US010646493B2

(12) United States Patent
Alexander et al.

(10) Patent No.: US 10,646,493 B2
(45) **Date of Patent: *May 12, 2020**

(54) SUBSTITUTED AMINOPURINE COMPOUNDS, COMPOSITIONS THEREOF, AND METHODS OF TREATMENT THEREWITH

(71) Applicant: Signal Pharmaceuticals, LLC, San Diego, CA (US)

(72) Inventors: Matthew Alexander, San Diego, CA (US); Sogole Bahmanyar, Rancho Santa Fe, CA (US); John Frederick Boylan, Bedminster, NJ (US); Joshua Hansen, La Jolla, CA (US); Dehua Huang, San Diego, CA (US); Robert Hubbard, San Diego, CA (US); Brandon Jeffy, San Diego, CA (US); Jim Leisten, San Marcos, CA (US); Mehran Moghaddam, Carlsbad, CA (US); Raj K. Raheja, Poway, CA (US); Heather Raymon, San Diego, CA (US); Kimberly Schwarz, San Diego, CA (US); Marianne Sloss, San Diego, CA (US); Eduardo Torres, San Diego, CA (US); Tam Minh Tran, San Diego, CA (US); Shuichan Xu, San Diego, CA (US); JingJing Zhao, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,749

(22) Filed: Jul. 17, 2019

(65) Prior Publication Data

US 2019/0336507 A1 Nov. 7, 2019

Related U.S. Application Data

(60) Continuation of application No. 16/169,414, filed on Oct. 24, 2018, now Pat. No. 10,398,700, which is a division of application No. 15/641,383, filed on Jul. 5, 2017, now Pat. No. 10,149,849, which is a continuation of application No. 15/335,619, filed on Oct. 27, 2016, now Pat. No. 9,737,541, which is a continuation of application No. 14/874,513, filed on Oct. 5, 2015, now Pat. No. 9,512,124.

(60) Provisional application No. 62/060,339, filed on Oct. 6, 2014.

(51) Int. Cl.

| | |
|---|---|
| *A61K 31/52* | (2006.01) |
| *C07D 473/32* | (2006.01) |
| *A61P 35/00* | (2006.01) |
| *A61K 31/5377* | (2006.01) |

(52) U.S. Cl.

CPC .......... *A61K 31/52* (2013.01); *A61K 31/5377* (2013.01); *A61P 35/00* (2018.01); *C07D 473/32* (2013.01)

(58) Field of Classification Search

CPC .............................. A61K 31/52; C07D 473/32

USPC ..................................................... 514/263.22

See application file for complete search history.

(56) References Cited

U.S. PATENT DOCUMENTS

| | | | |
|---|---|---|---|
| 5,858,968 | A | 1/1999 | Weiner et al. |
| 7,521,446 | B2 | 4/2009 | Albers et al. |
| 7,723,340 | B2 | 5/2010 | Albers et al. |
| 7,759,342 | B2 | 7/2010 | Bennett et al. |
| 8,101,588 | B2 | 1/2012 | Albers et al. |
| 8,158,635 | B2 | 4/2012 | Beauchamps et al. |
| 8,324,225 | B2 | 12/2012 | Brain et al. |
| 8,440,661 | B2 | 5/2013 | Bennett et al. |
| 8,491,930 | B2 | 7/2013 | Fernandez De Gatta Garcia et al. |

(Continued)

FOREIGN PATENT DOCUMENTS

| | | | |
|---|---|---|---|
| WO | WO 1999/015155 | A1 | 4/1999 |
| WO | WO 2006/076595 | A1 | 7/2006 |

(Continued)

OTHER PUBLICATIONS

Aljaberi et al., 2009, "Functional performance of silicified microcrystalline cellulose versus microcrystalline cellulose: a case study," Drug Development and Industrial Pharmacy 35(9): 1066-1071.

(Continued)

*Primary Examiner* — Kahsay Habte
(74) *Attorney, Agent, or Firm* — Jones Day

(57) ABSTRACT

Provided herein are Aminopurine Compounds having the following structures:

(I)

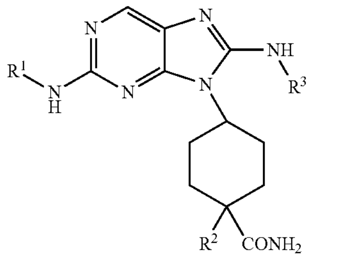

wherein $R^1$, $R^2$, and $R^3$ are as defined herein, compositions comprising an effective amount of an Aminopurine Compound, and methods for treating or preventing a cancer, for example, melanoma.

20 Claims, No Drawings

(56) References Cited

U.S. PATENT DOCUMENTS

| | | | | |
|---|---|---|---|---|
| 8,603,527 | B2 | 12/2013 | Bhat et al. | |
| 8,680,076 | B2 | 3/2014 | Bennett et al. | |
| 9,187,479 | B2 | 11/2015 | Clareen et al. | |
| 9,198,866 | B2 | 12/2015 | Bhat et al. | |
| 9,512,124 | B2 * | 12/2016 | Alexander | C07D 473/32 |
| 9,737,541 | B2 * | 8/2017 | Alexander | C07D 473/32 |
| 2003/0191086 | A1 | 10/2003 | Hanus et al. | |
| 2009/0312320 | A1 | 12/2009 | Albers et al. | |
| 2012/0115890 | A1 | 5/2012 | Beauchamps et al. | |
| 2013/0034495 | A1 | 2/2013 | Beauchamps et al. | |
| 2016/0039822 | A1 | 2/2016 | Clareen et al. | |

FOREIGN PATENT DOCUMENTS

| | | | |
|---|---|---|---|
| WO | WO 2007/062338 | A2 | 5/2007 |
| WO | WO 2007/127382 | A1 | 11/2007 |
| WO | WO 2008/057252 | A2 | 5/2008 |
| WO | WO 2011/071491 | A1 | 6/2011 |
| WO | WO 2014/172616 | A2 | 10/2014 |
| WO | WO 2015/086505 | A1 | 6/2015 |

OTHER PUBLICATIONS

Edge et al., 1999, "Polysaccharide engineering: Silicified microcrystalline cellulose as a novel high-functionality pharmaceutical material", in: *Polysaccharide Applications: Cosmetics and Pharmaceuticals*, American Chemical Society Symposium Series 737, Chapter 7, pp. 98-112.

Tobyn et al., 1998, "Physiochemical comparison between microcrystalline cellulose and silicified microcrystalline cellulose," International Journal of Pharmaceutics 169(2):183-194.

Chen, X., et al., (2014) "SKLB-287, a novel oral multikinase inhibitor of EGFR and VEGFR2, exhibits potent antitumor activity in LoVo colorectal tumor model," *Neoplasma*, 61.5 (2014): 514-522.

Krenitsky et al. Bioorganic & Medicinal Chemistry Letters (2012),22(3), 1427-1432.

* cited by examiner

SUBSTITUTED AMINOPURINE COMPOUNDS, COMPOSITIONS THEREOF, AND METHODS OF TREATMENT THEREWITH

This application is a continuation of U.S. patent application Ser. No. 16/169,414, filed Oct. 24, 2018, currently allowed, which is a divisional of U.S. patent application Ser. No. 15/641,383, filed Jul. 5, 2017, now U.S. Pat. No. 10,149,849, issued Dec. 11, 2018, which is a continuation of U.S. patent application Ser. No. 15/335,619, filed Oct. 27, 2016, now U.S. Pat. No. 9,737,541, issued Aug. 22, 2017, which is a continuation of U.S. patent application Ser. No. 14/874,513, filed Oct. 5, 2015, now U.S. Pat. No. 9,512,124, issued Dec. 6, 2016, which claims the benefit of U.S. Provisional Application No. 62/060,339, filed Oct. 6, 2014, the entire contents of which are incorporated herein by reference.

FIELD

Provided herein are certain aminopurine compounds, compositions comprising an effective amount of such compounds, and methods for treating or preventing a cancer, for example, melanoma, comprising administering an effective amount of such aminopurine compounds compounds to a subject in need thereof.

BACKGROUND

Melanoma is a cancer characterized by the uncontrolled growth of pigment-producing cells (melanocytes). Malignant melanoma develops from a neoplastic transformation of melanocytes, which are predominantly found in the basal layer of the epidermis and the eye. (Spagnolo F et al., *Archives of Dermatology Research,* 2012, 304: 177-184; Hurst E A et al., *Archives of Dermatology Research,* 2003, 139: 1067-1073). Malignant melanoma is the most aggressive form of skin cancer. In 2014, it is estimated that there will be 76,100 new cases of melanoma of the skin and an estimated 9,710 people will die of this disease. (SEER Stat Fact Sheets: Melanoma of the Skin, *Surveillance Epidemiology and End Results Program,*—accessed on Jun. 2, 2014 at http://seer.cancer.gov/statfacts/html/melan.html).

Although surgical removal of early melanoma lesions leads to a cure rate of 90%, advanced melanoma resists chemotherapy and tends to quickly metastasize (Spagnolo F et al., *Archives of Dermatology Research,* 2012, 304: 177-184); for these reasons, prognosis for advanced melanoma is poor, with 5-year survival rates of 78% for patients with stage IIIA, 59% for patients with stage IIIB, and 40% for patients with stage IIIC, respectively. (Balch C M et al., *Journal of Clinical Oncology,* 2009, 27(36): 6199-6206). For patients with distant metastases, the prognosis significantly worsens, with 1 year survival rates of 62% for stage M1a, 53% for stage M1b and only 33% for stage M1c. (Balch C M et al., *Journal of Clinical Oncology,* 2009, 27(36): 6199-6206).

The treatment options for metastatic melanoma are limited. Prior to 2011, only two therapies for metastatic melanoma had been approved by the FDA:dacarbazine and high dose interleukin 2 ("HD IL-2"), neither of which increased median overall survival. (Hill G et al., *Cancer,* 1984, 53:1299-1305; Atkins M et al., *Journal of Clinical Oncology,* 1999, 17(7): 2105-2116; Phan G et al., *Journal of Clinical Oncology,* 2001, 19(15): 3477-3482). Moreover, dacarbazine is limited by a low response rate of 10% to 15%, while HD IL-2 has an even lower response rate of 6% to 10%. (Finn L et al., *BMC Medicine,* 2012, 10:23). During 2011, the FDA approved two more therapies for advanced melanoma, vemurafenib (Zelboraf™) and ipilimumab. (Finn L et al., *BMC Medicine,* 2012, 10:23). While vemurafenib has demonstrated good clinical activity with a high response rate and low toxicity, its applicability is limited to the 40%-60% of melanoma patients who harbor an activating mutation in the BRAF gene that leads to constitutive activation of the mitogen-activated protein kinase pathway ("MAPK"), which causes increased cellular proliferation as well as increased oncogenic activity. (Finn L et al., *BMC Medicine,* 2012, 10:23). Additionally, most patients who initially respond to treatment with BRAF inhibitors relapse, indicating the development of drug resistance and demonstrating the limitations of targeting only one pathway to eradicate melanoma. (Villanueva J et al., *Cancer Cell,* 2010, 18(6): 683-695; Spagnolo F et al., *Archives of Dermatology Research,* 2012, 304: 177-184). Ipilmumab can induce long-term responses in a subset of patients, but its utility is limited by its low response rate of 10% to 15% and by the fact that it improves median survival time by only two months. (Finn L et al., *BMC Medicine,* 2012, 10:23). Thus, there remains a serious need for additional therapies for treatment of melanoma.

Citation or identification of any reference in Section 2 of this application is not to be construed as an admission that the reference is prior art to the present application.

SUMMARY

Provided herein are compounds having the following formula (I):

(I)

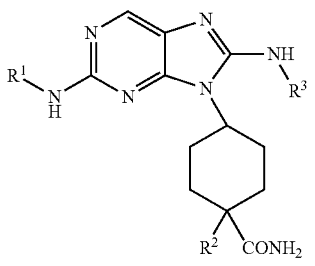

and pharmaceutically acceptable salts, tautomers, isotopologues, and stereoisomers thereof, wherein $R^1$, $R^2$ and $R^3$ are as defined herein.

A compound of formula (I) or a pharmaceutically acceptable salt, tautomer, isotopologue, or stereoisomer thereof (each being referred to herein as an "Aminopurine Compound") can be used in the methods provided herein. The compound of formula (I) or a pharmaceutically acceptable salt, tautomer, isotopologue, or stereoisomer thereof is useful for treating or preventing a cancer, for example, melanoma.

In one aspect, provided herein are Aminopurine Compounds as described in the instant disclosure, such as, for example, in Table 1.

In one aspect, provided herein are pharmaceuticals comprising an effective amount of an Aminopurine Compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing melanoma, comprising administering to a subject in need thereof an effective amount of an Aminopurine Compound as described herein; and a pharmaceutically acceptable carrier, excipient or vehicle. In another aspect, provided herein are methods for treating or preventing melanoma, comprising administering to a subject in need thereof an effective amount of an Aminopurine Compound. The Aminopurine Compound as provided herein is for use in methods for treating or preventing melanoma, comprising administering to a subject in need thereof an effective amount of the Aminopurine Compound. The Aminopurine Compound as provided herein is for use in methods for treating or preventing melanoma, comprising administering to a subject in need thereof an effective amount of the Aminopurine Compound; and a pharmaceutically acceptable carrier, excipient or vehicle.

In a further aspect, provided herein is a method of inhibiting a kinase in a cell expressing said kinase, comprising contacting said cell with an effective amount of the Aminopurine Compound as described herein. The method is an in vitro or an ex vivo method. Also provided is the Aminopurine Compound for use in said methods.

In another aspect provided herein are methods for preparing Aminopurine Compounds as described herein.

The present embodiments can be understood more fully by reference to the detailed description and examples, which are intended to exemplify non-limiting embodiments.

DETAILED DESCRIPTION

Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. Examples of unsaturated alkyl groups include, but are not limited to, vinyl, allyl, $—CH{=}CH(CH_3)$, $—CH{=}C(CH_3)_2$, $—C(CH_3){=}CH_2$, $—C(CH_3){=}CH(CH_3)$, $—C(CH_2CH_3){=}CH_2$, $—C{\equiv}CH$, $—C{\equiv}C(CH_3)$, $—C{\equiv}C(CH_2CH_3)$, $—CH_2C{\equiv}CH$, $—CH_2C{\equiv}C(CH_3)$ and $—CH_2C{\equiv}C(CH_2CH_3)$, among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; $B(OH)_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A “cycloalkylalkyl” group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An “aralkyl” group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An “heterocyclylalkyl” group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridin-3-yl methyl, tetrahydrofuran-2-yl ethyl, and indol-2-yl propyl.

A “halogen” is chloro, iodo, bromo, or fluoro.

A “hydroxyalkyl” group is an alkyl group as described herein substituted with one or more hydroxy groups.

An “alkoxy” group is —O-(alkyl), wherein alkyl is defined herein.

An “alkoxyalkyl” group is -(alkyl)-O-(alkyl), wherein alkyl is defined herein.

An “amine” group is a radical of the formula: $—NH_2$.

A “hydroxyl amine” group is a radical of the formula: $—N(R^{\#})OH$ or —NHOH, wherein $R^{\#}$ is a substituted or unsubstituted alkyl, cycloalkyl, cycloalkylalkyl, aryl, aralkyl, heterocyclyl or heterocyclylalkyl group as defined herein.

An “alkoxyamine” group is a radical of the formula: $—N(R^{\#})O$-alkyl or —NHO-alkyl, wherein $R^{\#}$ and alkyl are as defined herein.

An “aryloxyamine” group is a radical of the formula: $—N(R^{\#})O$-aryl or —NHO-aryl, wherein $R^{\#}$ and aryl are as defined herein.

An “aralkoxyamine” group is a radical of the formula: $—N(R^{\#})O$-aralkyl or —NHO-aralkyl, wherein $R^{\#}$ and aralkyl as defined herein.

An “alkylamine” group is a radical of the formula: —NH-alkyl or $—N(alkyl)_2$, wherein each alkyl is independently as defined herein.

An “aminocarbonyl” group is a radical of the formula: $—C(═O)N(R^{\#})_2$, $—C(═O)NH(R^{\#})$ or $—C(═O)NH_2$, wherein each $R^{\#}$ is as defined herein.

An “acylamino” group is a radical of the formula: $—NHC(═O)(R^{\#})$ or $—N(alkyl)C(═O)(R^{\#})$, wherein each alkyl and $R^{\#}$ are independently as defined herein.

An “O(alkyl)aminocarbonyl” group is a radical of the formula: $—O(alkyl)C(═O)N(R^{\#})_2$, $—O(alkyl)C(═O)NH(R^{\#})$ or $—O(alkyl)C(═O)NH_2$, wherein each $R^{\#}$ and alkyl are independently as defined herein.

An “N-oxide” group is a radical of the formula: $—N^+—O^-$.

A “carboxy” group is a radical of the formula: —C(═O)OH.

A “ketone” group is a radical of the formula: $—C(═O)(R^{\#})$, wherein $R^{\#}$ is as defined herein.

An “aldehyde” group is a radical of the formula: —CH(═O).

An “ester” group is a radical of the formula: $—C(═O)O(R^{\#})$ or $—OC(═O)(R^{\#})$, wherein $R^{\#}$ is as defined herein.

A “urea” group is a radical of the formula: $—N(alkyl)C(═O)N(R^{\#})_2$, $—N(alkyl)C(═O)NH(R^{\#})$, $—N(alkyl)C(═O)NH_2$, $—NHC(═O)N(R^{\#})_2$, $—NHC(═O)NH(R^{\#})$, or $—NHC(═O)NH_2\#$, wherein each alkyl and $R^{\#}$ are independently as defined herein.

An "imine" group is a radical of the formula: —N═C$(R^{\#})_2$ or —C$(R^{\#})$═N$(R^{\#})$, wherein each $R^{\#}$ is independently as defined herein.

An "imide" group is a radical of the formula: —C(═O)N$(R^{\#})$C(═O)$(R^{\#})$ or —N((C═O)$(R^{\#}))_2$, wherein each $R^{\#}$ is independently as defined herein.

A "urethane" group is a radical of the formula: —OC(═O)N$(R^{\#})_2$, —OC(═O)NH$(R^{\#})$, —N$(R^{\#})$C(═O)O$(R^{\#})$, or —NHC(═O)O$(R^{\#})$, wherein each $R^{\#}$ is independently as defined herein.

An "amidine" group is a radical of the formula: —C(═N$(R^{\#})$)N$(R^{\#})_2$, —C(═N$(R^{\#})$)NH$(R^{\#})$, —C(═N$(R^{\#})$)$NH_2$, —C(═NH)N$(R^{\#})_2$, —C(═NH)NH$(R^{\#})$, —C(═NH)$NH_2$, —N═C$(R^{\#})$N$(R^{\#})_2$, —N═C$(R^{\#})$NH$(R^{\#})$, —N═C$(R^{\#})$$NH_2$, —N$(R^{\#})$C$(R^{\#})$═N$(R^{\#})$, —NHC$(R^{\#})$═N$(R^{\#})$, —N$(R^{\#})$C$(R^{\#})$═NH, or —NHC$(R^{\#})$═NH, wherein each $R^{\#}$ is independently as defined herein.

A "guanidine" group is a radical of the formula: —N$(R^{\#})$C(═N$(R^{\#})$)N$(R^{\#})_2$, —NHC(═N$(R^{\#})$)N$(R^{\#})_2$, —N$(R^{\#})$C(═NH)N$(R^{\#})_2$, —N$(R^{\#})$C(═N$(R^{\#})$)NH$(R^{\#})$, —N$(R^{\#})$C(═N$(R^{\#})$)$NH_2$, —NHC(═NH)$NH_2$, —N═C(N$(R^{\#})_2)_2$, —N═C(NH$(R^{\#}))_2$, or —N═C$(NH_2)_2$, wherein each $R^{\#}$ is independently as defined herein.

A "enamine" group is a radical of the formula: —N$(R^{\#})$C$(R^{\#})$═C$(R^{\#})_2$, —NHC$(R^{\#})$═C$(R^{\#})_2$, —C(N$(R^{\#})_2$)═C$(R^{\#})_2$, —C(NH$(R^{\#})$)═C$(R^{\#})_2$, —C$(NH_2)$═C$(R^{\#})_2$, —C$(R^{\#})$═C$(R^{\#})$(N$(R^{\#})_2$), —C$(R^{\#})$═C$(R^{\#})$(NH$(R^{\#})$) or —C$(R^{\#})$═C$(R^{\#})$$(NH_2)$, wherein each $R^{\#}$ is independently as defined herein.

An "oxime" group is a radical of the formula: —C(═NO$(R^{\#})$)$(R^{\#})$, —C(═NOH)$(R^{\#})$, —CH(═NO$(R^{\#})$), or —CH(═NOH), wherein each $R^{\#}$ is independently as defined herein.

A "hydrazide" group is a radical of the formula: —C(═O)N$(R^{\#})$N$(R^{\#})_2$, —C(═O)NHN$(R^{\#})_2$, —C(═O)N$(R^{\#})$NH$(R^{\#})$, —C(═O)N$(R^{\#})$$NH_2$, —C(═O)NHNH$(R^{\#})_2$, or —C(═O)$NHNH_2$, wherein each $R^{\#}$ is independently as defined herein.

A "hydrazine" group is a radical of the formula: —N$(R^{\#})$N$(R^{\#})_2$, —NHN$(R^{\#})_2$, —N$(R^{\#})$NH$(R^{\#})$, —N$(R^{\#})$$NH_2$, —NHNH$(R^{\#})_2$, or —$NHNH_2$, wherein each $R^{\#}$ is independently as defined herein.

A "hydrazone" group is a radical of the formula: —C(═N—N$(R^{\#})_2$)$(R^{\#})_2$, —C(═N—NH$(R^{\#})$)$(R^{\#})_2$, —C(═N—$NH_2$)$(R^{\#})_2$, —N$(R^{\#})$(N═C$(R^{\#})_2$), or —NH(N═C$(R^{\#})_2$), wherein each $R^{\#}$ is independently as defined herein.

An "azide" group is a radical of the formula: —$N_3$.

An "isocyanate" group is a radical of the formula: —N═C═O.

An "isothiocyanate" group is a radical of the formula: —N═C═S.

A "cyanate" group is a radical of the formula: —OCN.

A "thiocyanate" group is a radical of the formula: —SCN.

A "thioether" group is a radical of the formula; —S$(R^{\#})$, wherein $R^{\#}$ is as defined herein.

A "thiocarbonyl" group is a radical of the formula: —C(═S)$(R^{\#})$, wherein $R^{\#}$ is as defined herein.

A "sulfinyl" group is a radical of the formula: —S(═O)$(R^{\#})$, wherein $R^{\#}$ is as defined herein.

A "sulfone" group is a radical of the formula: —S$(═O)_2$$(R^{\#})$, wherein $R^{\#}$ is as defined herein.

A "sulfonylamino" group is a radical of the formula: —$NHSO_2$$(R^{\#})$ or —N(alkyl)$SO_2$$(R^{\#})$, wherein each alkyl and $R^{\#}$ are defined herein.

A "sulfonamide" group is a radical of the formula: —S$(═O)_2$N$(R^{\#})_2$, or —S$(═O)_2$NH$(R^{\#})$, or —S$(═O)_2$$NH_2$, wherein each $R^{\#}$ is independently as defined herein.

A "phosphonate" group is a radical of the formula: —P(═O)(O$(R^{\#}))_2$, —P(═O)$(OH)_2$, —OP(═O)(O$(R^{\#})$)$(R^{\#})$, or —OP(═O)(OH)$(R^{\#})$, wherein each $R^{\#}$ is independently as defined herein.

A "phosphine" group is a radical of the formula: —P$(R^{\#})_2$, wherein each $R^{\#}$ is independently as defined herein.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; oxygen (═O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "Aminopurine Compound" refers to compounds of formula (I) as well as to further embodiments provided herein. In one embodiment, an "Aminopurine Compound" is a compound set forth in Table 1. The term "Aminopurine Compound" includes pharmaceutically acceptable salts, tautomers, isotopologues, and stereoisomers of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences,* $18^{th}$ eds., Mack Publishing, Easton Pa.

(1990) or *Remington: The Science and Practice of Pharmacy,* $19^{th}$ eds., Mack Publishing, Easton Pa. (1995).

As used herein and unless otherwise indicated, the term "stereoisomer" or "stereomerically pure" means one stereoisomer of an Aminopurine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Aminopurine Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Aminopurine Compounds, as well as the use of mixtures of those forms, are encompassed by the embodiments disclosed herein. For example, mixtures comprising equal or unequal amounts of the enantiomers of a particular Aminopurine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. *L., Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Aminopurine Compounds can include E and Z isomers, or a mixture thereof, and cis and trans isomers or a mixture thereof. In certain embodiments, the Aminopurine Compounds are isolated as either the E or Z isomer. In other embodiments, the Aminopurine Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

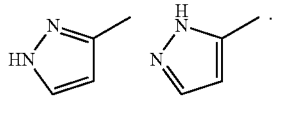

As readily understood by one skilled in the art, a wide variety of functional groups and other structures may exhibit tautomerism and all tautomers of compounds of formula (I) are within the scope of the present invention.

It should also be noted the Aminopurine Compounds can contain unnatural proportions of atomic isotopes at one or more of the atoms. For example, the compounds may be radiolabeled with radioactive isotopes, such as for example tritium ($^{3}H$), iodine-125 ($^{125}I$), sulfur-35 ($^{35}S$), or carbon-14 ($^{14}C$), or may be isotopically enriched, such as with deuterium ($^{2}H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically encriched compounds are useful as therapeutic agents, e.g., cancer and inflammation therapeutic agents, research reagents, e.g., binding assay reagents, and diagnostic agents, e.g., in vivo imaging agents. All isotopic variations of the Aminopurine Compounds as described herein, whether radioactive or not, are intended to be encompassed within the scope of the embodiments provided herein. In some embodiments, there are provided isotopologues of the Aminopurine Compounds, for example, the isotopologues are deuterium, carbon-13, or nitrogen-15 enriched Aminopurine Compounds.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is melanoma.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is melanoma, as described herein, or symptoms thereof.

The term "effective amount" in connection with an Aminopurine Compound means an amount capable of treating or preventing a disorder, disease or condition, or symptoms thereof, disclosed herein. In one embodiment, the disorder is melanoma.

The term "subject" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having melanoma, or a symptom thereof.

Aminopurine Compounds

Provided herein are compounds having the following formula (I):

(I)

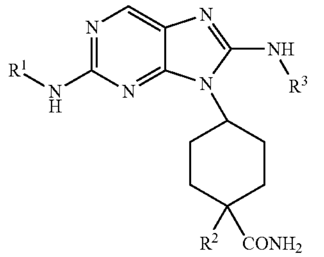

and pharmaceutically acceptable salts, tautomers, stereoisomers, enantiomers, and isotopologues thereof, wherein:

$R^1$ is substituted or unsubstituted $C_{1-8}$ alkyl, substituted or unsubstituted cycloalkyl, substituted or unsubstituted cycloalkylalkyl, or substituted or unsubstituted non-aromatic heterocyclyl;

$R^2$ is H or substituted or unsubstituted $C_{1-3}$ alkyl;

$R^3$ is phenyl, substituted with one or more halogen, optionally further substituted with one or more substitutents independently selected from substituted or unsubstituted $C_{1-3}$ alkyl, CN, and —OR', wherein each R' is independently substituted or unsubstituted $C_{1-3}$ alkyl;

provided the compound is not 4-[2-[(1-methylethyl)amino]-8-[(2,4,6-trifluorophenyl)amino]-9H-purin-9-yl]-cis-cyclohexanecarboxamide

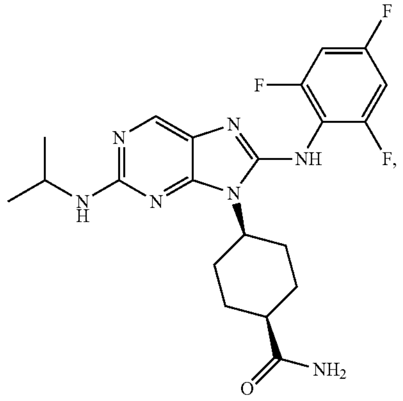 [SMILES: CC(C)Nc1ncc2nc(Nc3c(F)cc(F)cc3F)n([C@H]3CC[C@@H](C(N)=O)CC3)c2n1]

or 4-[8-[(2,4-difluorophenyl)amino]-2-[(trans-4-hydroxycyclohexyl)amino]-9H-purin-9-yl]-cis-cyclohexanecarboxamide

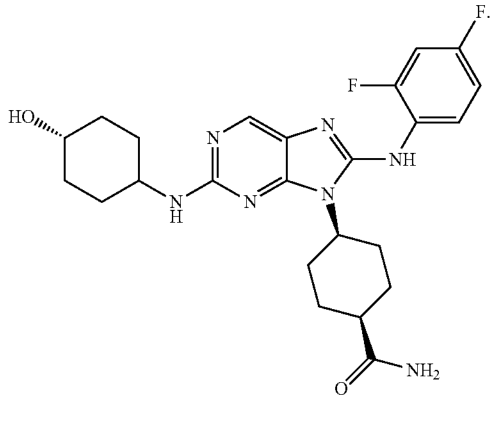

In one embodiment, the compound is a compound of formula (II):

(II)

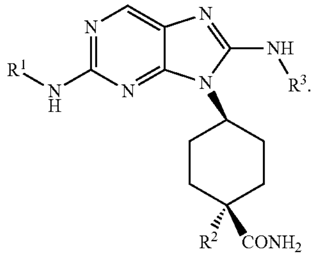

In some embodiments or compounds of formula (I), $R^1$ is substituted or unsubstituted $C_{1-8}$ alkyl. In some embodiments, $R^1$ is substituted or unsubstituted methyl, ethyl, n-propyl, isopropyl, n-butyl, sec-butyl, isobutyl, tert-butyl, n-pentyl, 2-methylpentyl, 3-methylpentyl, isopentyl, or neopentyl. In some embodiments, $R^1$ is substituted with one or more substituents independently selected from halogen and OR, wherein each R is independently H or substituted or unsubstituted $C_{1-3}$ alkyl. For example, $R^1$ is substituted with one or more substituents independently selected from F, OH, and $OCH_3$. In some embodiments, $R^1$ is ethyl, isopropyl, isobutyl, tert-butyl, $CH_2CH_2F$, $CH_2CHF_2$, $CH_2CF_3$, $CH_2CH(CH_3)OH$, $CH_2CH(CH_3)OCH_3$, $CH(CH_3)CH_2OH$, $CH(CH_3)CH_2OCH_3$, $CH_2C(F_2)CH_2OH$, $CH_2C(F_2)CH_2OCH_3$, $CH(CF_3)CH_2OH$, $CH(CF_3)CH_2OCH_3$, $CH(CH_2OH)CH_2CH_3$, $CH(CH_2OCH_3)CH_2CH_3$, $CH_2C(CH_3)_2CH_2OH$, or $CH_2C(CH_3)_2CH_2OCH_3$. For example, $R^1$ is isopropyl, isobutyl, tert-butyl, $CH_2CF_3$, $CH_2CH(CH_3)OH$, $CH(CH_3)CH_2OH$, $CH(CH_3)CH_2OCH_3$, $CH_2C(F_2)CH_2OH$, $CH(CF_3)CH_2OH$, $CH(CH_2OH)CH_2CH_3$, or $CH_2C(CH_3)_2CH_2OH$.

In one embodiment, $R^1$ is isopropyl, $CH(CH_3)CH_2OH$, or $CH(CH_2OH)CH_2CH_3$. In some embodiments, $R^1$ is (S)-2-propan-1-ol:

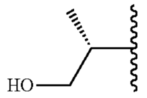 [SMILES: *[C@@H](C)CO]

In some embodiments, $R^1$ is substituted or unsubstituted cycloalkyl. In some embodiments, $R^1$ is substituted or unsubstituted cyclopropyl, cyclobutyl, cyclopentyl, cyclohexyl, or cycloheptyl. In some embodiments, $R^1$ is substituted with one or more substituents independently selected from halogen, OR, $SO_2R'$, substituted or unsubstituted $C_{1-3}$ alkyl, and substituted or unsubstituted heterocyclyl, wherein each R is independently H or substituted or unsubstituted $C_{1-3}$ alkyl, and each R' is independently substituted or unsubstituted $C_{1-3}$ alkyl. In some embodiments, $R^1$ is substituted with one or more substituents independently selected from F, OH, $OCH_3$, $SO_2CH_3$, methyl, and substituted or unsubstituted 5-membered heterocyclyl, for example, pyrrolidinedionyl, or oxadiazolyl. In some other embodiments, $R^1$ is cyclobutyl, cyclopentyl, cyclohexyl, or cycloheptyl, optionally substituted with one or more substituents independently selected from F, OH, $OCH_3$, $SO_2CH_3$, methyl, pyrrolidinedionyl, and oxadiazolyl. In some embodiments, $R^1$ is

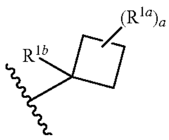

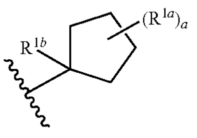

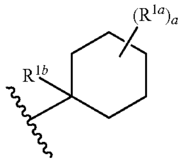

or

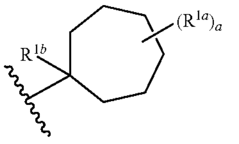

wherein each $R^{1a}$ is independently F, OH, $OCH_3$, $SO_2CH_3$, or methyl;

$R^{1b}$ is H or $CH_3$;

and a is 0-4.

In some embodiments, $R^1$ is substituted or unsubstituted cycloalkylalkyl. In some embodiments, $R^1$ is substituted or unsubstituted ($C_{1-3}$ alkyl)-($C_{1-8}$ cycloalkyl), for example, $R^1$ is substituted or unsubstituted $CH_2$-cyclopropyl, $CH_2$-cyclobutyl, $CH_2$-cyclopentyl, $CH_2$-cyclohexyl, or $CH_2$-cycloheptyl. In some embodiments, $R^1$ is substituted with one or more substituents independently selected from ($C_{1-3}$ alkyl) OR or OR, wherein each R is independently H or substituted or unsubstituted $C_{1-3}$ alkyl. For example, $R^1$ is $CH_2$-cyclopropyl, $CH_2$-cyclobutyl, $CH_2$-cyclopentyl, or $CH_2$-cyclohexyl, optionally substituted with one or more $CH_2OH$ or OH.

In some embodiments, $R^1$ is substituted or unsubstituted non-aromatic heterocyclyl. In some embodiments, $R^1$ is substituted or unsubstituted oxetanyl, tetrahydrofuranyl, tetrahydropyranyl, tetrahydro-thiopyrandioxide, piperidyl, oxepanyl, or oxaspiroheptyl. In some embodiments, $R^1$ is substituted with one or more substituents independently selected from halogen, OR, $SO_2R^4$, C(=O)$R^5$, C(=O)O$R^6$, C(=O)N$RR^7$, substituted or unsubstituted $C_{1-3}$ alkyl, substituted or unsubstituted aryl, substituted or unsubstituted heteroaryl, substituted or unsubstituted or alkylaryl, wherein each R is independently H or substituted or unsubstituted $C_{1-3}$ alkyl; $R^4$ is substituted or unsubstituted $C_{1-3}$ alkyl, or substituted or unsubstituted aryl; $R^5$ is substituted or unsubstituted $C_{1-3}$ alkyl; $R^6$ is substituted or unsubstituted $C_{1-6}$ alkyl; and $R^7$ is substituted or unsubstituted $C_{1-3}$ alkyl, or substituted or unsubstituted aryl. For example, $R^1$ is oxetanyl, tetrahydrofuranyl, tetrahydropyranyl, tetrahydro-thiopyrandioxide, piperidyl, oxepanyl, or oxaspiroheptyl, optionally substituted with one or more substituents independently selected from F, OH, $SO_2CH_3$, $SO_2$-tosyl, C(=O)$CH_3$, C(=O)$OCH_3$, C(=O)O-tert-butyl, C(=O)O-isopropyl, C(=O)$NHCH_3$, C(=O)NH-phenyl, methyl, ethyl, isopropyl, $CH_2OH$, phenyl, pyridyl, or benzyl. In one embodiment, $R^1$ is

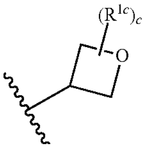

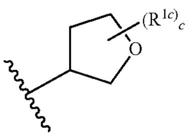

-continued

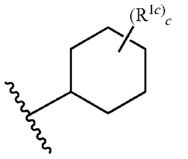

or

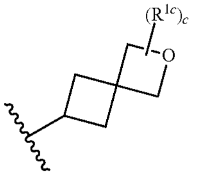

wherein each $R^{1c}$ is independently F, OH, methyl, or $CH_2OH$;

and c is 0-3.

In some such embodiments, $R^{1c}$ is F or methyl and c is 1 or 2.

In some embodiments of compounds of formula (I), $R^2$ is H. In others, $R^2$ is $CH_3$.

In some embodiments of compounds of formula (I), $R^3$ is ortho-halogen substituted phenyl. In one embodiment $R^3$ is o-fluoro or o-chloro substituted phenyl. In some embodiments, the phenyl is additionally para substituted, for example, the phenyl is additionally substituted with p-chloro, p-bromo, p-fluoro, p-CN, p-methyl, p-$CF_3$, or p-$OCH_3$. In other embodiments, $R^3$ is para-halogen substituted phenyl. In some embodiments, $R^3$ is p-fluoro or p-chloro substituted phenyl. In some embodiments, the phenyl is additionally ortho substituted, for example, the phenyl is additionally substituted with o-chloro, o-fluoro, or o-methyl. In other embodiments, $R^3$ is para-CN substituted phenyl. In some embodiments, the phenyl is additionally ortho substituted, for example, the phenyl is additionally substituted with o-chloro, or o-fluoro. In yet other embodiments, $R^3$ is ortho, ortho-dihalogen substituted phenyl. In one embodiment $R^3$ is o,o-difluoro or o,o-dichloro substituted phenyl. In some embodiments, the phenyl is additionally para substituted, for example, the phenyl is additionally substituted with p-chloro, p-bromo, p-fluoro, p-CN, p-methyl, p-$CF_3$, or p-$OCH_3$. In yet other embodiments, $R^3$ is ortho, para-dihalogen substituted phenyl. In one embodiment $R^3$ is o,p-difluoro substituted phenyl or o,p-dichloro substituted phenyl. In some embodiments, the phenyl is additionally ortho substituted, for example, the phenyl is additionally substituted with o-chloro, o-fluoro, or o-methyl. In still other embodiments, $R^3$ is 2,4,6-trihalogen substituted phenyl. In one embodiment $R^3$ is 2,4,6-trifluoro substituted phenyl, 4-chloro-2,6-difluoro substituted phenyl, or 2,4,6-trichloro substituted phenyl. In yet another embodiment, $R^3$ is ortho-halogen, para-CN substituted phenyl. In one embodiment $R^3$ is o-fluoro-p-CN substituted phenyl, or o-chloro-para-CN substituted phenyl. In some embodiments, the phenyl is additionally ortho substituted, for example, the phenyl is additionally substituted with o-chloro, or o-fluoro.

In some embodiments of compounds of formula (I), $R^3$ is

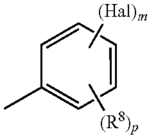

wherein each Hal is independently halogen;

each $R^8$ is independently substituted or unsubstituted $C_{1-3}$ alkyl, CN, or OR';

each R' is independently substituted or unsubstituted $C_{1-3}$ alkyl;

m is 1-3;

and p is 0-2.

In some embodiments, each Hal is independently Cl or F. In others, each $R^8$ is independently $CH_3$, $CF_3$, CN, or $OCH_3$. In yet others, m is 2 or 3. In still others, p is 0 or 1.

In some embodiments of compounds of formula (I), $R^3$ is

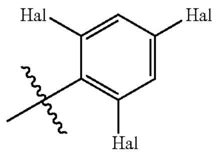

or

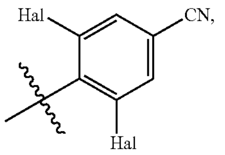

and each Hal is independently halogen.

In some embodiments, each Hal is independently F or Cl.

Further embodiments provided herein include combinations of one or more of the particular embodiments set forth above.

Representative compounds of formula (I) are set forth in Table 1.

Aminopurine Compounds set forth in Table 1 were tested in the Lox-IMVI anti-proliferative assay described herein and were found to have activity therein. In one embodiment, the Aminopurine Compound is a compound as described herein, wherein the compound at a concentration of 10 μM inhibits melanoma cell proliferation (for example, of a subject's cell, or a cell line, for example Lox-IMVI) by at least about 50% or more.

Methods for Making Aminopurine Compounds

The Aminopurine Compounds can be made using conventional organic syntheses and commercially available starting materials. By way of example and not limitation, Aminopurine Compounds of formula (I) can be prepared as described in U.S. Pat. Nos. 7,723,340, and 8,158,635, or as outlined in Scheme 1, shown below, as well as in the examples set forth herein. It should be noted that one skilled in the art would know how to modify the procedures set forth in the illustrative schemes and examples to arrive at the desired products.

Scheme 1

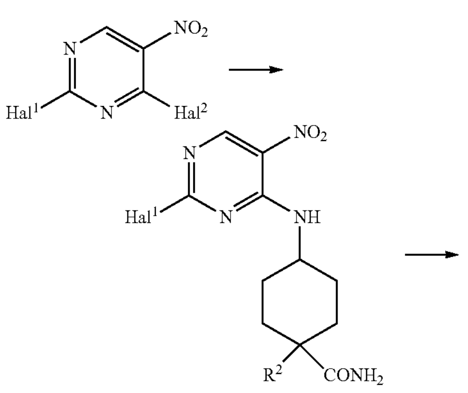

-continued

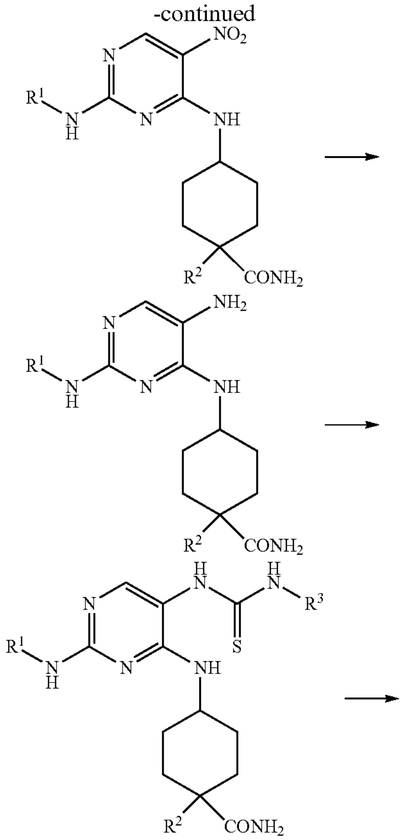

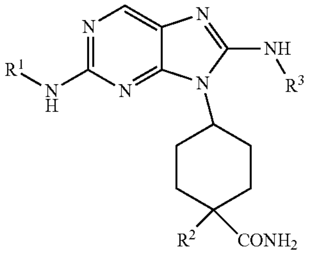

(I)

As shown in Scheme 1, compounds of formula (I), wherein $R^1$, $R^2$ and $R^3$ are as defined herein, can be prepared starting from an appropriately derivatized nitropyrimidine, wherein $Hal^1$ is Cl, and $Hal^2$ is Cl. Treatment of the dihalogenated nitropyrimidine with the appropriate 4-aminocyclohexane-1-carboxamide derivative, in the presence of a base, such as, for example, DIEA, TEA, or pyridine, in a solvent, such as for example, DCM or THF, at reduced temperature (for example, −78° C.), provided incorporation of the cyclohexylamide sidechain. Treatment of this product with $R^1NH_2$, in the presence of a base, such as DIEA, TEA, or pyridine, in a solvent such as DCM, THF, dioxane or DMF, at elevated temperature (for example 25-80° C.), resulted in incorporation of the $R^1$ sidechain. Reduction of the nitro moiety, using, for example hydrogen in the presence of a catalyst such as Pd/C, in a solvent, such as MeOH or ethyl acetate, provided the aminopyrimidine derivative. The aminopyrimidine derivative was treated with $R^3NCS$, in a solvent, such as THF, DMF, NMP, dioxane, or EtOH, to obtain the (optionally isolated) thiourea derivative, which was cyclized, using for example, EDC or DIC, in a solvent, for example, THF, dioxane, NMP or DMF, optionally at elevated temperature (for example, 40-80° C.), to provide compounds of formula (I).

Scheme 2

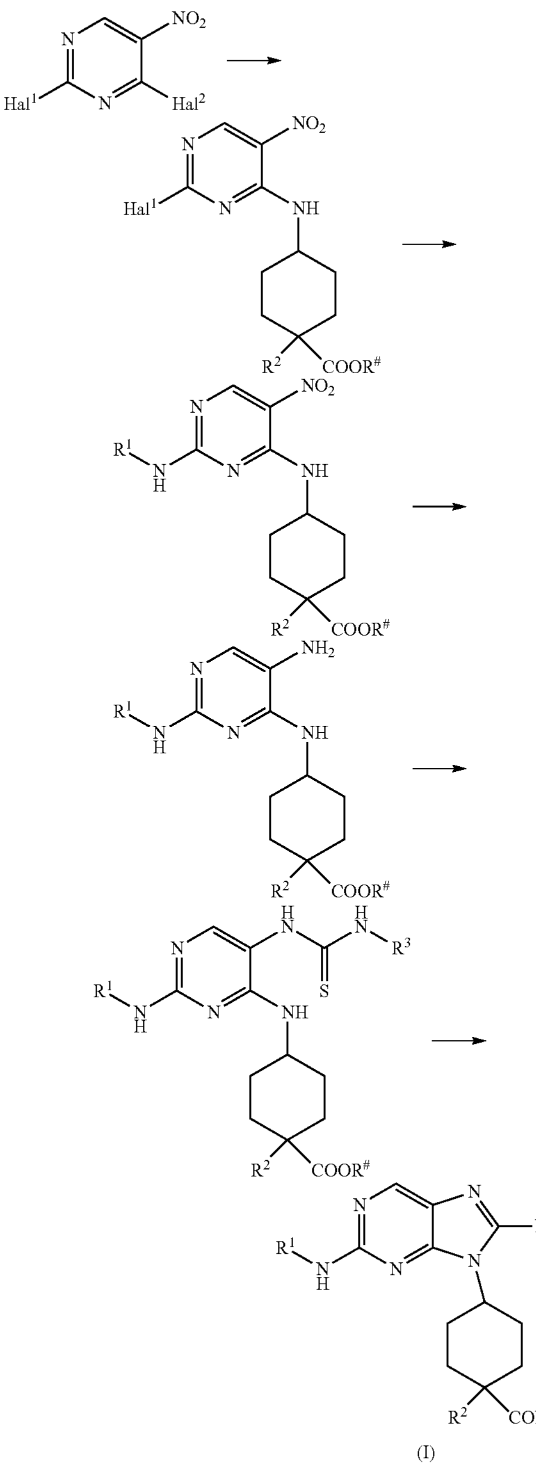

(I)

Alternatively, as shown in Scheme 2, compounds of formula (I), wherein $R^1$, $R^2$ and $R^3$ are as defined herein, and $R^\#$ is $C_{1-2}$ alkyl, can be prepared starting from, as before, an appropriately derivatized nitropyrimidine, wherein $Hal^1$ is Cl, and $Hal^2$ is Cl. Treatment of the dihalogenated nitropyrimidine with the appropriate 4-aminocyclohexane-1-carboxylate alkyl ester derivative, in the presence of a base, such as DIEA, TEA or pyridine, in a solvent, such as DCM or THF, at reduced temperature (for example, −78° C.), provided incorporation of the cyclohexylalkyl ester sidechain. Treatment of this product with $R^1NH_2$, in the presence of a base, such as DIEA, TEA, or pyridine, in a solvent such as DCM, THF, dioxane or DMF, at elevated temperature (for example 25-80° C.), resulted in incorporation of the $R^1$ sidechain. Reduction of the nitro moiety, using, for example hydrogen in the presence of a catalyst such as Pd/C, in a solvent, such as MeOH or ethyl acetate, provided the aminopyrimidine derivative. The aminopyrimidine derivative was treated with $R^3NCS$, in a solvent, such as THF, DMF, NMP, dioxane, or EtOH, to obtain the (optionally isolated) thiourea derivative, which was cyclized, using for example, EDC or DIC, in a solvent, for example, THF, NMP, dioxane, or DMF, optionally at elevated temperature (for example, 40° C. to 80° C.), to provide the derivatized diaminopurine derivative. Saponification of the alkyl ester, using a base (such as lithium hydroxide, sodium hydroxide, or potassium hydroxide), in a solvent (such as aqueous THF, MeOH, or EtOH), optionally at elevated temperature (for example, 40-80° C.), followed by amide formation, via treatment with $NH_4Cl$, in the presence of a coupling agent (such as, for example, HATU, CDI, HBTU, EDC, optionally in combination with HOBt, or ethyl chloroformate) and a base (such as DIEA, TEA, pyridine, DBU, or NMM), in a solvent, for example, DMF, provided the compounds of formula (I).

Scheme 3

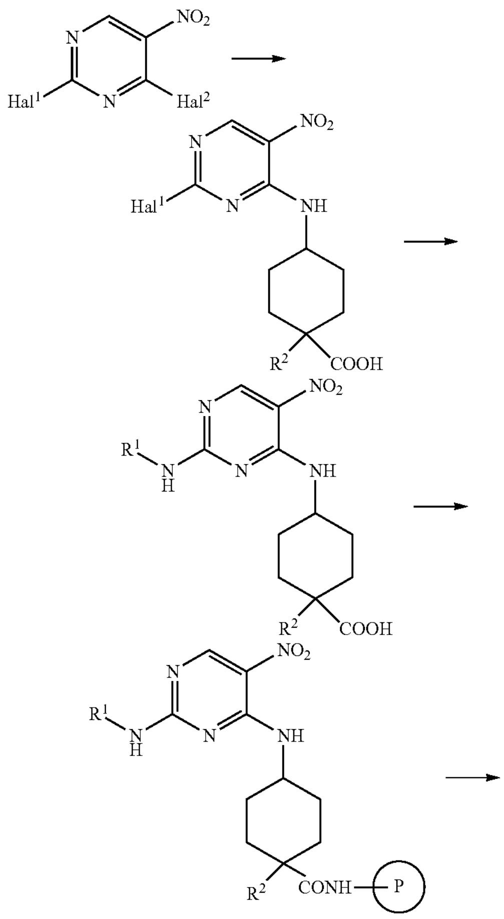

-continued

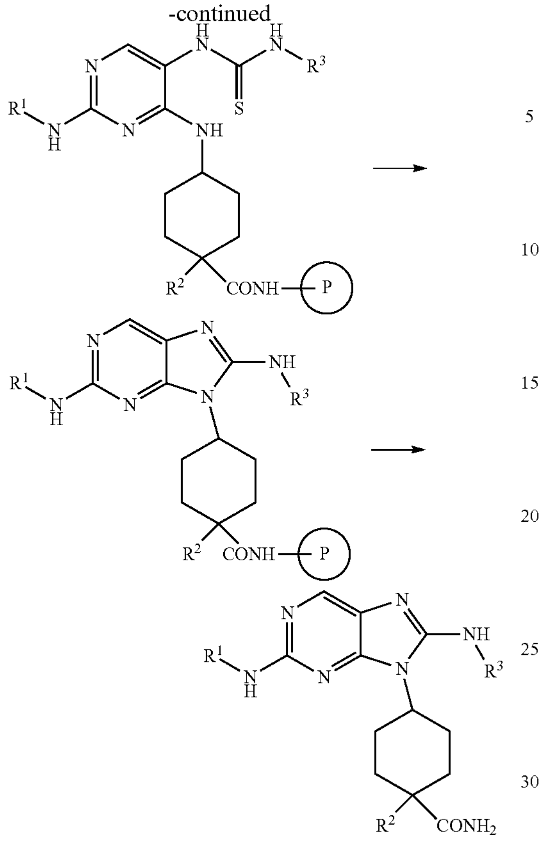

(I)

In a third approach, compounds of formula (I), wherein $R^1$, $R^2$ and $R^3$ are as defined herein, and P is a solid support, such as a resin, can be prepared starting from, as before, an appropriately derivatized nitropyrimidine, wherein $Hal^1$ is Cl, and $Hal^2$ is Cl. Treatment of the dihalogenated nitropyrimidine with the appropriate 4-aminocyclohexane-1-carboxylate derivative, in the presence of a base, such as DIEA, TEA or pyridine, in a solvent, such as DCM or THF, at reduced temperature (for example, −78° C.), provided incorporation of the cyclohexylalkyl carboxylate sidechain. Treatment of this product with $R^1NH_2$, in the presence of a base, such as DIEA, TEA, or pyridine, in a solvent such as DCM, THF, dioxane or DMF, at elevated temperature (for example 25-80° C.), resulted in incorporation of the $R^1$ sidechain. This intermediate was coupled to a solid support, such as a polymeric resin (for example, Rink-H resin) using a coupling agent (for example, HATU, CDI, HBTU, EDC, optionally in combination with HOBt, or ethyl chloroformate), in a solvent, for example DMF, at elevated temperature, for example 50° C. Treatment of the resin-bound intermediate with a reducing agent (such as chromium(II) chloride), in a solvent (such as DMF/MeOH mixture), resulted in reduction of the nitro group. The resulting amine moiety was reacted with $R^3NCS$, in a solvent, for example, EtOH, at elevated temperature, for example, 40° C. to 60° C., providing the thiourea derivative intermediate. This intermediate was cyclized using, for example, EDC or DIC, in a solvent, for example, THF, NMP, dioxane, or DMF, optionally at elevated temperature (for example, 40° C. to 80° C.), to provide the resin-bound diaminopurine derivative. Finally, acid treatment (for example, treatment with TFA in a solvent such as DCM), resulted in cleavage of compounds of formula (I) from the resin.

In one aspect, provided herein are methods for preparing a compound of formula (I):

(I)

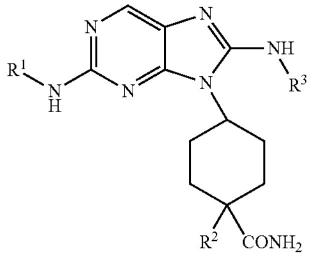

the methods comprising contacting a compound of formula (Ia)

(Ia)

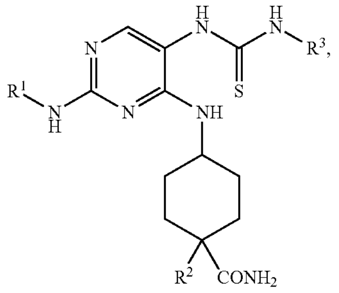

with EDC or DIC, in a solvent, under conditions suitable to provide a compound of formula (I), wherein:

$R^1$ is substituted or unsubstituted $C_{1-8}$ alkyl, substituted or unsubstituted cycloalkyl, substituted or unsubstituted cycloalkylalkyl, or substituted or unsubstituted non-aromatic heterocyclyl;

$R^2$ is H or substituted or unsubstituted $C_{1-3}$ alkyl;

$R^3$ is phenyl, substituted with one or more halogen, optionally further substituted with one or more substitutents selected from substituted or unsubstituted $C_{1-3}$ alkyl, CN, and —OR', wherein each R' is independently substituted or unsubstituted $C_{1-3}$ alkyl.

In one embodiment, the compound of formula (I) is not 4-[2-[(1-methylethyl)amino]-8-[(2,4,6-trifluorophenyl)amino]-9H-purin-9-yl]-cis-cyclohexanecarboxamide, or 4-[8-[(2,4-difluorophenyl)amino]-2-[(trans-4-hydroxycyclohexyl)amino]-9H-purin-9-yl]-cis-cyclohexanecarboxamide.

In one embodiment, the solvent is THF, dioxane, NMP or DMF. In some embodiments, the contacting is performed at elevated temperature, for example, from about 40° C. to about 80° C.

In some embodiments, the methods further comprise preparing a compound of formula (Ia):

(Ia)

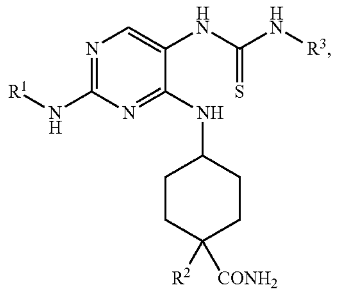

the methods comprising contacting a compound of formula (Ib)

(Ib)

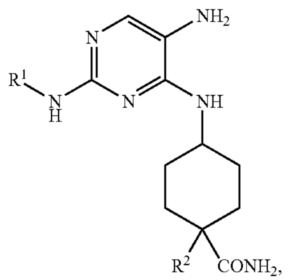

with $R^3NCS$, in a solvent, under conditions suitable to provide a compound of formula (Ia).

In one embodiment, the solvent is THF, DMF, NMP, dioxane, or EtOH.

In some embodiments, the methods further comprise preparing a compound of formula (Ib):

(Ib)

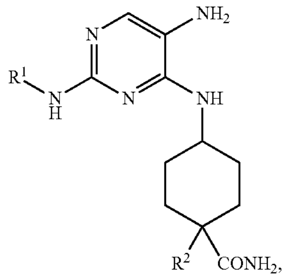

the methods comprising reducing a compound of formula (Ic)

(Ic)

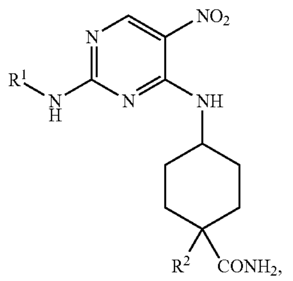

with a reducing agent, in the presence of a catalyst, in a solvent, under conditions suitable to provide a compound of formula (Ib).

In one embodiment, the reducing agents is $H_2$. In some embodiments, the catalyst Pd/C. In other embodiments, the solvent is MeOH or ethyl acetate.

In some embodiments, the methods further comprise preparing a compound of formula (Ic):

(Ic)

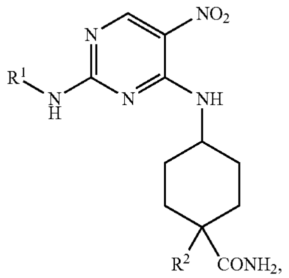

the methods comprising contacting a compound of formula (Id)

(Id)

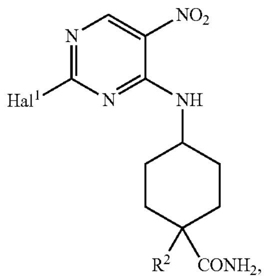

with $R^1NH_2$, in the presence of a base, in a solvent, under conditions suitable to provide a compound of formula (Ic), wherein $Hal^1$ is a halogen.

In one embodiment, $Hal^1$ is Cl. In some embodiments, the base is DIEA, TEA, or pyridine. In other embodiments, the solvent is DCM, THF, dioxane or DMF. In some embodiments, the contacting is performed at elevated temperature, for example, from about 25° C. to about 80° C.

In some embodiments, the methods further comprise preparing a compound of formula (Id):

(Id)

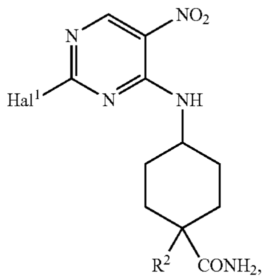

the methods comprising contacting a compound of formula (Ie)

(Ie)

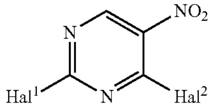

with

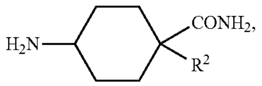

in the presence of a base, in a solvent, under conditions suitable to provide a compound of formula (Id), wherein $Hal^2$ is a halogen.

In one embodiment, $Hal^2$ is Cl. In some embodiments, the base is DIEA, TEA, or pyridine. In other embodiments, the solvent is DCM, or THF. In some embodiments, the contacting is performed at reduced temperature, for example, about −78° C.

In another aspect, provided herein are methods for preparing a compound of formula (I):

(I)

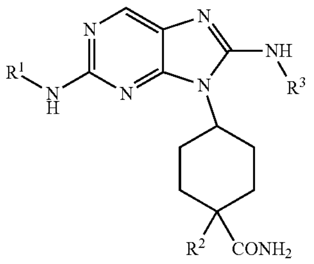

the methods comprising contacting a compound of formula (If)

(If)

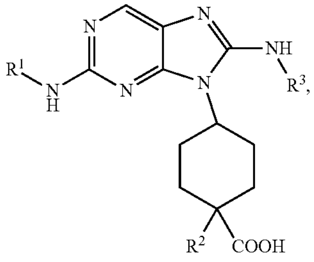

with $NH_4Cl$, in the presence of a coupling agent and a base, in a solvent, under conditions suitable to provide a compound of formula (I), wherein:

$R^1$ is substituted or unsubstituted $C_{1-8}$ alkyl, substituted or unsubstituted cycloalkyl, substituted or unsubstituted cycloalkylalkyl, or substituted or unsubstituted non-aromatic heterocyclyl;

$R^2$ is H or substituted or unsubstituted $C_{1-3}$ alkyl;

$R^3$ is phenyl, substituted with one or more halogen, optionally further substituted with one or more substitutents selected from substituted or unsubstituted $C_{1-3}$ alkyl, CN, and —OR', wherein each R' is independently substituted or unsubstituted $C_{1-3}$ alkyl.

In one embodiment, the compound of formula (I) is not 4-[2-[(1-methylethyl)amino]-8-[(2,4,6-trifluorophenyl) amino]-9H-purin-9-yl]-cis-cyclohexanecarboxamide, or 4-[8-[(2,4-difluorophenyl)amino]-2-[(trans-4-hydroxycyclohexyl)amino]-9H-purin-9-yl]-cis-cyclohexanecarboxamide.

In some embodiments, the coupling agent is HATU, CDI, HBTU, EDC, optionally in combination with HOBt, or ethyl chloroformate. For example, the coupling agent is HATU. In some embodiments, the base is DIEA, TEA, pyridine, DBU, or NMM. In one embodiment, the solvent is DMF.

In some embodiments, the methods further comprise preparing a compound of formula (If)

(If)

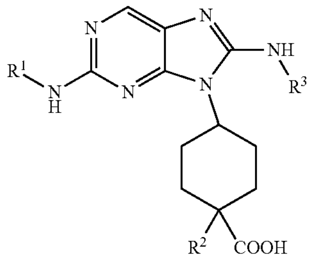

the methods comprising contacting a compound of formula (Ig)

(Ig)

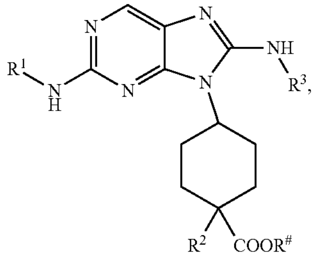

with a base, in a solvent, under conditions suitable to provide a compound of formula (If), wherein $R^{\#}$ is $C_{1-2}$ alkyl.

In one embodiment, the base is lithium hydroxide, sodium hydroxide, or potassium hydroxide. In some embodiments, the solvent is aqueous THF, MeOH, or EtOH. In some embodiments, the contacting is performed at elevated temperature, for example, from about 40° C. to about 80° C.

In some embodiments, the methods further comprise preparing a compound of formula (Ig):

(Ig)

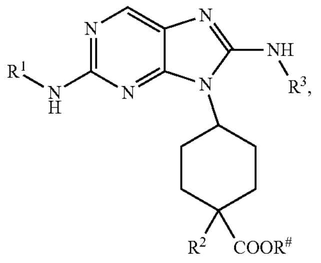

the methods comprising contacting a compound of formula (Ih)

(Ih)

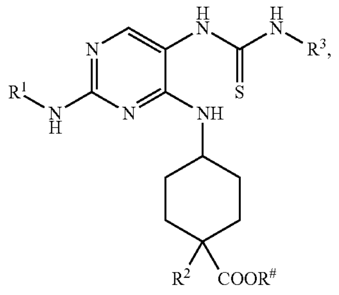

with with EDC or DIC, in a solvent, under conditions suitable to provide a compound of formula (Ig).

In one embodiment, the solvent is THF, dioxane, NMP or DMF. In some embodiments, the contacting is performed at elevated temperature, for example, from about 40° C. to about 80° C.

In some embodiments, the methods further comprise preparing a compound of formula (Ih):

(Ih)

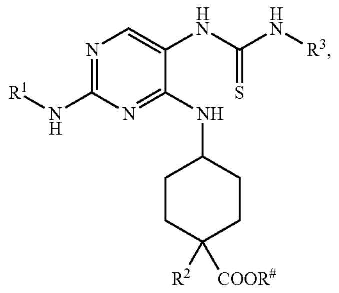

the methods comprising contacting a compound of formula (Ii)

(Ii)

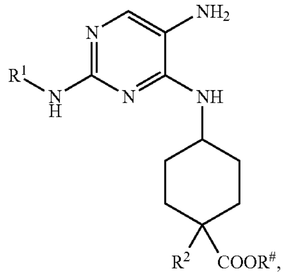

with $R^3NCS$, in a solvent, under conditions suitable to provide a compound of formula (Ih).

In one embodiment, the solvent is THF, DMF, NMP, dioxane, or EtOH.

In some embodiments, the methods further comprise preparing a compound of formula (Ii):

(Ii)

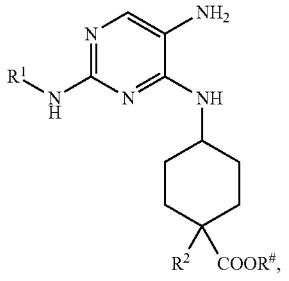

the methods comprising reducing a compound of formula (Ij)

(Ij)

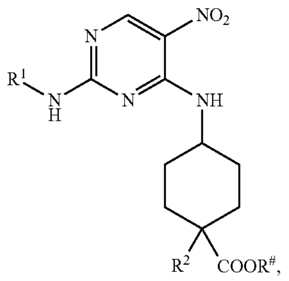

with a reducing agent, in the presence of a catalyst, in a solvent, under conditions suitable to provide a compound of formula (Ii).

In one embodiment, the reducing agents is $H_2$. In some embodiments, the catalyst Pd/C. In other embodiments, the solvent is MeOH or ethyl acetate.

In some embodiments, the methods further comprise preparing a compound of formula (Ij):

(Ij)

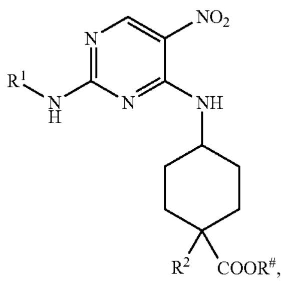

the methods comprising contacting a compound of formula (Ik)

(Ik)

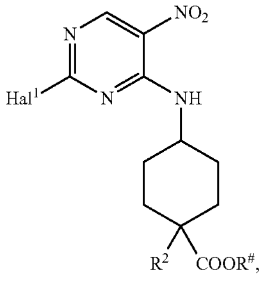

with $R^1NH_2$, in the presence of a base, in a solvent, under conditions suitable to provide a compound of formula (Ij), wherein $Hal^1$ is a halogen.

In one embodiment, $Hal^1$ is Cl. In some embodiments, the base is DIEA, TEA, or pyridine. In other embodiments, the solvent is DCM, THF, dioxane or DMF. In some embodiments, the contacting is performed at elevated temperature, for example, from about 25° C. to about 80° C.

In some embodiments, the methods further comprise preparing a compound of formula (Ik):

(Ik)

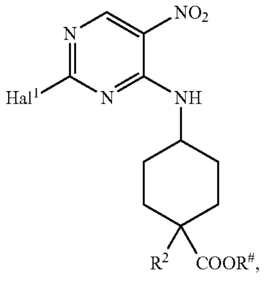

the methods comprising contacting a compound of formula (Ie)

(Ie)

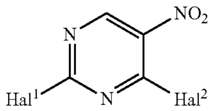

with

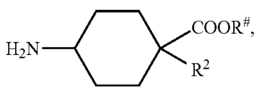

in the presence of a base, in a solvent, under conditions suitable to provide a compound of formula (Ik), wherein $Hal^2$ is a halogen.

In one embodiment, $Hal^2$ is Cl. In some embodiments, the base is DIEA, TEA, or pyridine. In other embodiments, the solvent is DCM, or THF. In some embodiments, the contacting is performed at reduced temperature, for example, about −78° C.

In yet another aspect, provided herein are methods for preparing a compound of formula (I):

(I)

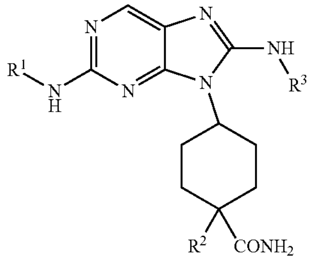

the methods comprising contacting a compound of formula (Im)

(Im)

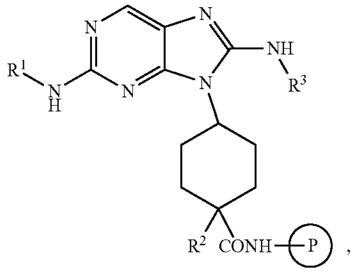

with an acid, in a solvent, under conditions suitable to provide a compound of formula (I), wherein:

$R^1$ is substituted or unsubstituted $C_{1-8}$ alkyl, substituted or unsubstituted cycloalkyl, substituted or unsubstituted cycloalkylalkyl, or substituted or unsubstituted non-aromatic heterocyclyl;

$R^2$ is H or substituted or unsubstituted $C_{1-3}$ alkyl;

$R^3$ is phenyl, substituted with one or more halogen, optionally further substituted with one or more substitutents selected from substituted or unsubstituted $C_{1-3}$ alkyl, CN, and —OR', wherein each R' is independently substituted or unsubstituted $C_{1-3}$ alkyl; and P is a resin.

In one embodiment, the compound of formula (I) is not 4-[2-[(1-methylethyl)amino]-8-[(2,4,6-trifluorophenyl)amino]-9H-purin-9-yl]-cis-cyclohexanecarboxamide, or 4-[8-[(2,4-difluorophenyl)amino]-2-[(trans-4-hydroxycyclohexyl)amino]-9H-purin-9-yl]-cis-cyclohexanecarboxamide.

In some embodiments, the acid is TFA. In some embodiments, the solvent is DCM. In other embodiments, the resin is Rink resin.

In some embodiments, the methods further comprise preparing a compound of formula (Im)

(Im)

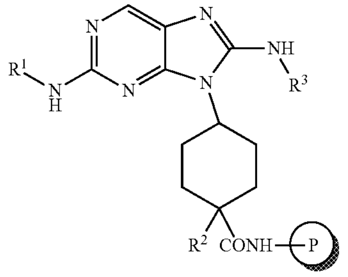

the methods comprising contacting a compound of formula (In)

(In)

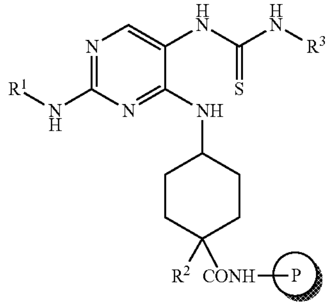

, with with EDC or DIC, in a solvent, under conditions suitable to provide a compound of formula (Im).

In one embodiment, the solvent is THF, NMP, dioxane, or DMF. In some embodiments, the contacting is performed at elevated temperature, for example, from about 40° C. to about 80° C.

In some embodiments, the methods further comprise preparing a compound of formula (In):

(In)

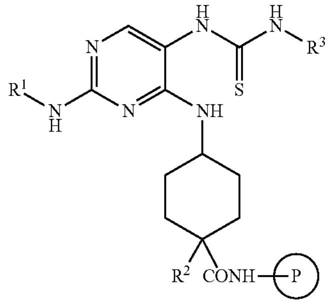

, the methods comprising contacting a compound of formula (Io)

(Io)

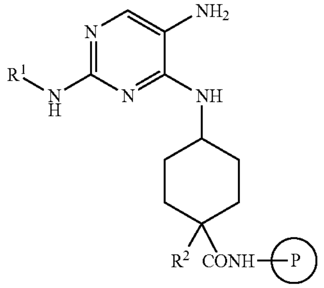

, with with $R^3NCS$, in a solvent, under conditions suitable to provide a compound of formula (In).

In one embodiment, the solvent is EtOH. In some embodiments, the contacting is performed at elevated temperature, for example, from about 40° C. to about 60° C.

In some embodiments, the methods further comprise preparing a compound of formula (Io):

(Io)

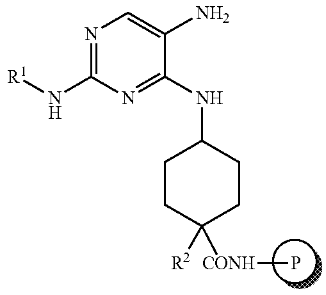

, the methods comprising contacting a compound of formula (Ip)

(Ip)

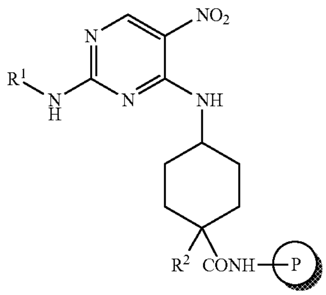

, with a reducing agent, in a solvent, under conditions suitable to provide a compound of formula (Io).

In one embodiment, the reducing agent is chromium(II) chloride. In one embodiment, the solvent is DMF, MeOH or mixtures thereof.

In some embodiments, the methods further comprise preparing a compound of formula (Ip):

(Ip)

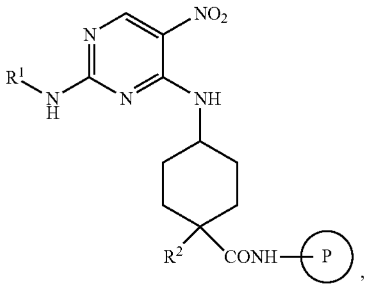

the methods comprising contacting a compound of formula (Iq)

(Iq)

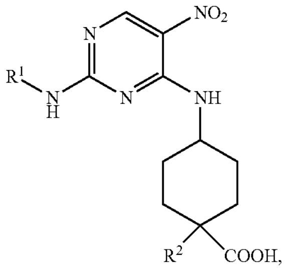

with a polymeric resin, in the presence of a coupling agent, in a solvent, under conditions suitable to provide a compound of formula (Ip).

In one embodiment, the coupling agent is HATU, CDI, HBTU, EDC, optionally in combination with HOBt, or ethyl chloroformate. In other embodiments, the solvent is for example DMF. In some embodiments, the contacting is performed at elevated temperature, for example about 50° C.

In some embodiments, the methods further comprise preparing a compound of formula (Iq):

(Iq)

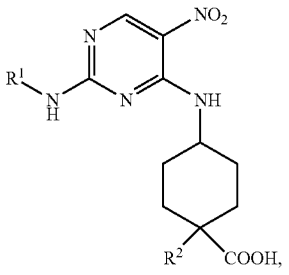

the methods comprising contacting a compound of formula (Ir)

(Ir)

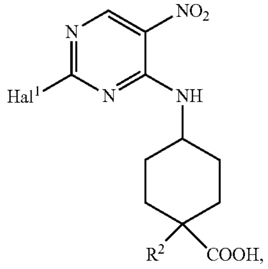

with $R^1NH_2$, in the presence of a base, in a solvent, under conditions suitable to provide a compound of formula (Iq), wherein $Hal^1$ is a halogen.

In one embodiment, $Hal^1$ is Cl. In some embodiments, the base is DIEA, TEA, or pyridine. In other embodiments, the solvent is DCM, THF, dioxane or DMF. In some embodiments, the contacting is performed at elevated temperature, for example, from about 25° C. to about 80° C.

In some embodiments, the methods further comprise preparing a compound of formula (Ir):

(Ir)

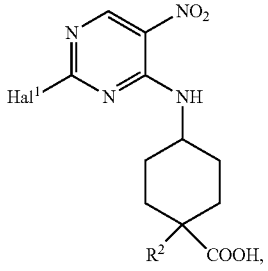

the methods comprising contacting a compound of formula (Ie)

(Ie)

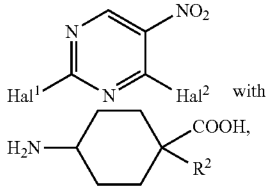

with in the presence of a base, in a solvent, under conditions suitable to provide a compound of formula (Ir), wherein $Hal^2$ is a halogen.

In one embodiment, $Hal^2$ is Cl. In some embodiments, the base is DIEA, TEA, or pyridine. In other embodiments, the solvent is DCM, or THF. In some embodiments, the contacting is performed at reduced temperature, for example, about −78° C.

Methods of Use

The Aminopurine Compounds have utility as pharmaceuticals to treat, prevent or improve conditions in animals or humans. Accordingly, provided herein can be used in all the methods as provided herein. Particularly, the Aminopurine Compounds as provided herein are for uses in the treatment or prevention of melanoma. The methods provided herein comprise the administration of an effective amount of one or more Aminopurine Compound(s) to a subject in need thereof.

In another aspect provided herein are methods for treating or preventing melanoma, comprising administering to a subject in need thereof an effective amount of an Aminopurine Compound, as described herein. Provided herein are the Aminopurine Compounds for use in said methods.

Pharmaceutical Compositions and Routes of Administration

The Aminopurine Compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Aminopurine Compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of an Aminopurine Compound to be administered to a subject is rather widely variable and can be subject to the judgment of a health-care practitioner. In general, the Aminopurine Compounds can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the Aminopurine Compound administered will depend on such factors as the solubility of the active component, the formulation used and the route of administration. In one embodiment, application of a topical concentration provides intracellular exposures or concentrations of about 0.01-10 μM.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of an Aminopurine Compound to a subject in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of an Aminopurine Compound to a subject in need thereof. In a particular embodiment, the methods disclosed herein comprise the administration of 400 mg/day, 600 mg/day or 800 mg/day of an Aminopurine Compound to a subject in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of an Aminopurine Compound.

In a particular embodiment, provided herein are unit dosage formulations comprising about 100 mg or 400 mg of an Aminopurine Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of an Aminopurine Compound.

An Aminopurine Compound can be administered once, twice, three, four or more times daily. In a particular embodiment, doses of 600 mg or less are administered as a once daily dose and doses of more than 600 mg are administered twice daily in an amount equal to one half of the total daily dose.

An Aminopurine Compound can be administered orally for reasons of convenience. In one embodiment, when administered orally, an Aminopurine Compound is administered with a meal and water. In another embodiment, the Aminopurine Compound is dispersed in water or juice (e.g., apple juice or orange juice) and administered orally as a suspension.

The Aminopurine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing an Aminopurine Compound without an additional carrier, excipient or vehicle.

In another embodiment, provided herein are compositions comprising an effective amount of an Aminopurine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing an Aminopurine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer an Aminopurine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Aminopurine Compound can be delayed or prolonged by proper formulation. For example, a slowly soluble pellet of the Aminopurine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Aminopurine Compound in oily or emulsified vehicles that allow it to disperse slowly in the serum.

EXAMPLES

The following Examples are presented by way of illustration, not limitation. Compounds are named using the automatic name generating tool provided in Chemdraw Ultra 9.0 (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations used:

| | |
|---|---|
| Cbz | Carboxybenzyl |
| CDI | Carbonyldiimidazole |
| DAST | Diethylaminosulfur trifluoride |
| DBU | 1 8-Diazabicyclo 5.4.0 undec-7-ene |
| DCM | Dichloromethane |
| DEA | Diethylamine |
| DIC | Diisopropylcarbodiimide |
| DIEA | Diisopropylethylamine |
| DMA | N,N-Dimethylacetamide |
| DME | 1,2-Dimethoxyethane |
| DMF | N,N-Dimethylformamide |
| DMSO | Dimethylsulfoxide |
| DPPA | Diphenylphosphoryl azide |
| EDC | Ethyl-(N',N'-dimethylamino)propylcarbodiimide hydrochloride |
| ESI | Electrospray ionization |
| EtOH | Ethanol |
| HATU | O-(7-Azabenzotriazol-1-yl)-N,N,N',N'-tetramethyluronium hexafluorophosphate |
| HBTU | O-(Benzotriazol-1-yl)-N,N,N',N'-tetramethyluronium hexafluorophosphate |
| HMPA | Hexamethylphosphoramide |
| HOBt | 1-Hydroxybenzotriazole |
| HPLC | High performance liquid chromatography |
| HTRF | Homogeneous time resolved fluorescence |
| LCMS | Liquid chromatography mass spectrometry |
| mCPBA | Meta-chloroperoxybenzoic acid |
| MeOH | Methanol |
| MS | Mass spectrometry |
| MTBE | tert-Butyl Methyl ether |
| NMM | N-Methylmorpholine |
| NMP | N-methylpyrrolidone |
| NMR | Nuclear magnetic resonance |
| pTSA | p-Toluenesulfonic acid |
| SFC | Supercritical fluid chromatography |
| TBTU | O-Benzotriazol-1-yl-N,N,N',N'-tetra-methyluronium tetrafluoroborate |
| t-BuOH | Tert-butanol |
| TEA | Triethylamine |
| TFA | Trifluoracetic acid |
| THF | Tetrahydrofuran |
| TLC | Thin layer chromatography |
| TMS | Trimethylsilane |

Compound Synthesis

Example 1. (1s,4s)-4-(8-((4-Chloro-2,6-difluorophenyl)amino)-2-((tetrahydro-2H-pyran-4-yl)amino)-9H-purin-9-yl)cyclohexane-1-carboxamide

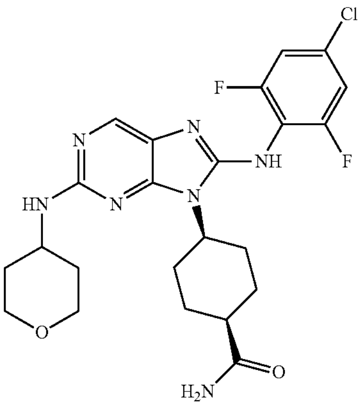 [SMILES: NC(=O)[C@H]1CC[C@@H](n2c(Nc3c(F)cc(Cl)cc3F)nc3cnc(NC4CCOCC4)nc32)CC1]

cis-(4-Carbamoyl-cyclohexyl)-carbamic acid tert-butyl ester cis-4-tert-Butoxycarbonylamino-cyclohexanecarboxylic acid (1 equiv.) and TEA (1.1 equiv.) were dissolved in 0.3 M THF and the mixture was cooled to 0° C. Ethyl chloroformate (1.1 equiv.) was added drop-wise. After stirring at 0° C. for 30 min, $NH_3$ in THF was added. The mixture was allowed to stir at −78° C. for 2 h. The mixture was diluted with water, and the solvent was evaporated until only water remained. The resulting precipitate was collected by filtration and dried under vacuum to give cis (4-carbamoyl-cyclohexyl)-carbamic acid tert-butyl ester (45%) as a white solid. $^1$H NMR (400 MHz, DMSO-$d_6$) δ ppm 7.10 (brs, 1H), 6.69 (brs, 2H), 3.41 (brs, 1H), 2.10 (m, 1H), 1.72 (m, 2H), 1.53 (m, 2H), 1.42 (m, 4H), 1.36 (s, 9H).

cis-4-Amino-cyclohexanecarboxylic acid amide hydrochloride

To a solution of cis-(4-carbamoyl-cyclohexyl)-carbamic acid tert-butyl ester (1 equiv.) in 1/1 DCM/TFA. The mixture was stirred for 1 h. The solvents were evaporated under reduced pressure. To the resulting residue was added 2M HCl/ether to give a white solid. The solvent was evaporated. The resulting solid was treated with ether and filtered to give cis-4-amino-cyclohexanecarboxylic acid amide hydrochloride (100%) as a white solid. $^1$H NMR (400 MHz, DMSO-$d_6$) δ ppm: 8.08 (brs, 3H), 7.28 (s, 1H), 6.78 (s, 1H), 3.06 (m, 1H), 2.22 (m, 1H), 1.86 (m, 2. H), 1.66 (m, 4H), 1.48 (m, 2H).

(1s,4s)-4-((2-Chloro-5-nitropyrimidin-4-yl)amino)cyclohexanecarboxamide (1s,4s)-4-Aminocyclohexanecarboxamide hydrochloride (0.56 mol) and 2,4-dichloro-5-nitropyrimidine (1 equiv.) were dissolved in DCM (0.16 M). The mixture was cooled to −78° C. An addition funnel was charged with DIEA (3 equiv.) and DCM (1.0M). The DIEA solution was added dropwise via an addition funnel. After the addition was complete, the reaction was stirred for an additional 2 h at −78° C. The reaction was monitored by LCMS. Once the reaction was completed, the reaction mixture was partitioned between DCM and water, the organic layer was separated and dried over anhydrous sodium sulfate. The mixture was filtered, then the filtrate was concentrated and washed with a mixture of petroleum ether and ethyl acetate (1:1) to give (1s,4s)-4-((2-chloro-5-nitropyrimidin-4-yl)amino)cyclohexanecarboxamide (65%) as a yellow solid. $^1$H NMR (400 MHz, DMSO-$d_6$) δ ppm: 9.01 (s, 1H), 8.51 (d, J=7.6 Hz, 1H), 7.23 (s, 1H), 6.75 (s, 1H), 4.26 (s, 1H), 2.24 (s, 1H), 1.60-1.83 (m, 8H).

5-Chloro-1,3-difluoro-2-isothiocyanatobenzene

To a solution of 4-chloro-2,6-difluoroaniline (1 equiv.) in anhydrous DCM (0.24 M) was added DIEA (2.5 equiv) in one portion. After stirring for 30 min at room temperature, the mixture was cooled to 0° C. and thiophosgene (1.8 equiv) was added dropwise over 1 h at this temperature. TLC (petroleum ether) showed that the reaction was finished. The mixture was concentrated, the residue was purified by silica gel column chromatography to give 5-chloro-1,3-difluoro-2-isothiocyanatobenzene (97%) as a colorless oil. $^1$H NMR (400 MHz, DMSO-$d_6$) δ ppm: 7.02 (d, J=7.2 Hz, 2H).

(1s,4s)-4-((5-Nitro-2-((tetrahydro-2H-pyran-4-yl)amino)pyrimidin-4-yl)amino)cyclohexanecarboxamide (1s,4s)-4-((2-Chloro-5-nitropyrimidin-4-yl)amino)cyclohexanecarboxamide (1 equiv.) and tetrahydro-2H-pyran-4-amine hydrochloride (1 equiv.) were dissolved in THF (0.5 M) and DIEA (2.5 equiv.) was added. The reaction was stirred at 70° C. for 3 h, diluted with water, and filtered to give (1s,4s)-4-((5-nitro-2-((tetrahydro-2H-pyran-4-yl)amino)pyrimidin-4-yl)amino)cyclohexanecarboxamide (98% yield) as a yellow solid. $^1$H NMR (400 MHz, DMSO-$d_6$) δ ppm: 8.84 (s, 1H); 8.52 (d, J=7.1 Hz, 1H); 8.39 (d, J=7.1 Hz, 1H); 7.23 (s, 1H); 6.74 (s, 1H); 4.24 (s, 1H); 3.87 (m, 3H); 3.58 (s, 1H); 3.10 (s, 1H); 2.22 (m, 2H); 1.61 (m, 13H); 1.25 (m, 5H).

(1s,4s)-4-((5-Amino-2-((tetrahydro-2H-pyran-4-yl)amino)pyrimidin-4-yl)amino)cyclohexanecarboxamide To a round-bottom flask was added (1s,4s)-4-((5-nitro-2-((tetrahydro-2H-pyran-4-yl)amino)pyrimidin-4-yl)amino)cyclohexanecarboxamide (1 equiv.) and Pd—C (0.1 equiv., 10% Pd by wt.) in MeOH (0.15 M) to give a black suspension. The suspension was stirred under 1 atm of $H_2$ overnight. The reaction was complete as shown by LCMS. The reaction mixture was filtered, and washed with additional MeOH. The filtrate was concentrated in vacuo to give (1s,4s)-4-((5-amino-2-((tetrahydro-2H-pyran-4-yl)amino)pyrimidin-4-yl)amino)cyclohexanecarboxamide (87%). MS (ESI) m/z=335.1 $[M+1]^+$.

(1s,4s)-4-((5-(3-(4-Chloro-2,6-difluorophenyl)thioureido)-2-((tetrahydro-2H-pyran-4-yl)amino)pyrimidin-4-yl)amino)cyclohexanecarboxamide In a three-necked flask was added (1s,4s)-4-((5-amino-2-((tetrahydro-2H-pyran-4-yl)amino)pyrimidin-4-yl)amino)cyclohexanecarboxamide (1 equiv.) and 5-chloro-1,3-difluoro-2-isothiocyanatobenzene (1 equiv.) in THF/DMF (3/1, 0.5 M) to give a purple suspension. The reaction was stirred at room temperature for 72 h. LCMS showed that a small amount of starting material remained. The reaction was partitioned between DCM and water. The organic layer was separated, dried over $Na_2SO_4$, filtered and evaporated in vacuo to afford (1s,4s)-4-((5-(3-(4-chloro-2,6-difluorophenyl)thioureido)-2-((tetrahydro-2H-pyran-4-yl)amino)pyrimidin-4-yl)amino)cyclohexanecarboxamide (79% yield). MS (ESI) m/z 540=[M+1]$^+$.

(1s,4s)-4-(8-((4-Chloro-2,6-difluorophenyl)amino)-2-((tetrahydro-2H-pyran-4-yl)amino)-9H-purin-9-yl) cyclohexanecarboxamide In a round-bottom flask was added (1s,4s)-4-((5-(3-(4-chloro-2,6-difluorophenyl)thioureido)-2-((tetrahydro-2H-pyran-4-yl)amino)pyrimidin-4-yl)amino)cyclohexanecarboxamide (1 equiv.) and EDC (2 equiv.) in THF (0.2 M) to give an off-white suspension. The suspension was heated to 60° C. for 1 h. Standard work-up and purification methods afforded (1s,4s)-4-(8-((4-chloro-2,6-difluorophenyl)amino)-2-((tetrahydro-2H-pyran-4-yl)amino)-9H-purin-9-yl)cyclohexanecarboxamide (57% yield). $^1$H NMR (400 MHz, DMSO-$d_6$) δ ppm: 8.37 (br. s., 1H) 8.02 (br. s., 1H) 7.46 (d, J=6.31 Hz, 2H) 7.26 (br. s., 1H) 6.72 (br. s., 1H) 4.52 (br. s., 1H) 4.08 (br. s., 1H) 3.86 (dt, J=11.74, 3.74 Hz, 2H) 3.64 (t, J=10.56 Hz, 2H) 2.59-2.72 (m, 2H) 2.21 (d, J=12.93 Hz, 2H) 1.93 (d, J=9.77 Hz, 2H) 1.68 (d, J=10.72 Hz, 2H) 1.55-1.65 (m, 2H) 1.44-1.55 (m, 2H). MS (ESI) m/z=506.2 [M+1]$^+$.

Example 2. (1s,4s)-4-(2-((Tetrahydro-2H-pyran-4-yl)amino)-8-((2,4,6-trichlorophenyl)amino)-9H-purin-9-yl)cyclohexane-1-carboxamide

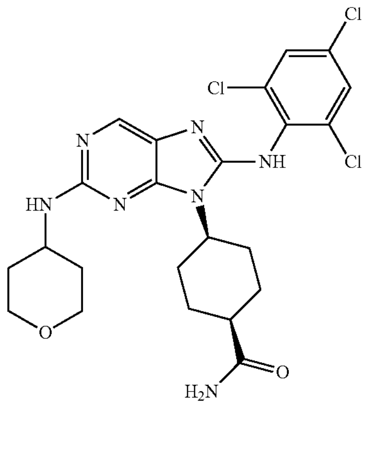 [SMILES: NC(=O)[C@H]1CC[C@@H](n2c(Nc3c(Cl)cc(Cl)cc3Cl)nc3cnc(NC4CCOCC4)nc32)CC1]

(1s,4s)-4-(2-((Tetrahydro-2H-pyran-4-yl)amino)-8-((2,4,6-trichlorophenyl)amino)-9H-purin-9-yl)cyclohexane-1-carboxamide A mixture of (1s,4s)-4-((5-amino-2-((tetrahydro-2H-pyran-4-yl)amino)pyrimidin-4-yl)amino)cyclohexanecarboxamide (1 equiv.) and 1,3,5-trichloro-2-isothiocyanatobenzene (1 equiv.) was stirred at room temperature for 2 h. EDC (2 equiv.) in THF (0.17 M) was added and the reaction was heated to 60° C. and stirred for 1 h. The reaction was cooled, and the organic solvents were fully concentrated. The resulting residue was diluted with water, stirred for 30 min, and filtered. Standard work-up and purification methods afforded (1s,4s)-4-(2-((tetrahydro-2H-pyran-4-yl)amino)-8-((2,4,6-trichlorophenyl)amino)-9H-purin-9-yl)cyclohexanecarboxamide (79% yield). $^1$H NMR (400 MHz, DMSO-$d_6$) δ ppm: 8.11 (br. s., 1H) 7.69 (br. s., 2H) 7.23 (br. s., 1H) 6.71 (br. s., 1H) 4.47 (br. s., 1H) 4.05 (br. s., H) 3.86 (dt, J=11.59, 3.66 Hz, 2H) 3.61 (d, J=11.03 Hz, 2H) 2.59-2.74 (m, 2H) 2.20 (d, J=13.24 Hz, 2H) 1.90 (d, J=10.40 Hz, 2H) 1.69 (br. s., 2H) 1.41-1.64 (m, 4H). MS (ESI) m/z=540.2 [M+H]$^+$.

Example 3. (1s,4s)-4-(8-((2-Chloro-4,5-difluorophenyl)amino)-2-((tetrahydro-2H-pyran-4-yl)amino)-9H-purin-9-yl)cyclohexanecarboxamide

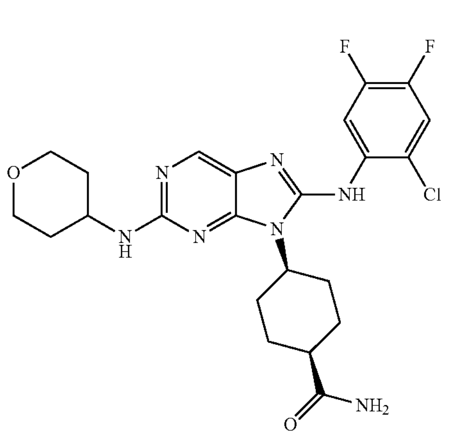 [SMILES: NC(=O)[C@H]1CC[C@@H](n2c(Nc3cc(F)c(F)cc3Cl)nc3cnc(NC4CCOCC4)nc32)CC1]

1-Chloro-4,5-difluoro-2-isothiocyanatobenzene

To a mixture of 2-chloro-4,5-difluoroaniline (1 equiv.) and sodium hydroxide (3 equiv.) in DCM (0.24 M) and water (0.24 M) was added dropwise thiophosgene (3 equiv.) at 0° C. The reaction mixture was stirred at 25° C. overnight. TLC showed the reaction was complete. The organic phase was separated and dried over $MgSO_4$, then concentrated to give 1-chloro-4,5-difluoro-2-isothiocyanatobenzene (53%) as a white solid.

(1s,4s)-4-(8-((2-Chloro-4,5-difluorophenyl)amino)-2-((tetrahydro-2H-pyran-4-yl)amino)-9H-purin-9-yl) cyclohexanecarboxamide To a solution of (1s,4s)-4-((5-amino-2-((tetrahydro-2H-pyran-4-yl)amino)pyrimidin-4-yl)amino)cyclohexanecarboxamide (1 equiv.) in DMF (0.24 M) was added 1-chloro-4,5-difluoro-2-isothiocyanatobenzene (1.1 equiv.) in one portion. The mixture was stirred at room temperature for 2 h. EDC (2.5 equiv.) was added to the reaction solution. The resulting mixture was stirred at room temperature overnight. Standard work-up and purification methods afforded (1s,4s)-4-(8-((2-chloro-4,5-difluorophenyl)amino)-2-((tetrahydro-2H-pyran-4-yl)amino)-9H-purin-9-yl)cyclohexanecarboxamide (35%). $^1$H NMR (400 MHz, DMSO-$d_6$) δ ppm: 10.21-8.21 (m, 1H), 8.02-7.54 (m, 2H), 7.24 (s, 1H), 6.74 (s, 1H), 6.53 (d, J=6.0 Hz, 1H), 4.34-4.20 (m, 1H), 3.85-3.83 (m, 3H), 3.60-3.45 (m, 2H), 2.73-2.51 (m, 2H), 2.48-2.39 (m, 1H), 2.23 (d, J=13.3 Hz, 2H), 1.91-1.79 (m, 2H), 1.74-1.37 (m, 6H). MS (ESI) m/z=506.1 [M+1]$^+$.

Example 4. (1s,4s)-4-(8-((2-Chloro-4-fluoro-6-methylphenyl)amino)-2-((tetrahydro-2H-pyran-4-yl)amino)-9H-purin-9-yl)cyclohexane-1-carboxamide

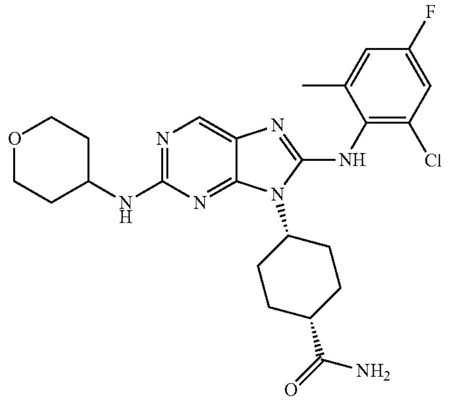 [SMILES: Cc1cc(F)cc(Cl)c1Nc1nc2cnc(NC3CCOCC3)nc2n1[C@H]1CC[C@@H](C(N)=O)CC1]

2-Chloro-4-fluoro-6-methylaniline

To a mixture of 4-fluoro-2-methylaniline (1 equiv.) in acetonitrile (0.4 M) was added NCS (1 equiv.) at 90° C. The mixture was stirred at 90° C. for 1 h. The mixture was concentrated to a residue, the residue was purified via silica gel chromatography to give 2-chloro-4-fluoro-6-methylaniline (24%) as a yellow oil. $^1$H NMR (400 MHz, $CDCl_3$) δ ppm: 7.87 (dd, J=8.4, 2.8 Hz, 1H), 7.73 (dd, J=8.8, 2.8 Hz 2.8 Hz, 1H), 2.17 (s, 3H).

1-Chloro-5-fluoro-2-isothiocyanato-3-methylbenzene

To a mixture of 2-chloro-4-fluoro-6-methylaniline 2 (0.3 g, 1.9 mmol) in $DCM/H_2O$ (1/2, 0.15 M) was added NaOH (21 equiv.) and $SCCl_2$ (5 equiv.) at 0° C. After addition, the mixture was allowed to warm to room temperature and stirred for 16 h. The mixture was filtered, and the filtrate was extracted with DCM. The combined organic layers were dried over $Na_2SO_4$, and concentrated to a residue. The residue was purified by silica chromatography to give 1-chloro-5-fluoro-2-isothiocyanato-3-methylbenzene (52%) as a yellow oil.

cis-4-(8-((2-Chloro-4-fluoro-6-methylphenyl)amino)-2-((tetrahydro-2H-pyran-4-yl)amino)-9H-purin-9-yl)cyclohexanecarboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in DMF (0.12 M) was added 1-chloro-5-fluoro-2-isothiocyanato-3-methylbenzene (1 equiv.). The reaction mixture was stirred at room temperature for 1 h, and DIC (2 equiv.) was added. The mixture was stirred at room temperature for 16 h. Standard work-up and purification methods provided cis-4-(8-((2-chloro-4-fluoro-6-methylphenyl)amino)-2-((tetrahydro-2H-pyran-4-yl)amino)-9H-purin-9-yl)cyclohexanecarboxamide (50%). $^1$H NMR (400 MHz, Methanol-$d_4$) δ ppm: 7.93 (s, 1H), 7.21 (t, J=7.2 Hz, 1H), 7.09 (d, J=7.6 Hz, 1H), 4.34 (s, 1H), 4.07-3.96 (m, 3H), 3.71-3.66 (s, 2H), 2.93-2.90 (m, 2H), 2.67 (s, 1H), 2.35-231 (m, 5H), 2.04-2.01 (m, 2H), 1.82-1.80 (m, 4H), 1.58-1.51 (m, 2H). MS (ESI) m/z=502.2 $[M+1]^+$.

Example 5. (1s,4s)-4-(8-((2,3-Difluoro-4-methylphenyl)amino)-2-((tetrahydro-2H-pyran-4-yl)amino)-9H-purin-9-yl)cyclohexane-1-carboxamide

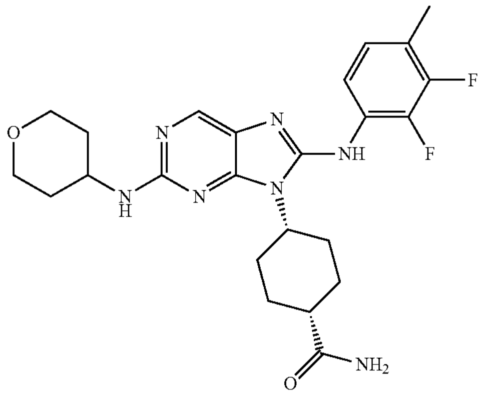 [SMILES: Cc1ccc(Nc2nc3cnc(NC4CCOCC4)nc3n2[C@H]2CC[C@@H](C(N)=O)CC2)c(F)c1F]

2,3-Difluoro-4-methylaniline

To a mixture of 2-chloro-6-fluoro-3-methylbenzoic acid (1 equiv.) in THF (0.45 M) was added DPPA (1.07 equiv.) and TEA (3 equiv.) at 25° C. The mixture was stirred at 25° C. for 2 h, then the mixture was heated to reflux for 2 h. Water was added to the reaction and the mixture was refluxed for 1 h. The mixture was concentrated to a residue, which was purified by silica gel chromatography to give 2-chloro-6-fluoro-3-methylaniline (46%) as a yellow oil. $^1$H NMR (400 MHz, $CDCl_3$) δ ppm: 6.83 (dd, J=8.4, 10.3 Hz, 1H), 6.56 (dd, J=5.8, 8.3 Hz, 1H), 4.08 (br.s., 1H), 2.31 (s, 1H).

2,3-Difluoro-1-isothiocyanato-4-methylbenzene

To a mixture of 2-chloro-6-fluoro-3-methylaniline (1 equiv.) in DCM/water (1/2, 0.1 M) was added NaOH (6 equiv.) and $SCCl_2$ (3 equiv.) at 0° C. After addition, the mixture was allowed to warm to room temperature and was stirred for 16 h. The mixture was filtered, the filtrate was extracted with DCM, and the combined organic layers were dried over $Na_2SO_4$, and concentrated to a residue. The residue was purified by silica gel chromatography to give 2,3-difluoro-1-isothiocyanato-4-methylbenzene (63%) as a yellow oil. $^1$H NMR (400 MHz, $CDCl_3$) δ ppm: 7.09 (dd, J=5.7, 8.6 Hz, 1H), 7.01-6.93 (m, 1H), 2.36 (s, 3H).

(1s,4s)-4-(8-((2,3-Difluoro-4-methylphenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in DMF (0.12 M) was added 2,3-difluoro-1-isothiocyanato-4-methylbenzene (1 equiv.). The reaction mixture was stirred at 25° C. for 1 h. DIC (2 equiv.) was added to the mixture and stirring at 25° C. was continued for 16 h. Standard work-up and purification methods provided cis-4-(8-((2-chloro-6-fluoro-3-methylphenyl)amino)-2-((tetrahydro-2H-pyran-4-yl)amino)-9H-purin-9-yl)cyclohexanecarboxamide (42%). $^1$H NMR (400 MHz, $CDCl_3$) δ ppm: 7.96 (s, 1H), 7.31-6.92 (m, 2H), 4.42 (s, 1H), 4.12-3.91 (m, 3H), 3.68 (t, J=11.3 Hz, 2H), 2.89 (d, J=11.7 Hz, 2H), 2.65 (s, 1H), 2.45-2.23 (m, 5H), 2.09-1.97 (m, 2H), 1.92-1.68 (m, 4H), 1.62-1.47 (m, 2H). MS (ESI) m/z=486.3 $[M+1]^+$.

Example 6. (1s,4s)-4-(8-((2-Chloro-3-fluoro-4-methylphenyl)amino)-2-((tetrahydro-2H-pyran-4-yl)amino)-9H-purin-9-yl)cyclohexane-1-carboxamide

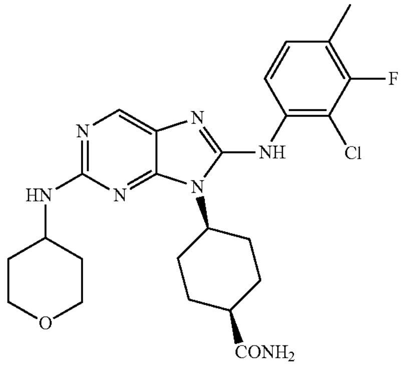 [SMILES: Cc1ccc(Nc2nc3cnc(NC4CCOCC4)nc3n2[C@H]2CC[C@@H](C(N)=O)CC2)c(Cl)c1F]

2-Chloro-3-fluoro-4-methylaniline

To a cooled (0° C.) solution of 3-fluoro-4-methylaniline (1 equiv.) in DMF (1.6 M) was added NCS (1 equiv.). After the addition was finished, the reaction was allowed to warm to room temperature and stirred for 18 h. The reaction was diluted with ethyl acetate, washed with saturated $Na_2SO_3$, dried over $Na_2SO_4$, filtered and concentrated. The resulting residue was purified via silica gel column chromatography providing 2-chloro-3-fluoro-4-methylaniline (8%) as a yellow solid. $^1H$ NMR (400 MHz, $CDCl_3$) δ ppm: 6.87 (t, J=8.1 Hz, 1H), 6.49 (dd, J=1.2, 8.2 Hz, 1H), 4.02 (s, 2H), 2.20 (d, J=1.8 Hz, 3H).

2-Chloro-3-fluoro-1-isothiocyanato-4-methylbenzene

To a cooled solution of 2-chloro-3-fluoro-4-methylaniline (1 equiv.) in DCM/$H_2O$ (1/1, 0.3 M) was added NaOH (3 equiv.), followed by dropwise $SCCl_2$ (3 equiv.) for 10 min. After the addition, the mixture was stirred for 60 min at room temperature. The reaction was diluted with petroleum ether, and filtered through a pad of silica gel. The filtrate was concentrated to afford 2-chloro-3-fluoro-1-isothiocyanato-4-methylbenzene (48%) as a yellow oil.

(1s,4s)-4-(8-((2-Chloro-3-fluoro-4-methylphenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in anhydrous DMF (0.15 M) was added 2-chloro-3-fluoro-1-isothiocyanato-4-methylbenzene (3 equiv.), and the mixture was stirred at room temperature for 90 min. DIC (6 equiv.) was added and the mixture was stirred at room temperature. Standard work-up and purification methods afforded cis-4-(8-((2-chloro-3-fluoro-4-methylphenyl)amino)-2-((tetrahydro-2H-pyran-4-yl)amino)-9H-purin-9-yl)cyclohexanecarboxamide (40%). $^1H$ NMR (400 MHz, MeOH-$d_4$) δ ppm: 8.07 (s, 1H), 7.34-7.12 (m, 2H), 4.37 (s, 1H), 4.11-3.92 (m, 3H), 3.71 (t, J=11.0 Hz, 2H), 2.89 (d, J=11.0 Hz, 2H), 2.67 (s, 1H), 2.47-2.17 (m, 5H), 2.04 (d, J=11.5 Hz, 2H), 1.89-1.71 (m, 4H), 1.64-1.47 (m, 2H). MS (ESI) m/z=502.2 $[M+1]^+$.

Example 7. (1s,4s)-4-(8-((4-Chloro-2,5-difluorophenyl)amino)-2-((tetrahydro-2H-pyran-4-yl)amino)-9H-purin-9-yl)cyclohexane-1-carboxamide

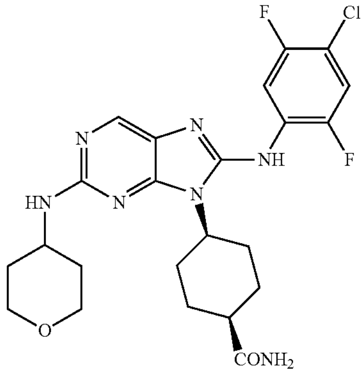 [SMILES: NC(=O)[C@H]1CC[C@@H](n2c(Nc3cc(F)c(Cl)cc3F)nc3cnc(NC4CCOCC4)nc32)CC1]

4-Chloro-2,5-difluoroaniline

To a mixture of 1-chloro-2,5-difluoro-4-nitrobenzene (1 equiv.) in acetic acid (0.5 M) was added Fe (5 equiv.), which was heated to reflux at 110° C. for 3 h. The mixture was filtered, the filtrate was concentrated to give the crude product, which was purified by silica gel chromatography to give 4-chloro-2,5-difluoroaniline (80%) as a white solid. $^1H$ NMR (400 MHz, $CDCl_3$) δ ppm: 7.08-6.99 (m, 1H), 6.65 (dd, J=7.8, 10.7 Hz, 1H).

1-Chloro-2,5-difluoro-4-isothiocyanatobenzene

To a mixture of 4-chloro-2,5-difluoroaniline (1.0 g, 6.1 mmol) in DCM/water (0.1 M, 1/2) added NaOH (6 equiv.) and $SCCl_2$ (3 equiv.) at 0° C. After addition, the mixture was allowed to warm to room temperature and stirred for 16 h. The mixture was filtered, and the filtrate was extracted with DCM. The combined organic layers were dried over $Na_2SO_4$, and concentrated to a residue. The residue was purified by silica gel chromatography to give 1-chloro-2,5-difluoro-4-isothiocyanatobenzene (48%) as a yellow oil. $^1H$ NMR (400 MHz, $CDCl_3$) δ ppm: 7.26-7.22 (m, 1H), 7.00 (dd, J=6.7, 8.5 Hz, 1H).

(1s,4s)-4-(8-((4-Chloro-2,5-difluorophenyl)amino)-2-((tetrahydro-2H-pyran-4-yl)amino)-9H-purin-9-yl)cyclohexanecarboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in DMF (0.37 M) was added 1-chloro-2,5-difluoro-4-isothiocyanatobenzene (1 equiv.). The reaction mixture was stirred at 25° C. for 1 h. DIC (1 equiv.) was added and the mixture was stirred at 25° C. for 16 h. Standard work-up and purification methods afforded (1s,4s)-4-(8-((4-chloro-2,5-difluorophenyl)amino)-2-((tetrahydro-2H-pyran-4-yl)amino)-9H-purin-9-yl)cyclohexanecarboxamide (32%). $^1H$ NMR (400 MHz, MeOH-$d_4$) δ ppm: 8.16 (s, 1H), 7.75 (s, 1H), 7.38 (s, 1H), 4.34 (s, 1H), 4.11-3.84 (m, 3H), 3.69 (t, J=11.2 Hz, 2H), 2.87 (d, J=11.7 Hz, 2H), 2.65 (s, 1H), 2.31 (d, J=12.9 Hz, 2H), 2.02 (d, J=12.8 Hz, 2H), 1.75 (s, 4H), 1.64-1.45 (m, 2H). MS (ESI) m/z=506.2 [M+1]$^+$.

Example 8. (1s,4s)-4-(8-((4-Chloro-2,3-difluorophenyl)amino)-2-((tetrahydro-2H-pyran-4-yl)amino)-9H-purin-9-yl)cyclohexane-1-carboxamide

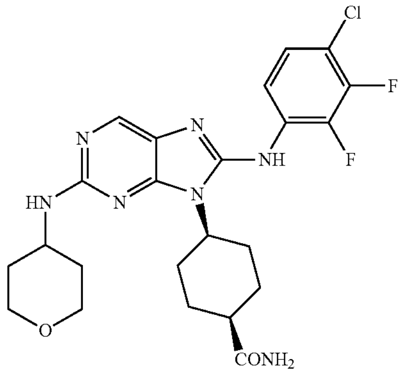 [SMILES: NC(=O)[C@H]1CC[C@@H](n2c(Nc3ccc(Cl)c(F)c3F)nc3cnc(NC4CCOCC4)nc32)CC1]

4-Chloro-2,3-difluoroaniline

To a mixture of 1-chloro-2,3-difluoro-4-nitrobenzene (1 equiv.) in acetic acid (0.5 M) was added Fe (5 equiv.). After addition, the mixture was refluxed for 3 h. The mixture was filtered, the filtrate was concentrated to give a residue. The residue was purified by silica gel chromatography to give 4-chloro-2,3-difluoroaniline (41%) as a yellow oil. $^1$H NMR (400 MHz, DMSO-d$_6$) δ ppm: 7.05-6.98 (m, 1H), 6.62-6.53 (m, 1H), 5.67 (br.s, 2H).

1-Chloro-2,3-difluoro-4-isothiocyanatobenzene

To a mixture of 4-chloro-2,3-difluoroaniline (1 equiv.) in DCM/water (0.3 M, 1/27) was added NaOH (3 equiv.) and $SCCl_2$ (3 equiv.) at 0° C. After addition, the mixture was allowed to warm to 25° C. and was stirred for 2 h. The mixture was filtered, and the filtrate was extracted with DCM. The combined organic layers were dried over $Na_2SO_4$, and concentrated to give a residue. The residue was purified by silica gel chromatography to give 1-chloro-2,3-difluoro-4-isothiocyanatobenzene (68%) as a yellow oil. $^1$H NMR (400 MHz, DMSO-d$_6$) δ ppm: 7.54-7.47 (m, 1H), 7.41-7.34 (m, 1H).

(1s,4s)-4-(8-((4-Chloro-2,3-difluorophenyl)amino)-2-((tetrahydro-2H-pyran-4-yl)amino)-9H-purin-9-yl)cyclohexanecarboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in DMF (0.3 M) was added 1-chloro-2,3-difluoro-4-isothiocyanatobenzene 2 (1.2 equiv.). The reaction mixture was stirred at 30° C. for 1 h. DIC (2 equiv.) was added, and the mixture was stirred at 30° C. for 16 h. Standard work-up and purification methods afforded (1s,4s)-4-(8-((4-chloro-2,3-difluorophenyl)amino)-2-((tetrahydro-2H-pyran-4-yl)amino)-9H-purin-9-yl)cyclohexanecarboxamide (26%). $^1$H NMR (400 MHz, MeOH-d$_4$) δ ppm: 8.11 (s, 1H), 7.46-7.36 (m, 1H), 7.33-7.23 (m, 1H), 4.42-4.29 (m, 1H), 4.11-3.94 (m, 3H), 3.77-3.65 (m, 2H), 3.00-2.79 (m, 2H), 2.70-2.64 (m, 1H), 2.39-2.28 (m, 2H), 2.09-1.98 (m, 2H), 1.85-1.71 (m, 4H), 1.64-1.52 (m, 2H). MS (ESI) m/z=506.2 [M+1]$^+$.

Example 9. (1s,4s)-4-(8-((2,4-Difluoro-6-methylphenyl)amino)-2-((tetrahydro-2H-pyran-4-yl)amino)-9H-purin-9-yl)cyclohexane-1-carboxamide

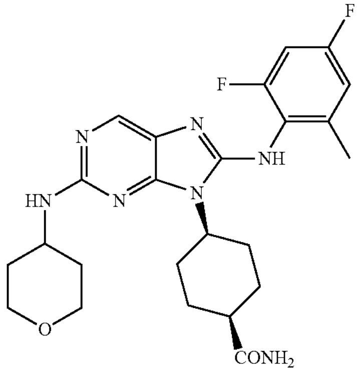 [SMILES: Cc1cc(F)cc(F)c1Nc1nc2cnc(NC3CCOCC3)nc2n1[C@H]1CC[C@@H](C(N)=O)CC1]

2,4-Difluoro-6-((methylthio)methyl)aniline

To a mixture of 2,4-difluoroaniline (1 equiv.) in DCM (0.5 M) was added $Me_2S$ (1 equiv.), NCS (1 equiv.) and TEA (1 equiv.) at −15° C. After addition, the mixture was allowed to warm to room temperature. The mixture was heated to reflux for 16 h. The mixture was concentrated in vacuo. The residue was purified by silica gel chromatography to afford 2,4-difluoro-6-((methylthio)methyl)aniline (40%) as a brown oil. $^1$H NMR (400 MHz, $CDCl_3$) δ ppm: 6.75 (ddd, J=2.9, 8.3, 10.8 Hz, 1H), 6.62 (td, J=2.2, 8.8 Hz, 1H), 3.67 (s, 2H), 2.01 (s, 3H).

2,4-Difluoro-6-methylaniline

To a mixture of 2,4-difluoro-6-((methylthio)methyl)aniline (1 equiv.) in EtOH (0.32 M) was added Raney Ni under $N_2$. The mixture was stirred under $H_2$ (50 psi) for 16 h. The mixture was filtered, and the filtrate was concentrated to give 2,4-difluoro-6-methylaniline 3 (0.8 g, yield: 89%) as a yellow oil. $^1$H NMR (400 MHz, $CDCl_3$) δ ppm: 6.74-6.53 (m, 2H), 3.63-3.34 (m, 2H), 2.19 (s, 3H).

1,5-Difluoro-2-isothiocyanato-3-methylbenzene

To a mixture of 2,4-difluoro-6-methylaniline (1 equiv.) in DCM/water (1/2, 0.2 M) was added NaOH (6 equiv.) and $SCCl_2$ (3 equiv.) at 0° C. After addition, the mixture was allowed to warm to room temperature and stirred for 16 h. The mixture was filtered, and the filtrate was extracted with DCM. The combined organic layers were dried over $Na_2SO_4$, and concentrated to a residue. The residue was purified by silica gel chromatography to provide 1,5-difluoro-2-isothiocyanato-3-methylbenzene (48%) as a yellow oil. $^1$H NMR (400 MHz, $CDCl_3$) δ ppm: 6.80-6.72 (m, 2H), 2.39 (s, 3H).

(1s,4s)-4-(8-((2,4-Difluoro-6-methylphenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in DMF (0.12 M) was added 1,5-difluoro-2-isothiocyanato-3-methylbenzene (1 equiv.). The reaction mixture was stirred at 25° C. for 1 h. To the reaction was added DIC (2 equiv.), and the mixture was stirred at 25° C. for 16 h. Standard work-up and purification methods afforded (1s,4s)-4-(8-((2,4-Difluoro-6-methylphenyl)amino)-2-((tetrahydro-2H-pyran-4-yl)amino)-9H-purin-9-yl)cyclohexane-1-carboxamide (54%). $^1$H NMR (400 MHz, MeOH-$d_4$) δ ppm: 7.93 (s, 1H), 6.98-6.79 (m, 2H), 4.39 (t, J=12.0 Hz, 1H), 4.09-3.90 (m, 3H), 3.67 (dt, J=1.9, 11.5 Hz, 2H), 2.99-2.79 (m, 2H), 2.66 (s, 1H), 2.37-2.17 (m, 5H), 2.06-1.95 (m, 2H), 1.87-1.71 (m, 4H), 1.63-1.47 (m, 2H). MS (ESI) m/z=486.3 [M+1]$^+$.

Example 10. (1s,4s)-4-(8-((2-Chloro-6-fluoro-3-methylphenyl)amino)-2-((tetrahydro-2H-pyran-4-yl)amino)-9H-purin-9-yl)cyclohexane-1-carboxamide

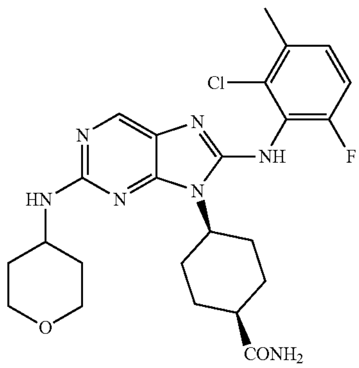 [SMILES: Cc1ccc(F)c(Nc2nc3cnc(NC4CCOCC4)nc3n2[C@H]2CC[C@@H](C(N)=O)CC2)c1Cl]

2-Chloro-6-fluoro-3-methylaniline

To a mixture of 2-chloro-6-fluoro-3-methylbenzoic acid (1 equiv.) in THF (0.3 M) was added DPPA (1.07 equiv.), and TEA (3 equiv.) at 25° C. The mixture was stirred at 25° C. for 2 h, then the mixture was heated to reflux for 2 h. Water was added and the reaction was refluxed for 1 h. The mixture was concentrated to a residue, which was purified via silica gel chromatography to give 2-chloro-6-fluoro-3-methylaniline (46%) as a yellow oil. $^1$H NMR (400 MHz, $CDCl_3$) δ ppm: 6.83 (dd, J=8.4, 10.3 Hz, 1H), 6.56 (dd, J=5.8, 8.3 Hz, 1H), 4.08 (br.s., 1H), 2.31 (s, 1H).

2-Chloro-4-fluoro-3-isothiocyanato-1-methylbenzene

To a mixture of 2-chloro-6-fluoro-3-methylaniline (1 equiv.) in DCM/water (1/2, 0.1 M) was added NaOH (6 equiv.) and $SCCl_2$ (3 equiv.) at 0° C. After addition, the mixture was allowed to warm to room temperature and stirred for 16 h. The mixture was filtered. The filtrate was extracted with DCM. The combined organic layers were dried over $Na_2SO_4$, and concentrated to a residue. The residue was purified via silica gel chromatography (petroleum ether) to give 2-chloro-4-fluoro-3-isothiocyanato-1-methylbenzene (63%) as a yellow oil. $^1$H NMR (400 MHz, $CDCl_3$) δ ppm: 7.09 (dd, J=5.7, 8.6 Hz, 1H), 7.01-6.93 (m, 1H), 2.36 (s, 3H).

(1s,4s)-4-(8-((2-chloro-6-fluoro-3-methylphenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in DMF (0.1 M) was added 2-chloro-4-fluoro-3-isothiocyanato-1-methylbenzene (1 equiv.). The reaction mixture was stirred at 25° C. for 1 h. To the reaction mixture was added DIC (2 equiv.). The mixture was stirred at 25° C. for 16 h. Standard work-up and purification methods provided cis-4-(8-((2-chloro-6-fluoro-3-methylphenyl)amino)-2-((tetrahydro-2H-pyran-4-yl)amino)-9H-purin-9-yl)cyclohexanecarboxamide (42%). $^1$H NMR (400 MHz, MeOH-$d_4$) δ ppm: 7.96 (s, 1H), 7.31-6.92 (m, 2H), 4.42 (s, 1H), 4.12-3.91 (m, 3H), 3.68 (t, J=11.3 Hz, 2H), 2.89 (d, J=11.7 Hz, 2H), 2.65 (s, 1H), 2.45-2.23 (m, 5H), 2.09-1.97 (m, 2H), 1.92-1.68 (m, 4H), 1.62-1.47 (m, 2H). MS (ESI) m/z=502.1 [M+1]$^+$.

Example 11. (1s,4s)-4-(8-((3,4-Dichloro-2-fluorophenyl)amino)-2-((tetrahydro-2-pyran-4-yl)amino)-9H-purin-9-yl)cyclohexanecarboxamide

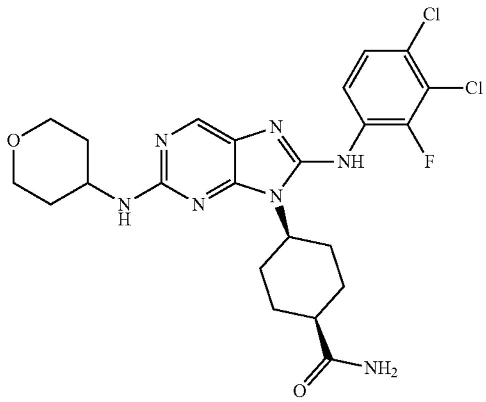 [SMILES: NC(=O)[C@H]1CC[C@@H](n2c(Nc3ccc(Cl)c(Cl)c3F)nc3cnc(NC4CCOCC4)nc32)CC1]

1,2-Dichloro-3-fluoro-4-isothiocyanatobenzene

A solution of sodium hydroxide (3 equiv.) in water (0.5 M) was added to a solution of 3,4-dichloro-2-fluoroaniline (1 equiv.) in DCM (1 M). The mixture was cooled to 0° C. and thiophosgene (3 equiv.) was added dropwise via syringe. The reaction mixture was allowed to warm to room temperature for 16 h. The mixture was extracted with DCM, the combined organic layers were dried over sodium sulfate and concentrated under vacuum. The residue was purified by column chromatography to afford 1,2-dichloro-3-fluoro-4-isothiocyanatobenzene (79%) as a white solid. $^1$H NMR (400 MHz, $CDCl_3$) δ ppm: 7.24 (dd, J=8.8, 2.0 Hz, 1H), 7.06 (t, J=8.2 Hz, 1H).

(1s,4s)-4-(8-((3,4-Dichloro-2-fluorophenyl)amino)-2-((tetrahydro-2H-pyran-4-yl)amino)-9H-purin-9-yl)cyclohexanecarboxamide A solution of (1s,4s)-4-((5-amino-2-((tetrahydro-2H-pyran-4-yl)amino)pyrimidin-4-yl)amino)cyclohexanecarboxamide (1 equiv.) (prepared as described herein) and 1,2-dichloro-3-fluoro-4-isothiocyanatobenzene (1.2 equiv.) in DMF (0.5 M) was stirred at room temperature for 2 h. LCMS showed that the intermediate thiourea was formed. Then EDC (2.5 equiv.) was added and the reaction was stirred for another 16 h. Standard work-up and purification methods afforded (1s,4s)-4-(8-((3,4-dichloro-2-fluorophenyl)amino)-2-((tetrahydro-2H-pyran-4-yl)amino)-9H-purin-9-yl)cyclohexanecarboxamide (31%). $^1$H NMR (400 MHz, Methanol-$d_4$) δ ppm: 8.01 (brs, 1H), 7.47 (s, 1H), 7.35 (dd, J=8.8, 2.0 Hz, 1H), 4.39-4.35 (m, 1H), 4.04-3.96 (m, 3H), 3.72-3.66 (m, 2H), 2.89-2.85 (m, 2H), 2.65 (s, 1H), 2.32 (d, J=12.4 Hz, 2H), 2.02 (d, J=10.8 Hz, 2H), 1.78-1.55 (m, 4H), 1.16-1.12 (m, 2H). MS (ESI) m/z=522.2 $[M+1]^+$.

Example 12. (1s,4s)-4-((5-(3-(2-Chloro-4-cyano-6-fluorophenyl)thioureido)-2-((tetrahydro-2H-pyran-4-yl)amino)pyrimidin-4-yl)amino)cyclohexanecarboxamide

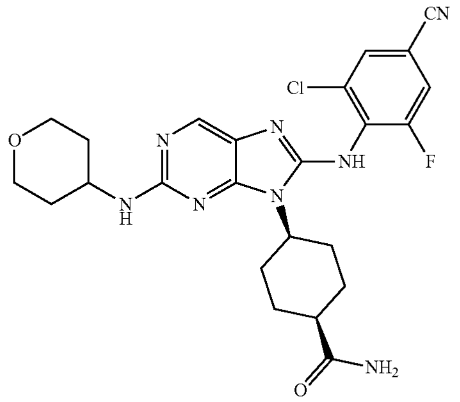 [SMILES: N#Cc1cc(F)c(Nc2nc3cnc(NC4CCOCC4)nc3n2[C@H]2CC[C@@H](C(N)=O)CC2)c(Cl)c1]

4-Amino-3-chloro-5-fluorobenzonitrile

A mixture of 4-amino-3-fluorobenzonitrile (1 equiv.) and N-chlorosuccinimide (1.5 equiv.) in acetonitrile (0.24 M) was stirred at 85° C. for 5 h. The solvent was removed by concentration and the residue was partitioned between ethyl acetate and 5% NaOH. The organic phase was washed with 5% NaOH and brine. Then the organic phase was dried over $MgSO_4$ and dried in vacuum to afford 4-amino-3-chloro-5-fluorobenzonitrile (88%) as a beige solid. $^1H$ NMR (400 MHz, $CDCl_3$) δ ppm: 7.41 (t, J=6 Hz, 1H), 7.24 (dd, J=1.8, 10.2 Hz, 1H), 4.66 (s, 2H).

3-Chloro-5-fluoro-4-isothiocyanatobenzonitrile

To a mixture of 4-amino-3-chloro-5-fluorobenzonitrile (1 equiv.) and DIEA (3.5 equiv.) in DCM (1 M) was added thiophosgene (3.5 equiv.) at 0° C. The reaction was stirred at room temperature overnight. The solvent was removed and the residue was purified by preparative TLC to give 3-chloro-5-fluoro-4-isothiocyanatobenzonitrile (34%) as a yellow solid. $^1H$ NMR (400 MHz, $CDCl_3$) δ ppm: 7.55 (t, J=1.6 Hz, 1H), 7.40 (dd, J=1.7, 8.5 Hz, 1H).

(1s,4s)-4-((5-(3-(2-Chloro-4-cyano-6-fluorophenyl)thioureido)-2-((tetrahydro-2H-pyran-4-yl)amino)pyrimidin-4-yl)amino)cyclohexanecarboxamide A mixture of 3-chloro-5-fluoro-4-isothiocyanatobenzonitrile (1 equiv.) and (1s,4s)-4-((5-amino-2-((tetrahydro-2H-pyran-4-yl)amino)pyrimidin-4-yl)amino)cyclohexanecarboxamide (1 equiv.) (prepared as described herein) in DMF was stirred at room temperature overnight. The solvent was removed and the residue was purified by preparative TLC to give (1s,4s)-4-((5-(3-(2-chloro-4-cyano-6-fluorophenyl)thioureido)-2-((tetrahydro-2H-pyran-4-yl)amino)pyrimidin-4-yl)amino)cyclohexanecarboxamide (33%) as a yellow solid. MS (ESI) m/z=547.2 $[M+1]^+$.

(1s,4s)-4-(8-((2-Chloro-4-cyano-6-fluorophenyl)amino)-2-((tetrahydro-2H-pyran-4-yl)amino)-9H-purin-9-yl)cyclohexanecarboxamide To a solution of (1s,4s)-4-((5-(3-(2-chloro-4-cyano-6-fluorophenyl)thioureido)-2-((tetrahydro-2H-pyran-4-yl)amino)pyrimidin-4-yl)amino)cyclohexanecarboxamide (1 equiv.) in DMF was added EDC (2.5 equiv.) in one portion. The resulting mixture was stirred at room temperature overnight. Standard work-up and purification methods afforded (1s,4s)-4-(8-((2-chloro-4-cyano-6-fluorophenyl)amino)-2-((tetrahydro-2H-pyran-4-yl)amino)-9H-purin-9-yl)cyclohexanecarboxamide (43%). $^1H$ NMR (400 MHz, Methanol-$d_4$) δ ppm: 7.71 (s, 1H), 7.56 (d, J=9.7 Hz, 1H), 4.54 (t, J=12.2 Hz, 1H), 4.06-3.95 (m, 3H), 3.69 (t, J=11.3 Hz, 2H), 2.92-2.78 (m, 2H), 2.68-2.63 (m, 1H), 2.33 (d, J=14.2 Hz, 2H), 2.03 (d, J=13.7 Hz, 2H), 1.83-1.70 (m, 4H), 1.64-1.52 (m, 2H). MS (ESI) m/z 531.2 $[M+1]^+$.

Example 13. (1s,4s)-4-(8-((4-Cyano-2,6-difluorophenyl)amino)-2-((tetrahydro-2H-pyran-4-yl)amino)-9H-purin-9-yl)cyclohexane-1-carboxamide

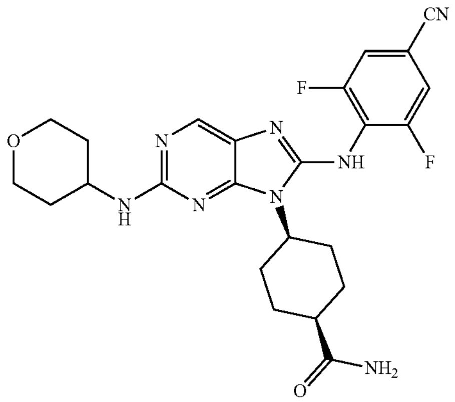 [SMILES: N#Cc1cc(F)c(Nc2nc3cnc(NC4CCOCC4)nc3n2[C@H]2CC[C@@H](C(N)=O)CC2)c(F)c1]

3,5-Difluoro-4-isothiocyanatobenzonitrile

To a cooled (0° C.) solution of 4-amino-3,5-difluorobenzonitrile (1 equiv.) in anhydrous DCM (0.2 M) was added DIEA (2.5 equiv.) in one portion. Then sulfonyl chloride (1.5 equiv.) was added dropwise over 20 min. After the addition, the reaction mixture was stirred for about 3 h at 0° C. The solvent was evaporated to give a brown solid, which was purified by column chromatography to give 3,5-difluoro-4-isothiocyanatobenzonitrile (67%) as a light yellow solid.

(1s,4s)-4-(8-((4-Cyano-2,6-difluorophenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexanecarboxamide (prepared as described herein) in anhydrous DMF (3.0 mL) was added 3,5-difluoro-4-isothiocyanatobenzonitrile (1 equiv.). After the addition, the reaction mixture was stirred for 1 h at room temperature. EDC (2.5 equiv.) was added in one portion. The reaction mixture was stirred for 16 h at room temperature. Standard work-up and purification methods afforded (1s,4s)-4-(8-((4-cyano-2,6-difluorophenyl)amino)-2-((tetrahydro-2H-pyran-4-yl)amino)-9H-purin-9-yl)cyclohexane-1-carboxamide (9%). $^1$H NMR (400 MHz, Methanol-$d_4$) δ ppm: 8.14 (s, 1H), 7.70-7.41 (m, 2H), 4.55 (s, 1H), 3.99 (d, J=11.67 Hz, 3H), 3.70 (t, J=10.79 Hz, 2H), 2.86 (s, 2H), 2.66 (s, 1H), 2.33 (d, J=12.55 Hz, 2H), 2.02 (d, J=11.54 Hz, 2H), 1.76 (s, 4H), 1.67-1.47 (m, 2H). MS (ESI) m/z=497.2 $[M+1]^+$.

Example 14. (1s,4s)-4-(8-((3-Cyano-2,6-difluorophenyl)amino)-2-((tetrahydro-2H-pyran-4-yl)amino)-9H-purin-9-yl)cyclohexane-1-carboxamide

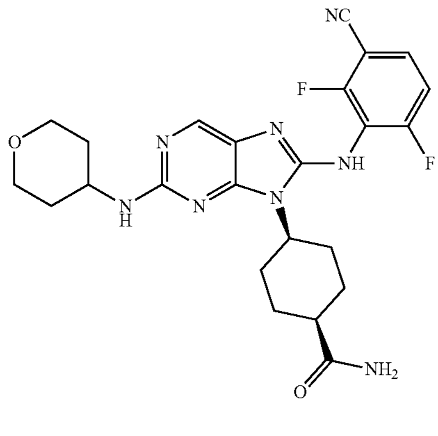 [SMILES: N#Cc1ccc(F)c(Nc2nc3cnc(NC4CCOCC4)nc3n2[C@H]2CC[C@@H](C(N)=O)CC2)c1F]

3-Cyano-2,6-difluorobenzoic acid

To a cooled (0° C.) solution of diisopropylamine (1.15 equiv.) in anhydrous THF was added n-BuLi (1.15 equiv.) dropwise over a period of 10 min. After the addition, the solution was stirred for about 30 mins at 0° C. The mixture was cooled to −78° C. and stirred for about 30 mins. A solution of 2,4-difluorobenzonitrile (1 equiv.) in THF was added dropwise over a period of 20 min. The reaction solution was stirred for 10 mins at −78° C. and $CO_2$ was bubbled into the mixture via a syringe for 15 min. The reaction was stirred at −78° C. for 2 h. HCl (6 M) was added into the reaction to pH=3-4. The aqueous phase was extracted with DCM/MeOH. The combined organic layers were washed with saturated sodium chloride solution, dried over sodium sulfate, filtered and concentrated in vacuum to give a white residue, which was purified by column chromatography on silica gel to give to 3-cyano-2,6-difluorobenzoic acid (53%) as a white solid.

tert-Butyl (3-cyano-2,6-difluorophenyl)carbamate

To a solution of 3-cyano-2,6-difluorobenzoic acid (1 equiv.) in 1:4 t-BuOH/dioxane was added DPPA (1.1 equiv.), di-t-butyl dicarbonate (1.2 equiv.) and triethanolamine (3.5 equiv.). After the addition, the reaction was heated to 100° C., and stirred for about 6 h. The solvent was concentrated to give a white residue, and water was added to the residue. The aqueous phase was extracted with ethyl acetate. The combined organic layers were washed with saturated sodium chloride solution, dried over sodium sulfate, filtered and concentrated in vacuum to give a white residue, which was purified by column chromatography on silica gel to give to tert-butyl (3-cyano-2,6-difluorophenyl)carbamate (38%) as a white solid.

3-Amino-2,4-difluorobenzonitrile tert-Butyl (3-cyano-2,6-difluorophenyl)carbamate (1 equiv.) was dissolved in 4 M HCl/1,4-Dioxane (0.2 M). The reaction mixture was stirred for 4 h at room temperature. The solvent was concentrated to give 3-amino-2,4-difluorobenzonitrile (93%) as a yellow solid. $^1$H NMR (400 MHz, DMSO-$d_6$) δ ppm: 7.19-7.09 (m, 1H), 7.09-6.99 (m, 1H), 5.85 (s, 2H).

2,4-Difluoro-3-isothiocyanatobenzonitrile

To a cooled (0° C.) solution of 3-amino-2,4-difluorobenzonitrile (1 equiv.) in anhydrous DCM (1.0 mL) was added DIEA (4 equiv.) in one portion. Sulfonyl chloride (5 equiv.) was added dropwise over 10 min. After the addition, the reaction mixture was stirred for about 0.5 h at 0° C. The reaction was warmed to room temperature and stirred for 3 h. The solvent was evaporated to give a brown solid, which was purified by column chromatography on silica gel to give 2,4-difluoro-3-isothiocyanatobenzonitrile (31%) as a white solid. $^1$H NMR (400 MHz, $CDCl_3$) δ ppm: 7.60-7.45 (m, 1H), 7.13 (td, J=8.72, 1.64 Hz, 1H).

(1s,4s)-4-(8-((3-Cyano-2,6-difluorophenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in anhydrous DMF was added 2,4-difluoro-3-isothiocyanatobenzonitrile (1.1 equiv.). After the addition, the reaction mixture was stirred for 2 h at room temperature. DIC (1.1 equiv.) was added in one portion. The reaction mixture was stirred for 16 h at room temperature. Standard work-up and purification methods provided cis-4-(8-((3-cyano-2,6-difluorophenyl)amino)-2-((tetrahydro-2H-pyran-4-yl)amino)-9H-purin-9-yl)cyclohexanecarboxamide (15%). $^1$H NMR (400 MHz, Methanol-$d_4$) δ ppm: 8.00 (s, 1H), 7.79-7.56 (m, 1H), 7.33-7.06 (m, 1H), 4.49 (s, 1H), 4.12-3.91 (m, 3H), 3.70 (t, J=10.98 Hz, 2H), 3.00-2.75 (m, 2H), 2.67 (s, 1H), 2.34 (d, J=13.68 Hz, 2H), 2.03 (d, J=11.04 Hz, 2H), 1.89-1.68 (m, 4H), 1.46-1.65 (m, 2H). MS (ESI) m/z 497.3=$[M+1]^+$.

Example 15. (1s,4s)-4-(8-((2-Chloro-6-fluoro-4-(trifluoromethyl)phenyl)amino)-2-((tetrahydro-2H-pyran-4-yl)amino)-9H-purin-9-yl)cyclohexane-1-carboxamide

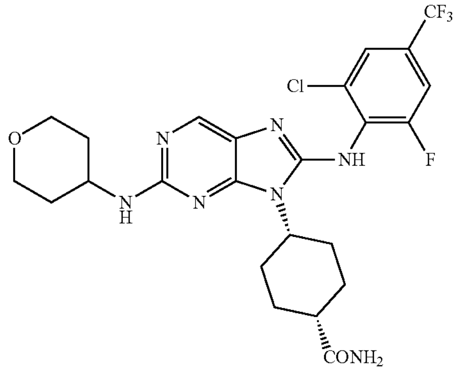 [SMILES: NC(=O)[C@H]1CC[C@@H](n2c(Nc3c(F)cc(C(F)(F)F)cc3Cl)nc3cnc(NC4CCOCC4)nc32)CC1]

2-Chloro-6-fluoro-4-(trifluoromethyl)aniline

To a mixture of 2-fluoro-4-(trifluoromethyl)aniline (1 equiv.) in acetonitrile (10 mL) was added N-chlorosuccinimide (1.15 equiv.) at 90° C. The reaction mixture was stirred at 90° C. for 5 h. The mixture was concentrated to give a residue. The residue was purified via silica gel chromatography to give the desired product 2-chloro-6-fluoro-4-(trifluoromethyl)aniline (50%). $^1$H NMR (400 MHz, $CDCl_3$) δ ppm: 7.36 (s, 1H), 7.20 (d, J=10.4 Hz, 1H), 4.41 (s, 2H).

1-Chloro-3-fluoro-2-isothiocyanato-5-(trifluoromethyl)benzene

To a solution of 2-chloro-6-fluoro-4-(trifluoromethyl)aniline (1 equiv.) in DCM (5 mL) was added DIEA (3 equiv.) and thiocarbonyl dichloride (3 equiv.). After addition, the mixture was heated to 50° C. and stirred for 2 h. TLC (petroleum ether/ethyl acetate=50:1) showed 2-chloro-6-fluoro-4-(trifluoromethyl)aniline was consumed completely. The mixture was concentrated and purified with silica gel chromatography to give the desired product 1-chloro-3-fluoro-2-isothiocyanato-5-(trifluoromethyl)benzene (67%) as a yellow solid. $^1$H NMR (400 MHz, $CDCl_3$) δ ppm: 7.51 (s, 1H), 7.35 (d, J=8.8 Hz, 1H).

(1s,4s)-4-(8-((2-Chloro-6-fluoro-4-(trifluoromethyl)phenyl)amino)-2-((tetrahydro-2H-pyran-4-yl)amino)-9H-purin-9-yl)cyclohexanecarboxamide To a solution of (1s,4s)-4-((5-amino-2-((tetrahydro-2H-pyran-4-yl)amino)pyrimidin-4-yl)amino)cyclohexanecarboxamide (prepared as described herein) (1 equiv.), in DMF was added 1-chloro-3-fluoro-2-isothiocyanato-5-(trifluoromethyl)benzene (1 equiv.). The reaction mixture was stirred at 30° C. for 2 h. To the reaction mixture was added EDC (2 equiv.), the mixture was stirred at 30° C. for 16 h. Standard work-up and purification methods afforded (1s,4s)-4-(8-((2-chloro-6-fluoro-4-(trifluoromethyl)phenyl)amino)-2-((tetrahydro-2H-pyran-4-yl)amino)-9H-purin-9-yl)cyclohexanecarboxamide (32%). $^1$H NMR (400 MHz, Methanol-$d_4$) δ ppm: 7.63-7.53 (m, 2H), 7.48-7.39 (m, 1H), 4.60-4.47 (m, 1H), 4.07-3.90 (m, 3H), 3.75-3.62 (m, 2H), 2.97-2.75 (m, 2H), 2.66-2.59 (m, 1H), 2.37-2.27 (m, 2H), 2.04-1.95 (m, 2H), 1.88-1.68 (m, 4H), 1.62-1.47 (m, 2H). MS (ESI) m/z=556.2 $[M+1]^+$.

Example 16. (1s,4s)-4-(8-((3-Chloro-2-methylphenyl)amino)-2-((tetrahydro-2H-pyran-4-yl)amino)-9H-purin-9-yl)cyclohexane-1-carboxamide

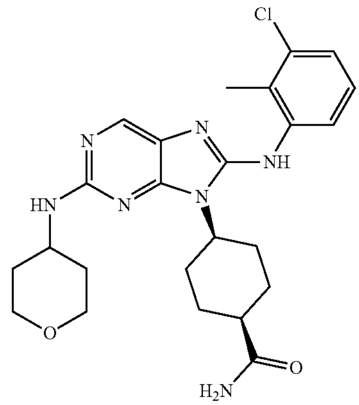 [SMILES: Cc1c(Cl)cccc1Nc1nc2cnc(NC3CCOCC3)nc2n1[C@H]1CC[C@@H](C(N)=O)CC1]

(1s,4s)-4-((2-Chloro-5-nitropyrimidin-4-yl)amino)cyclohexane-1-carboxylic acid 2,4-Dichloro-5-nitropyrimidine (1 equiv.) and (1s,4s)-4-aminocyclohexanecarboxylic acid (1 equiv.) were suspended in THF and cooled to −78° C. DIEA (3 equiv.) was added drop wise and the reaction was stirred at −78° C. for 45 min. The cooling bath was removed and the reaction was stirred at room temperature overnight. The solvent was removed under reduced pressure to give the desired product (1s,4s)-4-((2-chloro-5-nitropyrimidin-4-yl)amino)cyclohexanecarboxylic acid (84%), which was filtered and used without further purification. MS (ESI) m/z 301.2 $[M+1]^+$.

(1s,4s)-4-((5-Nitro-2-((tetrahydro-2H-pyran-4-yl)amino)pyrimidin-4-yl)amino)cyclohexane-1-carboxylic acid (1s,4s)-4-((2-Chloro-5-nitropyrimidin-4-yl)amino)cyclohexanecarboxylic acid (1 equiv.) and tetrahydro-2H-pyran-4-amine hydrochloride (1 equiv.) were suspended in THF followed by the addition of DIEA (4 equiv.). The reaction was stirred at 50° C. overnight. The solvent was reduced in vacuo to give the desired product (1s,4s)-4-((5-nitro-2-((tetrahydro-2H-pyran-4-yl)amino)pyrimidin-4-yl)amino)cyclohexanecarboxylic acid (69%). The product was used without further purification. MS (ESI) m/z 366.4 $[M+1]^+$.

Resin bound-(1s,4s)-4-((5-nitro-2-((tetrahydro-2H-pyran-4-yl)amino)pyrimidin-4-yl)amino)cyclohexane-1-carboxamide (1s,4s)-4-((5-Nitro-2-((tetrahydro-2H-pyran-4-yl)amino)pyrimidin-4-yl)amino)cyclohexanecarboxylic acid (1 equiv.) was dissolved in DMF, followed by the addition of Rink-H resin (1 equiv.) and HOBt (1.5 equiv.). The reaction mixture was stirred overnight followed by the addition of EDC (2.3 equiv.), and the reaction mixture was heated at 50° C. for 1 h. The resin was washed with three portions of MeOH, three portions of DCM, three portions of MeOH, and two portions of ether. The resin was taken forward into the next step. MS (ESI) m/z 484.2 $[M+1]^+$.

Resin bound-(1s,4s)-4-((5-(3-(3-chloro-2-methylphenyl)thioureido)-2-((tetrahydro-2H-pyran-4-yl)amino)pyrimidin-4-yl)amino)cyclohexane-1-carboxamide Resin bound (1s,4s)-N-methyl-4-((5-nitro-2-((tetrahydro-2H-pyran-4-yl)amino)pyrimidin-4-yl)amino)cyclohexanecarboxamide (1 equiv.) was treated with DMF:MeOH (3:1) ratio followed by the addition of chromium(II) chloride (3 equiv.) The reaction mixture was stirred overnight at room temperature followed by the addition of 1-chloro-3-isothiocyanato-2-methylbenzene (5 equiv.). The resin was washed with three portions of MeOH followed by three portions of DCM, then rinsed with EtOH. The resin once washed was taken into the next step. MS (ESI) m/z 519.2 $[M+1]^+$.

(1s,4s)-4-(8-((3-Chloro-2-methylphenyl)amino)-2-((tetrahydro-2H-pyran-4-yl)amino)-9H-purin-9-yl)cyclohexane-1-carboxamide Resin bound (1s,4s)-4-((5-(3-(3-chloro-2-methylphenyl)thioureido)-2-((tetrahydro-2H-pyran-4-yl)amino)pyrimidin-4-yl)amino)cyclohexane-1-carboxamide (1 equiv.) was suspended in EtOH followed by the addition of EDC (5 equiv.). The reaction mixture was heated to 50° C. for 3 h. The resin was washed with three portions of MeOH followed by three portions of DCM, then MeOH/DCM alternating the wash three times each. The resin was then transferred to a vial and 50% DCM/TFA was used to cleave the compound from the resin. The mixture was left to stir for 30 min, filtered, the resin was rinsed with DCM and the filtrate was concentrated under reduced pressure to afford (1s,4s)-4-(8-((3-chloro-2-methylphenyl)amino)-2-((tetrahydro-2H-pyran-4-yl)amino)-9H-purin-9-yl)cyclohexane-1-carboxamide as the TFA salt. Standard workup and purification methods afforded (1s,4s)-4-(8-((3-chloro-2-methylphenyl)amino)-2-((tetrahydro-2H-pyran-4-yl)amino)-9H-purin-9-yl)cyclohexane-1-carboxamide (7%). $^1$H NMR (400 MHz, DMSO-$d_6$) δ ppm: 8.31 (s, 1H), 8.10 (s, 1H), 7.56 (d, J=7.81 Hz, 1H), 7.32 (d, J=1.17 Hz, 1H), 7.10-7.28 (m, 2H), 6.76 (br. s., 1H), 6.45 (d, J=7.81 Hz, 1H), 4.30 (br. s., 1H), 3.78-3.94 (m, 3H), 3.53 (t, J=10.94 Hz, 2H), 2.57-2.76 (m, 2H), 2.13-2.36 (m, 5H), 1.85 (d, J=12.50 Hz, 2H), 1.34-1.71 (m, 7H). MS (ESI) m/z=484.2 $[M+1]^+$.

Example 17. (1s,4s)-4-(8-((2-Chloro-4-cyanophenyl)amino)-2-((tetrahydro-2H-pyran-4-yl)amino)-9H-purin-9-yl)cyclohexane-1-carboxamide

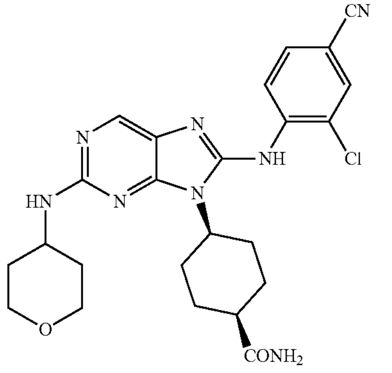 [SMILES: N#Cc1ccc(Nc2nc3cnc(NC4CCOCC4)nc3n2[C@H]2CC[C@@H](C(N)=O)CC2)c(Cl)c1]

3-Chloro-4-isothiocyanatobenzonitrile

To a cooled (0° C.) solution of 4-amino-3-chlorobenzonitrile (1 equiv.) in anhydrous DCM (0.65 M) was added DIEA (3 equiv.) in one portion. Then $CSCl_2$ (3 equiv.) was added dropwise over 20 min. After the addition, the reaction mixture was stirred for about 2 h at 0° C. The solvent was evaporated to give a brown solid, which was purified by column chromatography on silica gel) to give 3-chloro-4-isothiocyanatobenzonitrile (61%) as a light yellow solid.

(1s,4s)-4-(8-((2-Chloro-4-cyanophenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexanecarboxamide (1 equiv.) (prepared as described herein) in anhydrous DMF (0.3 M) was added 3-chloro-4-isothiocyanatobenzonitrile (1 equiv.). After the addition, the reaction mixture was stirred for 1 h at room temperature. DIC (2 equiv.) was added in one portion. The reaction mixture was stirred for 16 h at room temperature. Standard work-up and purification methods afforded (1s,4s)-4-(8-((2-chloro-4-cyanophenyl)amino)-2-((tetrahydro-2H-pyran-4-yl)amino)-9H-purin-9-yl)cyclohexane-1-carboxamide (14%). $^1$H NMR (400 MHz, Methanol-$d_4$) δ ppm: 8.29 (s, 1H), 7.88 (s, 1H), 7.76-7.52 (m, 2H), 4.32 (s, 1H), 4.10-3.96 (m, 4H), 3.76-3.66 (m, 2H), 2.87 (d, J=10.67 Hz, 2H), 2.66 (s, 1H), 2.33 (d, J=13.55 Hz, 2H), 2.03 (s, 2H), 1.82-1.70 (m, 4H), 1.60 (d, J=11.80 Hz, 2H). MS (ESI) m/z=495.2 $[M+1]^+$.

Example 18. (1s,4s)-4-(8-((2,3-Difluoro-4-(trifluoromethoxy)phenyl)amino)-2-((tetrahydro-2H-pyran-4-yl)amino)-9H-purin-9-yl)cyclohexane-1-carboxamide

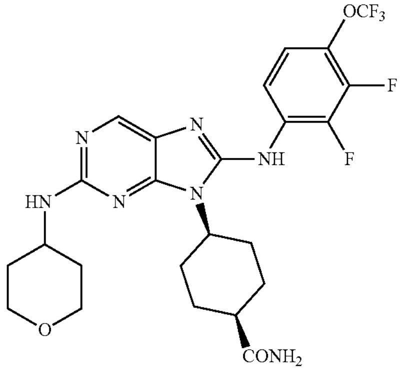 [SMILES: NC(=O)[C@H]1CC[C@@H](n2c(Nc3ccc(OC(F)(F)F)c(F)c3F)nc3cnc(NC4CCOCC4)nc32)CC1]

2,3-Difluoro-4-methoxyaniline

To a mixture of 2,3-difluoro-1-methoxy-4-nitrobenzene 1 (1 equiv.) in EtOH (0.5 M) was added $SnCl_2$ (5 equiv.). Then HCl (25 mL) was added and the reaction was stirred at room temperature for 16 h. Ethyl acetate and $H_2O$ were added, and the aqueous layer was extracted with ethyl acetate. The combined organic layers were dried over $Na_2SO_4$, and filtered, then the filtrate was concentrated in vacuo to give 2,3-difluoro-4-methoxyaniline (90%) as a brown solid.

2,3-Difluoro-1-isothiocyanato-4-methoxybenzene

To a solution of 2,3-difluoro-4-methoxyaniline (1 equiv.) in DCM (0.8 M) was added DIEA (2.5 equiv.) at 0° C., then $SCCl_2$ (5 equiv.) was added drop-wise at 0° C. The reaction mixture was stirred at room temperature for 2 h. The organic solvent was condensed in vacuo and purified via silica gel to give 2,3-difluoro-1-isothiocyanato-4-methoxybenzene (94%) as a yellow solid. $^1H$ NMR (400 MHz, DMSO-$d_6$) δ ppm: 7.42-7.27 (m, 1H), 7.08 (dt, J=2.1, 8.9 Hz, 1H), 3.99-3.83 (m, 3H).

(1s,4s)-4-(8-((2,3-Difluoro-4-(trifluoromethoxy)phenyl)amino)-2-((tetrahydro-2H-pyran-4-yl)amino)-9H-purin-9-yl)cyclohexane-1-carboxamide To a solution of 2,3-difluoro-1-isothiocyanato-4-methoxybenzene (1 equiv.) in DMF (0.5 M) was added (is, 4s)-4-((5-amino-2-((tetrahydro-2H-pyran-4-yl)amino)pyrimidin-4-yl)amino)cyclohexanecarboxamide (1 equiv.) (prepared as described herein). The mixture was stirred at room temperature for 1 h. To the mixture obtained in the previous step was added DIC (2 equiv.). The mixture was stirred at room temperature for 12 h. Standard work-up and purification methods afforded (is, 4s)-4-(8-((2,3-difluoro-4-methoxyphenyl)amino)-2-((tetrahydro-2H-pyran-4-yl)amino)-9H-purin-9-yl)cyclohexanecarboxamide (5%). $^1H$ NMR (400 MHz, $CDCl_3$) δ ppm: 8.33 (s, 1H), 7.76 (dt, J=2.5, 8.8 Hz, 1H), 7.37 (s, 1H), 6.96-6.75 (m, 1H), 5.61-5.39 (m, 2H), 4.81-4.55 (m, 2H), 4.19-3.98 (m, 3H), 3.92 (s, 3H), 3.67-3.54 (m, 2H), 2.85-2.66 (m, 2H), 2.63 (brs., 1H), 2.22 (d, J=15.4 Hz, 2H), 2.14-2.03 (m, 2H), 1.94-1.72 (m, 4H), 1.58-1.46 (m, 2H). MS (ESI) m/z=502.3 $[M+1]^+$.

Example 19. (1s,4s)-4-(8-((4-Fluorophenyl)amino)-2-((tetrahydro-2H-pyran-4-yl)amino)-9H-purin-9-yl)cyclohexane-1-carboxamide

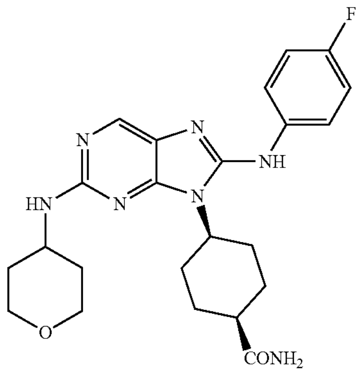 [SMILES: NC(=O)[C@H]1CC[C@@H](n2c(Nc3ccc(F)cc3)nc3cnc(NC4CCOCC4)nc32)CC1]

Methyl (1s,4s)-4-aminocyclohexane-1-carboxylate hydrochloride

To a solution of cis-4-aminocyclohexanecarboxylic acid (1 equiv.) in dry methanol (0.5 M), was added dropwise sulfurous dichloride (4 equiv.). The reaction was stirred at room temperature for 2 h. The solvent was removed in vacuum to give methyl (1s,4s)-4-aminocyclohexane-1-carboxylate hydrochloride (96%) as a white solid. $^1H$ NMR (400 MHz, $CDCl_3$-$d_4$) δ ppm: 8.34 (br. s., 3H), 3.80-3.66 (m, 3H), 3.32 (br. s., 1H), 2.58 (br. s., 1H), 2.31-1.50 (m, 8H).

Methyl (1s,4s)-4-((2-chloro-5-nitropyrimidin-4-yl)amino)cyclohexane-1-carboxylate 2,4-Dichloro-5-nitropyrimidine (1 equiv.) and methyl (1s, 4s)-4-aminocyclohexane-1-carboxylate hydrochloride (1 equiv.) were dissolved in THE (0.5 M) and cooled to −78° C. DIEA (2.5 equiv.) was added dropwise and the reaction was stirred at −78° C. for 45 min. The cooling bath was removed and the reaction was stirred at room temperature for 4 h. The solvent was removed in vacuo to give methyl (1s,4s)-4-((2-chloro-5-nitropyrimidin-4-yl)amino)cyclohexane-1-carboxylate (95%) as a yellow solid, which was used directly into the next step without further purification. MS (ESI) m/z=315.1 $[M+1]^+$.

Methyl (1s,4s)-4-((5-nitro-2-((tetrahydro-2H-pyran-4-yl)amino)pyrimidin-4-yl)amino)cyclohexane-1-carboxylate To a mixture of methyl (1s,4s)-4-((2-chloro-5-nitropyrimidin-4-yl)amino)cyclohexane-1-carboxylate (1 equiv.) and tetrahydro-2H-pyran-4-amine (1.2 equiv.) in THF (0.3 M) was added DIEA (3 equiv.). The mixture was stirred at 70° C. overnight. Water and ethyl acetate were added to the mixture and the layers were separated. The aqueous layer was extracted with ethyl acetate. The combined organic layers were dried over $Na_2SO_4$ and concentrated in vacuo to give methyl (1s,4s)-4-((5-nitro-2-((tetrahydro-2H-pyran-4-yl)amino)pyrimidin-4-yl)amino)cyclohexane-1-carboxylate (60%) as yellow solid. $^1H$ NMR (400 MHz, $CDCl_3$) δ ppm: 9.06-8.90 (m, 1H), 8.64-8.35 (m, 1H), 5.70-5.30 (m, 1H), 4.2 (m, 1H), 4.07-3.95 (m, 3H), 3.72 (m, 3H), 3.60-3.46 (m, 2H), 2.60-2.47 (m, 1H), 2.04-1.92 (m, 4H), 1.89-1.69 (m, 6H), 1.65-1.55 (m, 2H). MS (ESI) m/z=380.2 $[M+1]^+$.

Methyl (1s,4s)-4-((5-amino-2-((tetrahydro-2H-pyran-4-yl)amino)pyrimidin-4-yl)amino)cyclohexane-1-carboxylate To methyl (1s,4s)-4-((5-nitro-2-((tetrahydro-2H-pyran-4-yl)amino)pyrimidin-4-yl)amino)cyclohexane-1-carboxylate (1 equiv.) in MeOH (0.3 M) was added Pd/C (0.1 equiv, 10% Pd by wt.) under nitrogen atmosphere. The mixture was hydrogenated overnight under $H_2$ (1 atm). The reaction was filtered over Celite and washed with MeOH. The filtrate was concentrated in vacuo to give methyl (1s,4s)-4-((5-amino-2-((tetrahydro-2H-pyran-4-yl)amino)pyrimidin-4-yl)amino)cyclohexane-1-carboxylate, which was used into the next step without further purification. $^1H$ NMR (400 MHz, DMSO-$d_6$) δ ppm: 7.23 (s, 1H), 5.78 (d, J=7.2 Hz, 1H), 5.54 (d, J=8.0 Hz, 1H), 4.01-3.90 (m, 1H), 3.89-3.77 (m, 4H), 3.75-3.65 (m, 1H), 3.63 (s, 3H), 3.34-3.28 (m, 2H), 2.61-2.53 (m, 1H), 2.00-1.90 (m, 2H), 1.79 (dd, J=1.9, 12.4 Hz, 2H), 1.75-1.67 (m, 2H), 1.62-1.35 (m, 6H).

Methyl (1s,4s)-4-(8-((4-fluorophenyl)amino)-2-((tetrahydro-2H-pyran-4-yl)amino)-9H-purin-9-yl)cyclohexane-1-carboxylate To methyl (1s,4s)-4-((5-amino-2-((tetrahydro-2H-pyran-4-yl)amino)pyrimidin-4-yl)amino)cyclohexane-1-carboxylate (1 equiv.) in DMF (0.2 M) was added 1-fluoro-4-isothiocyanatobenzene (1 equiv.). The reaction was stirred at room temperature for 2 h. The reaction solution was used directly in the next step without further purification. To the reaction solution from above was added DIC (1 equiv.). The reaction was stirred at 50° C. overnight. Water and ethyl acetate were added to the solution and the layers were separated. The aqueous layer was extracted with ethyl acetate. The combined organic layers were washed with water, then dried over $Na_2SO_4$ and concentrated in vacuo. The residue was washed with ethyl acetate to give methyl (1s,4s)-4-(8-((4-fluorophenyl)amino)-2-((tetrahydro-2H-pyran-4-yl)amino)-9H-purin-9-yl)cyclohexane-1-carboxylate (64%) as white solid. MS (ESI) m/z=469.3 $[M+1]^+$.

(1s,4s)-4-(8-((4-Fluorophenyl)amino)-2-((tetrahydro-2H-pyran-4-yl)amino)-9H-purin-9-yl)cyclohexane-1-carboxylic acid A mixture of methyl (1s,4s)-4-(8-((4-fluorophenyl)amino)-2-((tetrahydro-2H-pyran-4-yl)amino)-9H-purin-9-yl)cyclohexane-1-carboxylate (1 equiv.), LiOH (1 equiv.) and THF/$H_2O$ (4/1, 0.1 M) was stirred at 70° C. overnight. Water was added to the residue, the pH of the mixture was adjusted to 6 with 1N HCl, and the solution was filtered to give (1s,4s)-4-(8-((4-fluorophenyl)amino)-2-((tetrahydro-2H-pyran-4-yl)amino)-9H-purin-9-yl)cyclohexane-1-carboxylic acid (88%) as white solid. $^1$H NMR (400 MHz, Methanol-$d_4$) δ ppm: 8.01 (s, 1H), 7.67-7.58 (m, 2H), 7.13 (t, J=8.8 Hz, 2H), 4.46-4.35 (m, 1H), 4.18-4.06 (m, 1H), 4.03-3.94 (m, 2H), 3.77 (dt, J=11.2, 1.8 Hz, 2H), 2.89-2.73 (m, 3H), 2.41 (d, J=13.7 Hz, 2H), 2.08-2.03 (m, 2H), 1.88-1.74 (m, 4H), 1.71-1.54 (m, 2H).

(1s,4s)-4-(8-((4-Fluorophenyl)amino)-2-((tetrahydro-2H-pyran-4-yl)amino)-9H-purin-9-yl)cyclohexane-1-carboxamide To a solution of (1s,4s)-4-(8-((4-Fluorophenyl)amino)-2-((tetrahydro-2H-pyran-4-yl)amino)-9H-purin-9-yl)cyclohexane-1-carboxylic acid (1 equiv.) in DMF (0.2 M) was added $NH_4Cl$ (3.3 equiv.), DIEA (4 equiv.) and HATU (1.2 equiv.). The reaction was stirred at room temperature overnight. Standard work-up and purification methods provided (1s,4s)-4-(8-((4-fluorophenyl)amino)-2-((tetrahydro-2H-pyran-4-yl)amino)-9H-purin-9-yl)cyclohexane-1-carboxylic acid (36%). $^1$H NMR (400 MHz, Methanol-$d_4$) δ ppm: 7.95 (s, 1H), 7.76-7.71 (m, 2H), 7.20-7.13 (m, 2H), 4.51 (tt, J=12.0, 4.0 Hz, 1H), 4.27-4.14 (m, 1H), 4.01 (td, J=11.2, 3.6 Hz, 2H), 3.76 (t, J=11.2 2H), 2.95-2.82 (m, 2H), 2.74-2.68 (m, 1H), 2.32 (d, J=13.6 Hz, 2H), 2.05 (dd, J=12.8, 2.4 Hz, 2H), 1.89-1.78 (m, 4H), 1.73-1.61 (m, 2H). MS (ESI) m/z=454.3 $[M+H]^+$.

Example 20. (1s,4s)-4-(8-((2,6-Dichloro-4-fluorophenyl)amino)-2-((tetrahydro-2H-pyran-4-yl)amino)-9H-purin-9-yl)cyclohexane-1-carboxamide

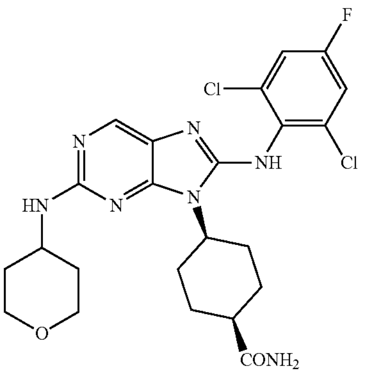 [SMILES: NC(=O)[C@H]1CC[C@@H](n2c(Nc3c(Cl)cc(F)cc3Cl)nc3cnc(NC4CCOCC4)nc32)CC1]

Methyl (1s,4s)-4-((5-(3-(2,6-dichloro-4-fluorophenyl)thioureido)-2-((tetrahydro-2H-pyran-4-yl)amino)pyrimidin-4-yl)amino)cyclohexane-1-carboxylate To a solution of (1s,4s)-methyl 4-((5-amino-2-((tetrahydro-2H-pyran-4-yl)amino)pyrimidin-4-yl)amino)cyclohexanecarboxylate (1 equiv.) (prepared as described herein) in DMF (0.3 M) was added 1,3-dichloro-5-fluoro-2-isothiocyanatobenzene (1 equiv.). The reaction was stirred at 25° C. for 2 h. The mixture was used directly in next step without further purification. MS (ESI) m/z=571.1 $[M+H]^+$.

(1s,4s)-Methyl 4-(8-((2,6-dichloro-4-fluorophenyl)amino)-2-((tetrahydro-2H-pyran-4-yl)amino)-9H-purin-9-yl)cyclohexanecarboxylate To the solution from above was added DIC (2 equiv.). The mixture was stirred at 40° C. for 16 h. The mixture was diluted with brine and filtered. The filter cake was crystallized with ethyl acetate to give (1s,4s)-methyl 4-(8-((2,6-dichloro-4-fluorophenyl)amino)-2-((tetrahydro-2H-pyran-4-yl)amino)-9H-purin-9-yl)cyclohexanecarboxylate (82%). $^1$H NMR (400 MHz, Methanol-$d_4$) δ ppm: 8.44-8.13 (m, 1H), 7.17 (d, J=7.6 Hz, 2H), 4.94-4.79 (m, 1H), 4.59-4.44 (m, 1H), 4.12-3.95 (m, 3H), 3.74 (s, 3H), 3.68-3.57 (m, 2H), 2.83-2.75 (m, 1H), 2.75-2.60 (m, 2H), 2.39-2.28 (m, 2H), 2.11-2.01 (m, 2H), 1.81-1.61 (m, 4H), 1.60-1.46 (m, 2H).

(1s,4s)-4-(8-((2,6-Dichloro-4-fluorophenyl)amino)-2-((tetrahydro-2H-pyran-4-yl)amino)-9H-purin-9-yl)cyclohexanecarboxylic acid To a mixture of (1s,4s)-methyl 4-(8-((2,6-dichloro-4-fluorophenyl)amino)-2-((tetrahydro-2H-pyran-4-yl)amino)-9H-purin-9-yl)cyclohexanecarboxylate (1 equiv.) in THF/water (5/1, 0.12 M) was added LiOH (5 equiv.). The reaction was stirred at 60° C. for 16 h. Water was added to the mixture and the pH was adjusted to 6 with 1N HCl, then the mixture was concentrated to give the crude product, which was used directly in next step without further purification. MS (ESI) m/z=523.1 $[M+H]^+$.

(1s,4s)-4-(8-((2,6-Dichloro-4-fluorophenyl)amino)-2-((tetrahydro-2H-pyran-4-yl)amino)-9H-purin-9-yl)cyclohexanecarboxamide To a solution of (1s,4s)-4-(8-((2,6-dichloro-4-fluorophenyl)amino)-2-((tetrahydro-2H-pyran-4-yl)amino)-9H-purin-9-yl)cyclohexanecarboxylic acid (1 equiv.) in DMF (0.2 M) was added DIEA (2 equiv.), HATU (1.2 equiv.) and $NH_4Cl$ (2 equiv.). The reaction was stirred at room temperature for 2 h. Standard work-up and purification methods afforded (1s,4s)-4-(8-((2,6-dichloro-4-fluorophenyl)amino)-2-((tetrahydro-2H-pyran-4-yl)amino)-9H-purin-9-yl)cyclohexanecarboxamide (30%). $^1$H NMR (400 MHz, Methanol-$d_4$) δ ppm: 8.04-7.87 (m, 1H), 7.48-7.18 (m, 2H), 4.53-4.34 (m, 1H), 4.08-3.91 (m, 3H), 3.74-3.61 (m, 2H), 2.97-2.77 (m, 2H), 2.70-2.62 (m, 1H), 2.38-2.26 (m, 2H), 2.06-1.96 (m, 2H), 1.88-1.71 (m, 4H), 1.63-1.48 (m, 2H). MS (ESI) m/z=522.2 $[M+H]^+$.

Example 21. (1s,4s)-4-(8-((2,6-Difluorophenyl) amino)-2-((tetrahydro-2H-pyran-4-yl)amino)-9H-purin-9-yl)-1-methylcyclohexane-1-carboxamide

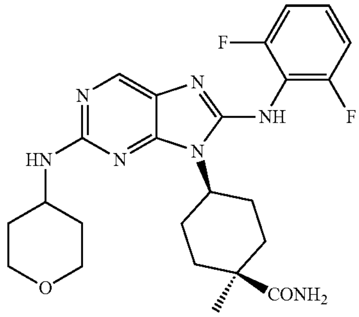 [SMILES: C[C@]1(C(N)=O)CC[C@@H](n2c(Nc3c(F)cccc3F)nc3cnc(NC4CCOCC4)nc32)CC1]

cis-Ethyl 4-(8-((2,6-Difluorophenyl)amino)-2-((tetrahydro-2H-pyran-4-yl)amino)-9H-purin-9-yl)-1-methylcyclohexanecarboxylate To a solution of ethyl (1s,4s)-4-((5-amino-2-((tetrahydro-2H-pyran-4-yl)amino)pyrimidin-4-yl)amino)-1-methylcyclohexane-1-carboxylate (prepared as described herein) (1 equiv.) in anhydrous DMF (0.36 M) was added 1,3-difluoro-2-isothiocyanatobenzene (1 equiv.). The mixture was stirred at room temperature for 90 min. DIC (2 equiv.) was added and stirring was continued at room temperature. The reaction was diluted with water, and extracted with ethyl acetate. The combined extracts were evaporated. The residue was purified by column chromatography to afford cis-ethyl 4-(8-((2,6-difluorophenyl)amino)-2-((tetrahydro-2H-pyran-4-yl) amino)-9H-purin-9-yl)-1-methylcyclohexanecarboxylate (80%) as a yellow solid. MS (ESI) m/z=515.3 $[M+H]^+$.

(1s,4s)-4-(8-((2,6-Difluorophenyl)amino)-2-((tetrahydro-2H-pyran-4-yl)amino)-9H-purin-9-yl)-1-methylcyclohexane-1-carboxylic acid To cis-ethyl 4-(8-((2,6-difluorophenyl)amino)-2-((tetrahydro-2H-pyran-4-yl)amino)-9H-purin-9-yl)-1-methylcyclohexanecarboxylate (1 equiv.) in MeOH/water (0.1 M, 3/1) was added KOH (7 equiv.). The reaction was refluxed for 72 h. The reaction was concentrated, diluted with water, and extracted with ethyl acetate. The aqueous layer was acidified with 6 M HCl to pH=3-5, and extracted with ethyl acetate. The combined extracts were evaporated to afford (1s,4s)-4-(8-((2,6-difluorophenyl)amino)-2-((tetrahydro-2H-pyran-4-yl)amino)-9H-purin-9-yl)-1-methylcyclohexane-1-carboxylic acid (67%) as a yellow solid, which was used directly into the next step without further purification.

To a solution of (1s,4s)-4-(8-((2,6-difluorophenyl) amino)-2-((tetrahydro-2H-pyran-4-yl)amino)-9H-purin-9-yl)-1-methylcyclohexane-1-carboxylic acid (1 equiv.) in DMF (0.3 M) were added HATU (2 equiv.), TEA (2 equiv.) and $NH_4Cl$ (2 equiv.). The reaction was stirred at room temperature overnight. Standard work-up and purification methods afforded (1s,4s)-4-(8-((2,6-difluorophenyl)amino)-2-((tetrahydro-2H-pyran-4-yl)amino)-9H-purin-9-yl)-1-methylcyclohexane-1-carboxamide (88%). $^1H$ NMR (400 MHz, Methanol-$d_4$) δ ppm: 8.00 (br. s., 1H), 7.45-6.92 (m, 3H), 4.37 (br. s., 1H), 4.07-3.93 (m, 3H), 3.72 (t, J=10.7 Hz, 2H), 2.79 (d, J=12.0 Hz, 2H), 2.41 (d, J=13.1 Hz, 2H), 2.04 (d, J=13.7 Hz, 2H), 1.84 (d, J=11.0 Hz, 2H), 1.65-1.53 (m, 2H), 1.46 (dt, J=3.1, 13.8 Hz, 2H), 1.26 (s, 3H). MS (ESI) m/z=486.2 $[M+H]^+$.

Example 22. (1s,4s)-1-Methyl-4-(2-((tetrahydro-2H-pyran-4-yl)amino)-8-((2,4,6-trifluorophenyl)amino)-9H-purin-9-yl)cyclohexane-1-carboxamide

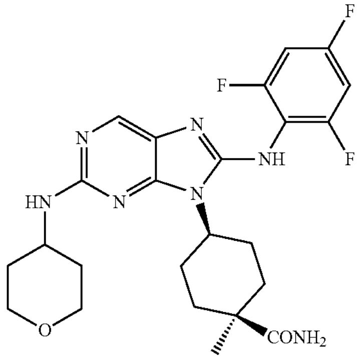 [SMILES: C[C@]1(C(N)=O)CC[C@@H](n2c(Nc3c(F)cc(F)cc3F)nc3cnc(NC4CCOCC4)nc32)CC1]

Ethyl 1,4-dioxaspiro[4.5]decane-8-carboxylate

To a solution of ethyl 4-oxocyclohexanecarboxylate (1 equiv.) in DCM (0.6 M) were added ethane-1,2-diol (2 equiv.), triethoxymethane (2 equiv.) and pTSA (0.05 equiv.). The reaction was stirred at room temperature overnight. The reaction was concentrated in vacuum. The resulting residue was diluted with petroleum/ethyl acetate, filtered through a pad of silica gel. The filtrate was concentrated to give ethyl 1,4-dioxaspiro[4.5]decane-8-carboxylate (100%). $^1H$ NMR (400 MHz, $CDCl_3$) δ ppm: 4.11 (q, J=7.2 Hz, 2H), 3.93 (s, 4H), 2.37-2.26 (m, 1H), 1.98-1.87 (m, 2H), 1.85-1.71 (m, 4H), 1.59-1.48 (m, 2H), 1.22 (t, J=7.2 Hz, 3H).

Ethyl 8-methyl-1,4-dioxaspiro[4.5]decane-8-carboxylate

To a cooled (0° C.) solution of DIA (1.2 equiv.) in anhydrous THF (1 M) was added n-BuLi (1.6 equiv.) dropwise for 20 min. The mixture was stirred for 30 min at 0° C. and then cooled to −78° C. A solution of ethyl 1,4-dioxaspiro[4.5]decane-8-carboxylate (1 equiv.) in THF (1 M) was added dropwise for 30 min, followed by iodomethane (3 equiv.). The reaction mixture was stirred overnight at room temperature. The reaction was diluted with brine and extracted with ethyl acetate. The combined organic layers were washed with brine, dried over $Na_2SO_4$ and filtered. The filtrate was concentrated to give ethyl 8-methyl-1,4-dioxaspiro[4.5]decane-8-carboxylate 3 (100%). $^1H$ NMR (400 MHz, $CDCl_3$) δ ppm: 4.16 (q, J=7.1 Hz, 2H), 3.95 (s, 4H), 2.19-2.11 (m, 2H), 1.72-1.57 (m, 4H), 1.57-1.45 (m, 2H), 1.30-1.24 (m, 3H), 1.20 (s, 3H).

Ethyl 1-methyl-4-oxocyclohexane-1-carboxylate

To a solution of ethyl 8-methyl-1,4-dioxaspiro[4.5]decane-8-carboxylate (1 equiv.) in acetone/$H_2O$ (0.5 M, 1/1) was added pTSA.$H_2O$ (1 equiv.). The mixture was refluxed overnight, then concentrated to remove acetone. The resulting solution was diluted with ethyl acetate, and the layers were separated. The organic phase was washed with saturated $NaHCO_3$, dried over $Na_2SO_4$ and filtered. The filtrate was concentrated to afford ethyl 1-methyl-4-oxocyclohexanecarboxylate (67%). $^1$H NMR (400 MHz, $CDCl_3$) δ ppm: 4.23 (q, J=7.2 Hz, 2H), 2.49-2.39 (m, 4H), 2.37-2.27 (m, 2H), 1.75-1.64 (m, 2H), 1.34-1.28 (m, 6H).

Ethyl 4-(hydroxyimino)-1-methylcyclohexane-1-carboxylate

To a solution of ethyl 1-methyl-4-oxocyclohexane-1-carboxylate (1.8 g, 9.78 mmol) in $CH_3OH/H_2O$ (0.3 M, 4/1) were added $NH_2OH$—HCl (1.1 equiv.) and NaOAc (1.1 equiv). The reaction was refluxed overnight and evaporated to remove MeOH. The resulting residue was diluted with water, and extracted with ethyl acetate. The combined extracts were evaporated in vacuo. Purification of the residue by column chromatography on silica gel gave ethyl 4-(hydroxyimino)-1-methylcyclohexane-1-carboxylate (72%). $^1$H NMR (400 MHz, $CDCl_3$) δ ppm: 4.20 (q, J=7.1 Hz, 2H), 3.04 (td, J=4.5, 15.1 Hz, 1H), 2.38-2.21 (m, 4H), 2.20-2.08 (m, 1H), 1.53-1.37 (m, 2H), 1.29 (t, J=7.0 Hz, 2H), 1.24 (s, 3H).

Ethyl 4-amino-1-methylcyclohexane-1-carboxylate hydrochloride

To a solution of ethyl 4-(hydroxyimino)-1-methylcyclohexane-1-carboxylate (1 equiv.) in MeOH (0.3 M) was added Raney-Ni under $N_2$ atmosphere. The suspension was degassed under vacuum and purged with several times, and stirred at 50° C. under 50 psi of $H_2$ overnight. The reaction was filtered through a pad of celite, washed with MeOH, and treated with 4 M HCl/Dioxane. The resulting solution was evaporated under reduced pressure to afford ethyl 4-amino-1-methylcyclohexane-1-carboxylate hydrochloride (77%).

Ethyl (1r,4r)-4-((2-chloro-5-nitropyrimidin-4-yl)amino)-1-methylcyclohexane-1-carboxylate and ethyl (1s,4s)-4-((2-chloro-5-nitropyrimidin-4-yl)amino)-1-methylcyclohexane-1-carboxylate To a cooled (−78° C.) solution of 2,4-dichloro-5-nitropyrimidine (1 equiv.) and ethyl 4-amino-1-methylcyclohexane-1-carboxylate hydrochloride (1 equiv.) in anhydrous THF (0.46 M) was added DIEA (3 equiv.) dropwise over 30 min. After the addition, stirring was continued for 45 min at −78° C., then for 2 h at room temperature. The mixture was diluted with ethyl acetate, washed with brine, dried over $Na_2SO_4$, filtered and concentrated. The residue was purified to afford ethyl (1r,4r)-4-((2-chloro-5-nitropyrimidin-4-yl)amino)-1-methylcyclohexane-1-carboxylate (46%), $^1$H NMR (400 MHz, Benzene-$d_6$) δ ppm: 8.55 (s, 1H), 8.08 (d, J=6.8 Hz, 1H), 4.03 (q, J=7.1 Hz, 2H), 3.97-3.80 (m, 1H), 1.87 (ddd, J=3.8, 9.5, 13.6 Hz, 2H), 1.68-1.57 (m, 2H), 1.48-1.37 (m, 2H), 1.32-1.18 (m, 2H), 1.09 (s, 3H), 1.04 (t, J=7.1 Hz, 3H); and ethyl (1s,4s)-4-((2-chloro-5-nitropyrimidin-4-yl)amino)-1-methylcyclohexane-1-carboxylate (27%), $^1$H NMR (400 MHz, Benzene-$d_6$) δ ppm: 8.44 (s, 1H), 7.85 (d, J=7.0 Hz, 1H), 4.00-3.90 (m, 2H), 3.79 (tdt, J=4.0, 7.7, 11.6 Hz, 1H), 2.19-2.07 (m, 2H), 1.76-1.65 (m, 2H), 1.36-1.22 (m, 2H), 0.98 (s, 2H), 0.95-0.90 (m, 2H), 0.85 (dt, J=3.6, 13.4 Hz, 1H).

Ethyl (1s,4s)-1-methyl-4-((5-nitro-2-((tetrahydro-2H-pyran-4-yl)amino)pyrimidin-4-yl)amino)cyclohexane-1-carboxylate To a solution of ethyl (1s,4s)-4-((2-chloro-5-nitropyrimidin-4-yl)amino)-1-methylcyclohexane-1-carboxylatecarboxylate (1.0 equiv.) in anhydrous DMF (0.4 M) were added tetrahydro-2H-pyran-4-amine hydrochloride (1.2 equiv.) and DIEA (3 equiv.). The mixture was stirred at room temperature for 3 h. The reaction was diluted with ethyl acetate, the organic layer was washed with brine, dried over $Na_2SO_4$, filtered and concentrated. The resulting residue was slurried with ethyl acetate and filtered to afford ethyl (1s,4s)-1-methyl-4-((5-nitro-2-((tetrahydro-2H-pyran-4-yl)amino)pyrimidin-4-yl)amino)cyclohexane-1-carboxylate (80%). MS (ESI) m/z=408.1 $[M+H]^+$.

Ethyl (1s,4s)-4-((5-amino-2-((tetrahydro-2H-pyran-4-yl)amino)pyrimidin-4-yl)amino)-1-methylcyclohexane-1-carboxylate To a solution of ethyl (1s,4s)-1-methyl-4-((5-nitro-2-((tetrahydro-2H-pyran-4-yl)amino)pyrimidin-4-yl)amino)cyclohexane-1-carboxylate (1 equiv.) in MeOH (0.1 M) was added Pd/C (0.1 g, 10% Pd by wt.) under $N_2$. The suspension was degassed under vacuum and purged with hydrogen. The suspension was stirred under hydrogen balloon at room temperature for 3 h. The reaction was filtered through a pad of celite, and washed with MeOH. The filtrate was concentrated to afford ethyl (1s,4s)-4-((5-amino-2-((tetrahydro-2H-pyran-4-yl)amino)pyrimidin-4-yl)amino)-1-methylcyclohexane-1-carboxylate (100%).

Ethyl (1s,4s)-1-methyl-4-(2-((tetrahydro-2H-pyran-4-yl)amino)-8-((2,4,6-trifluorophenyl)amino)-9H-purin-9-yl)cyclohexane-1-carboxylate To a solution of ethyl (1s,4s)-4-((5-amino-2-((tetrahydro-2H-pyran-4-yl)amino)pyrimidin-4-yl)amino)-1-methylcyclohexane-1-carboxylate (1 equiv.) in anhydrous DMF (0.36 M) was added 1,3,5-trifluoro-2-isothiocyanatobenzene (1 equiv.), and the reaction was stirred at room temperature for 90 min. DIC (2 equiv.) was added and stirring was continued at room temperature. The reaction was diluted with water, and extracted with ethyl acetate. The combined extracts were evaporated. The resulting residue was purified by column chromatography to afford ethyl (1s,4s)-1-methyl-4-(2-((tetrahydro-2H-pyran-4-yl)amino)-8-((2,4,6-trifluorophenyl)amino)-9H-purin-9-yl)cyclohexane-1-carboxylate (49%). MS (ESI) m/z=533.3 $[M+H]^+$.

(1s,4s)-1-Methyl-4-(2-((tetrahydro-2H-pyran-4-yl)amino)-8-((2,4,6-trifluorophenyl)amino)-9H-purin-9-yl)cyclohexane-1-carboxylic acid To ethyl (1s,4s)-1-methyl-4-(2-((tetrahydro-2H-pyran-4-yl)amino)-8-((2,4,6-trifluorophenyl)amino)-9H-purin-9-yl)cyclohexane-1-carboxylate (1 equiv.) in $MeOH/H_2O$ (0.1 M, 4/1) was added KOH (8 equiv.). The reaction was refluxed for 72 h. The reaction was concentrated, diluted with water, and extracted with ethyl acetate. The aqueous layer was acidified with 6 M HCl to pH=3-5, and extracted with ethyl acetate. The combined extracts were evaporated under reduced pressure to afford (1s,4s)-1-methyl-4-(2-((tetrahydro-2H-pyran-4-yl)amino)-8-((2,4,6-trifluorophenyl)amino)-9H-purin-9-yl)cyclohexane-1-carboxylic acid (70%).

(1s,4s)-1-Methyl-4-(2-((tetrahydro-2H-pyran-4-yl)amino)-8-((2,4,6-trifluorophenyl)amino)-9H-purin-9-yl)cyclohexane-1-carboxamide To a solution of (1s,4s)-1-methyl-4-(2-((tetrahydro-2H-pyran-4-yl)amino)-8-((2,4,6-trifluorophenyl)amino)-9H-purin-9-yl)cyclohexane-1-carboxylic acid (1 equiv.) in DMF (0.2 M) were added HATU (2 equiv.), TEA (2 equiv.) and $NH_4Cl$ (2 equiv.). The reaction was stirred at room temperature overnight. Standard work-up and purification methods afforded (1s,4s)-1-Methyl-4-(2-((tetrahydro-2H-pyran-4-yl) amino)-8-((2,4,6-trifluorophenyl)amino)-9H-purin-9-yl)cyclohexane-1-carboxamide (56%). $^1$H NMR (400 MHz, Methanol-$d_4$) δ ppm: 8.01 (s, 1H), 7.02 (s, 2H), 4.33 (s, 1H), 4.08-3.93 (m, 3H), 3.72 (t, J=11.2 Hz, 2H), 2.91-2.66 (m, 2H), 2.43-2.40 (m, 2H), 2.05-2.01 (m, 2H), 1.85-1.82 (m, 2H), 1.65-1.53 (m, 2H), 1.46-1.43 (m, 2H), 1.26 (s, 3H). MS (ESI) m/z=504.2 $[M+H]^+$.

Example 23. (1s,4s)-4-(8-((2,4-Dichloro-6-fluorophenyl)amino)-2-((tetrahydro-2H-pyran-4-yl)amino)-9H-purin-9-yl)cyclohexane-1-carboxamide

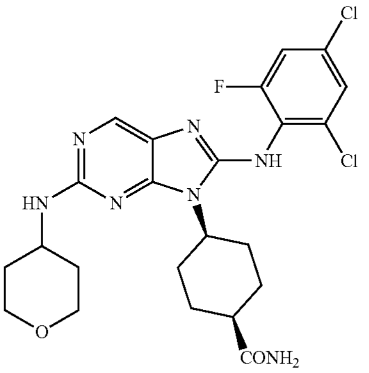 [SMILES: NC(=O)[C@H]1CC[C@@H](n2c(Nc3c(F)cc(Cl)cc3Cl)nc3cnc(NC4CCOCC4)nc32)CC1]

2,4-Dichloro-6-fluoro-aniline

To a solution of 2-fluoroaniline (1 equiv.) in MeOH (0.9 M) was added NCS (1 equiv.) in portions at 65° C. under $N_2$. The mixture was stirred at this temperature for 60 min. The mixture was evaporated to remove MeOH, diluted with ethyl acetate and filtered to afford the crude product. Purification via silica gel chromatography provided product. Trituration of the material with petroleum ether at 0° C. yielded 2,4-dichloro-6-fluoro-aniline (36%). $^1$H NMR (400 MHz, $CDCl_3$) δ ppm: 7.07 (s, 1H), 6.94-6.97 (m, 1H), 4.06 (s, 2H).

1,5-Dichloro-3-fluoro-2-isothiocyanatobenzene

To a solution of 2,4-dichloro-6-fluoro-aniline (1 equiv.) in anhydrous toluene (0.76 M) was added a catalytic amount of DMF (0.05 equiv.) and thiocarbonyl dichloride (2.5 equiv.) drop-wise over 10 min under nitrogen. The mixture was slowly heated at 90-100° C. for 2 h. After 2 h, the reaction was complete. The mixture was filtered and the filtrate was concentrated to give crude product, which was purified by silica gel column chromatography to give 1,5-dichloro-3-fluoro-2-isothiocyanato-benzene (66%). $^1$H NMR (400 MHz, $CDCl_3$) δ ppm: 7.25-7.28 (m, 1H), 7.11 (d, J=2.0 Hz, 1H).

Methyl (1s,4s)-4-((5-(3-(2,4-dichloro-6-fluorophenyl)thioureido)-2-((tetrahydro-2H-pyran-4-yl)amino) pyrimidin-4-yl)amino)cyclohexane-1-carboxylate To a solution of ethyl (1s,4s)-4-((5-amino-2-((tetrahydro-2H-pyran-4-yl)amino)pyrimidin-4-yl)amino)-1-methylcyclohexane-1-carboxylate (1 equiv.) (prepared as described herein) in DMF (0.28 M) was added 1,5-dichloro-3-fluoro-2-isothiocyanatobenzene (1.1 equiv.). The reaction was stirred at 25° C. for 2 h. The mixture was used directly in the next step without further purification. DIC (2 equiv.) was added to the reaction mixture and stirring was continued at 40° C. for 16 h. LCMS showed the reaction was complete. To the mixture was added brine, and the precipitate was filtered. The filter cake was crystallized with ethyl acetate to give (1s,4s)-methyl 4-(8-((2,4-dichloro-6-fluorophenyl) amino)-2-((tetrahydro-2H-pyran-4-yl)amino)-9H-purin-9-yl)cyclohexanecarboxylate (65%) as a white solid. $^1$H NMR (400 MHz, Methanol-$d_4$) δ ppm: 8.01 (s, 1H), 7.62-7.13 (m, 2H), 4.57-4.28 (m, 1H), 4.12-4.02 (m, 1H), 4.02-3.94 (m, 2H), 3.78 (s, 3H), 3.76-3.64 (m, 2H), 2.89-2.63 (m, 3H), 2.42-2.28 (m, 2H), 2.07-1.94 (m, 2H), 1.89-1.67 (m, 4H), 1.63-1.49 (m, 2H). MS (ESI) m/z=537.2 $[M+H]^+$.

(1s,4s)-4-(8-((2,4-Dichloro-6-fluorophenyl)amino)-2-((tetrahydro-2H-pyran-4-yl)amino)-9H-purin-9-yl) cyclohexanecarboxylic acid To a mixture of (1s,4s)-methyl 4-(8-((2,4-dichloro-6-fluorophenyl)amino)-2-((tetrahydro-2H-pyran-4-yl)amino)-9H-purin-9-yl)cyclohexanecarboxylate (1 equiv.) in THF/water (5/1, 0.5 M) was added LiOH (5 equiv.). The reaction was stirred at 60° C. for 16 h. Water was added to the mixture and the pH was adjusted to 6 by addition of 1N HCl, then the mixture was concentrated to give crude product which was used directly in next step without further purification. MS (ESI) m/z=523.1 $[M+H]^+$.

(1s,4s)-4-(8-((2,4-Dichloro-6-fluorophenyl)amino)-2-((tetrahydro-2H-pyran-4-yl)amino)-9H-purin-9-yl) cyclohexanecarboxamide To a solution of (1s,4s)-4-(8-((2,4-dichloro-6-fluorophenyl)amino)-2-((tetrahydro-2H-pyran-4-yl)amino)-9H-purin-9-yl)cyclohexanecarboxylic acid (1 equiv.) in DMF (1.2 M) was added DIEA (2 equiv.), HATU (436 mg, 1.15 mmol) and $NH_4Cl$ (1.2 equiv.). The reaction was stirred at room temperature for 2 h. Standard work-up and purification methods afforded (1s,4s)-4-(8-((2,4-dichloro-6-fluorophenyl)amino)-2-((tetrahydro-2H-pyran-4-yl)amino)-9H-purin-9-yl)cyclohexanecarboxamide (16%). $^1$H NMR (400 MHz, Methanol-$d_4$) δ ppm: 10.32 (brs, 1H), 7.61 (s, 1H), 7.48-7.37 (m, 1H), 7.27-7.14 (m, 1H), 6.77-6.66 (m, 1H), 6.57-6.45 (m, 1H), 4.45-4.30 (m, 1H), 3.92-3.76 (m, 3H), 3.61-3.44 (m, 2H), 2.71-2.55 (m, 2H), 2.45-2.39 (m, 1H), 2.27-2.16 (m, 2H), 1.90-1.77 (m, 2H), 1.72-1.36 (m, 6H). MS (ESI) m/z=522.2 $[M+H]^+$.

Example 24. (1s,4s)-4-(8-((2-Chloro-3-methylphenyl)amino)-2-((tetrahydro-2H-pyran-4-yl)amino)-9H-purin-9-yl)cyclohexane-1-carboxamide

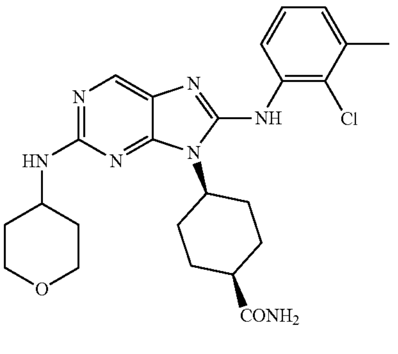 [SMILES: Cc1cccc(Nc2nc3cnc(NC4CCOCC4)nc3n2[C@H]2CC[C@@H](C(N)=O)CC2)c1Cl]

2-Chloro-3-methylaniline

To 2-chloro-1-methyl-3-nitrobenzene (1 equiv.) in acetic acid (0.5M) was added Fe (4 equiv.). The reaction was heated at 100° C. for 2 h. The solvent was removed and MeOH was added to the residue. The mixture was stirred at room temperature for 12 h then filtered. The filtrate was concentrated and purified by silica gel chromatography to give 2-chloro-3-methylaniline (60%) as a red oil. $^1$H NMR (400 MHz, DMSO-$d_6$) δ ppm: 6.90 (t, J=7.7 Hz, 1H), 6.66 (d, J=7.9 Hz, 1H), 6.50 (d, J=7.4 Hz, 1H), 5.23 (brs, 2H), 2.24 (s, 3H).

2-Chloro-1-isothiocyanato-3-methylbenzene

To 2-chloro-3-methylaniline (1 equiv.) in DCM/water (0.5 M, 1/2) at 0° C. was added NaOH (3 equiv.), the solution was stirred at 0° C. for 5 min, then $CSCl_2$ (3 equiv.) was added. The reaction was stirred at room temperature overnight. The reaction was extracted with DCM. The combined organic layers were concentrated to dryness to give crude 2-chloro-1-isothiocyanato-3-methylbenzene. The crude product was purified by column chromatography on silica gel with petroleum ether to give 2-chloro-1-isothiocyanato-3-methylbenzene (61%) as a colorless oil. $^1$H NMR (400 MHz, $CDCl_3$) δ ppm: 7.19-7.09 (m, 3H), 2.42 (s, 3H).

cis-4-(8-((2-Chloro-3-methylphenyl)amino)-2-((tetrahydro-2H-pyran-4-yl)amino)-9H-purin-9-yl)cyclohexanecarboxamide To a solution of (1s,4s)-4-((5-amino-2-((tetrahydro-2H-pyran-4-yl)amino)pyrimidin-4-yl)amino)cyclohexane-1-carboxamide (1 equiv.) (prepared as described herein) in DMF (0.3 M) was added 2-chloro-1-isothiocyanato-3-methylbenzene (1.1 equiv.). The reaction was stirred for 2 h at room temperature, and then DIC (3 equiv.) was added, and the reaction was stirred at room temperature overnight. Standard work-up and purification methods afforded (1s,4s)-4-(8-((2-chloro-3-methylphenyl)amino)-2-((tetrahydro-2H-pyran-4-yl)amino)-9H-purin-9-yl)cyclohexane-1-carboxamide (58%). $^1$H NMR (400 MHz, Methanol-$d_4$) δ ppm: 8.07 (s, 1H), 7.48-7.34 (m, 1H), 7.24 (t, J=7.7 Hz, 1H), 7.16 (d, J=7.4 Hz, 1H), 4.38 (t, J=11.8 Hz, 1H), 4.10-3.94 (m, 3H), 3.77-3.65 (m, 2H), 2.96-2.81 (m, 2H), 2.71-2.63 (m, 1H), 2.44 (s, 3H), 2.34 (d, J=13.4 Hz, 2H), 2.05 (d, J=10.5 Hz, 2H), 1.88-1.72 (m, 4H), 1.65-1.52 (m, 2H). MS (ESI) m/z=484.2 $[M+H]^+$.

Example 25. (1s,4s)-4-(8-((4-Chloro-2-fluoro-5-methylphenyl)amino)-2-((tetrahydro-2H-pyran-4-yl)amino)-9H-purin-9-yl)cyclohexane-1-carboxamide

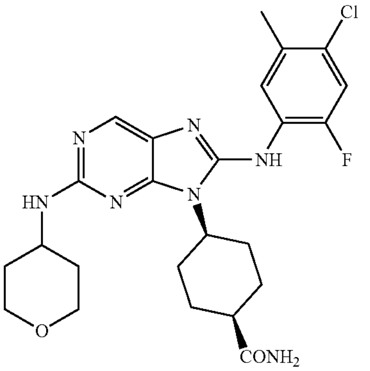 [SMILES: Cc1cc(Nc2nc3cnc(NC4CCOCC4)nc3n2[C@H]2CC[C@@H](C(N)=O)CC2)c(F)cc1Cl]

1-Chloro-5-fluoro-2-methyl-4-nitrobenzene

To a cooled (−5° C.) solution of 2-fluoro-5-methylaniline (1 equiv.) in concentrated $H_2SO_4$ (0.7 M) was added $KNO_3$ (1.3 equiv.) in several portions within 1 h. The reaction was allowed to warm to room temperature and stirred overnight. The reaction mixture was poured into ice-water slowly, and extracted with MTBE, washed with saturated $NaHCO_3$ and brine, dried over $Na_2SO_4$, filtered and concentrated. The resulted residue was recrystallized from ethyl acetate and petroleum ether to afford 1-chloro-5-fluoro-2-methyl-4-nitrobenzene (61%) as a yellow solid. $^1$H NMR (400 MHz, $CDCl_3$) δ ppm: 8.00 (d, J=8.0 Hz, 1H), 7.35 (d, J=10.4 Hz, 1H), 2.45 (s, 3H).

4-Chloro-2-fluoro-5-methylaniline

To a suspension of 1-chloro-5-fluoro-2-methyl-4-nitrobenzene (1 equiv) in EtOH (2 M) was added Fe (5 equiv.), followed by concentrated HCl (2 M). The reaction was refluxed for 3 h. The reaction was filtered through a pad of celite. The filtrate was concentrated. The resulting residue was purified by column chromatography to afford 4-chloro-2-fluoro-5-methylaniline (32%) as a purple solid. $^1$H NMR (400 MHz, $CDCl_3$) δ ppm: 7.41 (d, J=7.03 Hz, 1H), 6.97-7.13 (m, 2H), 2.33 (s, 3H).

1-Chloro-5-fluoro-4-isothiocyanato-2-methylbenzene

To a cooled solution of 4-chloro-2-fluoro-5-methylaniline 3 (1.0 g, 6.3 mmol) in DCM/$H_2O$ (0.6 M, 1/1) was added NaOH (3 equiv.), followed by dropwise addition of $SCCl_2$ (3 equiv.) for 10 min. After the addition, the mixture was stirred for 60 min at room temperature. The filtrate was concentrated to afford 1-chloro-5-fluoro-4-isothiocyanato-2-methylbenzene (75%) as a colorless oil.

cis-4-(8-((5-Chloro-2-fluoro-4-methylphenyl)amino)-2-((tetrahydro-2H-pyran-4-yl)amino)-9H-purin-9-yl)cyclohexanecarboxamide To a solution of cis-4-((5-amino-2-((tetrahydro-2H-pyran-4-yl)amino)pyrimidin-4-yl)amino)cyclohexanecarboxamide (1 equiv.) (prepared as described herein) in anhydrous DMF (0.3 M) was added 1-chloro-5-fluoro-4-isothiocyanato-2-methylbenzene (1 equiv.), and the solution was stirred at room temperature for 90 min. DIC (3 equiv.) was added and stirring was continued at room temperature for 12 h. Standard work-up and purification methods afforded cis-4-(8-((5-chloro-2-fluoro-4-methylphenyl)amino)-2-((tetrahydro-2H-pyran-4-yl)amino)-9H-purin-9-yl)cyclohexanecarboxamide (58%). $^1$H NMR (400 MHz, Methanol-$d_4$) δ ppm: 8.09 (s, 1H), 7.55 (d, J=9.5 Hz, 1H), 7.27 (d, J=10.0 Hz, 1H), 4.34 (d, J=15.6 Hz, 1H), 4.11-3.91 (m, 3H), 3.80-3.63 (m, 2H), 2.98-2.80 (m, 2H), 2.67 (s, 1H), 2.46-2.26 (m, 5H), 2.12-1.93 (m, 2H), 1.88-1.67 (m, 4H), 1.66-1.38 (m, 2H). MS (ESI) m/z=502.2 $[M+H]^+$.

Example 26. (1s,4s)-4-(8-((4-Chloro-2-fluoro-6-methylphenyl)amino)-2-((tetrahydro-2H-pyran-4-yl)amino)-9H-purin-9-yl)cyclohexane-1-carboxamide

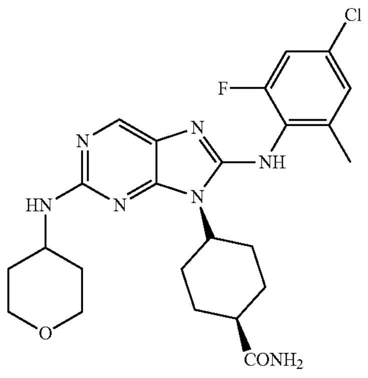

4-Chloro-2-fluoro-6-methylaniline

To a solution of 2-fluoro-6-methylaniline (1 equiv.) in DMF (0.8 M) was added NCS (1.2 equiv.). The reaction was stirred at room temperature. Water and ethyl acetate were added to the solution and the layers were separated. The organic layer was washed with $H_2O$, dried with $Na_2SO_4$ and concentrated. The resulting residue was purified by column chromatography on silica gel to give 4-chloro-2-fluoro-6-methylaniline (58%) as a brown oil. $^1$H NMR (400 MHz, DMSO-$d_6$) δ ppm: 10.33 (dd, J=10.8, 2.0 Hz, 1H), 6.87 (s, 1H), 4.53 (brs. 2H), 2.11 (s, 3H).

5-Chloro-1-fluoro-2-isothiocyanato-3-methylbenzene

To a solution of 4-chloro-2-fluoro-6-methylaniline (1 equiv.) in DCM/water (0.8 M, 1/2) at 0° C. was added NaOH (3 equiv.). The solution was stirred at 0° C. for 5 min and $CSCl_2$ (2 equiv.) was added. The reaction was stirred at room temperature for 3 h. The mixture was filtered through a pad of silica gel and the pad was washed with DCM. The combined filtrates were concentrated to dryness to give 5-chloro-1-fluoro-2-isothiocyanato-3-methylbenzene (43%) as brown oil. $^1$H NMR (400 MHz, DMSO-$d_6$) δ ppm: 7.52 (dd, J=9.2, 2.4 Hz, 1H), 2.35 (s, 3H).

(1s,4s)-4-(8-((4-Chloro-2-fluoro-6-methylphenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexane-1-carboxamide (1 equiv.) (prepared as described herein) in DMF (0.3 M) was added 5-chloro-1-fluoro-2-isothiocyanato-3-methylbenzene (1.1 equiv.). The reaction was stirred at room for 2 h then DIC (3 equiv.) was added. The reaction was stirred at room temperature overnight. Standard work-up and purification methods afforded cis-4-(8-((4-chloro-2-fluoro-6-methylphenyl)amino)-2-((tetrahydro-2H-pyran-4-yl)amino)-9H-purin-9-yl)cyclohexanecarboxamide (30%). $^1$H NMR (400 MHz, Methanol-$d_4$) δ ppm: 8.01-7.93 (m, 1H), 7.24-7.12 (m, 2H), 4.50-4.33 (m, 1H), 4.10-3.95 (m, 3H), 3.75-3.65 (m, 2H), 2.98-2.83 (m, 2H), 2.72-2.65 (m, 1H), 2.34 (d, J=14.1 Hz, 2H), 2.27 (s, 3H), 2.06-1.99 (m, 2H), 1.82 (d, J=11.2 Hz, 4H), 1.64-1.50 (m, 2H). MS (ESI) m/z=502.2 $[M+H]^+$.

Example 27. (1s,4s)-4-(8-((2,3-Dichloro-4-methylphenyl)amino)-2-((tetrahydro-2H-pyran-4-yl)amino)-9H-purin-9-yl)cyclohexane-1-carboxamide

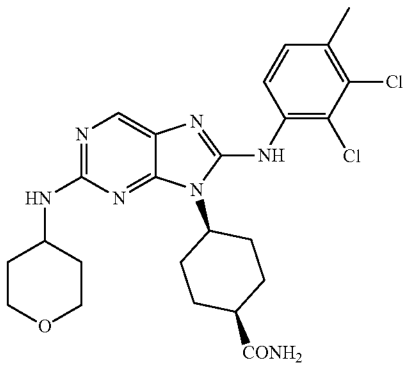 [SMILES: Cc1ccc(Nc2nc3cnc(NC4CCOCC4)nc3n2[C@H]2CC[C@@H](C(N)=O)CC2)c(Cl)c1Cl]

2,3-Dichloro-4-methylaniline

To a solution of 3-chloro-4-methylaniline (1 equiv.) in DMF (0.7 M) at 0° C. was added NCS (1 equiv.) in DMF dropwise. The reaction was stirred at room temperature overnight. Water and ethyl acetate was added to the solution and the layers were separated. The organic layer was washed with $H_2O$, dried over $Na_2SO_4$ and concentrated. The resulting residue was purified by column chromatography on silica gel to give 2,3-dichloro-4-methylaniline (26%). $^1$H NMR (400 MHz, DMSO-$d_6$) δ ppm: 6.98 (d, J=8.4 Hz, 1H), 6.69 (d, J=8.4 Hz, 1H), 5.41 (brs. 2H), 2.20 (s, 3H). and 2,5-dichloro-4-methylaniline (16%). $^1$H NMR (400 MHz, DMSO-$d_6$) δ ppm: 7.17 (s, 1H), 6.85 (s, 1H), 5.38 (brs. 2H), 2.15 (s, 3H).

2,3-Dichloro-1-isothiocyanato-4-methylbenzene

To a solution of 2,3-dichloro-4-methylaniline (500 mg, 2.86 mmol) in DCM/water (0.4 M, 1/2) at 0° C. was added NaOH (3 equiv.) and $H_2O$ (4 mL). The solution was stirred at 0° C. for 5 min then $CSCl_2$ (3 equiv.) was added. The reaction was stirred at room temperature for 3 h. The mixture was filtered through a pad of celite and the pad was washed with DCM. The combined filtrates were concentrated to dryness to give crude 2,3-dichloro-1-isothiocyanato-4-methylbenzene. The crude product was purified by silica gel chromatography to give 2,3-dichloro-1-isothiocyanato-4-methylbenzene (66%) as a colorless oil. $^1$H NMR (400 MHz, DMSO-$d_6$) δ ppm: 7.48-7.40 (m, 2H), 2.40 (s, 3H).

(1s,4s)-4-(8-((2,3-Dichloro-4-methylphenyl)amino)-2-((tetrahydro-2H-pyran-4-yl)amino)-9H-purin-9-yl) cyclohexane-1-carboxamide To a solution (1s,4s)-4-((5-amino-2-((tetrahydro-2H-pyran-4-yl)amino)pyrimidin-4-yl)amino)cyclohexane-1-carboxamide (1 equiv.) (prepared as described herein) in DMF (0.3 M) was added 2,3-dichloro-1-isothiocyanato-4-methylbenzene (1.1 equiv.). The reaction was stirred at room temperature for 2 h. DIC (2 equiv.) was added and the reaction was stirred at room temperature overnight. Standard work-up and purification methods afforded (1s,4s)-4-(8-((2,3-Dichloro-4-methylphenyl)amino)-2-((tetrahydro-2H-pyran-4-yl)amino)-9H-purin-9-yl)cyclohexane-1-carboxamide (38%). $^1$H NMR (400 MHz, Methanol-$d_4$) δ ppm: 8.07 (s, 1H), 7.43 (d, J=8.0 Hz, 1H), 7.30 (d, J=8.0 Hz, 1H), 4.43-4.30 (m, 1H), 4.10-3.94 (m, 3H), 3.71 (t, J=10.9 Hz, 2H), 2.96-2.81 (m, 2H), 2.72-2.64 (m, 1H), 2.45 (s, 3H), 2.39-2.29 (m, 2H), 2.04 (d, J=11.4 Hz, 2H), 1.88-1.72 (m, 4H), 1.65-1.52 (m, 2H). MS (ESI) m/z=518.2 [M+H]$^+$.

Example 28. (1s,4s)-4-(8-((4-chloro-2-fluoro-3-methylphenyl)amino)-2-((tetrahydro-2H-pyran-4-yl) amino)-9H-purin-9-yl)cyclohexane-1-carboxamide

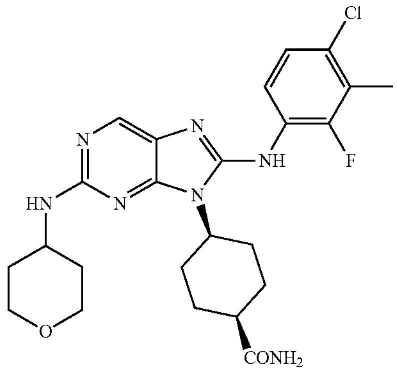 [SMILES: Cc1c(Cl)ccc(Nc2nc3cnc(NC4CCOCC4)nc3n2[C@H]2CC[C@@H](C(N)=O)CC2)c1F]

4-Chloro-2-fluoro-3-methylaniline

To a solution of 2-fluoro-3-methylaniline (1 equiv.) in DMF (0.8 M) was added NCS (1 equiv.). The reaction was stirred at room temperature overnight. Water and ethyl acetate was added to the solution and the layers were separated. The organic layer was washed with $H_2O$, dried over $Na_2SO_4$ and concentrated. The resulting residue was purified by column chromatography on silica gel to give 4-chloro-2-fluoro-3-methylaniline (22%) as yellow oil. $^1$H NMR (400 MHz, $CDCl_3$) δ ppm: 6.92 (dd, J=1.2, 8.4 Hz, 1H), 6.61 (t, J=9.2 Hz, 1H), 5.20 (s, 2H), 2.18 (d, J=2.5 Hz, 3H).

1-Chloro-2-fluoro-4-isothiocyanato-3-methylbenzene

To a solution of 4-chloro-2-fluoro-3-methylaniline (1 equiv.) in DCM/water (0.3 M, 1/2) at 0° C. was added NaOH (7 equiv.). The solution was stirred at 0° C. for 5 min. $CSCl_2$ (7 equiv.) was added. The reaction was stirred at room temperature for 3 h. The mixture was filtered through a pad of silica gel and the pad was washed with DCM. The combined filtrates were concentrated to dryness to give 1-chloro-2-fluoro-4-isothiocyanato-3-methylbenzene (91%) as brown oil. $^1$H NMR (400 MHz, $CDCl_3$) δ ppm: 7.38-7.34 (m, 2H), 2.28 (d, J=2.4 Hz, 3H).

(1s,4s)-4-(8-((4-chloro-2-fluoro-3-methylphenyl) amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexane-1-carboxamide (1 equiv.) (prepared as described herein) in DMF (0.4 M) was added 1-chloro-2-fluoro-4-isothiocyanato-3-methylbenzene (1.1 equiv.). The reaction was stirred at room temperature for 2 hours then DIC (3 equiv.) was added. The reaction was stirred at room temperature overnight. Standard work-up and purification methods afforded (1s,4s)-4-(8-((4-chloro-2-fluoro-3-methylphenyl)amino)-2-((tetrahydro-2H-pyran-4-yl)amino)-9H-purin-9-yl)cyclohexane-1-carboxamide (40%). $^1$H NMR (400 MHz, Methanol-$d_4$) δ ppm: 8.08 (s, 1H), 7.43 (t, J=8.4 Hz, 1H), 7.22 (d, J=8.8 Hz, 1H), 4.43-4.28 (m, 1H), 4.11-3.93 (m, 3H), 3.78-3.65 (m, 2H), 2.98-2.78 (m, 2H), 2.73-2.63 (m, 1H), 2.40-2.27 (m, 5H), 2.04 (d, J=10.4 Hz, 2H), 1.85-1.70 (m, 4H), 1.66-1.50 (m, 2H). MS (ESI) m/z=502.2 [M+H]$^+$.

Example 29. (1s,4s)-4-(8-((2,3-Dichloro-6-fluorophenyl)amino)-2-((tetrahydro-2H-pyran-4-yl) amino)-9H-purin-9-yl)cyclohexane-1-carboxamide

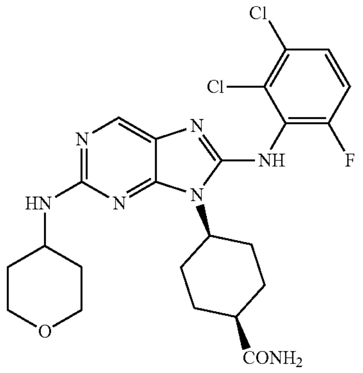 [SMILES: NC(=O)[C@H]1CC[C@@H](n2c(Nc3c(F)ccc(Cl)c3Cl)nc3cnc(NC4CCOCC4)nc32)CC1]

4-Bromo-5-chloro-2-fluoroaniline

To a mixture of 5-chloro-2-fluoroaniline (1 equiv.) in acetonitrile (0.5 M) was added N-bromosuccinimide (1 equiv.) at 25° C. The mixture was stirred at 25° C. for 1 h. The mixture was concentrated to a residue, the residue was purified via silica gel chromatography to give 4-bromo-5-chloro-2-fluoroaniline (91%) as a yellow oil. $^1$H NMR (400 MHz, $CDCl_3$) δ ppm: 7.23 (d, J=10.2 Hz, 1H), 6.88 (d, J=8.4 Hz, 1H), 3.92-2.64 (br, 2H).

4-Bromo-2,3-dichloro-6-fluoroaniline

To a mixture of 4-bromo-5-chloro-2-fluoroaniline (1 equiv.) in acetonitrile (0.36 M) was added NCS (1 equiv.) portion-wise at 90° C. over 30 min. The mixture was stirred at 90° C. for 1 h. The residue was purified by chromatography to give 4-bromo-2,3-dichloro-6-fluoroaniline (76%) as a brown solid. $^1$H NMR (400 MHz, $CDCl_3$) δ ppm: 7.35 (d, J=10.5 Hz, 1H).

2,3-Dichloro-6-fluoroaniline

To a mixture of 4-bromo-2,3-dichloro-6-fluoroaniline (1 equiv.) in THF (0.28 M) was added n-BuLi (2 equiv.) dropwise at −78° C. over 10 min. After addition, the mixture was warmed to −30° C. and stirred for 1 h, and then the mixture was cooled to −78° C. To the mixture was added $H_2O$. The mixture was warmed to 25° C., and extracted with ethyl acetate. The combined organic layers were dried over $Na_2SO_4$, filtered and concentrated to give a residue. The residue was purified by chromatography to give 2,3-dichloro-6-fluoroaniline (43%) as a yellow solid. $^1H$ NMR (400 MHz, $CDCl_3$) δ ppm: 6.93-6.85 (m, 1H), 6.83-6.76 (m, 1H), 4.23 (brs., 2H)

1,2-Dichloro-4-fluoro-3-isothiocyanatobenzene

To a mixture of 2,3-dichloro-6-fluoroaniline (1 equiv.) in DCM (0.1 M, 1/2) was added NaOH (5 equiv.) and $SCCl_2$ (3 equiv.) at 0° C. After addition, the mixture was allowed to warm to room temperature and stirred for 16 h. The mixture was filtered, and the filtrate was extracted with DCM. The combined organic layers were dried over $Na_2SO_4$, and concentrated to a residue. The residue was purified by chromatography to give 1,2-dichloro-4-fluoro-3-isothiocyanatobenzene (59%) as a yellow solid. $^1H$ NMR (400 MHz, $CDCl_3$) δ ppm: 7.05 (t, J=8.78 Hz, 1H) 7.33 (dd, J=9.03, 5.14 Hz, 1H)

cis-4-(8-((2,3-Dichloro-6-fluorophenyl)amino)-2-((tetrahydro-2H-pyran-4-yl)amino)-9H-purin-9-yl)cyclohexanecarboxamide To a solution of (1s,4s)-4-((5-amino-2-((tetrahydro-2H-pyran-4-yl)amino)pyrimidin-4-yl)amino)cyclohexane-1-carboxamide (1 equiv.) (prepared as described herein) in DMF (0.8 M) was added 1,2-dichloro-4-fluoro-3-isothiocyanatobenzene (1 equiv.). The reaction mixture was stirred at 25° C. for 1 h. DIC (2 equiv.) was added and stirring continued at 25° C. for 16 h. Standard work-up and purification methods afforded (1s,4s)-4-(8-((2,3-dichloro-6-fluorophenyl)amino)-2-((tetrahydro-2H-pyran-4-yl)amino)-9H-purin-9-yl)cyclohexane-1-carboxamide (38%). $^1H$ NMR (400 MHz, Methanol-$d_4$) δ ppm: 7.79 (s, 1H), 7.39-7.32 (m, 1H), 7.20 (t, J=9.1 Hz, 1H), 4.58-4.39 (m, 1H), 4.11-3.90 (m, 3H), 3.81-3.61 (m, 2H), 2.97-2.79 (m, 2H), 2.67 (s, 1H), 2.34 (d, J=13.8 Hz, 2H), 2.13-1.98 (m, 2H), 1.88-1.70 (m, 4H), 1.64-1.49 (m, 2H). MS (ESI) m/z=522.4 $[M+H]^+$.

Example 30. (1s,4s)-4-(8-((4-Chloro-3-fluoro-2-methylphenyl)amino)-2-((tetrahydro-2H-pyran-4-yl)amino)-9H-purin-9-yl)cyclohexane-1-carboxamide

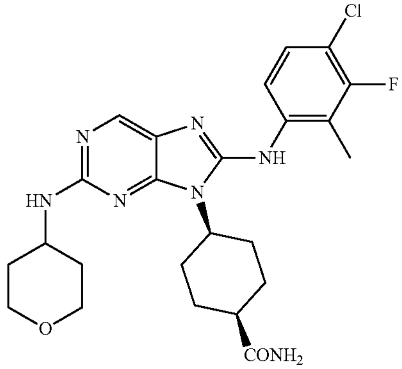 [SMILES: Cc1c(Nc2nc3cnc(NC4CCOCC4)nc3n2[C@H]2CC[C@@H](C(N)=O)CC2)ccc(Cl)c1F]

4-Chloro-3-fluoro-2-methylaniline

To a solution of 3-fluoro-2-methylaniline (1 equiv.) in DMF (0.8 M) was added NCS (1 equiv.). The reaction was stirred at room temperature overnight. Water and ethyl acetate were added to the solution and the layers were separated. The organic layer was washed with $H_2O$, dried over $Na_2SO_4$ and concentrated. The resulting residue was purified by column chromatography on silica gel to give 4-chloro-3-fluoro-2-methylaniline (12%) as a brown oil. $^1H$ NMR (400 MHz, $CDCl_3$) δ ppm: 7.02 (t, J=8.0 Hz, 1H), 6.42 (dd, J=1.6, 8.8 Hz, 1H), 3.71 (brs, 2H), 2.11 (d, J=1.6 Hz, 3H).

1-Chloro-2-fluoro-4-isothiocyanato-3-methylbenzene

To a solution of 4-chloro-3-fluoro-2-methylaniline (1 equiv.) in DCM/water (0.3 M, 1/2) at 0° C. was added NaOH (2 equiv.). The solution was stirred at 0° C. for 5 min then $CSCl_2$ (2 equiv.) was added. The reaction was stirred at room temperature for 3 h. The mixture was filtered through a pad of silica gel and the pad was washed with DCM. The combined filtrates were concentrated to dryness to give 1-chloro-2-fluoro-4-isothiocyanato-3-methylbenzene (75%) as a brown oil. $^1H$ NMR (400 MHz, $CDCl_3$) δ ppm: 7.22 (t, J=8.0 Hz, 1H), 7.00 (dd, J=1.6, 8.4 Hz, 1H), 2.35 (d, J=2.4 Hz, 3H).

(1s,4s)-4-(8-((4-Chloro-3-fluoro-2-methylphenyl)amino)-2-((tetrahydro-2H-pyran-4-yl)amino)-9H-purin-9-yl)cyclohexane-1-carboxamide To a solution of (1s,4s)-4-((5-amino-2-((tetrahydro-2H-pyran-4-yl)amino)pyrimidin-4-yl)amino)cyclohexane-1-carboxamide (1 equiv.) (prepared as described herein) in DMF (0.4 M) was added 1-chloro-2-fluoro-4-isothiocyanato-3-methylbenzene (1.1 equiv.). The reaction was stirred at room temperature for 2 h then DIC (3 equiv.) was added. The reaction was stirred at room temperature overnight. Standard work-up and purification methods afforded (1s,4s)-4-(8-((4-chloro-3-fluoro-2-methylphenyl)amino)-2-((tetrahydro-2H-pyran-4-yl)amino)-9H-purin-9-yl)cyclohexane-1-carboxamide (31%). $^1H$ NMR (400 MHz, Methanol-$d_4$) δ ppm: 8.00 (s, 1H), 7.33 (t, J=8.4 Hz, 1H), 7.18-7.05 (m, 1H), 4.44-4.30 (m, 1H), 4.11-3.91 (m, 3H), 3.79-3.64 (m, 2H), 2.98-2.82 (m, 2H), 2.73-2.63 (m, 1H), 2.34 (d, J=14.1 Hz, 2H), 2.18 (d, J=2.4 Hz, 3H), 2.09-1.98 (m, 2H), 1.87-1.72 (m, 4H), 1.65-1.50 (m, 2H). MS (ESI) m/z=502.2 $[M+H]^+$.

Example 31. (1s,4s)-4-(8-((6-Chloro-2,3-difluorophenyl)amino)-2-((tetrahydro-2H-pyran-4-yl)amino)-9H-purin-9-yl)cyclohexane-1-carboxamide

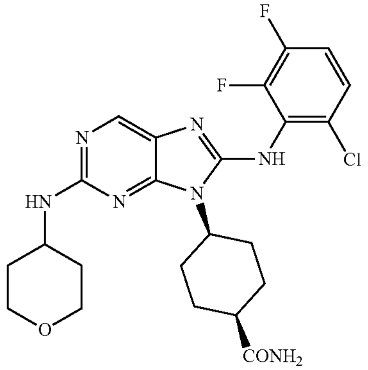 [SMILES: NC(=O)[C@H]1CC[C@@H](n2c(Nc3c(Cl)ccc(F)c3F)nc3cnc(NC4CCOCC4)nc32)CC1]

4-Bromo-2,3-difluoroaniline

To a solution of 2,3-difluoroaniline (1 equiv.), N-bromosuccinimide (1 equiv.) in acetonitrile (1 M). The mixture was stirred at 35° C. for 2 h, and then reduced in vacuo to afford a residue. The residue was poured into water and extracted with ethyl acetate, then concentrated to give the crude product, which was purified by silica gel chromatography to afford the desired product 4-bromo-2,3-difluoroaniline (68%).

4-Bromo-6-chloro-2,3-difluoroaniline

To a solution of 4-bromo-2,3-difluoroaniline (1 equiv.) in acetonitrile (3 M). The solution was warmed to reflux, and then NCS (1.1 equiv.) was added in portions. The reaction was stirred at 70° C. The solution was concentrated in vacuo to give a residue, which was poured into water, extracted with ethyl acetate. The organics were collected, concentrated to give crude product. The crude product was purified by silica gel column to give the desired product 4-bromo-6-chloro-2,3-difluoroaniline (78%). $^1$H NMR (400 MHz, $CDCl_3$) δ ppm: 7.24-7.22 (m, 1H), 4.21 (brs, 2H).

6-Chloro-2,3-difluoroaniline

To a solution of 4-bromo-6-chloro-2,3-difluoroaniline (1 equiv.) in THF (1.6 M). The solution was cooled to −78° C. and then n-BuLi (2 equiv.) was added drop-wise. The reaction was stirred at −78° C. for 1.5 h, and then quenched with water. The solution was extracted with ethyl acetate. The organic layer was concentrated in vacuo to afford the crude product, which was purified by silica gel column to give the desired product 6-chloro-2,3-difluoroaniline (55%). $^1$H NMR (400 MHz, $CDCl_3$) δ ppm: 6.99-6.95 (m, 1H), 6.53-6.48 (m, 1H), 4.19 (brs, 2H).

(1s,4s)-4-(8-((6-Chloro-2,3-difluorophenyl)amino)-2-((tetrahydro-2H-pyran-4-yl)amino)-9H-purin-9-yl) cyclohexanecarboxamide To a solution of 6-chloro-2,3-difluoroaniline (1 equiv.), KOH (6 equiv.) in DCM/$H_2O$ (1.2 M, 1/2). The solution was cooled to 0° C. and stirred for 20 min, and then $SCCl_2$ (6 equiv.) was added drop-wise. The reaction was stirred at 36° C.-40° C. for 10 h. The solution was extracted with ethyl acetate. The organic layer was concentrated in vacuo to get the crude product, which was used directly into the next step without further purification. To a solution of 1-chloro-3,4-difluoro-2-isothiocyanatobenzene (1 equiv.) and (1s,4s)-4-((5-amino-2-((tetrahydro-2H-pyran-4-yl)amino)pyrimidin-4-yl)amino)cyclohexane-1-carboxamide (1 equiv.) (prepared as described herein) in DMF (1.2 M), DIC (2 equiv.) was added drop wise. The reaction was stirred at 31° C.-35° C. for 12 h. Standard work-up and purification methods provided (1s,4s)-4-(8-((6-chloro-2,3-difluorophenyl)amino)-2-((tetrahydro-2H-pyran-4-yl)amino)-9H-purin-9-yl)cyclohexanecarboxamide (23%). $^1$H NMR (400 MHz, DMSO-$d_6$) δ ppm: 10.37 (br. s., 1H) 7.65 (br. s., 1H) 7.30 (br. s., 1H) 7.20 (br. s., 1H) 7.07 (br. s., 1H) 6.71 (br. s., 1H) 6.51 (br. s., 1H) 4.40 (t, J=11.86 Hz, 1H) 3.80-3.94 (m, 3H) 3.52 (d, J=10.92 Hz, 2H) 2.55-2.77 (m, 2H) 2.44 (br. s., 1H) 2.24 (d, J=13.20 Hz, 2H) 1.84 (d, J=12.80 Hz, 2H) 1.38-1.70 (m, 6H). MS (ESI) m/z=506.1 $[M+H]^+$.

Example 32. (1S,4s)-4-(2-(((3S,4R)-3-Fluorotetrahydro-2H-pyran-4-yl)amino)-8-((2,4,6-trichlorophenyl)amino)-9H-purin-9-yl)cyclohexane-1-carboxamide

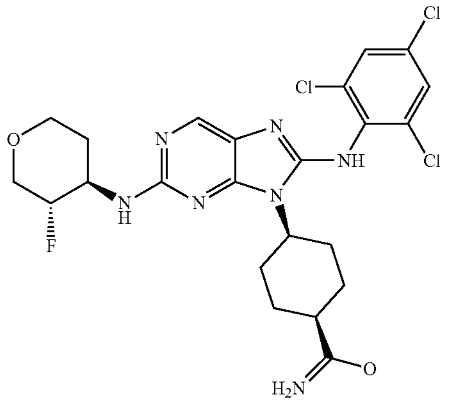 [SMILES: N=C(O)[C@H]1CC[C@@H](n2c(Nc3c(Cl)cc(Cl)cc3Cl)nc3cnc(N[C@@H]4CCOC[C@H]4F)nc32)CC1]

4,4-Dimethoxytetrahydro-2H-pyran $CH(OMe)_3$ (1.2 equiv) was added dropwise over a period of 20 min to a solution of dihydro-2H-pyran-4(3H)-one (1 equiv.) and pTSA (0.03 equiv.) in anhydrous MeOH (8 M), while the reactants were maintained under gentle refluxing. After 15 min, the products were neutralized with sodium methoxide/MeOH (1 M) and distilled to give 4,4-dimethoxytetrahydro-2H-pyran (41%) as a colorless oil. $^1$H NMR (400 MHz, $CDCl_3$) δ ppm: 3.68 (t, J=5.2 Hz, 4H), 3.22 (s, 6H), 1.77 (t, J=5.6 Hz, 4H).

4-Methoxy-3,6-dihydro-2H-pyran 4,4-dimethoxytetrahydro-2H-pyran (1 equiv.) and pTSA (0.01 equiv.) were placed together in a distillation apparatus. The reaction was heated (bath temperature: 160° C.) at atmospheric pressure. When the theoretical amount of MeOH had been collected, the reaction was distilled under reduced pressure (water pump) to give 4-methoxy-3,6-dihydro-2H-pyran (21%) as a colorless oil. $^1$H NMR (400 MHz, $CDCl_3$) δ ppm: 4.55-4.68 (m, 1H), 4.20 (q, J=2.3 Hz, 2H), 3.80-3.87 (m, 2H), 3.53-3.57 (m, 3H), 2.19 (ttd, J=5.6 Hz, 2.2 Hz, 1.1 Hz, 2H).

3-Fluorodihydro-2H-pyran-4(3H)-one

To a solution of SelectFluor (0.85 equiv.) in acetonitrile/$H_2O$ (1/1, 0.4 M) was added a solution of 4-methoxy-3,6-dihydro-2H-pyran (1 equiv.) in acetonitrile dropwise keeping the temperature at 0-5° C. After the addition, the reaction was stirred at 0° C. for 30 min, and the reaction was stirred at room temperature for 24 h. Solid NaCl (40.0 g) was added, the mixture was extracted with MTBE, dried over $Na_2SO_4$, filtered and concentrated to afford 3-fluorodihydro-2H-pyran-4(3H)-one (42%) as a colorless oil. $^1$H NMR (400 MHz, $CDCl_3$) δ ppm: 4.85-5.05 (m, 1H), 4.36-4.42 (m, 1H), 4.16-4.24 (m, 1H), 3.60-3.78 (m, 2H), 2.61-2.76 (m, 2H).

trans-N-Benzyl-3-fluorotetrahydro-2H-pyran-4-amine and cis-N-benzyl-3-fluorotetrahydro-2H-pyran-4-amine To a cooled (0° C.) solution of 3-fluorodihydro-2H-pyran-4(3H)-one (1 equiv.) in MeOH (0.3 M) was added benzylamine (1.05 equiv.), $NaBH_3CN$ (1.4 equiv.) and acetic acid (1 equiv.). The reaction was stirred at room temperature overnight. The reaction was concentrated, diluted with water, extracted with ethyl acetate, dried over $Na_2SO_4$, filtered and concentrated. The resulted residue was purified with preparative HPLC to afford trans-N-benzyl-3-fluorotetrahydro-2H-pyran-4-amine and cis-N-benzyl-3-fluorotetrahydro-2H-pyran-4-amine as a colorless oil. trans-diastereomer—$^1$H NMR (400 MHz, $CDCl_3$) δ ppm: 7.34-7.40 (m, 1H), 7.25-7.33 (m, 1H), 4.33-4.54 (m, 1H), 4.08 (dt, J=11.1, 5.6 Hz, 1H), 3.82-3.97 (m, 3H), 3.41 (td, J=11.4, 2.5 Hz, 1H), 3.33 (ddd, J=11.2, 9.2, 4.6 Hz, 1H), 2.94 (dddd, J=11.4, 10.4, 8.2, 4.8 Hz, 1H), 2.00-2.09 (m, 1H), 1.47-1.63 (m, 1H). cis-diastereomer—$^1$H NMR (400 MHz, $CDCl_3$) δ ppm: 7.33-7.42 (m, 4H), 7.26-7.32 (m, 1H), 4.64-4.84 (m, 1H), 4.14-4.25 (m, 1H), 4.03 (dtd, J=11.4, 3.6, 1.1 Hz, 1H), 3.82-3.97 (m, 2H), 3.52 (dd, J=13.1, 0.9 Hz, 1H), 3.37-3.46 (m, 2H), 2.72-2.86 (m, 1H), 1.80-1.88 (m, 2H).

(3R,4S)—N-Benzyl-3-fluorotetrahydro-2H-pyran-4-amine and (3S,4R)—N-benzyl-3-fluorotetrahydro-2H-pyran-4-amine trans-N-Benzyl-3-fluorotetrahydro-2H-pyran-4-amine was separated by chiral-HPLC (AD-3 S_3_5_40_3ML Column: Chiralpak AD-3 100×4.6 mm I.D., 3 um Mobile phase: MeOH (0.05% DEA) in $CO_2$ from 5% to 40% Flow rate: 3 mL/min Wavelength: 220 nm) to afford (3R,4S)—N-benzyl-3-fluorotetrahydro-2H-pyran-4-amine and (3S,4R)—N-benzyl-3-fluorotetrahydro-2H-pyran-4-amine as a colorless oil.

(3R,4S)-3-Fluorotetrahydro-2H-pyran-4-amine hydrochloride

To a solution of (3R,4S)—N-benzyl-3-fluorotetrahydro-2H-pyran-4-amine (1 equiv.) in anhydrous MeOH (0.3 M) was added Pd/C (0.1 equiv, 10% Pd by wt.) under $N_2$ atmosphere. The suspension was degassed under vacuum and purged with hydrogen several times. The reaction mixture was stirred under hydrogen balloon for 3 h at room temperature. Then the reaction was filtered through a pad of celite and washed with MeOH. The filtrate was treated with 4 M HCl and concentrated to afford (3R,4S)-3-fluorotetrahydro-2H-pyran-4-amine hydrochloride as a white solid (100%).

(3S,4R)-3-Fluorotetrahydro-2H-pyran-4-amine hydrochloride

To a solution of (3S,4R)—N-benzyl-3-fluorotetrahydro-2H-pyran-4-amine (1 equiv.) in anhydrous MeOH (0.3 M) was added Pd/C (0.1 equiv., 10% Pd by wt.) under $N_2$ atmosphere. The suspension was degassed under vacuum and purged with hydrogen several times. The reaction mixture was stirred under hydrogen balloon for 3 h at room temperature. The reaction was filtered through a pad of celite and washed with MeOH. The filtrate was treated with 4 M HCl and concentrated to afford (3S,4R)-3-fluorotetrahydro-2H-pyran-4-amine hydrochloride as a white solid (100%).

(3R,4R)—N-Benzyl-3-fluorotetrahydro-2H-pyran-4-amine and (3S,4S)—N-benzyl-3-fluorotetrahydro-2H-pyran-4-amine cis-N-benzyl-3-fluorotetrahydro-2H-pyran-4-amine was separated by chiral-HPLC (AS-3S_5_5_40_3 ML Column: Chiralpak AS-3 150×4.6 mm I.D., 3 um Mobile phase: EtOH (0.05% DEA) in $CO_2$ from 5% to 40% Flow rate: 3 mL/min Wavelength: 220 nm) to afford (3R,4R)—N-benzyl-3-fluorotetrahydro-2H-pyran-4-amine and (3S,4S)—N-benzyl-3-fluorotetrahydro-2H-pyran-4-amine as a colorless oil.

(3R,4R)-3-Fluorotetrahydro-2H-pyran-4-amine hydrochloride

To a solution of (3R,4R)—N-benzyl-3-fluorotetrahydro-2H-pyran-4-amine (1 equiv.) in anhydrous MeOH (0.2 M) was added Pd/C (0.1 equiv., 10% Pd/C) under $N_2$ atmosphere. The suspension was degassed under vacuum and purged with hydrogen several times. The reaction mixture was stirred under hydrogen balloon for 3 h at room temperature. The reaction was filtered through a pad of celite and washed with MeOH. The filtrate was treated with 4 M HCl and concentrated to afford (3R,4R)-3-fluorotetrahydro-2H-pyran-4-amine hydrochloride as a white solid (100%).

(3S,4S)-3-Fluorotetrahydro-2H-pyran-4-amine hydrochloride

To a solution of (3 S, 4S)—N-benzyl-3-fluorotetrahydro-2H-pyran-4-amine (1 equiv.) in anhydrous MeOH (0.2 M) was added Pd/C (0.1 equiv., 10% Pd/C) under $N_2$ atmosphere. The suspension was degassed under vacuum and purged with hydrogen several times. The reaction mixture was stirred under hydrogen balloon for 3 h at room temperature. The reaction was filtered through a pad of celite and washed with MeOH. The filtrate was treated with 4 M HCl and concentrated to afford (3S,4S)-3-fluorotetrahydro-2H-pyran-4-amine hydrochloride a white solid (100%).

(1S,4R)-4-((2-(((3R,4S)-3-Fluorotetrahydro-2H-pyran-4-yl)amino)-5-nitropyrimidin-4-yl)amino) cyclohexanecarboxamide To a solution of (1s,4s)-4-((2-chloro-5-nitropyrimidin-4-yl)amino)cyclohexane-1-carboxamide (1 equiv.) (prepared as described herein) in anhydrous DMF (0.3 M) were added (3S,4R)-3-fluorotetrahydro-2H-pyran-4-amine hydrochloride (1 equiv.) and DIEA (3 equiv.). The formed precipitated solid was collected by filtration to give (1S,4R)-4-((2-(((3R,4S)-3-fluorotetrahydro-2H-pyran-4-yl)amino)-5-nitropyrimidin-4-yl)amino)cyclohexanecarboxamide (38%). $^1$H NMR (400 MHz, DMSO-$d_6$) δ ppm: 8.99-8.85 (m, 1H), 8.75-8.29 (m, 2H), 7.35-7.14 (m, 1H), 6.87-6.65 (m, 1H), 4.65-3.78 (m, 5H), 3.49-3.41 (m, 1H), 2.38-2.19 (m, 1H), 2.09-1.45 (m, 11H).

(1S,4r)-4-((5-Amino-2-(((3R,4S)-3-fluorotetrahydro-2H-pyran-4-yl)amino)pyrimidin-4-yl)amino)cyclohexane-1-carboxamide To a solution of (1S,4R)-4-((2-(((3R,4S)-3-fluorotetrahydro-2H-pyran-4-yl)amino)-5-nitropyrimidin-4-yl)amino) cyclohexanecarboxamide in MeOH (0.1 M) was added Pd/C (0.1 equiv, 10% Pd/C) under nitrogen atmosphere. The suspension was degassed under vacuum and purged with hydrogen several times. The reaction mixture was stirred under hydrogen balloon for 16 h at room temperature. The reaction was filtered through a pad of celite and washed with MeOH. The filtrate was concentrated in vacuum to afford (1S,4r)-4-((5-amino-2-(((3R,4S)-3-fluorotetrahydro-2H-pyran-4-yl)amino)pyrimidin-4-yl)amino)cyclohexane-1-carboxamide a purple solid (88%). MS (ESI) m/z=353.1 $[M+H]^+$.

(1S,4s)-4-(2-(((3S,4R)-3-fluorotetrahydro-2H-pyran-4-yl)amino)-8-((2,4,6-trichlorophenyl)amino)-9H-purin-9-yl)cyclohexane-1-carboxamide To a solution of (1S,4r)-4-((5-amino-2-(((3R,4S)-3-fluorotetrahydro-2H-pyran-4-yl)amino)pyrimidin-4-yl)amino) cyclohexane-1-carboxamide (1 equiv.) in anhydrous DMF (0.2 M) was added 1,3,5-trichloro-2-isothiocyanatobenzene (1 equiv.). The reaction was stirred for 90 min at room temperature. Then DIC (1 equiv.) was added and stirring was continued at room temperature overnight. Standard work-up and purification methods provided (1S,4s)-4-(8-((2,4-dichloro-6-fluorophenyl)amino)-2-(((3S,4R)-3-fluorotetrahydro-2H-pyran-4-yl)amino)-9H-purin-9-yl)cyclohexane-1-carboxamide. $^1H$ NMR (400 MHz, DMSO-$d_6$) δ ppm: 10.29 (s, 1H), 8.10-7.56 (m, 2H), 7.33-7.17 (m, 1H), 6.95-6.62 (m, 1H), 4.64-4.29 (m, 2H), 4.18 (s, 1H), 4.00 (s, 1H), 3.79 (d, J=9.40 Hz, 1H), 3.60 (s, 1H), 3.48-3.42 (m, 1H), 2.68 (t, J=12.42 Hz, 2H), 2.45-2.33 (m, 1H), 2.22 (s, 2H), 2.00 (d, J=11.92 Hz, 1H), 1.76-1.37 (m, 5H). MS (ESI) m/z=556.5 $[M+H]^+$.

Example 33. (1S,4s)-4-(8-((2,4-Dichloro-6-fluorophenyl)amino)-2-(((3S,4R)-3-fluorotetrahydro-2H-pyran-4-yl)amino)-9H-purin-9-yl)cyclohexane-1-carboxamide

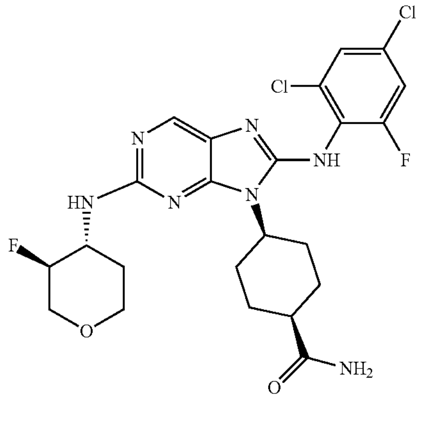 [SMILES: NC(=O)[C@H]1CC[C@@H](n2c(Nc3c(F)cc(Cl)cc3Cl)nc3cnc(N[C@@H]4CCOC[C@H]4F)nc32)CC1]

(1S,4s)-4-(8-((2,4-Dichloro-6-fluorophenyl)amino)-2-(((3S,4R)-3-fluorotetrahydro-2H-pyran-4-yl) amino)-9H-purin-9-yl)cyclohexanecarboxamide To a mixture of (1S,4s)-4-((5-amino-2-(((3S,4R)-3-fluorotetrahydro-2H-pyran-4-yl)amino)pyrimidin-4-yl)amino) cyclohexanecarboxamide (1 equiv.) in DMF (0.2 M) was added 1,5-dichloro-3-fluoro-2-isothiocyanatobenzene (1.1 equiv., prepared as described herein). The mixture was stirred at room temperature and DIC (2 equiv.) was added. The mixture was stirred at room temperature for 16 h. Standard work-up and purification methods afforded (1S,4s)-4-(8-((2,4-dichloro-6-fluorophenyl)amino)-2-(((3S,4R)-3-fluorotetrahydro-2H-pyran-4-yl)amino)-9H-purin-9-yl) cyclohexanecarboxamide (34%). $^1H$ NMR (400 MHz, DMSO-$d_6$) δ ppm: 10.37 (s, 1H), 7.66-7.45 (m, 2H), 7.44-7.18 (m, 2H), 6.90-6.68 (m, 2H), 4.62-4.44 (m, 1H) 4.43-4.33 (m, 1H) 4.19 (s, 1H) 4.05-3.96 (m, 1H) 3.80-3.65 (m, 1H) 3.64-3.58 (m, 1H) 3.44-3.38 (m, 1H) 2.77-2.60 (m, 2H) 2.46-2.40 (m, 1H), 2.24-2.18 (m, 2H) 2.05-1.97 (m, 1H) 1.71-1.42 (m, 5H). MS (ESI) m/z=540.1 $[M+H]^+$.

Example 34. (1S,4s)-4-(8-((2-Chloro-4,6-difluorophenyl)amino)-2-(((3S,4R)-3-fluorotetrahydro-2H-pyran-4-yl)amino)-9H-purin-9-yl)-1-methylcyclohexane-1-carboxamide

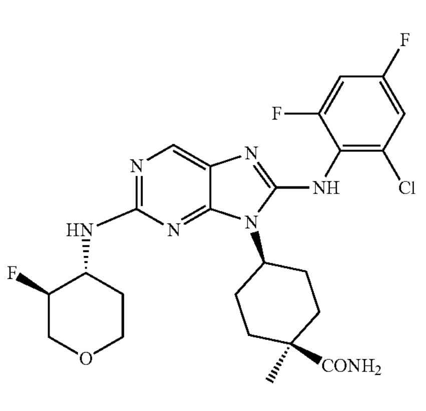 [SMILES: C[C@]1(C(N)=O)CC[C@@H](n2c(Nc3c(F)cc(F)cc3Cl)nc3cnc(N[C@@H]4CCOC[C@H]4F)nc32)CC1]

(1S,4s)-4-(8-((2-Chloro-4,6-difluorophenyl)amino)-2-(((3S,4R)-3-fluorotetrahydro-2H-pyran-4-yl) amino)-9H-purin-9-yl)-1-methylcyclohexane-1-carboxamide To a mixture of (1S,4s)-4-((5-amino-2-(((3S,4R)-3-fluorotetrahydro-2H-pyran-4-yl)amino)pyrimidin-4-yl)amino) cyclohexanecarboxamide (1 equiv., prepared as described herein) in DMF (0.24 M) was added 1-chloro-3,5-difluoro-2-isothiocyanatobenzene (1 equiv.) in one portion. The mixture was stirred at room temperature for 3 h. DIC (2 equiv.) was added. The mixture was stirred at room temperature for 16 h, and stirring was continued at 30° C. for 14 h. Standard workup and purification conditions afforded (1S,4s)-4-(8-((2-chloro-4,6-difluorophenyl)amino)-2-(((3S,4R)-3-fluorotetrahydro-2H-pyran-4-yl)amino)-9H-purin-9-yl)cyclohexanecarboxamide (36%) as a white solid. $^1H$ NMR (500 MHz, DMSO-$d_6$) δ ppm: 8.55-10.38 (m, 1.0H) 7.55-8.21 (m, 0.9H) 7.40-7.51 (m, 0.8H) 7.24-7.40 (m, 1.6H) 7.20 (br. s., 0.6H) 6.81 (d, J=8.2 Hz, 1.0H) 6.60-6.78 (m, 1.0H), 4.44-4.62 (m, 1.0H) 4.33-4.44 (m, 1.0H) 4.11-4.28 (m, 1.0H) 3.93-4.06 (m, 1.0H) 3.74-3.86 (m, 1.0H) 3.52-3.70 (m, 1.0H) 3.38-3.50 (m, 1.0H) 2.58-2.86 (m, 2.1H) 2.36-2.48 (m, 1.2H) 2.15-2.31 (m, 2.0H) 1.93-2.10 (m, 1.0H) 1.39-1.77 (m, 5.1H). MS (ESI) m/z=524.2 $[M+H]^+$.

Example 35. (1R,4s)-4-(8-((2,4-Dichloro-6-fluorophenyl)amino)-2-(((3S,4S)-3-fluorotetrahydro-2H-pyran-4-yl)amino)-9H-purin-9-yl)cyclohexane-1-carboxamide

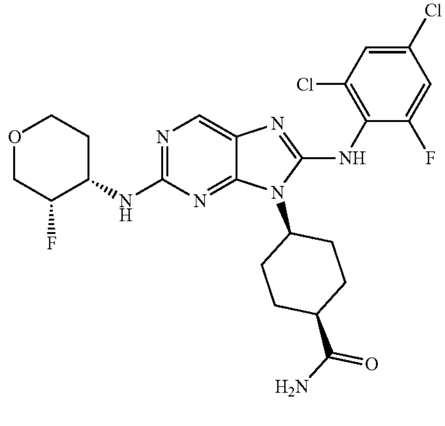 [SMILES: NC(=O)[C@H]1CC[C@@H](n2c(Nc3c(F)cc(Cl)cc3Cl)nc3cnc(N[C@H]4CCOC[C@H]4F)nc32)CC1]

(1R,4s)-4-((2-(((3S,4S)-3-Fluorotetrahydro-2H-pyran-4-yl)amino)-5-nitropyrimidin-4-yl)amino) cyclohexane-1-carboxamide To a solution of (1s,4s)-4-((2-chloro-5-nitropyrimidin-4-yl)amino)cyclohexane-1-carboxamide (1 equiv.) (prepared as described herein) in anhydrous DMF (0.3 M) were added (3S,4S)-3-fluorotetrahydro-2H-pyran-4-amine hydrochloride (prepared as described herein) (1.1 equiv.) and DIEA (3 equiv.). The formed precipitated solid was collected by filtration to give (1R,4s)-4-((2-(((3S,4S)-3-fluorotetrahydro-2H-pyran-4-yl)amino)-5-nitropyrimidin-4-yl)amino)cyclohexane-1-carboxamide (100%). MS (ESI) m/z=383.1 $[M+H]^+$.

(1R,4s)-4-((5-Amino-2-(((3S,4S)-3-fluorotetrahydro-2H-pyran-4-yl)amino)pyrimidin-4-yl)amino)cyclohexane-1-carboxamide To a solution of (1R,4s)-4-((2-(((3S,4S)-3-fluorotetrahydro-2H-pyran-4-yl)amino)-5-nitropyrimidin-4-yl)amino) cyclohexane-1-carboxamide (1 equiv.) in MeOH (0.18 M) was added Pd/C (0.1 equiv., 10% Pd by wt.) under nitrogen atmosphere. The suspension was degassed under vacuum and purged with hydrogen several times. The reaction mixture was stirred under hydrogen balloon for 3 h at room temperature. The reaction was filtered through a pad of celite and washed with MeOH. The filtrate was concentrated in vacuum to afford (1R,4s)-4-((5-amino-2-(((3S,4 S)-3-fluorotetrahydro-2H-pyran-4-yl)amino)pyrimidin-4-yl)amino) cyclohexane-1-carboxamide as a purple solid (100%).

(1R,4s)-4-(8-((2,4-Dichloro-6-fluorophenyl)amino)-2-(((3S,4S)-3-fluorotetrahydro-2H-pyran-4-yl) amino)-9H-purin-9-yl)cyclohexane-1-carboxamide To a solution of (1R,4s)-4-((5-amino-2-(((3S,4S)-3-fluorotetrahydro-2H-pyran-4-yl)amino)pyrimidin-4-yl)amino) cyclohexane-1-carboxamide (1 equiv.) in anhydrous DMF (0.2 M) was added 1,5-dichloro-3-fluoro-2-isothiocyanatobenzene (prepared as described herein) (1 equiv.). The reaction was stirred for 1 h at room temperature. DIC (1 equiv.) was added and stirring was continued for 18 h at room temperature. Standard work-up and purification methods afforded (1R,4s)-4-(8-((2,4-dichloro-6-fluorophenyl) amino)-2-(((3S,4 S)-3-fluorotetrahydro-2H-pyran-4-yl) amino)-9H-purin-9-yl)cyclohexane-1-carboxamide (21%). $^1$H NMR (400 MHz, DMSO-$d_6$) δ ppm: 10.34 (s, 1H), 7.78-7.63 (m, 2H), 7.25 (s, 1H), 6.77 (s, 1H), 6.56 (s, 1H), 4.81-4.64 (m, 1H), 4.40 (s, 1H), 4.10-3.87 (m, 4H), 3.90-3.52 (m, 1H), 2.70-2.58 (m, 2H), 2.45 (s, 1H), 2.18 (s, 2H), 1.92-1.88 (m, 1H), 1.63-1.56 (m, 5H). MS (ESI) m/z=540.2 $[M+1]^+$.

Example 36. (1R,4s)-4-(8-((2,4-Dichloro-6-fluorophenyl)amino)-2-(((3S,4S)-3-fluorotetrahydro-2H-pyran-4-yl)amino)-9H-purin-9-yl)-1-methylcyclohexane-1-carboxamide

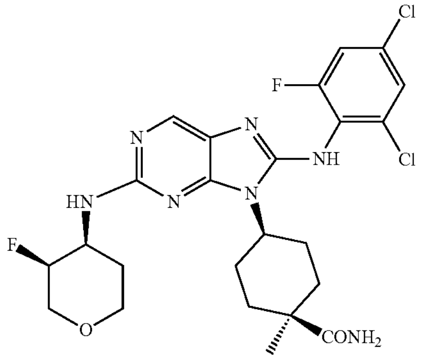 [SMILES: C[C@]1(C(N)=O)CC[C@@H](n2c(Nc3c(F)cc(Cl)cc3Cl)nc3cnc(N[C@H]4CCOC[C@H]4F)nc32)CC1]

(1R,4s)-4-((2-(((3S,4S)-3-Fluorotetrahydro-2H-pyran-4-yl)amino)-5-nitropyrimidin-4-yl)amino)-1-methylcyclohexanecarboxamide To a mixture of (1s,4s)-4-((2-chloro-5-nitropyrimidin-4-yl)amino)-1-methylcyclohexane-1-carboxamide (1 equiv., prepared as described herein) and (3S,4S)-3-fluorotetrahydro-2H-pyran-4-amine hydrochloride (1.1 equiv., prepared as described herein) in DMF (0.3 M) was added DIEA (3 equiv.) in one portion at 20° C. under $N_2$. The mixture was stirred at 20° C. for 18 h. The mixture was diluted with ethyl acetate, the organic layer was separated, washed with brine, dried over $Na_2SO_4$, filtered and concentrated. The residue was recrystallized from ethyl acetate to afford (1R,4s)-4-((2-(((3S,4S)-3-fluorotetrahydro-2H-pyran-4-yl)amino)-5-nitropyrimidin-4-yl)amino)-1-methylcyclohexanecarboxamide (95%). $^1$H NMR (400 MHz, DMSO-$d_6$) δ ppm: 8.87 (s, 1H), 8.48-8.22 (m, 1H), 8.12 (t, J=8.4 Hz, 1H), 7.16 (s, 1H), 6.83 (s, 1H), 4.89-4.59 (m, 1H), 4.34-3.82 (m, 4H), 3.64-3.44 (m, 2H), 2.23-2.08 (m, 2H), 2.04-1.91 (m, 1H), 1.89-1.75 (m, 2H), 1.70-1.57 (m, 1H), 1.50-1.32 (m, 2H), 1.28-1.12 (m, 2H), 1.07 (s, 3H).

(1R,4s)-4-((5-Amino-2-(((3S,4S)-3-fluorotetrahydro-2H-pyran-4-yl)amino)pyrimidin-4-yl)amino)-1-methylcyclohexanecarboxamide To a solution of (1R,4s)-4-((2-(((3S,4S)-3-fluorotetrahydro-2H-pyran-4-yl)amino)-5-nitropyrimidin-4-yl) amino)-1-methylcyclohexanecarboxamide (1 equiv.) in MeOH (0.13 M) was added Pd/C (0.1 equiv, 10% Pd by wt.) under $N_2$. The suspension was degassed under vacuum and purged with $H_2$ several times. The mixture was stirred under $H_2$ (20 psi) at 20° C. for 3 h. The reaction mixture was filtered and the filtrate was concentrated to give (1R,4s)-4-((5-amino-2-(((3S,4 S)-3-fluorotetrahydro-2H-pyran-4-yl) amino)pyrimidin-4-yl)amino)-1-methylcyclohexanecarboxamide (98%). $^1$H NMR (400 MHz, DMSO-$d_6$) δ ppm: 7.33 (s, 1H), 4.77-4.61 (m, 1H), 4.15-3.95 (m, 3H), 3.95-3.85 (m, 1H), 3.54 (s, 2H), 2.28-2.18 (m, 2H), 2.01-1.75 (m, 4H), 1.49-1.27 (m, 4H), 1.19 (s, 3H).

(1R,4s)-4-(8-((2,4-dichloro-6-fluorophenyl)amino)-2-(((3S,4S)-3-fluorotetrahydro-2H-pyran-4-yl) amino)-9H-purin-9-yl)-1-methylcyclohexane-1-carboxamide To a solution of (1R,4s)-4-((5-amino-2-(((3S,4S)-3-fluorotetrahydro-2H-pyran-4-yl)amino)pyrimidin-4-yl)amino)-1-methylcyclohexanecarboxamide (1 equiv.) in anhydrous DMF (0.25 M) was added 1,5-dichloro-3-fluoro-2-isothiocyanatobenzene (prepared as described herein) (1.1 equiv.) and the mixture was stirred at 20° C. for 90 min. DIC (2 equiv.) was added and stirring was continued at 20° C. for 18 h. Standard work-up and purification methods afforded (1R,4s)-4-(8-((2,4-dichloro-6-fluorophenyl)amino)-2-(((3S, 4 S)-3-fluorotetrahydro-2H-pyran-4-yl)amino)-9H-purin-9-yl)-1-methylcyclohexanecarboxamide (41%). $^1$H NMR (500 MHz, Methanol-$d_4$) δ ppm: 8.06 (s, 1H), 7.64-7.18 (m, 2H), 4.84-4.65 (m, 1H), 4.59-4.33 (m, 1H), 4.29-3.99 (m, 3H), 3.98-3.72 (m, 2H), 2.89-2.59 (m, 2H), 2.46-2.33 (m, 2H), 2.04-1.91 (m, 1H), 1.91-1.76 (m, 3H), 1.52-1.38 (m, 2H), 1.26 (s, 3H). MS (ESI) m/z=554.1 [M+1]$^+$.

Example 37. (1R,4s)-4-(2-(((3S,4S)-3-Fluorotetrahydro-2H-pyran-4-yl)amino)-8-((2,4,6-trichlorophenyl)amino)-9H-purin-9-yl)cyclohexane-1-carboxamide

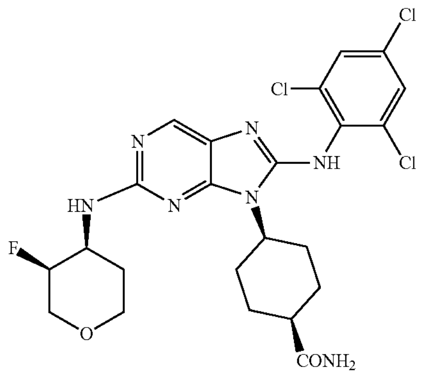 [SMILES: NC(=O)[C@H]1CC[C@@H](n2c(Nc3c(Cl)cc(Cl)cc3Cl)nc3cnc(N[C@H]4CCOC[C@H]4F)nc32)CC1]

(1R,4s)-4-(2-(((3S,4S)-3-Fluorotetrahydro-2H-pyran-4-yl)amino)-8-((2,4,6-trichlorophenyl)amino)-9H-purin-9-yl)cyclohexane-1-carboxamide To a solution of cis-4-((5-amino-2-(((3S,4S)-3-fluorotetrahydro-2H-pyran-4-yl)amino)pyrimidin-4-yl)amino)cyclohexanecarboxamide (1 equiv.) (prepared as described herein) in anhydrous DMF (0.2 M) was added 1,3,5-trichloro-2-isothiocyanatobenzene (1 equiv.). The reaction was stirred for 1 h at room temperature. DIC (1 equiv.) was added and stirring was continued for 18 h at room temperature. Standard work-up and purification methods afforded cis-4-(2-(((3S,4S)-3-fluorotetrahydro-2H-pyran-4-yl) amino)-8-((2,4,6-trichlorophenyl)amino)-9H-purin-9-yl)cyclohexanecarboxamide (21%). $^1$H NMR (400 MHz, DMSO-$d_6$) δ ppm: 10.34 (s, 1H), 7.78-7.63 (m, 2H), 7.25 (s, 1H), 6.77 (s, 1H), 6.56 (s, 1H), 4.81-4.64 (m, 1H), 4.40 (s, 1H), 4.10-3.87 (m, 4H), 3.90-3.52 (m, 1H), 2.70-2.58 (m, 2H), 2.45 (s, 1H), 2.18 (s, 2H), 1.92-1.88 (m, 1H), 1.63-1.56 (m, 5H). MS (ESI) m/z=557.2 [M+1]$^+$.

Example 38. (1s,4s)-4-(8-((2,6-dichloro-4-cyanophenyl)amino)-2-((tetrahydro-2H-pyran-4-yl) amino)-9H-purin-9-yl)cyclohexane-1-carboxamide

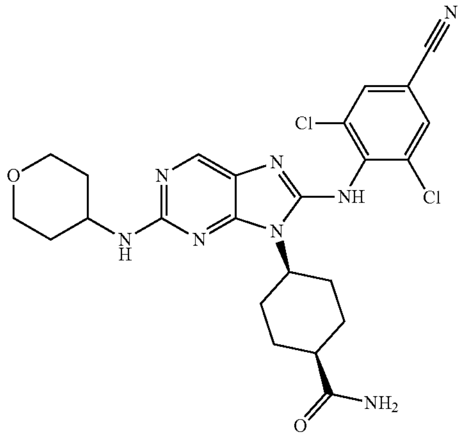 [SMILES: N#Cc1cc(Cl)c(Nc2nc3cnc(NC4CCOCC4)nc3n2[C@H]2CC[C@@H](C(N)=O)CC2)c(Cl)c1]

3,5-Dichloro-4-isothiocyanatobenzonitrile

To a cooled (0° C.) solution of 4-amino-3,5-dichlorobenzonitrile (1 equiv.) in anhydrous DCM (0.5 M) was added DIEA (3 equiv.) in one portion. $SCCl_2$ (3 equiv.) was added dropwise over 20 min. After the addition, the reaction mixture was stirred for about 5 h at 0° C. The solvent was evaporated to give a brown solid, which was purified by column chromatography on silica gel (petroleum/ethyl acetate=25/1) to give 3,5-dichloro-4-isothiocyanatobenzonitrile as a light yellow solid (75%).

(1s,4s)-4-(8-((2,6-Dichloro-4-cyanophenyl)amino)-2-((tetrahydro-2H-pyran-4-yl)amino)-9H-purin-9-yl) cyclohexane-1-carboxamide To a solution of 3,5-dichloro-4-isothiocyanatobenzonitrile (1 equiv.) in anhydrous DMF (0.3 M) was added cis-4-((5-amino-2-((tetrahydro-2H-pyran-4-yl)amino)pyrimidin-4-yl)amino)cyclohexanecarboxamide (1 equiv.) (prepared as described herein). After the addition, the reaction mixture was stirred for 1 h at room temperature. DIC (1 equiv.) was added in one portion. The reaction mixture stirred for 16 h at room temperature. Standard work-up and purification methods afforded (1s,4s)-4-(8-((2,6-dichloro-4-cyanophenyl)amino)-2-((tetrahydro-2H-pyran-4-yl)amino)-9H-purin-9-yl)cyclohexane-1-carboxamide (18%). $^1$H NMR (400 MHz, Methanol-$d_4$) δ ppm: 7.85-7.59 (m, 2H), 7.47 (s, 1H), 4.61-4.42 (m, 1H), 4.00 (d, J=11.29 Hz, 3H), 3.68 (t, J=10.85 Hz, 2H), 2.85 (d, J=10.79 Hz, 2H), 2.65 (s, 1H), 2.34 (d, J=14.31 Hz, 2H), 2.08-1.93 (m, 2H), 1.80-1.68 (m, 4H), 1.65-1.49 (m, 2H). MS (ESI) m/z 529.1 [M]$^+$.

Example 39. (1R,4s)-4-(8-((2,6-Dichloro-4-cyanophenyl)amino)-2-(((S)-1-hydroxypropan-2-yl)amino)-9H-purin-9-yl)cyclohexane-1-carboxamide

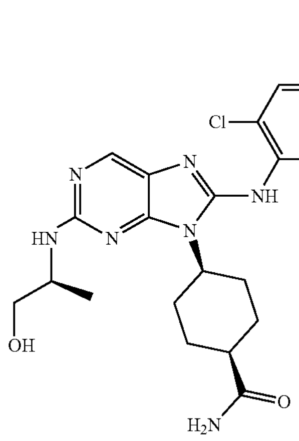

(1R,4s)-4-((2-(((S)-1-hydroxypropan-2-yl)amino)-5-nitropyrimidin-4-yl)amino)cyclohexane-1-carboxamide To a mixture of (1s,4s)-4-((2-chloro-5-nitropyrimidin-4-yl)amino)cyclohexanecarboxamide (1 equiv.) (prepared as described herein) in DMF (0.3 M) was added (S)-2-aminopropan-1-ol (1 equiv.), DIEA (1 equiv.) at 25° C. The mixture was stirred at room temperature for 12 h. The mixture was poured into water and extracted with ethyl acetate. The organic solvents were concentrated to give the crude product. The solid was purified by column chromatography to give (1R,4s)-4-((2-(((S)-1-hydroxypropan-2-yl)amino)-5-nitropyrimidin-4-yl)amino)cyclohexane-1-carboxamide (69%) as a brown solid. MS (ESI) m/z=339.1 $[M+H]^+$.

(1R,4s)-4-((5-Amino-2-(((S)-1-hydroxypropan-2-yl)amino)pyrimidin-4-yl)amino)cyclohexane-1-carboxamide To a mixture of (1R,4s)-4-((2-(((S)-1-hydroxypropan-2-yl)amino)-5-nitropyrimidin-4-yl)amino)cyclohexanecarboxamide (1 equiv.) in MeOH (0.05 M) was added Pd/C (0.1 equiv., 10% Pd by wt.). The mixture was stirred under $H_2$ balloon at 25° C. for 12 h. The mixture was filtered, the organic solvent was concentrated to give (1R,4s)-4-((5-amino-2-(((S)-1-hydroxypropan-2-yl)amino)pyrimidin-4-yl)amino)cyclohexane-1-carboxamide (81%).

(1R,4s)-4-(8-((2,6-Dichloro-4-cyanophenyl)amino)-2-(((S)-1-hydroxypropan-2-yl)amino)-9H-purin-9-yl)cyclohexanecarboxamide To a solution of (1R,4s)-4-((5-amino-2-(((S)-1-hydroxypropan-2-yl)amino)pyrimidin-4-yl)amino)cyclohexane-1-carboxamide (1 equiv.) in DMF (0.4 M) was added 3,5-dichloro-4-isothiocyanatobenzonitrile (1.1 equiv.) (prepared as described herein). The reaction mixture was stirred at 30° C. for 2 h. To the reaction mixture was added DIC (2 equiv.), and the mixture was stirred at 30° C. for 16 h. Standard work-up and purification methods afforded (1R,4s)-4-(8-((2,6-dichloro-4-cyanophenyl)amino)-2-(((S)-1-hydroxypropan-2-yl)amino)-9H-purin-9-yl)cyclohexanecarboxamide (31%). $^1$H NMR (400 MHz, Methanol-$d_4$) δ ppm: 10.49 (s, 1H), 8.01 (s, 2H), 7.67 (s, 1H), 7.31 (s, 1H), 6.86 (s, 1H), 6.26 (s, 1H), 4.75-4.72 (m, 1H), 4.37-4.35 (m, 1H), 3.82-3.90 (m, 1H), 3.51-3.59 (m, 1H), 3.24-3.10 (m, 1H), 2.63-2.74 (m, 2H), 2.45 (s., 1H), 2.23-2.18 (m, 2H), 1.51-1.66 (m, 4H), 1.14 (d, J=6.5 Hz, 3H). MS (ESI) m/z=503.1 $[M+H]^+$.

Example 40. (1S,4s)-4-(8-((4-Chloro-2,6-difluorophenyl)amino)-2-(((R)-3,3-difluorocyclopentyl)amino)-9H-purin-9-yl)cyclohexane-1-carboxamide

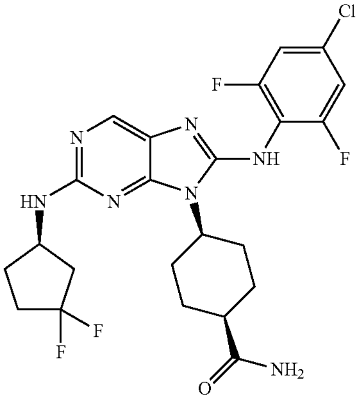 [SMILES: NC(=O)[C@H]1CC[C@@H](n2c(Nc3c(F)cc(Cl)cc3F)nc3cnc(N[C@@H]4CCC(F)(F)C4)nc32)CC1]

3-Azidocyclopentanone

To a mixture of $TMSN_3$ (5 equiv.) and acetic acid (5 equiv.) in DCM (1 M) was added cyclopent-2-enone (1 equiv.) and TEA (0.20 equiv.) in one portion at room temperature under $N_2$. The mixture was stirred at room temperature for 18 h. To the mixture was added saturated $NaHCO_3$ and stirring was continued for 20 min, then the aqueous phase was extracted with DCM. The combined organic phase was washed with saturated brine dried over anhydrous $Na_2SO_4$, filtered and concentrated in vacuum to give 3-azidocyclopentanone as a crude product. The crude product was used directly in the next step without purification.

tert-Butyl (3-oxocyclopentyl)carbamate

To a solution of 3-azidocyclopentanone (1.00 equiv.) in ethyl acetate (1.2 M) was added di-tert-butyl dicarbonate (1.20 equiv.) and Pd/C (0.1 equiv. 10% by wt.) under $N_2$. The suspension was degassed under vacuum and purged with $H_2$ several times. The mixture was stirred under $H_2$ (50 psi) at 15° C. for 5 h. The reaction mixture was filtered and the filtrate was concentrated. The crude product was purified by silica gel chromatography (29%) as a white solid. $^1$H NMR (400 MHz, $CDCl_3$) δ ppm: 4.68-4.67 (m, 1H), 4.23 (s, 1H), 2.66 (dd, J=18.45, 7.15 Hz, 1H), 2.38-2.34 (m, 2H), 2.25-2.13 (m, 2H), 1.85-1.84 (m, 1H), 1.45 (s, 9H).

tert-Butyl (3,3-difluorocyclopentyl)carbamate

To a mixture of tert-butyl (3-oxocyclopentyl)carbamate (1 equiv.) in DCM (0.2 M) was added DAST (5.00 equiv.) in one portion at room temperature under $N_2$. The mixture was stirred at room temperature for 20 h. The mixture was poured into ice-water (w/w=1/1) and stirred for 20 min. The aqueous phase was extracted with DCM. The combined organic phase was washed with saturated brine, dried over anhydrous $Na_2SO_4$, filtered and concentrated in vacuum to give a residue. The residue was purified by silica gel chromatography to afford tert-butyl (3,3-difluorocyclopentyl)carbamate (36%) as a white solid. $^1$H NMR (400 MHz, $CDCl_3$) δ ppm: 4.68 (s, 1H), 4.19-4.17 (m, 1H), 2.54 (qd, J=14.28, 7.97 Hz, 1H), 2.23-2.21 (m, 2H), 2.21-2.09 (m, 2H), 1.70-1.68 (m, 1H), 1.46 (s, 9H).

3,3-Difluorocyclopentanamine Hydrochloride

The mixture of tert-butyl (3,3-difluorocyclopentyl)carbamate (1 equiv.) in HCl/ethyl acetate (2.00 equiv.) was stirred at room temperature for 1 h. The solid was precipitated. The mixture was filtered and the filter cake was dried in vacuum to afford 3,3-difluorocyclopentanamine hydrochloride (73%) as a white solid.

(R)-Benzyl (3,3-difluorocyclopentyl)carbamate and (S)-benzyl (3,3-difluorocyclopentyl)carbamate To a mixture of 3,3-difluorocyclopentanamine hydrochloride (1 equiv.) and CbzCl (1.5 equiv.) in DCM (1.3 M) was added TEA (3 equiv.) in one portion. The mixture was stirred at room temperature for 2 h. To the mixture was added water, stirring was continued for 20 min, and the aqueous phase was extracted with DCM. The combined organic phase was washed with saturated brine, dried with anhydrous sodium sulfate, filtered and concentrated in vacuum to give benzyl (3,3-difluorocyclopentyl)carbamate (yield: 62%) as a white solid. SFC separation of the mixture via OD-3S_4_5%-40%_3ML Column: Chiralcel OD-3 100×4.6 mm I.D., 3 m Mobile phase: iso-propanol (0.05% DEA) in $CO_2$ from 5% to 40% Flow rate: 3 mL/min Wavelength: 220 nm) gave (R)-benzyl (3,3-difluorocyclopentyl)carbamate and (S)-benzyl (3,3-difluorocyclopentyl)carbamate. $^1$H NMR (400 MHz, $CDCl_3$) δ ppm: 67.40-7.33 (m, 5H), 5.14-5.10 (m, 2H), 4.93 (s, 1H), 4.27-4.22 (m, 1H), 2.51 (qd, J=14.26, 8.28 Hz, 1H), 2.24-2.01 (m, 4H) 1.71-1.70 (m, 1H). MS (ESI) m/z=256.3 $[M+H]^+$.

(R)-3,3-Difluorocyclopentanamine

To a solution of (R)-benzyl (3,3-difluorocyclopentyl)carbamate (1 equiv.) in MeOH (0.15 M) was added Pd/C (0.1 equiv., 10% Pd by wt.) under $N_2$. The suspension was degassed under vacuum and purged with $H_2$ several times. The mixture was stirred under $H_2$ (20 psi) at room temperature for 18 h. The reaction mixture was filtered and the filtrate was concentrated in vacuum to give (R)-3,3-difluorocyclopentanamine (57%) as a yellow oil. $^1$H NMR (400 MHz, DMSO-$d_6$) δ ppm: 3.37-3.30 (m, 1H), 3.16 (s, 2H), 2.35-2.20 (m, 2H), 1.93-1.89 (m, 3H), 1.46-1.41 (m, 1H).

cis-4-((2-(((R)-3,3-Difluorocyclopentyl)amino)-5-nitropyrimidin-4-yl)amino)cyclohexanecarboxamide To a mixture of (R)-3,3-difluorocyclopentanamine (1.00 equiv.) and cis-4-((2-chloro-5-nitropyrimidin-4-yl)amino) cyclohexanecarboxamide (1.50 equiv.) (prepared as described herein) in DMF (0.5 M) was added DIEA (2 equiv.) in one portion at room temperature. The mixture was stirred at room temperature for 18 h. The mixture was purified by prep-HPLC to afford cis-4-((2-(((R)-3,3-difluorocyclopentyl)amino)-5-nitropyrimidin-4-yl)amino)cyclohexanecarboxamide (60%) as a yellow solid. $^1$H NMR (400 MHz, $CDCl_3$) δ ppm: 9.02-8.96 (m, 1H), 8.69-8.48 (m, 1H), 5.90 (d, J=5.65 Hz, 1H), 5.49 (s, 2H), 4.45-4.28 (m, 2H), 2.64 (qd, J=13.85, 8.03 Hz, 1H), 2.29-2.39 (m, 5H), 1.96-1.84 (m, 9H). MS (ESI) m/z=385.1 $[M+H]^+$.

cis-4-((5-Amino-2-(((R)-3,3-difluorocyclopentyl)amino)pyrimidin-4-yl)amino)cyclohexanecarboxamide To a solution of cis-4-((2-(((R)-3,3-difluorocyclopentyl)amino)-5-nitropyrimidin-4-yl)amino)cyclohexanecarboxamide (1.00 equiv.) in MeOH (0.02 M) was added Pd/C (0.1 equiv., 10% Pd by wt.) under $N_2$. The suspension was degassed under vacuum and purged with $H_2$ several times. The mixture was stirred under $H_2$ (20 psi) at room temperature for 18 h. The reaction mixture was filtered and the filtrate was concentrated in vacuum to give cis-4-((5-amino-2-(((R)-3,3-difluorocyclopentyl)amino)pyrimidin-4-yl)amino)cyclohexanecarboxamide (94%) as a violet solid. MS (ESI) m/z=355.2 $[M+H]^+$.

cis-4-(8-((2,4-Dichloro-6-fluorophenyl)amino)-2-(((R)-3,3-difluorocyclopentyl)amino)-9H-purin-9-yl)cyclohexanecarboxamide To a mixture of cis-4-((5-amino-2-(((R)-3,3-difluorocyclopentyl)amino)pyrimidin-4-yl)amino)cyclohexanecarboxamide (1 equiv.) in DMF (0.35 M) was added 1,5-dichloro-3-fluoro-2-isothiocyanatobenzene (1 equiv., prepared as described herein). The mixture was stirred at room temperature for 1.5 h. To the mixture was added DIC (2 equiv.), and the mixture was stirred at room temperature for 18 h. Standard work-up and purification afforded cis-4-(8-((2,4-dichloro-6-fluorophenyl)amino)-2-(((R)-3,3-difluorocyclopentyl)amino)-9H-purin-9-yl)cyclohexanecarboxamide (30%). $^1$H NMR (400 MHz, Methanol-$d_4$) δ ppm: 8.01 (s, 1H), 7.62-7.24 (m, 2H), 4.54-4.52 (m, 2H), 2.89-2.65 (m, 2H), 2.71-2.62 (m, 2H), 2.35-2.24 (m, 5H), 2.11-2.04 (m, 1H), 1.81-1.74 (m, 5H). MS (ESI) m/z=542.1 $[M+H]^+$.

Example 41. (1S,4s)-4-(8-((2,6-Dichloro-4-cyanophenyl)amino)-2-(((3S,4R)-3-methyltetrahydro-2H-pyran-4-yl)amino)-9H-purin-9-yl)cyclohexane-1-carboxamide

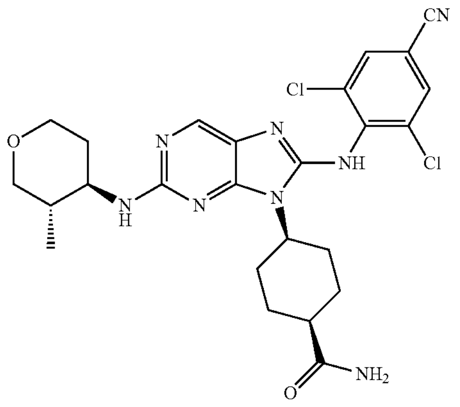 [SMILES: C[C@@H]1COCC[C@H]1Nc1ncc2nc(Nc3c(Cl)cc(C#N)cc3Cl)n([C@H]3CC[C@@H](C(N)=O)CC3)c2n1]

3-Methyltetrahydropyran-4-one

To a cooled (0° C.) solution of DIA (1.1 equiv.) in of anhydrous THF (0.6 M) was added n-BuLi (1.2 equiv., 2.5

M in hexane) dropwise over 40 min. After the addition, the mixture was stirred for 30 min at 0° C. and then cooled to −78° C. A solution of tetrahydropyran-4-one (1 equiv.) and HMPA (1 equiv.) in THF (6 M) was added dropwise over 2 h. Methyliodide (3 equiv.) was added dropwise at −78° C. The reaction mixture was stirred overnight at room temperature, then quenched by addition of citric acid and extracted with ethyl acetate. The combined organic layer was dried over $Na_2SO_4$ and concentrated in vacuo. The residue was purified via silica gel chromatography to give 3-methyltetrahydropyran-4-one as a yellow oil (15%). $^1H$ NMR (400 MHz, $CDCl_3$) δ ppm: 4.30-4.23 (m, 1H), 4.22-4.15 (m, 1H), 3.73 (dt, J=3.1, 11.5 Hz, 1H), 3.34 (t, J=10.9 Hz, 1H), 2.74-2.61 (m, 2H), 2.41 (td, J=2.7, 14.1 Hz, 1H), 1.01 (d, J=6.7 Hz, 3H).

trans-N-Benzyl-3-methyltetrahydro-2H-pyran-4-amine 4 trans and cis-N-benzyl-3-methyltetrahydro-2H-pyran-4-amine To a mixture of 3-methyltetrahydropyran-4-one (1.1 equiv.) and phenylmethanamine (1 equiv.) in MeOH (0.9 M) were added acetic acid (1 equiv.) and $NaBH_3CN$ (1.5 equiv.) at 0° C. The reaction mixture was stirred at room temperature overnight. The solvent was removed in vacuum and partitioned between DCM and aqueous potassium carbonate. The separated organic phase was dried over $Na_2SO_4$ and concentrated. The residue was purified by prep-HPLC to give trans-N-benzyl-3-methyltetrahydro-2H-pyran-4-amine (12%) and cis-N-benzyl-3-methyltetrahydro-2H-pyran-4-amine as a white solid (13%). trans-$^1H$ NMR (400 MHz, $CDCl_3$) δ ppm: 7.46-7.41 (m, 2H), 7.37 (t, J=7.3 Hz, 2H), 7.33-7.27 (m, 1H), 4.03-4.0 (m, 2H), 3.86 (dd, J=4.6, 11.5 Hz, 1H), 3.82-3.78 (m, 1H), 3.38 (dt, J=2.2, 11.8 Hz, 1H), 3.01 (t, J=11.0 Hz, 1H), 2.40 (dt, J=4.1, 10.3 Hz, 1H), 2.01 (tdd, J=2.1, 4.2, 13.0 Hz, 1H), 1.82-1.67 (m, 1H), 1.66-1.53 (m, 1H), 0.96 (d, J=6.5 Hz, 3H). cis-$^1H$ NMR (400 MHz, MeOH-$d_4$) δ ppm: 7.40-7.31 (m, 4H), 7.29-7.23 (m, 1H), 3.92 (td, J=3.4, 11.4 Hz, 1H), 3.82-3.74 (m, 2H), 3.72 (dd, J=2.4, 9.0 Hz, 1H), 3.49 (dd, J=2.5, 11.4 Hz, 1H), 3.40 (dt, J=3.0, 11.4 Hz, 1H), 2.85 (td, J=4.3, 10.8 Hz, 1H), 1.98 (dq, J=4.0, 6.7 Hz, 1H), 1.75-1.63 (m, 1H), 1.05 (d, J=7.2 Hz, 3H).

(3R,4S)—N-Benzyl-3-methyltetrahydro-2H-pyran-4-amine and (3S,4R)—N-benzyl-3-methyltetrahydro-2H-pyran-4-amine Trans-N-benzyl-3-methyltetrahydro-2H-pyran-4-amine 5A trans (2.6 g 12.6 mmol) was separated by chiral-HPLC (AD-3S_3_5_40_3ML Column: Chiralpak AD-3 100×4.6 mm I.D., 3 um Mobile phase: MeOH (0.05% DEA) in $CO_2$ from 5% to 40% Flow rate: 3 mL/min Wavelength: 220 nm) to afford (3R,4S)—N-benzyl-3-methyltetrahydro-2H-pyran-4-amine as a colorless oil and (3S,4R)—N-benzyl-3-methyltetrahydro-2H-pyran-4-amine as a white solid.

(3S,4R)-3-Methyltetrahydro-2H-pyran-4-amine hydrochloride

To a solution of (3S,4R)—N-benzyl-3-methyltetrahydro-2H-pyran-4-amine (1 equiv.) in anhydrous MeOH (0.12 M) was added Pd/C (0.1 equiv., 10% Pd/C by wt.) under $N_2$ atmosphere. The suspension was degassed under vacuum and purged with hydrogen several times. The reaction mixture was stirred under hydrogen balloon for 3 h at room temperature. The reaction was filtered through a pad of celite and washed with MeOH. The filtrate was treated with 4 M HCl/MeOH and concentrated to afford (3S,4R)-3-methyltetrahydro-2H-pyran-4-amine hydrochloride as a white solid (86%).

(1S,4s)-4-((2-(((3S,4R)-3-methyltetrahydro-2H-pyran-4-yl)amino)-5-nitropyrimidin-4-yl)amino)cyclohexane-1-carboxamide To a solution of (1s,4s)-4-((2-chloro-5-nitropyrimidin-4-yl)amino)cyclohexane-1-carboxamide (1 equiv.) (prepared as described herein) in anhydrous DMF (0.5 M) were added (3S,4R)-3-methyltetrahydro-2H-pyran-4-amine hydrochloride (1 equiv.) and DIEA (3 equiv.). The reaction solution was diluted with brine. The formed precipitated solid was collected by filtration to give (1S,4s)-4-((2-(((3S,4R)-3-methyltetrahydro-2H-pyran-4-yl)amino)-5-nitropyrimidin-4-yl)amino)cyclohexane-1-carb oxamide (63%).

(1S,4s)-4-((5-Amino-2-(((3S,4R)-3-methyltetrahydro-2H-pyran-4-yl)amino)pyrimidin-4-yl)amino)cyclohexane-1-carboxamide To a solution of (1s,4s)-4-((2-chloro-5-nitropyrimidin-4-yl)amino)cyclohexane-1-carboxamide (1 equiv.) in MeOH (0.1 M) was added Pd/C (0.1 equiv, 10% Pd by wt.) under nitrogen atmosphere. The suspension was degassed under vacuum and purged with hydrogen several times. The reaction mixture was stirred under hydrogen balloon for 16 h at room temperature. The reaction was filtered through a pad of celite and washed with MeOH. The filtrate was concentrated in vacuum to afford (1S,4s)-4-((5-Amino-2-(((3S,4R)-3-methyltetrahydro-2H-pyran-4-yl)amino)pyrimidin-4-yl)amino)cyclohexane-1-carboxamide (82%). $^1H$ NMR (400 MHz, $CDCl_3$) δ ppm: 7.51 (s, 1H), 5.58-5.28 (m, 3H), 4.38 (d, J=8.92 Hz, 1H), 4.14 (s, 1H), 4.02-3.93 (m, 1H), 3.89 (dd, J=11.54, 4.38 Hz, 1H), 3.69-3.56 (m, 1H), 3.55-3.42 (m, 1H), 3.12 (t, J=11.12 Hz, 1H), 2.48 (s, 2H), 2.33 (td, J=8.30, 3.94 Hz, 1H), 2.12-2.00 (m, 1H), 1.94-1.70 (m, 8H), 1.45 (qd, J=12.02, 4.58 Hz, 1H), 0.90 (d, J=6.68 Hz, 3H).

(1S,4s)-4-(8-((2,6-Dichloro-4-cyanophenyl)amino)-2-(((3S,4R)-3-methyltetrahydro-2H-pyran-4-yl)amino)-9H-purin-9-yl)cyclohexane-1-carboxamide To a solution of (1S,4s)-4-((5-Amino-2-(((3S,4R)-3-methyltetrahydro-2H-pyran-4-yl)amino)pyrimidin-4-yl)amino)cyclohexane-1-carboxamide (1 equiv.) in anhydrous DMF (0.17 M) was added 3,5-dichloro-4-isothiocyanatobenzonitrile (1 equiv.) (prepared as described herein). The reaction was stirred for 90 min at room temperature. Then DIC (2 equiv.) was added and stirring was continued at room temperature overnight. Standard work-up and purification methods afforded (1S,4s)-4-(8-((2,6-dichloro-4-cyanophenyl)amino)-2-(((3S,4R)-3-methyltetrahydro-2H-pyran-4-yl)amino)-9H-purin-9-yl)cyclohexane-1-carboxamide (59%). $^1H$ NMR (400 MHz, Methanol-$d_4$) δ ppm: 7.82 (s, 2H), 7.58 (s, 1H), 4.63-4.41 (m, 1H), 3.99 (dd, J=11.42, 4.02 Hz, 1H), 3.91 (dd, J=11.48, 4.32 Hz, 1H), 3.84-3.61 (m, 2H), 3.32-3.22 (m, 1H), 2.86 (d, J=12.56 Hz, 2H), 2.66 (s, 1H), 2.35 (d, J=13.04 Hz, 2H), 2.07-1.95 (m, 1H), 1.87-1.65 (m, 5H), 1.54 (qd, J=12.16, 4.52 Hz, 1H), 0.93 (d, J=6.64 Hz, 3H). MS (ESI) m/z=544 $[M+H]^+$.

Example 42. (1S,4s)-1-Methyl-4-(2-(((3S,4R)-3-methyltetrahydro-2H-pyran-4-yl)amino)-8-((2,4,6-trichlorophenyl)amino)-9H-purin-9-yl)cyclohexane-1-carboxamide

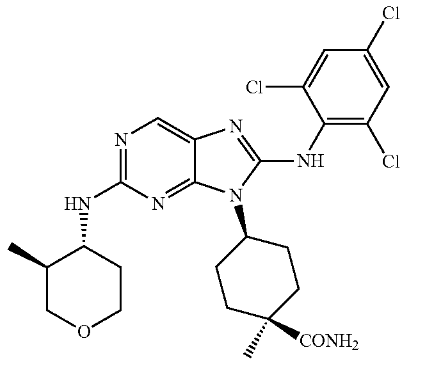 [SMILES: C[C@@H]1COCC[C@H]1Nc1ncc2nc(Nc3c(Cl)cc(Cl)cc3Cl)n([C@H]3CC[C@@](C)(C(N)=O)CC3)c2n1]

Ethyl (1S,4s)-1-methyl-4-(2-(((3S,4R)-3-methyltetrahydro-2H-pyran-4-yl)amino)-8-((2,4,6-trichlorophenyl)amino)-9H-purin-9-yl)cyclohexane-1-carboxylate To a mixture of ethyl (1S,4s)-4-((5-amino-2-(((3S,4R)-3-methyltetrahydro-2H-pyran-4-yl)amino)pyrimidin-4-yl)amino)-1-methylcyclohexane-1-carboxylate (1 equiv., prepared as described herein) in DMF (0.35 M) was added 1,3,5-trichloro-2-isothiocyanatobenzene (1 equiv.). The mixture was stirred at 15-20° C. for 1.5 h. DIC (1 equiv.) was added to the reaction in one portion. The mixture was stirred at 15-20° C. for 16 h. The reaction was diluted with water, extracted with ethyl acetate, dried over $Na_2SO_4$, filtered and concentrated. The residue was purified with column chromatography (petroleum/Ethyl acetate=5:1-1:1) to give (1S,4s)-ethyl 1-methyl-4-(2-(((3S,4R)-3-methyltetrahydro-2H-pyran-4-yl)amino)-8-((2,4,6-trichlorophenyl)amino)-9H-purin-9-yl)cyclohexanecarboxylate (88%) as a yellow solid.

(1S,4s)-1-Methyl-4-(2-(((3S,4R)-3-methyltetrahydro-2H-pyran-4-yl)amino)-8-((2,4,6-trichlorophenyl)amino)-9H-purin-9-yl)cyclohexane-1-carboxylic acid To a solution of (1S,4s)-ethyl 1-methyl-4-(2-(((3S,4R)-3-methyltetrahydro-2H-pyran-4-yl)amino)-8-((2,4,6-trichlorophenyl)amino)-9H-purin-9-yl)cyclohexanecarboxylate (1 equiv.) in MeOH/water (4/1, 0.1 M) was added NaOH (6 equiv.). The reaction was refluxed for 30 h. The reaction was concentrated, diluted with water, and extracted with ethyl acetate. The aqueous phase was acidified with 3M HCl to pH=3-5, extracted with DCM, dried over $Na_2SO_4$, filtered and concentrated to give (1S,4s)-1-Methyl-4-(2-(((3S,4R)-3-methyltetrahydro-2H-pyran-4-yl)amino)-8-((2,4,6-trichlorophenyl)amino)-9H-purin-9-yl)cyclohexane-1-carboxylic acid. (53%) as a yellow solid. MS (ESI) m/z=567.1 $[M+H]^+$.

(1S,4s)-1-Methyl-4-(2-(((3S,4R)-3-methyltetrahydro-2H-pyran-4-yl)amino)-8-((2,4,6-trichlorophenyl)amino)-9H-purin-9-yl)cyclohexane-1-carboxamide To a mixture of cis-1-methyl-4-(2-(((3S,4R)-3-methyltetrahydro-2H-pyran-4-yl)amino)-8-((2,4,6-trichlorophenyl)amino)-9H-purin-9-yl)cyclohexanecarboxylic acid (1 equiv.) in DMF (0.4 M) was added HATU (1 equiv.), DIEA (2 equiv.) and $NH_4Cl$ (3 equiv.) in one portion at room temperature. The mixture was stirred at room temperature for 24 h. Standard work-up and purification methods afforded (1S,4s)-1-methyl-4-(2-(((3S,4R)-3-methyltetrahydro-2H-pyran-4-yl)amino)-8-((2,4,6-trichlorophenyl)amino)-9H-purin-9-yl)cyclohexanecarboxamide (19%). $^1H$ NMR (400 MHz, Methanol-$d_4$) δ ppm: 7.99 (s, 1H), 7.61-7.48 (m, 2H), 4.51-4.40 (m, 1H), 4.05-3.96 (m, 1H), 3.94-3.90 (m, 1H), 3.80-3.64 (m, 2H), 3.32-3.23 (m, 1H), 2.88-2.69 (m, 2H), 2.48-2.33 (m, 2H), 2.01-1.98 (m, 1H), 1.84-1.73 (m, 3H), 1.59-1.36 (m, 3H), 1.25 (s, 3H), 0.92 (d, J=6.7 Hz, 3H). MS (ESI) m/z=566.2 $[M+H]^+$.

Example 43. (1S,4s)-4-(2-(((3S,4R)-3-Methyltetrahydro-2H-pyran-4-yl)amino)-8-((2,4,6-trifluorophenyl)amino)-9H-purin-9-yl)cyclohexane-1-carboxamide

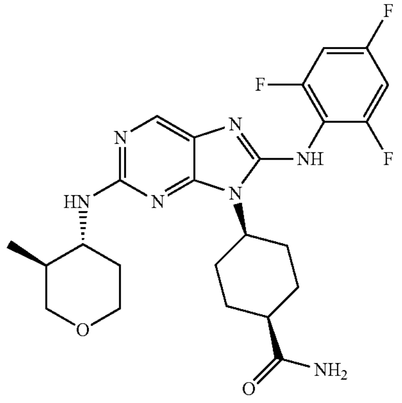 [SMILES: C[C@@H]1COCC[C@H]1Nc1ncc2nc(Nc3c(F)cc(F)cc3F)n([C@H]3CC[C@@H](C(N)=O)CC3)c2n1]

(1s,4s)-4-(2-(((3S,4R)-3-Methyltetrahydro-2H-pyran-4-yl)amino)-8-((2,4,6-trifluorophenyl)amino)-9H-purin-9-yl)cyclohexanecarboxamide To a mixture of (1S,4s)-4-((5-amino-2-(((3S,4R)-3-methyltetrahydro-2H-pyran-4-yl)amino)pyrimidin-4-yl)amino)cyclohexanecarboxamide (prepared as described herein) (1 equiv.) in DMF (0.2 M) was added 1,3,5-trifluoro-2-isothiocyanatobenzene (1.2 equiv.) in one portion. The mixture was stirred at room temperature for 3 h. DIC (2 equiv.) was added and stirring was continued at room temperature for 20 h. LCMS showed the reaction was complete. Standard work-up and purification methods afforded (1s,4s)-4-(2-(((3S,4R)-3-methyltetrahydro-2H-pyran-4-yl)amino)-8-((2,4,6-trifluorophenyl)amino)-9H-purin-9-yl)cyclohexanecarboxamide (47%). $^1H$ NMR (400 MHz, Methanol-$d_4$) δ ppm: 8.00 (s, 1H), 7.07-6.83 (m, 2H), 4.38 (s, 1H), 4.02-3.97 (m, 1H), 3.91 (dd, J=4.3, 11.5 Hz, 1H), 3.86-3.69 (m, 2H), 3.38-3.34 (m, 1H), 2.92 (d, J=11.4 Hz, 2H), 2.68 (s, 1H), 2.35 (d, J=12.5 Hz, 2H), 2.02 (s, 1H), 1.86-1.69 (m, 5H), 1.60-1.48 (m, 1H), 0.93 (d, J=6.5 Hz, 3H). MS (ESI) m/z=504.4 $[M+H]^+$.

Example 44. (1S,4s)-4-(8-((4-Chloro-2,6-difluoro-phenyl)amino)-2-(((3S,4R)-3-methyltetrahydro-2H-pyran-4-yl)amino)-9H-purin-9-yl)cyclohexane-1-carboxamide

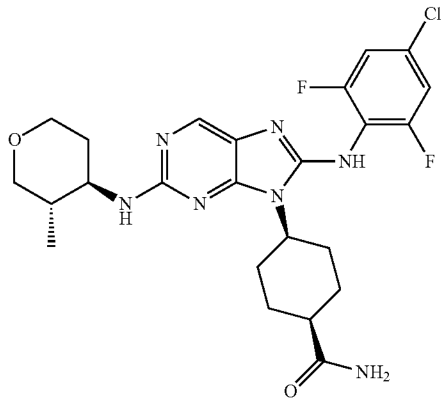 [SMILES: C[C@@H]1COCC[C@H]1Nc1ncc2nc(Nc3c(F)cc(Cl)cc3F)n([C@H]3CC[C@@H](C(N)=O)CC3)c2n1]

(1S,4s)-4-(8-((4-Chloro-2,6-difluorophenyl)amino)-2-(((3S,4R)-3-methyltetrahydro-2H-pyran-4-yl)amino)-9H-purin-9-yl)cyclohexanecarboxamide To a mixture of (1S,4s)-4-((5-amino-2-(((3S,4R)-3-methyltetrahydro-2H-pyran-4-yl)amino)pyrimidin-4-yl)amino)cyclohexanecarboxamide (prepared as described herein (1 equiv.) in DMF (0.09 M) was added 5-chloro-1,3-difluoro-2-isothiocyanatobenzene (prepared as described herein) (1.2 equiv.) in one portion. The mixture was stirred at room temperature for 8 h. DIC (2 equiv.) was added and stirring was continued at room temperature for 20 h. Standard work-up and purification methods afforded (1S,4s)-4-(8-((4-chloro-2,6-difluorophenyl)amino)-2-(((3S,4R)-3-methyltetrahydro-2H-pyran-4-yl)amino)-9H-purin-9-yl)cyclohexanecarboxamide (44%). $^1$H NMR (400 MHz, Methanol-$d_4$) δ ppm: 8.02 (s, 1H), 7.29-7.06 (m, 2H), 4.58-4.33 (m, 1H), 3.99 (d, J=7.9 Hz, 1H), 3.91 (dd, J=4.3, 11.5 Hz, 1H), 3.85-3.69 (m, 2H), 3.37 (s, 1H), 2.90 (s, 2H), 2.68 (s, 1H), 2.35 (d, J=12.5 Hz, 2H), 2.03 (d, J=12.8 Hz, 1H), 1.77 (d, J=11.8 Hz, 5H), 1.60-1.48 (m, 1H), 0.93 (d, J=6.7 Hz, 3H). MS (ESI) m/z=520.3 [M+H]$^+$.

Example 45. (1S,4s)-4-(8-((2,4-Dichloro-6-fluoro-phenyl)amino)-2-(((3S,4R)-3-methyltetrahydro-2H-pyran-4-yl)amino)-9H-purin-9-yl)cyclohexane-1-carboxamide

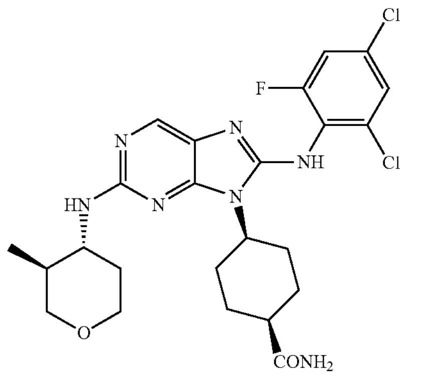 [SMILES: C[C@@H]1COCC[C@H]1Nc1ncc2nc(Nc3c(F)cc(Cl)cc3Cl)n([C@H]3CC[C@@H](C(N)=O)CC3)c2n1]

(1S,4s)-4-(8-((2,4-Dichloro-6-fluorophenyl)amino)-2-(((3S,4R)-3-methyltetrahydro-2H-pyran-4-yl)amino)-9H-purin-9-yl)cyclohexane-1-carboxamide To a solution (1S,4s)-4-((5-amino-2-(((3S,4R)-3-methyltetrahydro-2H-pyran-4-yl)amino)pyrimidin-4-yl)amino)cyclohexanecarboxamide (prepared as described herein (1 equiv.) in anhydrous DMF (0.2 M) was added 1,5-dichloro-3-fluoro-2-isothiocyanatobenzene (1 equiv., prepared as described herein). The reaction was stirred for 90 min at room temperature. DIC (2 equiv.) was added and stirring was continued at room temperature overnight. Standard work-up and purification methods afforded (1S,4s)-4-(8-((2,4-dichloro-6-fluorophenyl)amino)-2-(((3S,4R)-3-methyltetrahydro-2H-pyran-4-yl)amino)-9H-purin-9-yl)cyclohexane-1-carboxamide (40%). $^1$H NMR (400 MHz, Methanol-$d_4$) δ ppm: 8.00 (s, 1H), 7.63-7.20 (m, 2H), 4.45 (s, 1H), 3.99 (dd, J=11.36, 4.08 Hz, 1H), 3.91 (dd, J=11.48, 4.32 Hz, 1H), 3.86-3.66 (m, 2H), 3.32-3.25 (s, 1H), 3.01-2.77 (s, 2H), 2.67 (s, 1H), 2.35 (d, J=13.04 Hz, 2H), 2.02 (d, J=12.80 Hz, 1H), 1.88-1.64 (m, 5H), 1.62-1.44 (m, 1H), 0.93 (d, J=6.64 Hz, 3H). MS (ESI) m/z=536.2 [M+H]$^+$.

Example 46. (1s,4s)-4-(8-((4-Chloro-2,6-difluoro-phenyl)amino)-2-((tetrahydro-2H-pyran-4-yl)amino)-9H-purin-9-yl)-1-methylcyclohexane-1-carboxamide

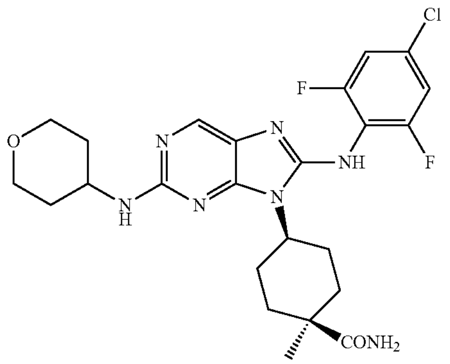 [SMILES: C[C@]1(C(N)=O)CC[C@@H](n2c(Nc3c(F)cc(Cl)cc3F)nc3cnc(NC4CCOCC4)nc32)CC1]

1,4-Dioxaspiro[4.5]decane-8-carbonitrile. To a −10° C. solution of 1,4 dioxaspiro[4.5]decan-8-one (1 equiv.), ethanol (1.78 equiv.) and toluenesulfonylmethyl isocyanide (1.3 equiv.) in DME (0.3 M) was added potassium 2-methylpropan-2-olate (2.3 equiv.) portion wise. The reaction was stirred at −10° C. for 1 h, and 15 h at room temperature. The reaction mixture was concentrated to a beige solid, dissolved in water and extracted with ether. The combined extracts were washed with brine and dried. Concentration under reduced pressure gave an orange oil. This material was purified by distillation [(103° C. (oil bath 150° C.) at about 2-3 mbar] to give 1,4-dioxaspiro[4.5]decan-8-one as a colorless oil (87% yield). $^1$H NMR (400 MHz, $CDCl_3$) δ ppm: 3.88-4.02 (m, 4H), 2.56-2.74 (m, 1H), 1.79-2.05 (m, 6H), 1.50-1.71 (m, 2H).

Methyl-4-oxo-cyclohexanecarbonitrile

To a 0° C. solution of 1,4-dioxaspiro[4.5]decane-8-carbonitrile (1 equiv.) in THF (0.5 M) was added 1 M lithium bis(trimethylsilyl)amide in THF (1.25 equiv.) dropwise. The resulting solution was stirred for 1 h at 0° C. before iodomethane (1.5 eq) was added. After 1 h stirring at 0° C., the reaction was stirred at room temperature for 15 h. The reaction mixture was quenched with saturated aqueous ammonium chloride and extracted with ethyl acetate. The organic phases were combined and washed with saturated aqueous sodium chloride. The organic layer was dried over anhydrous $MgSO_4$, filtered, and concentrated. The crude product was stirred with hydrochloric acid (2 equiv.) in acetone (0.3 M) at 25° C. for 5 h. The reaction mixture was cooled to 0° C. and the pH was adjusted to 8 with 3N sodium hydroxide. The mixture was extracted with ether. The organic portions were combined, dried over $MgSO_4$, and concentrated. The crude product was purified by silica gel column chromatography to afford 1-methyl-4-oxo-cyclohexanecarbonitrile as a white solid (56% yield). $^1H$ NMR (400 MHz, DMSO-$d_6$) δ ppm: 2.41-2.48 (m, 2H), 2.23-2.34 (m, 2H), 2.09-2.23 (m, 2H), 1.86 (td, J=13.18, 4.49 Hz, 2H), 1.37-1.47 (m, 3H). MS (ESI) m/z 138.3 $[M+H]^+$.

(1s,4s)-4-(Benzylamino)-1-methylcyclohexanecarbonitrile

To a solution of 1-methyl-4-oxocyclohexanecarbonitrile (1 equiv.) in MeOH (0.5 M) was added phenylmethanamine (3 equiv.). The resulting solution was stirred for 2 h at room temperature. The solution was cooled to −78° C. and lithium borohydride (2M in THF, 1.1 equiv.) was added dropwise. The solution was allowed to slowly warm to room temperature overnight. After 12 h, the reaction mixture was quenched with saturated aqueous sodium bicarbonate and extracted with ethyl acetate. The organic phase was combined and washed with saturated aqueous sodium bicarbonate. The organic layer was dried over $MgSO_4$, filtered, and concentrated. The crude product was purified to afford the title compound ((1s,4s)-4-(benzylamino)-1-methylcyclohexanecarbonitrile as a white solid (8:1 cis:trans). $^1H$ NMR (400 MHz, $CHCl_3$) δ ppm: 7.29-7.40 (m, 4H), 7.23-7.28 (m, 1H), 3.83 (s, 2H), 2.46 (tt, J 10.98, 3.66 Hz, 1H), 1.95-2.06 (m, 4H), 1.45-1.58 (m, 2H), 1.23-1.40 (m, 5H). MS (ESI) m/z 229.2 $[M+H]^+$.

(1s,4s)-4-(Benzylamino)-1-methylcyclohexane-1-carboxamide

To a solution of (1s,4s)-4-(benzylamino)-1-methylcyclohexanecarbonitrile (1 equiv.) in 1,4-dioxane (4.75 M) was added sulfuric acid 95-98% (5 equiv.). The reaction was stirred at 100° C. for 2 h. The reaction mixture was cooled to room temperature and quenched with saturated aqueous sodium bicarbonate and adjusted to pH to 8 with sodium carbonate. The solution was extracted with DCM/MeOH. The organic phases were combined, and washed with saturated aqueous sodium bicarbonate. The organic layer was dried over sodium sulfate, filtered, and concentrated. The crude product was purified by silica gel column chromatography to afford an 8/1 mixture of diastereomers of (1s,4s)-4-(benzylamino)-1-methylcyclohexane-1-carboxamide as a white solid (83% yield). $^1H$ NMR (400 MHz, DMSO-$d_6$) δ ppm: 7.25-7.35 (m, 4H), 7.14-7.24 (m, 1H), 7.08 (s, 1H), 6.77 (s, 1H), 3.69 (s, 2H), 2.24-2.35 (m, 1H), 2.07 (d, J=12.50 Hz, 2H), 1.63-1.75 (m, 2H), 0.92-1.17 (m, 7H). MS (ESI) m/z 247.2 $[M+H]^+$.

(1s,4s)-4-Amino-1-methylcyclohexane-1-carboxamide

To a solution of (1s,4s)-4-(benzylamino)-1-methylcyclohexanecarboxamide (1 equiv.) in MeOH (0.5 M) was added Pd/C (0.015 equiv, 10% by wt.). The solution was stirred under hydrogen (1 atm) at room temperature for 15 h. The reaction mixture was filtered through celite and concentrated to afford (1s,4s)-4-amino-1-methylcyclohexane-1-carboxamide as a white solid (100%). $^1H$ NMR (400 MHz, DMSO-$d_6$) δ ppm: 7.07 (br. s., 1H), 6.75 (br. s., 1H), 2.38-2.48 (m, 1H), 1.97-2.13 (m, 2H), 1.45-1.60 (m, 2H), 0.96-1.11 (m, 7H). MS (ESI) m/z=157.2 $[M+H]^+$.

(1s,4s)-4-((2-Chloro-5-nitropyrimidin-4-yl)amino)-1-methylcyclohexane-1-carboxamide To a −78° C. solution of (1s,4s)-4-amino-1-methylcyclohexanecarboxamide (1 equiv), DIEA (1.5 equiv.) in DCM (0.5 M) was added the suspension of 2,4-dichloro-5-nitropyrimidine (1.0 equiv.) in THF (1.5 M) dropwise. The reaction was stirred at −78° C. for 1 h, and allowed to warm up to room temperature over 2 h. The reaction was stirred for another h at room temperature. The reaction mixture was concentrated. The crude was purified by silica gel column chromatography. The resulting solid was triturated several times in ethyl acetate to afford (1s,4s)-4-((2-chloro-5-nitropyrimidin-4-yl)amino)-1-methylcyclohexane-1-carboxamide as yellow solid (65% yield). $^1H$ NMR (400 MHz, DMSO-$d_6$) δ ppm: 8.54 (d, J=8.20 Hz, 1H), 7.18 (s, 1H), 6.86 (s, 1H), 3.98-4.15 (m, 1H), 2.16 (d, J=13.28 Hz, 2H), 1.73 (dd, J=12.69, 3.32 Hz, 2H), 1.50-1.65 (m, 2H), 1.16-1.28 (m, 2H), 1.06 (s, 3H). MS (ESI) m/z=314.0 $[M+H]^+$.

(1s,4s)-1-Methyl-4-((5-nitro-2-((tetrahydro-2H-pyran-4-yl)amino)pyrimidin-4-yl)amino)cyclohexane-1-carboxamide (1s,4s)-4-((2-chloro-5-nitropyrimidin-4-yl)amino)-1-methylcyclohexane-1-carboxamide (1 equiv.) and tetrahydro-2H-pyran-4-amine hydrochloride (1 equiv.) were slurried in THF (0.06 M) at room temperature. DIEA (4 equiv.) was added and the reaction was stirred at 50° C. overnight. The reaction mixture volume was reduced in vacuo and used directly in the next step.

(1s,4s)-4-((5-Amino-2-((tetrahydro-2H-pyran-4-yl)amino)pyrimidin-4-yl)amino)-1-methylcyclohexane-1-carboxamide To a MeOH solution (0.05 M) of (1s,4s)-1-methyl-4-((5-nitro-2-((tetrahydro-2H-pyran-4-yl)amino)pyrimidin-4-yl)amino)cyclohexane-1-carboxamide (1 equiv.) was added Pd/C (0.1 equiv, 10% Pd by wt.). The reaction was stirred under 1 atm of $H_2$ overnight. The reaction was filtered through celite and the filtrate was reduced in vacuo to afford (1s,4s)-4-((5-amino-2-((tetrahydro-2H-pyran-4-yl)amino)pyrimidin-4-yl)amino)-1-methylcyclohexanecarboxamide (91% yield). MS (ESI) m/z=349.3$[M+1]^+$.

(1s,4s)-4-(8-((4-Chloro-2,6-difluorophenyl)amino)-2-((tetrahydro-2H-pyran-4-yl)amino)-9H-purin-9-yl)-1-methylcyclohexane-1-carboxamide To a (1s,4s)-4-((5-amino-2-((tetrahydro-2H-pyran-4-yl)amino)pyrimidin-4-yl)amino)-1-methylcyclohexanecarboxamide (1 equiv.) solution of DMF (0.15 M) was added 5-chloro-1,3-difluoro-2-isothiocyanatobenzene (prepared as described herein) (1.09 equiv.) to give a yellow solution. The solution was stirred at room temperature for 1 h. To the reaction mixture was added EDC (1.09 equiv.) and the mixture was heated at 50° C. for 1.5 h. Standard work-up and purification methods afforded (1s,4s)-4-(8-((4-chloro-2, 6-difluorophenyl)amino)-2-((tetrahydro-2H-pyran-4-yl) amino)-9H-purin-9-yl)-1-methylcyclohexanecarboxamide (38%). $^1$H NMR (400 MHz, DMSO-$d_6$) δ ppm: 7.59 (s, 1H) 7.43 (d, J=7.81 Hz, 1H) 7.21-7.30 (m, 1H) 7.10-7.21 (m, 1H) 6.67 (d, J=8.20 Hz, 1H) 6.49 (d, J=7.03 Hz, 1H) 4.17-4.44 (m, 1H) 3.71-3.86 (m, 3H) 3.42-3.62 (m, 2H) 2.49-2.67 (m, 1H) 2.26 (t, J=12.89 Hz, 2H) 1.72-1.88 (m, 2H) 1.61 (d, J=10.54 Hz, 1H) 1.54 (d, J=10.54 Hz, 1H) 1.33-1.47 (m, 2H) 1.11-1.27 (m, 2H) 0.95-1.09 (m, 3H). MS (ESI) m/z=520.2 $[M]^+$.

Example 47. (1R,4s)-4-(2-(((S)-1-Hydroxypropan-2-yl)amino)-8-((2,4,6-trichlorophenyl)amino)-9H-purin-9-yl)-1-methylcyclohexane-1-carboxamide

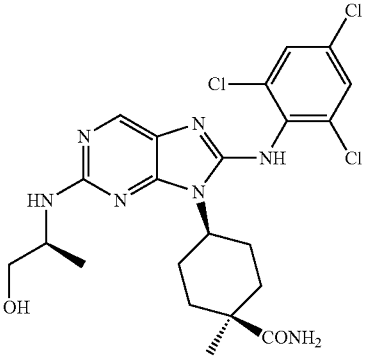 [SMILES: C[C@@H](CO)Nc1ncc2nc(Nc3c(Cl)cc(Cl)cc3Cl)n([C@H]3CC[C@@](C)(C(N)=O)CC3)c2n1]

(1R,4s)-4-((2-(((S)-1-Hydroxypropan-2-yl)amino)-5-nitropyrimidin-4-yl)amino)-1-methylcyclohexane-1-carboxamide (1s,4s)-4-((2-Chloro-5-nitropyrimidin-4-yl)amino)-1-methylcyclohexane-1-carboxamide (1 equiv.) and (S)-2-aminopropan-1-ol (1.03 equiv.) were slurried in THF (0.3 M) and DIEA (4 equiv.) was added. The reaction was stirred at 50° C. overnight. The reaction mixture was concentrated and used without further purification.

(1R,4s)-4-((5-amino-2-(((S)-1-hydroxypropan-2-yl) amino)pyrimidin-4-yl)amino)-1-methylcyclohexane-1-carboxamide To a solution of (1R,4s)-4-((2-(((S)-1-hydroxypropan-2-yl)amino)-5-nitropyrimidin-4-yl)amino)-1-methylcyclohexane-1-carboxamide (1 equiv.) in MeOH (0.1 M) was added Pd/C (0.1 equiv., 10% Pd by wt.) and the reaction was purged in vacuo followed by $H_2$. The reaction was stirred at room temperature under $H_2$. The reaction was filtered through celite and concentrated to afford (1R,4s)-4-((5-amino-2-(((S)-1-hydroxypropan-2-yl)amino)pyrimidin-4-yl)amino)-1-methylcyclohexane-1-carboxamide (99%). MS (ESI) m/z=323.4$[M+1]^+$.

(1R,4s)-4-(2-(((S)-1-Hydroxypropan-2-yl)amino)-8-((2,4,6-trichlorophenyl)amino)-9H-purin-9-yl)-1-methylcyclohexane-1-carboxamide (1R,4s)-4-((5-Amino-2-(((S)-1-hydroxypropan-2-yl) amino)pyrimidin-4-yl)amino)-1-methylcyclohexane-1-carboxamide (1 equiv.) and 1,3,5-trichloro-2-isothiocyanatobenzene (1.1 equiv.) in DMF (0.15 M) were stirred at room temperature for 1 h. To this reaction, EDC (2 equiv.) was added and the mixture was heated to 50° C. for 1.5 h. Standard work-up and purification methods afforded (1R, 4s)-4-(2-(((S)-1-hydroxypropan-2-yl)amino)-8-((2,4,6-trichlorophenyl)amino)-9H-purin-9-yl)-1-methylcyclohexane-1-carboxamide (28%). $^1$H NMR (400 MHz, DMSO-$d_6$) δ ppm: 7.51-7.64 (m, 2H), 7.25 (br.s., 1H), 6.81 (s, 1H), 6.12 (d, J=6.31 Hz, 1H), 4.70 (t, J=5.99 Hz, 1H), 4.39 (t, J=3.94 Hz, 1H), 3.77-3.93 (m, 1H), 3.42-3.57 (m, 1H), 3.21-3.30 (m, 1H), 2.58-2.73 (m, 3H), 2.29 (t, J=10.56 Hz, 1H), 1.63 (br. s., 1H), 1.20-1.35 (m, 2H), 1.11-1.19 (m, 2H), 1.09 (s, 2H). MS (ESI) m/z=527 $[M+H]^+$.

Example 48. (1R,4s)-4-(8-((2,4-Dichloro-6-fluorophenyl)amino)-2-(((S)-1-hydroxypropan-2-yl) amino)-9H-purin-9-yl)-1-methylcyclohexane-1-carboxamide

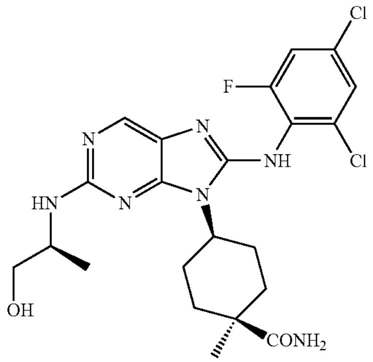 [SMILES: C[C@@H](CO)Nc1ncc2nc(Nc3c(F)cc(Cl)cc3Cl)n([C@H]3CC[C@@](C)(C(N)=O)CC3)c2n1]

(1R,4s)-4-(8-((2,4-Dichloro-6-fluorophenyl)amino)-2-(((S)-1-hydroxypropan-2-yl)amino)-9H-purin-9-yl)-1-methylcyclohexane-1-carboxamide ((1R,4s)-4-((5-Amino-2-(((S)-1-hydroxypropan-2-yl) amino)pyrimidin-4-yl)amino)-1-methylcyclohexane-1-carboxamide 1 equiv., prepared as disclosed herein) and 1,5-dichloro-3-fluoro-2-isothiocyanatobenzene (prepared as described herein) (1.1 equiv.) were stirred in DMF (0.15 M) for 1 h. EDC (2 equiv.) was added to the reaction mixture and stirring was continued at 50° C. for 1.5 h. Standard work-up and purification methods afforded (1R,4s)-4-(8-((2, 4-dichloro-6-fluorophenyl)amino)-2-(((S)-1-hydroxypropan-2-yl)amino)-9H-purin-9-yl)-1-methylcyclohexane-1-carboxamide (22%). $^1$H NMR (500 MHz, DMSO-$d_6$) δ ppm: 7.52-7.64 (m, 1H) 7.36-7.49 (m, 1H) 7.26 (br. s., 1H) 6.74-6.93 (m, 1H) 6.12 (br. s., 1H) 4.67-4.81 (m, 1H) 4.28-4.49 (m, 1H) 3.86 (dt, J=12.53, 6.50 Hz, 1H) 3.45-3.63 (m, 1H) 3.21-3.28 (m, 1H) 2.72 (d, J=17.65 Hz, 1H) 2.56-2.69 (m, 2H) 2.18-2.33 (m, 1H) 1.60 (br. s., 2H) 1.19-1.32 (m, 2H) 1.07-1.19 (m, 4H). MS (ESI) m/z=510.2 $[M+H]^+$.

Example 49. (1R,4s)-4-(8-((2,6-Dichloro-4-cyanophenyl)amino)-2-(((S)-1-hydroxypropan-2-yl)amino)-9H-purin-9-yl)-1-methylcyclohexane-1-carboxamide

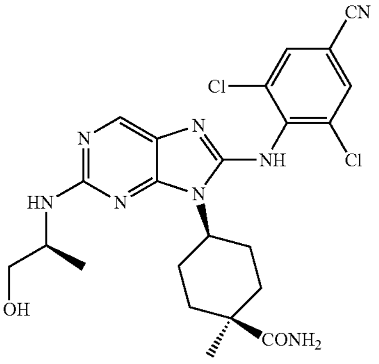 [SMILES: C[C@@H](CO)Nc1ncc2nc(Nc3c(Cl)cc(C#N)cc3Cl)n([C@H]3CC[C@@](C)(C(N)=O)CC3)c2n1]

(1R,4s)-4-(8-((2,6-Dichloro-4-cyanophenyl)amino)-2-(((S)-1-hydroxypropan-2-yl)amino)-9H-purin-9-yl)-1-methylcyclohexane-1-carboxamide ((1R,4s)-4-((5-Amino-2-(((S)-1-hydroxypropan-2-yl)amino)pyrimidin-4-yl)amino)-1-methylcyclohexane-1-carboxamide (1 equiv., prepared as disclosed herein) and 3,5-dichloro-4-isothiocyanatobenzonitrile (1.1 equiv.) were stirred in DMF (0.15 M). The solution was stirred at room temperature for 1 h. EDC (2 equiv.) was added to the reaction mixture, and the reaction was stirred at 50° C. for 1.5 h. Standard work-up and purification methods afforded (1R,4s)-4-(8-((2,6-dichloro-4-cyanophenyl)amino)-2-(((S)-1-hydroxypropan-2-yl)amino)-9H-purin-9-yl)-1-methylcyclohexane-1-carboxamide (6%). $^1$H NMR (500 MHz, DMSO-$d_6$) δ ppm: 8.01 (s, 1H) 7.68 (s, 1H) 7.25 (br. s., 1H) 6.82 (s, 1H) 6.21 (br. s., 1H) 4.71 (t, J=5.99 Hz, 1H) 4.31-4.48 (m, 1H) 3.77-3.92 (m, 1H) 3.53 (dt, J=10.40, 4.89 Hz, 1H) 3.20-3.30 (m, 1H) 2.53-2.74 (m, 3H) 2.28 (t, J=10.56 Hz, 1H) 1.62 (br. s., 1H) 1.20-1.34 (m, 1H) 1.10-1.20 (m, 2H) 1.09 (s, 2H). MS (ESI) m/z=5172 $[M+H]^+$.

Example 50. (1S,4s)-4-(8-((2,6-Dichloro-4-cyanophenyl)amino)-2-(((3S,4R)-3-fluorotetrahydro-2H-pyran-4-yl)amino)-9H-purin-9-yl)-1-methylcyclohexane-1-carboxamide

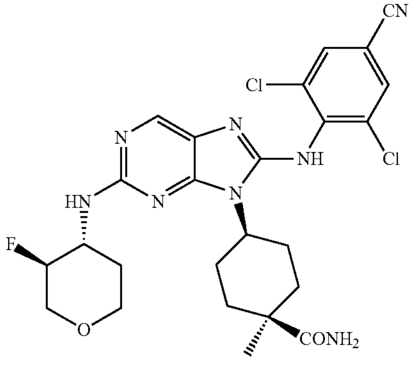 [SMILES: C[C@]1(C(N)=O)CC[C@@H](n2c(Nc3c(Cl)cc(C#N)cc3Cl)nc3cnc(N[C@@H]4CCOC[C@H]4F)nc32)CC1]

(1S,4s)-4-((2-(((3S,4R)-3-Fluorotetrahydro-2H-pyran-4-yl)amino)-5-nitropyrimidin-4-yl)amino)-1-methylcyclohexane-1-carboxamide To a mixture of (1s,4s)-4-((2-chloro-5-nitropyrimidin-4-yl)amino)-1-methylcyclohexane-1-carboxamide (1.00 equiv.) and (3S,4R)-3-fluorotetrahydro-2H-pyran-4-amine hydrochloride (1.02 equiv.) in DMF (0.3 M) was added DIEA (2.2 equiv.). The mixture was stirred at 30° C. for 16 h. The mixture was diluted with $H_2O$ and extracted with ethyl acetate. The combined organic phase was washed with saturated brine, dried over anhydrous $Na_2SO_4$, filtered and concentrated in vacuum to afford (1S,4s)-4-((2-(((3S,4R)-3-fluorotetrahydro-2H-pyran-4-yl)amino)-5-nitropyrimidin-4-yl)amino)-1-methylcyclohexane-1-carboxamide (99% yield) as a yellow solid. The crude product was used without further purification. MS (ESI) m/z=397.1 $[M+H]^+$.

(1S,4s)-4-((5-Amino-2-(((3S,4R)-3-fluorotetrahydro-2H-pyran-4-yl)amino)pyrimidin-4-yl)amino)-1-methylcyclohexane-1-carboxamide To a solution of (1S,4s)-4-((2-(((3S,4R)-3-fluorotetrahydro-2H-pyran-4-yl)amino)-5-nitropyrimidin-4-yl)amino)-1-methylcyclohexane-1-carboxamide (1.0 equiv.) in MeOH (0.25 M) was added Pd/C (0.1 equiv, 10% Pd by wt.). The suspension was degassed under vacuum and purged with $H_2$ several times. The reaction was stirred under $H_2$ balloon (15 psi) at 30° C. for 2 h. The mixture was filtered and concentrated in vacuum to afford (1S,4s)-4-((5-amino-2-(((3S,4R)-3-fluorotetrahydro-2H-pyran-4-yl)amino)pyrimidin-4-yl)amino)-1-methylcyclohexane-1-carboxamide (90%) as a violet solid. The crude product was used directly in the next step without further purification. MS (ESI) m/z=367.2 $[M+H]^+$.

(1S,4s)-4-(8-((2,6-Dichloro-4-cyanophenyl)amino)-2-(((3S,4R)-3-fluorotetrahydro-2H-pyran-4-yl)amino)-9H-purin-9-yl)-1-methylcyclohexane-1-carboxamide To a solution of (1S,4s)-4-((5-amino-2-(((3S,4R)-3-fluorotetrahydro-2H-pyran-4-yl)amino)pyrimidin-4-yl)amino)-1-methylcyclohexane-1-carboxamide (1 equiv.) in DMF (0.14 M) was added 3,5-dichloro-4-isothiocyanatobenzonitrile (1.00 equiv) (prepared as described herein). The mixture was stirred at 30° C. for 2 h. DIC (2 equiv.) was added and the mixture was stirred at 30° C. for 16 h. The mixture was diluted with $H_2O$ and extracted with ethyl acetate. The combined organic phases were washed with saturated brine, dried over anhydrous $Na_2SO_4$, filtered and concentrated in vacuo. Standard work-up and purification methods afforded (1S,4s)-4-(8-((2,6-dichloro-4-cyanophenyl)amino)-2-(((3S,4R)-3-fluorotetrahydro-2H-pyran-4-yl)amino)-9H-purin-9-yl)-1-methylcyclohexane-1-carboxamide (64%). $^1$H NMR (400 MHz, Methanol-$d_4$) δ ppm: 7.82 (s, 2H), 7.60 (s, 1H), 4.62-4.45 (m, 2H), 4.27-4.17 (m, 1H), 4.11-4.05 (m, 1H), 3.93-3.90 (m, 1H), 3.74-3.69 (m, 1H), 3.62-3.56 (m, 1H), 2.79-2.73 (m, 2H), 2.41-2.38 (m, 2H), 2.23-2.20 (m, 1H), 1.84-1.81 (m, 2H), 1.68-1.61 (m, 1H), 1.45-1.39 (m, 2H), 1.25 (s, 3H). MS (ESI) m/z=561.1 $[M+H]^+$.

Example 51. (1S,4s)-4-(8-((2,4-dichloro-6-fluorophenyl)amino)-2-(((3S,4R)-3-methyltetrahydro-2H-pyran-4-yl)amino)-9H-purin-9-yl)-1-methylcyclohexane-1-carboxamide

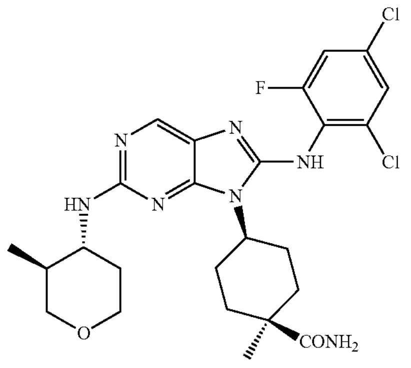

Ethyl (1S,4s)-1-methyl-4-((2-(((3S,4R)-3-methyltetrahydro-2H-pyran-4-yl)amino)-5-nitropyrimidin-4-yl)amino)cyclohexane-1-carboxylate To a mixture of ethyl (1s,4s)-4-((2-chloro-5-nitropyrimidin-4-yl)amino)-1-methylcyclohexane-1-carboxylate (1 equiv.) and (3S,4R)-3-methyltetrahydro-2H-pyran-4-amine hydrochloride (1.05 equiv.) in DMF (0.4 M) was added DIEA (2.3 equiv.) in one portion at room temperature under $N_2$. The mixture was stirred at room temperature for 16 h. The reaction was diluted with water, and extracted with ethyl acetate. The combined organic layers were dried over $Na_2SO_4$, filtered and concentrated to give ethyl (1S,4s)-1-methyl-4-((2-(((3S,4R)-3-methyltetrahydro-2H-pyran-4-yl)amino)-5-nitropyrimidin-4-yl)amino)cyclohexane-1-carboxylate (98%). MS (ESI) m/z 422.2 $[M+1]^+$.

Ethyl (1S,4s)-4-((5-amino-2-(((3S,4R)-3-methyltetrahydro-2H-pyran-4-yl)amino)pyrimidin-4-yl)amino)-1-methylcyclohexane-1-carboxylate To a solution of ethyl (1S,4s)-1-methyl-4-((2-(((3S,4R)-3-methyltetrahydro-2H-pyran-4-yl)amino)-5-nitropyrimidin-4-yl)amino)cyclohexane-1-carboxylate (1 equiv.) in MeOH (0.2 M) was added Pd/C (0.1 equiv, 10% Pd by wt.) under $N_2$. The suspension was degassed under vacuum and purged with $H_2$ several times. The mixture was stirred under $H_2$ at room temperature overnight. The reaction mixture was filtered through a pad of celite and the filtrate was concentrated to give ethyl (1S,4s)-4-((5-amino-2-(((3S,4R)-3-methyltetrahydro-2H-pyran-4-yl)amino)pyrimidin-4-yl)amino)-1-methylcyclohexane-1-carboxylate (99%).

Ethyl (1S,4s)-4-(8-((2,4-dichloro-6-fluorophenyl)amino)-2-(((3S,4R)-3-methyltetrahydro-2H-pyran-4-yl)amino)-9H-purin-9-yl)-1-methylcyclohexane-1-carboxylate To a mixture of ethyl (1S,4s)-4-((5-amino-2-(((3S,4R)-3-methyltetrahydro-2H-pyran-4-yl)amino)pyrimidin-4-yl)amino)-1-methylcyclohexane-1-carboxylate (1 equiv.) in DMF (0.1 M) was added 1,5-dichloro-3-fluoro-2-isothiocyanatobenzene (prepared as described herein) (1 equiv.). The mixture was stirred at 15-20° C. for 1.5 h. DIC (2 equiv.) was added to the reaction in one portion. The mixture was stirred at room temperature for 16 h. The reaction was diluted with water, extracted with ethyl acetate, dried over $Na_2SO_4$, filtered and concentrated. The resulted residue was purified via column chromatography to give ethyl (1S,4s)-4-(8-((2,4-dichloro-6-fluorophenyl)amino)-2-(((3S,4R)-3-methyltetrahydro-2H-pyran-4-yl)amino)-9H-purin-9-yl)-1-methylcyclohexane-1-carboxylate (90%) as a yellow solid.

(1S,4s)-4-(8-((2,4-Dichloro-6-fluorophenyl)amino)-2-(((3S,4R)-3-methyltetrahydro-2H-pyran-4-yl)amino)-9H-purin-9-yl)-1-methylcyclohexane-1-carboxylic acid To a solution of ethyl (1S,4s)-4-(8-((2,4-dichloro-6-fluorophenyl)amino)-2-(((3S,4R)-3-methyltetrahydro-2H-pyran-4-yl)amino)-9H-purin-9-yl)-1-methylcyclohexane-1-carboxylate (1 equiv.) in MeOH/water (0.2M. 4/1) was added NaOH (3 equiv). The reaction was refluxed for 48 h. The reaction was concentrated, diluted with water, and extracted with ethyl acetate. The aqueous phase was acidified with 3 M HCl to pH=3-5, extracted with DCM, the organic layer was dried over $Na_2SO_4$, filtered and concentrated to give (1S,4s)-4-(8-((2,4-dichloro-6-fluorophenyl)amino)-2-(((3S,4R)-3-methyltetrahydro-2H-pyran-4-yl)amino)-9H-purin-9-yl)-1-methylcyclohexane-1-carboxylic acid (53%) as a yellow solid. $^1H$ NMR (400 MHz, Methanol-$d_4$) δ ppm: 7.70 (s, 1H), 7.47-7.31 (m, 2H), 4.02-3.75 (m, 4H), 3.42-3.37 (m, 1H), 2.27-2.61 (m, 1H), 2.45-2.41 (m, 2H), 1.98-1.91 (m, 3H), 1.85-1.81 (m, 1H), 1.70-1.60 (m, 1H), 1.51-1.43 (m, 2H), 1.29 (s, 3H), 0.94 (d, J=8.0 Hz, 3H).

(1S,4s)-4-(8-((2,4-dichloro-6-fluorophenyl)amino)-2-(((3S,4R)-3-methyltetrahydro-2H-pyran-4-yl)amino)-9H-purin-9-yl)-1-methylcyclohexane-1-carboxamide To a mixture of (1S,4s)-4-(8-((2,4-dichloro-6-fluorophenyl)amino)-2-(((3S,4R)-3-methyltetrahydro-2H-pyran-4-yl)amino)-9H-purin-9-yl)-1-methylcyclohexanecarboxylic acid (1 equiv.) in DMF (0.19 M) were added HATU (1.1 equiv.), TEA (1.1 equiv.) and $NH_4Cl$ (1.1 equiv.) in one portion at room temperature. The mixture was stirred at room temperature for 24 h. Standard work-up and purification methods afforded (1S,4s)-4-(8-((2,4-dichloro-6-fluorophenyl)amino)-2-(((3S,4R)-3-methyltetrahydro-2H-pyran-4-yl)amino)-9H-purin-9-yl)-1-methylcyclohexane-1-carboxamide (37%). $^1H$ NMR (400 MHz, $CHCl_3$) δ ppm: 7.87 (s, 1H), 7.47-7.30 (m, 2H), 4.40-4.34 (m, 1H), 4.02-3.98 (m, 1H), 3.94-3.90 (m, 1H), 3.76-3.70 (m, 2H), 2.80-2.67 (m, 2H), 2.46-2.34 (m, 2H), 2.03-1.95 (m, 1H), 1.88-1.78 (m, 2H), 1.77-1.70 (m, 1H), 1.61-1.41 (m, 3H), 1.25 (s, 3H), 0.92 (d, J=8.0 Hz, 3H). MS (ESI) m/z=550.2 $[M+H]^+$.

Example 52. (1R,4s)-4-(8-((2-Chloro-4,6-difluorophenyl)amino)-2-(((3S,4S)-3-fluorotetrahydro-2H-pyran-4-yl)amino)-9H-purin-9-yl)-1-methylcyclohexane-1-carboxamide

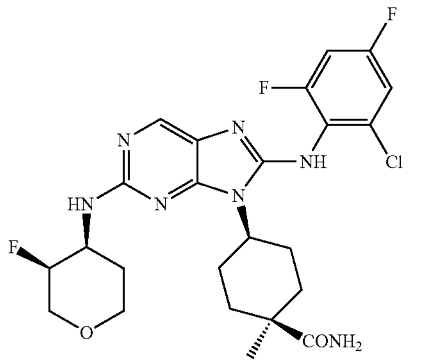 [SMILES: C[C@]1(C(N)=O)CC[C@@H](n2c(Nc3c(F)cc(F)cc3Cl)nc3cnc(N[C@H]4CCOC[C@H]4F)nc32)CC1]

Ethyl (1R,4s)-4-((2-(((3S,4S)-3-fluorotetrahydro-2H-pyran-4-yl)amino)-5-nitropyrimidin-4-yl)amino)-1-methylcyclohexane-1-carboxylate To a mixture of ethyl (1s,4s)-4-((2-chloro-5-nitropyrimidin-4-yl)amino)-1-methylcyclohexane-1-carboxylate (1 equiv., prepared as described herein) and (3S,4S)-3-fluorotetrahydro-2H-pyran-4-amine hydrochloride (1.1 equiv., prepared as described herein) in DMF (0.1 M) was added DIEA (3 equiv.), and the reaction stirred at room temperature for 16 h. The reaction was diluted with water, and extracted with ethyl acetate. The combined organic solvents were dried over $Na_2SO_4$, filtered and concentrated to give ethyl (1R,4s)-4-((2-(((3S,4 S)-3-fluorotetrahydro-2H-pyran-4-yl)amino)-5-nitropyrimidin-4-yl)amino)-1-methylcyclohexane-1-carboxylate (96%). MS (ESI) m/z=426.2 $[M+H]^+$.

Ethyl (1R,4s)-4-((5-amino-2-(((3S,4S)-3-fluorotetrahydro-2H-pyran-4-yl)amino)pyrimidin-4-yl)amino)-1-methylcyclohexane-1-carboxylate To a solution of ethyl (1R,4s)-4-((2-(((3S,4S)-3-fluorotetrahydro-2H-pyran-4-yl)amino)-5-nitropyrimidin-4-yl)amino)-1-methylcyclohexane-1-carboxylate (1 equiv.) in MeOH (0.2 M) was added Pd/C (0.1 equiv., 10% Pd by wt.) under $N_2$ atmosphere. The suspension was degassed under vacuum and purged with $H_2$ several times. The reaction was stirred under a $H_2$ balloon at room temperature for 16 h. The reaction was filtered through a pad of celite and concentrated to give ethyl (1R,4s)-4-((5-amino-2-(((3S,4S)-3-fluorotetrahydro-2H-pyran-4-yl)amino)pyrimidin-4-yl)amino)-1-methylcyclohexane-1-carboxylate (95%) as a purple solid. MS (ESI) m/z=396.2 $[M+H]^+$.

Ethyl (1R,4s)-4-(8-((2-chloro-4,6-difluorophenyl)amino)-2-(((3S,4S)-3-fluorotetrahydro-2H-pyran-4-yl)amino)-9H-purin-9-yl)-1-methylcyclohexane-1-carboxylate To a solution of ethyl (1R,4s)-4-((5-amino-2-(((3S,4S)-3-fluorotetrahydro-2H-pyran-4-yl)amino)pyrimidin-4-yl)amino)-1-methylcyclohexane-1-carboxylate (1 equiv.) in DMF (0.4 M) was added 1-chloro-3,5-difluoro-2-isothiocyanatobenzene (1 equiv.). The solution was stirred at room temperature for 90 min. DIC (2 equiv.) was added at room temperature and the reaction mixture was stirred for 18 h. The reaction was diluted with water, extracted with ethyl acetate, dried over $Na_2SO_4$, filtered and concentrated. The resulting residue was purified by column chromatography to give ethyl (1R,4s)-4-(8-((2-chloro-4,6-difluorophenyl)amino)-2-(((3S,4S)-3-fluorotetrahydro-2H-pyran-4-yl)amino)-9H-purin-9-yl)-1-methylcyclohexane-1-carboxylate (86%) as a yellow solid. MS (ESI) m/z=567.2 $[M+H]^+$.

(1R,4s)-4-(8-((2-chloro-4,6-difluorophenyl)amino)-2-(((3S,4S)-3-fluorotetrahydro-2H-pyran-4-yl)amino)-9H-purin-9-yl)-1-methylcyclohexane-1-carboxylic acid To a solution of ethyl (1R,4s)-4-(8-((2-chloro-4,6-difluorophenyl)amino)-2-(((3S,4 S)-3-fluorotetrahydro-2H-pyran-4-yl)amino)-9H-purin-9-yl)-1-methylcyclohexane-1-carboxylate (1 equiv.) in MeOH/water (0.1 M, 4/1) was added NaOH (5 equiv). The reaction was refluxed for 48 h. The reaction was diluted with water, and extracted with ethyl acetate. The aqueous phase was adjusted with 3 M HCl to pH=3-5, extracted with DCM, the organic layer was dried over $Na_2SO_4$, filtered and concentrated to give (1R,4s)-4-(8-((2-chloro-4,6-difluorophenyl)amino)-2-(((3S,4S)-3-fluorotetrahydro-2H-pyran-4-yl)amino)-9H-purin-9-yl)-1-methylcyclohexane-1-carboxylic acid (51%) as a yellow solid. $^1H$ NMR (400 MHz, Methanol-$d_4$) δ ppm: 7.86 (s, 1H), 7.39-6.92 (m, 2H), 4.84-4.71 (m, 1H), 4.58-4.43 (m, 1H), 4.41-4.25 (m, 1H), 4.20-4.13 (m, 1H), 4.06-3.77 (m, 3H), 2.74-2.67 (m, 2H), 2.46-2.33 (m, 2H), 2.01-1.81 (m, 4H), 1.51-1.44 (m, 2H), 1.30 (s, 3H).

(1R,4s)-4-(8-((2-Chloro-4,6-difluorophenyl)amino)-2-(((3S,4S)-3-fluorotetrahydro-2H-pyran-4-yl)amino)-9H-purin-9-yl)-1-methylcyclohexane-1-carboxamide To a mixture of (1R,4s)-4-(8-((2-chloro-4,6-difluorophenyl)amino)-2-(((3S,4 S)-3-fluorotetrahydro-2H-pyran-4-yl)amino)-9H-purin-9-yl)-1-methylcyclohexane-1-carboxylic acid (1 equiv.) in DMF (0.1 M) was added HATU (1.1 equiv.), TEA (2 equiv.) and $NH_4Cl$ (2 equiv.) in one portion at room temperature. The mixture was stirred for 24 h. Standard work-up and purification methods (1R,4s)-4-(8-((2-chloro-4,6-difluorophenyl)amino)-2-(((3S,4 S)-3-fluorotetrahydro-2H-pyran-4-yl)amino)-9H-purin-9-yl)-1-methylcyclohexane-1-carboxamide (15%). $^1H$ NMR (400 MHz, Methanol-$d_4$) δ ppm: 7.92 (s, 1H), 7.29-7.03 (m, 2H), 4.85-4.60 (m, 1H), 4.50-4.35 (m, 1H), 4.26-4.11 (m, 2H), 4.07-3.70 (m, 3H), 2.85-2.69 (m, 2H), 2.42-2.38 (m, 2H), 2.04-1.91 (m, 1H), 1.86-1.84 (m, 3H), 1.55-1.38 (m, 2H), 1.25 (s, 3H). MS (ESI) m/z=538.2 $[M+H]^+$.

Example 53. (1S,4s)-4-(2-(((3S,4R)-3-Fluorotetrahydro-2H-pyran-4-yl)amino)-8-((2,4,6-trichlorophenyl)amino)-9H-purin-9-yl)-1-methylcyclohexane-1-carboxamide

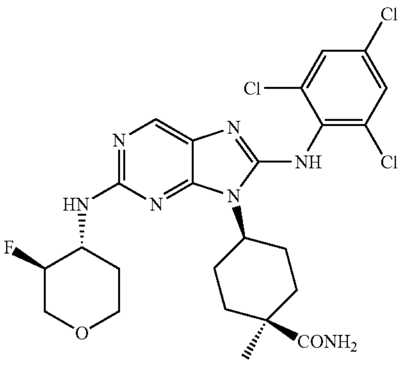 [SMILES: C[C@]1(C(N)=O)CC[C@@H](n2c(Nc3c(Cl)cc(Cl)cc3Cl)nc3cnc(N[C@@H]4CCOC[C@H]4F)nc32)CC1]

(1S,4s)-4-((2-(((3S,4R)-3-Fluorotetrahydro-2H-pyran-4-yl)amino)-5-nitropyrimidin-4-yl)amino)-1-methylcyclohexane-1-carboxamide To a mixture of (1s,4s)-4-((2-chloro-5-nitropyrimidin-4-yl)amino)-1-methylcyclohexane-1-carboxamide (1 equiv., prepared as described herein) and (3S,4R)-3-fluorotetrahydro-2H-pyran-4-amine hydrochloride (1.02 equiv, prepared as described herein) in DMF (0.3 M) was added DIEA (2.20 equiv.), and the mixture was stirred at 30° C. for 16 h. The mixture was diluted with $H_2O$ and extracted with ethyl acetate. The combined organic phases were washed with saturated brine, dried over anhydrous $Na_2SO_4$, filtered and concentrated in vacuum to afford (1S,4s)-4-((2-(((3S,4R)-3-fluorotetrahydro-2H-pyran-4-yl)amino)-5-nitropyrimidin-4-yl)amino)-1-methylcyclohexane-1-carboxamide (99%). The crude product was used in the next step without further purification. MS (ESI) m/z=397.1 $[M+H]^+$.

(1S,4s)-4-((5-Amino-2-(((3S,4R)-3-fluorotetrahydro-2H-pyran-4-yl)amino)pyrimidin-4-yl)amino)-1-methylcyclohexane-1-carboxamide To a solution of (1S,4s)-4-((2-(((3S,4R)-3-fluorotetrahydro-2H-pyran-4-yl)amino)-5-nitropyrimidin-4-yl)amino)-1-methylcyclohexane-1-carboxamide (1.0 equiv.) in MeOH (0.1 M) was added Pd/C (0.1 equiv, 10% Pd by wt.). The suspension was degassed under vacuum and purged with $H_2$ several times. The reaction was stirred under $H_2$ at room temperature for 2 h. The mixture was filtered and concentrated in vacuum to afford (1S,4s)-4-((5-amino-2-(((3S,4R)-3-fluorotetrahydro-2H-pyran-4-yl)amino)pyrimidin-4-yl)amino)-1-methylcyclohexane-1-carboxamide (90%). The crude product was used directly in the next step without further purification. MS (ESI) m/z=367.2 $[M+H]^+$.

(1S,4s)-4-(2-(((3S,4R)-3-Fluorotetrahydro-2H-pyran-4-yl)amino)-8-((2,4,6-trichlorophenyl)amino)-9H-purin-9-yl)-1-methylcyclohexane-1-carboxamide To the solution (1S,4s)-4-((5-amino-2-(((3S,4R)-3-fluorotetrahydro-2H-pyran-4-yl)amino)pyrimidin-4-yl)amino)-1-methylcyclohexane-1-carboxamide (1.0 equiv.) in DMF (0.4 M) was added 1,3,5-trichloro-2-isothiocyanatobenzene (1.0 equiv.). The mixture was stirred at 30° C. for 2 h. DIC (2.0 equiv.) was added and the reaction was stirred at room temperature for 16 h. The mixture was diluted with $H_2O$ and extracted with ethyl acetate. The combined organic phase was washed with saturated brine, dried over anhydrous $Na_2SO_4$, filtered and concentrated in vacuo. Standard work-up and purification methods afforded (1S,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide (40%). $^1H$ NMR (400 MHz, Methanol-$d_4$) δ ppm: 8.02 (s, 1H), 7.56-7.49 (m, 2H), 4.63-4.46 (m, 2H), 4.22 (s, 1H), 4.11-4.05 (m, 1H), 3.93-3.90 (m, 1H), 3.73 (s, 1H), 3.62-3.60 (m, 1H), 2.76-2.68 (m, 2H), 2.42-2.38 (m, 2H), 2.21 (s, 1H), 1.85 (s, 2H), 1.68-1.61 (m, 1H), 1.47-1.41 (m, 2H), 1.25 (s, 3H). MS (ESI) m/z=570.1 $[M+H]^+$.

Example 54. (1S,4s)-4-(8-((2-Chloro-4,6-difluorophenyl)amino)-2-(((3S,4R)-3-methyltetrahydro-2H-pyran-4-yl)amino)-9H-purin-9-yl)-1-methylcyclohexane-1-carboxamide

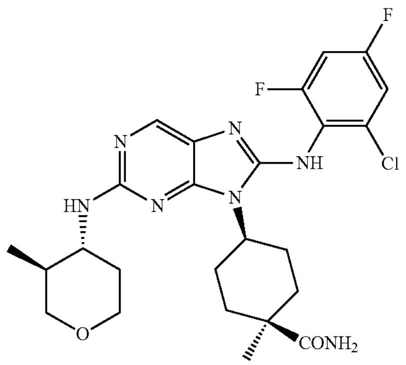 [SMILES: C[C@@H]1COCC[C@H]1Nc1ncc2nc(Nc3c(F)cc(F)cc3Cl)n([C@H]3CC[C@@](C)(C(N)=O)CC3)c2n1]

(1S,4s)-Ethyl 4-(8-((2-chloro-4,6-difluorophenyl)amino)-2-(((3S,4R)-3-methyltetrahydro-2H-pyran-4-yl)amino)-9H-purin-9-yl)-1-methylcyclohexanecarboxylate To a mixture of ethyl (1S,4s)-4-((5-amino-2-(((3S,4R)-3-methyltetrahydro-2H-pyran-4-yl)amino)pyrimidin-4-yl)amino)-1-methylcyclohexane-1-carboxylate (1 equiv., prepared as described herein) in DMF (0.03 M) was added 1-chloro-3,5-difluoro-2-isothiocyanatobenzene (1 equiv.). The mixture was stirred at room temperature for 1.5 h. DIC (2 equiv.) was added to the reaction in one portion. The mixture was stirred at room temperature for 16 h. The reaction was diluted with water, extracted with ethyl acetate, dried over $Na_2SO_4$, filtered and concentrated. The resulting residue was purified via column chromatography to give ethyl (1S,4s)-4-(8-((2-chloro-4,6-difluorophenyl)amino)-2-(((3S,4R)-3-methyltetrahydro-2H-pyran-4-yl)amino)-9H-purin-9-yl)-1-methylcyclohexane-1-carboxylate (97%) as a yellow solid. MS (ESI) m/z=563.3 $[M+H]^+$.

(1S,4s)-4-(8-((2-Chloro-4,6-difluorophenyl)amino)-2-(((3S,4R)-3-methyltetrahydro-2H-pyran-4-yl)amino)-9H-purin-9-yl)-1-methylcyclohexane-1-carboxylic acid To a solution of ethyl (1S,4s)-4-(8-((2-chloro-4,6-difluorophenyl)amino)-2-(((3S,4R)-3-methyltetrahydro-2H- pyran-4-yl)amino)-9H-purin-9-yl)-1-methylcyclohexane-1-carboxylate (1 equiv.) in MeOH/water (0.1 M, 4/1) was added NaOH (5 equiv.). The reaction was refluxed for 48 h. The reaction was diluted with water, and extracted with ethyl acetate. The aqueous phase was adjusted with 3 M HCl to pH=3-5, extracted with DCM, the organic layer was dried over $Na_2SO_4$, filtered and concentrated to give (1S,4s)-4-(8-((2-chloro-4,6-difluorophenyl)amino)-2-(((3S,4R)-3-methyltetrahydro-2H-pyran-4-yl)amino)-9H-purin-9-yl)-1-methylcyclohexane-1-carboxylic acid (51%) as a yellow solid.

(1S,4s)-4-(8-((2-Chloro-4,6-difluorophenyl)amino)-2-(((3S,4R)-3-methyltetrahydro-2H-pyran-4-yl)amino)-9H-purin-9-yl)-1-methylcyclohexane-1-carboxamide To a solution of (1S,4s)-4-(8-((2-chloro-4,6-difluorophenyl)amino)-2-(((3S,4R)-3-methyltetrahydro-2H-pyran-4-yl)amino)-9H-purin-9-yl)-1-methylcyclohexane-1-carboxylic acid (1 equiv.) in DMF (0.3 M) were added HATU (1.2 equiv.), TEA (3 equiv.) and $NH_4Cl$ (3 equiv.) in one portion at room temperature. The reaction was stirred at room temperature for 24 h. Standard work-up and purification methods afforded (1S,4s)-4-(8-((2-chloro-4,6-difluorophenyl)amino)-2-(((3S,4R)-3-methyltetrahydro-2H-pyran-4-yl)amino)-9H-purin-9-yl)-1-methylcyclohexane-1-carboxamide (15%). $^1$H NMR (400 MHz, Methanol-$d_4$) δ ppm: 7.98 (s, 1H), 7.34-6.80 (m, 2H), 4.38-4.35 (m, 1H), 4.05-3.89 (m, 2H), 3.71-3.65 (m, 2H), 3.28-3.25 (m, 1H), 2.88-2.75 (m, 2H), 2.46-2.42 (m, 2H), 2.08-1.96 (m, 1H), 1.95-1.64 (m, 3H), 1.61-1.44 (m, 1H), 1.43-1.32 (m, 2H), 1.23 (s, 3H), 0.91 (d, J=6.7 Hz, 3H). MS (ESI) m/z=534.2 $[M+H]^+$.

Assays

Cell Assays

Determination of the Growth Inhibitory Effect of Aminopurine Compounds.

The Lox-IMVI melanoma cell line (Source: NCI-DCTD, catalog No. 0507283) was maintained and tested in RPMI+10% FBS. The seeding density for the cell line was optimized to ensure assay linearity in 384-well plates.

Increasing concentrations of Aminopurine Compound (0.5 nM to 10 μM) were spotted in a 10-point serial dilution fashion (3-fold dilution) in duplicate within the plate via an acoustic dispenser (EDC ATS-100) into an empty 384-well plate. The dimethyl sulfoxide (DMSO) concentration was kept constant for a final assay concentration of 0.2% DMSO. Prior to testing, cells were grown and expanded in culture flasks to provide sufficient amounts of starting material. Cells were then diluted to their desired densities and added directly to the compound-spotted 384-well plates. Cells were allowed to grow for 72 hours in 5% $CO_2$ at 37° C. At the time when exposure of cells to compound began (to), initial cell number was assessed via a viability assay (Cell Titer-Glo) by quantifying the level of luminescence generated by adenosine-5'-triphosphate (ATP) present in viable cells. After 72 hours, cell viability of compound-treated cells was assessed via Cell Titer-Glo Luminescent Cell Viability Assay (Promega Corporation, Madison, Wis.) and read for luminescence.

All data was normalized and represented as a percentage of the DMSO-treated control cells after 72 h. Results were expressed as a $IC_{50}$ value, which is the compound concentration required to inhibit 50% of the untreated control cells during the 72 hours of treatment.

A Four Parameter Logistic Model (Sigmoidal Dose-Response Model) was used to determine the compound's $IC_{50}$.

$$y=(A+((B-A)/(1+((C/x)^D))))$$

wherein:

$A=Y_{Min}$ $B=Y_{Max}$ $C=EC_{50}$

D=Hill Slope $IC_{50}$ is the compound concentration when Y=50% of DMSO control

Y=Luminescence unit

All inhibition curves were processed and evaluated using XLFit and Activity Base (IDBS).

Animal Models

Xenograft Model.

For xenograft model studies human melanoma cancer cell lines were injected into SCID (severe combined immunodeficiency) mice. Cancer cell lines were propagated in culture in vitro. Tumor bearing animals were generated by injecting precisely determined numbers of cells into mice. Following inoculation of animals, the tumors were allowed to grow to a certain size prior to randomization. The mice bearing xenograft tumors ranging between pre-determined sizes were pooled together and randomized into various treatment groups. A typical efficacy study design involved administering one or more compounds at various dose levels to tumor-bearing mice. Additionally, reference chemotherapeutic agents (positive control) and negative controls were similarly administered and maintained. Tumor measurements and body weights were taken over the course of the study.

Mice were anesthetized with inhaled isoflurane and then inoculated with LOX-IMVI tumor cells subcutaneously above the right hind leg with 0.1 mL of a single cell suspension in PBS using a sterile 1 mL syringe fitted with a 26-gauge needle. Following inoculation of the animals, tumors were allowed to grow to approximately 75-125 $mm^3$ or in some cases 250-400 $mm^3$ prior to randomization of the mice. The tumor of each animal was measured and animals with tumors in the appropriate range were included in the study. Animals from the study pool were then distributed randomly into various cages and the cages were randomly assigned to vehicle, positive control, or test article groups. All of the mice were tagged with metal ear tags on the right ear. A typical group consisted of 8-10 animals. For a typical xenograft study, SCID mice bearing tumors were randomized and dosed with compounds ranging from, for example, 100 mg/kg to 0.1 mg/kg with different dose scheduling, including, but not limited to, qd, q2d, q3d, q5d, q7d and bid. The mice were dosed for 1-4 weeks. Tumors were measured twice a week using calipers and tumor volumes were calculated using the formula of $W^2 \times L/2$.

In this melanoma model, Aminopurine Compounds have, or are expected to have, an $ED_{50}$ value of <100 mg/kg, with some compounds having an $ED_{50}$ of <10 mg/kg and others an $ED_{50}$ of <1 mg/kg.

ACTIVITY TABLES

Each of the compounds in Table 1 was tested in one or more of the assays and was found to have activity therein, with all of the compounds having an $IC_{50}$ below 10 μM in the cell-based assay, with some compounds having an $IC_{50}$ above 1 μM (activity level A), some an $IC_{50}$ between 500 nM and 1 μM (activity level B), some an $IC_{50}$ between 250 nM and 500 nM (activity level C), and others having an $IC_{50}$ below 250 nM (activity level D).

TABLE 1

| Cmpd No. | Structure | Name | MH+ | Ac-tivi-ty |
|---|---|---|---|---|
| 1 | 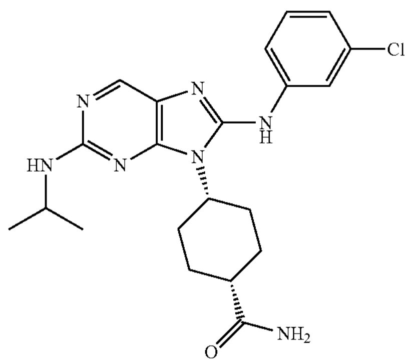 [SMILES: CC(C)Nc1ncc2nc(Nc3cccc(Cl)c3)n([C@H]3CC[C@@H](C(N)=O)CC3)c2n1] | (1s,4s)-4-(8-(3-chlorophenylamino)-2-(isopropylamino)-9H-purin-9-yl)cyclohexanecarboxamide | 428.4 | A |
| 2 | 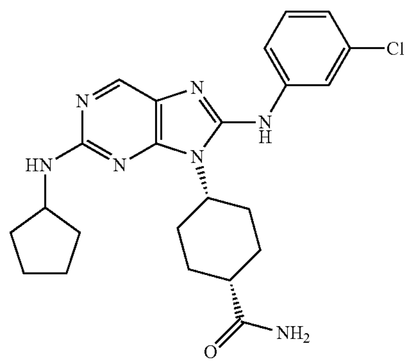 [SMILES: NC(=O)[C@H]1CC[C@@H](n2c(Nc3cccc(Cl)c3)nc3cnc(NC4CCCC4)nc32)CC1] | (1s,4s)-4-(8-(3-chlorophenylamino)-2-(cyclopentylamino)-9H-purin-9-yl)cyclohexanecarboxamide | 454.4 | A |
| 3 | 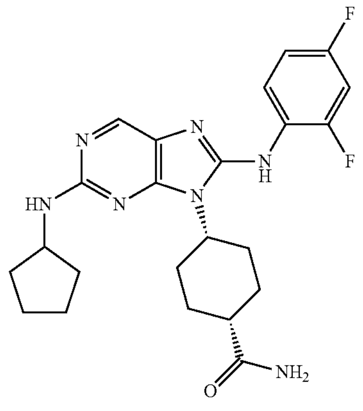 [SMILES: NC(=O)[C@H]1CC[C@@H](n2c(Nc3ccc(F)cc3F)nc3cnc(NC4CCCC4)nc32)CC1] | (1s,4s)-4-(2-(cyclopentylamino)-8-(2,4-difluorophenylamino)-9H-purin-9-yl)cyclohexanecarboxamide | 456.3 | A |

TABLE 1-continued
| Cmpd No. | Structure | Name | MH+ | Activity |
|---|---|---|---|---|
| 4 | 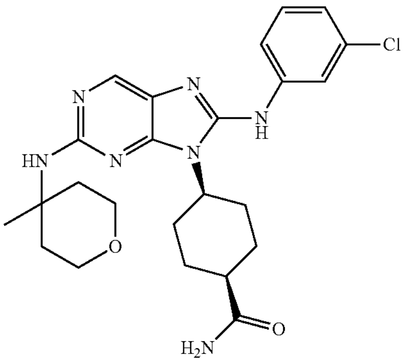 [SMILES: CC1(Nc2ncc3nc(Nc4cccc(Cl)c4)n([C@H]4CC[C@@H](C(N)=O)CC4)c3n2)CCOCC1] | (1s,4s)-4-(8-(3-chlorophenylamino)-2-(4-methyltetrahydro-2H-pyran-4-ylamino)-9H-purin-9-yl)cyclohexanecarboxamide | 484.2 | A |
| 5 | 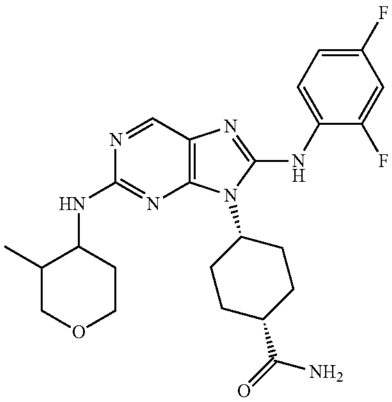 [SMILES: CC1COCCC1Nc1ncc2nc(Nc3ccc(F)cc3F)n([C@H]3CC[C@@H](C(N)=O)CC3)c2n1] | (1s,4s)-4-(8-(2,4-difluorophenylamino)-2-(3-methyltetrahydro-2H-pyran-4-ylamino)-9H-purin-9-yl)cyclohexanecarboxamide | 486.5 | A |
| 6 | 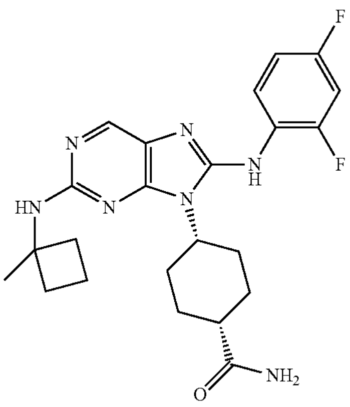 [SMILES: CC1(Nc2ncc3nc(Nc4ccc(F)cc4F)n([C@H]4CC[C@@H](C(N)=O)CC4)c3n2)CCC1] | (1s,4s)-4-(8-(2,4-difluorophenylamino)-2-(1-methylcyclobutylamino)-9H-purin-9-yl)cyclohexanecarboxamide | 456.5 | A |

TABLE 1-continued
| Cmpd No. | Structure | Name | MH+ | Activity |
|---|---|---|---|---|
| 7 | 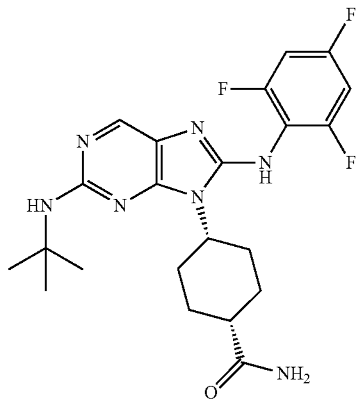 [SMILES: CC(C)(C)Nc1ncc2nc(Nc3c(F)cc(F)cc3F)n([C@H]3CC[C@@H](C(N)=O)CC3)c2n1] | (1s,4s)-4-(2-(tert-butylamino)-8-(2,4,6-trifluorophenylamino)-9H-purin-9-yl)cyclohexanecarboxamide | 462.5 | A |
| 8 | 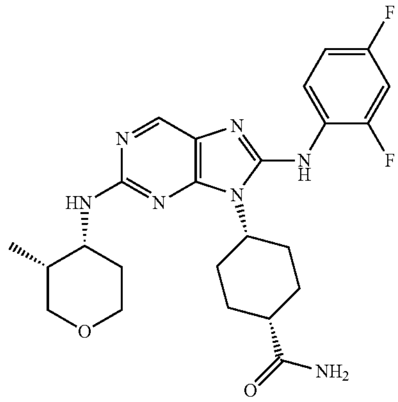 [SMILES: C[C@H]1COCC[C@H]1Nc1ncc2nc(Nc3ccc(F)cc3F)n([C@H]3CC[C@@H](C(N)=O)CC3)c2n1] | (1S,4s)-4-(8-(2,4-difluorophenylamino)-2-((3R,4R)-3-methyltetrahydro-2H-pyran-4-ylamino)-9H-purin-9-yl)cyclohexanecarboxamide | 486.1 | A |
| 9 | 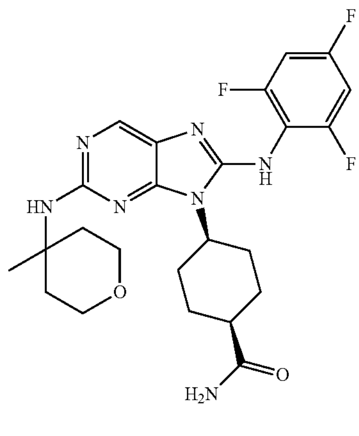 [SMILES: CC1(Nc2ncc3nc(Nc4c(F)cc(F)cc4F)n([C@H]4CC[C@@H](C(N)=O)CC4)c3n2)CCOCC1] | (1s,4s)-4-(2-(4-methyltetrahydro-2H-pyran-4-ylamino)-8-(2,4,6-trifluorophenylamino)-9H-purin-9-yl)cyclohexanecarboxamide | 504.1 | A |

TABLE 1-continued

| Cmpd No. | Structure | Name | MH+ | Activity |
|---|---|---|---|---|
| 10 | 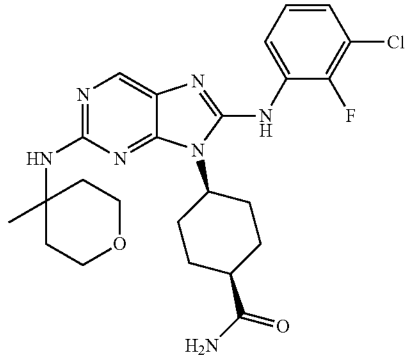 [SMILES: CC1(Nc2ncc3nc(Nc4cccc(Cl)c4F)n([C@H]4CC[C@@H](C(N)=O)CC4)c3n2)CCOCC1] | (1s,4s)-4-(8-(3-chloro-2-fluorophenylamino)-2-(4-methyltetrahydro-2H-pyran-4-ylamino)-9H-purin-9-yl)cyclohexanecarboxamide | 502.2 | A |
| 11 | 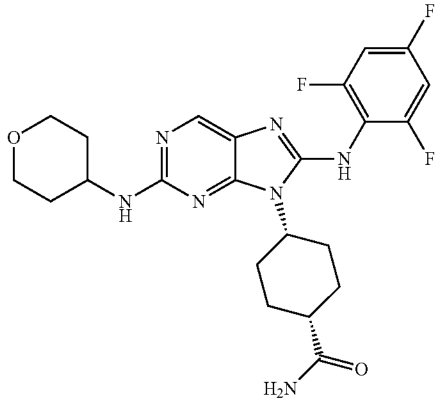 [SMILES: NC(=O)[C@H]1CC[C@@H](n2c(Nc3c(F)cc(F)cc3F)nc3cnc(NC4CCOCC4)nc32)CC1] | (1s,4s)-4-(2-(tetrahydro-2H-pyran-4-ylamino)-8-(2,4,6-trifluorophenylamino)-9H-purin-9-yl)cyclohexanecarboxamide | 490.2 | D |
| 12 | 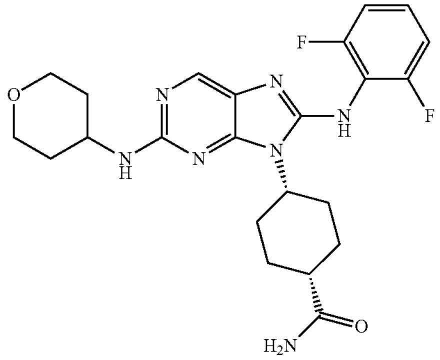 [SMILES: NC(=O)[C@H]1CC[C@@H](n2c(Nc3c(F)cccc3F)nc3cnc(NC4CCOCC4)nc32)CC1] | (1s,4s)-4-(8-(2,6-difluorophenylamino)-2-(tetrahydro-2H-pyran-4-ylamino)-9H-purin-9-yl)cyclohexanecarboxamide | 472.2 | C |
| 13 | 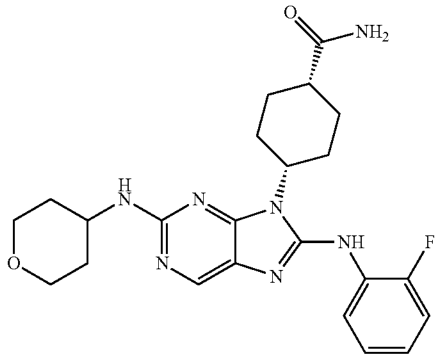 [SMILES: NC(=O)[C@H]1CC[C@@H](n2c(Nc3ccccc3F)nc3cnc(NC4CCOCC4)nc32)CC1] | (1s,4s)-4-(8-(2-fluorophenylamino)-2-(tetrahydro-2H-pyran-4-ylamino)-9H-purin-9-yl)cyclohexanecarboxamide | 454.2 | B |

TABLE 1-continued

| Cmpd No. | Structure | Name | MH+ | Activity |
|---|---|---|---|---|
| 14 | 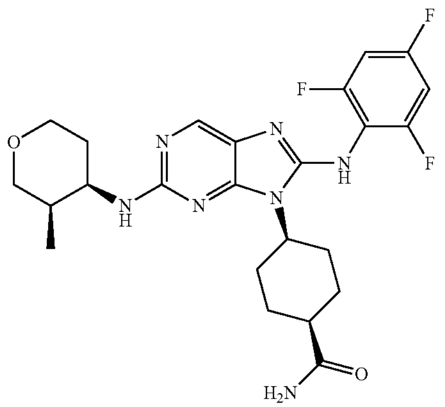 [SMILES: C[C@H]1COCC[C@H]1Nc1ncc2nc(Nc3c(F)cc(F)cc3F)n([C@H]3CC[C@@H](C(N)=O)CC3)c2n1] | (1S,4s)-4-(2-((3R,4R)-3-methyltetrahydro-2H-pyran-4-ylamino)-8-(2,4,6-trifluorophenylamino)-9H-purin-9-yl)cyclohexanecarboxamide | 504.3 | B |
| 15 | 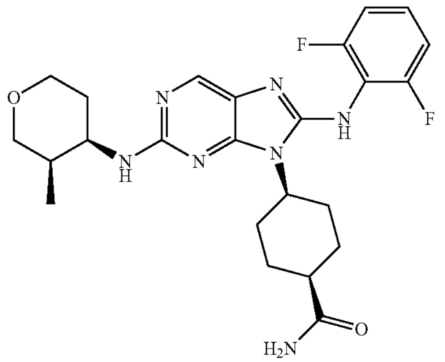 [SMILES: C[C@H]1COCC[C@H]1Nc1ncc2nc(Nc3c(F)cccc3F)n([C@H]3CC[C@@H](C(N)=O)CC3)c2n1] | (1S,4s)-4-(8-(2,6-difluorophenylamino)-2-((3R,4R)-3-methyltetrahydro-2H-pyran-4-ylamino)-9H-purin-9-yl)cyclohexanecarboxamide | 486.3 | A |
| 16 | 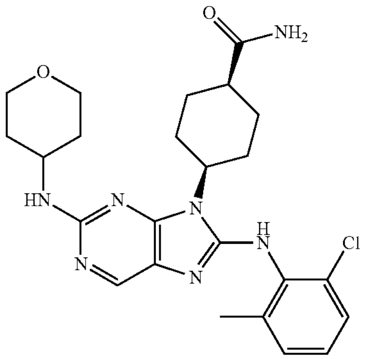 [SMILES: Cc1cccc(Cl)c1Nc1nc2cnc(NC3CCOCC3)nc2n1[C@H]1CC[C@@H](C(N)=O)CC1] | (1s,4s)-4-(8-(2-chloro-6-methylphenylamino)-2-(tetrahydro-2H-pyran-4-ylamino)-9H-purin-9-yl)cyclohexanecarboxamide | 484.2 | A |
| 17 | 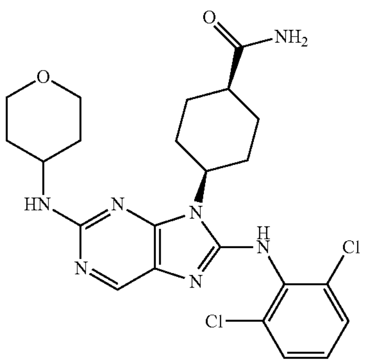 [SMILES: NC(=O)[C@H]1CC[C@@H](n2c(Nc3c(Cl)cccc3Cl)nc3cnc(NC4CCOCC4)nc32)CC1] | (1s,4s)-4-(8-(2,6-dichlorophenylamino)-2-(tetrahydro-2H-pyran-4-ylamino)-9H-purin-9-yl)cyclohexanecarboxamide | 504.2 | D |

TABLE 1-continued
| Cmpd No. | Structure | Name | MH+ | Ac-tivi-ty |
|---|---|---|---|---|
| 18 | 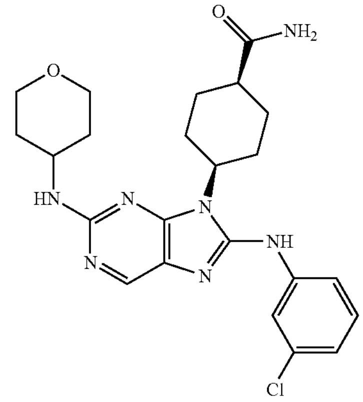 [SMILES: NC(=O)[C@H]1CC[C@@H](n2c(Nc3cccc(Cl)c3)nc3cnc(NC4CCOCC4)nc32)CC1] | (1s,4s)-4-(8-(3-chlorophenylamino)-2-(tetrahydro-2H-pyran-4-ylamino)-9H-purin-9-yl)cyclohexanecarboxamide | 470.2 | A |
| 19 | 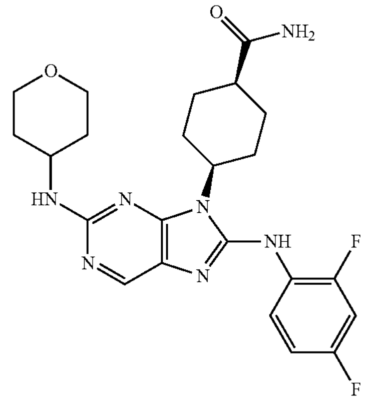 [SMILES: NC(=O)[C@H]1CC[C@@H](n2c(Nc3ccc(F)cc3F)nc3cnc(NC4CCOCC4)nc32)CC1] | (1s,4s)-4-(8-(2,4-difluorophenylamino)-2-(tetrahydro-2H-pyran-4-ylamino)-9H-purin-9-yl)cyclohexanecarboxamide | 472.2 | A |
| 20 | 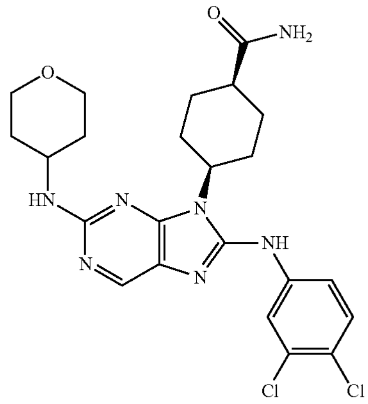 [SMILES: NC(=O)[C@H]1CC[C@@H](n2c(Nc3ccc(Cl)c(Cl)c3)nc3cnc(NC4CCOCC4)nc32)CC1] | (1s,4s)-4-(8-(3,4-dichlorophenylamino)-2-(tetrahydro-2H-pyran-4-ylamino)-9H-purin-9-yl)cyclohexanecarboxamide | 504.2 | A |

TABLE 1-continued

| Cmpd No. | Structure | Name | MH+ | Activity |
|---|---|---|---|---|
| 21 | 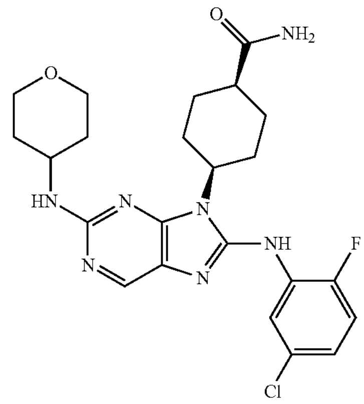 [SMILES: NC(=O)[C@H]1CC[C@@H](n2c(Nc3cc(Cl)ccc3F)nc3cnc(NC4CCOCC4)nc32)CC1] | (1s,4s)-4-(8-(5-chloro-2-fluorophenylamino)-2-(tetrahydro-2H-pyran-4-ylamino)-9H-puriin-9-yl)cyclohexanecarboxamide | 488.3 | A |
| 22 | 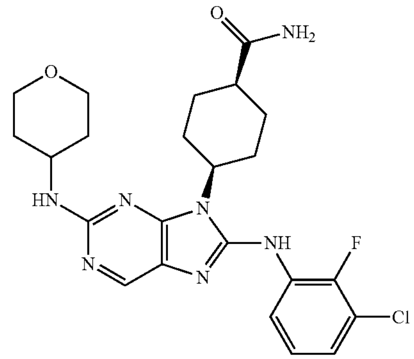 [SMILES: NC(=O)[C@H]1CC[C@@H](n2c(Nc3cccc(Cl)c3F)nc3cnc(NC4CCOCC4)nc32)CC1] | (1s,4s)-4-(8-(3-chloro-2-fluorophenylamino)-2-(tetrahydro-2H-pyran-4-ylamino)-9H-purin-9-yl)cyclohexanecarboxamide | 488.1 | A |
| 23 | 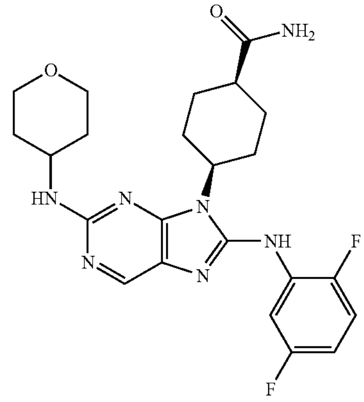 [SMILES: NC(=O)[C@H]1CC[C@@H](n2c(Nc3cc(F)ccc3F)nc3cnc(NC4CCOCC4)nc32)CC1] | (1s,4s)-4-(8-(2,5-difluorophenylamino)-2-(tetrahydro-2H-pyran-4-ylamino)-9H-purin-9-yl)cyclohexanecarboxamide | 472.2 | A |
| 24 | 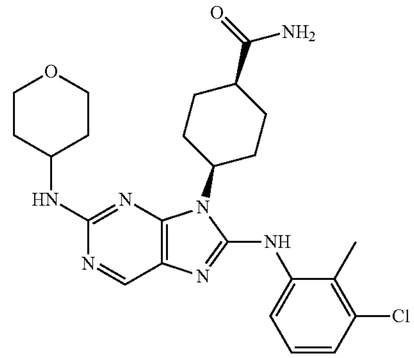 [SMILES: Cc1c(Cl)cccc1Nc1nc2cnc(NC3CCOCC3)nc2n1[C@H]1CC[C@@H](C(N)=O)CC1] | (1s,4s)-4-(8-(3-chloro-2-methylphenylamino)-2-(tetrahydro-2H-pyran-4-ylamino)-9H-purin-9-yl)cyclohexanecarboxamide | 484.2 | A |

TABLE 1-continued
| Cmpd No. | Structure | Name | MH+ | Activity |
|---|---|---|---|---|
| 25 | 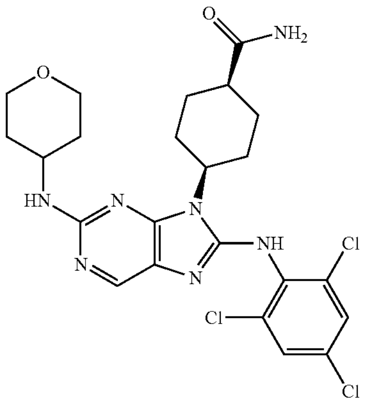 [SMILES: NC(=O)[C@H]1CC[C@@H](n2c(Nc3c(Cl)cc(Cl)cc3Cl)nc3cnc(NC4CCOCC4)nc32)CC1] | (1s,4s)-4-(2-(tetrahydro-2H-pyran-4-ylamino)-8-(2,4,6-trichlorophenylamino)-9H-purin-9-yl)cyclohexanecarboxamide | 538.1 | D |
| 26 | 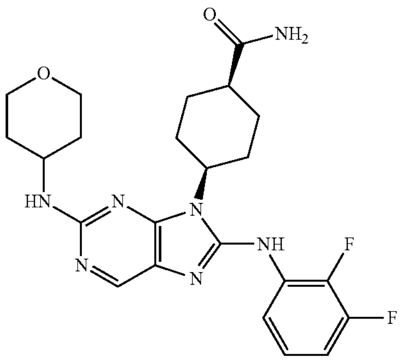 [SMILES: NC(=O)[C@H]1CC[C@@H](n2c(Nc3cccc(F)c3F)nc3cnc(NC4CCOCC4)nc32)CC1] | (1s,4s)-4-(8-(2,3-difluorophenylamino)-2-(tetrahydro-2H-pyran-4-ylamino)-9H-purin-9-yl)cyclohexanecarboxamide | 472.2 | A |
| 27 | 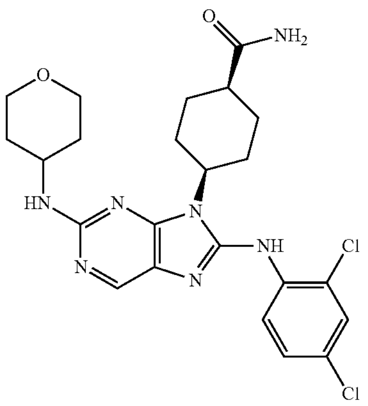 [SMILES: NC(=O)[C@H]1CC[C@@H](n2c(Nc3ccc(Cl)cc3Cl)nc3cnc(NC4CCOCC4)nc32)CC1] | (1s,4s)-4-(8-(2,4-dichlorophenylamino)-2-(tetrahydro-2H-pyran-4-ylamino)-9H-purin-9-yl)cyclohexanecarboxamide | 504.2 | A |

TABLE 1-continued
| Cmpd No. | Structure | Name | MH+ | Activity |
| --- | --- | --- | --- | --- |
| 28 | 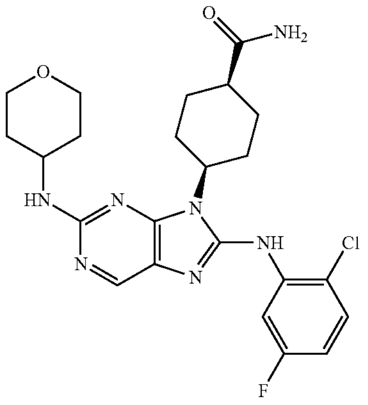 [SMILES: NC(=O)[C@H]1CC[C@@H](n2c(Nc3cc(F)ccc3Cl)nc3cnc(NC4CCOCC4)nc32)CC1] | (1s,4s)-4-(8-(2-chloro-5-fluorophenylamino)-2-(tetrahydro-2H-pyran-4-ylamino)-9H-purin-9-yl)cyclohexanecarboxamide | 488.1 | A |
| 29 | 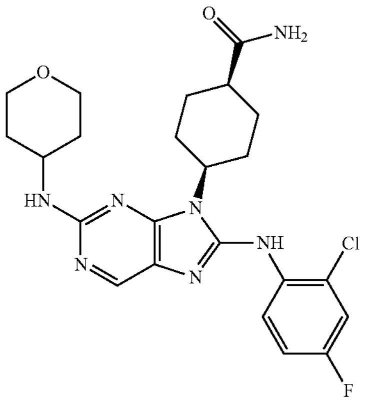 [SMILES: NC(=O)[C@H]1CC[C@@H](n2c(Nc3ccc(F)cc3Cl)nc3cnc(NC4CCOCC4)nc32)CC1] | (1s,4s)-4-(8-(2-chloro-4-fluorophenylamino)-2-(tetrahydro-2H-pyran-4-ylamino)-9H-purin-9-yl)cyclohexanecarboxamide | 488.2 | A |
| 30 | 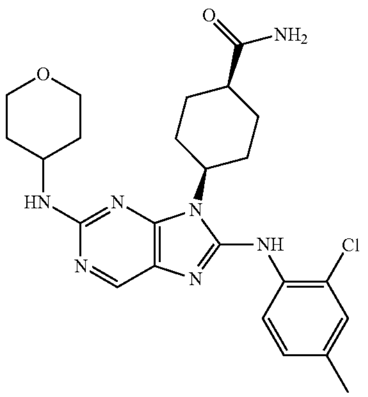 [SMILES: Cc1ccc(Nc2nc3cnc(NC4CCOCC4)nc3n2[C@H]2CC[C@@H](C(N)=O)CC2)c(Cl)c1] | (1s,4s)-4-(8-(2-chloro-4-methylphenylamino)-2-(tetrahydro-2H-pyran-4-ylamino)-9H-purin-9-yl)cyclohexanecarboxamide | 484.4 | A |

TABLE 1-continued
| Cmpd No. | Structure | Name | MH+ | Ac-tivi-ty |
|---|---|---|---|---|
| 31 | 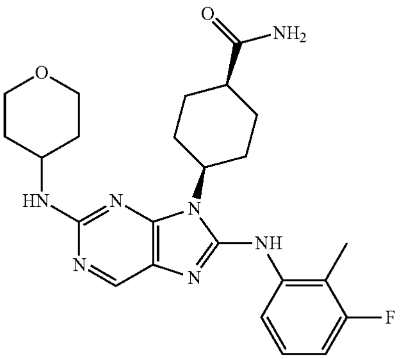 [SMILES: Cc1c(F)cccc1Nc1nc2cnc(NC3CCOCC3)nc2n1[C@H]1CC[C@@H](C(N)=O)CC1] | (1s,4s)-4-(8-(3-fluoro-2-methylphenylamino)-2-(tetrahydro-2H-pyran-4-ylamino)-9H-purin-9-yl)cyclohexanecarboxamide | 468.4 | A |
| 32 | 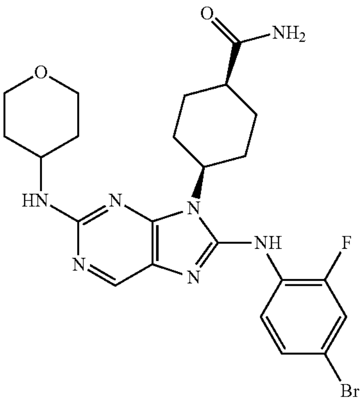 [SMILES: NC(=O)[C@H]1CC[C@@H](n2c(Nc3ccc(Br)cc3F)nc3cnc(NC4CCOCC4)nc32)CC1] | (1s,4s)-4-(8-(4-bromo-2-fluroophenylamino)-2-(tetrahydro-2H-pyran-4-ylamino)-9H-purin-9-yl)cyclohexanecarboxamide | 532.1 | B |
| 33 | 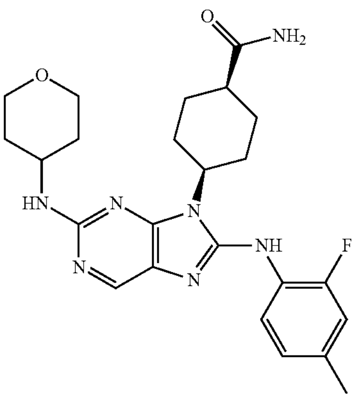 [SMILES: Cc1ccc(Nc2nc3cnc(NC4CCOCC4)nc3n2[C@H]2CC[C@@H](C(N)=O)CC2)c(F)c1] | (1s,4s)-4-(8-(2-fluoro-4-methylphenylamino)-2-(tetrahydro-2H-pyran-4-ylamino)-9H-purin-9-yl)cyclohexanecarboxamide | 468.2 | A |

TABLE 1-continued
| Cmpd No. | Structure | Name | MH+ | Activity |
|---|---|---|---|---|
| 34 | 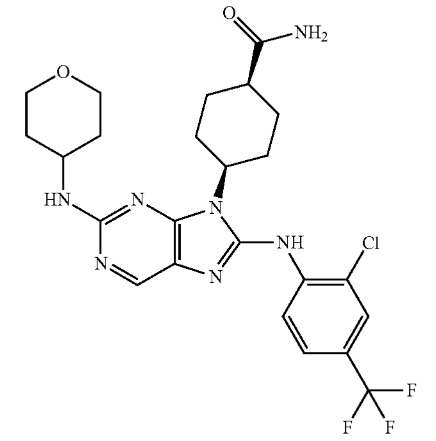 [SMILES: NC(=O)[C@H]1CC[C@@H](n2c(Nc3ccc(C(F)(F)F)cc3Cl)nc3cnc(NC4CCOCC4)nc32)CC1] | (1s,4s)-4-(8-(2-chloro-4-(trifluoromethyl)phenylamino)-2-(tetrahydro-2H-pyran-4-ylamino)-9H-purin-9-yl)cyclohexanecarboxamide | 538.1 | A |
| 35 | 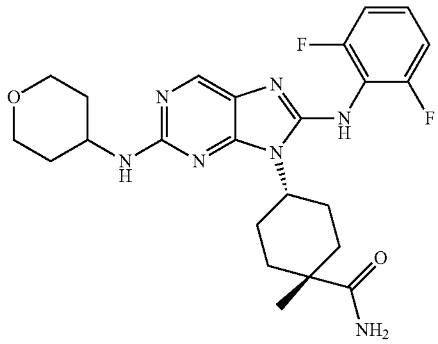 [SMILES: C[C@]1(C(N)=O)CC[C@@H](n2c(Nc3c(F)cccc3F)nc3cnc(NC4CCOCC4)nc32)CC1] | (1s,4s)-4-(8-(2,6-difluorophenylamino)-2-(tetrahydro-2H-pyran-4-ylamino)-9H-purin-9-yl)-1-methylcyclohexanecarboxamide | 486.2 | B |
| 36 | 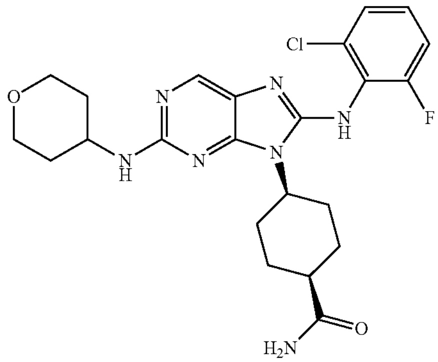 [SMILES: NC(=O)[C@H]1CC[C@@H](n2c(Nc3c(F)cccc3Cl)nc3cnc(NC4CCOCC4)nc32)CC1] | (1s,4s)-4-(8-(2-chloro-6-fluorophenylamino)-2-(tetrahydro-2H-pyran-4-ylamino)-9H-purin-9-yl)cyclohexanecarboxamide | 488.2 | C |

TABLE 1-continued
| Cmpd No. | Structure | Name | MH+ | Activity |
|---|---|---|---|---|
| 37 | 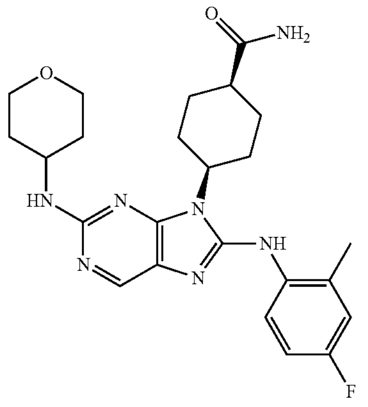 [SMILES: Cc1cc(F)ccc1Nc1nc2cnc(NC3CCOCC3)nc2n1[C@H]1CC[C@@H](C(N)=O)CC1] | (1s,4s)-4-(8-(4-fluoro-2-methylphenylamino)-2-(tetrahydro-2H-pyran-4-ylamino)-9H-purin-9-yl)cyclohexanecarboxamide | 468.4 | A |
| 38 | 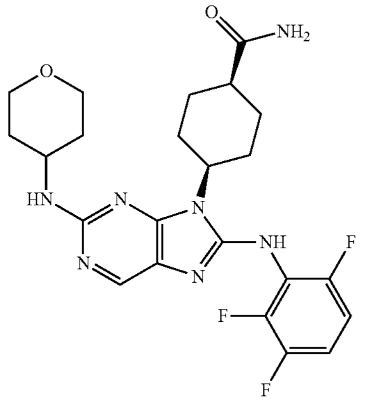 [SMILES: NC(=O)[C@H]1CC[C@@H](n2c(Nc3c(F)ccc(F)c3F)nc3cnc(NC4CCOCC4)nc32)CC1] | (1s,4s)-4-(2-(tetrahydro-2H-pyran-4-ylamino)-8-(2,3,6-trifluorophenylamino)-9H-purin-9-yl)cyclohexanecarboxamide | 490.2 | B |
| 39 | 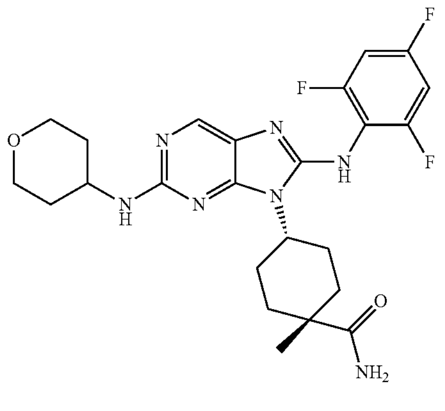 [SMILES: C[C@]1(C(N)=O)CC[C@@H](n2c(Nc3c(F)cc(F)cc3F)nc3cnc(NC4CCOCC4)nc32)CC1] | (1s,4s)-1-methyl-4-(2-(tetrahydro-2H-pyran-4-ylamino)-8-(2,4,6-trifluorophenylamino)-9H-purin-9-yl)cyclohexanecarboxamide | 504.2 | C |

TABLE 1-continued
| Cmpd No. | Structure | Name | MH+ | Activity |
|---|---|---|---|---|
| 40 | 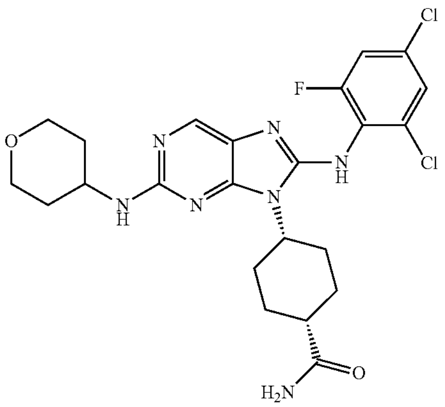 [SMILES: NC(=O)[C@H]1CC[C@@H](n2c(Nc3c(F)cc(Cl)cc3Cl)nc3cnc(NC4CCOCC4)nc32)CC1] | (1s,4s)-4-(8-(2,4-dichloro-6-fluorophenylamino)-2-(tetrahydro-2H-pyran-4-ylamino)-9H-purin-9-yl)cyclohexanecarboxamide | 522.2 | D |
| 41 | 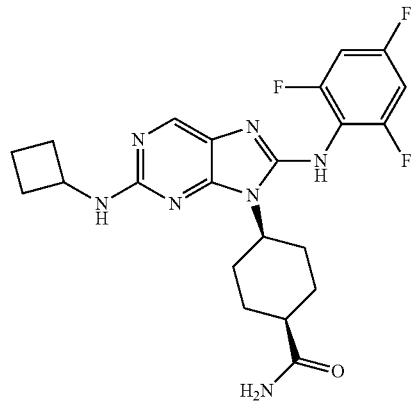 [SMILES: NC(=O)[C@H]1CC[C@@H](n2c(Nc3c(F)cc(F)cc3F)nc3cnc(NC4CCC4)nc32)CC1] | (1s,4s)-4-(2-(cyclobutylamino)-8-(2,4,6-trifluorophenylamino)-9H-purin-9-yl)cyclohexanecarboxamide | 460.1 | C |
| 42 | 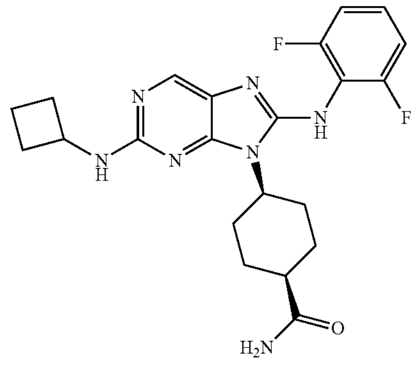 [SMILES: NC(=O)[C@H]1CC[C@@H](n2c(Nc3c(F)cccc3F)nc3cnc(NC4CCC4)nc32)CC1] | (1s,4s)-4-(2-(cyclobutylamino)-8-(2,6-difluorophenylamino)-9H-purin-9-yl)cyclohexanecarboxamide | 442.1 | A |

TABLE 1-continued

| Cmpd No. | Structure | Name | MH+ | Ac-tivi-ty |
|---|---|---|---|---|
| 43 | 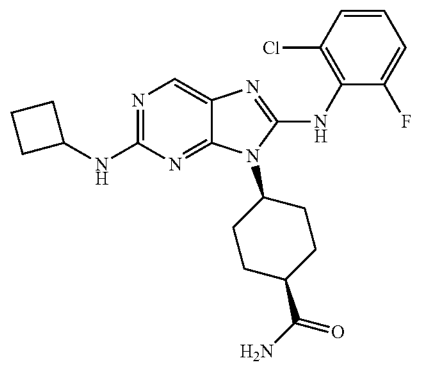 [SMILES: NC(=O)[C@H]1CC[C@@H](n2c(Nc3c(F)cccc3Cl)nc3cnc(NC4CCC4)nc32)CC1] | (1s,4s)-4-(8-(2-chloro-6-fluorophenyl)-2-(cyclobutylamino)-9H-purin-9-yl)cyclohexanecarboxamide | 458.1 | B |
| 44 | 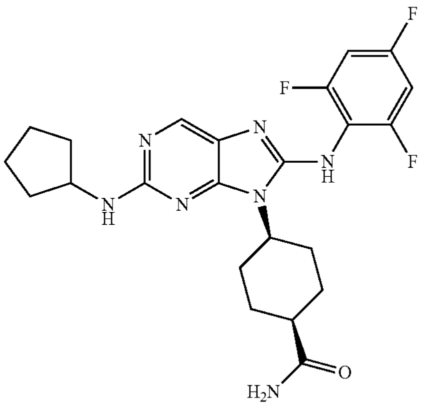 [SMILES: NC(=O)[C@H]1CC[C@@H](n2c(Nc3c(F)cc(F)cc3F)nc3cnc(NC4CCCC4)nc32)CC1] | (1s,4s)-4-(2-(cyclopentylamino)-8-(2,4,6-trifluorophenylamino)-9H-purin-9-yl)cyclohexanecarboxamide | 474.2 | C |
| 45 | 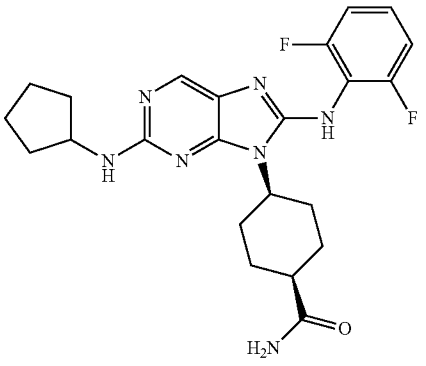 [SMILES: NC(=O)[C@H]1CC[C@@H](n2c(Nc3c(F)cccc3F)nc3cnc(NC4CCCC4)nc32)CC1] | (1s,4s)-4-(2-(cyclopentylamino)-8-(2,6-difluorophenylamino)-9H-purin-9-yl)cyclohexanecarboxamide | 456.2 | B |
| 46 | 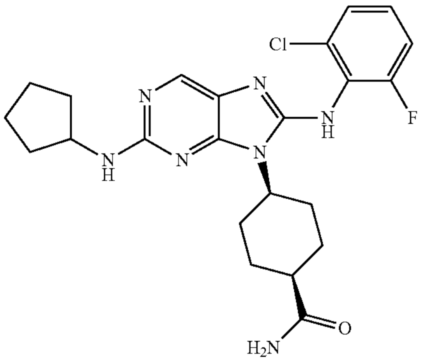 [SMILES: NC(=O)[C@H]1CC[C@@H](n2c(Nc3c(F)cccc3Cl)nc3cnc(NC4CCCC4)nc32)CC1] | (1s,4s)-4-(8-(2-chloro-6-fluorophenylamino)-2-(cyclopentylamino)-9H-purin-9-yl)cyclohexanecarboxamide | 472.2 | B |

TABLE 1-continued
| Cmpd No. | Structure | Name | MH+ | Activity |
|---|---|---|---|---|
| 47 | 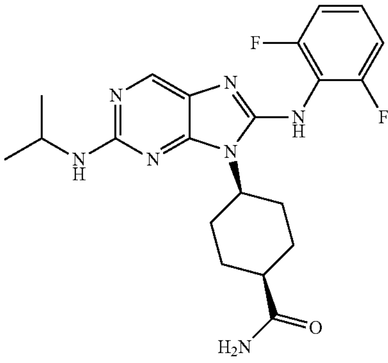 [SMILES: CC(C)Nc1ncc2nc(Nc3c(F)cccc3F)n([C@H]3CC[C@@H](C(N)=O)CC3)c2n1] | (1s,4s)-4-(8-(2,6-difluorophenylamino)-2-(isopropylamino)-9H-purin-9-yl)cyclohexanecarboxamide | 430.2 | A |
| 48 | 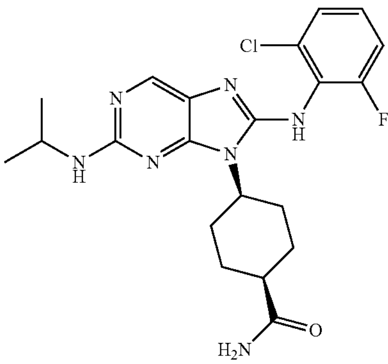 [SMILES: CC(C)Nc1ncc2nc(Nc3c(F)cccc3Cl)n([C@H]3CC[C@@H](C(N)=O)CC3)c2n1] | (1s,4s)-4-(8-(2-chloro-6-fluorophenylamino)-2-(isopropylamino)-9H-purin-9-yl)cyclohexanecarboxamide | 446.2 | A |
| 49 | 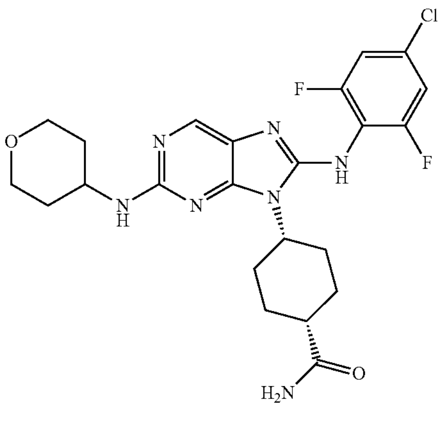 [SMILES: NC(=O)[C@H]1CC[C@@H](n2c(Nc3c(F)cc(Cl)cc3F)nc3cnc(NC4CCOCC4)nc32)CC1] | (1s,4s)-4-(8-(4-chloro-2,6-difluorophenylamino)-2-(tetrahydro-2H-pyran-4-ylamino)-9H-purin-9-yl)cyclohexanecarboxamide | 506.1 | D |

TABLE 1-continued
| Cmpd No. | Structure | Name | MH+ | Activity |
|---|---|---|---|---|
| 50 | 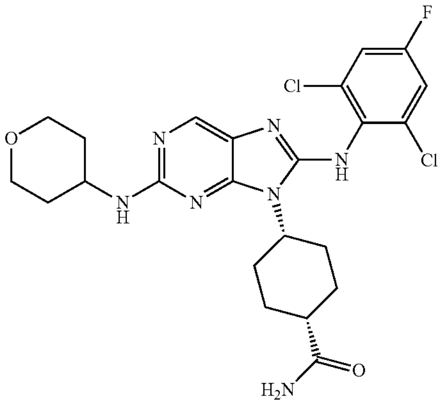 [SMILES: NC(=O)[C@H]1CC[C@@H](n2c(Nc3c(Cl)cc(F)cc3Cl)nc3cnc(NC4CCOCC4)nc32)CC1] | (1s,4s)-4-(8-(2,6-dichloro-4-fluorophenylamino)-2-(tetrahydro-2H-pyran-4-ylamino)-9H-purin-9-yl)cyclohexanecarboxamide | 522.1 | D |
| 51 | 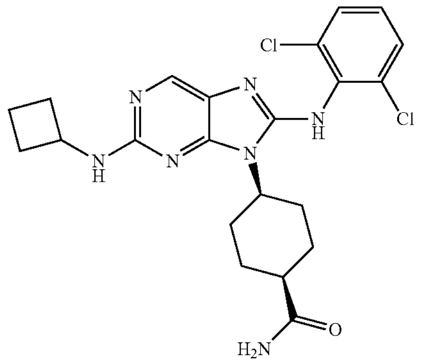 [SMILES: NC(=O)[C@H]1CC[C@@H](n2c(Nc3c(Cl)cccc3Cl)nc3cnc(NC4CCC4)nc32)CC1] | (1s,4s)-4-(2-(cyclobutylamino)-8-(2,6-dichlorophenylamino)-9H-purin-9-yl)cyclohexanecarboxamide | 474.1 | B |
| 52 | 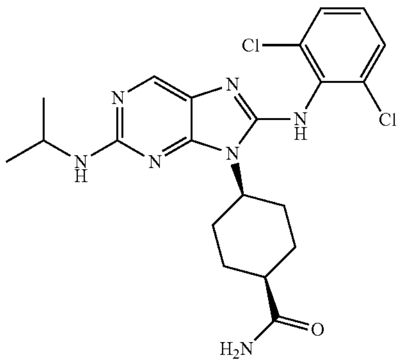 [SMILES: CC(C)Nc1ncc2nc(Nc3c(Cl)cccc3Cl)n([C@H]3CC[C@@H](C(N)=O)CC3)c2n1] | (1s,4s)-4-(8-(2,6-dichlorophenylamino)-2-(isopropylamino)-9H-purin-9-yl)cyclohexanecarboxamide | 462.1 | A |

TABLE 1-continued
| Cmpd No. | Structure | Name | MH+ | Activity |
|---|---|---|---|---|
| 53 | 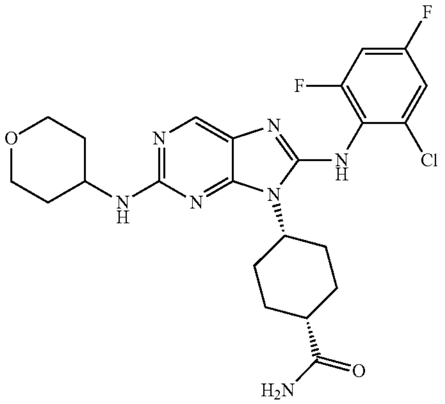 | (1s,4s)-4-(8-(2-chloro-4,6-difluorophenylamino)-2-(tetrahydro-2H-pyran-4-ylamino)-9H-purin-9-yl)cyclohexanecarboxamide | 506.1 | D |
| 54 | 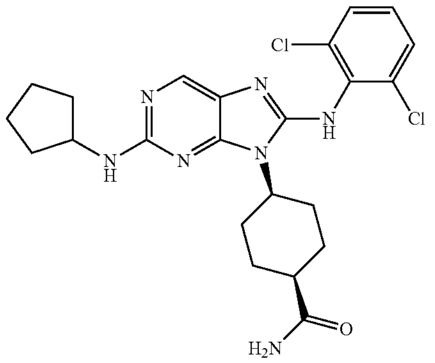 [SMILES: NC(=O)[C@H]1CC[C@@H](n2c(Nc3c(Cl)cccc3Cl)nc3cnc(NC4CCCC4)nc32)CC1] | (1s,4s)-4-(2-(cyclopentylamino)-8-(2,6-dichlorophenylamino)-9H-purin-9-yl)cyclohexanecarboxamide | 488.2 | B |
| 55 | 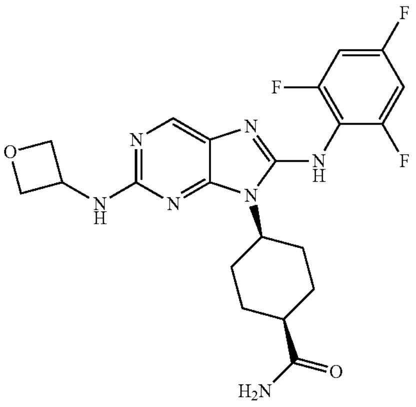 [SMILES: NC(=O)[C@H]1CC[C@@H](n2c(Nc3c(F)cc(F)cc3F)nc3cnc(NC4COC4)nc32)CC1] | (1s,4s)-4-(2-(oxetan-3-ylamino)-8-(2,4,6-trifluorophenylamino)-9H-purin-9-yl)cyclohexanecarboxamide | 462.2 | A |

TABLE 1-continued
| Cmpd No. | Structure | Name | MH+ | Activity |
|---|---|---|---|---|
| 56 | 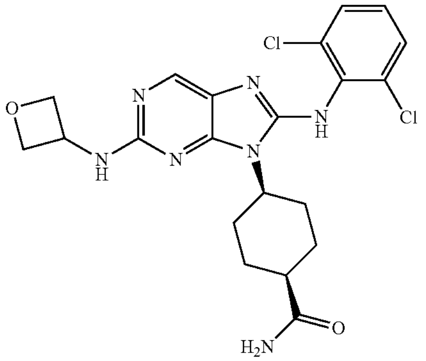 [SMILES: NC(=O)[C@H]1CC[C@@H](n2c(Nc3c(Cl)cccc3Cl)nc3cnc(NC4COC4)nc32)CC1] | (1s,4s)-4-(8-(2,6-dichlorophenylamino)-2-(oxetan-3-ylamino)-9H-puriin-9-yl)cyclohexanecarboxamide | 476.1 | A |
| 57 | 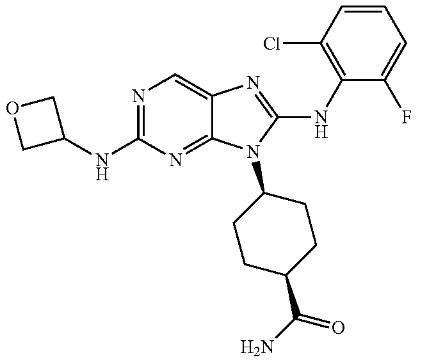 [SMILES: NC(=O)[C@H]1CC[C@@H](n2c(Nc3c(F)cccc3Cl)nc3cnc(NC4COC4)nc32)CC1] | (1s,4s)-4-(8-(2-chloro-6-fluorophenylamino)-2-(oxetan-3-ylamino)-9H-purin-9-yl)cyclohexanecarboxamide | 460.1 | A |
| 58 | 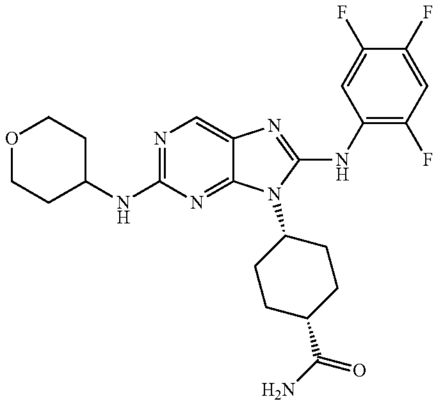 [SMILES: NC(=O)[C@H]1CC[C@@H](n2c(Nc3cc(F)c(F)cc3F)nc3cnc(NC4CCOCC4)nc32)CC1] | (1s,4s)-4-(2-(tetrahydro-2H-pyran-4-ylamino)-8-(2,4,5-trifluorophenylamino)-9H-purin-9-yl)cyclohexanecarboxamide | 490.2 | B |

TABLE 1-continued

| Cmpd No. | Structure | Name | MH+ | Activity |
|---|---|---|---|---|
| 59 | 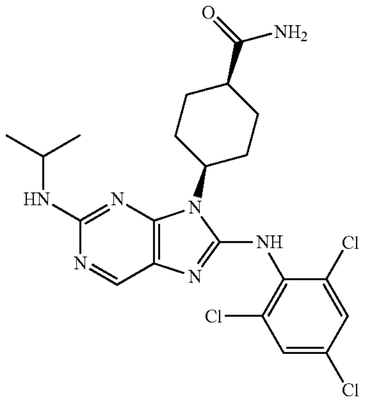 [SMILES: CC(C)Nc1ncc2nc(Nc3c(Cl)cc(Cl)cc3Cl)n([C@H]3CC[C@@H](C(N)=O)CC3)c2n1] | (1s,4s)-4-(2-(isopropylamino)-8-(2,4,6-trichlorophenylamino)-9H-purin-9-yl)cyclohexanecarboxamide | 496.2 | B |
| 60 | 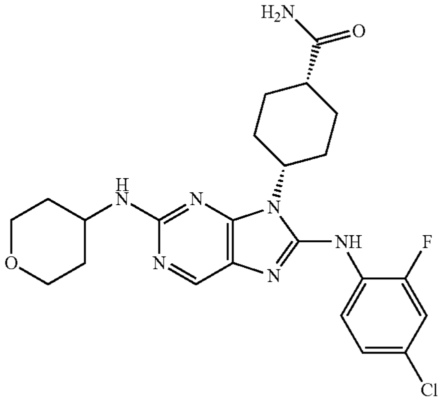 [SMILES: NC(=O)[C@H]1CC[C@@H](n2c(Nc3ccc(Cl)cc3F)nc3cnc(NC4CCOCC4)nc32)CC1] | (1s,4s)-4-(8-(4-chloro-2-fluorophenylamino)-2-(tetrahydro-2H-pyran-4-ylamino)-9H-purin-9-yl)cyclohexanecarboxamide | 488.1 | B |
| 61 | 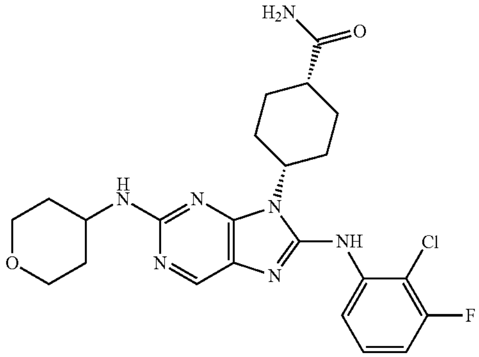 [SMILES: NC(=O)[C@H]1CC[C@@H](n2c(Nc3cccc(F)c3Cl)nc3cnc(NC4CCOCC4)nc32)CC1] | (1s,4s)-4-(8-(2-chloro-3-fluorophenylamino)-2-(tetrahydro-2H-pyran-4-ylamino)-9H-purin-9-yl)cyclohexanecarboxamide | 488.2 | A |
| 62 | 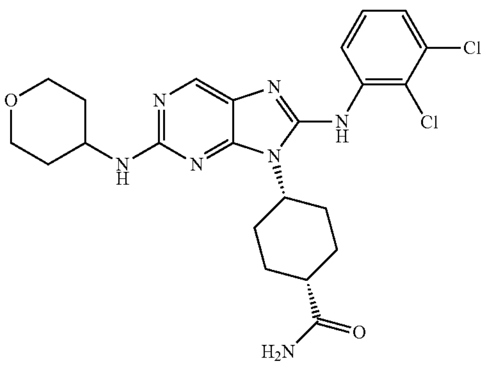 [SMILES: NC(=O)[C@H]1CC[C@@H](n2c(Nc3cccc(Cl)c3Cl)nc3cnc(NC4CCOCC4)nc32)CC1] | (1s,4s)-4-(8-(2,3-dichlorophenylamino)-2-(tetrahydro-2H-pyran-4-ylamino)-9H-purin-9-yl)cyclohexanecarboxamide | 504.1 | A |

TABLE 1-continued
| Cmpd No. | Structure | Name | MH+ | Activity |
|---|---|---|---|---|
| 63 | 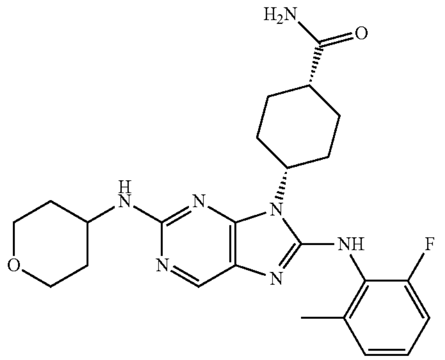 [SMILES: Cc1cccc(F)c1Nc1nc2cnc(NC3CCOCC3)nc2n1[C@H]1CC[C@@H](C(N)=O)CC1] | (1s,4s)-4-(8-(2-fluoro-6-methylphenylamino)-2-(tetrahydro-2H-pyran-4-ylamino)-9H-purin-9-yl)cyclohexanecarboxamide | 468.2 | A |
| 64 | 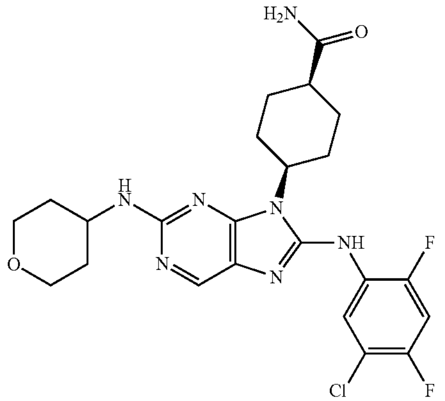 [SMILES: NC(=O)[C@H]1CC[C@@H](n2c(Nc3cc(Cl)c(F)cc3F)nc3cnc(NC4CCOCC4)nc32)CC1] | (1s,4s)-4-(8-(5-chloro-2,4-difluorophenylamino)-2-(tetrahydro-2H-pyran-4-ylamino)-9H-purin-9-yl)cyclohexanecarboxamide | 506.2 | A |
| 65 | 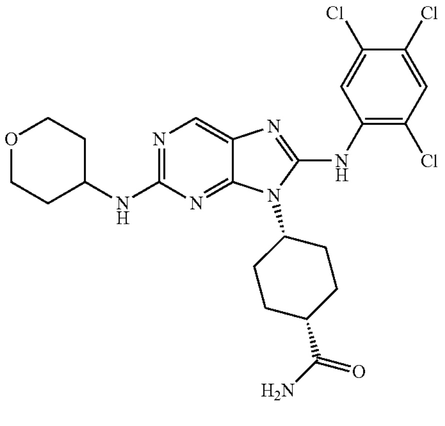 [SMILES: NC(=O)[C@H]1CC[C@@H](n2c(Nc3cc(Cl)c(Cl)cc3Cl)nc3cnc(NC4CCOCC4)nc32)CC1] | (1s,4s)-4-(2-(tetrahydro-2H-pyran-4-ylamino)-8-(2,4,5-trichlorophenylamino)-9H-purin-9-yl)cyclohexanecarboxamide | 504.1 | A |

TABLE 1-continued
| Cmpd No. | Structure | Name | MH+ | Activity |
|---|---|---|---|---|
| 66 | 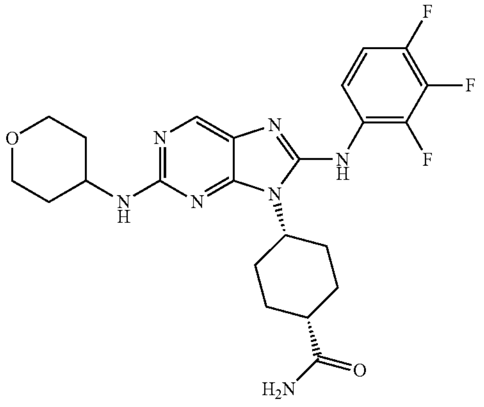 | (1s,4s)-4-(2-(tetrahydro-2H-pyran-4-ylamino)-8-(2,3,4-trifluorophenylamino)-9H-purin-9-yl)cyclohexanecarboxamide | 490.2 | B |
| 67 | 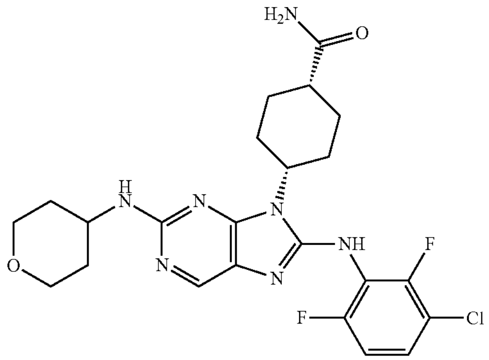 [SMILES: NC(=O)[C@H]1CC[C@@H](n2c(Nc3c(F)ccc(Cl)c3F)nc3cnc(NC4CCOCC4)nc32)CC1] | (1s,4s)-4-(8-(3-chloro-2,6-difluorophenylamino)-2-(tetrahydro-2H-pyran-4-ylamino)-9H-purin-9-yl)cyclohexanecarboxamide | 506.2 | A |
| 68 | 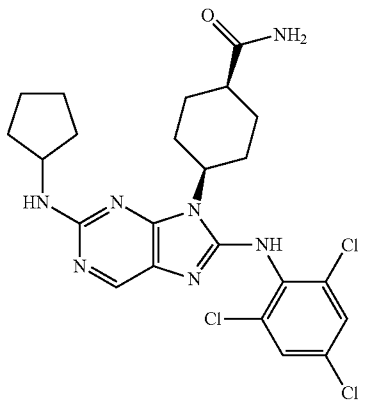 [SMILES: NC(=O)[C@H]1CC[C@@H](n2c(Nc3c(Cl)cc(Cl)cc3Cl)nc3cnc(NC4CCCC4)nc32)CC1] | (1s,4s)-4-(2-(cyclopentylamino)-8-(2,4,6-trichlorophenylamino)-9H-purin-9-yl)cyclohexanecarboxamide | 524.1 | B |

TABLE 1-continued
| Cmpd No. | Structure | Name | MH+ | Activity |
|---|---|---|---|---|
| 69 | 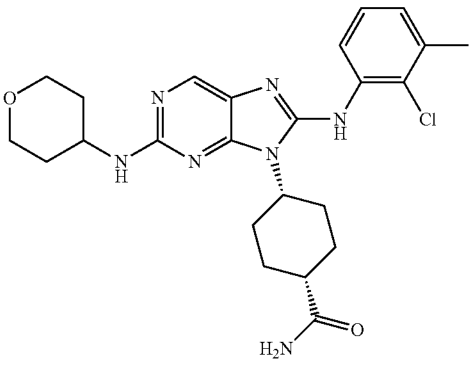 [SMILES: Cc1cccc(Nc2nc3cnc(NC4CCOCC4)nc3n2[C@H]2CC[C@@H](C(N)=O)CC2)c1Cl] | (1s,4s)-4-(8-(2-chloro-3-methylphenylamino)-2-(tetrahydro-2H-pyran-4-ylamino)-9H-purin-9-yl)cyclohexanecarboxamide | 484.2 | A |
| 70 | 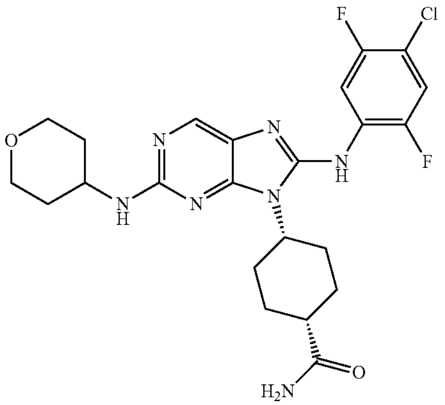 [SMILES: NC(=O)[C@H]1CC[C@@H](n2c(Nc3cc(F)c(Cl)cc3F)nc3cnc(NC4CCOCC4)nc32)CC1] | (1s,4s)-4-(8-(4-chloro-2,5-difluorophenylamino)-2-(tetrahydro-2H-pyran-4-ylamino)-9H-purin-9-yl)cyclohexanecarboxamide | 506.2 | B |
| 71 | 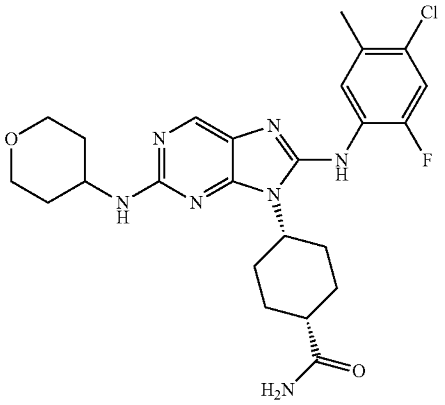 [SMILES: Cc1cc(Nc2nc3cnc(NC4CCOCC4)nc3n2[C@H]2CC[C@@H](C(N)=O)CC2)c(F)cc1Cl] | (1s,4s)-4-(8-(4-chloro-2-fluoro-5-methylphenylamino)-2-(tetrahydro-2H-pyran-4-ylamino)-9H-purin-9-yl)cyclohexanecarboxamide | 502.2 | A |

TABLE 1-continued
| Cmpd No. | Structure | Name | MH+ | Activity |
|---|---|---|---|---|
| 72 | 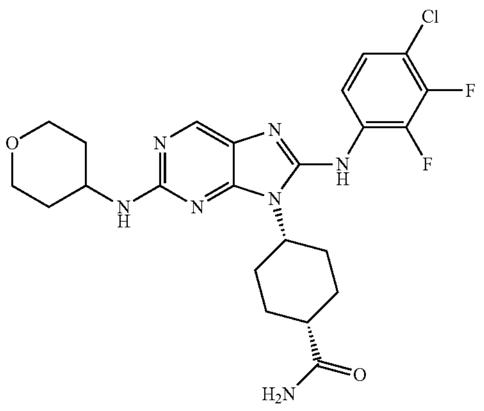 | (1s,4s)-4-(8-(4-chloro-2,3-difluorophenylamino)-2-(tetrahydro-2H-pyran-4-ylamino)-9H-purin-9-yl)cyclohexanecarboxamide | 506.2 | C |
| 73 | 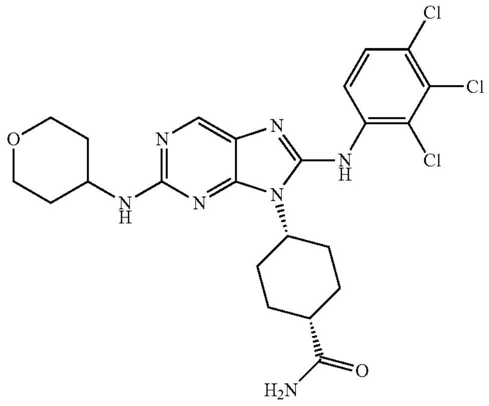 [SMILES: NC(=O)[C@H]1CC[C@@H](n2c(Nc3ccc(Cl)c(Cl)c3Cl)nc3cnc(NC4CCOCC4)nc32)CC1] | (1s,4s)-4-(2-(tetrahydro-2H-pyran-4-ylamino)-8-(2,3,4-trichlorophenylamino)-9H-purin-9-yl)cyclohexanecarboxamide | 538.1 | A |
| 74 | 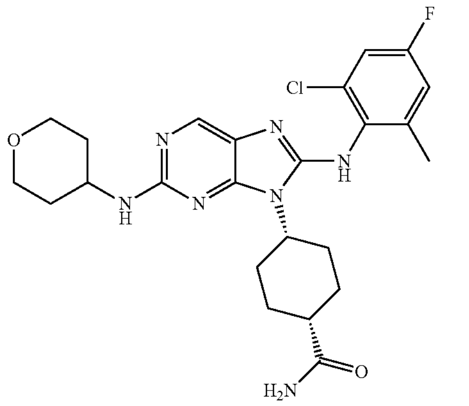 [SMILES: Cc1cc(F)cc(Cl)c1Nc1nc2cnc(NC3CCOCC3)nc2n1[C@H]1CC[C@@H](C(N)=O)CC1] | (1s,4s)-4-(8-(2-chloro-4-fluoro-6-methylphenylamino)-2-(tetrahydro-2H-pyran-4-ylamino)-9H-purin-9-yl)cyclohexanecarboxamide | 502.2 | A |

TABLE 1-continued
| Cmpd No. | Structure | Name | MH+ | Activity |
|---|---|---|---|---|
| 75 | 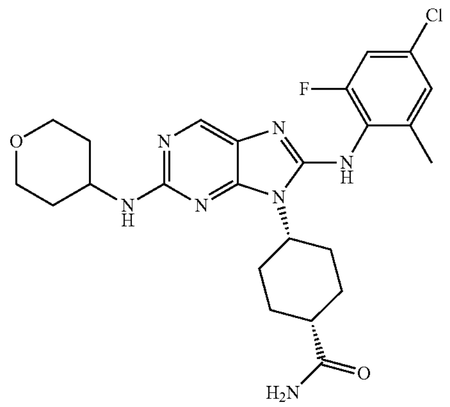 | (1s,4s)-4-(8-(4-chloro-2-fluoro-6-methylphenylamino)-2-(tetrahydro-2H-pyran-4-ylamino)-9H-purin-9-yl)cylcohexanecarboxamide | 502.2 | A |
| 76 | 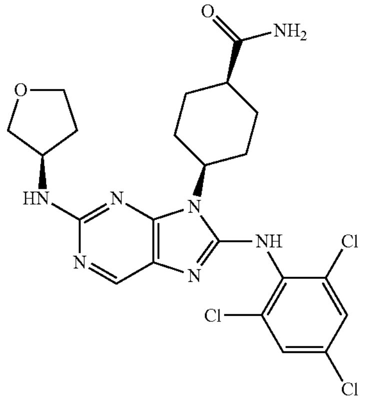 [SMILES: NC(=O)[C@H]1CC[C@@H](n2c(Nc3c(Cl)cc(Cl)cc3Cl)nc3cnc(N[C@@H]4CCOC4)nc32)CC1] | (1S,4s)-4-(2-((R)-tetrahydrofuran-3-ylamino)-8-(2,4,6-trichlorophenyalmino)-9H-purin-9-yl)cyclohexanecarboxamide | 524.2 | C |
| 77 | 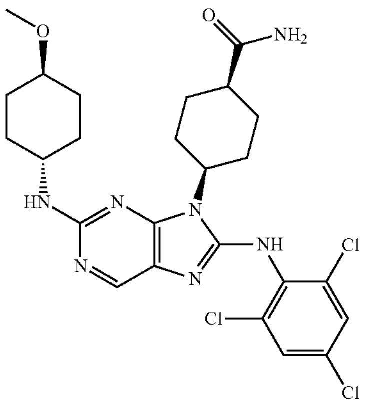 [SMILES: CO[C@H]1CC[C@H](Nc2ncc3nc(Nc4c(Cl)cc(Cl)cc4Cl)n([C@H]4CC[C@@H](C(N)=O)CC4)c3n2)CC1] | (1s,4s)-4-(2-((1r,4r)-4-methoxycyclohexylamino)-8-(2,4,6-trichlorophenylamino)-9H-purin-9-yl)cyclohexanecarboxamide | 566.2 | B |

TABLE 1-continued
| Cmpd No. | Structure | Name | MH+ | Activity |
|---|---|---|---|---|
| 78 | 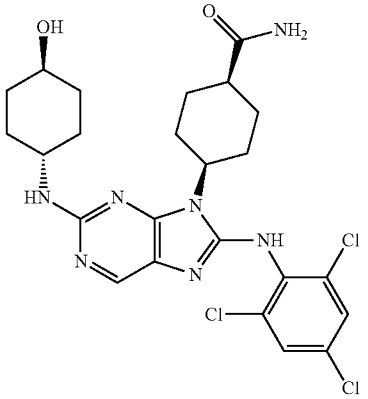 [SMILES: NC(=O)[C@H]1CC[C@@H](n2c(Nc3c(Cl)cc(Cl)cc3Cl)nc3cnc(N[C@H]4CC[C@H](O)CC4)nc32)CC1] | (1s,4s)-4-(2-((1r,4r)-4-hydroxycyclohexylamino)-8-(2,4,6-trichlorophenylamino)-9H-purin-9-yl)cyclohexanecarboxamide | 552.2 | A |
| 79 | 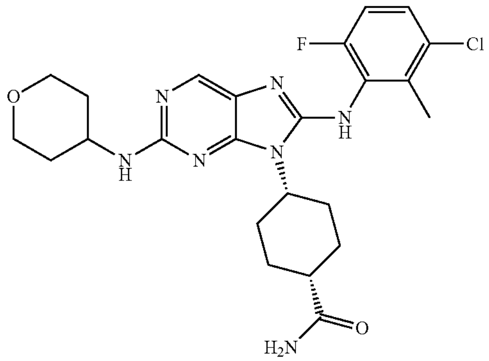 [SMILES: Cc1c(Cl)ccc(F)c1Nc1nc2cnc(NC3CCOCC3)nc2n1[C@H]1CC[C@@H](C(N)=O)CC1] | (1s,4s)-4-(8-(3-chloro-6-fluoro-2-methylphenylamino)-2-(tetrahydro-2H-pyran-4-ylamino)-9H-purin-9-yl)cyclohexanecarboxamide | 502.2 | A |
| 80 | 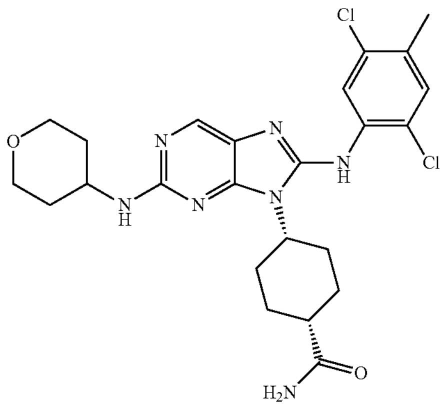 [SMILES: Cc1cc(Cl)c(Nc2nc3cnc(NC4CCOCC4)nc3n2[C@H]2CC[C@@H](C(N)=O)CC2)cc1Cl] | (1s,4s)-4-(8-(2,5-dichloro-4-methylphenylamino)-2-(tetrahydro-2H-pyran-4-ylamino)-9H-purin-9-yl)cyclohexanecarboxamide | 518.1 | B |

TABLE 1-continued
| Cmpd No. | Structure | Name | MH+ | Activity |
| --- | --- | --- | --- | --- |
| 81 | 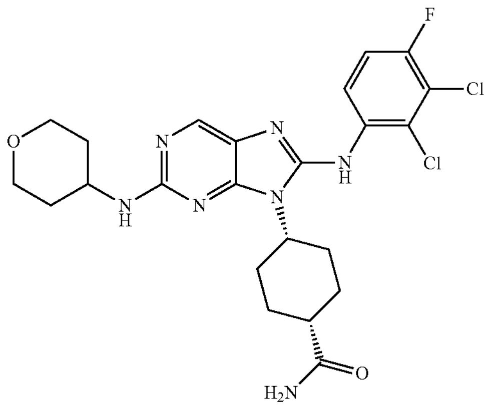 | (1s,4s)-4-(8-(2,3-dichloro-4-fluorophenylamino)-2-(tetrahydro-2H-pyran-4-ylamino)-9H-purin-9-yl)cyclohexanecarboxamide | 522 | A |
| 82 | 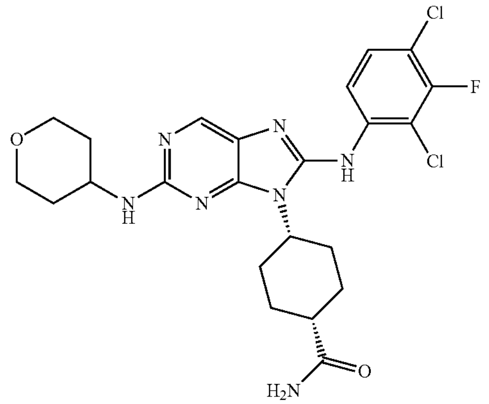 [SMILES: NC(=O)[C@H]1CC[C@@H](n2c(Nc3ccc(Cl)c(F)c3Cl)nc3cnc(NC4CCOCC4)nc32)CC1] | (1s,4s)-4-(8-(2,4-dichloro-3-fluorophenylamino)-2-(tetrahydro-2H-pyran-4-ylamino)-9H-purin-9-yl)cyclohexanecarboxamide | 522.1 | A |
| 83 | 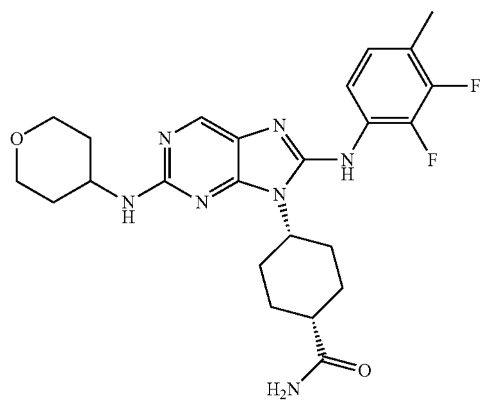 [SMILES: Cc1ccc(Nc2nc3cnc(NC4CCOCC4)nc3n2[C@H]2CC[C@@H](C(N)=O)CC2)c(F)c1F] | (1s,4s)-4-(8-(2,3-difluoro-4-methylphenylamino)-2-(tetrahydro-2H-pyran-4-ylamino)-9H-purin-9-yl)cyclohexanecarboxamide | 486.3 | B |

TABLE 1-continued
| Cmpd No. | Structure | Name | MH+ | Activity |
|---|---|---|---|---|
| 84 | 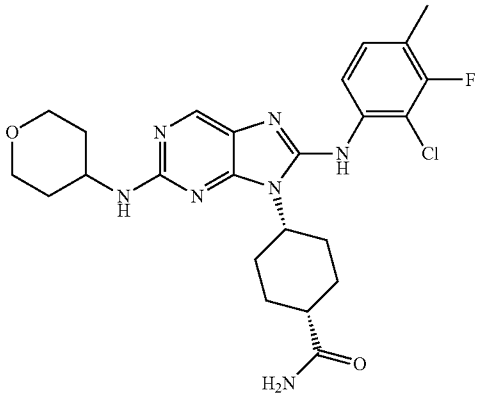 [SMILES: Cc1ccc(Nc2nc3cnc(NC4CCOCC4)nc3n2[C@H]2CC[C@@H](C(N)=O)CC2)c(Cl)c1F] | (1s,4s)-4-(8-(2-chloro-3-fluoro-4-methylphenylamino)-2-(tetrahydro-2H-pyran-4-ylamino)-9H-purin-9-yl)cyclohexanecarboxamide | 502.2 | B |
| 85 | 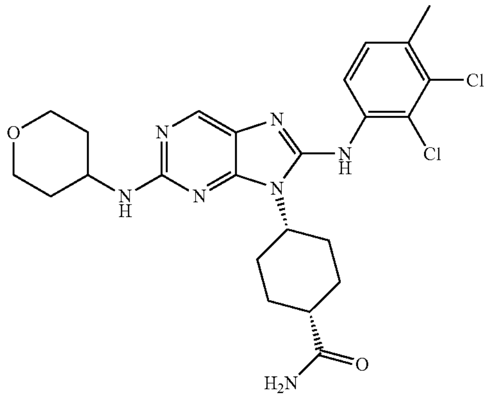 [SMILES: Cc1ccc(Nc2nc3cnc(NC4CCOCC4)nc3n2[C@H]2CC[C@@H](C(N)=O)CC2)c(Cl)c1Cl] | (1s,4s)-4-(8-(2,3-dichloro-4-methylphenylamino)-2-(tetrahydro-2H-pyran-4-ylamino)-9H-purin-9-yl)cyclohexanecarboxamide | 518.2 | A |
| 86 | 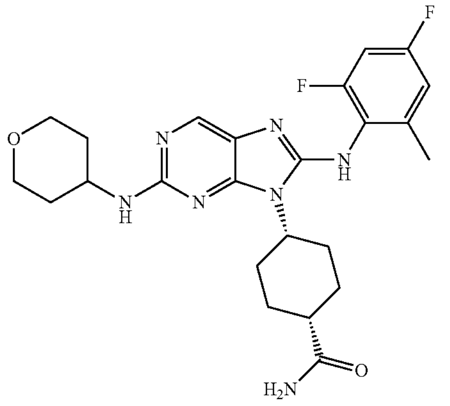 | (1s,4s)-4-(8-(2,4-difluoro-6-methylphenylamino)-2-(tetrahydro-2H-pyran-4-ylamino)-9H-purin-9-yl)cyclohexanecarboxamide | 486.3 | A |

TABLE 1-continued
| Cmpd No. | Structure | Name | MH+ | Activity |
| --- | --- | --- | --- | --- |
| 87 | 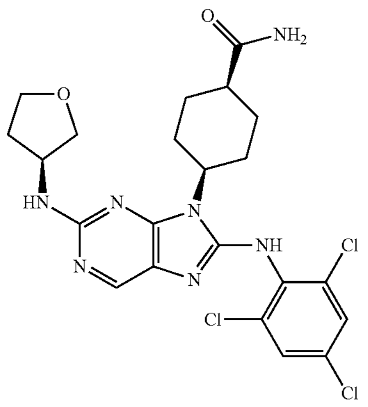 [SMILES: NC(=O)[C@H]1CC[C@@H](n2c(Nc3c(Cl)cc(Cl)cc3Cl)nc3cnc(N[C@H]4CCOC4)nc32)CC1] | (1R,4s)-4-(2-((S)-tetrahydrofuran-3-ylamino)-8-(2,4,6-trichlorophenylamino)-9H-purin-9-yl)cyclohexanecarboxamide | 525.2 | B |
| 88 | 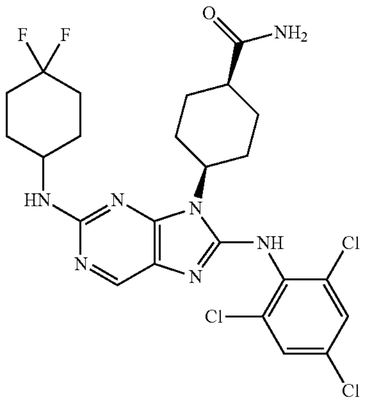 [SMILES: NC(=O)[C@H]1CC[C@@H](n2c(Nc3c(Cl)cc(Cl)cc3Cl)nc3cnc(NC4CCC(F)(F)CC4)nc32)CC1] | (1s,4s)-4-(2-(4,4-difluorocyclohexylamino)-8-(2,4,6-trichlorophenylamino)-9H-purin-9-yl)cyclohexanecarboxamide | 572.1 | B |
| 89 | 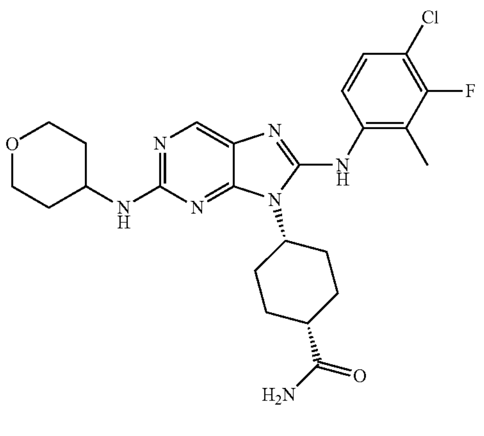 [SMILES: Cc1c(Nc2nc3cnc(NC4CCOCC4)nc3n2[C@H]2CC[C@@H](C(N)=O)CC2)ccc(Cl)c1F] | (1s,4s)-4-(8-(4-chloro-3-fluoro-2-methylphenylamino)-2-(tetrahydro-2H-pyran-4-ylamino)-9H-purin-9-yl)cyclohexanecarboxamide | 502.1 | A |

TABLE 1-continued
| Cmpd No. | Structure | Name | MH+ | Activity |
|---|---|---|---|---|
| 90 | 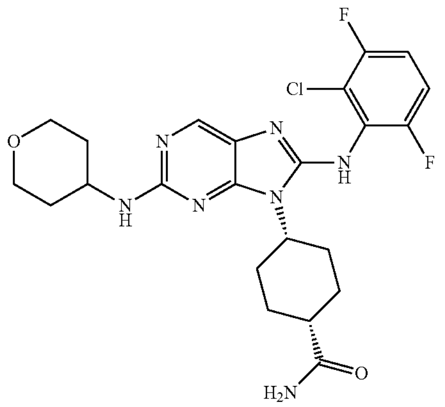 | (1s,4s)-4-(8-(2-chloro-3,6-difluorophenylamino)-2-(tetrahydro-2H-pyran-4-ylamino)-9H-purin-9-yl)cyclohexanecarboxamide | 506.1 | C |
| 91 | 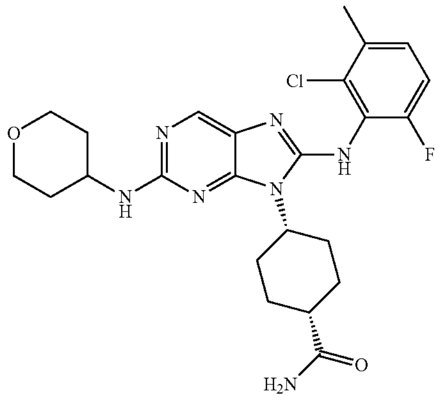 [SMILES: Cc1ccc(F)c(Nc2nc3cnc(NC4CCOCC4)nc3n2[C@H]2CC[C@@H](C(N)=O)CC2)c1Cl] | (1s,4s)-4-(8-(2-chloro-6-fluoro-3-methylphenylamino)-2-(tetrahydro-2H-pyran-4-ylamino)-9H-purin-9-yl)cyclohexanecarboxamide | 502.1 | A |
| 92 | 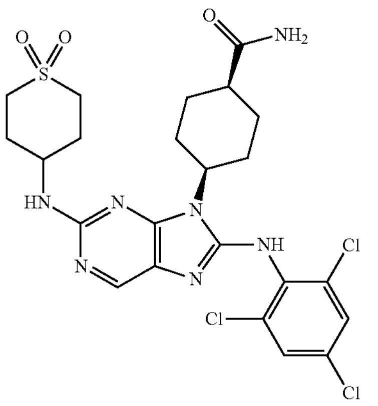 [SMILES: NC(=O)[C@H]1CC[C@@H](n2c(Nc3c(Cl)cc(Cl)cc3Cl)nc3cnc(NC4CCS(=O)(=O)CC4)nc32)CC1] | (1s,4s)-4-(2-((1,1-dioxidotetrahydro-2H-thiopyran-4-yl)amino)-8-((2,4,6-trichlorophenyl)amino)-9H-purin-9-yl)cyclohexane-1-carboxamide | 586 | A |

TABLE 1-continued
| Cmpd No. | Structure | Name | MH+ | Ac-tivi-ty |
|---|---|---|---|---|
| 93 | 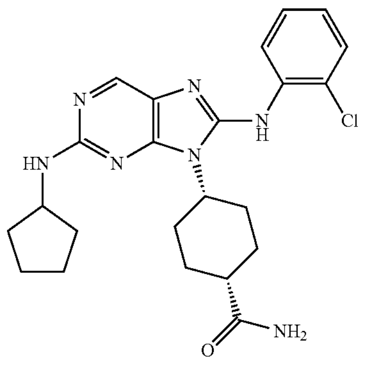 [SMILES: NC(=O)[C@H]1CC[C@@H](n2c(Nc3ccccc3Cl)nc3cnc(NC4CCCC4)nc32)CC1] | (1s,4s)-4-(8-(2-chlorophenylamino)-2-(cyclopentylamino)-9H-purin-9-yl)cyclohexanecarboxamide | 545.3 | A |
| 94 | 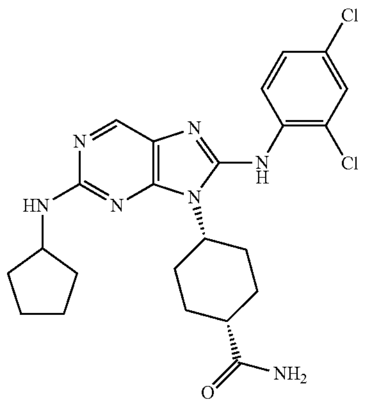 [SMILES: NC(=O)[C@H]1CC[C@@H](n2c(Nc3ccc(Cl)cc3Cl)nc3cnc(NC4CCCC4)nc32)CC1] | (1s,4s)-4-(2-(cyclopentylamino)-8-(2,4-dichlorophenylamino)-9H-purin-9-yl)cyclohexanecarboxamide | 488.2 | A |
| 95 | 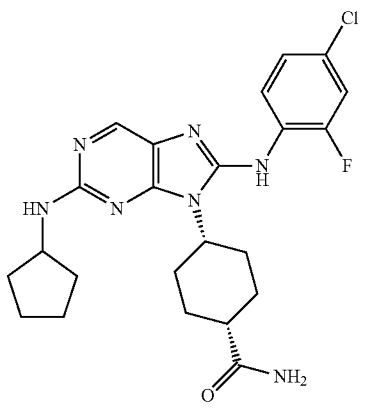 [SMILES: NC(=O)[C@H]1CC[C@@H](n2c(Nc3ccc(Cl)cc3F)nc3cnc(NC4CCCC4)nc32)CC1] | (1s,4s)-4-(8-(4-chloro-2-fluorophenylamino)-2-(cyclopentylamino)-9H-purin-9-yl)cyclohexanecarboxamide | 472.3 | A |

TABLE 1-continued
| Cmpd No. | Structure | Name | MH+ | Activity |
|---|---|---|---|---|
| 96 | 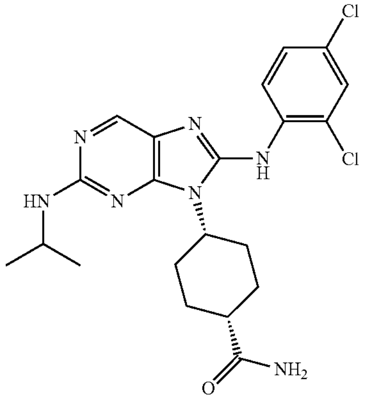 [SMILES: CC(C)Nc1ncc2nc(Nc3ccc(Cl)cc3Cl)n([C@H]3CC[C@@H](C(N)=O)CC3)c2n1] | (1s,4s)-4-(8-(2,4-dichlorophenylamino)-2-(isopropylamino)-9H-purin-9-yl)cyclohexanecarboxamide | 462.2 | A |
| 97 | 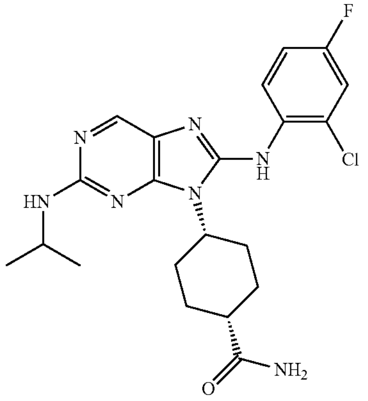 [SMILES: CC(C)Nc1ncc2nc(Nc3ccc(F)cc3Cl)n([C@H]3CC[C@@H](C(N)=O)CC3)c2n1] | (1s,4s)-4-(8-(2-chloro-4-fluorophenylamino)-2-(isopropylamino)-9H-purin-9-yl)cyclohexanecarboxamide | 446.2 | A |
| 98 | 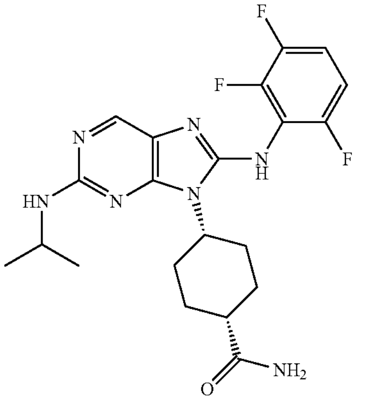 [SMILES: CC(C)Nc1ncc2nc(Nc3c(F)ccc(F)c3F)n([C@H]3CC[C@@H](C(N)=O)CC3)c2n1] | (1s,4S)-4-(2-(isopropylamino)-8-(2,3,6-trifluorophenylamino)-9H-purin-9-yl)cyclohexanecarboxamide | 448.2 | A |

TABLE 1-continued
| Cmpd No. | Structure | Name | MH+ | Activity |
|---|---|---|---|---|
| 99 | 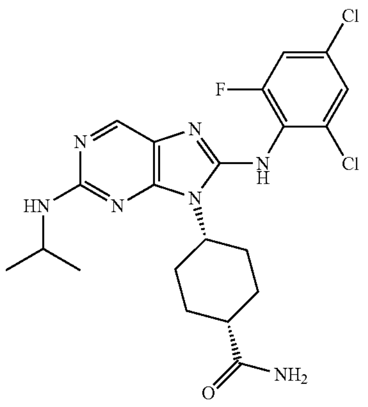 [SMILES: CC(C)Nc1ncc2nc(Nc3c(F)cc(Cl)cc3Cl)n([C@H]3CC[C@@H](C(N)=O)CC3)c2n1] | (1s,4s)-4-(8-(2,4-dichloro-6-fluorophenylamino)-2-(isopropylamino)-9H-purin-9-yl)cyclohexanecarboxamide | 480.1 | C |
| 100 | 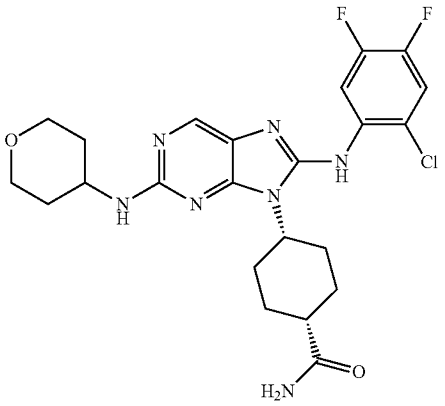 | (1s,4s)-4-(8-(2-chloro-4,5-difluorophenylamino)-2-(tetrahydro-2H-pyran-4-ylamino)-9H-purin-9-yl)cyclohexanecarboxamide | 506.1 | A |
| 101 | 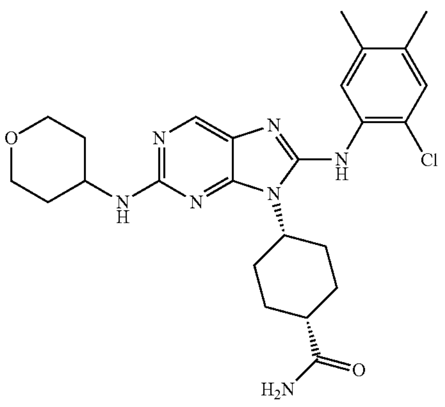 [SMILES: Cc1cc(Cl)c(Nc2nc3cnc(NC4CCOCC4)nc3n2[C@H]2CC[C@@H](C(N)=O)CC2)cc1C] | (1s,4s)-4-(8-(2-chloro-4,5-dimethylphenylamino)-2-(tetrahydro-2H-pyran-4-ylamino)-9H-purin-9-yl)cyclohexanecarboxamide | 498.2 | A |

TABLE 1-continued
| Cmpd No. | Structure | Name | MH+ | Activity |
|---|---|---|---|---|
| 102 | 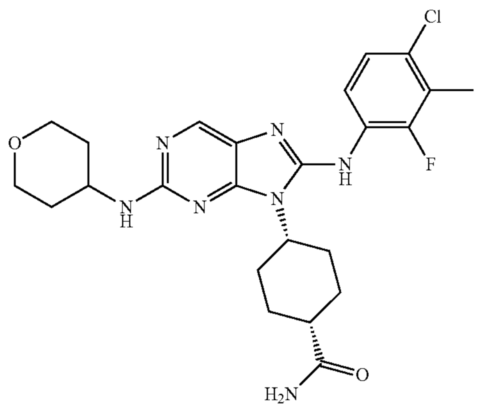 [SMILES: Cc1c(Cl)ccc(Nc2nc3cnc(NC4CCOCC4)nc3n2[C@H]2CC[C@@H](C(N)=O)CC2)c1F] | (1s,4s)-4-(8-(4-chloro-2-fluoro-3-methylphenylamino)-2-(tetrahydro-2H-pyran-4-ylamino)-9H-purin-9-yl)cyclohexanecarboxamide | 502.1 | A |
| 103 | 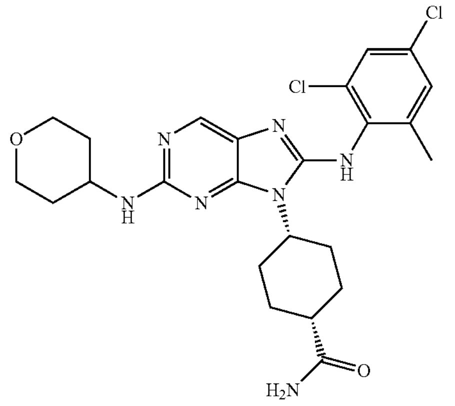 | (1s,4s)-4-(8-(2,4-dichloro-6-methylphenylamino)-2-(tetrahydro-2H-pyran-4-ylamino)-9H-purin-9-yl)cyclohexanecarboxamide | 518.1 | A |
| 104 | 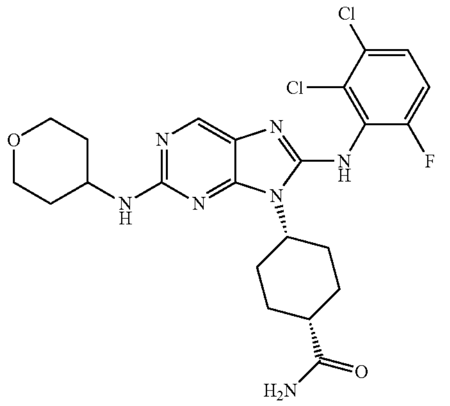 [SMILES: NC(=O)[C@H]1CC[C@@H](n2c(Nc3c(F)ccc(Cl)c3Cl)nc3cnc(NC4CCOCC4)nc32)CC1] | (1s,4s)-4-(8-(2,3-dichloro-6-fluorophenylamino)-2-(tetrahydro-2H-pyran-4-ylamino)-9H-purin-9-yl)cyclohexanecarboxamide | 522.1 | C |

TABLE 1-continued
| Cmpd No. | Structure | Name | MH+ | Activity |
|---|---|---|---|---|
| 105 | 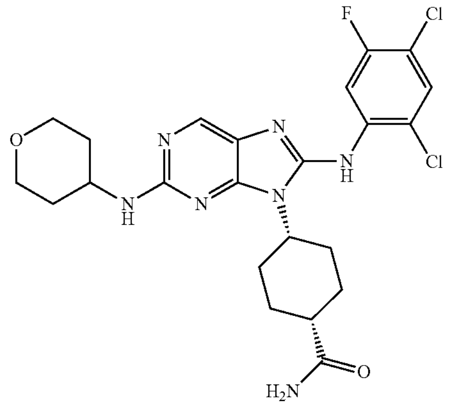 [SMILES: NC(=O)[C@H]1CC[C@@H](n2c(Nc3cc(F)c(Cl)cc3Cl)nc3cnc(NC4CCOCC4)nc32)CC1] | (1s,4s)-4-(8-(2,4-dichloro-5-fluorophenylamino)-2-(tetrahydro-2H-pyran-4-ylamino)-9H-purin-9-yl)cyclohexanecarboxamide | 522.1 | A |
| 106 | 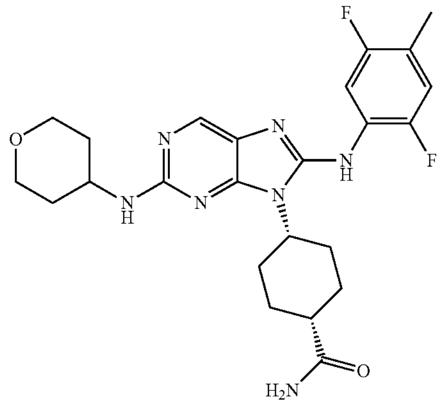 | (1s,4s)-4-(8-(2,5-difluoro-4-methylphenylamino)-2-(tetrahydro-2H-pyran-4-ylamino)-9H-purin-9-yl)cyclohexanecarboxamide | 486.2 | A |
| 107 | 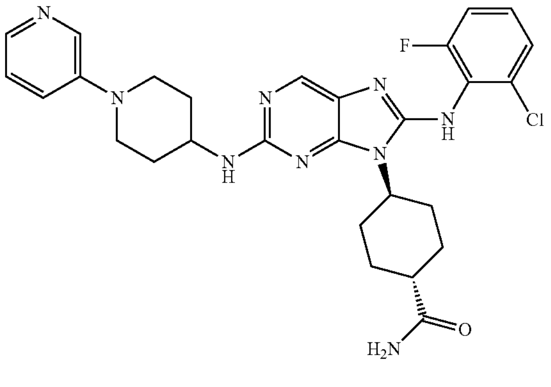 [SMILES: NC(=O)[C@H]1CC[C@H](n2c(Nc3c(F)cccc3Cl)nc3cnc(NC4CCN(c5cccnc5)CC4)nc32)CC1] | (1s,4s)-4-(8-(2-chloro-6-fluorophenylamino)-2-(1-(pyridin-3-yl)piperiidn-4-ylamino)-9H-purin-9-yl)cyclohexanecarboxamide | 564.2 | A |

TABLE 1-continued
| Cmpd No. | Structure | Name | MH+ | Activity |
|---|---|---|---|---|
| 108 | 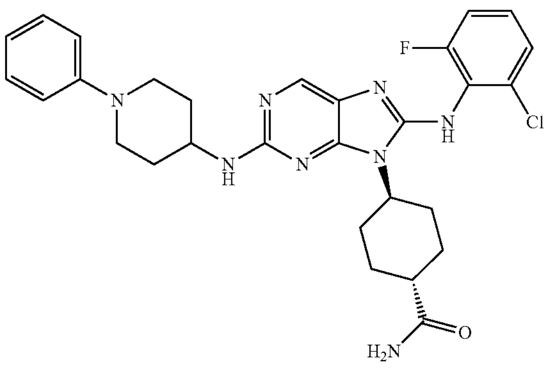 [SMILES: NC(=O)[C@H]1CC[C@H](n2c(Nc3c(F)cccc3Cl)nc3cnc(NC4CCN(c5ccccc5)CC4)nc32)CC1] | (1s,4s)-4-(8-(2-chloro-6-fluorophenylamino)-2-(1-phenylpiperidin-4-ylamino)-9H-purin-9-yl)cyclohexanecarboxamide | 563.2 | A |
| 109 | 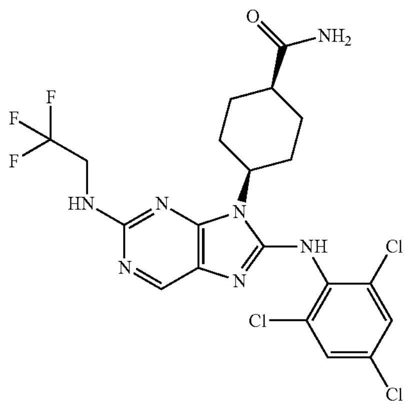 [SMILES: NC(=O)[C@H]1CC[C@@H](n2c(Nc3c(Cl)cc(Cl)cc3Cl)nc3cnc(NCC(F)(F)F)nc32)CC1] | (1s,4s)-4-(8-(2,4,6-trichlorophenylamino)-2-(2,2,2-trifluoroethylamino)-9H-purin-9-yl)cyclohexanecarboxamide | 526.2 | A |
| 110 | 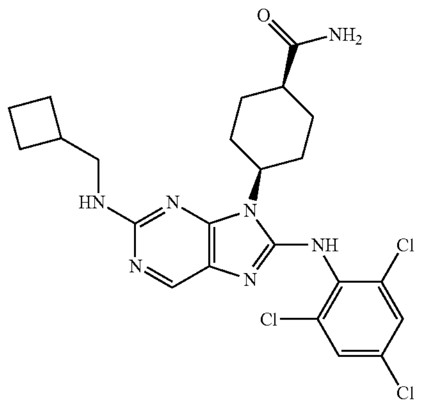 [SMILES: NC(=O)[C@H]1CC[C@@H](n2c(Nc3c(Cl)cc(Cl)cc3Cl)nc3cnc(NCC4CCC4)nc32)CC1] | (1s,4s)-4-(2-(cyclobutylmethylamino)-8-(2,4,6-trichlorophenylamino)-9H-purin-9-yl)cyclohexanecarboxamide | 524.1 | B |

TABLE 1-continued
| Cmpd No. | Structure | Name | MH+ | Activity |
|---|---|---|---|---|
| 111 | 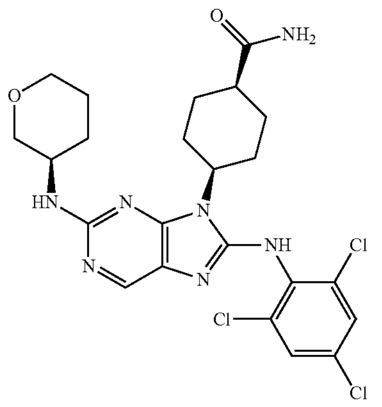 [SMILES: NC(=O)[C@H]1CC[C@@H](n2c(Nc3c(Cl)cc(Cl)cc3Cl)nc3cnc(N[C@@H]4CCCOC4)nc32)CC1] | (1S,4s)-4-(2-((R)-tetrahydro-2H-pyran-3-ylamino)-8-(2,4,6-trichlorophenylamino)-9H-purin-9-yl)cyclohexanecarboxamide | 539 | A |
| 112 | 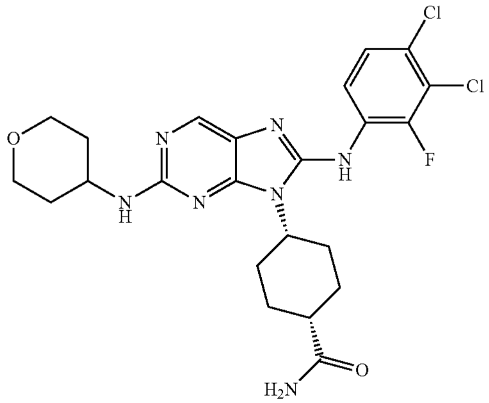 [SMILES: NC(=O)[C@H]1CC[C@@H](n2c(Nc3ccc(Cl)c(Cl)c3F)nc3cnc(NC4CCOCC4)nc32)CC1] | (1s,4s)-4-(8-(3,4-dichloro-2-fluorophenylamino)-2-(tetrahydro-2H-pyran-4-ylamino)-9H-purin-9-yl)cyclohexanecarboxamide | 522.2 | C |
| 113 | 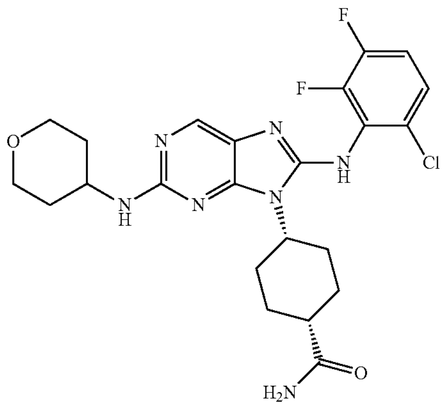 [SMILES: NC(=O)[C@H]1CC[C@@H](n2c(Nc3c(Cl)ccc(F)c3F)nc3cnc(NC4CCOCC4)nc32)CC1] | (1s,4s)-4-(8-(6-chloro-2,3-difluorophenylamino)-2-(tetrahydro-2H-pyran-4-ylamino)-9H-purin-9-yl)cyclohexanecarboxamide | 506.1 | B |

TABLE 1-continued
| Cmpd No. | Structure | Name | MH+ | Activity |
|---|---|---|---|---|
| 114 | 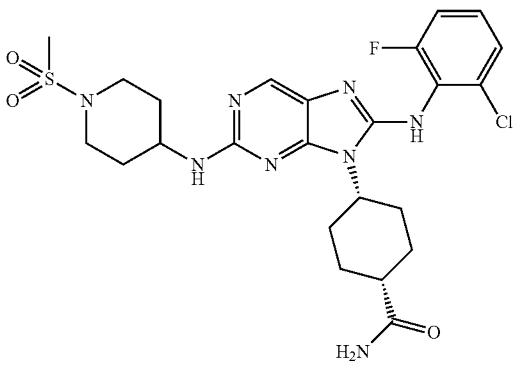 [SMILES: CS(=O)(=O)N1CCC(Nc2ncc3nc(Nc4c(F)cccc4Cl)n([C@H]4CC[C@@H](C(N)=O)CC4)c3n2)CC1] | (1s,4s)-4-(8-(2-chloro-6-fluorophenylamino)-2-(1-(methylsulfonyl)piperidin-4-ylamino)-9H-purin-9-yl)cyclohexanecarboxamide | 565.1 | A |
| 115 | 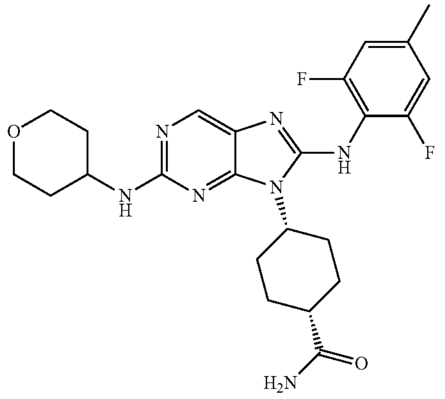 [SMILES: Cc1cc(F)c(Nc2nc3cnc(NC4CCOCC4)nc3n2[C@H]2CC[C@@H](C(N)=O)CC2)c(F)c1] | (1s,4s)-4-(8-(2,6-difluoro-4-methylphenylamino)-2-(tetrahydro-2H-pyran-4-ylamino)-9H-purin-9-yl)cyclohexanecarboxamide | 486.2 | B |
| 116 | 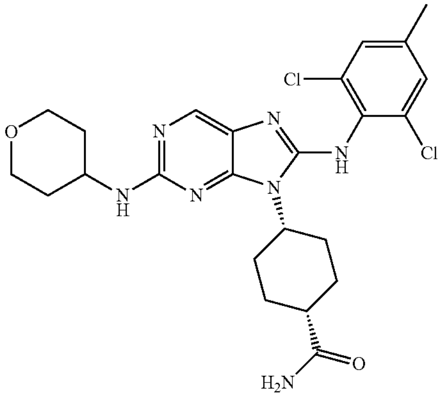 [SMILES: Cc1cc(Cl)c(Nc2nc3cnc(NC4CCOCC4)nc3n2[C@H]2CC[C@@H](C(N)=O)CC2)c(Cl)c1] | (1s,4s)-4-(8-(2,6-dichloro-4-methylphenylamino)-2-(tetrahydro-2H-pyran-4-ylamino)-9H-purin-9-yl)cyclohexanecarboxamide | 518.2 | A |

TABLE 1-continued
| Cmpd No. | Structure | Name | MH+ | Activity |
|---|---|---|---|---|
| 117 | 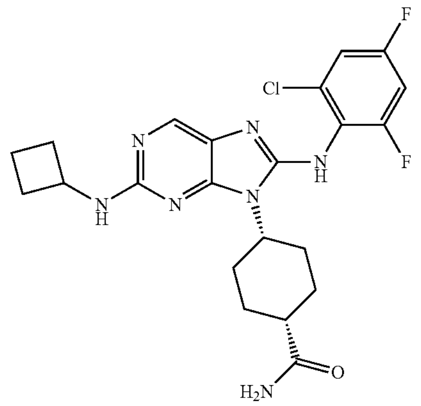 [SMILES: NC(=O)[C@H]1CC[C@@H](n2c(Nc3c(F)cc(F)cc3Cl)nc3cnc(NC4CCC4)nc32)CC1] | (1s,4s)-4-(8-(2-chloro-4,6-difluorophenylamino)-2-(cyclobutylamino)-9H-purin-9-yl)cyclohexanecarboxamide | 476.2 | B |
| 118 | 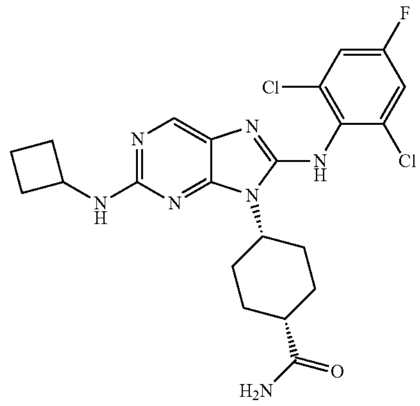 [SMILES: NC(=O)[C@H]1CC[C@@H](n2c(Nc3c(Cl)cc(F)cc3Cl)nc3cnc(NC4CCC4)nc32)CC1] | (1s,4s)-4-(2-(cyclobutylamino)-8-(2,6-dichloro-4-fluorophenylamino)-9H-purin-9-yl)cyclohexanecarboxamide | 492.1 | B |
| 119 | 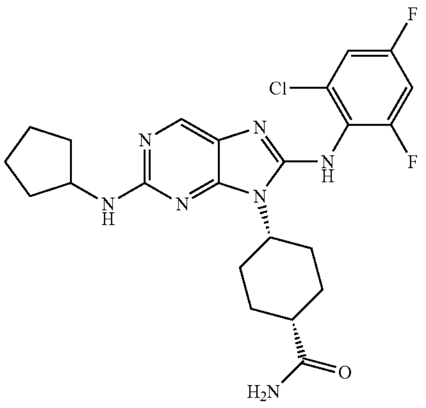 [SMILES: NC(=O)[C@H]1CC[C@@H](n2c(Nc3c(F)cc(F)cc3Cl)nc3cnc(NC4CCCC4)nc32)CC1] | (1s,4s)-4-(8-(2-chloro-4,6-difluorophenylamino)-2-(cyclopentylamino)-9H-purin-9-yl)cyclohexanecarboxamide | 490.1 | C |

TABLE 1-continued
| Cmpd No. | Structure | Name | MH+ | Activity |
|---|---|---|---|---|
| 120 | 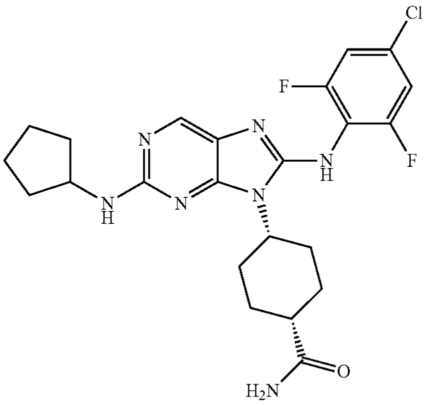 [SMILES: NC(=O)[C@H]1CC[C@@H](n2c(Nc3c(F)cc(Cl)cc3F)nc3cnc(NC4CCCC4)nc32)CC1] | (1s,4s)-4-(8-(4-chloro-2,6-difluorophenylamino)-2-(cyclopentylamino)-9H-purin-9-yl)cyclohexanecarboxamide | 490.2 | C |
| 121 | 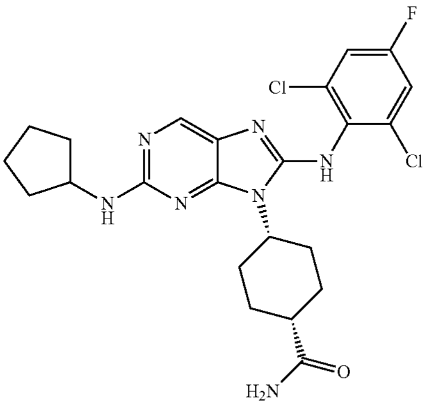 [SMILES: NC(=O)[C@H]1CC[C@@H](n2c(Nc3c(Cl)cc(F)cc3Cl)nc3cnc(NC4CCCC4)nc32)CC1] | (1s,4s)-4-(2-(cyclopentylamino)-8-(2,6-dichloro-4-fluorophenylamino)-9H-purin-9-yl)cyclohexanecarboxamide | 506.1 | B |
| 122 | 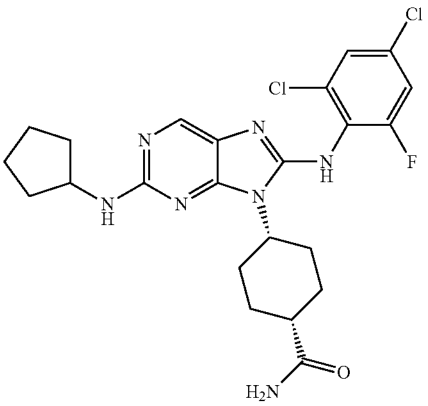 [SMILES: NC(=O)[C@H]1CC[C@@H](n2c(Nc3c(F)cc(Cl)cc3Cl)nc3cnc(NC4CCCC4)nc32)CC1] | (1s,4s)-4-(2-(cyclopentylamino)-8-(2,4-dichloro-6-fluorophenylamino)-9H-purin-9-yl)cyclohexanecarboxamide | 506.2 | C |

TABLE 1-continued
| Cmpd No. | Structure | Name | MH+ | Activity |
|---|---|---|---|---|
| 123 | 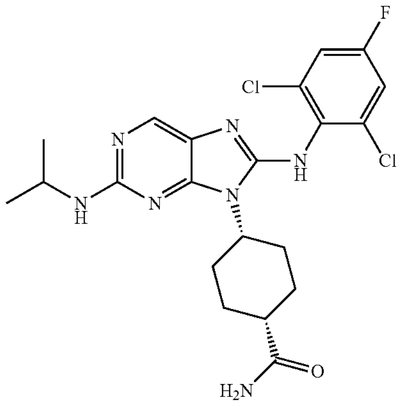 [SMILES: CC(C)Nc1ncc2nc(Nc3c(Cl)cc(F)cc3Cl)n([C@H]3CC[C@@H](C(N)=O)CC3)c2n1] | (1s,4s)-4-(8-(2,6-dichloro-4-fluorophenylamino)-2-(isopropylamino)-9H-purin-9-yl)cyclohexanecarboxamide | 480.1 | B |
| 124 | 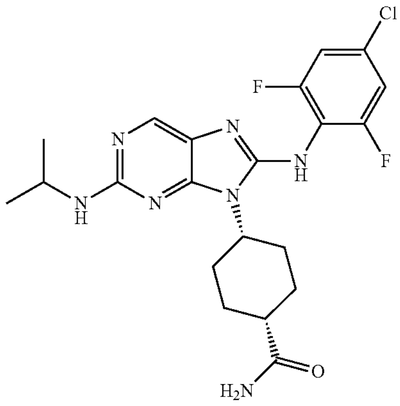 [SMILES: CC(C)Nc1ncc2nc(Nc3c(F)cc(Cl)cc3F)n([C@H]3CC[C@@H](C(N)=O)CC3)c2n1] | (1s,4s)-4-(8-(4-chloro-2,6-difluorophenylamino)-2-(isopropylamino)-9H-purin-9-yl)cyclohexanecarboxamide | 464.1 | A |
| 125 | 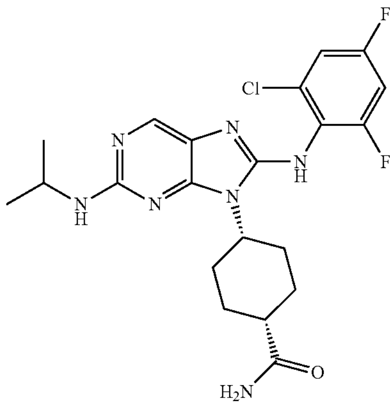 [SMILES: CC(C)Nc1ncc2nc(Nc3c(F)cc(F)cc3Cl)n([C@H]3CC[C@@H](C(N)=O)CC3)c2n1] | (1s,4s)-4-(8-(2-chloro-4,6-difluorophenylamino)-2-(isopropylamino)-9H-purin-9-yl)cyclohexanecarboxamide | 464.2 | B |

TABLE 1-continued

| Cmpd No. | Structure | Name | MH+ | Activity |
|---|---|---|---|---|
| 126 | 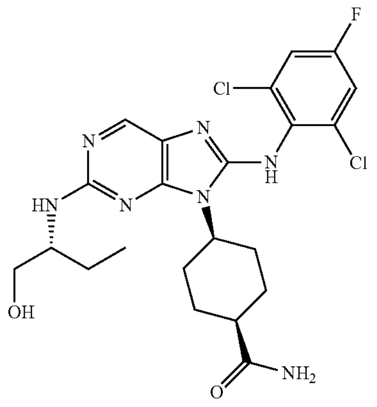 [SMILES: CC[C@H](CO)Nc1ncc2nc(Nc3c(Cl)cc(F)cc3Cl)n([C@H]3CC[C@@H](C(N)=O)CC3)c2n1] | (1S,4s)-4-(8-(2,6-dichloro-4-fluorophenylamino)-2-((R)-1-hydroxybutan-2-ylamino)-9H-purin-9-yl)cyclohexanecarboxamide | 510.1 | A |
| 127 | 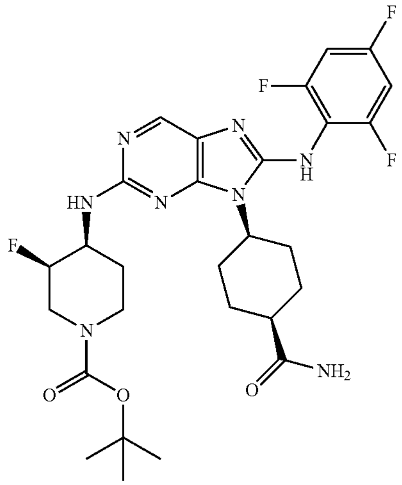 [SMILES: CC(C)(C)OC(=O)N1CC[C@H](Nc2ncc3nc(Nc4c(F)cc(F)cc4F)n([C@H]4CC[C@@H](C(N)=O)CC4)c3n2)[C@H](F)C1] | (3R,4S)-tert-butyl 4-(9-((1s,4R)-4-carbamoylcyclohexyl)-8-(2,4,6-trifluorophenylamino)-9H-purin-2-ylamino)-3-fluoropipeiridne-1-carboxylate | 607.2 | A |
| 128 | 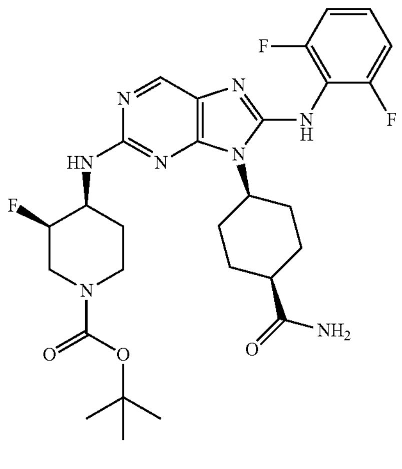 [SMILES: CC(C)(C)OC(=O)N1CC[C@H](Nc2ncc3nc(Nc4c(F)cccc4F)n([C@H]4CC[C@@H](C(N)=O)CC4)c3n2)[C@H](F)C1] | (3R,4S)-tert-butyl 4-(9-((1s,4R)-4-carbamoylcyclohexyl)-8-(2,6-difluorophenylamino)-9H-purin-2-ylamino)-3-fluoropiperidine-1-carboxamide | 589.2 | A |

TABLE 1-continued
| Cmpd No. | Structure | Name | MH+ | Activity |
|---|---|---|---|---|
| 129 | 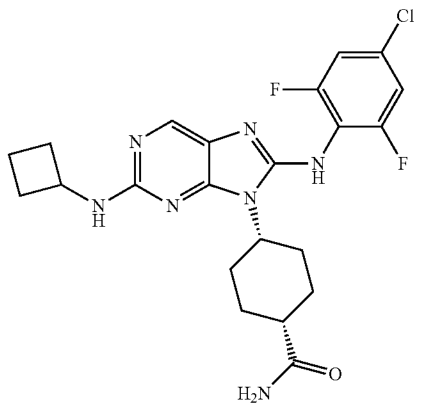 [SMILES: NC(=O)[C@H]1CC[C@@H](n2c(Nc3c(F)cc(Cl)cc3F)nc3cnc(NC4CCC4)nc32)CC1] | (1s,4s)-4-(8-(4-chloro-2,6-difluorophenylamino)-2-(cyclobutylamino)-9H-purin-9-yl)cyclohexanecarboxamide | 476.2 | A |
| 130 | 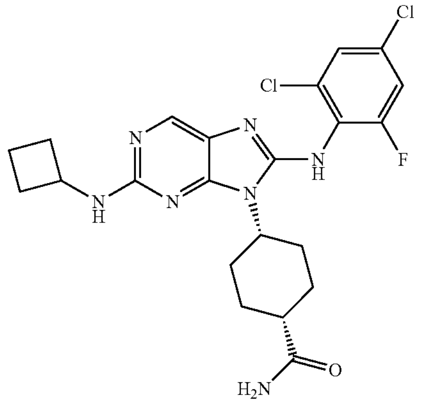 [SMILES: NC(=O)[C@H]1CC[C@@H](n2c(Nc3c(F)cc(Cl)cc3Cl)nc3cnc(NC4CCC4)nc32)CC1] | (1s,4s)-4-(2-(cyclobutylamino)-8-(2,4-dichloro-6-fluorophenylamino)-9H-purin-9-yl)cyclohexanecarboxamide | 492.1 | A |
| 131 | 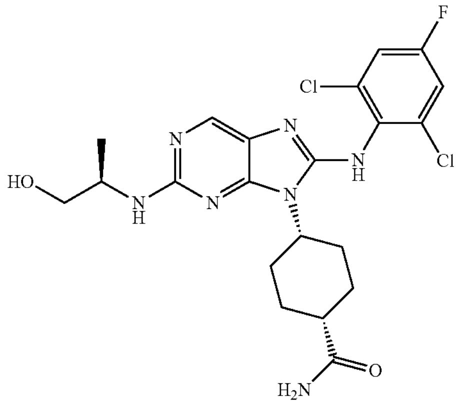 | (1S,4s)-4-(8-(2,6-dichloro-4-fluorophenylamino)-2-((R)-1-hydroxypropan-2-ylamino)-9H-purin-9-yl)cyclohexanecarboxamide | 496.2 | A |

TABLE 1-continued
| Cmpd No. | Structure | Name | MH+ | Activity |
|---|---|---|---|---|
| 132 | 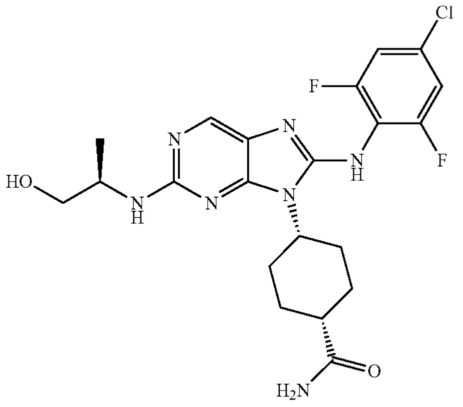 [SMILES: C[C@H](CO)Nc1ncc2nc(Nc3c(F)cc(Cl)cc3F)n([C@H]3CC[C@@H](C(N)=O)CC3)c2n1] | (1S,4s)-4-(8-(4-chloro-2,6-difluorophenylamino)-2-((R)-1-hydroxypropan-2-ylamino)-9H-purin-9-yl)cyclohexanecarboxamide | 480.2 | A |
| 133 | 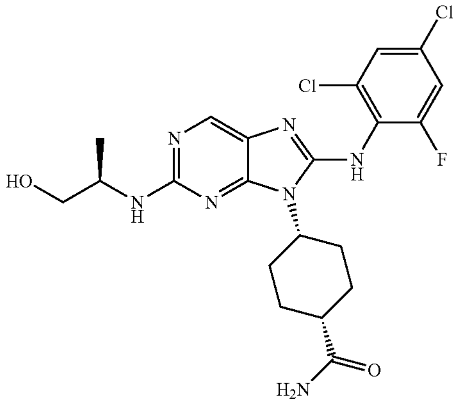 [SMILES: C[C@H](CO)Nc1ncc2nc(Nc3c(F)cc(Cl)cc3Cl)n([C@H]3CC[C@@H](C(N)=O)CC3)c2n1] | (1S,4s)-4-(8-(2,4-dichloro-6-fluorophenylamino)-2-((R)-1-hydroxypropaon-2-ylamino)-9H-purin-9-yl)cyclohexanecarboxamide | 496.1 | B |
| 134 | 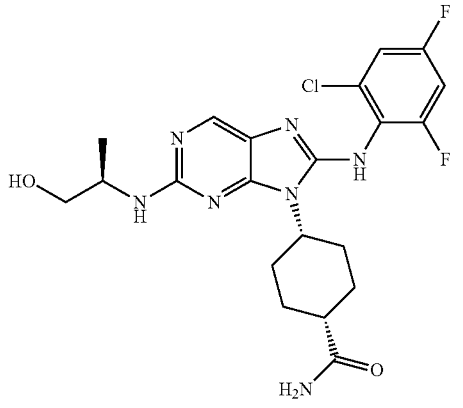 [SMILES: C[C@H](CO)Nc1ncc2nc(Nc3c(F)cc(F)cc3Cl)n([C@H]3CC[C@@H](C(N)=O)CC3)c2n1] | (1S,4s)-4-(8-(2-chloro-4,6-difluorophenylamino)-2-((R)-1-hydroxypropan-2-ylamino)-9H-purin-9-yl)cyclohexanecarboxamide | 480.1 | A |

TABLE 1-continued
| Cmpd No. | Structure | Name | MH+ | Activity |
|---|---|---|---|---|
| 135 | 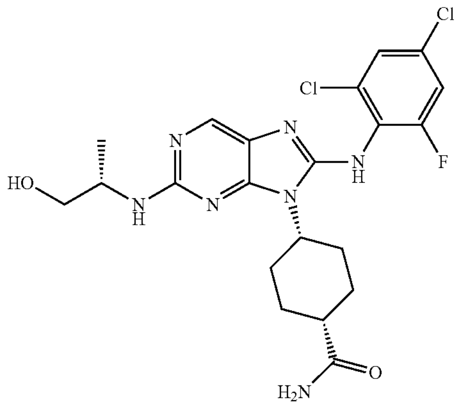 [SMILES: C[C@@H](CO)Nc1ncc2nc(Nc3c(F)cc(Cl)cc3Cl)n([C@H]3CC[C@@H](C(N)=O)CC3)c2n1] | (1R,4s)-4-(8-(2,4-dichloro-6-fluorophenylamino)-2-((S)-1-hydroxypropan-2-ylamino)-9H-purin-9-yl)cyclohexanecarboxamide | 496.1 | D |
| 136 | 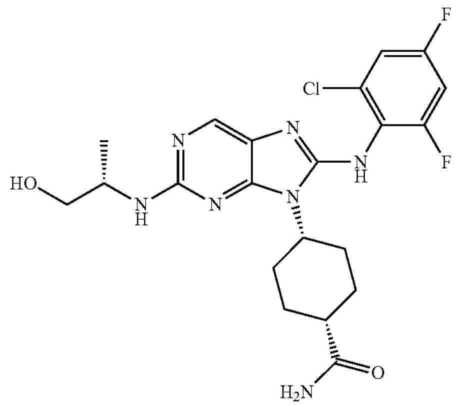 [SMILES: C[C@@H](CO)Nc1ncc2nc(Nc3c(F)cc(F)cc3Cl)n([C@H]3CC[C@@H](C(N)=O)CC3)c2n1] | (1R,4s)-4-(8-(2-chloro-4,6-difluorophenylamino)-2-((S)-1-hydroxypropan-2-ylamino)-9H-purin-9-yl)cyclohexanecarboxamide | 480.1 | B |
| 137 | 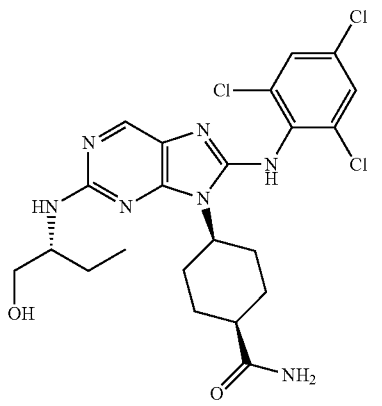 [SMILES: CC[C@H](CO)Nc1ncc2nc(Nc3c(Cl)cc(Cl)cc3Cl)n([C@H]3CC[C@@H](C(N)=O)CC3)c2n1] | (1S,4s)-4-(2-((R)-1-hydroxybutan-2-ylamino)-8-(2,4,6-trichlorophenylamino)-9H-purin-9-yl)cyclohexanecarboxamide | 526.1 | A |

TABLE 1-continued

| Cmpd No. | Structure | Name | MH+ | Activity |
|---|---|---|---|---|
| 138 | 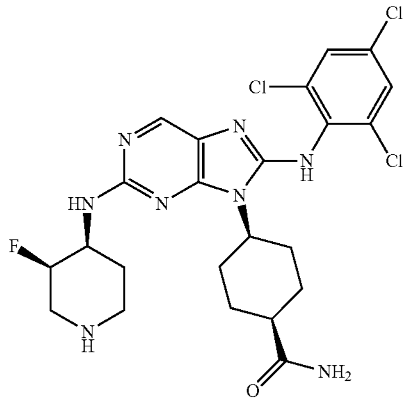 [SMILES: NC(=O)[C@H]1CC[C@@H](n2c(Nc3c(Cl)cc(Cl)cc3Cl)nc3cnc(N[C@H]4CCNC[C@H]4F)nc32)CC1] | (1R,4s)-4-(2-((3R,4S)-3-fluoropiperidin-4-ylamino)-8-(2,4,6-trichlorophenylamino)-9H-purin-9-yl)cyclohexanecarboxamide | 555.1 | A |
| 139 | 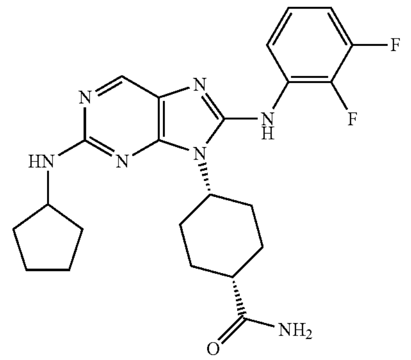 [SMILES: NC(=O)[C@H]1CC[C@@H](n2c(Nc3cccc(F)c3F)nc3cnc(NC4CCCC4)nc32)CC1] | (1s,4s)-4-(2-(cyclopentylamino)-8-(2,3-difluorophenylamino)-9H-purin-9-yl)cyclohexanecarboxamide | 456.4 | A |
| 140 | 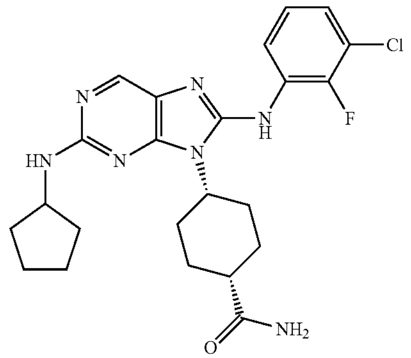 [SMILES: NC(=O)[C@H]1CC[C@@H](n2c(Nc3cccc(Cl)c3F)nc3cnc(NC4CCCC4)nc32)CC1] | (1s,4s)-4-(8-(3-chloro-2-fluorophenylamino)-2-(cyclopentylamino)-9H-purin-9-yl)cyclohexanecarboxamide | 472 | A |
| 141 | 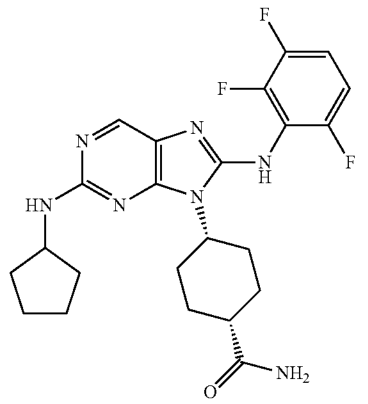 [SMILES: NC(=O)[C@H]1CC[C@@H](n2c(Nc3c(F)ccc(F)c3F)nc3cnc(NC4CCCC4)nc32)CC1] | (1s,4s)-4-(2-(cyclopentylamino)-8-(2,3,6-trifluorophenylamino)-9H-purin-9-yl)cyclohexanecarboxamide | 474.1 | B |

TABLE 1-continued
| Cmpd No. | Structure | Name | MH+ | Activity |
| --- | --- | --- | --- | --- |
| 142 | 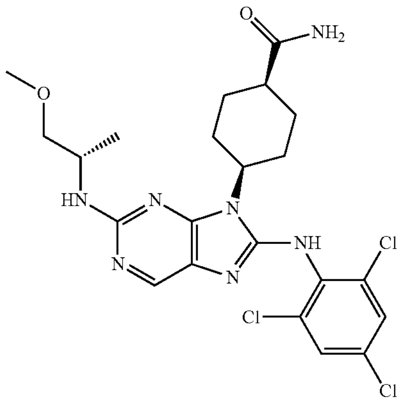 [SMILES: COC[C@H](C)Nc1ncc2nc(Nc3c(Cl)cc(Cl)cc3Cl)n([C@H]3CC[C@@H](C(N)=O)CC3)c2n1] | (1R,4s)-4-(2-((S)-1-methoxypropan-2-ylamino)-8-(2,4,6-trichlorophenylamino)-9H-purin-9-yl)cyclohexanecarboxamide | 526.2 | A |
| 143 | 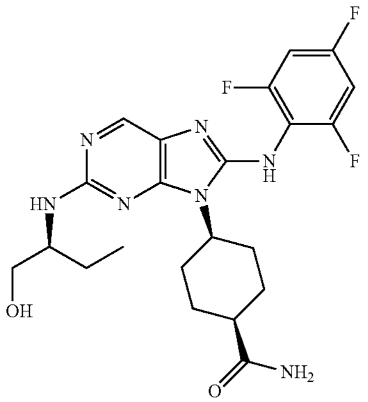 [SMILES: CC[C@@H](CO)Nc1ncc2nc(Nc3c(F)cc(F)cc3F)n([C@H]3CC[C@@H](C(N)=O)CC3)c2n1] | (1R,4s)-4-(2-((S)-1-hydroxybutan-2-ylamino)-8-(2,4,6-trifluorophenylamino)-9H-purin-9-yl)cyclohexanecarboxamide | 478.4 | A |
| 144 | 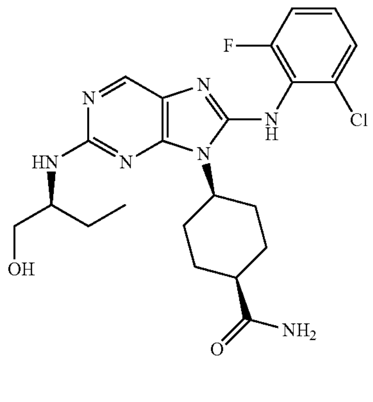 [SMILES: CC[C@@H](CO)Nc1ncc2nc(Nc3c(F)cccc3Cl)n([C@H]3CC[C@@H](C(N)=O)CC3)c2n1] | (1R,4s)-4-(8-(2-chloro-6-fluorophenylamino)-2-((S)-1-hydroxybutan-2-ylamino)-9H-purin-9-yl)cyclohexanecarboxamide | 476.1 | A |

TABLE 1-continued
| Cmpd No. | Structure | Name | MH+ | Activity |
|---|---|---|---|---|
| 145 | 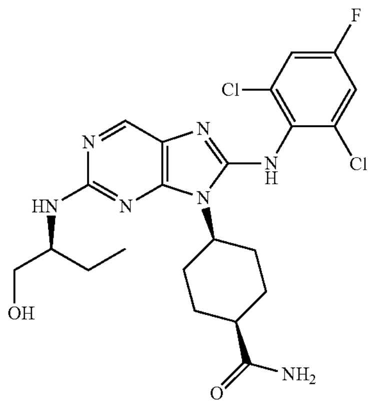 [SMILES: CC[C@@H](CO)Nc1ncc2nc(Nc3c(Cl)cc(F)cc3Cl)n([C@H]3CC[C@@H](C(N)=O)CC3)c2n1] | (1R,4s)-4-(8-(2,6-dichloro-4 fluorophenylamino)-2-((S)-1-hydroxybutan-2-ylamino)-9H-purin-9-yl)cyclohexanecarboxamide | 510.1 | A |
| 146 | 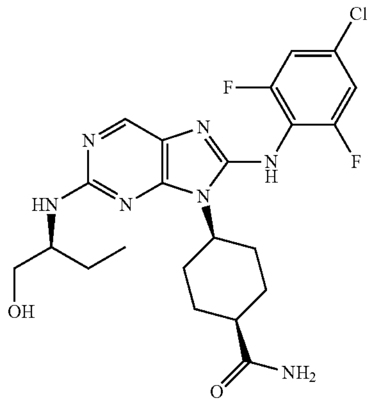 [SMILES: CC[C@@H](CO)Nc1ncc2nc(Nc3c(F)cc(Cl)cc3F)n([C@H]3CC[C@@H](C(N)=O)CC3)c2n1] | (1R,4s)-4-(8-(4-chloro-2,6-difluorophenylamino)-2-((S)-1-hydroxybutan-2-ylamino)-9H-purin-9-yl)cyclohexanecarboxamide | 494.2 | B |
| 147 | 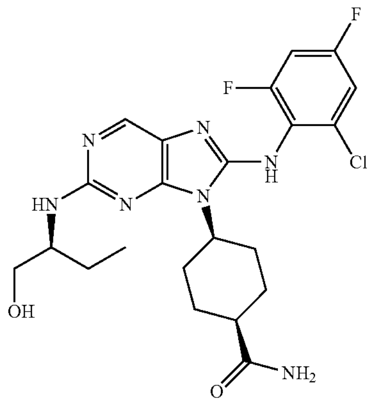 [SMILES: CC[C@@H](CO)Nc1ncc2nc(Nc3c(F)cc(F)cc3Cl)n([C@H]3CC[C@@H](C(N)=O)CC3)c2n1] | (1R,4s)-4-(8-(2-chloro-4,6-difluorophenylamino)-2-((S)-1-hydroxybutan-2-ylamino)-9H-purin-9-yl)cyclohexanecarboxamide | 494.1 | A |

TABLE 1-continued

| Cmpd No. | Structure | Name | MH+ | Ac-tivi-ty |
|---|---|---|---|---|
| 148 | 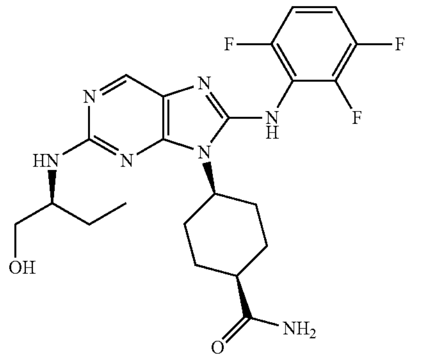 [SMILES: CC[C@@H](CO)Nc1ncc2nc(Nc3c(F)ccc(F)c3F)n([C@H]3CC[C@@H](C(N)=O)CC3)c2n1] | (1R,4s)-4-(2-((S)-1-hydroxybutan-2-ylamino)-8-(2,3,6-trifluorophenylamino)-9H-purin-9-yl)cyclohexanecarboxamide | 478.2 | A |
| 149 | 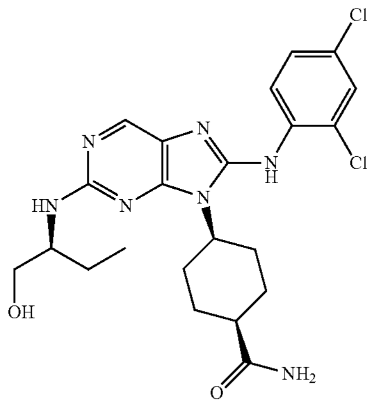 [SMILES: CC[C@@H](CO)Nc1ncc2nc(Nc3ccc(Cl)cc3Cl)n([C@H]3CC[C@@H](C(N)=O)CC3)c2n1] | (1R,4s)-4-(8-(2,4-dichlorophenylamino)-2-((S)-1-hydroxybutan-2-ylamino)-9H-pyrin-9-yl)cyclohexanecarboxamide | 492.1 | A |
| 150 | 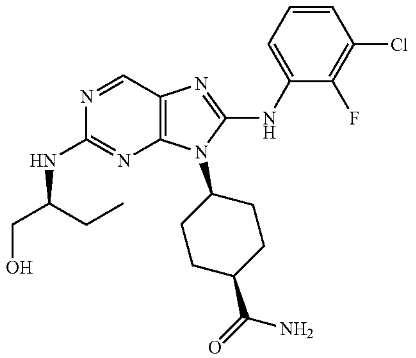 [SMILES: CC[C@@H](CO)Nc1ncc2nc(Nc3cccc(Cl)c3F)n([C@H]3CC[C@@H](C(N)=O)CC3)c2n1] | (1R,4s)-4-(8-(3-chloro-2-fluorophenylamino)-2-((S)-1-hydroxybutan-2-ylamino)-9H-purin-9-yl)cyclohexanecarboxamide | 476.1 | A |
| 151 | 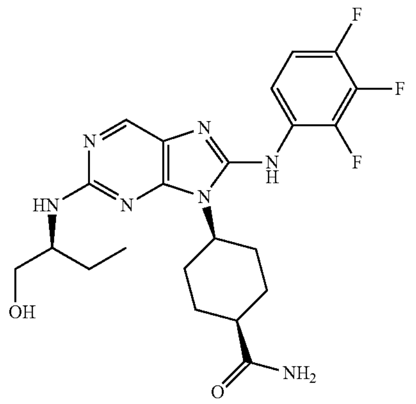 [SMILES: CC[C@@H](CO)Nc1ncc2nc(Nc3ccc(F)c(F)c3F)n([C@H]3CC[C@@H](C(N)=O)CC3)c2n1] | (1R,4s)-4-(2-((S)-1-hydroxybutan-2-ylamino)-8-(2,3,4-trifluorophenylamino)-9H-purin-9-yl)cyclohexanecarboxamide | 478.2 | A |

TABLE 1-continued
| Cmpd No. | Structure | Name | MH+ | Activity |
|---|---|---|---|---|
| 152 | 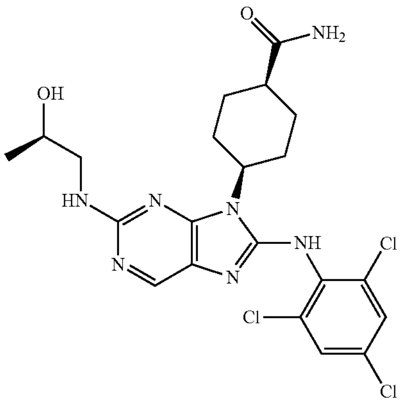 [SMILES: C[C@@H](O)CNc1ncc2nc(Nc3c(Cl)cc(Cl)cc3Cl)n([C@H]3CC[C@@H](C(N)=O)CC3)c2n1] | (1S,4s)-4-(2-((R)-2-hydroxypropylamino)-8-(2,4,6-trichlorophenylamino)-9H-purin-9-yl)cyclohexanecarboxamide | 512.2 | A |
| 153 | 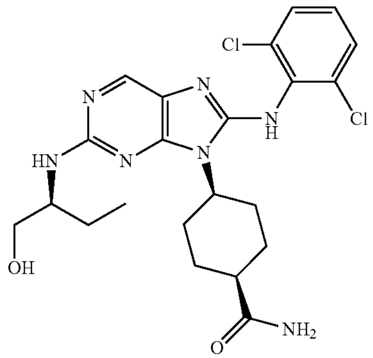 [SMILES: CC[C@@H](CO)Nc1ncc2nc(Nc3c(Cl)cccc3Cl)n([C@H]3CC[C@@H](C(N)=O)CC3)c2n1] | (1R,4s)-4-(8-(2,6-dichlorophenylamino)-2-((S)-1-hydroxybutan-2-ylamino)-9H-purin-9-yl)cyclohexanecarboxamide | 492.1 | A |
| 154 | 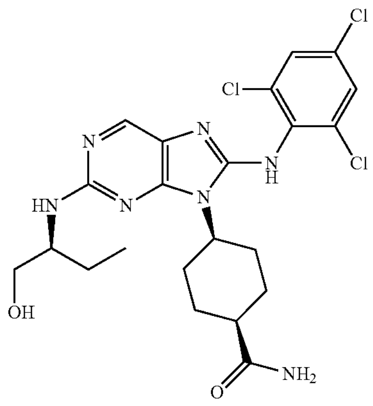 [SMILES: CC[C@@H](CO)Nc1ncc2nc(Nc3c(Cl)cc(Cl)cc3Cl)n([C@H]3CC[C@@H](C(N)=O)CC3)c2n1] | (1R,4s)-4-(2-((S)-1-hydroxybutan-2-ylamino)-8-(2,4,6-trichlorophenylamino)-9H-purin-9-yl)cyclohexanecarboxamide | 526 | A |

TABLE 1-continued

| Cmpd No. | Structure | Name | MH+ | Activity |
|---|---|---|---|---|
| 155 | 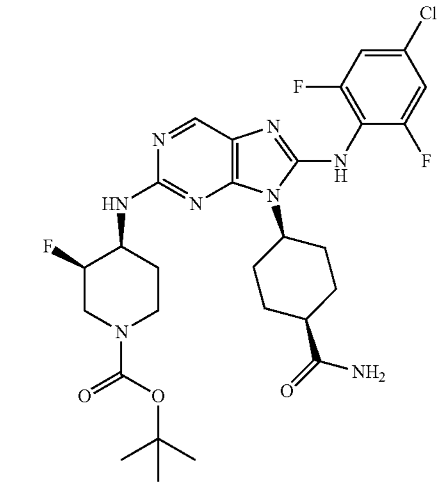 [SMILES: CC(C)(C)OC(=O)N1CC[C@H](Nc2ncc3nc(Nc4c(F)cc(Cl)cc4F)n([C@H]4CC[C@@H](C(N)=O)CC4)c3n2)[C@H](F)C1] | (3R,4S)-tert-butyl 4-(9-((1s,4R)-4-carbamoylcyclohexyl)-8-(4-chloro-2,6-difluorophenylamino)-9H-purin-2-ylamino)-3-fluoropiperidine-1-carboxylate | 623.2 | A |
| 156 | 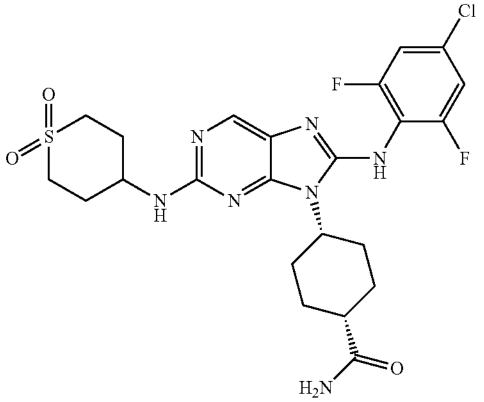 [SMILES: NC(=O)[C@H]1CC[C@@H](n2c(Nc3c(F)cc(Cl)cc3F)nc3cnc(NC4CCS(=O)(=O)CC4)nc32)CC1] | (1s,4s)-4-(8-((4-chloro-2,6-difluorophenyl)amino)-2-((1,1-dioxidotetrahydro-2H-thiopyran-4-yl)amino)-9H-purin-9-yl)cyclohexane-1-carboxamide | 554.1 | A |
| 157 | 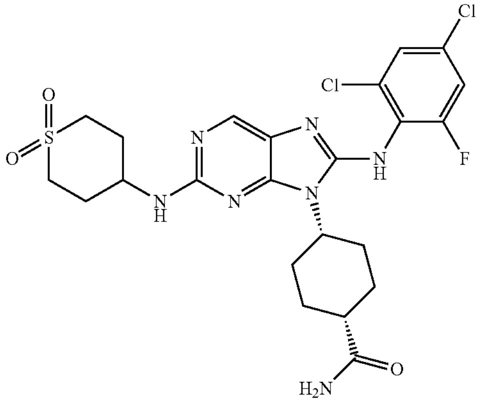 [SMILES: NC(=O)[C@H]1CC[C@@H](n2c(Nc3c(F)cc(Cl)cc3Cl)nc3cnc(NC4CCS(=O)(=O)CC4)nc32)CC1] | (1s,4s)-4-(8-(((2,4-dichloro-6-fluorophenyl)amino)-2-((1,1-dioxidotetrahydro-2H-thiopyran-4-yl)amino)-9H-purin-9-yl)cyclohexane-1-carboxamide | 570.1 | A |

TABLE 1-continued

| Cmpd No. | Structure | Name | MH+ | Ac-tivi-ty |
|---|---|---|---|---|
| 158 | 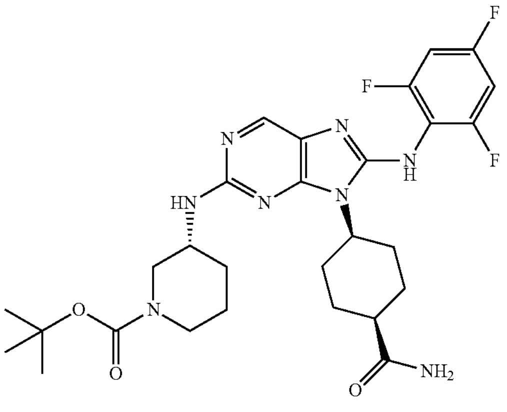 [SMILES: CC(C)(C)OC(=O)N1CCC[C@@H](Nc2ncc3nc(Nc4c(F)cc(F)cc4F)n([C@H]4CC[C@@H](C(N)=O)CC4)c3n2)C1] | (R)-tert-butyl 3-(9-((1s,4S)-4-carbamoylcyclohexyl)-8-(2,4,6-trifluorophenylamino)-9H-purin-2-ylamino)piperidine-1-carboxylate | 589.2 | A |
| 159 | 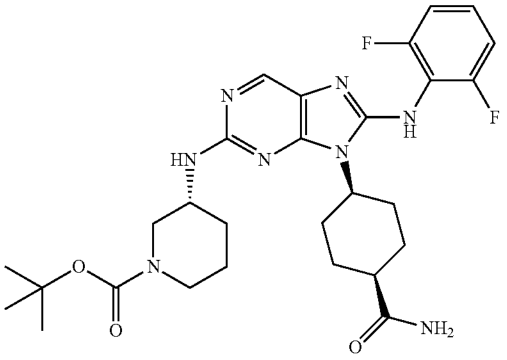 [SMILES: CC(C)(C)OC(=O)N1CCC[C@@H](Nc2ncc3nc(Nc4c(F)cccc4F)n([C@H]4CC[C@@H](C(N)=O)CC4)c3n2)C1] | (R)-tert-butyl 3-(9-((1s,4S)-4-carbamoylcyclohexyl)-8-(2,6-difluorophenylamino)-9H-purin-2-ylamino)piperidine-1-carboxylate | 571.2 | A |
| 160 | 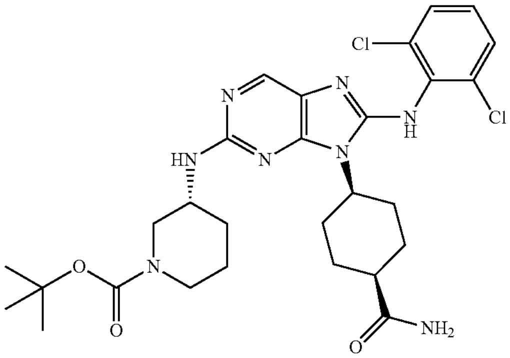 [SMILES: CC(C)(C)OC(=O)N1CCC[C@@H](Nc2ncc3nc(Nc4c(Cl)cccc4Cl)n([C@H]4CC[C@@H](C(N)=O)CC4)c3n2)C1] | (R)-tert-butyl 3-(9-((1s,4S)-4-carbamoylcyclohexyl)-8-(2,6-dichlorophenylamino)-9H-purin-2-ylamino)piperidine-1-carboxylate | 603.2 | A |
| 161 | 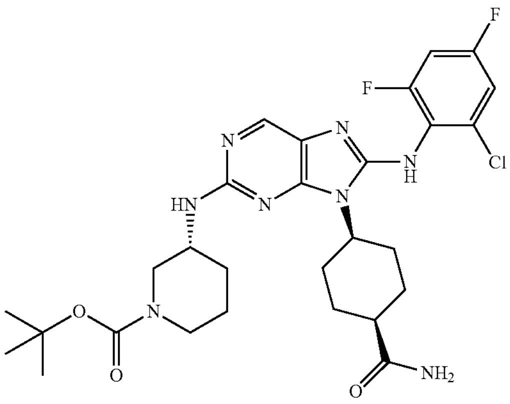 [SMILES: CC(C)(C)OC(=O)N1CCC[C@@H](Nc2ncc3nc(Nc4c(F)cc(F)cc4Cl)n([C@H]4CC[C@@H](C(N)=O)CC4)c3n2)C1] | (R)-tert-butyl 3-(9-((1s,4S)-4-carbamoylcyclohexyl)-8-(2-chloro-4,6-difluorophenylamino)-9H-purin-2-ylamino)piperidine-1-carboxylate | 605.3 | A |

TABLE 1-continued
| Cmpd No. | Structure | Name | MH+ | Activity |
|---|---|---|---|---|
| 162 | 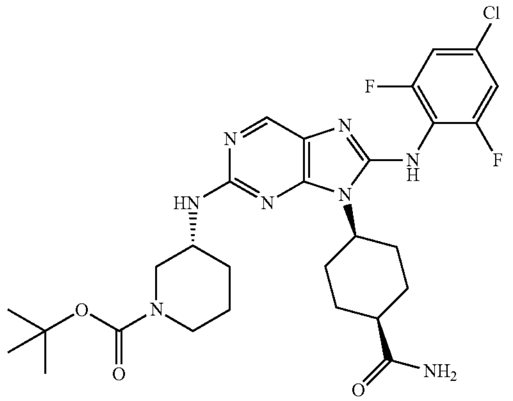 [SMILES: CC(C)(C)OC(=O)N1CCC[C@@H](Nc2ncc3nc(Nc4c(F)cc(Cl)cc4F)n([C@H]4CC[C@@H](C(N)=O)CC4)c3n2)C1] | (R)-tert-butyl 3-(9-((1s,4S)-4-carbamoylcyclohexyl)-8-(4-chloro-2,6-difluorophenylamino)-9H-purin-2-ylamino)piperidine-1-carboxylate | 605.2 | A |
| 163 | 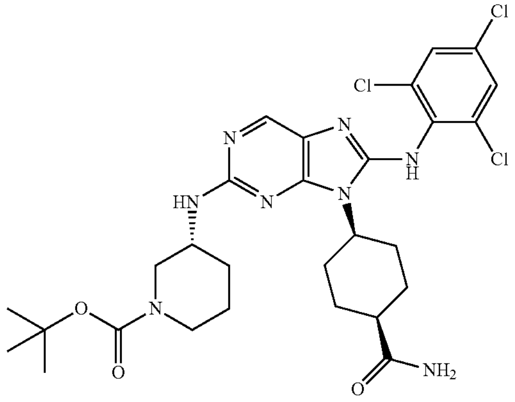 [SMILES: CC(C)(C)OC(=O)N1CCC[C@@H](Nc2ncc3nc(Nc4c(Cl)cc(Cl)cc4Cl)n([C@H]4CC[C@@H](C(N)=O)CC4)c3n2)C1] | (R)-tert-butyl 3-(9-((1s,4S)-4-carbamoylcyclohexyl)-8-(2,4,6-trichlorophenylamino)-9H-purin-2-ylamino)piperidine-1-carboxylate | 637.2 | A |
| 164 | 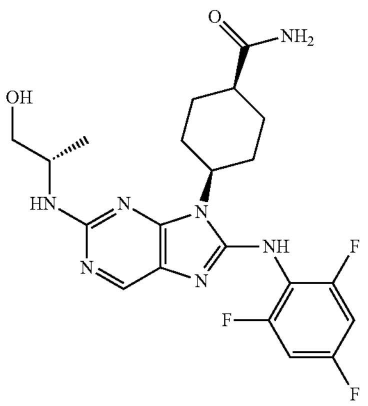 [SMILES: C[C@@H](CO)Nc1ncc2nc(Nc3c(F)cc(F)cc3F)n([C@H]3CC[C@@H](C(N)=O)CC3)c2n1] | (1R,4s)-4-(2-((S)-1-hydroxypropan-2-ylamino)-8-(2,4,6-trifluorophenylamino)-9H-purin-9-yl)cyclohexanecarboxamide | 464.1 | A |

TABLE 1-continued

| Cmpd No. | Structure | Name | MH+ | Activity |
| --- | --- | --- | --- | --- |
| 165 | 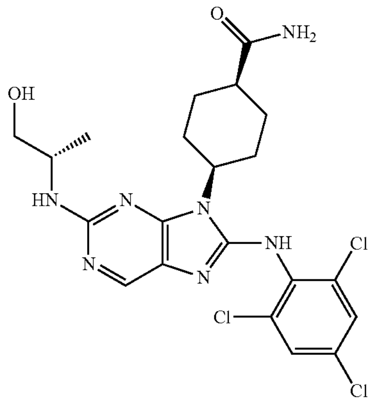 [SMILES: C[C@@H](CO)Nc1ncc2nc(Nc3c(Cl)cc(Cl)cc3Cl)n([C@H]3CC[C@@H](C(N)=O)CC3)c2n1] | (1R,4s)-4-(2-((S)-1-hydroxypropan-2-ylamino)-8-(2,4,6-trichlorophenylamino)-9H-purin-9-yl)cyclohexanecarboxamide | 512.1 | C |
| 166 | 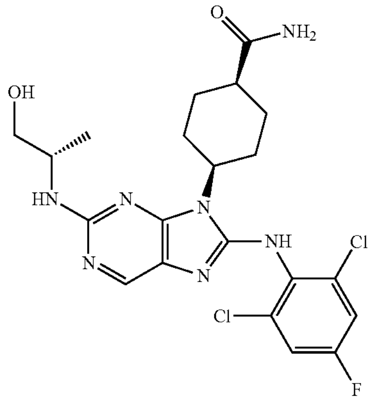 [SMILES: C[C@@H](CO)Nc1ncc2nc(Nc3c(Cl)cc(F)cc3Cl)n([C@H]3CC[C@@H](C(N)=O)CC3)c2n1] | (1R,4s)-4-(8-(2,6-dichloro-4-fluorophenylamino)-2-((S)-1-hydroxypropan-2-ylamino)-9H-purin-9-yl)cyclohexanecarboxamide | 496.1 | B |
| 167 | 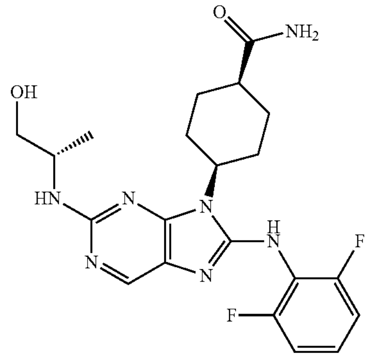 [SMILES: C[C@@H](CO)Nc1ncc2nc(Nc3c(F)cccc3F)n([C@H]3CC[C@@H](C(N)=O)CC3)c2n1] | (1R,4s)-4-(8-(2,6-difluorophenylamino)-2-((S)-1 hydroxypropan-2-ylamino)-9H-purin-9-yl)cyclohexanecarboxamide | 446.1 | A |
| 168 | 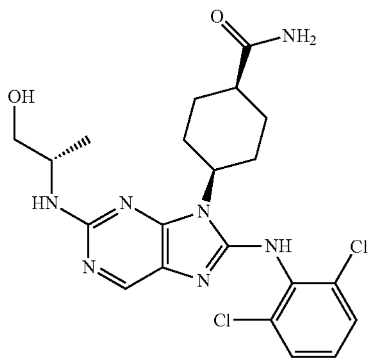 [SMILES: C[C@@H](CO)Nc1ncc2nc(Nc3c(Cl)cccc3Cl)n([C@H]3CC[C@@H](C(N)=O)CC3)c2n1] | (1R,4s)-4-(8-(2,6-dichlorophenylamino)-2-((S)-1-hydroxypropan-2-ylamino)-9H-purin-9-yl)cyclohexanecarboxamide | 479.1 | A |

TABLE 1-continued
| Cmpd No. | Structure | Name | MH+ | Activity |
|---|---|---|---|---|
| 169 | 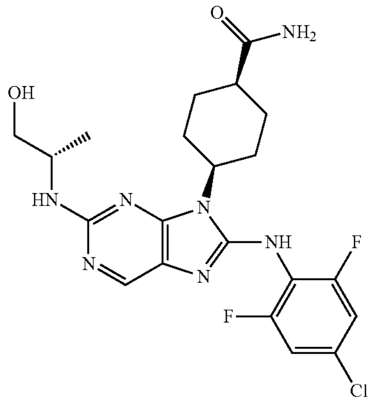 [SMILES: C[C@@H](CO)Nc1ncc2nc(Nc3c(F)cc(Cl)cc3F)n([C@H]3CC[C@@H](C(N)=O)CC3)c2n1] | (1R,4s)-4-(8-(4-chloro-2,6-difluorophenylamino)-2-((S)-1-hydroxypropan-2-ylamino)-9H-purin-9-yl)cyclohexanecarboxamide | 480.1 | B |
| 170 | 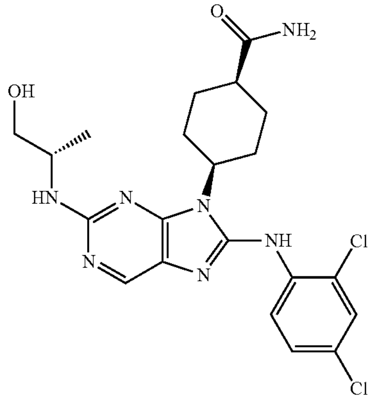 [SMILES: C[C@@H](CO)Nc1ncc2nc(Nc3ccc(Cl)cc3Cl)n([C@H]3CC[C@@H](C(N)=O)CC3)c2n1] | (1R,4s)-4-(8-(2,4-dichlorophenylamino)-2-((S)-1-hydroxypropan-2-ylamino)-9H-purin-9-yl)cyclohexanecarboxamide | 478 | A |
| 171 | 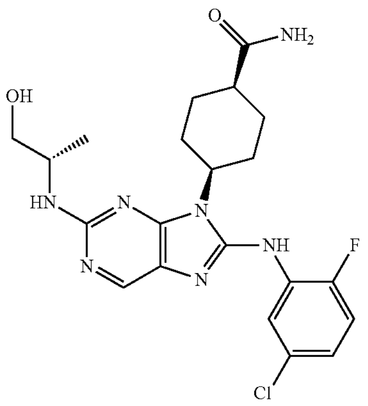 [SMILES: C[C@@H](CO)Nc1ncc2nc(Nc3cc(Cl)ccc3F)n([C@H]3CC[C@@H](C(N)=O)CC3)c2n1] | (1R,4s)-4-(8-(5-chloro-2-fluorophenylamino)-2-((S)-1-hydroxypropan-2-ylamino)-9H-purin-9-yl)cyclohexanecarboxamide | 462.1 | A |

TABLE 1-continued

| Cmpd No. | Structure | Name | MH+ | Ac-tivi-ty |
|---|---|---|---|---|
| 172 | 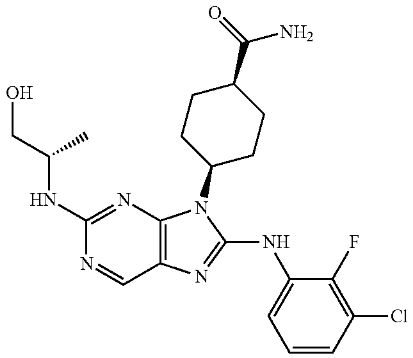 [SMILES: C[C@@H](CO)Nc1ncc2nc(Nc3cccc(Cl)c3F)n([C@H]3CC[C@@H](C(N)=O)CC3)c2n1] | (1R,4s)-4-(8-(3-chloro-2-fluorophenylamino)-2-((S)-1-hydroxypropan-2-ylamino)-9H-purin-9-yl)cyclohexanecarboxamide | 462.1 | A |
| 173 | 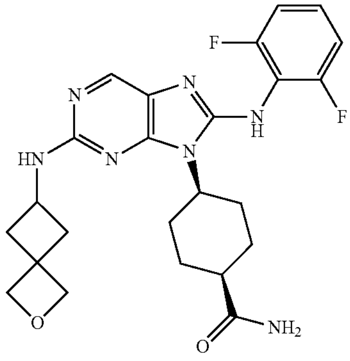 [SMILES: NC(=O)[C@H]1CC[C@@H](n2c(Nc3c(F)cccc3F)nc3cnc(NC4CC5(COC5)C4)nc32)CC1] | (1s,4s)-4-(2-(2-oxaspiro[3.3]heptan-6-ylamino)-8-(2,6-difluorophenylamino)-9H-purin-9-yl)cyclohexanecarboxamide | 484.5 | A |
| 174 | 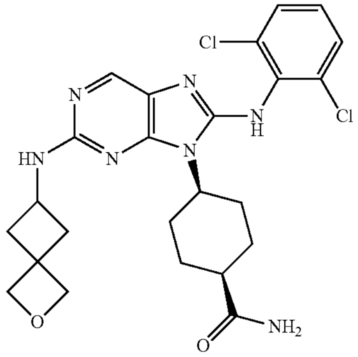 [SMILES: NC(=O)[C@H]1CC[C@@H](n2c(Nc3c(Cl)cccc3Cl)nc3cnc(NC4CC5(COC5)C4)nc32)CC1] | (1s,4s)-4-(2-(2-oxaspiro[3.3]heptan-6-ylamino)-8-(2,6-dichlorophenylamino)-9H-purin-9-yl)cyclohexanecarboxamide | 516.2 | A |
| 175 | 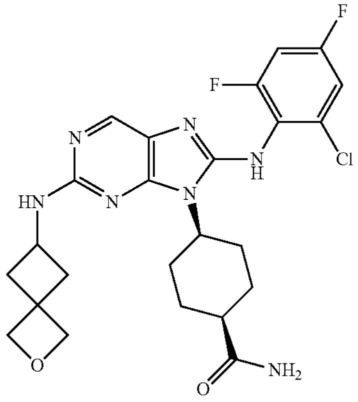 [SMILES: NC(=O)[C@H]1CC[C@@H](n2c(Nc3c(F)cc(F)cc3Cl)nc3cnc(NC4CC5(COC5)C4)nc32)CC1] | (1s,4s)-4-(2-(2-oxaspiro[3.3]heptan-6-ylamino)-8-(2-chloro-,6-difluorophenylamino)-9H-purin-9-yl)cyclohexanecarboxamide | 518.4 | B |

TABLE 1-continued
| Cmpd No. | Structure | Name | MH+ | Activity |
|---|---|---|---|---|
| 176 | 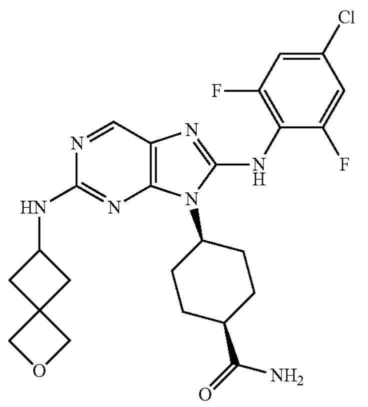 [SMILES: NC(=O)[C@H]1CC[C@@H](n2c(Nc3c(F)cc(Cl)cc3F)nc3cnc(NC4CC5(COC5)C4)nc32)CC1] | (1s,4s)-4-(2-(2-oxaspiro[3.3]heptan-6-ylamino)-8-(4-chloro-2,6-difluorophenylamino)-9H-purin-9-yl)cyclohexanecarboxamide | 518.1 | A |
| 177 | 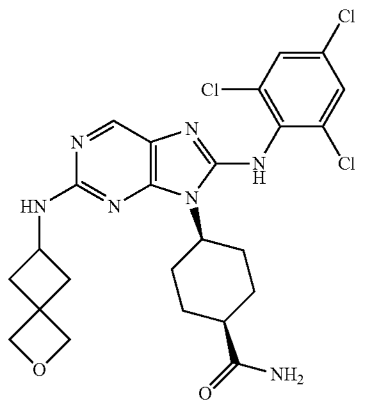 [SMILES: NC(=O)[C@H]1CC[C@@H](n2c(Nc3c(Cl)cc(Cl)cc3Cl)nc3cnc(NC4CC5(COC5)C4)nc32)CC1] | (1s,4s)-4-(2-(2-oxaspiro[3.3]heptan-6-ylamino)-8-(2,4,6-trichlorophenylamino)-9H-purin-9-yl)cyclohexanecarboxamide | 550 | C |
| 178 | 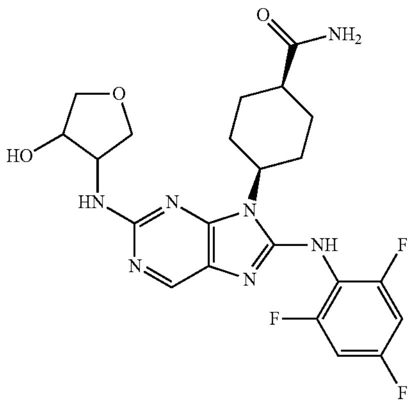 [SMILES: NC(=O)[C@H]1CC[C@@H](n2c(Nc3c(F)cc(F)cc3F)nc3cnc(NC4COCC4O)nc32)CC1] | (1s,4s)-4-(2-(4-hydroxytetrahydrofuran-3-ylamino)-8-(2,4,6-trifluorophenylamino)-9H-purin-9-yl)cyclohexanecarboxamide | 492 | A |

TABLE 1-continued
| Cmpd No. | Structure | Name | MH+ | Activity |
|---|---|---|---|---|
| 179 | 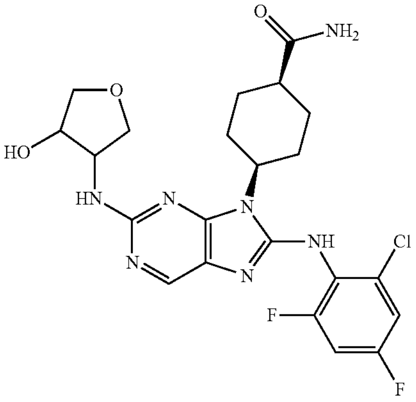 [SMILES: NC(=O)[C@H]1CC[C@@H](n2c(Nc3c(F)cc(F)cc3Cl)nc3cnc(NC4COCC4O)nc32)CC1] | (1s,4s)-4-(8-(2-chloro-4,6-difluorophenylamino)-2-(4-hydroxytetrahydrofuran-3-ylamino)-9H-purin-9-yl)cyclohexanecarboxamide | 508 | A |
| 180 | 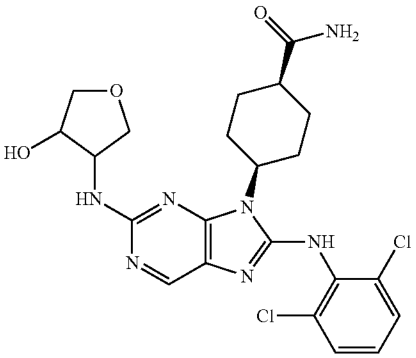 [SMILES: NC(=O)[C@H]1CC[C@@H](n2c(Nc3c(Cl)cccc3Cl)nc3cnc(NC4COCC4O)nc32)CC1] | (1s,4s)-4-(8-(2,6-dichlorophenylamino)-2-(4-hydroxytetrahydrofuran-3-ylamino)-9H-purin-9-yl)cyclohexanecarboxamide | 506.1 | A |
| 181 | 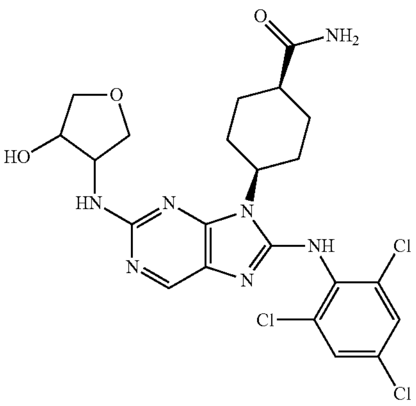 [SMILES: NC(=O)[C@H]1CC[C@@H](n2c(Nc3c(Cl)cc(Cl)cc3Cl)nc3cnc(NC4COCC4O)nc32)CC1] | (1s,4s)-4-(2-(4-hydroxytetrahydrofuran-3-ylamino)-8-(2,4,6-trichlorophenylamino)-9H-purin-9-yl)cyclohexanecarboxamide | 540 | B |

TABLE 1-continued

| Cmpd No. | Structure | Name | MH+ | Activity |
| --- | --- | --- | --- | --- |
| 182 | 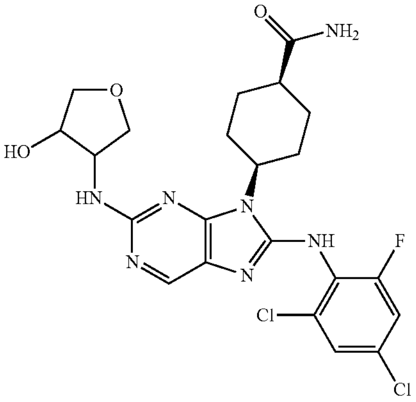 [SMILES: NC(=O)[C@H]1CC[C@@H](n2c(Nc3c(F)cc(Cl)cc3Cl)nc3cnc(NC4COCC4O)nc32)CC1] | (1s,4s)-4-(8-(2,4-dichloro-6-fluorophenylamino)-2-(4-hydroxytetrahydrofuran-3-ylamino)-9H-purin-9-yl)cyclohexanecarboxamide | 524.1 | A |
| 183 | 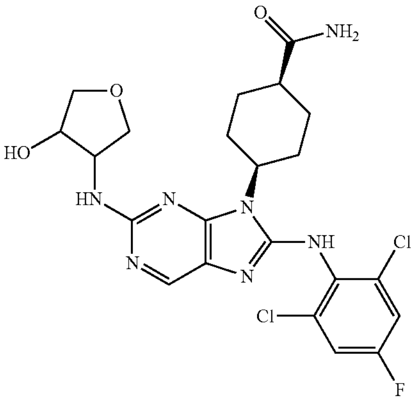 [SMILES: NC(=O)[C@H]1CC[C@@H](n2c(Nc3c(Cl)cc(F)cc3Cl)nc3cnc(NC4COCC4O)nc32)CC1] | (1s,4s)-4-(8-(2,6-dichloro-4-fluorophenylamino)-2-(4-hydroxytetrahydrofuran-3-ylamino)-9H-purin-9-yl)cyclohexanecarboxamide | 524.1 | A |
| 184 | 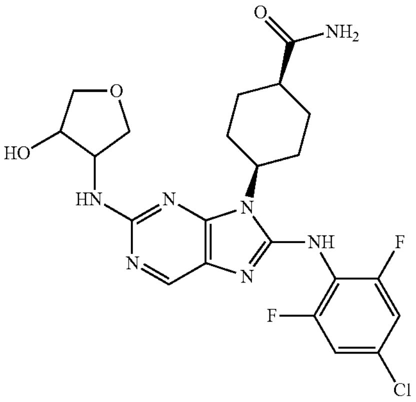 [SMILES: NC(=O)[C@H]1CC[C@@H](n2c(Nc3c(F)cc(Cl)cc3F)nc3cnc(NC4COCC4O)nc32)CC1] | (1s,4s)-4-(8-(4-chloro-2,6-difluorophenylamino)-2-(4-hydroxytetrahydrofuran-3-ylamino)-9H-purin-9-yl)cyclohexanecarboxamide | 508 | A |

TABLE 1-continued
| Cmpd No. | Structure | Name | MH+ | Activity |
| --- | --- | --- | --- | --- |
| 185 | 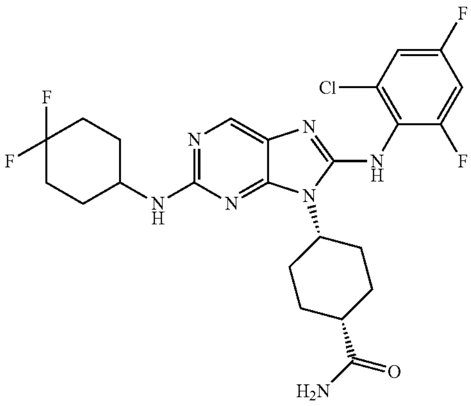 [SMILES: NC(=O)[C@H]1CC[C@@H](n2c(Nc3c(F)cc(F)cc3Cl)nc3cnc(NC4CCC(F)(F)CC4)nc32)CC1] | (1s,4s)-4-(8-(2-chloro-4,6-difluorophenylamino)-2-(4,4-difluorocyclohexylamino)-9H-purin-9-yl)cyclohexanecarboxamide | 540.2 | D |
| 186 | 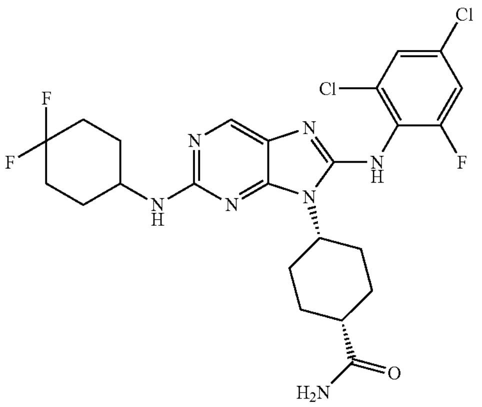 [SMILES: NC(=O)[C@H]1CC[C@@H](n2c(Nc3c(F)cc(Cl)cc3Cl)nc3cnc(NC4CCC(F)(F)CC4)nc32)CC1] | (1s,4S)-4-(8-(2,4-dichloro-6-fluorophenylamino)-2-(4,4-difluorocyclohexylamino)-9H-purin-9-yl)cyclohexanecarboxamide | 556.1 | D |
| 187 | 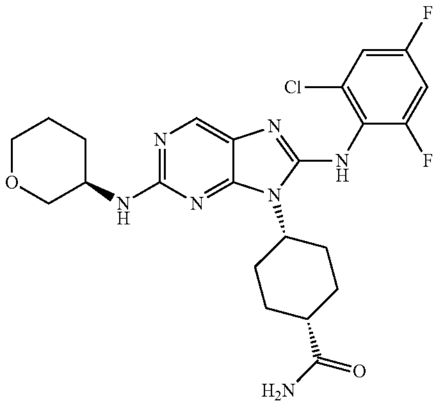 [SMILES: NC(=O)[C@H]1CC[C@@H](n2c(Nc3c(F)cc(F)cc3Cl)nc3cnc(N[C@@H]4CCCOC4)nc32)CC1] | (1S,4s)-4-(8-(2-chloro-4,6-difluorophenylamino)-2-((R)-tetrahydro-2H-pyran-3-ylamino)-9H-purin-9-yl)cyclohexanecarboxamide | 506.1 | A |

TABLE 1-continued
| Cmpd No. | Structure | Name | MH+ | Ac-tivi-ty |
|---|---|---|---|---|
| 188 | 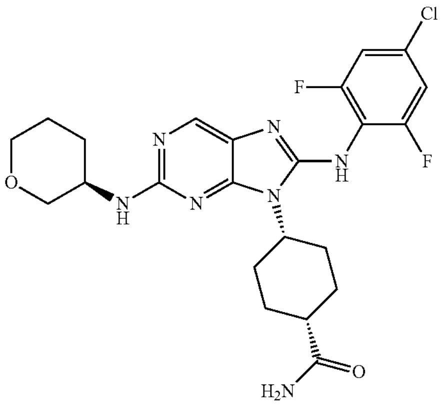 [SMILES: NC(=O)[C@H]1CC[C@@H](n2c(Nc3c(F)cc(Cl)cc3F)nc3cnc(N[C@@H]4CCCOC4)nc32)CC1] | (1S,4s)-4-(8-(4-chloro-2,6-difluorophenylamino)-2-((R)-tetrahydro-2H-pyran-3-ylamino)-9H-purin-9-yl)cyclohexanecarboxamide | 506.2 | A |
| 189 | 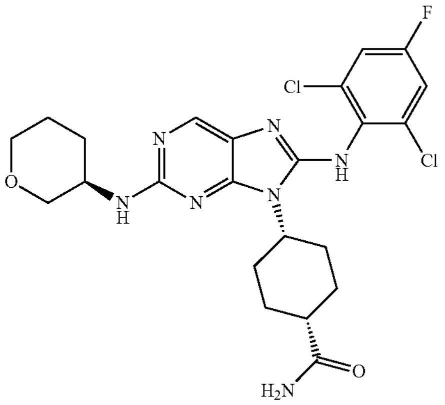 [SMILES: NC(=O)[C@H]1CC[C@@H](n2c(Nc3c(Cl)cc(F)cc3Cl)nc3cnc(N[C@@H]4CCCOC4)nc32)CC1] | (1S,4s)-4-(8-(2,6-dichloro-4-fluorophenylamino)-2-((R)-tetrahydro-2H-pyran-3-ylamino)-9H-purin-9-yl)cyclohexanecarboxamide | 522.1 | A |
| 190 | 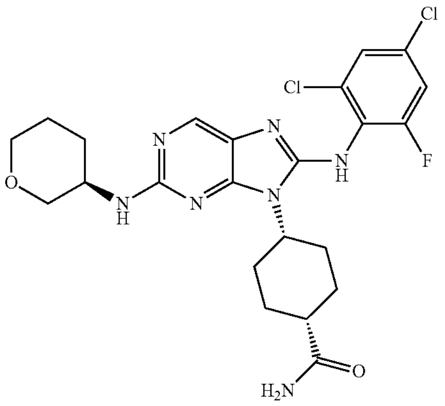 [SMILES: NC(=O)[C@H]1CC[C@@H](n2c(Nc3c(F)cc(Cl)cc3Cl)nc3cnc(N[C@@H]4CCCOC4)nc32)CC1] | (1S,4s)-4-(8-(2,4-dichloro-6-fluorophenylamino)-2-((R)-tetrahydro-2H-pyran-3-ylamino)-9H-purin-9-yl)cyclohexanecarboxamide | 522.1 | A |

TABLE 1-continued
| Cmpd No. | Structure | Name | MH+ | Activity |
|---|---|---|---|---|
| 191 | 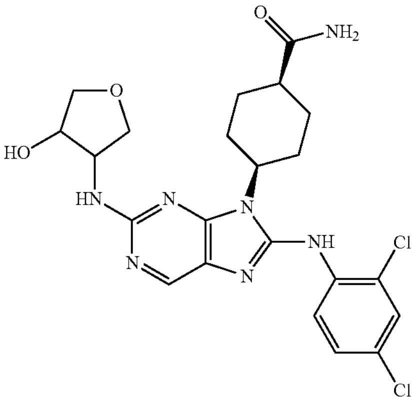 [SMILES: NC(=O)[C@H]1CC[C@@H](n2c(Nc3ccc(Cl)cc3Cl)nc3cnc(NC4COCC4O)nc32)CC1] | (1s,4s)-4-(8-(2,4-dichlorophenylamino)-2-(4-hydroxytetrahydrofuran-3-ylamino)-9H-purin-9-yl)cyclohexanecarboxamide | 506.2 | A |
| 192 | 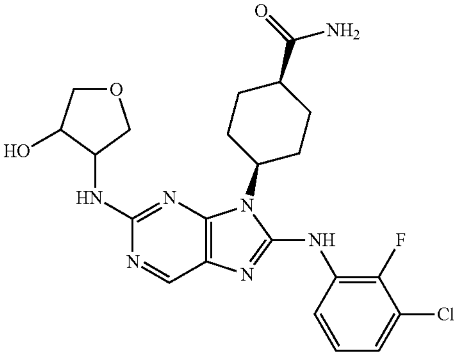 [SMILES: NC(=O)[C@H]1CC[C@@H](n2c(Nc3cccc(Cl)c3F)nc3cnc(NC4COCC4O)nc32)CC1] | (1s,4s)-4-(8-(3-chloro-2-fluorophenylamino)-2-(4-hydroxytetrahydrofuran-3-ylamino)-9H-purin-9-yl)cyclohexanecarboxamide | 490.1 | A |
| 193 | 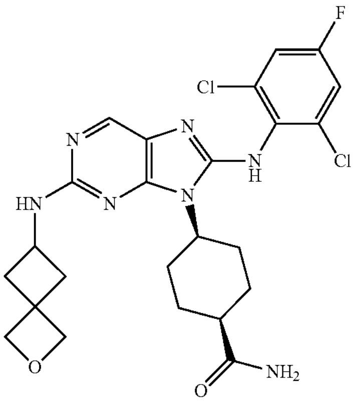 | (1s,4s)-4-(2-(2-oxaspiro[3.3]heptan-6-ylamino)-8-(2,6-dichloro-4-fluorophenylamino)-9H-purin-9-yl)cyclohexanecarboxamide | 534.1 | A |

TABLE 1-continued
| Cmpd No. | Structure | Name | MH+ | Activity |
|---|---|---|---|---|
| 194 | 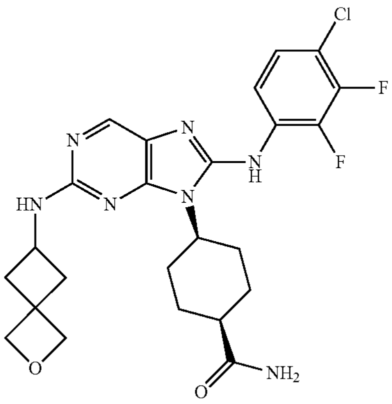 [SMILES: NC(=O)[C@H]1CC[C@@H](n2c(Nc3ccc(Cl)c(F)c3F)nc3cnc(NC4CC5(COC5)C4)nc32)CC1] | (1s,4s)-4-(2-(2-oxaspiro[3.3]heptan-6-ylamino)-8-(4-chloro-2,3-difluorophenylamino)-9H-purin-9-yl)cyclohexanecarboxamide | 518.1 | A |
| 195 | 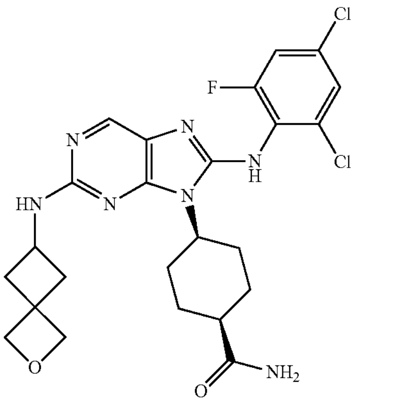 | (1s,4s)-4-(2-(2-oxaspiro[3.3]heptan-6-ylamino)-8-(2,4-dichloro-6-fluorophenylamino)-9H-purin-9-yl)cyclohexanecarboxamide | 534 | C |
| 196 | 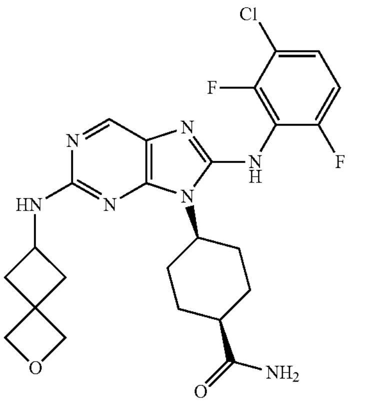 [SMILES: NC(=O)[C@H]1CC[C@@H](n2c(Nc3c(F)ccc(Cl)c3F)nc3cnc(NC4CC5(COC5)C4)nc32)CC1] | (1s,4s)-4-(2-(2-oxaspiro[3.3]heptan-6-ylamino)-8-(3-chloro-2,6-difluorophenylamino)-9H-purin-9-yl)cyclohexanecarboxamide | 518.2 | A |

TABLE 1-continued
| Cmpd No. | Structure | Name | MH+ | Activity |
|---|---|---|---|---|
| 197 | 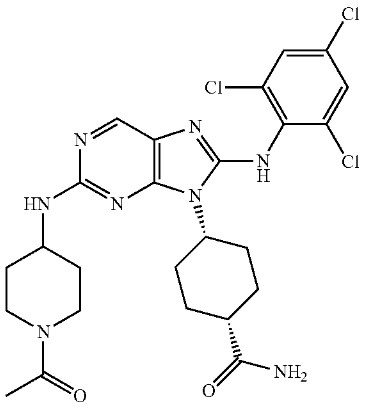 [SMILES: CC(=O)N1CCC(Nc2ncc3nc(Nc4c(Cl)cc(Cl)cc4Cl)n([C@H]4CC[C@@H](C(N)=O)CC4)c3n2)CC1] | (1s,4s)-4-(2-(1-acetylpiperidin-4-ylamino)-8-(2,4,6-trichlorophenylamino)-9H-purin-9-yl)cyclohexanecarboxamide | 579.2 | A |
| 198 | 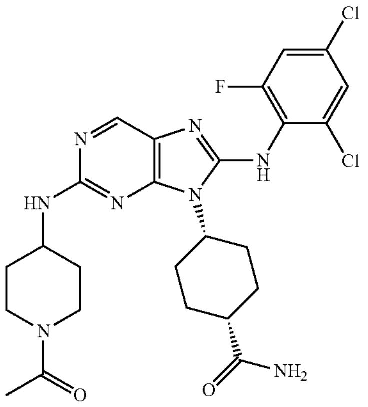 [SMILES: CC(=O)N1CCC(Nc2ncc3nc(Nc4c(F)cc(Cl)cc4Cl)n([C@H]4CC[C@@H](C(N)=O)CC4)c3n2)CC1] | (1s,4s)-4-(2-(1-acetylpiperidin-4-ylamino)-8-(2,4-dichloro-6-fluorophenylamino)-9H-purin-9-yl)cyclohexanecarboxamide | 563.2 | A |
| 199 | 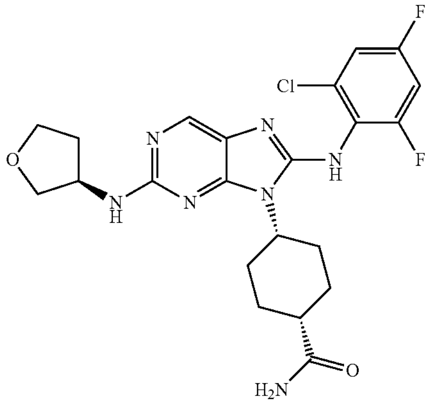 [SMILES: NC(=O)[C@H]1CC[C@@H](n2c(Nc3c(F)cc(F)cc3Cl)nc3cnc(N[C@@H]4CCOC4)nc32)CC1] | (1S,4s)-4-(8-(2-chloro-4,6-difluorophenylamino)-2-((R)-tetrahydrofuran-3-ylamino)-9H-purin-9-yl)cyclohexanecarboxamide | 492.4 | B |

TABLE 1-continued
| Cmpd No. | Structure | Name | MH+ | Activity |
| --- | --- | --- | --- | --- |
| 200 | 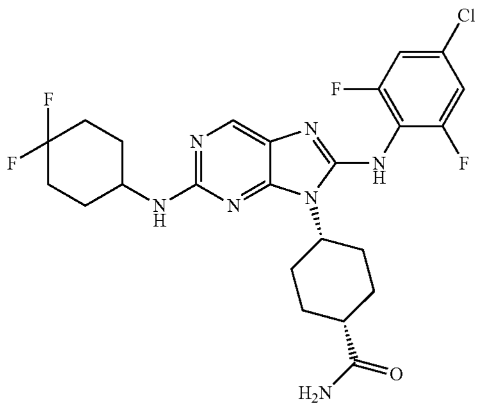 [SMILES: NC(=O)[C@H]1CC[C@@H](n2c(Nc3c(F)cc(Cl)cc3F)nc3cnc(NC4CCC(F)(F)CC4)nc32)CC1] | (1s,4s)-4-(8-(4-chloro-2,6-difluorophenylamino)-2-(4,4-difluorocyclohexylamino)-9H-purin-9-yl)cyclohexanecarboxamide | 540.1 | C |
| 201 | 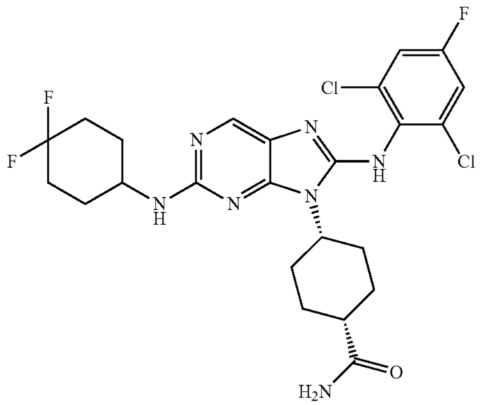 [SMILES: NC(=O)[C@H]1CC[C@@H](n2c(Nc3c(Cl)cc(F)cc3Cl)nc3cnc(NC4CCC(F)(F)CC4)nc32)CC1] | (1s,4s)-4-(8-(2,6-dichloro-4-fluuorophenylamino)-2-(4,4-difluorocyclohexylamino)-9H-purin-9-yl)cyclohexanecarboxamide | 556.2 | C |
| 202 | 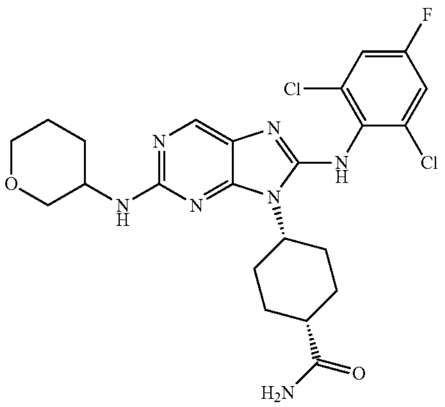 [SMILES: NC(=O)[C@H]1CC[C@@H](n2c(Nc3c(Cl)cc(F)cc3Cl)nc3cnc(NC4CCCOC4)nc32)CC1] | (1R,4s)-4-(8-(2,6-dichloro-4-fluorophenylamino)-2-((S)-tetrahydro-2H-pyran-3-ylamino)-9H-purin-9-yl)cyclohexanecarboxamide | 522.1 | A |

TABLE 1-continued
| Cmpd No. | Structure | Name | MH+ | Ac-tivi-ty |
|---|---|---|---|---|
| 203 | 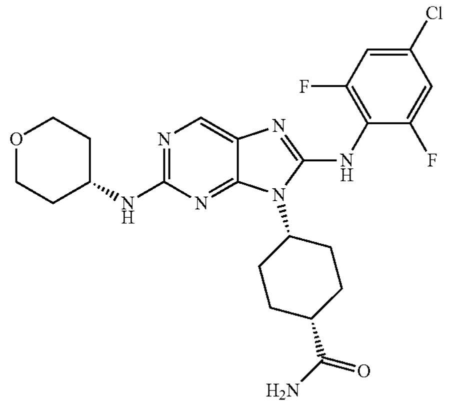 | (1R,4s)-4-(8-(4-chloro-2,6-difluorophenylamino)-2-((S)-tetrahydro-2H-pyran-3-ylamino)-9H-purin-9-yl)cyclohexanecarboxamide | 506.1 | A |
| 204 | 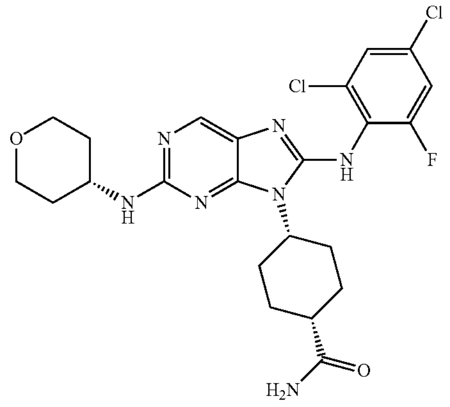 | (1R,4s)-4-(8-(2,4-dichloro-6-fluorophenylamino)-2-((S)-tetrahydro-2H-pyran-3-ylamino)-9H-purin-9-yl)cyclohexanecarboxamide | 522.1 | A |
| 205 | 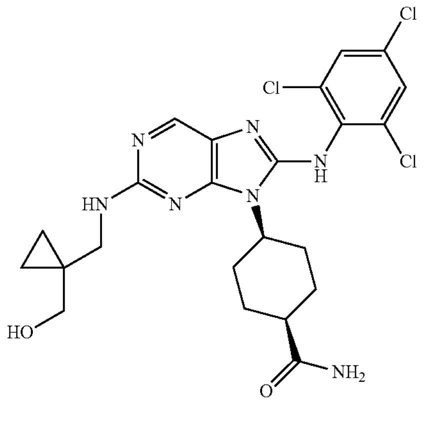 [SMILES: NC(=O)[C@H]1CC[C@@H](n2c(Nc3c(Cl)cc(Cl)cc3Cl)nc3cnc(NCC4(CO)CC4)nc32)CC1] | (1s,4s)-4-(2-((1-(hydroxymethyl)cyclopropyl)methyl-amino)-8-(2,4,6-trichlorophenylamino)-9H-purin-9-yl)cyclohexanecarboxamide | 538.2 | A |

TABLE 1-continued
| Cmpd No. | Structure | Name | MH+ | Ac-tivi-ty |
|---|---|---|---|---|
| 206 | 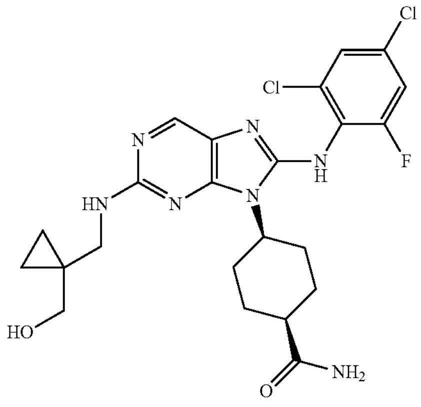 [SMILES: NC(=O)[C@H]1CC[C@@H](n2c(Nc3c(F)cc(Cl)cc3Cl)nc3cnc(NCC4(CO)CC4)nc32)CC1] | (1s,4s)-4-(8-(2,4-dichloro-6-fluorophenylamino)-2-((1-(hydroxymethyl)cyclopropyl)methyl-amino)-9H-purin-9-yl)cyclohexanecarboxamide | 522.2 | A |
| 207 | 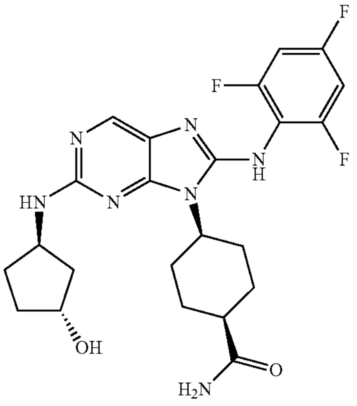 [SMILES: NC(=O)[C@H]1CC[C@@H](n2c(Nc3c(F)cc(F)cc3F)nc3cnc(N[C@@H]4CC[C@@H](O)C4)nc32)CC1] | (1S,4s)-4-(2-((1R,3R)-3-hydroxycyclopentylamino)-8-(2,4,6-trifluorophenylamino)-9H-purin-9-yl)cyclohexanecarboxamide | 490 | A |
| 208 | 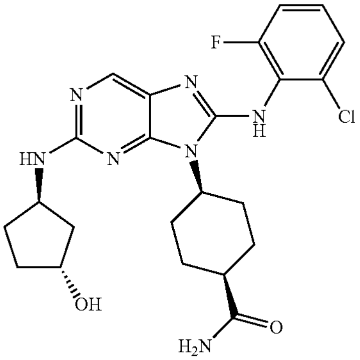 [SMILES: NC(=O)[C@H]1CC[C@@H](n2c(Nc3c(F)cccc3Cl)nc3cnc(N[C@@H]4CC[C@@H](O)C4)nc32)CC1] | (1S,4s)-4-(8-(2-chloro-6-fluorophenylamino)-2-((1R,3R)-3-hydroxycyclopentylamino)-9H-purin-9-yl)cyclohexanecarboxamide | 488.4 | A |

TABLE 1-continued
| Cmpd No. | Structure | Name | MH+ | Activity |
|---|---|---|---|---|
| 209 | 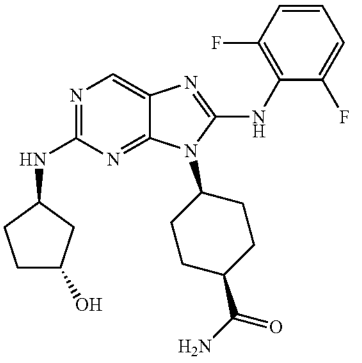 [SMILES: NC(=O)[C@H]1CC[C@@H](n2c(Nc3c(F)cccc3F)nc3cnc(N[C@@H]4CC[C@@H](O)C4)nc32)CC1] | (1S,4s)-4-(8-(2,6-difluorophenylamino)-2-((1R,3R)-3-hydroxycyclopentylamino)-9H-purin-9-yl)cyclohexanecarboxamide | 472.2 | A |
| 210 | 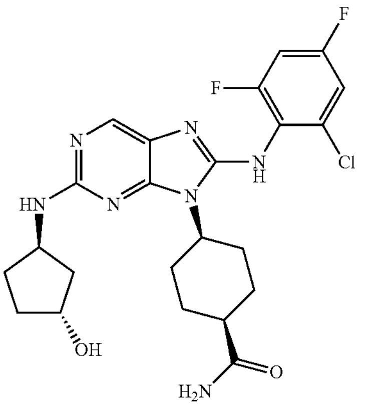 [SMILES: NC(=O)[C@H]1CC[C@@H](n2c(Nc3c(F)cc(F)cc3Cl)nc3cnc(N[C@@H]4CC[C@@H](O)C4)nc32)CC1] | (1S,4s)-4-(8-(2-chloro-4,6-difluorophenylamino)-2-((1R,3R)-3-hydroxycyclopentylamino)-9H-purin-9-yl)cyclohexanecarboxamide | 506.1 | A |
| 211 | 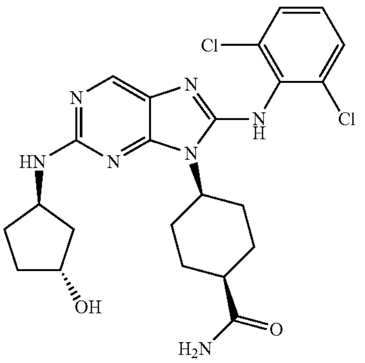 [SMILES: NC(=O)[C@H]1CC[C@@H](n2c(Nc3c(Cl)cccc3Cl)nc3cnc(N[C@@H]4CC[C@@H](O)C4)nc32)CC1] | (1S,4s)-4-(8-(2,6-dichlorophenylamino)-2-((1R,3R)-3-hydroxycyclopentylamino)-9H-purin-9-yl)cyclohexanecarboxamide | 504.2 | A |

TABLE 1-continued
| Cmpd No. | Structure | Name | MH+ | Activity |
|---|---|---|---|---|
| 212 | 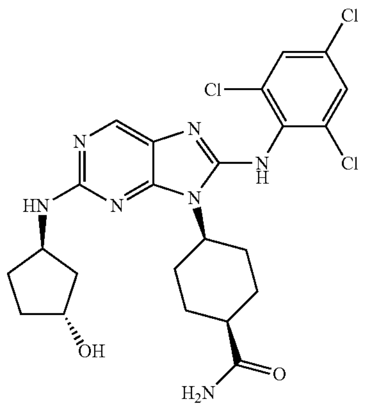 [SMILES: NC(=O)[C@H]1CC[C@@H](n2c(Nc3c(Cl)cc(Cl)cc3Cl)nc3cnc(N[C@@H]4CC[C@@H](O)C4)nc32)CC1] | (1S,4s)-4-(2-((1R,3R)-3-hydroxycyclopentylamino)-8-(2,4,6-trichlorophenylamino)-9H-purin-9-yl)cyclohexanecarboxamide | 538.1 | C |
| 213 | 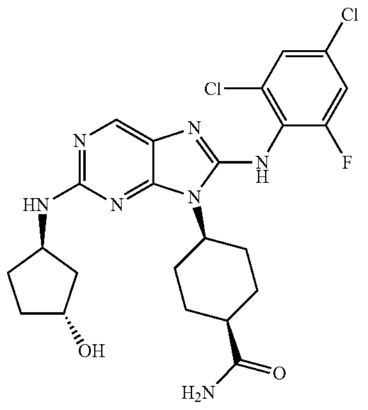 [SMILES: NC(=O)[C@H]1CC[C@@H](n2c(Nc3c(F)cc(Cl)cc3Cl)nc3cnc(N[C@@H]4CC[C@@H](O)C4)nc32)CC1] | (1S,4s)-4-(8-(2,4-dichlroo-6-fluorophenylamino)-2-((1R,3R)-3-hydroxycyclopentylamino)-9H-purin-9-yl)cyclohexanecarboxamide | 522.1 | C |
| 214 | 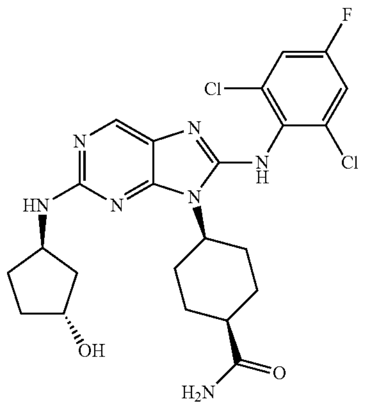 [SMILES: NC(=O)[C@H]1CC[C@@H](n2c(Nc3c(Cl)cc(F)cc3Cl)nc3cnc(N[C@@H]4CC[C@@H](O)C4)nc32)CC1] | (1S,4s)-4-(8-(2,6-dichloro-4-fluorophenylamino)-2-((1R,3R)-3-hydroxycyclopentylamino)-9H-purin-9-yl)cyclohexanecarboxamide | 522.1 | A |

TABLE 1-continued
| Cmpd No. | Structure | Name | MH+ | Activity |
|---|---|---|---|---|
| 215 | 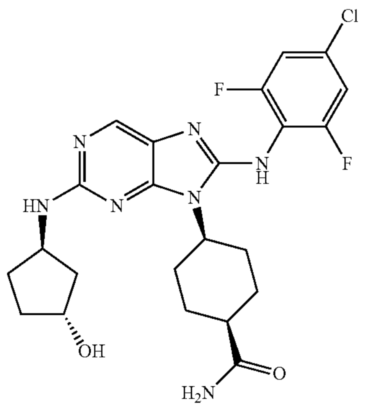 [SMILES: NC(=O)[C@H]1CC[C@@H](n2c(Nc3c(F)cc(Cl)cc3F)nc3cnc(N[C@@H]4CC[C@@H](O)C4)nc32)CC1] | (1S,4s)-4-(8-(4-chloro-2,6-difluorophenylamino)-2-((1R,3R)-3-hydroxycyclopentylamino)-9H-purin-9-yl)cyclohexanecarboxamide | 506.1 | C |
| 216 | 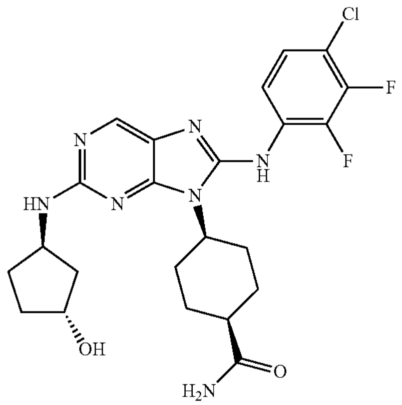 [SMILES: NC(=O)[C@H]1CC[C@@H](n2c(Nc3ccc(Cl)c(F)c3F)nc3cnc(N[C@@H]4CC[C@@H](O)C4)nc32)CC1] | (1S,4s)-4-(8-(4-chloro-2,3-difluorophenylamino)-2-((1R,3R)-3-hydroxycyclopentylamino)-9H-purin-9-yl)cyclohexanecarboxamide | 506.2 | A |
| 217 | 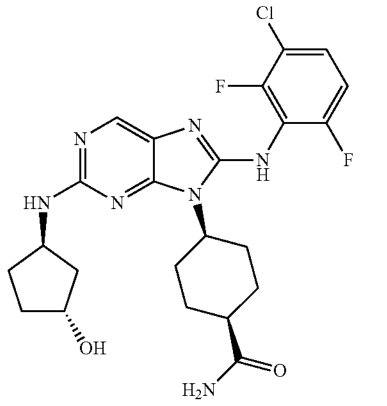 [SMILES: NC(=O)[C@H]1CC[C@@H](n2c(Nc3c(F)ccc(Cl)c3F)nc3cnc(N[C@@H]4CC[C@@H](O)C4)nc32)CC1] | (1S,4s)-4-(8-(3-chloro-2,6-difluorophenylamino)-2-((1R,3R)-3-hydroxycyclopentylamino)-9H-purin-9-yl)cyclohexanecarboxamide | 506.2 | A |

TABLE 1-continued
| Cmpd No. | Structure | Name | MH+ | Activity |
| --- | --- | --- | --- | --- |
| 218 | 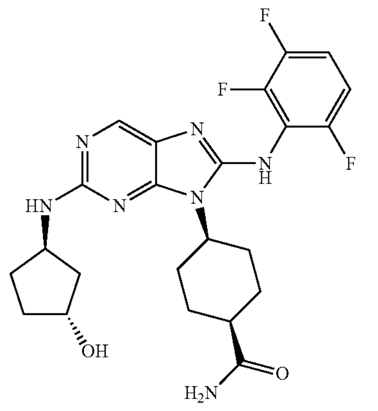 [SMILES: NC(=O)[C@H]1CC[C@@H](n2c(Nc3c(F)ccc(F)c3F)nc3cnc(N[C@@H]4CC[C@@H](O)C4)nc32)CC1] | (1S,4s)-4-(2-((1R,3R)-3-hydroxycyclopentylamino)-8-(2,3,6-trifluorophenylamino)-9H-purin-9-yl)cyclohexanecarboxamide | 490.2 | A |
| 219 | 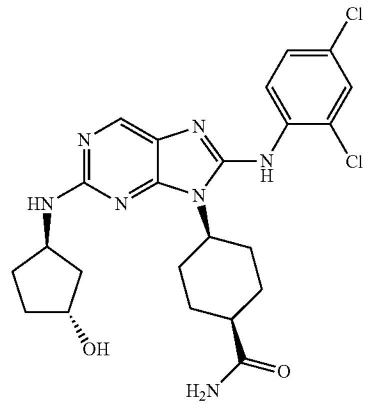 [SMILES: NC(=O)[C@H]1CC[C@@H](n2c(Nc3ccc(Cl)cc3Cl)nc3cnc(N[C@@H]4CC[C@@H](O)C4)nc32)CC1] | (1S,4s)-4-(8-(2,4-dichlorophenylamino)-2-((1R,3R)-3-hydroxycyclopentylamino)-9H-purin-9-yl)cyclohexanecarboxamide | 504.1 | A |
| 220 | 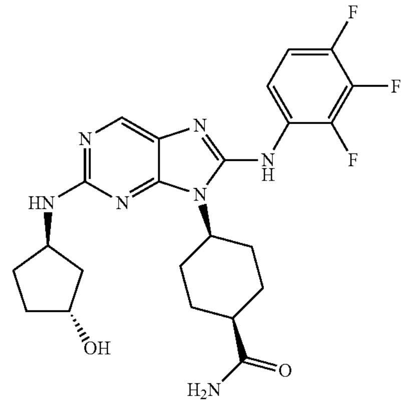 [SMILES: NC(=O)[C@H]1CC[C@@H](n2c(Nc3ccc(F)c(F)c3F)nc3cnc(N[C@@H]4CC[C@@H](O)C4)nc32)CC1] | (1S,4s)-4-(2-((1R,3R)-3-hydroxycyclopentylamino)-8-(2,3,4-trifluorophenylamino)-9H-purin-9-yl)cyclohexanecarboxamide | 490.2 | A |

TABLE 1-continued
| Cmpd No. | Structure | Name | MH+ | Activity |
|---|---|---|---|---|
| 221 | 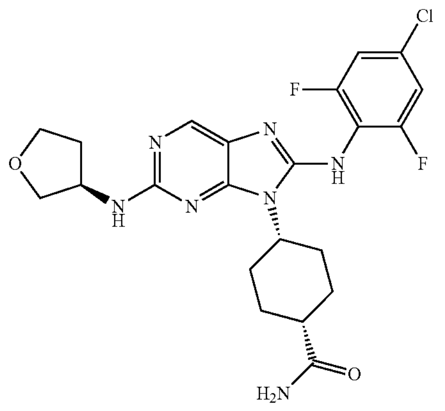 [SMILES: NC(=O)[C@H]1CC[C@@H](n2c(Nc3c(F)cc(Cl)cc3F)nc3cnc(N[C@@H]4CCOC4)nc32)CC1] | (1S,4s)-4-(8-(4-chloro-2,6-difluorophenylamino)-2-((R)-tetrahydrofuran-3-ylamino)-9H-purin-9-yl)cyclohexanecarboxamide | 492.1 | B |
| 222 | 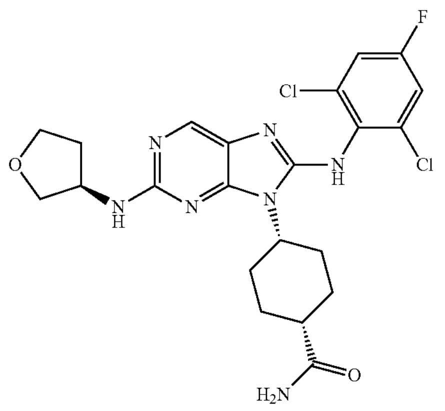 | (1S,4S)-4-(8-(2,6-dichloro-4-fluorophenylamino)-2-((R)-tetrahydrofuran-3-ylamino)-9H-purin-9-yl)cyclohexanecarboxamide | 508 | B |
| 223 | 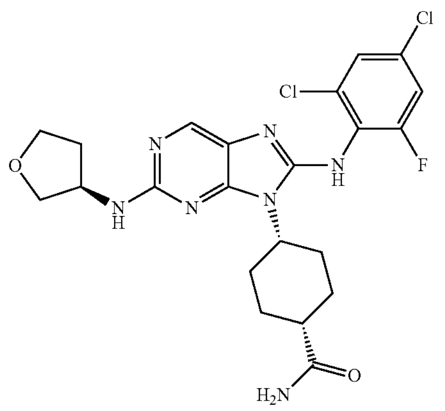 [SMILES: NC(=O)[C@H]1CC[C@@H](n2c(Nc3c(F)cc(Cl)cc3Cl)nc3cnc(N[C@@H]4CCOC4)nc32)CC1] | (1S,4s)-4-(8-(2,4-dichloro-6-fluorophenylamino)-2-((R)-tetrahydrofuran-3-ylamino)-9H-purin-9-yl)cyclohexanecarboxamide | 508.1 | C |

TABLE 1-continued

| Cmpd No. | Structure | Name | MH+ | Activity |
|---|---|---|---|---|
| 224 | 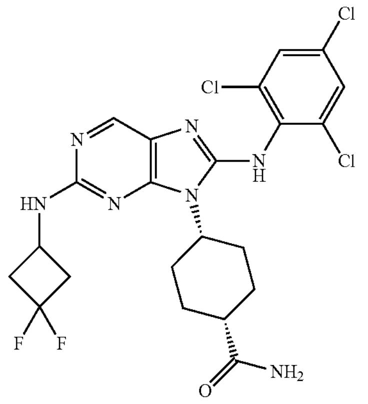 | (1s,4s)-4-(2-(3,3-difluorocyclobutylamino)-8-(2,4,6-trichlorophenylamino)-9H-purin-9-yl)cyclohexanecarboxamide | 544.1 | A |
| 225 | 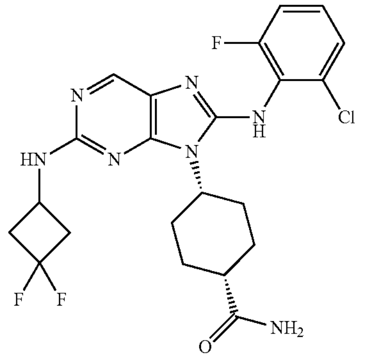 [SMILES: NC(=O)[C@H]1CC[C@@H](n2c(Nc3c(F)cccc3Cl)nc3cnc(NC4CC(F)(F)C4)nc32)CC1] | (1s,4s)-4-(8-(2-chloro-6-fluorophenylamino)-2-(3,3-difluorocyclobutylamino)-9H-purin-9-yl)cyclohexanecarboxamide | 494.1 | A |
| 226 | 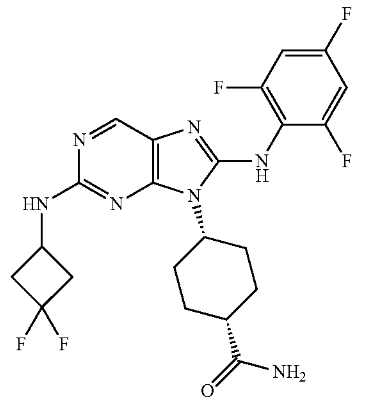 [SMILES: NC(=O)[C@H]1CC[C@@H](n2c(Nc3c(F)cc(F)cc3F)nc3cnc(NC4CC(F)(F)C4)nc32)CC1] | (1s,4s)-4-(2-(3,3-difluorocyclobutylamino)-8-(2,4,6-trifluorophenylamino)-9H-purin-9-yl)cyclohexanecarboxamide | 496.1 | A |
| 227 | 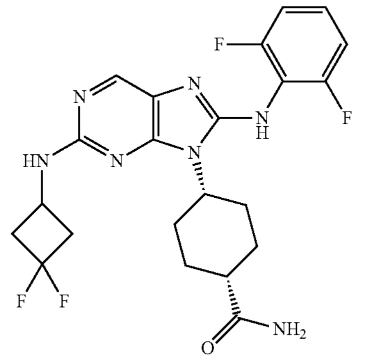 [SMILES: NC(=O)[C@H]1CC[C@@H](n2c(Nc3c(F)cccc3F)nc3cnc(NC4CC(F)(F)C4)nc32)CC1] | (1s,4s)-4-(2-(3,3-difluorocyclobutylamino)-8-(2,6-difluorophenylamino)-9H-purin-9-yl)cyclohexanecarboxamide | 478.2 | A |

TABLE 1-continued
| Cmpd No. | Structure | Name | MH+ | Activity |
| --- | --- | --- | --- | --- |
| 228 | 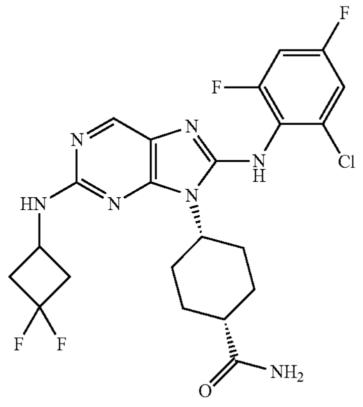 | (1s,4s)-4-(8-(2-chloro-4,6-difluorophenylamino)-2-(3,3-difluorocyclobutylamino)-9H-purin-9-yl)cyclohexanecarboxamide | 512.1 | B |
| 229 | 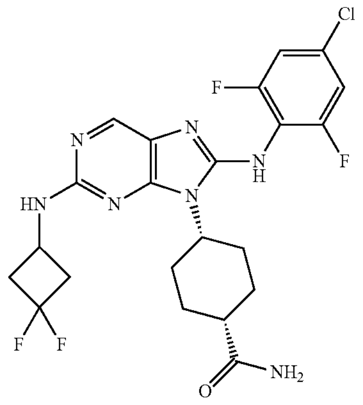 [SMILES: NC(=O)[C@H]1CC[C@@H](n2c(Nc3c(F)cc(Cl)cc3F)nc3cnc(NC4CC(F)(F)C4)nc32)CC1] | (1s,4s)-4-(8-(4-chloro-2,6-difluorophenylamino)-2-(3,3-difluorocyclobutylamino)-9H-purin-9-yl)cyclohexanecarboxamide | 512.1 | A |
| 230 | 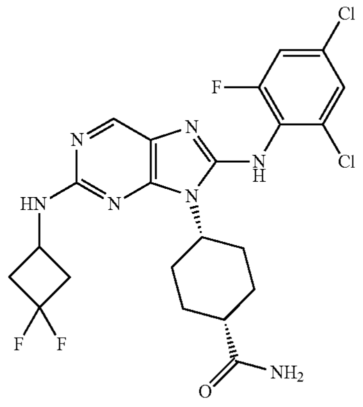 [SMILES: NC(=O)[C@H]1CC[C@@H](n2c(Nc3c(F)cc(Cl)cc3Cl)nc3cnc(NC4CC(F)(F)C4)nc32)CC1] | (1s,4s)-4-(8-(2,4-dichloro-6-fluorophenylamino)-2-(3,3-difluorocyclobutylamino)-9H-purin-9-yl)cyclohexanecarboxamide | 528.1 | C |

TABLE 1-continued
| Cmpd No. | Structure | Name | MH+ | Activity |
|---|---|---|---|---|
| 231 | 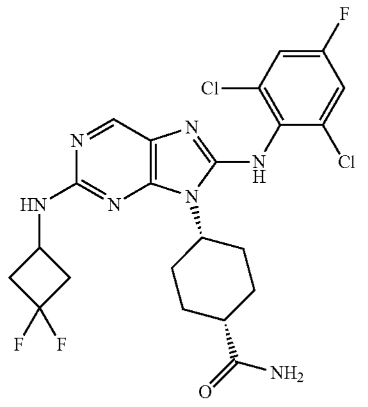 | (1s,4s)-4-(8-(2,6-dichloro-4-fluorophenylamino)-2-(3,3-difluorocyclobutylamino)-9H-purin-9-yl)cyclohexanecarboxamide | 528.1 | A |
| 232 | 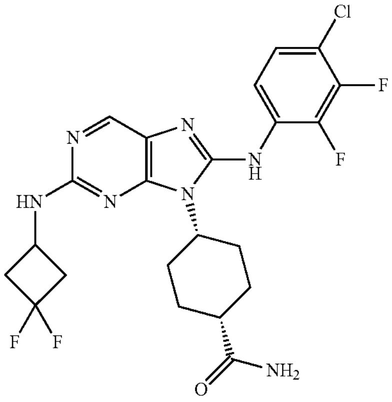 [SMILES: NC(=O)[C@H]1CC[C@@H](n2c(Nc3ccc(Cl)c(F)c3F)nc3cnc(NC4CC(F)(F)C4)nc32)CC1] | (1s,4s)-4-(8-(4-chloro-2,3-difluorophenylamino)-2-(3,3-difluorocyclobutylamino)-9H-purin-9-yl)cyclohexanecarboxamide | 512.1 | A |
| 233 | 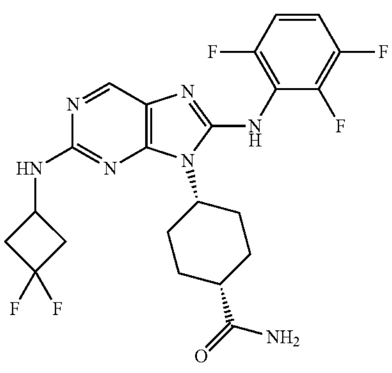 [SMILES: NC(=O)[C@H]1CC[C@@H](n2c(Nc3c(F)ccc(F)c3F)nc3cnc(NC4CC(F)(F)C4)nc32)CC1] | (1s,4s)-4-(2-(3,3-difluorocyclobutylamino)-8-(2,3,6-trifluorophenylamino)-9H-purin-9-yl)cyclohexanecarboxamide | 496.1 | B |

TABLE 1-continued

| Cmpd No. | Structure | Name | MH+ | Activity |
|---|---|---|---|---|
| 234 | 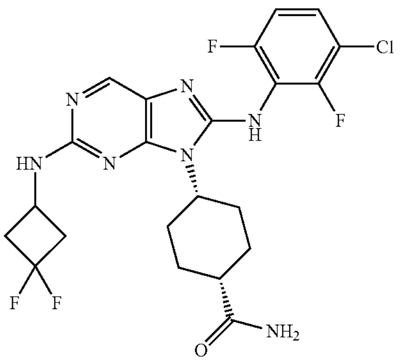 [SMILES: NC(=O)[C@H]1CC[C@@H](n2c(Nc3c(F)ccc(Cl)c3F)nc3cnc(NC4CC(F)(F)C4)nc32)CC1] | (1s,4s)-4-(8-(3-chloro-2,6-difluorophenylamino)-2-(3,3-difluorocyclobutylamino)-9H-purin-9-yl)cyclohexanecarboxamide | 512.1 | A |
| 235 | 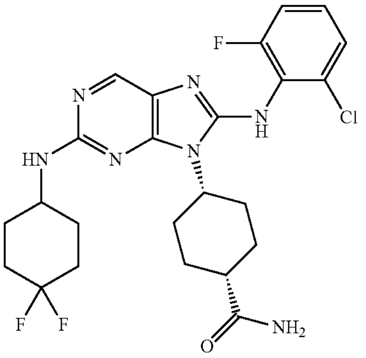 [SMILES: NC(=O)[C@H]1CC[C@@H](n2c(Nc3c(F)cccc3Cl)nc3cnc(NC4CCC(F)(F)CC4)nc32)CC1] | (1s,4s)-4-(8-(2-chloro-6-fluorophenylamino)-2-(4,4-difluorocyclohexylamino)-9H-purin-9-yl)cyclohexanecarboxamide | 522.1 | B |
| 236 | 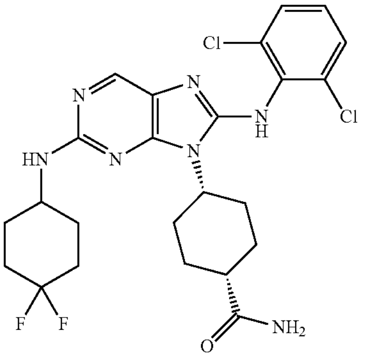 [SMILES: NC(=O)[C@H]1CC[C@@H](n2c(Nc3c(Cl)cccc3Cl)nc3cnc(NC4CCC(F)(F)CC4)nc32)CC1] | (1s,4s)-4-(8-(2,6-dichlorophenylamino)-2-(4,4-difluorocyclohexylamino)-9H-purin-9-yl)cyclohexanecarboxamide | 538.1 | C |
| 237 | 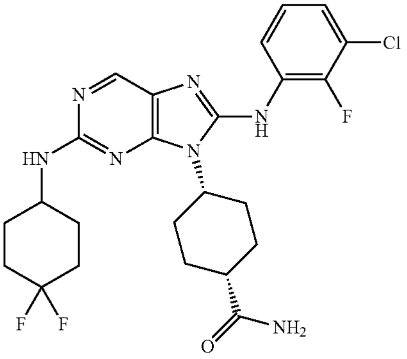 [SMILES: NC(=O)[C@H]1CC[C@@H](n2c(Nc3cccc(Cl)c3F)nc3cnc(NC4CCC(F)(F)CC4)nc32)CC1] | (1s,4s)-4-(8-(3-chloro-2-fluorophenylamino)-2-(4,4-difluorocyclohexylamino)-9H-purin-9-yl)cyclohexanecarboxamide | 522.1 | A |

TABLE 1-continued
| Cmpd No. | Structure | Name | MH+ | Activity |
|---|---|---|---|---|
| 238 | 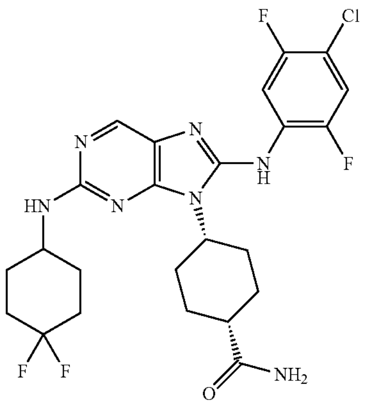 [SMILES: NC(=O)[C@H]1CC[C@@H](n2c(Nc3cc(F)c(Cl)cc3F)nc3cnc(NC4CCC(F)(F)CC4)nc32)CC1] | (1s,4s)-4-(8-(4-chloro-2,5-difluorophenylamino)-2-(4,4-difluorocyclohexylamino)-9H-purin-9-yl)cyclohexanecarboxamide | 540.2 | A |
| 239 | 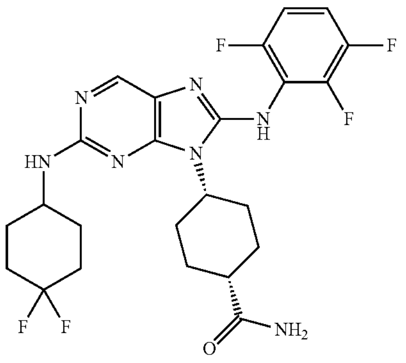 [SMILES: NC(=O)[C@H]1CC[C@@H](n2c(Nc3c(F)ccc(F)c3F)nc3cnc(NC4CCC(F)(F)CC4)nc32)CC1] | (1s,4s)-4-(2-(4,4-difluorocyclohexylamino)-8-(2,3,6-trifluorophenylamino)-9H-purin-9-yl)cyclohexanecarboxamide | 524.1 | B |
| 240 | 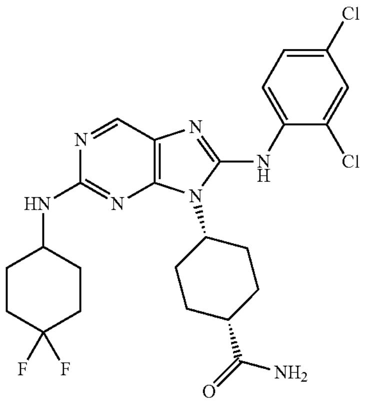 [SMILES: NC(=O)[C@H]1CC[C@@H](n2c(Nc3ccc(Cl)cc3Cl)nc3cnc(NC4CCC(F)(F)CC4)nc32)CC1] | (1s,4s)-4-(8-(2,4-dichlorophenylamino)-2-(4,4-difluorocyclohexylamino)-9H-purin-9-yl)cyclohexanecarboxamide | 538.2 | A |

TABLE 1-continued
| Cmpd No. | Structure | Name | MH+ | Activity |
|---|---|---|---|---|
| 241 | 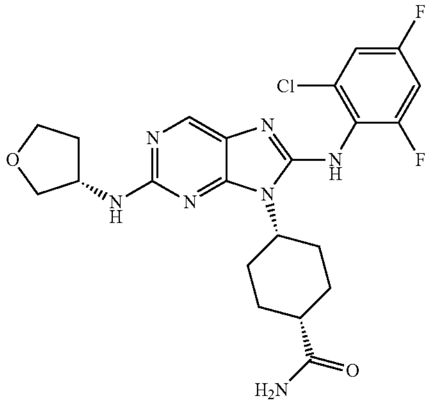 [SMILES: NC(=O)[C@H]1CC[C@@H](n2c(Nc3c(F)cc(F)cc3Cl)nc3cnc(N[C@H]4CCOC4)nc32)CC1] | (1R,4s)-4-(8-(2-chloro-4,6-difluorophenylamino)-2-((S)-tetrahydrofuran-3-ylamino)-9H-purin-9-yl)cylcohexanecarboxamide | 492.1 | A |
| 242 | 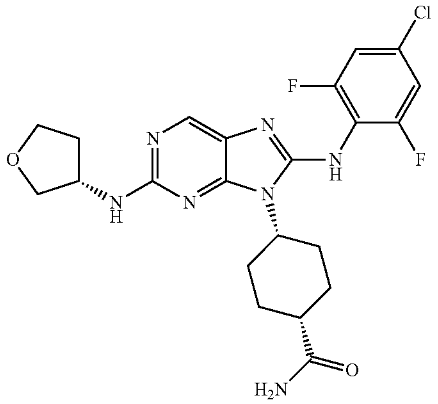 [SMILES: NC(=O)[C@H]1CC[C@@H](n2c(Nc3c(F)cc(Cl)cc3F)nc3cnc(N[C@H]4CCOC4)nc32)CC1] | (1R,4s)-4-(8-(4-chloro-2,6-difluorophenylamino)-2-((S)-tetrahydrofuran-3-ylamino)-9H-purin-9-yl)cyclohexanecarboxamide | 492.1 | B |
| 243 | 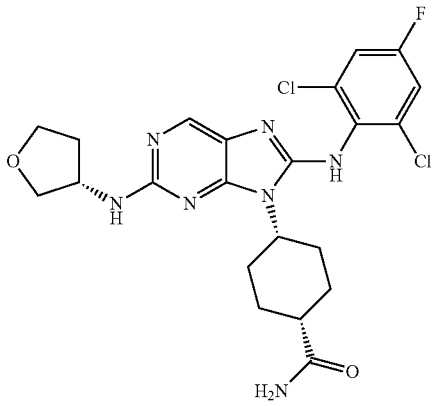 | (1R,4s)-4-(8-(2,6-dichloro-4-fluorophenylamino)-2-((S)-tetrahydrofuran-3-ylamino)-9H-purin-9-yl)cyclohexanecarboxamide | 508.1 | B |

TABLE 1-continued
| Cmpd No. | Structure | Name | MH+ | Activity |
|---|---|---|---|---|
| 244 | 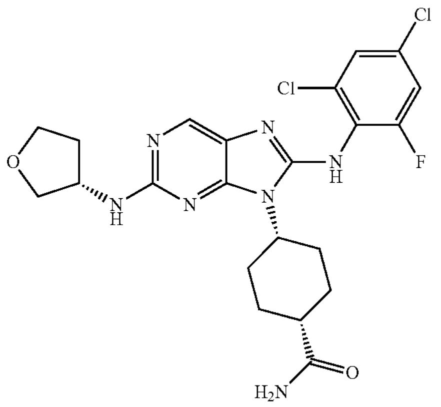 [SMILES: NC(=O)[C@H]1CC[C@@H](n2c(Nc3c(F)cc(Cl)cc3Cl)nc3cnc(N[C@H]4CCOC4)nc32)CC1] | (1R,4s)-4-(8-(2,4-dichloro-6-fluorophenylamino)-2-((S)-tetrahydrofuran-3-ylamino)-9H-purin-9-yl)cyclohexanecarboxamide | 508.1 | B |
| 245 | 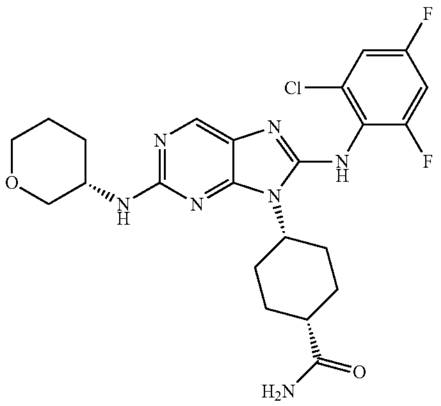 [SMILES: NC(=O)[C@H]1CC[C@@H](n2c(Nc3c(F)cc(F)cc3Cl)nc3cnc(N[C@H]4CCCOC4)nc32)CC1] | (1R,4s)-4-(8-(2-chloro-4,6-difluorophenylamino)-2-((S)-tetrahydro-2H-pyran-3-ylamino)-9H-purin-9-yl)cyclohexanecarboxamide | 506.1 | A |
| 246 | 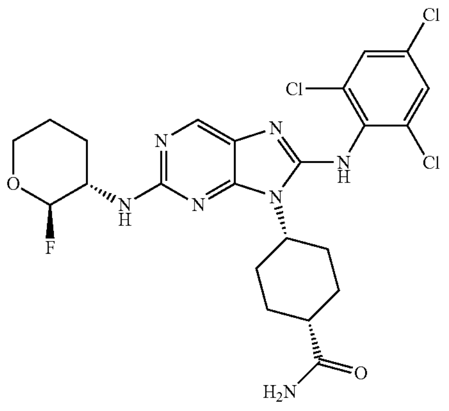 [SMILES: NC(=O)[C@H]1CC[C@@H](n2c(Nc3c(Cl)cc(Cl)cc3Cl)nc3cnc(N[C@H]4CCCO[C@@H]4F)nc32)CC1] | (1R,4s)-4-(2-((3R,4S)-3-fluorotetrahydro-2H-pyran-4-ylamino)-8-(2,4,6-trichlorophenylamino)-9H-purin-9-yl)cyclohexanecarboxamide | 556.1 | B |

TABLE 1-continued
| Cmpd No. | Structure | Name | MH+ | Activity |
|---|---|---|---|---|
| 247 | 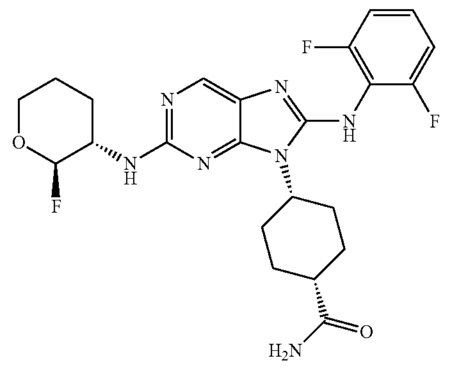 [SMILES: NC(=O)[C@H]1CC[C@@H](n2c(Nc3c(F)cccc3F)nc3cnc(N[C@H]4CCCO[C@@H]4F)nc32)CC1] | (1R,4s)-4-(8-(2,6-difluorophenylamino)-2-((3R,4S)-3-fluorotetrahydro-2H-pyran-4-ylamino)-9H-purin-9-yl)cyclohexanecarboxamide | 490.2 | A |
| 248 | 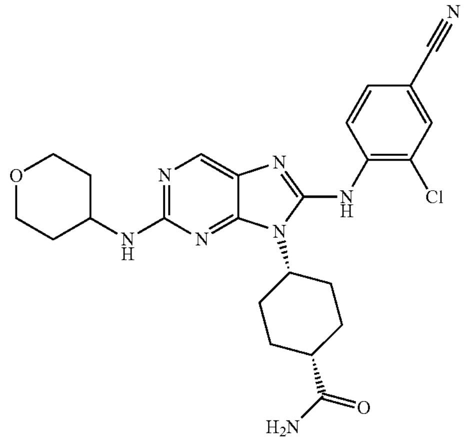 [SMILES: N#Cc1ccc(Nc2nc3cnc(NC4CCOCC4)nc3n2[C@H]2CC[C@@H](C(N)=O)CC2)c(Cl)c1] | (1s,4s)-4-(8-(2-chloro-4-cyanophenylamino)-2-(tetrahydro-2H-pyran-4-ylamino)-9H-purin-9-yl)cyclohexanecarboxamide | 495.2 | B |
| 249 | 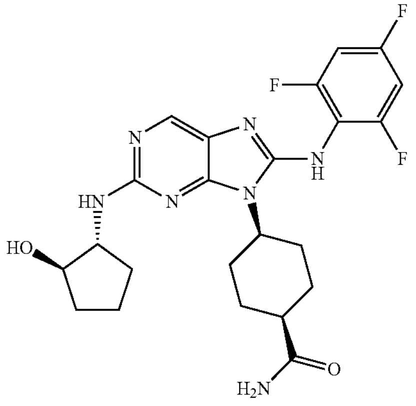 [SMILES: NC(=O)[C@H]1CC[C@@H](n2c(Nc3c(F)cc(F)cc3F)nc3cnc(N[C@@H]4CCC[C@H]4O)nc32)CC1] | (1S,4s)-4-(2-((1R,2R)-2-hydroxycyclopentylamino)-8-(2,4,6-trifluorophenylamino)-9H-purin-9-yl)cyclohexanecarboxamide | 490 | A |

TABLE 1-continued

| Cmpd No. | Structure | Name | MH+ | Ac-tivi-ty |
|---|---|---|---|---|
| 250 | 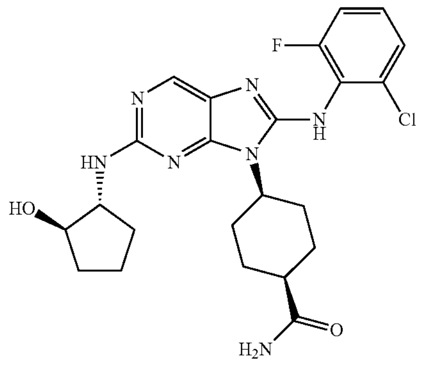 [SMILES: NC(=O)[C@H]1CC[C@@H](n2c(Nc3c(F)cccc3Cl)nc3cnc(N[C@@H]4CCC[C@H]4O)nc32)CC1] | (1S,4s)-4-(8-(2-chloro-6-fluorophenylamino)-2-((1R,2R)-2-hydroxycyclopentylamino)-9H-purin-9-yl)cyclohexanecarboxamide | 488 | A |
| 251 | 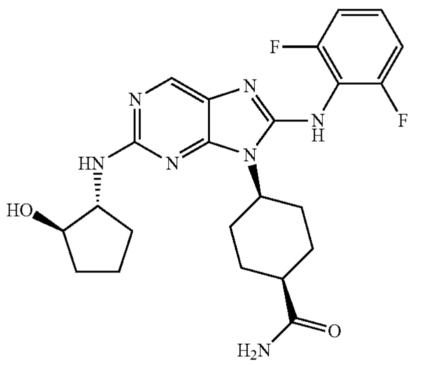 [SMILES: NC(=O)[C@H]1CC[C@@H](n2c(Nc3c(F)cccc3F)nc3cnc(N[C@@H]4CCC[C@H]4O)nc32)CC1] | (1S,4s)-4-(8-(2,6-difluorophenylamino)-2-((1R,2R)-2-hydroxycyclopentylamino)-9H-purin-9-yl)cyclohexanecarboxamide | 472 | A |
| 252 | 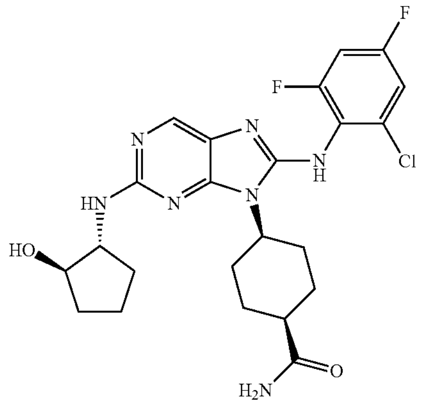 [SMILES: NC(=O)[C@H]1CC[C@@H](n2c(Nc3c(F)cc(F)cc3Cl)nc3cnc(N[C@@H]4CCC[C@H]4O)nc32)CC1] | (1S,4s)-4-(8-(2-chloro-4,6-difluorophenylamino)-2-((1R,2R)-2-hydroxycyclopentylamino)-9H-purin-9-yl)cyclohexanecarboxamide | 506.3 | A |
| 253 | 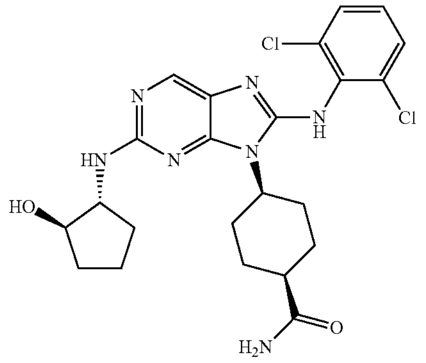 [SMILES: NC(=O)[C@H]1CC[C@@H](n2c(Nc3c(Cl)cccc3Cl)nc3cnc(N[C@@H]4CCC[C@H]4O)nc32)CC1] | (1S,4s)-4-(8-(2,6-dichlorophenylamino)-2-((1R,2R)-2-hydroxycyclopentylamino)-9H-purin-9-yl)cyclohexanecarboxamide | 503.3 | A |

TABLE 1-continued
| Cmpd No. | Structure | Name | MH+ | Activity |
|---|---|---|---|---|
| 254 | 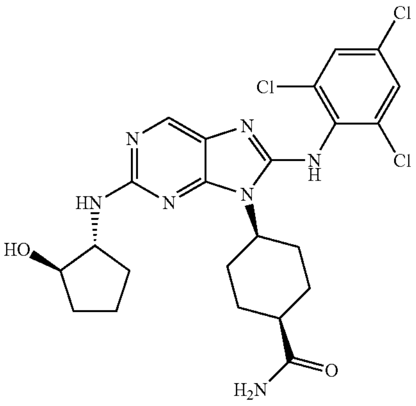 [SMILES: NC(=O)[C@H]1CC[C@@H](n2c(Nc3c(Cl)cc(Cl)cc3Cl)nc3cnc(N[C@@H]4CCC[C@H]4O)nc32)CC1] | (1S,4s)-4-(2-((1R,2R)-2-hydroxycyclopentyalmino)-8-(2,4,6-trichlorophenylamino)-9H-purin-9-yl)cyclohexanecarboxamide | 540 | B |
| 255 | 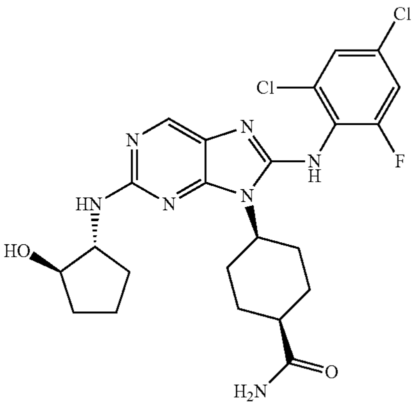 [SMILES: NC(=O)[C@H]1CC[C@@H](n2c(Nc3c(F)cc(Cl)cc3Cl)nc3cnc(N[C@@H]4CCC[C@H]4O)nc32)CC1] | (1S,4s)-4-(8-(2,4-dichloro-6-fluorophenylamino)-2-((1R,2R)-2-hydroxycyclopentylamino)-9H-purin-9-yl)cyclohexanecarboxamide | 522.2 | A |
| 256 | 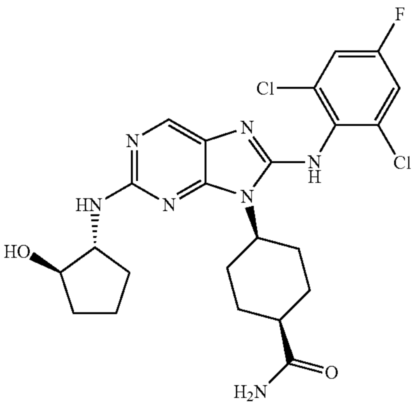 [SMILES: NC(=O)[C@H]1CC[C@@H](n2c(Nc3c(Cl)cc(F)cc3Cl)nc3cnc(N[C@@H]4CCC[C@H]4O)nc32)CC1] | (1S,4s)-4-(8-(2,6-dichloro-4-fluorophenylamino)-2-((1R,2R)-2-hydroxycyclopentylamino)-9H-purin-9-yl)cyclohexanecarboxamide | 522.1 | A |

TABLE 1-continued
| Cmpd No. | Structure | Name | MH+ | Activity |
|---|---|---|---|---|
| 257 | 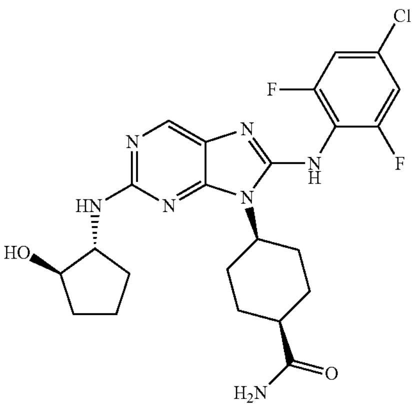 [SMILES: NC(=O)[C@H]1CC[C@@H](n2c(Nc3c(F)cc(Cl)cc3F)nc3cnc(N[C@@H]4CCC[C@H]4O)nc32)CC1] | (1S,4s)-4-(8-(4-chloro-2,6-difluorophenylamino)-2-((1R,2R)-2-hydroxycyclopentyalmino)-9H-purin-9-yl)cyclohexanecarboxamide | 506.2 | B |
| 258 | 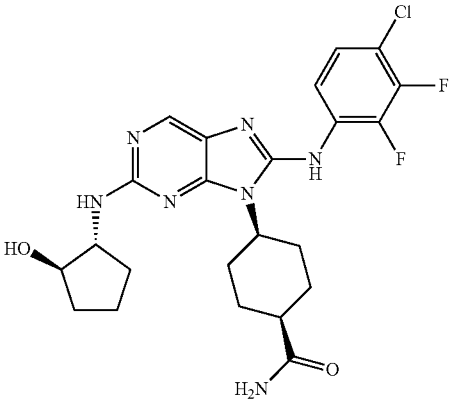 [SMILES: NC(=O)[C@H]1CC[C@@H](n2c(Nc3ccc(Cl)c(F)c3F)nc3cnc(N[C@@H]4CCC[C@H]4O)nc32)CC1] | (1S,4s)-4-(8-(4-chloro-2,3-difluorophenylamino)-2-((1R,2R)-2-hydroxycyclopentylamino)-9H-purin-9-yl)cyclohexanecarboxamide | 506.1 | A |
| 259 | 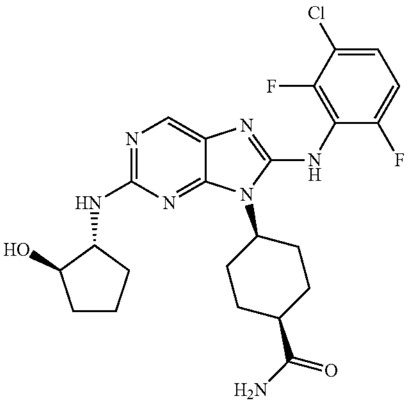 [SMILES: NC(=O)[C@H]1CC[C@@H](n2c(Nc3c(F)ccc(Cl)c3F)nc3cnc(N[C@@H]4CCC[C@H]4O)nc32)CC1] | (1S,4s)-4-(8-(3-chloro-2,6-difluorophenylamino)-2-((1R,2R)-2-hydroxycyclopentylamino)-9H-purin-9-yl)cyclohexanecarboxamide | 506.2 | A |

TABLE 1-continued
| Cmpd No. | Structure | Name | MH+ | Activity |
| --- | --- | --- | --- | --- |
| 260 | 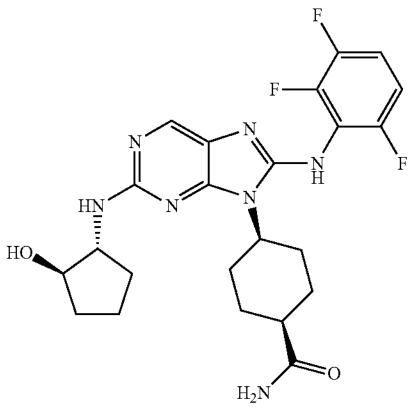 [SMILES: NC(=O)[C@H]1CC[C@@H](n2c(Nc3c(F)ccc(F)c3F)nc3cnc(N[C@@H]4CCC[C@H]4O)nc32)CC1] | (1S,4s)-4-(2-((1R,2R)-2-hydroxycyclopentylamino)-8-(2,3,6-trifluorophenylamino)-9H-purin-9-yl)cyclohexanecarboxamide | 490.2 | A |
| 261 | 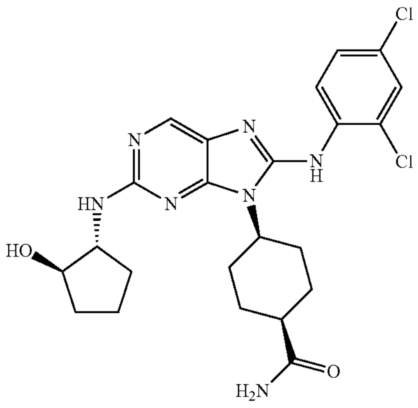 [SMILES: NC(=O)[C@H]1CC[C@@H](n2c(Nc3ccc(Cl)cc3Cl)nc3cnc(N[C@@H]4CCC[C@H]4O)nc32)CC1] | (1S,4s)-4-(8-(2,4-dichlorophenylamino)-2-((1R,2R)-2-hydroxycyclopentylamino)-9H-purin-9-yl)cyclohexanecarboxamide | 506.1 | A |
| 262 | 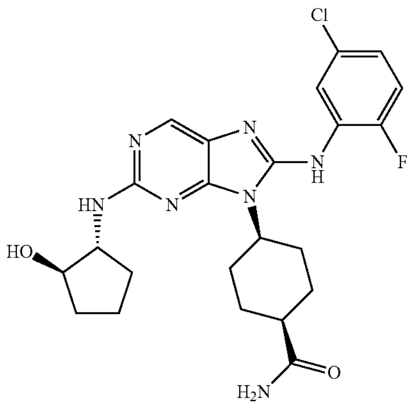 [SMILES: NC(=O)[C@H]1CC[C@@H](n2c(Nc3cc(Cl)ccc3F)nc3cnc(N[C@@H]4CCC[C@H]4O)nc32)CC1] | (1S,4s)-4-(8-(5-chloro-2-fluorophenylamino)-2-((1R,2R)-2-hydroxycyclopentylamino)-9H-purin-9-yl)cyclohexanecarboxamide | 488.1 | A |

TABLE 1-continued
| Cmpd No. | Structure | Name | MH+ | Activity |
| --- | --- | --- | --- | --- |
| 263 | 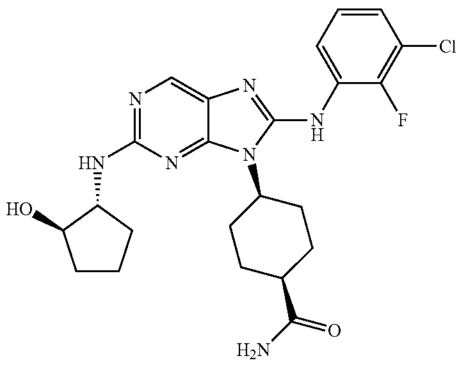 [SMILES: NC(=O)[C@H]1CC[C@@H](n2c(Nc3cccc(Cl)c3F)nc3cnc(N[C@@H]4CCC[C@H]4O)nc32)CC1] | (1S,4s)-4-(8-(3-chloro-2-fluorophenylamino)-2-((1R,2R)-2-hydroxycyclopentylamino)-9H-purin-9-yl)cyclohexanecarboxamide | 488.1 | A |
| 264 | 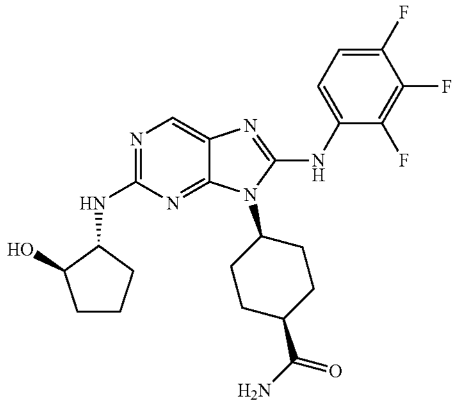 [SMILES: NC(=O)[C@H]1CC[C@@H](n2c(Nc3ccc(F)c(F)c3F)nc3cnc(N[C@@H]4CCC[C@H]4O)nc32)CC1] | (1S,4s)-4-(2-((1R,2R)-2-hydroxycyclopentylamino)-8-(2,3,4-trifluorophenylamino)-9H-purin-9-yl)cyclohexanecarboxamide | 490.2 | A |
| 265 | 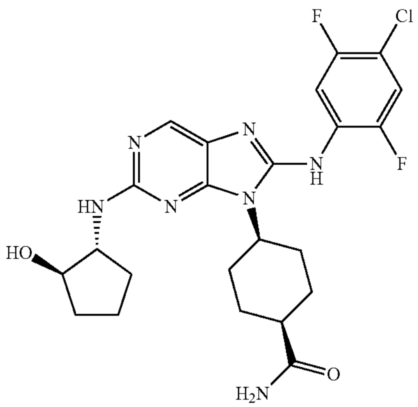 [SMILES: NC(=O)[C@H]1CC[C@@H](n2c(Nc3cc(F)c(Cl)cc3F)nc3cnc(N[C@@H]4CCC[C@H]4O)nc32)CC1] | (1S,4s)-4-(8-(4-chloro-2,5-difluorophenylamino)-2-((1R,2R)-2-hydroxycyclopentylamino)-9H-purin-9-yl)cyclohexanecarboxamide | 506.1 | A |

TABLE 1-continued

| Cmpd No. | Structure | Name | MH+ | Ac-tivi-ty |
|---|---|---|---|---|
| 266 | 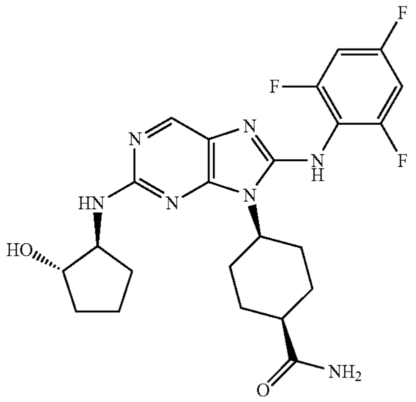 [SMILES: NC(=O)[C@H]1CC[C@@H](n2c(Nc3c(F)cc(F)cc3F)nc3cnc(N[C@H]4CCC[C@@H]4O)nc32)CC1] | (1R,4s)-4-(2-((1S,2S)-2-hydroxycyclopentylamino)-8-(2,4,6-trifluorophenylamino)-9H-purin-9-yl)cyclohexanecarboxamide | 490.3 | A |
| 267 | 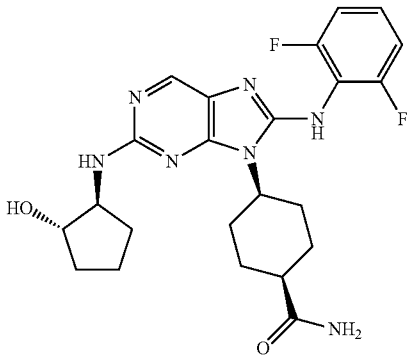 [SMILES: NC(=O)[C@H]1CC[C@@H](n2c(Nc3c(F)cccc3F)nc3cnc(N[C@H]4CCC[C@@H]4O)nc32)CC1] | (1R,4s)-4-(8-(2,6-difluorophenylamino)-2-((1S,2S)-2-hydroxycyclopentylamino)-9H-purin-9-yl)cyclohexanecarboxamide | 472.2 | A |
| 268 | 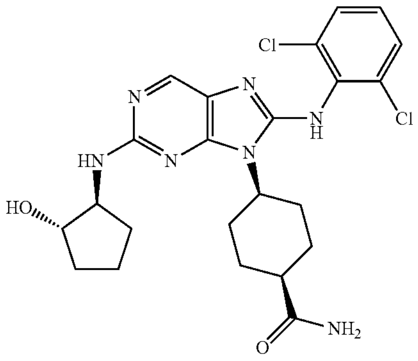 [SMILES: NC(=O)[C@H]1CC[C@@H](n2c(Nc3c(Cl)cccc3Cl)nc3cnc(N[C@H]4CCC[C@@H]4O)nc32)CC1] | (1R,4s)-4-(8-(2,6-dichlorophenylamino)-2-((1S,2S)-2-hydroxycyclopentylamino)-9H-purin-9-yl)cyclohexanecarboxamide | 504.2 | A |
| 269 | 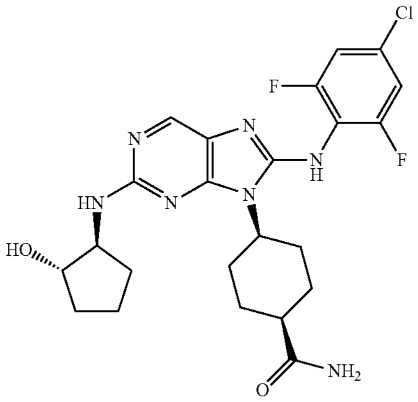 [SMILES: NC(=O)[C@H]1CC[C@@H](n2c(Nc3c(F)cc(Cl)cc3F)nc3cnc(N[C@H]4CCC[C@@H]4O)nc32)CC1] | (1R,4s)-4-(8-(4-chloro-2,6-difluorophenylamino)-2-((1S,2S)-2-hydroxycyclopentylamino)-9H-purin-9-yl)cyclohexanecarboxamide | 506.2 | A |

TABLE 1-continued
| Cmpd No. | Structure | Name | MH+ | Activity |
|---|---|---|---|---|
| 270 | 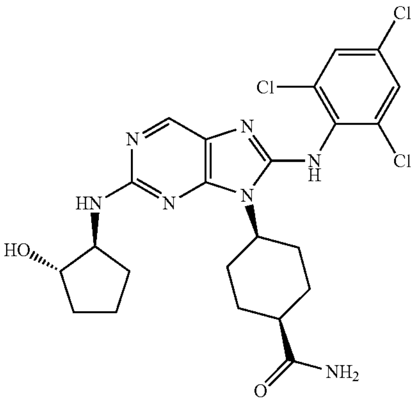 [SMILES: NC(=O)[C@H]1CC[C@@H](n2c(Nc3c(Cl)cc(Cl)cc3Cl)nc3cnc(N[C@H]4CCC[C@@H]4O)nc32)CC1] | (1R,4s)-4-(2-((1S,2S)-2-hydroxycyclopentylamino)-8-(2,4,6-trichlorophenylamino)-9H-purin-9-yl)cyclohexanecarboxamide | 504.2 | A |
| 271 | 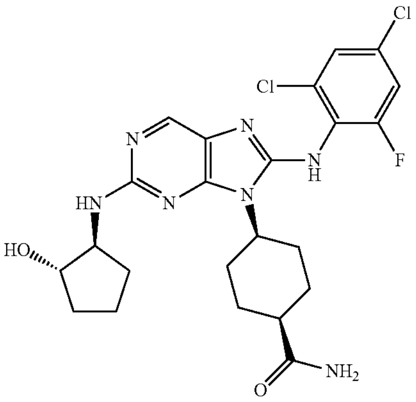 [SMILES: NC(=O)[C@H]1CC[C@@H](n2c(Nc3c(F)cc(Cl)cc3Cl)nc3cnc(N[C@H]4CCC[C@@H]4O)nc32)CC1] | (1R,4s)-4-(8-(2,4-dichloro-6-fluorophenylamino)-2-((1S,2S)-2-hydroxycyclopentylamino)-9H-purin-9-yl)cyclohexanecarboxamide | 522.2 | B |
| 272 | 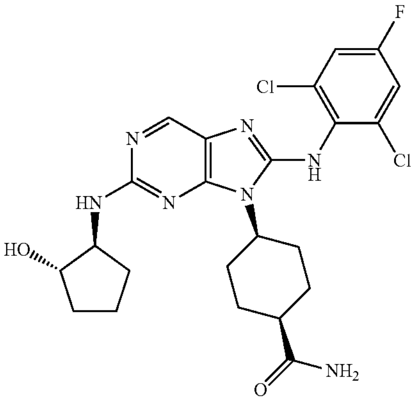 [SMILES: NC(=O)[C@H]1CC[C@@H](n2c(Nc3c(Cl)cc(F)cc3Cl)nc3cnc(N[C@H]4CCC[C@@H]4O)nc32)CC1] | (1R,4s)-4-(8-(2,6-dichloro-4-fluorophenylamino)-2-((1S,2S)-2-hydroxycyclopentylamino)-9H-purin-9-yl)cyclohexanecarboxamide | 522.2 | A |

TABLE 1-continued

| Cmpd No. | Structure | Name | MH+ | Activity |
|---|---|---|---|---|
| 273 | 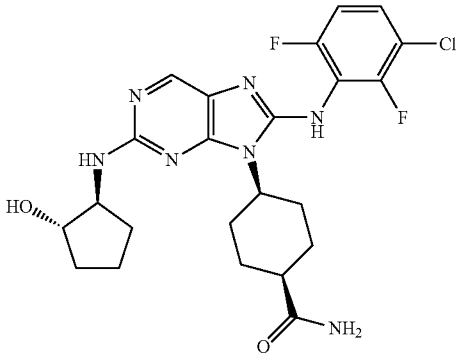 [SMILES: NC(=O)[C@H]1CC[C@@H](n2c(Nc3c(F)ccc(Cl)c3F)nc3cnc(N[C@H]4CCC[C@@H]4O)nc32)CC1] | (1R,4s)-4-(8-(3-chloro-2,6-difluorophenylamino)-2-((1S,2S)-2-hydroxycyclopentylamino)-9H-purin-9-yl)cyclohexanecarboxamide | 506.2 | A |
| 274 | 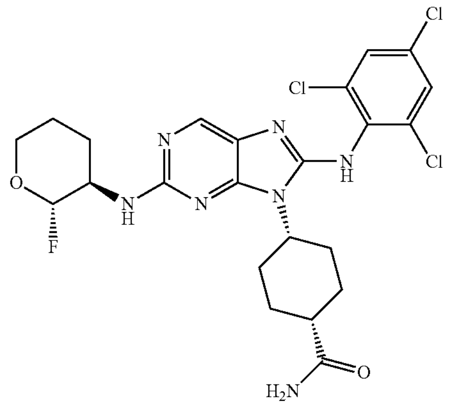 [SMILES: NC(=O)[C@H]1CC[C@@H](n2c(Nc3c(Cl)cc(Cl)cc3Cl)nc3cnc(N[C@@H]4CCCO[C@H]4F)nc32)CC1] | (1S,4s)-4-(2-((3S,4R)-3-fluorotetrahydro-2H-pyran-4-ylamino)-8-(2,4,6-trichlorophenylamino)-9H-purin-9-yl)cyclohexanecarboxamide | 556.5 | D |
| 275 | 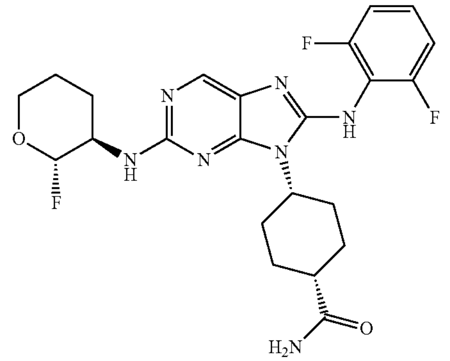 [SMILES: NC(=O)[C@H]1CC[C@@H](n2c(Nc3c(F)cccc3F)nc3cnc(N[C@@H]4CCCO[C@H]4F)nc32)CC1] | (1S,4s)-4-(8-(2,6-difluorophenylamino)-2-((3S,4R)-3-fluorotetrahydro-2H-pyran-4-ylamino)-9H-purin-9-yl)cyclohexanecarboxamide | 490.2 | C |
| 276 | 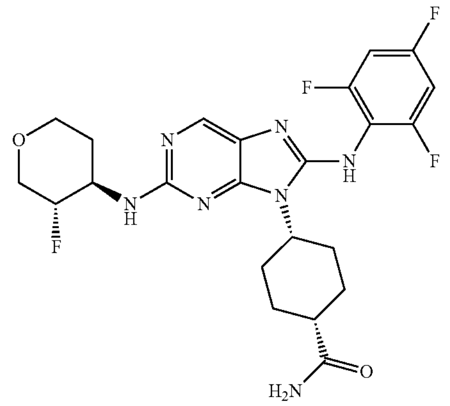 [SMILES: NC(=O)[C@H]1CC[C@@H](n2c(Nc3c(F)cc(F)cc3F)nc3cnc(N[C@@H]4CCOC[C@H]4F)nc32)CC1] | (1S,4s)-4-(2-((3S,4R)-3-fluorotetrahydro-2H-pyran-4-ylamino)-8-(2,4,6-trifluorophenylamino)-9H-purin-9-yl)cyclohexanecarboxamide | 508.2 | D |

TABLE 1-continued
| Cmpd No. | Structure | Name | MH+ | Activity |
|---|---|---|---|---|
| 277 | 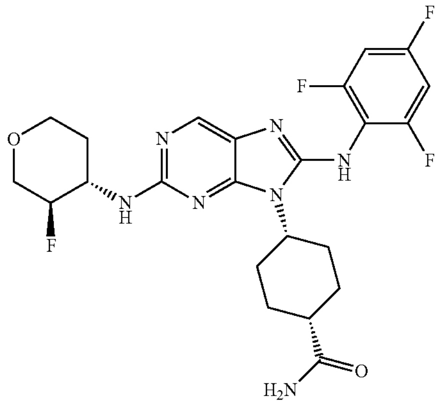 [SMILES: NC(=O)[C@H]1CC[C@@H](n2c(Nc3c(F)cc(F)cc3F)nc3cnc(N[C@H]4CCOC[C@@H]4F)nc32)CC1] | (1R,4s)-4-(2-((3R,4S)-3-fluorotetrahydro-2H-pyran-4-ylamino)-8-(2,4,6-trifluorophenylamino)-9H-purin-9-yl)cyclohexanecarboxamide | 508.2 | A |
| 278 | 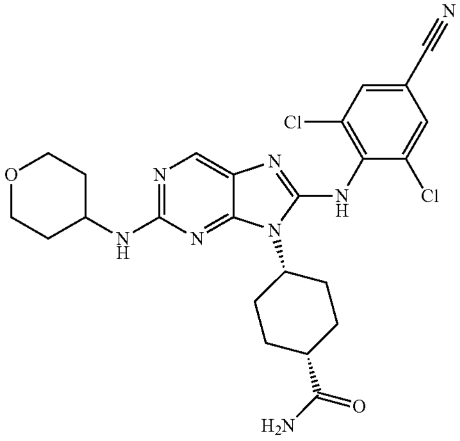 [SMILES: N#Cc1cc(Cl)c(Nc2nc3cnc(NC4CCOCC4)nc3n2[C@H]2CC[C@@H](C(N)=O)CC2)c(Cl)c1] | (1s,4s)-4-(8-(2,6-dichloro-4-cyanophenylamino)-2-(tetrahydro-2H-pyran-4-ylamino)-9H-purin-9-yl)cyclohexanecarboxamide | 529.1 | D |
| 279 | 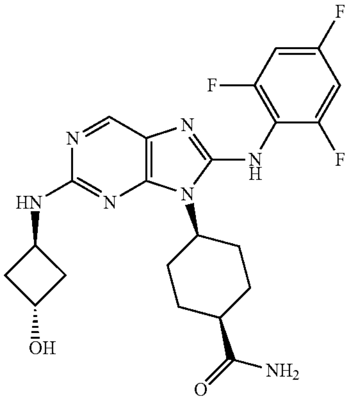 [SMILES: NC(=O)[C@H]1CC[C@@H](n2c(Nc3c(F)cc(F)cc3F)nc3cnc(N[C@H]4C[C@H](O)C4)nc32)CC1] | (1s,4s)-4-(2-((1r,3r)-3-hydroxycyclobutylamino)-8-(2,4,6-trifluorophenylamino)-9H-purin-9-yl)cyclohexanecarboxamide | 476.1 | A |

TABLE 1-continued

| Cmpd No. | Structure | Name | MH+ | Ac-tivi-ty |
|---|---|---|---|---|
| 280 | 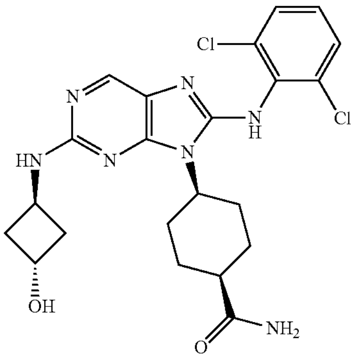 [SMILES: NC(=O)[C@H]1CC[C@@H](n2c(Nc3c(Cl)cccc3Cl)nc3cnc(N[C@H]4C[C@H](O)C4)nc32)CC1] | (1s,4s)-4-(8-(2,6-dichlorophenylamino)-2-((1r,3r)-3-hydroxycyclobutylamino)-9H-purin-9-yl)cyclohexanecarboxamide | 490 | A |
| 281 | 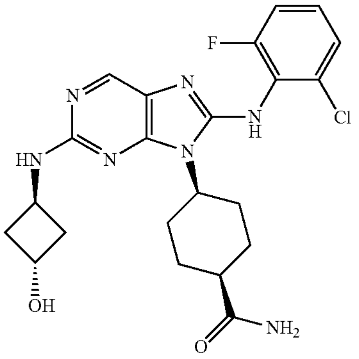 [SMILES: NC(=O)[C@H]1CC[C@@H](n2c(Nc3c(F)cccc3Cl)nc3cnc(N[C@H]4C[C@H](O)C4)nc32)CC1] | (1s,4s)-4-(8-(2-chloro-6-fluorophenylamino)-2-((1r,3r)-3-hydroxycyclobutylamino)-9H-purin-9-yl)cyclohexanecarboxamide | 474.1 | A |
| 282 | 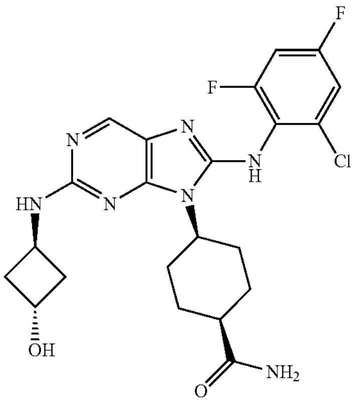 [SMILES: NC(=O)[C@H]1CC[C@@H](n2c(Nc3c(F)cc(F)cc3Cl)nc3cnc(N[C@H]4C[C@H](O)C4)nc32)CC1] | (1s,4s)-4-(8-(2-chloro-4,6-difluorophenylamino)-2-((1r,3r)-3-hydroxycyclobutylamino)-9H-purin-9-yl)cyclohexanecarboxamide | 492.1 | A |
| 283 | 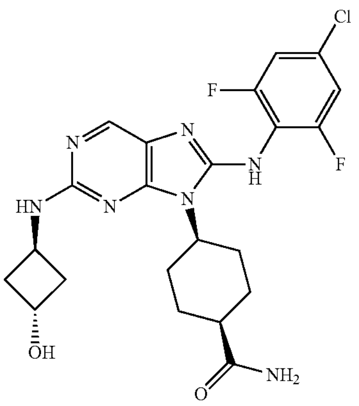 [SMILES: NC(=O)[C@H]1CC[C@@H](n2c(Nc3c(F)cc(Cl)cc3F)nc3cnc(N[C@H]4C[C@H](O)C4)nc32)CC1] | (1s,4s)-4-(8-(4-chloro-2,6-difluorophenylamino)-2-((1r,3r)-3-hydroxycyclobutylamino)-9H-purin-9-yl)cyclohexanecarboxamide | 492.1 | A |

TABLE 1-continued
| Cmpd No. | Structure | Name | MH+ | Activity |
|---|---|---|---|---|
| 284 | 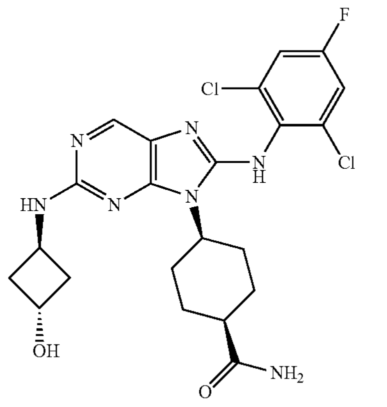 [SMILES: NC(=O)[C@H]1CC[C@@H](n2c(Nc3c(Cl)cc(F)cc3Cl)nc3cnc(N[C@H]4C[C@H](O)C4)nc32)CC1] | (1s,4s)-4-(8-(2,6-dichloro-4-fluorophenylamino)-2-((1r,3r)-3-hydroxycyclobutylamino)-9H-purin-9-yl)cyclohexanecarboxamide | 508.1 | A |
| 285 | 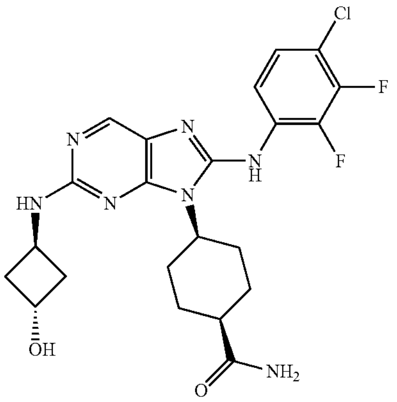 [SMILES: NC(=O)[C@H]1CC[C@@H](n2c(Nc3ccc(Cl)c(F)c3F)nc3cnc(N[C@H]4C[C@H](O)C4)nc32)CC1] | (1s,4s)-4-(8-(4-chloro-2,3-difluorophenylamino)-2-((1r,3r)-3-hydroxycyclobutylamino)-9H-purin-9-yl)cyclohexanecarboxamide | 492.1 | A |
| 286 | 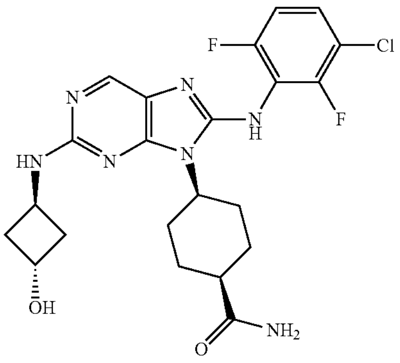 [SMILES: NC(=O)[C@H]1CC[C@@H](n2c(Nc3c(F)ccc(Cl)c3F)nc3cnc(N[C@H]4C[C@H](O)C4)nc32)CC1] | (1s,4s)-4-(8-(3-chloro-2,6-difluorophenylamino)-2-((1r,3r)-3-hydroxycyclobutylamino)-9H-purin-9-yl)cyclohexanecarboxamide | 492.1 | A |

TABLE 1-continued
| Cmpd No. | Structure | Name | MH+ | Activity |
|---|---|---|---|---|
| 287 | 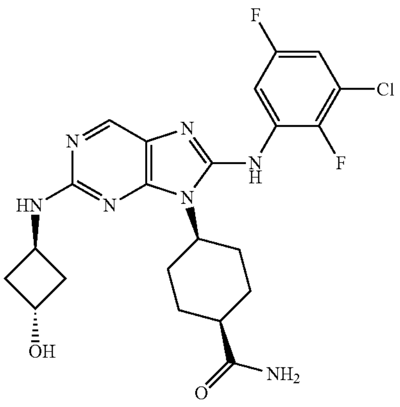 [SMILES: NC(=O)[C@H]1CC[C@@H](n2c(Nc3cc(F)cc(Cl)c3F)nc3cnc(N[C@H]4C[C@H](O)C4)nc32)CC1] | (1s,4s)-4-(8-(3-chloro-2,5-difluorophenylamino)-2-((1r,3r)-3-hydroxycyclobutylamino)-9H-purin-9-yl)cyclohexanecarboxamide | 492.1 | A |
| 288 | 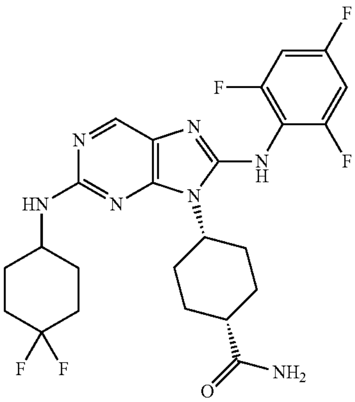 [SMILES: NC(=O)[C@H]1CC[C@@H](n2c(Nc3c(F)cc(F)cc3F)nc3cnc(NC4CCC(F)(F)CC4)nc32)CC1] | (1s,4s)-4-(2-(4,4-difluorocyclohexylamino)-8-(2,4,6-trifluorophenylamino)-9H-purin-9-yl)cyclohexanecarboxamide | 524.1 | C |
| 289 | 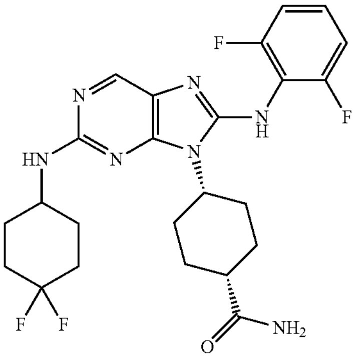 [SMILES: NC(=O)[C@H]1CC[C@@H](n2c(Nc3c(F)cccc3F)nc3cnc(NC4CCC(F)(F)CC4)nc32)CC1] | (1s,4s)-4-(2-(4,4-difluorocyclohexylamino)-8-(2,6-difluorophenylamino)-9H-purin-9-yl)cyclohexanecarboxamide | 506.1 | A |

TABLE 1-continued
| Cmpd No. | Structure | Name | MH+ | Activity |
|---|---|---|---|---|
| 290 | 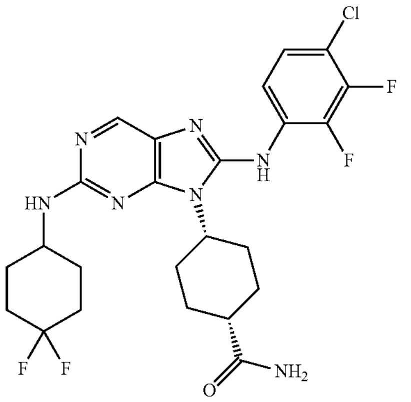 [SMILES: NC(=O)[C@H]1CC[C@@H](n2c(Nc3ccc(Cl)c(F)c3F)nc3cnc(NC4CCC(F)(F)CC4)nc32)CC1] | (1s,4s)-4-(8-(4-chloro-2,3-difluorophenylamino)-2-(4,4-difluorocyclohexylamino)-9H-purin-9-yl)cyclohexanecarboxamide | 540.2 | B |
| 291 | 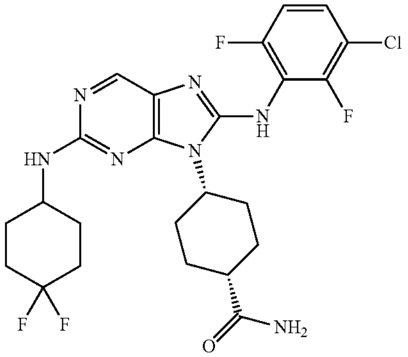 [SMILES: NC(=O)[C@H]1CC[C@@H](n2c(Nc3c(F)ccc(Cl)c3F)nc3cnc(NC4CCC(F)(F)CC4)nc32)CC1] | (1s,4s)-4-(8-(3-chloro-2,6-difluorophenylamino)-2-(4,4-difluorocyclohexylamino)-9H-purin-9-yl)cyclohexanecarboxamide | 540.2 | B |
| 292 | 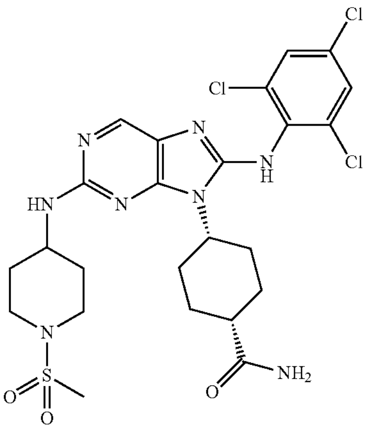 [SMILES: CS(=O)(=O)N1CCC(Nc2ncc3nc(Nc4c(Cl)cc(Cl)cc4Cl)n([C@H]4CC[C@@H](C(N)=O)CC4)c3n2)CC1] | (1s,4s)-4-(2-(1-(methylsulfonyl)piperidin-4-ylamino)-8-(2,4,6-trichlorophenylamino)-9H-purin-9-yl)cyclohexanecarobxamide | 617.1 | B |

TABLE 1-continued

| Cmpd No. | Structure | Name | MH+ | Ac-tivi-ty |
|---|---|---|---|---|
| 293 | 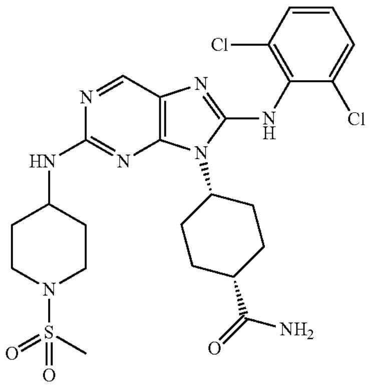 [SMILES: CS(=O)(=O)N1CCC(Nc2ncc3nc(Nc4c(Cl)cccc4Cl)n([C@H]4CC[C@@H](C(N)=O)CC4)c3n2)CC1] | (1s,4s)-4-(8-(2,6-dichlorophenylamino)-2-(1-(methylsulfonyl)piperidin-4-ylamino)-9H-purin-9-yl)cyclohexanecarboxamide | 581.1 | A |
| 294 | 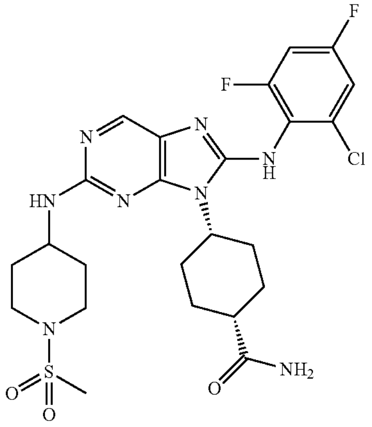 [SMILES: CS(=O)(=O)N1CCC(Nc2ncc3nc(Nc4c(F)cc(F)cc4Cl)n([C@H]4CC[C@@H](C(N)=O)CC4)c3n2)CC1] | (1s,4s)-4-(8-(2-chloro-4,6-difluorophenylamino)-2-(1-(methylsulfonyl)piperidin-4-ylamino)-9H-purin-9-yl)cyclohexanecarboxmaide | 583.2 | A |
| 295 | 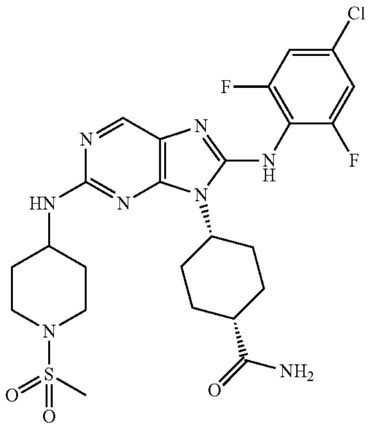 [SMILES: CS(=O)(=O)N1CCC(Nc2ncc3nc(Nc4c(F)cc(Cl)cc4F)n([C@H]4CC[C@@H](C(N)=O)CC4)c3n2)CC1] | (1s,4s)-4-(8-(4-chloro-2,6-difluorophenylamino)-2-(1-(methylsulfonyl)piperidin-4-ylamino)-9H-purin-9-yl)cyclohexanecarboxamide | 583.2 | A |

TABLE 1-continued

| Cmpd No. | Structure | Name | MH+ | Activity |
|---|---|---|---|---|
| 296 | 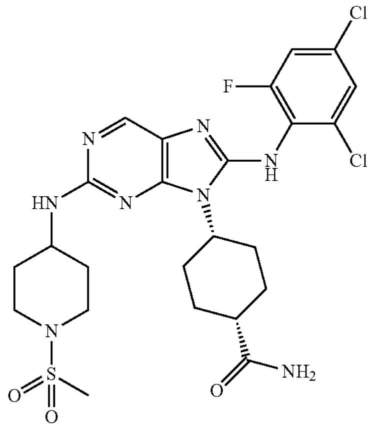 [SMILES: CS(=O)(=O)N1CCC(Nc2ncc3nc(Nc4c(F)cc(Cl)cc4Cl)n([C@H]4CC[C@@H](C(N)=O)CC4)c3n2)CC1] | (1s,4s)-4-(8-(2,4-dichloro-6-fluorophenylamino)-2-(1-(methylsulfonyl)piperidin-4-ylamino)-9H-purin-9-yl)cyclohexanecarboxamide | 599.1 | B |
| 297 | 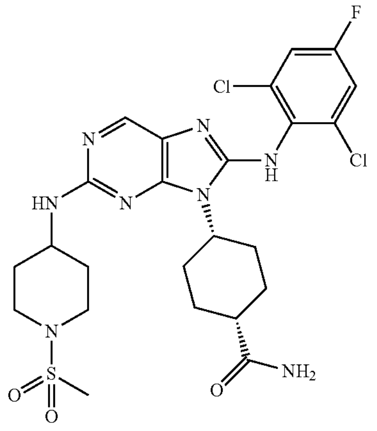 [SMILES: CS(=O)(=O)N1CCC(Nc2ncc3nc(Nc4c(Cl)cc(F)cc4Cl)n([C@H]4CC[C@@H](C(N)=O)CC4)c3n2)CC1] | (1s,4s)-4-(8-(2,6-dichloro-4-fluorophenylamino)-2-(1-(methylsulfonyl)piperidin-4-ylamino)-9H-purin-9-yl)cyclohexanecarboxamide | 599.1 | A |
| 298 | 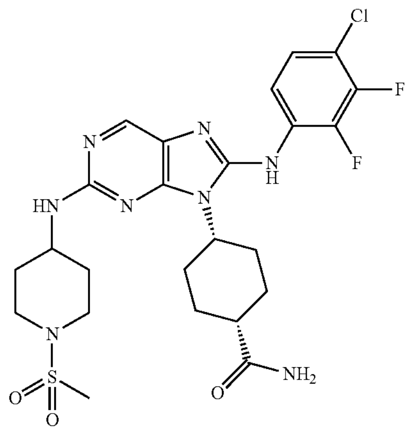 [SMILES: CS(=O)(=O)N1CCC(Nc2ncc3nc(Nc4ccc(Cl)c(F)c4F)n([C@H]4CC[C@@H](C(N)=O)CC4)c3n2)CC1] | (1s,4s)-4-(8-(4-chloro-2,3-difluorophenylamino)-2-(1-(methylsulfonyl)piperidin-4-ylamino)-9H-purin-9-yl)cyclohexanecarboxamide | 583.2 | A |

TABLE 1-continued
| Cmpd No. | Structure | Name | MH+ | Activity |
| --- | --- | --- | --- | --- |
| 299 | 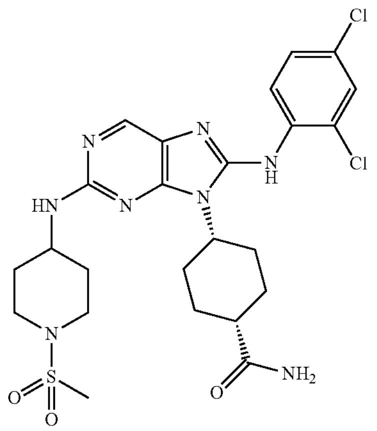 [SMILES: CS(=O)(=O)N1CCC(Nc2ncc3nc(Nc4ccc(Cl)cc4Cl)n([C@H]4CC[C@@H](C(N)=O)CC4)c3n2)CC1] | (1s,4s)-4-(8-(2,4-dichlorophenylamino)-2-(1-(methylsulfonyl)piperidin-4-ylamino)-9H-purin-9-yl)cyclohexanecarboxamide | 581.1 | A |
| 300 | 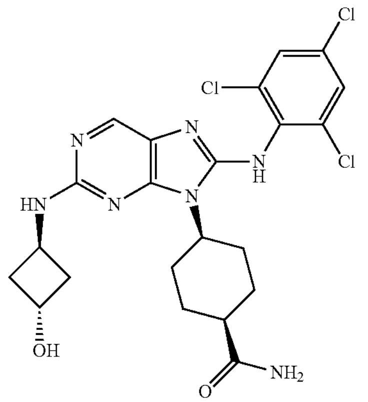 [SMILES: NC(=O)[C@H]1CC[C@@H](n2c(Nc3c(Cl)cc(Cl)cc3Cl)nc3cnc(N[C@H]4C[C@H](O)C4)nc32)CC1] | (1s,4s)-4-(2-((1r,3r)-3-hydroxycyclobutylamino)-8-(2,4,6-trichlorophenylamino)-9H-purin-9-yl)cyclohexanecarboxamide | 524.2 | B |
| 301 | 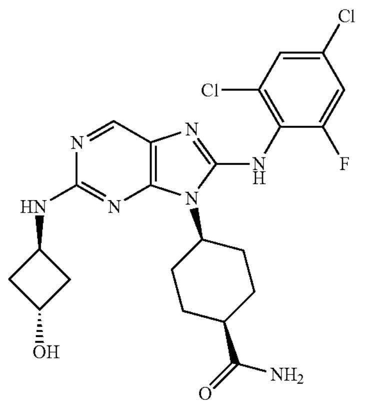 [SMILES: NC(=O)[C@H]1CC[C@@H](n2c(Nc3c(F)cc(Cl)cc3Cl)nc3cnc(N[C@H]4C[C@H](O)C4)nc32)CC1] | (1s,4s)-4-(8-(2,4-dichloro-6-fluorophenylamino)-2-((1r,3r)-3-hydroxycyclobutylamino)-9H-purin-9-yl)cyclohexanecarboxamide | 508.1 | B |

TABLE 1-continued
| Cmpd No. | Structure | Name | MH+ | Ac-tivi-ty |
|---|---|---|---|---|
| 302 | 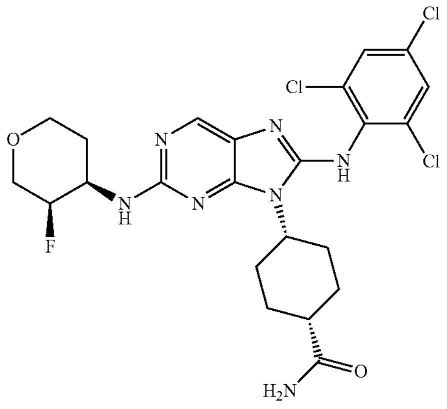 [SMILES: NC(=O)[C@H]1CC[C@@H](n2c(Nc3c(Cl)cc(Cl)cc3Cl)nc3cnc(N[C@@H]4CCOC[C@@H]4F)nc32)CC1] | (1S,4s)-4-(2-((3R,4R)-3-fluorotetrahydro-2H-pyran-4-ylamino)-8-(2,4,6-trichlorophenylamino)-9H-purin-9-yl-cyclohexanecarboxamide | 556.1 | B |
| 303 | 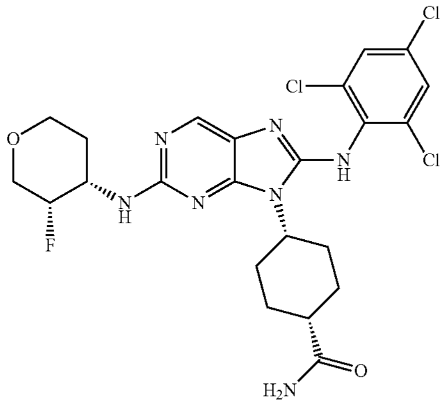 | (1R,4s)-4-(2-((3S,4S)-3-fluorotetrahydro-2H-pyran-4-ylamino)-8-(2,4,6-trichlorophenylamino)-9H-purin-9-yl)cyclohexanecarboxamide | 556.2 | D |
| 304 | 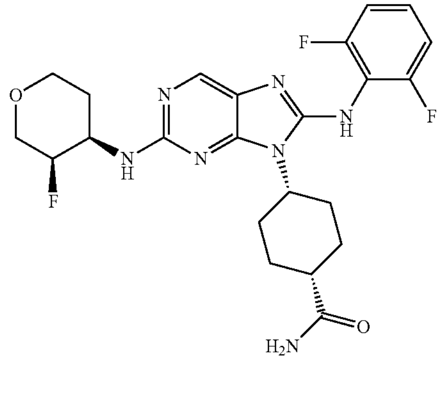 [SMILES: NC(=O)[C@H]1CC[C@@H](n2c(Nc3c(F)cccc3F)nc3cnc(N[C@@H]4CCOC[C@@H]4F)nc32)CC1] | (1S,4s)-4-(8-(2,6-difluorophenylamino)-2-((3R,4R)-3-fluorotetrahydro-2H-pyran-4-ylamino)-9H-purin-9-yl)cyclohexanecarboxamide | 490.2 | A |

TABLE 1-continued
| Cmpd No. | Structure | Name | MH+ | Activity |
|---|---|---|---|---|
| 305 | 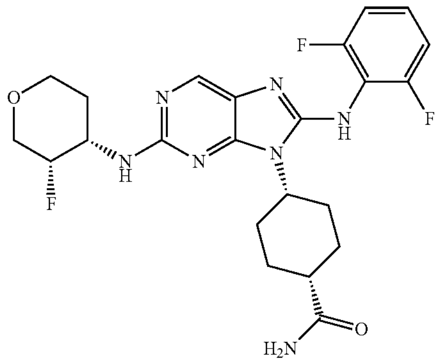 [SMILES: NC(=O)[C@H]1CC[C@@H](n2c(Nc3c(F)cccc3F)nc3cnc(N[C@H]4CCOC[C@H]4F)nc32)CC1] | (1R,4s)-4-(8-(2,6-difluorophenylamino)-2-((3S,4S)-3-fluorotetrahydro-2H-pyran-4-ylamino)-9H-purin-9-yl)cyclohexanecarboxamide | 490.2 | B |
| 306 | 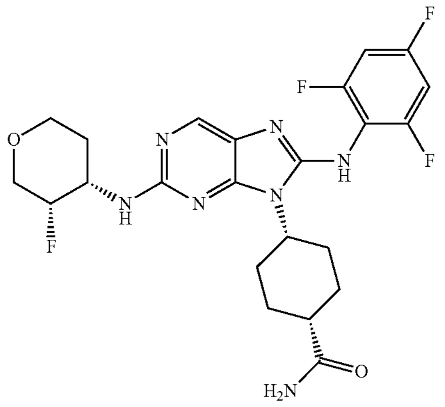 [SMILES: NC(=O)[C@H]1CC[C@@H](n2c(Nc3c(F)cc(F)cc3F)nc3cnc(N[C@H]4CCOC[C@H]4F)nc32)CC1] | (1R,4s)-4-(2-((3S,4S)-3-fluorotetrahydro-2H-pyran-4-ylamino)-8-(2,4,6-trifluorophenylamino)-9H-purin-9-yl)cyclohexanecarboxamide | 508.2 | C |
| 307 | 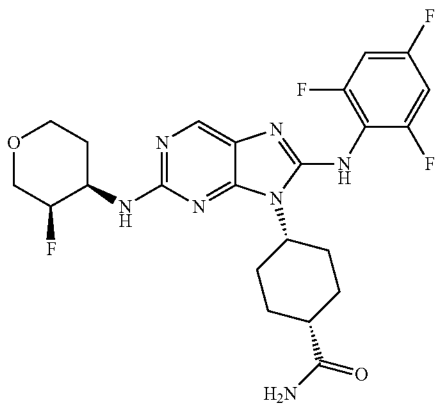 [SMILES: NC(=O)[C@H]1CC[C@@H](n2c(Nc3c(F)cc(F)cc3F)nc3cnc(N[C@@H]4CCOC[C@@H]4F)nc32)CC1] | (1S,4s)-4-(2-((3R,4R)-3-fluorotetrahydro-2H-pyran-4-ylamino)-8-(2,4,6-trifluorophenylamino)-9H-purin-9-yl)cyclohexanecarboxamide | 508.2 | A |

TABLE 1-continued
| Cmpd No. | Structure | Name | MH+ | Activity |
|---|---|---|---|---|
| 308 | 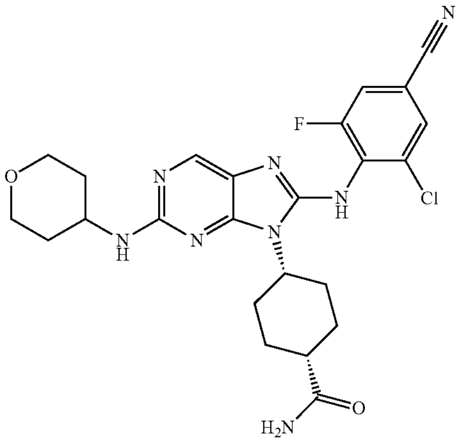 [SMILES: N#Cc1cc(F)c(Nc2nc3cnc(NC4CCOCC4)nc3n2[C@H]2CC[C@@H](C(N)=O)CC2)c(Cl)c1] | (1s,4s)-4-(8-(2-chloro-4-cyano-6-fluorophenylamino)-2-(tetrahydro-2H-pyran-4-ylamino)-9H-purin-9-yl)cyclohexanecarboxamide | 513.2 | D |
| 309 | 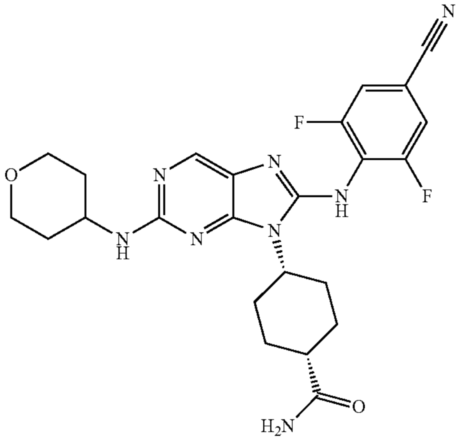 [SMILES: N#Cc1cc(F)c(Nc2nc3cnc(NC4CCOCC4)nc3n2[C@H]2CC[C@@H](C(N)=O)CC2)c(F)c1] | (1s,4s)-4-(8-(4-cyano-2,6-difluorophenylamino)-2-(tetrahydro-2H-pyran-4-ylamino)-9H-purin-9-yl)cyclohexanecarboxamide | 497.2 | D |
| 310 | 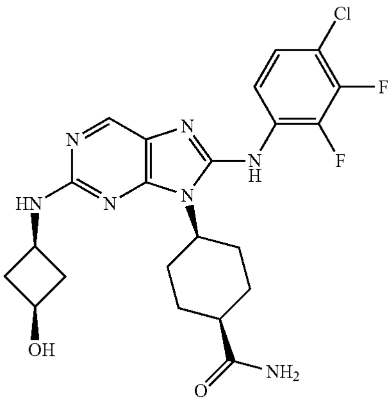 [SMILES: NC(=O)[C@H]1CC[C@@H](n2c(Nc3ccc(Cl)c(F)c3F)nc3cnc(N[C@H]4C[C@@H](O)C4)nc32)CC1] | (1s,4s)-4-(8-(4-chloro-2,3-difluorophenylamino)-2-((1s,3s)-3-hydroxycyclobutylamino)-9H-purin-9-yl)cyclohexanecarboxamide | 494.1 | A |

TABLE 1-continued

| Cmpd No. | Structure | Name | MH+ | Activity |
|---|---|---|---|---|
| 311 | 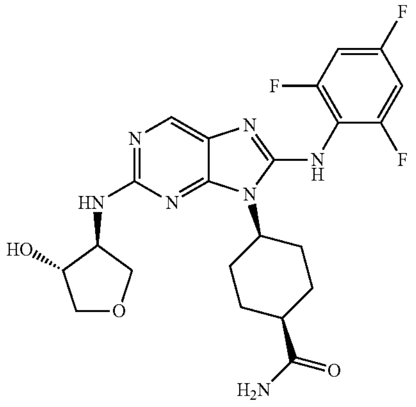 [SMILES: NC(=O)[C@H]1CC[C@@H](n2c(Nc3c(F)cc(F)cc3F)nc3cnc(N[C@H]4COC[C@@H]4O)nc32)CC1] | (1R,4s)-4-(2-((3S,4R)-4-hydroxytetrahydrofuran-3-ylamino)-8-(2,4,6-trifluorophenylamino)-9H-purin-9-yl)cyclohexanecarboxamide | 492.3 | A |
| 312 | 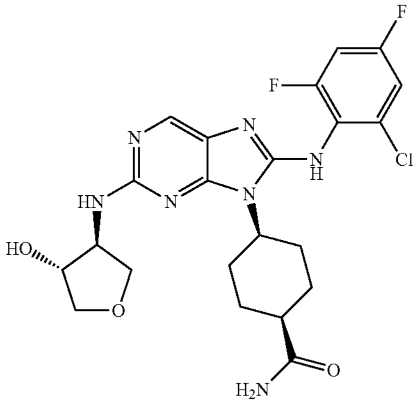 [SMILES: NC(=O)[C@H]1CC[C@@H](n2c(Nc3c(F)cc(F)cc3Cl)nc3cnc(N[C@H]4COC[C@@H]4O)nc32)CC1] | (1R,4s)-4-(8-(2-chloro-4,6-difluorophenylamino)-2-((3S,4R)-4-hydroxytetrahydrofuran-3-ylamino)-9H-purin-9-yl)cyclohexanecarboxamide | 508.2 | A |
| 313 | 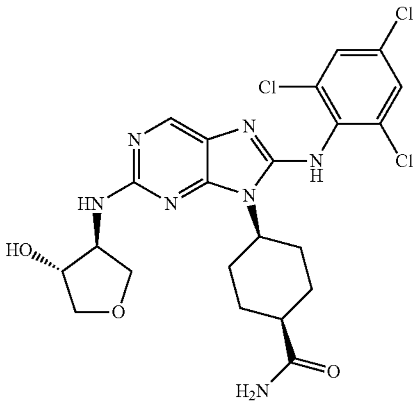 [SMILES: NC(=O)[C@H]1CC[C@@H](n2c(Nc3c(Cl)cc(Cl)cc3Cl)nc3cnc(N[C@H]4COC[C@@H]4O)nc32)CC1] | (1R,4s)-4-(2-((3S,4R)-4-hydroxytetrahydrofuran-3-ylamino)-8-(2,4,6-trichlorophenylamino)-9H-purin-9-yl)cyclohexanecarboxamide | 540 | B |

TABLE 1-continued

| Cmpd No. | Structure | Name | MH+ | Activity |
|---|---|---|---|---|
| 314 | 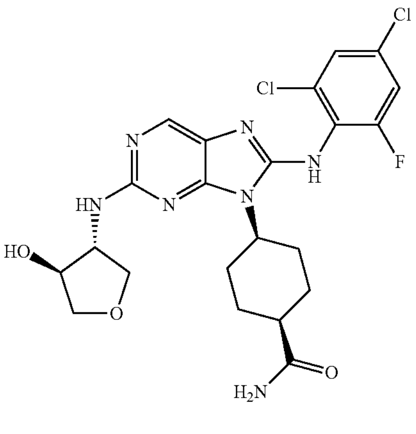 [SMILES: NC(=O)[C@H]1CC[C@@H](n2c(Nc3c(F)cc(Cl)cc3Cl)nc3cnc(N[C@@H]4COC[C@H]4O)nc32)CC1] | (1S,4s)-4-(8-(2,4-dichloro-6-fluorophenylamino)-2-((3R,4S)-4-hydroxytetrahydrofuran-3-ylamino)-9H-purin-9-yl)cyclohexanecarboxamide | 524.1 | A |
| 315 | 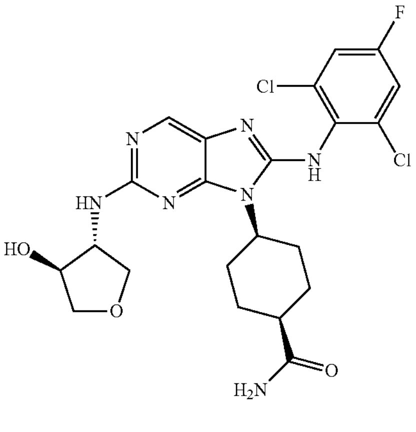 [SMILES: NC(=O)[C@H]1CC[C@@H](n2c(Nc3c(Cl)cc(F)cc3Cl)nc3cnc(N[C@@H]4COC[C@H]4O)nc32)CC1] | (1S,4s)-4-(8-(2,6-dichloro-4-fluorophenylamino)-2-((3R,4S)-4-hydroxytetrahydrofuran-3-ylamino)-9H-purin-9-yl)cyclohexanecarboxamide | 524.1 | A |
| 316 | 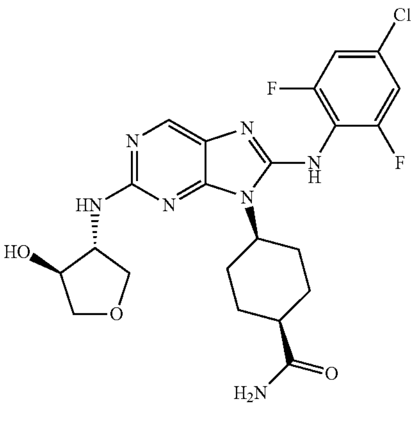 [SMILES: NC(=O)[C@H]1CC[C@@H](n2c(Nc3c(F)cc(Cl)cc3F)nc3cnc(N[C@@H]4COC[C@H]4O)nc32)CC1] | (1S,4s)-4-(8-(4-chloro-2,6-difluorophenylamino)-2-((3R,4S)-4-hydroxytetrahydrofuran-3-ylamino)-9H-purin-9-yl)cyclohexanecarboxamide | 508.1 | A |

TABLE 1-continued

| Cmpd No. | Structure | Name | MH+ | Activity |
|---|---|---|---|---|
| 317 | 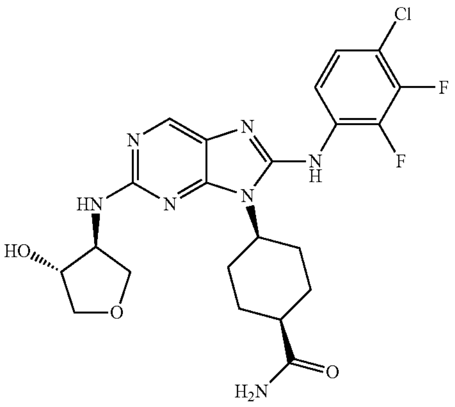 [SMILES: NC(=O)[C@H]1CC[C@@H](n2c(Nc3ccc(Cl)c(F)c3F)nc3cnc(N[C@H]4COC[C@@H]4O)nc32)CC1] | (1R,4s)-4-(8-(4-chloro-2,3-difluorophenylamino)-2-((3S,4R)-4-hydroxytetrahydrofuran-3-ylamino)-9H-purin-9-yl)cyclohexanecarboxamide | 508 | B |
| 318 | 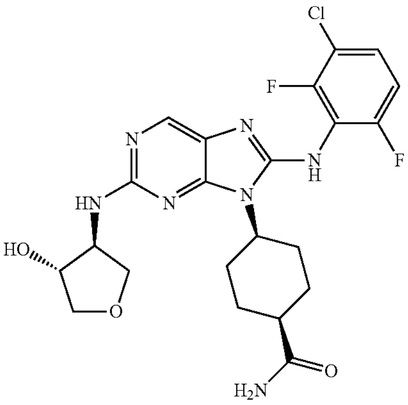 [SMILES: NC(=O)[C@H]1CC[C@@H](n2c(Nc3c(F)ccc(Cl)c3F)nc3cnc(N[C@H]4COC[C@@H]4O)nc32)CC1] | (1R,4s)-4-(8-(3-chloro-2,6-difluorophenylamino)-2-((3S,4R)-4-hydroxytetrahydrofuran-3-ylamino)-9H-purin-9-yl)cyclohexanecarboxamide | 508 | A |
| 319 | 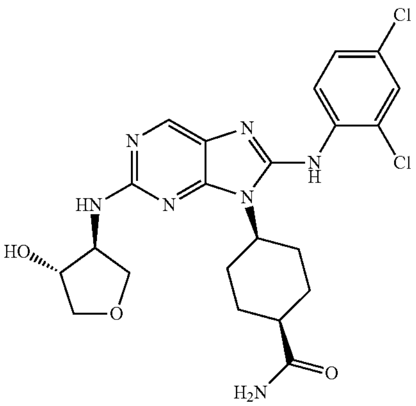 [SMILES: NC(=O)[C@H]1CC[C@@H](n2c(Nc3ccc(Cl)cc3Cl)nc3cnc(N[C@H]4COC[C@@H]4O)nc32)CC1] | (1R,4s)-4-(8-(2,4-dichlorophenylamino)-2-((3S,4R)-4-hydroxytetrahydrofuran-3-ylamino)-9H-purin-9-yl)cyclohexanecarboxamide | 506.1 | A |

TABLE 1-continued

| Cmpd No. | Structure | Name | MH+ | Activity |
|---|---|---|---|---|
| 320 | 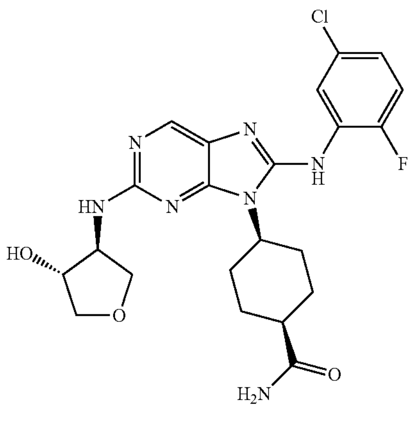 [SMILES: NC(=O)[C@H]1CC[C@@H](n2c(Nc3cc(Cl)ccc3F)nc3cnc(N[C@H]4COC[C@@H]4O)nc32)CC1] | (1R,4s)-4-(8-(5-chloro-2-fluorophenylamino)-2-((3S,4R)-4-hydroxytetrahydrofuran-3-ylamino)-9H-purin-9-yl)cyclohexanecarboxamide | 490 | A |
| 321 | 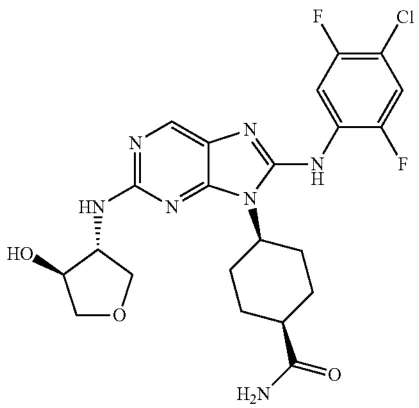 [SMILES: NC(=O)[C@H]1CC[C@@H](n2c(Nc3cc(F)c(Cl)cc3F)nc3cnc(N[C@@H]4COC[C@H]4O)nc32)CC1] | (1S,4s)-4-(8-(4-chloro-2,5-difluorophenylamino)-2-((3R,4S)-4-hydroxytetrahydrofuran-3-ylamino)-9H-purin-9-yl)cyclohexanecarboxamide | 508 | A |
| 322 | 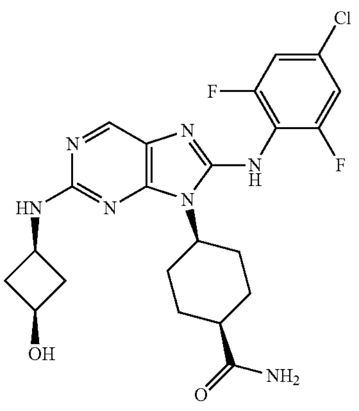 [SMILES: NC(=O)[C@H]1CC[C@@H](n2c(Nc3c(F)cc(Cl)cc3F)nc3cnc(N[C@H]4C[C@@H](O)C4)nc32)CC1] | (1s,4s)-4-(8-(4-chloro-2,6-difluorophenylamino)-2-((1s,3s)-3-hydroxycyclobutylamino)-9H-purin-9-yl)cyclohexanecarboxamide | 492.2 | A |

TABLE 1-continued
| Cmpd No. | Structure | Name | MH+ | Activity |
|---|---|---|---|---|
| 323 | 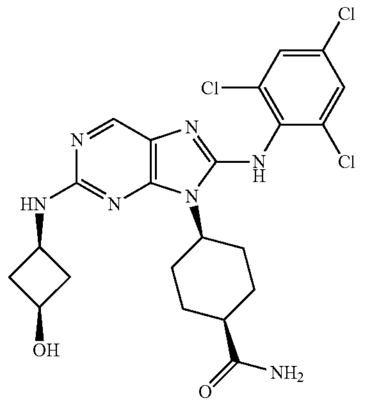 [SMILES: NC(=O)[C@H]1CC[C@@H](n2c(Nc3c(Cl)cc(Cl)cc3Cl)nc3cnc(N[C@H]4C[C@@H](O)C4)nc32)CC1] | (1s,4s)-4-(2-((1s,3s)-3-hydroxycyclobutylamino)-8-(2,4,6-trichlorophenylamino)-9H-purin-9-yl)cyclohexanecarboxamide | 524.2 | A |
| 324 | 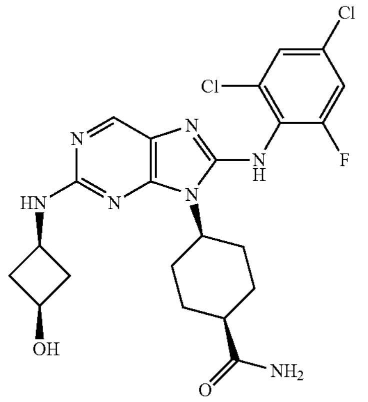 [SMILES: NC(=O)[C@H]1CC[C@@H](n2c(Nc3c(F)cc(Cl)cc3Cl)nc3cnc(N[C@H]4C[C@@H](O)C4)nc32)CC1] | (1s,4s)-4-(8-(2,4-dichloro-6-fluorophenylamino)-2-((1s,3s)-3-hydroxycyclobutylamino)-9H-purin-9-yl)cyclohexanecarboxamide | 508 | A |
| 325 | 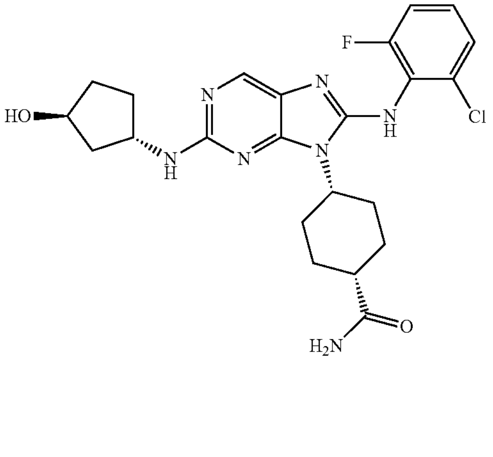 [SMILES: NC(=O)[C@H]1CC[C@@H](n2c(Nc3c(F)cccc3Cl)nc3cnc(N[C@H]4CC[C@H](O)C4)nc32)CC1] | (1R,4s)-4-(8-(2-chloro-6-fluorophenylamino)-2-((1S,3S)-3-hydroxycyclopentylamino)-9H-purin-9-yl)cyclohexanecarboxamide | 488.2 | A |

TABLE 1-continued
| Cmpd No. | Structure | Name | MH+ | Activity |
| --- | --- | --- | --- | --- |
| 326 | 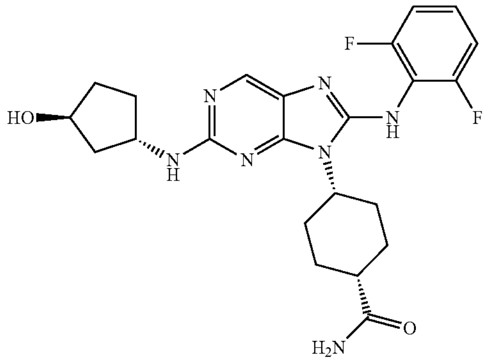 [SMILES: NC(=O)[C@H]1CC[C@@H](n2c(Nc3c(F)cccc3F)nc3cnc(N[C@H]4CC[C@H](O)C4)nc32)CC1] | (1R,4s)-4-(8-(2,6-difluorophenylamino)-2-((1S,3S)-3-hydroxycyclopentylamino)-9H-purin-9-yl)cyclohexanecarboxamide | 472.2 | A |
| 327 | 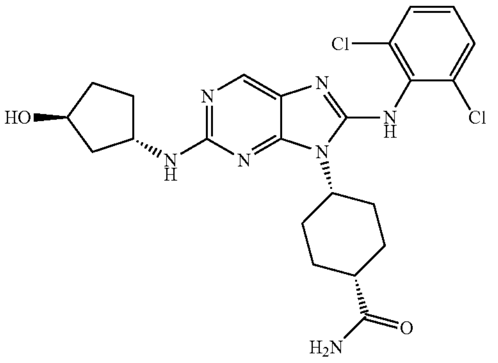 [SMILES: NC(=O)[C@H]1CC[C@@H](n2c(Nc3c(Cl)cccc3Cl)nc3cnc(N[C@H]4CC[C@H](O)C4)nc32)CC1] | (1R,4s)-4-(8-(2,6-dichlorophenylamino)-2-((1S,3S)-3-hydroxycyclopentylamino)-9H-purin-9-yl)cyclohexanecarboxamide | 504.1 | B |
| 328 | 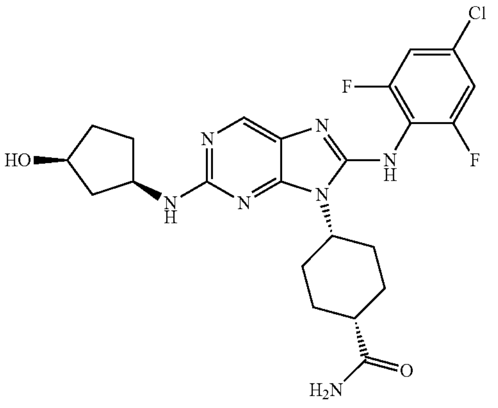 [SMILES: NC(=O)[C@H]1CC[C@@H](n2c(Nc3c(F)cc(Cl)cc3F)nc3cnc(N[C@@H]4CC[C@H](O)C4)nc32)CC1] | (1S,4s)-4-(8-(4-chloro-2,6-difluorophenylamino)-2-((1R,3S)-3-hydroxycyclopentylamino)-9H-purin-9-yl)cyclohexanecarboxamide | 506.2 | A |

TABLE 1-continued
| Cmpd No. | Structure | Name | MH+ | Activity |
| --- | --- | --- | --- | --- |
| 329 | 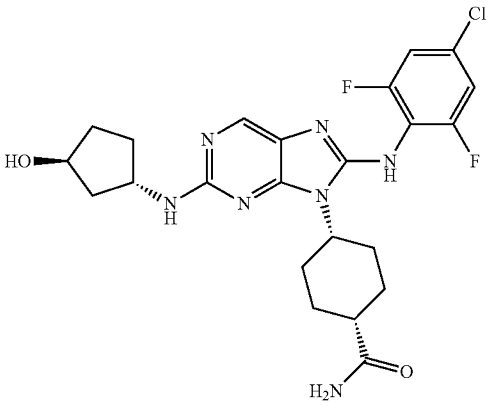 [SMILES: NC(=O)[C@H]1CC[C@@H](n2c(Nc3c(F)cc(Cl)cc3F)nc3cnc(N[C@H]4CC[C@H](O)C4)nc32)CC1] | (1R,4s)-4-(8-(4-chloro-2,6-difluorophenylamino)-2-((1S,3S)-3-hydroxycyclopentyalmino)-9H-purin-9-yl)cyclohexanecarboxamide | 506.2 | B |
| 330 | 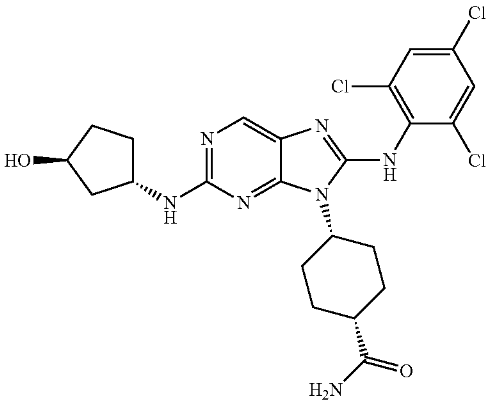 [SMILES: NC(=O)[C@H]1CC[C@@H](n2c(Nc3c(Cl)cc(Cl)cc3Cl)nc3cnc(N[C@H]4CC[C@H](O)C4)nc32)CC1] | (1R,4s)-4-(2-((1S,3S)-3-hydroxycyclopentylamino)-8-(2,4,6-trichlorophenylamino)-9H-purin-9-yl)cyclohexanecarboxamide | 538.1 | B |
| 331 | 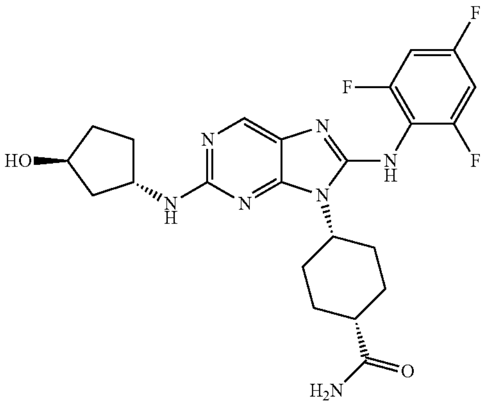 [SMILES: NC(=O)[C@H]1CC[C@@H](n2c(Nc3c(F)cc(F)cc3F)nc3cnc(N[C@H]4CC[C@H](O)C4)nc32)CC1] | (1R,4S)-4-(2-((1S,3S)-3-hydroxycyclopentylamino)-8-(2,4,6-trifluorophenylamino)-9H-purin-9-yl)cyclohexanecarboxamide | 490.2 | A |

TABLE 1-continued
| Cmpd No. | Structure | Name | MH+ | Activity |
|---|---|---|---|---|
| 332 | 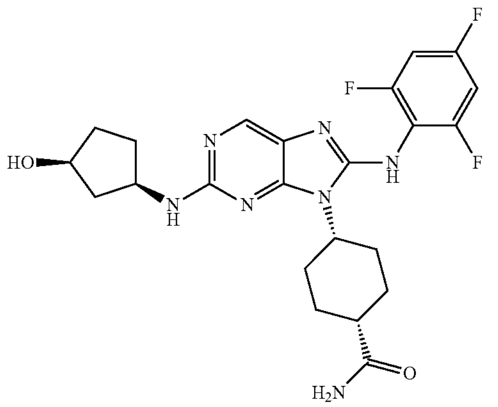 [SMILES: NC(=O)[C@H]1CC[C@@H](n2c(Nc3c(F)cc(F)cc3F)nc3cnc(N[C@@H]4CC[C@H](O)C4)nc32)CC1] | (1S,4s)-4-(2-((1R,3S)-3-hydroxycyclopentylamino)-8-(2,4,6-trifluorophenylamino)-9H-purin-9-yl)cyclohexanecarboxamide | 490.2 | A |
| 333 | 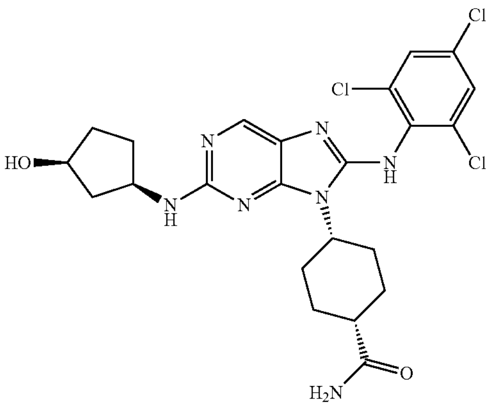 [SMILES: NC(=O)[C@H]1CC[C@@H](n2c(Nc3c(Cl)cc(Cl)cc3Cl)nc3cnc(N[C@@H]4CC[C@H](O)C4)nc32)CC1] | (1S,4s)-4-(2-((1R,3S)-3-hydroxycyclopentylamino)-8-(2,4,6-trichlorophenylamino)-9H-purin-9-yl)cyclohexanecarboxamide | 538.1 | B |
| 334 | 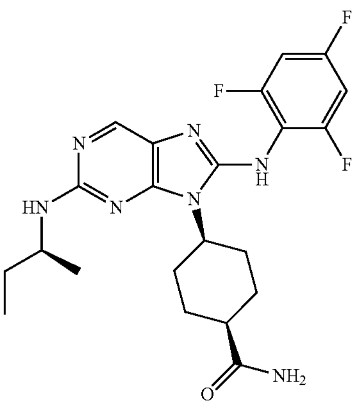 [SMILES: CC[C@H](C)Nc1ncc2nc(Nc3c(F)cc(F)cc3F)n([C@H]3CC[C@@H](C(N)=O)CC3)c2n1] | (1R,4s)-4-(2-(sec-butylamino)-8-(2,4,6-trifluorophenylamino)-9H-purin-9-yl)cyclohexanecarboxamide | 462.1 | B |

TABLE 1-continued

| Cmpd No. | Structure | Name | MH+ | Activity |
|---|---|---|---|---|
| 335 | 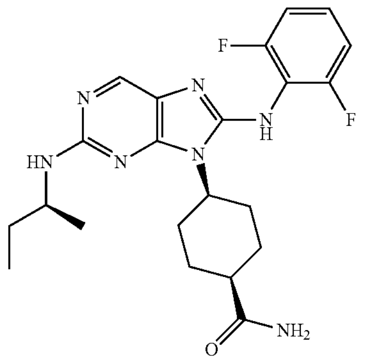 [SMILES: CC[C@H](C)Nc1ncc2nc(Nc3c(F)cccc3F)n([C@H]3CC[C@@H](C(N)=O)CC3)c2n1] | (1R,4s)-4-(2-(sec-butylamino)-8-(2,6-difluorophenylamino)-9H-purin-9-yl)cyclohexanecarboxamide | 444.2 | A |
| 336 | 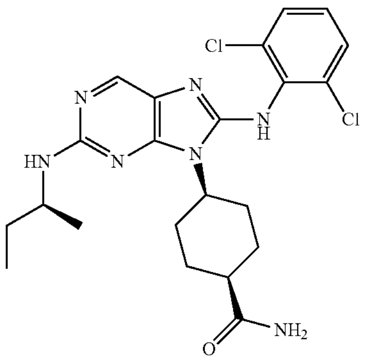 [SMILES: CC[C@H](C)Nc1ncc2nc(Nc3c(Cl)cccc3Cl)n([C@H]3CC[C@@H](C(N)=O)CC3)c2n1] | (1R,4s)-4-(2-(sec-butylamino)-8-(2,6-dichlorophenylamino)-9H-purin-9-yl)cyclohexanecarboxamide | 476.1 | A |
| 337 | 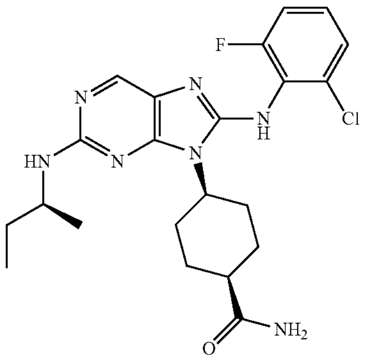 [SMILES: CC[C@H](C)Nc1ncc2nc(Nc3c(F)cccc3Cl)n([C@H]3CC[C@@H](C(N)=O)CC3)c2n1] | (1R,4s)-4-(2-(sec-butylamino)-8-(2-chloro-6-fluorophenylamino)-9H-purin-9-yl)cyclohexanecarboxamide | 460.2 | A |
| 338 | 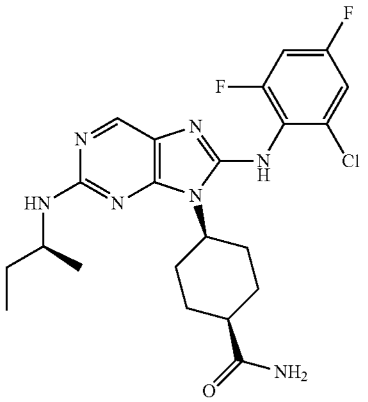 [SMILES: CC[C@H](C)Nc1ncc2nc(Nc3c(F)cc(F)cc3Cl)n([C@H]3CC[C@@H](C(N)=O)CC3)c2n1] | (1R,4s)-4-(2-(sec-butylamino)-8-(2-chloro-4,6-difluorophenylamino)-9H-purin-9-yl)cyclohexanecarboxamide | 478 | B |

TABLE 1-continued

| Cmpd No. | Structure | Name | MH+ | Activity |
|---|---|---|---|---|
| 339 | 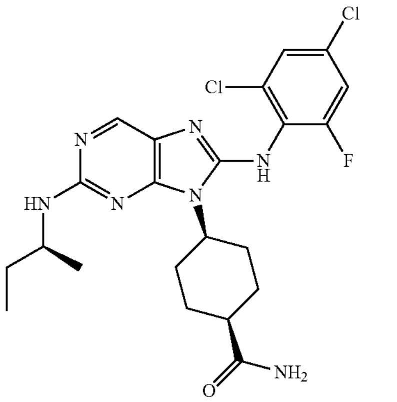 [SMILES: CC[C@H](C)Nc1ncc2nc(Nc3c(F)cc(Cl)cc3Cl)n([C@H]3CC[C@@H](C(N)=O)CC3)c2n1] | (1R,4s)-4-(2-(sec-butylamino)-8-(2,4-dichloro-6-fluorophenylamino)-9H-purin-9-yl)cyclohexanecarboxamide | 494.1 | B |
| 340 | 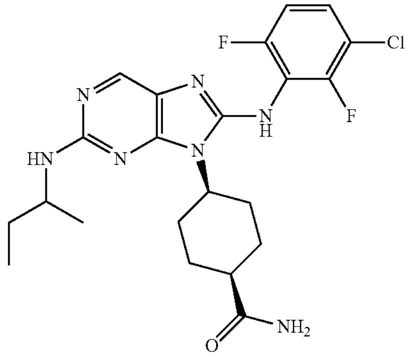 [SMILES: CCC(C)Nc1ncc2nc(Nc3c(F)ccc(Cl)c3F)n([C@H]3CC[C@@H](C(N)=O)CC3)c2n1] | (1R,4s)-4-(2-(sec-butylamino)-8-(3-chloro-2,6-difluorophenylamino)-9H-purin-9-yl)cyclohexanecarboxamide | 478 | A |
| 341 | 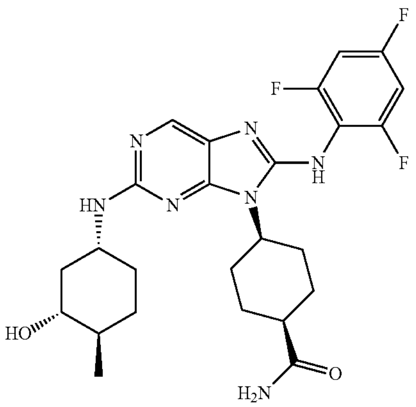 [SMILES: C[C@@H]1CC[C@@H](Nc2ncc3nc(Nc4c(F)cc(F)cc4F)n([C@H]4CC[C@@H](C(N)=O)CC4)c3n2)C[C@H]1O] | (1S,4s)-4-(2-((1R,3R,4R)-3-hydroxy-4-methylcyclohexylamino)-8-(2,4,6-trifluorophenylamino)-9H-purin-9-yl)cyclohexanecarboxamide | 518 | A |
| 342 | 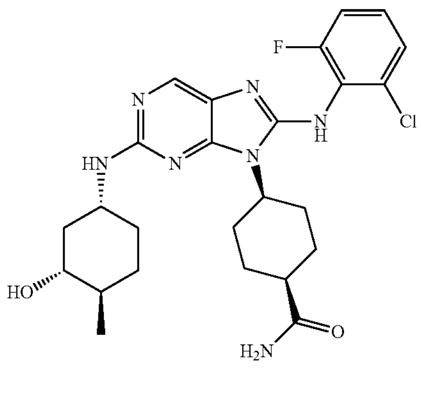 [SMILES: C[C@@H]1CC[C@@H](Nc2ncc3nc(Nc4c(F)cccc4Cl)n([C@H]4CC[C@@H](C(N)=O)CC4)c3n2)C[C@H]1O] | (1S,4s)-4-(8-(2-chloro-6-fluorophenylamino)-2-((1R,3R,4R)-3-hydroxy-4-methylcyclohexylamino)-9H-purin-9-yl)cyclohexanecarboxamide | 516.2 | A |

TABLE 1-continued
| Cmpd No. | Structure | Name | MH+ | Activity |
|---|---|---|---|---|
| 343 | 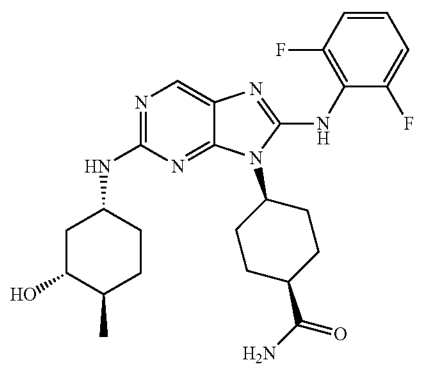 [SMILES: C[C@@H]1CC[C@@H](Nc2ncc3nc(Nc4c(F)cccc4F)n([C@H]4CC[C@@H](C(N)=O)CC4)c3n2)C[C@H]1O] | (1S,4s)-4-(8-(2,6-difluorophenylamino)-2-((1R,3R,4R)-3-hydroxy-4-methylcyclohexylamino)-9H-purin-9-yl)cyclohexanecarboxamide | 500 | A |
| 344 | 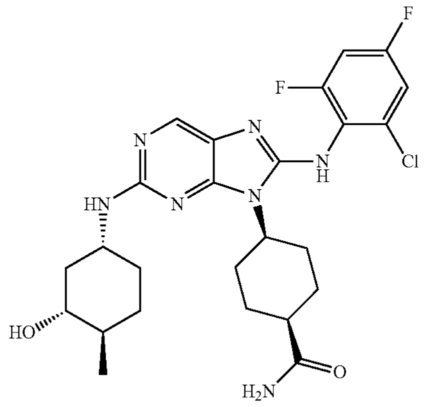 [SMILES: C[C@@H]1CC[C@@H](Nc2ncc3nc(Nc4c(F)cc(F)cc4Cl)n([C@H]4CC[C@@H](C(N)=O)CC4)c3n2)C[C@H]1O] | (1S,4s)-4-(8-(2-chloro-4,6-difluorophenylamino)-2-((1R,3R,4R)-3-hydroxy-4-methylcyclohexylamino)-9H-purin-9-yl)cyclohexanecarboxamide | 534 | A |
| 345 | 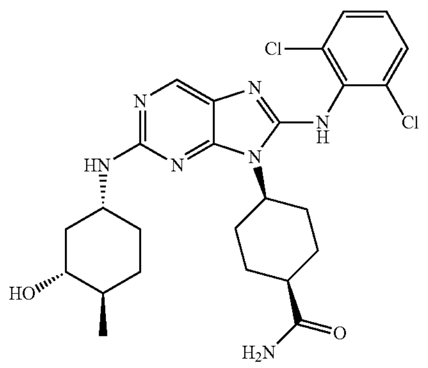 [SMILES: C[C@@H]1CC[C@@H](Nc2ncc3nc(Nc4c(Cl)cccc4Cl)n([C@H]4CC[C@@H](C(N)=O)CC4)c3n2)C[C@H]1O] | (1S,4s)-4-(8-(2,6-dichlorophenylamino)-2-((1R,3R,4R)-3-hydroxy-4-methylcyclohexylamino)-9H-purin-9-yl)cyclohexanecarboxamide | 533.2 | A |

TABLE 1-continued

| Cmpd No. | Structure | Name | MH+ | Activity |
| --- | --- | --- | --- | --- |
| 346 | 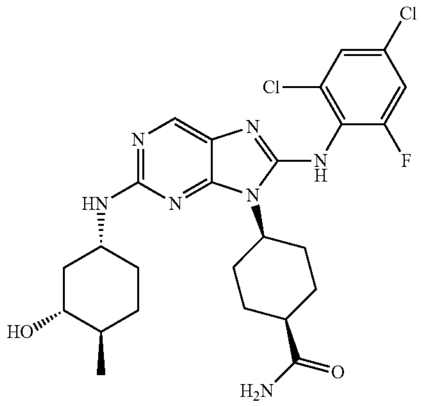 [SMILES: C[C@@H]1CC[C@@H](Nc2ncc3nc(Nc4c(F)cc(Cl)cc4Cl)n([C@H]4CC[C@@H](C(N)=O)CC4)c3n2)C[C@H]1O] | (1S,4s)-4-(8-(2,4-dichloro-6-fluorophenylamino)-2-((1R,3R,4R)-3-hydroxy-4-methylcyclohexylamino)-9H-purin-9-yl)cyclohexanecarboxamide | 550.2 | C |
| 347 | 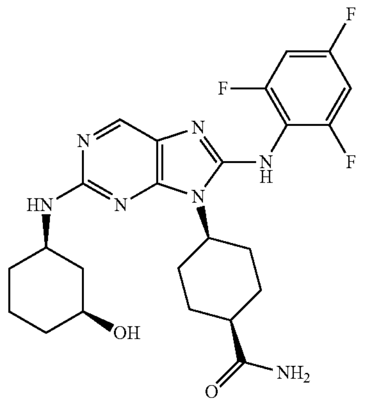 [SMILES: NC(=O)[C@H]1CC[C@@H](n2c(Nc3c(F)cc(F)cc3F)nc3cnc(N[C@@H]4CCC[C@H](O)C4)nc32)CC1] | (1S,4s)-4-(2-((1R,3S)-3-hydroxycyclohexylamino)-8-(2,4,6-trifluorophenylamino)-9H-purin-9-yl)cyclohexanecarboxamide | 504.2 | A |
| 348 | 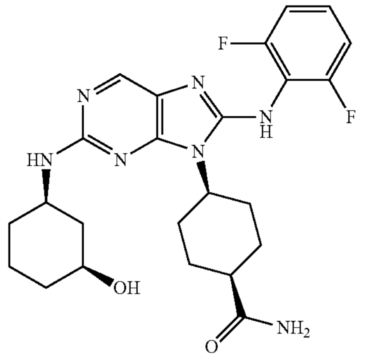 [SMILES: NC(=O)[C@H]1CC[C@@H](n2c(Nc3c(F)cccc3F)nc3cnc(N[C@@H]4CCC[C@H](O)C4)nc32)CC1] | (1S,4s)-4-(8-(2,6-difluorophenylamino)-2-((1R,3S)-3-hydroxycyclohexylamino)-9H-purin-9-yl)cyclohexanecarboxamide | 486.2 | A |
| 349 | 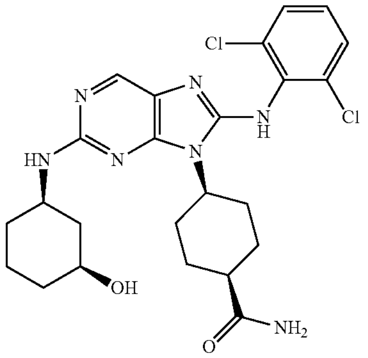 [SMILES: NC(=O)[C@H]1CC[C@@H](n2c(Nc3c(Cl)cccc3Cl)nc3cnc(N[C@@H]4CCC[C@H](O)C4)nc32)CC1] | (1S,4s)-4-(8-(2,6-dichlorophenylamino)-2-((1R,3S)-3-hydroxycyclohexylamino)-9H-purin-9-yl)cyclohexanecarboxamide | 518.1 | A |

TABLE 1-continued
| Cmpd No. | Structure | Name | MH+ | Activity |
|---|---|---|---|---|
| 350 | 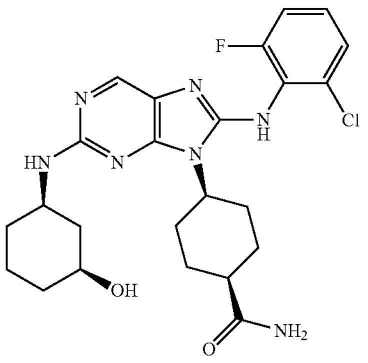 [SMILES: NC(=O)[C@H]1CC[C@@H](n2c(Nc3c(F)cccc3Cl)nc3cnc(N[C@@H]4CCC[C@H](O)C4)nc32)CC1] | (1S,4s)-4-(8-(2-chloro-6-fluorophenylamino)-2-((1R,3S)-3-hydroxycyclohexylamino)-9H-purin-9-yl)cyclohexanecarboxamide | 502.2 | B |
| 351 | 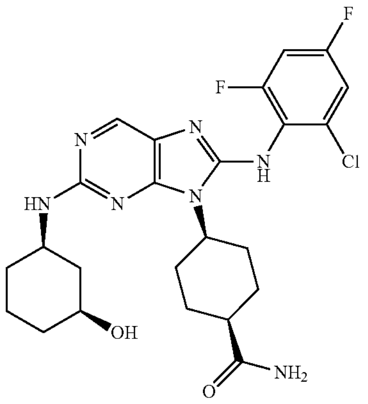 [SMILES: NC(=O)[C@H]1CC[C@@H](n2c(Nc3c(F)cc(F)cc3Cl)nc3cnc(N[C@@H]4CCC[C@H](O)C4)nc32)CC1] | (1S,4s)-4-(8-(2-chloro-4,6-difluorophenylamino)-2-((1R,3S)-3-hydroxycyclohexylamino)-9H-purin-9-yl)cyclohexanecarboxamide | 520.2 | A |
| 352 | 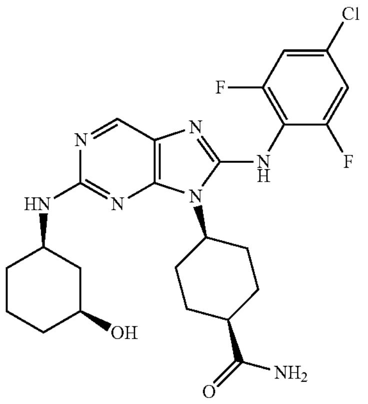 [SMILES: NC(=O)[C@H]1CC[C@@H](n2c(Nc3c(F)cc(Cl)cc3F)nc3cnc(N[C@@H]4CCC[C@H](O)C4)nc32)CC1] | (1S,4s)-4-(8-(4-chloro-2,6-difluorophenylamino)-2-((1R,3S)-3-hydroxycyclohexylamino)-9H-purin-9-yl)cyclohexanecarboxamide | 520.2 | B |

TABLE 1-continued
| Cmpd No. | Structure | Name | MH+ | Activity |
|---|---|---|---|---|
| 353 | 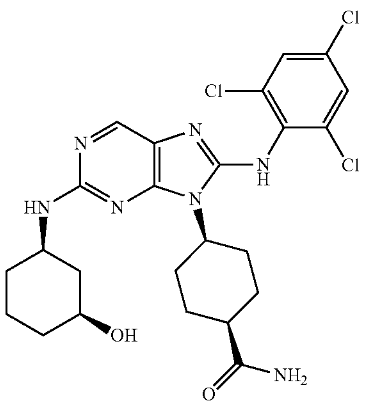 [SMILES: NC(=O)[C@H]1CC[C@@H](n2c(Nc3c(Cl)cc(Cl)cc3Cl)nc3cnc(N[C@@H]4CCC[C@H](O)C4)nc32)CC1] | (1S,4s)-4-(2-((1R,3S)-3-hydroxycyclohexylamino)-8-(2,4,6-trichlorophenylamino)-9H-purin-9-yl)cyclohexanecarboxamide | 552.1 | C |
| 354 | 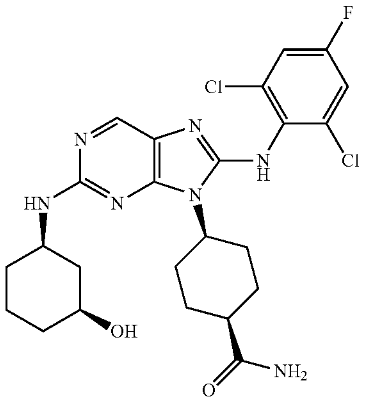 [SMILES: NC(=O)[C@H]1CC[C@@H](n2c(Nc3c(Cl)cc(F)cc3Cl)nc3cnc(N[C@@H]4CCC[C@H](O)C4)nc32)CC1] | (1S,4s)-4-(8-(2,6-dichloro-4-fluorophenylamino)-2-((1R,3S)-3-hydroxycyclohexylamino)-9H-purin-9-yl)cyclohexanecarboxamide | 536.1 | B |
| 355 | 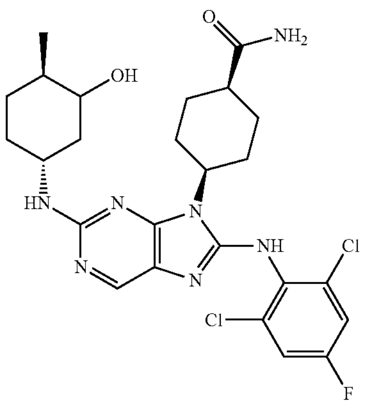 [SMILES: C[C@@H]1CC[C@@H](Nc2ncc3nc(Nc4c(Cl)cc(F)cc4Cl)n([C@H]4CC[C@@H](C(N)=O)CC4)c3n2)CC1O] | (1S,4s)-4-(8-(2,6-dichloro-4-fluorophenylamino)-2-((1R,3R,4R)-3-hydroxy-4-methylcyclohexylamino)-9H-purin-9-yl)cyclohexanecarboxamide | 550.2 | A |

TABLE 1-continued

| Cmpd No. | Structure | Name | MH+ | Activity |
|---|---|---|---|---|
| 356 | 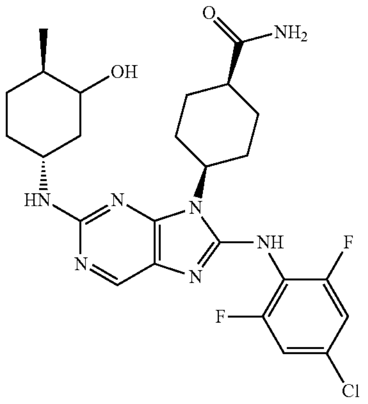 [SMILES: C[C@@H]1CC[C@@H](Nc2ncc3nc(Nc4c(F)cc(Cl)cc4F)n([C@H]4CC[C@@H](C(N)=O)CC4)c3n2)CC1O] | (1S,4s)-4-(8-(4-chloro-2,6-difluorophenylamino)-2-((1R,3R,4R)-3-hydroxy-4-methylcyclohexylamino)-9H-purin-9-yl)cyclohexanecarboxamide | 534.2 | A |
| 357 | 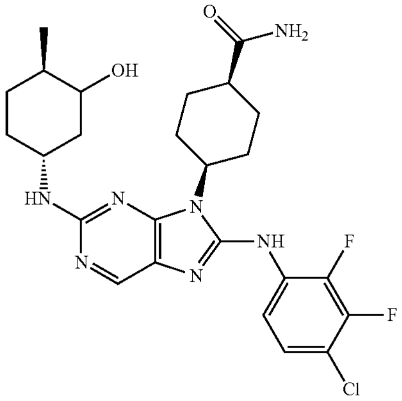 [SMILES: C[C@@H]1CC[C@@H](Nc2ncc3nc(Nc4ccc(Cl)c(F)c4F)n([C@H]4CC[C@@H](C(N)=O)CC4)c3n2)CC1O] | (1S,4s)-4-(8-(4-chloro-2,3-difluorophenylamino)-2-((1R,3R,4R)-3-hydroxy-4-methylcyclohexylamino)-9H-purin-9-yl)cyclohexanecarboxamide | 534.3 | A |
| 358 | 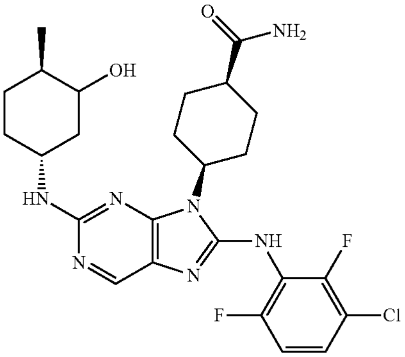 [SMILES: C[C@@H]1CC[C@@H](Nc2ncc3nc(Nc4c(F)ccc(Cl)c4F)n([C@H]4CC[C@@H](C(N)=O)CC4)c3n2)CC1O] | (1S,4s)-4-(8-(3-chloro-2,6-difluorophenylamino)-2-((1R,3R,4R)-3-hydroxy-4-methylcyclohexylamino)-9H-purin-9-yl)cyclohexanecarboxamide | 534.3 | A |
| 359 | 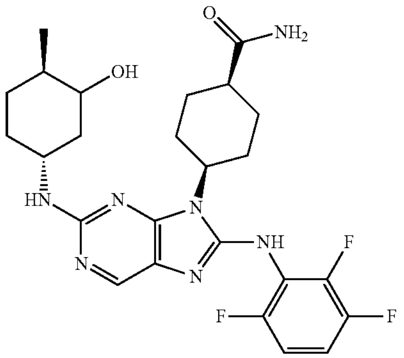 [SMILES: C[C@@H]1CC[C@@H](Nc2ncc3nc(Nc4c(F)ccc(F)c4F)n([C@H]4CC[C@@H](C(N)=O)CC4)c3n2)CC1O] | (1S,4s)-4-(2-((1R,3R,4R)-3-hydroxy-4-methylcyclohexylamino)-8-(2,3,6-trifluorophenylamino)-9H-purin-9-yl)cyclohexanecarboxamide | 518.3 | A |

TABLE 1-continued
| Cmpd No. | Structure | Name | MH+ | Activity |
|---|---|---|---|---|
| 360 | 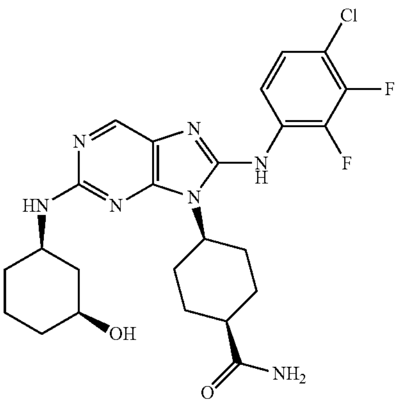 [SMILES: NC(=O)[C@H]1CC[C@@H](n2c(Nc3ccc(Cl)c(F)c3F)nc3cnc(N[C@@H]4CCC[C@H](O)C4)nc32)CC1] | (1S,4s)-4-(8-(4-chloro-2,3-difluorophenylamino)-2-((1R,3S)-3-hydroxycyclohexylamino)-9H-purin-9-yl)cyclohexanecarboxamide | 520.2 | A |
| 361 | 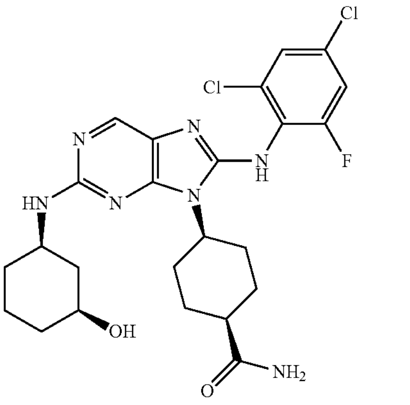 [SMILES: NC(=O)[C@H]1CC[C@@H](n2c(Nc3c(F)cc(Cl)cc3Cl)nc3cnc(N[C@@H]4CCC[C@H](O)C4)nc32)CC1] | (1S,4s)-4-(8-(2,4-dichloro-6-fluorophenylamino)-2-((1R,3S)-3-hydroxycyclohexylamino)-9H-purin-9-yl)cyclohexanecarboxamide | 536.1 | D |
| 362 | 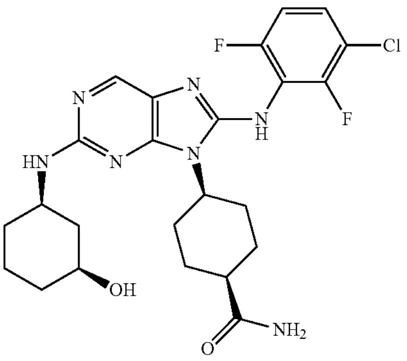 [SMILES: NC(=O)[C@H]1CC[C@@H](n2c(Nc3c(F)ccc(Cl)c3F)nc3cnc(N[C@@H]4CCC[C@H](O)C4)nc32)CC1] | (1S,4s)-4-(8-(3-chloro-2,6-difluorophenylamino)-2-((1R,3S)-3-hydroxycyclohexylamino)-9H-purin-9-yl)cyclohexanecarboxamide | 520.1 | A |

TABLE 1-continued
| Cmpd No. | Structure | Name | MH+ | Activity |
|---|---|---|---|---|
| 363 | 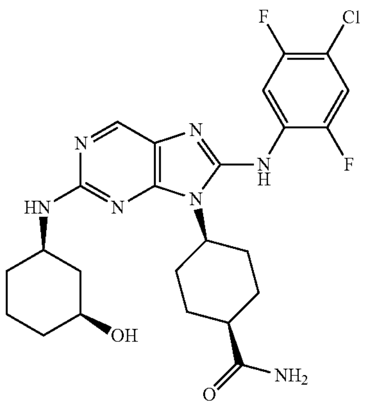 [SMILES: NC(=O)[C@H]1CC[C@@H](n2c(Nc3cc(F)c(Cl)cc3F)nc3cnc(N[C@@H]4CCC[C@H](O)C4)nc32)CC1] | (1S,4s)-4-(8-(4-chloro-2,5-difluorophenylamino)-2-((1R,3S)-3-hydroxycyclohexylamino)-9H-purin-9-yl)cyclohexanecarboxamide | 520.2 | A |
| 364 | 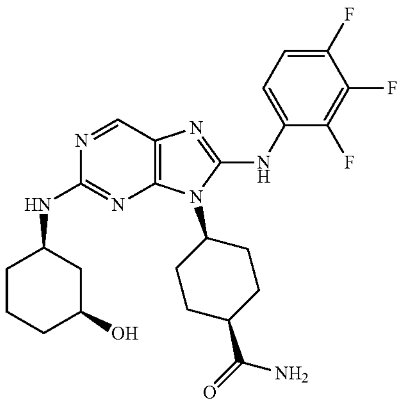 [SMILES: NC(=O)[C@H]1CC[C@@H](n2c(Nc3ccc(F)c(F)c3F)nc3cnc(N[C@@H]4CCC[C@H](O)C4)nc32)CC1] | (1S,4s)-4-(2-((1R,3S)-3-hydroxycyclohexylamino)-8-(2,3,4-trifluorophenylamino)-9H-purin-9-yl)cyclohexanecarboxamide | 504.2 | A |
| 365 | 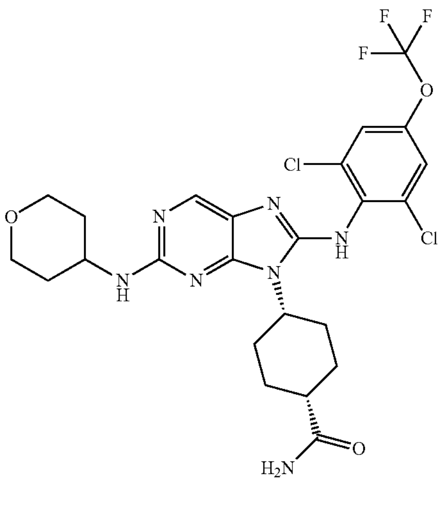 [SMILES: NC(=O)[C@H]1CC[C@@H](n2c(Nc3c(Cl)cc(OC(F)(F)F)cc3Cl)nc3cnc(NC4CCOCC4)nc32)CC1] | (1s,4s)-4-(8-(2,6-dichloro-4-(trifluoromethoxy)phenylamino)-2-(tetrahydro-2H-pyran-4-ylamino)-9H-purin-9-yl)cyclohexanecarboxamide | 588.2 | D |

TABLE 1-continued
| Cmpd No. | Structure | Name | MH+ | Activity |
|---|---|---|---|---|
| 366 | 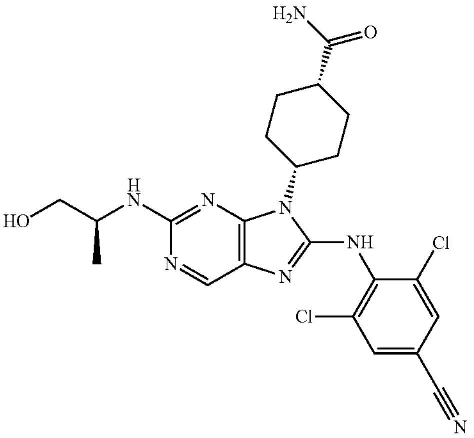 [SMILES: C[C@@H](CO)Nc1ncc2nc(Nc3c(Cl)cc(C#N)cc3Cl)n([C@H]3CC[C@@H](C(N)=O)CC3)c2n1] | (1R,4s)-4-(8-(2,6-dichloro-4-cyanophenylamino)-2-((S)-1-hydroxypropan-2-ylamino)-9H-purin-9-yl)cyclohexanecarboxamide | 503.2 | D |
| 367 | 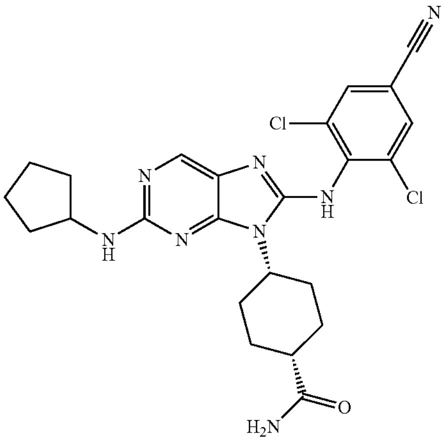 [SMILES: N#Cc1cc(Cl)c(Nc2nc3cnc(NC4CCCC4)nc3n2[C@H]2CC[C@@H](C(N)=O)CC2)c(Cl)c1] | (1s,4s)-4-(2-(cyclopentylamino)-8-(2,6-dichloro-4-cyanophenylamino)-9H-purin-9-yl)cyclohexanecarboxamide | 513.2 | D |
| 368 | 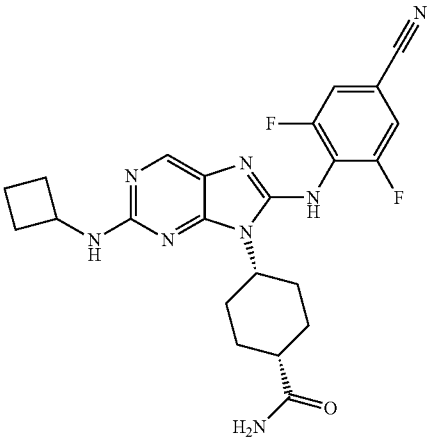 [SMILES: N#Cc1cc(F)c(Nc2nc3cnc(NC4CCC4)nc3n2[C@H]2CC[C@@H](C(N)=O)CC2)c(F)c1] | (1s,4s)-4-(8-(4-cyano-2,6-difluorophenylamino)-2-(cyclobutylamino)-9H-purin-9-yl)cyclohexanecarboxamide | 467.3 | B |

TABLE 1-continued
| Cmpd No. | Structure | Name | MH+ | Activity |
|---|---|---|---|---|
| 369 | 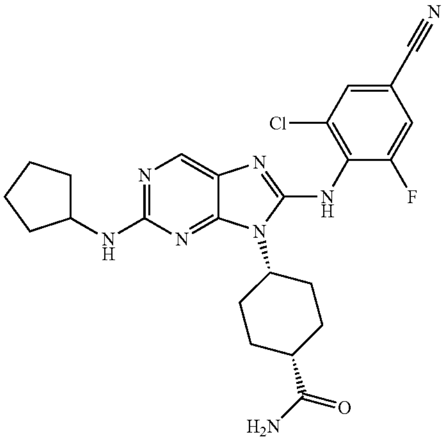 [SMILES: N#Cc1cc(F)c(Nc2nc3cnc(NC4CCCC4)nc3n2[C@H]2CC[C@@H](C(N)=O)CC2)c(Cl)c1] | (1s,4s)-4-(8-(2-chloro-4-cyano-6-fluorophenylamino)-2-(cyclopentylamino)-9H-purin-9-yl)cyclohexanecarboxamide | 497.3 | C |
| 370 | 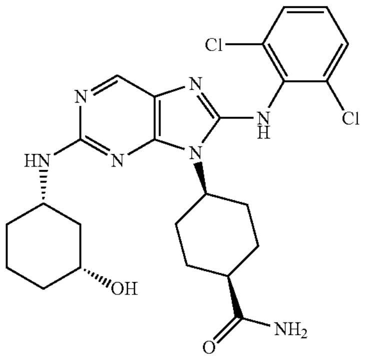 [SMILES: NC(=O)[C@H]1CC[C@@H](n2c(Nc3c(Cl)cccc3Cl)nc3cnc(N[C@H]4CCC[C@@H](O)C4)nc32)CC1] | (1R,4s)-4-(8-(2,6-dichlorophenylamino)-2-((1S,3R)-3-hydroxycyclohexylamino)-9H-purin-9-yl)cyclohexanecarboxamide | 518.2 | A |
| 371 | 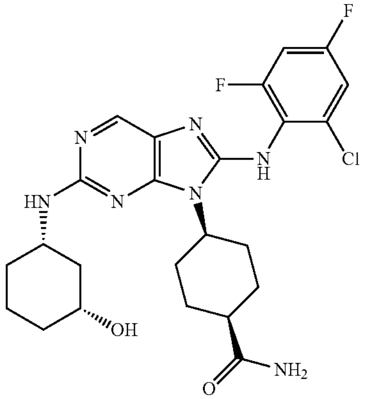 [SMILES: NC(=O)[C@H]1CC[C@@H](n2c(Nc3c(F)cc(F)cc3Cl)nc3cnc(N[C@H]4CCC[C@@H](O)C4)nc32)CC1] | (1R,4s)-4-(8-(2-chloro-4,6-difluorophenylamino)-2-((1S,3R)-3-hydroxycyclohexylamino)-9H-purin-9-yl)cyclohexanecarboxamide | 520.2 | A |

TABLE 1-continued
| Cmpd No. | Structure | Name | MH+ | Activity |
|---|---|---|---|---|
| 372 | 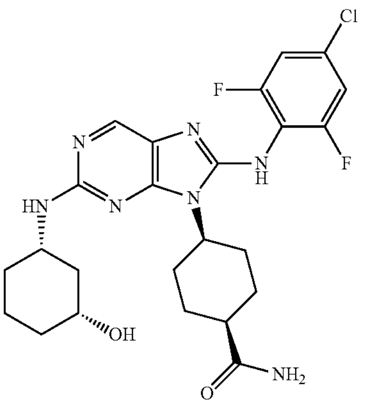 [SMILES: NC(=O)[C@H]1CC[C@@H](n2c(Nc3c(F)cc(Cl)cc3F)nc3cnc(N[C@H]4CCC[C@@H](O)C4)nc32)CC1] | (1R,4s)-4-(8-(4-chloro-2,6-difluorophenylamino)-2-((1S,3R)-3-hydroxycyclohexylamino)-9H-purin-9-yl)cyclohexanecarboxamide | 520.2 | A |
| 373 | 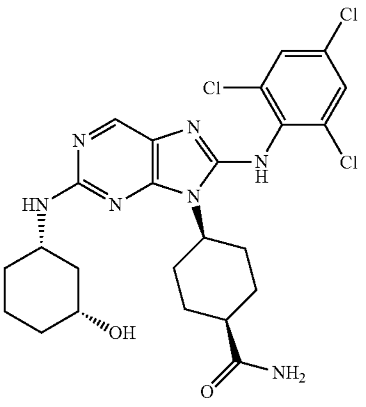 [SMILES: NC(=O)[C@H]1CC[C@@H](n2c(Nc3c(Cl)cc(Cl)cc3Cl)nc3cnc(N[C@H]4CCC[C@@H](O)C4)nc32)CC1] | (1R,4s)-4-(2-((1S,3R)-3-hydroxycyclohexylamino)-8-(2,4,6-trichlorophenylamino)-9H-purin-9-yl)cyclohexanecarboxamide | 552.1 | B |
| 374 | 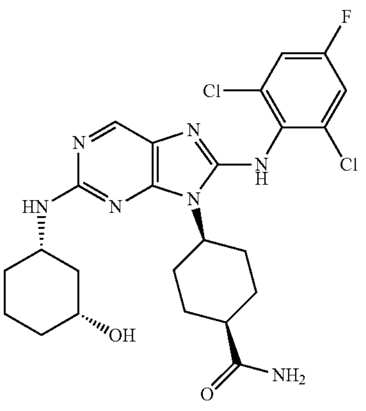 [SMILES: NC(=O)[C@H]1CC[C@@H](n2c(Nc3c(Cl)cc(F)cc3Cl)nc3cnc(N[C@H]4CCC[C@@H](O)C4)nc32)CC1] | (1R,4s)-4-(8-(2,6-dichloro-4-fluorophenylamino)-2-((1S,3R)-3-hydroxycyclohexylamino)-9H-purin-9-yl)cyclohexanecarboxamide | 536.1 | A |

TABLE 1-continued
| Cmpd No. | Structure | Name | MH+ | Activity |
|---|---|---|---|---|
| 375 | 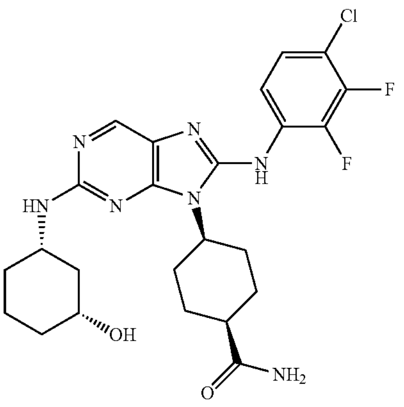 [SMILES: NC(=O)[C@H]1CC[C@@H](n2c(Nc3ccc(Cl)c(F)c3F)nc3cnc(N[C@H]4CCC[C@@H](O)C4)nc32)CC1] | (1R,4s)-4-(8-(4-chloro-2,3-difluorophenylamino)-2-((1S,3R)-3-hydroxycyclohexylamino)-9H-purin-9-yl)cyclohexanecarboxamide | 520.2 | A |
| 376 | 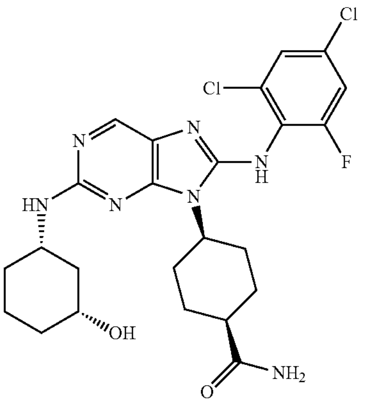 [SMILES: NC(=O)[C@H]1CC[C@@H](n2c(Nc3c(F)cc(Cl)cc3Cl)nc3cnc(N[C@H]4CCC[C@@H](O)C4)nc32)CC1] | (1R,4s)-4-(8-(2,4-dichloro-6-fluorophenylamino)-2-((1S,3R)-3-hydroxycyclohexylamino)-9H-purin-9-yl)cyclohexanecarboxamide | 536.1 | A |
| 377 | 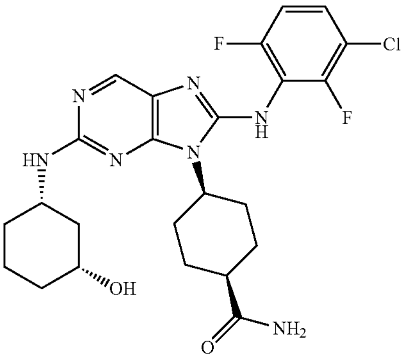 [SMILES: NC(=O)[C@H]1CC[C@@H](n2c(Nc3c(F)ccc(Cl)c3F)nc3cnc(N[C@H]4CCC[C@@H](O)C4)nc32)CC1] | (1R,4s)-4-(8-(3-chloro-2,6-difluorophenylamino)-2-((1S,3R)-3-hydroxycyclohexylamino)-9H-purin-9-yl)cyclohexanecarboxamide | 520.2 | A |

TABLE 1-continued
| Cmpd No. | Structure | Name | MH+ | Activity |
|---|---|---|---|---|
| 378 | 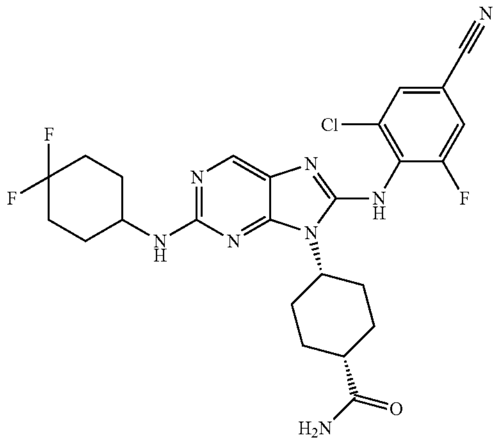 [SMILES: N#Cc1cc(F)c(Nc2nc3cnc(NC4CCC(F)(F)CC4)nc3n2[C@H]2CC[C@@H](C(N)=O)CC2)c(Cl)c1] | (1s,4s)-4-(8-(2-chloro-4-cyano-6-fluorophenylamino)-2-(4,4-difluorocyclohexylamino)-9H-purin-9-yl)cyclohexanecarboxamide | 547.3 | C |
| 379 | 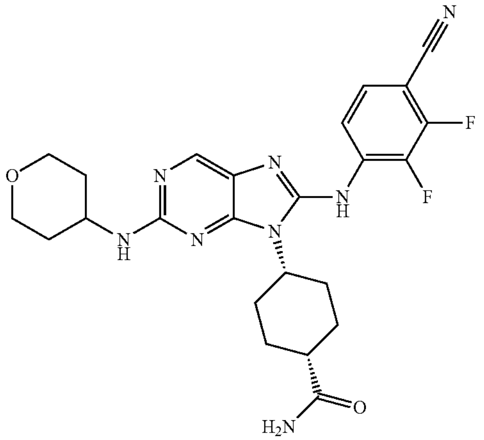 [SMILES: N#Cc1ccc(Nc2nc3cnc(NC4CCOCC4)nc3n2[C@H]2CC[C@@H](C(N)=O)CC2)c(F)c1F] | (1s,4s)-4-(8-(4-cyano-2,3-difluorophenylamino)-2-(tetrahydro-2H-pyran-4-ylamino)-9H-purin-9-yl)cyclohexanecarboxamide | 497.3 | A |
| 380 | 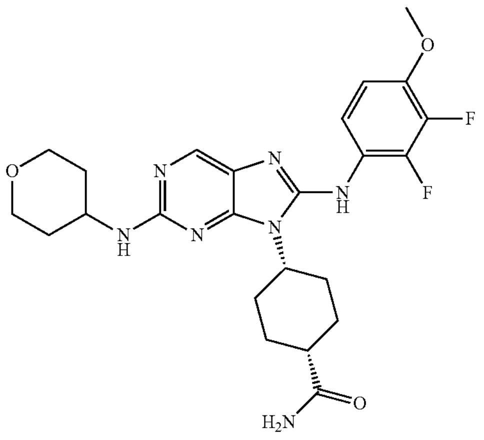 [SMILES: COc1ccc(Nc2nc3cnc(NC4CCOCC4)nc3n2[C@H]2CC[C@@H](C(N)=O)CC2)c(F)c1F] | (1s,4s)-4-(8-(2,3-difluoro-4-methoxyphenylamino)-2-(tetrahydro-2H-pyran-4-ylamino)-9H-purin-9-yl)cyclohexanecarboxamide | 502.3 | A |

TABLE 1-continued

| Cmpd No. | Structure | Name | MH+ | Activity |
|---|---|---|---|---|
| 381 | 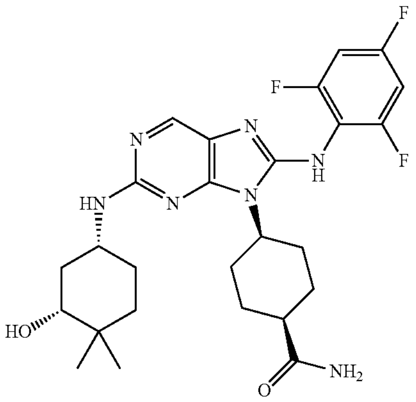 [SMILES: CC1(C)CC[C@@H](Nc2ncc3nc(Nc4c(F)cc(F)cc4F)n([C@H]4CC[C@@H](C(N)=O)CC4)c3n2)C[C@H]1O] | (1S,4s)-4-(2-((1R,3R)-3-hydroxy-4,4-dimethylcyclohexylamino)-8-(2,4,6-trifluorophenylamino)-9H-purin-9-yl)cyclohexanecarboxamide | 531.8 | A |
| 382 | 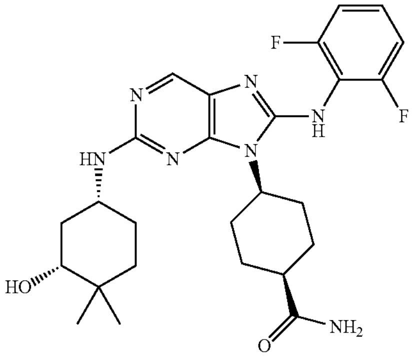 [SMILES: CC1(C)CC[C@@H](Nc2ncc3nc(Nc4c(F)cccc4F)n([C@H]4CC[C@@H](C(N)=O)CC4)c3n2)C[C@H]1O] | (1S,4s)-4-(8-(2,6-difluroophenylamino)-2-((1R,3R)-3-hydroxy-4,4-dimethylcyclohexylamino)-9H-purin-9-yl)cyclohexanecarboxamide | 513.8 | A |
| 383 | 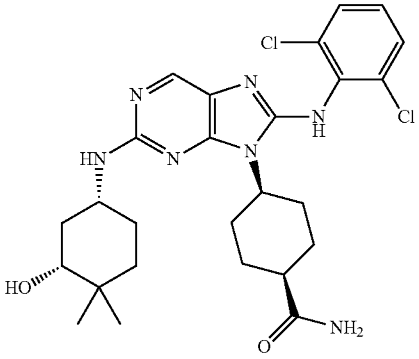 [SMILES: CC1(C)CC[C@@H](Nc2ncc3nc(Nc4c(Cl)cccc4Cl)n([C@H]4CC[C@@H](C(N)=O)CC4)c3n2)C[C@H]1O] | (1S,4s)-4-(8-(2,6-dichlorophenylamino)-2-((1R,3R)-3-hydroxy-4,4-dimethylcyclohexylamino)-9H-purin-9-yl)cyclohexanecarboxamide | 545.7 | A |
| 384 | 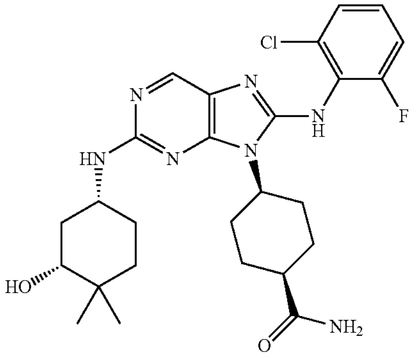 [SMILES: CC1(C)CC[C@@H](Nc2ncc3nc(Nc4c(F)cccc4Cl)n([C@H]4CC[C@@H](C(N)=O)CC4)c3n2)C[C@H]1O] | (1S,4s)-4-(8-(2-chloro-6-fluorophenylamino)-2-((1R,3R)-3-hydroxy-4,4-dimethylcyclohexylamino)-9H-purin-9-yl)cyclohexanecarboxamide | 530 | A |

TABLE 1-continued

| Cmpd No. | Structure | Name | MH+ | Activity |
|---|---|---|---|---|
| 385 | 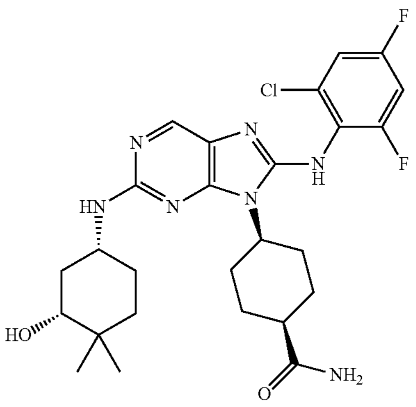 [SMILES: CC1(C)CC[C@@H](Nc2ncc3nc(Nc4c(F)cc(F)cc4Cl)n([C@H]4CC[C@@H](C(N)=O)CC4)c3n2)C[C@H]1O] | (1S,4s)-4-(8-(2-chloro-4,6-difluorophenylamino)-2-((1R,3R)-3-hydroxy-4,4-dimethylcyclohexylamino)-9H-purin-9-yl)cyclohexanecarboxamide | 547.7 | A |
| 386 | 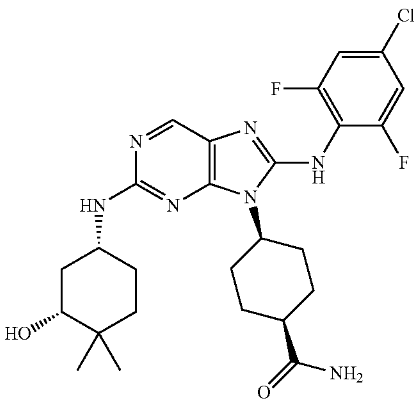 [SMILES: CC1(C)CC[C@@H](Nc2ncc3nc(Nc4c(F)cc(Cl)cc4F)n([C@H]4CC[C@@H](C(N)=O)CC4)c3n2)C[C@H]1O] | (1S,4s)-4-(8-(4-chloro-2,6-difluorophenylamino)-2-((1R,3R)-3-hydroxy-4,4-dimethylcyclohexylamino)-9H-purin-9-yl)cyclohexanecarboxamide | 547.7 | A |
| 387 | 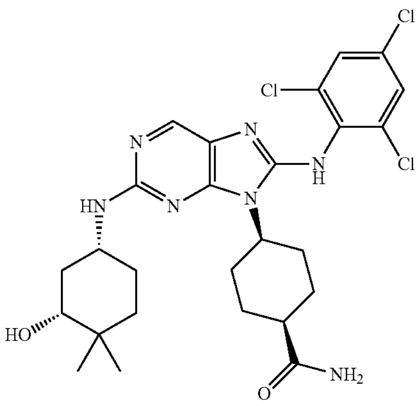 [SMILES: CC1(C)CC[C@@H](Nc2ncc3nc(Nc4c(Cl)cc(Cl)cc4Cl)n([C@H]4CC[C@@H](C(N)=O)CC4)c3n2)C[C@H]1O] | (1S,4s)-4-(2-((1R,3R)-3-hydroxy-4,4-dimethylcyclohexylamino)-8-(2,4,6-trichlorophenylamino)-9H-purin-9-yl)cyclohexanecarboxamide | 579.7 | A |

TABLE 1-continued

| Cmpd No. | Structure | Name | MH+ | Activity |
| --- | --- | --- | --- | --- |
| 388 | 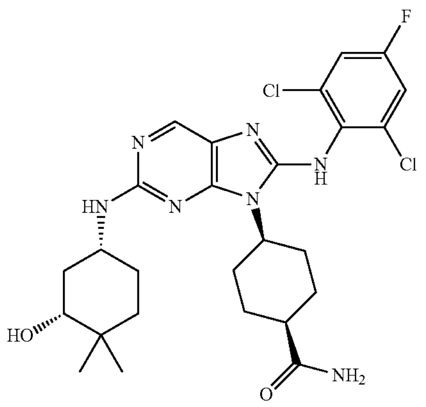 [SMILES: CC1(C)CC[C@@H](Nc2ncc3nc(Nc4c(Cl)cc(F)cc4Cl)n([C@H]4CC[C@@H](C(N)=O)CC4)c3n2)C[C@H]1O] | (1S,4s)-4-(8-(2,6-dichloro-4-fluorophenylamino)-2-((1R,3R)-3-hydroxy-4,4-dimethylcyclohexylamino)-9H-purin-9-yl)cyclohexanecarboxamide | 563.7 | A |
| 389 | 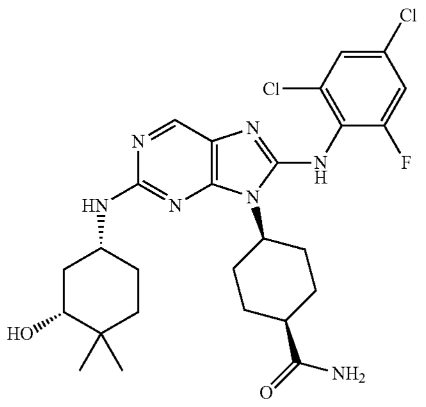 [SMILES: CC1(C)CC[C@@H](Nc2ncc3nc(Nc4c(F)cc(Cl)cc4Cl)n([C@H]4CC[C@@H](C(N)=O)CC4)c3n2)C[C@H]1O] | (1S,4s)-4-(8-(2,4-dichloro-6-fluorophenylamino)-2-((1R,3R)-3-hydroxy-4,4-dimethylcyclohexylamino)-9H-purin-9-yl)cyclohexanecarboxamide | 563.7 | A |
| 390 | 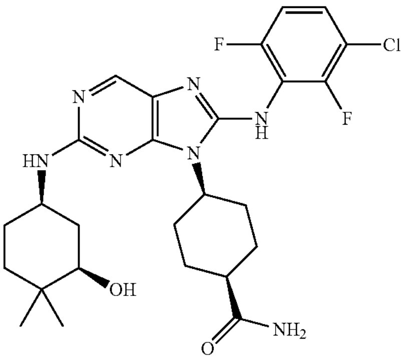 [SMILES: CC1(C)CC[C@@H](Nc2ncc3nc(Nc4c(F)ccc(Cl)c4F)n([C@H]4CC[C@@H](C(N)=O)CC4)c3n2)C[C@H]1O] | (1S,4s)-4-(8-(3-chloro-2,6-difluorophenylamino)-2-((1R,3R)-3-hydroxy-4,4-dimethylcyclohexylamino)-9H-purin-9-yl)cyclohexanecarboxamide | 547.7 | A |

TABLE 1-continued
| Cmpd No. | Structure | Name | MH+ | Activity |
|---|---|---|---|---|
| 391 | 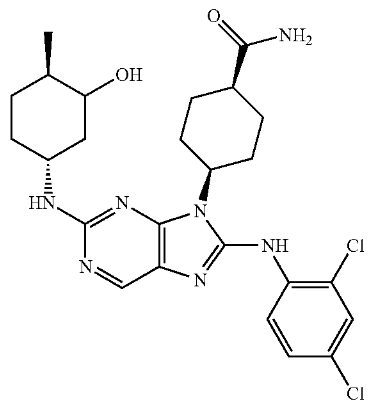 [SMILES: C[C@@H]1CC[C@@H](Nc2ncc3nc(Nc4ccc(Cl)cc4Cl)n([C@H]4CC[C@@H](C(N)=O)CC4)c3n2)CC1O] | (1S,4s)-4-(8-(2,4-dichlorophenylamino)-2-((1R,3R,4R)-3-hydroxy-4-methylcyclohexylamino)-9H-purin-9-yl)cyclohexanecarboxamide | 532.2 | A |
| 392 | 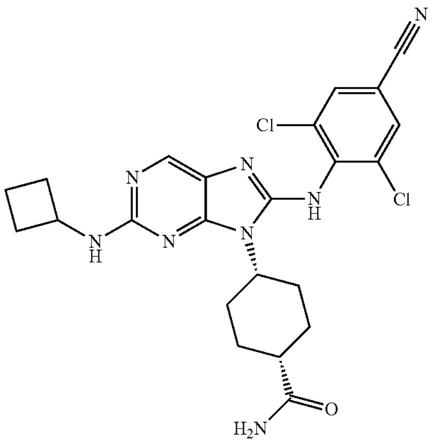 [SMILES: N#Cc1cc(Cl)c(Nc2nc3cnc(NC4CCC4)nc3n2[C@H]2CC[C@@H](C(N)=O)CC2)c(Cl)c1] | (1s,4s)-4-(2-(cyclobutylamino)-8-(2,6-dichloro-4-cyanophenylamino)-9H-purin-9-yl)cyclohexanecarboxamide | 499.2 | D |
| 393 | 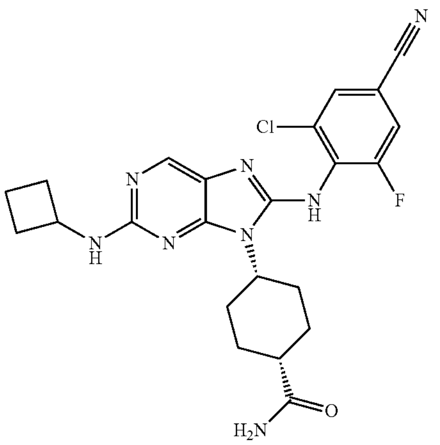 [SMILES: N#Cc1cc(F)c(Nc2nc3cnc(NC4CCC4)nc3n2[C@H]2CC[C@@H](C(N)=O)CC2)c(Cl)c1] | (1s,4s)-4-(8-(2-chloro-4-cyano-6-fluorophenylamino)-2-(cyclobutylamino)-9H-purin-9-yl)cyclohexanecarboxamide | 483.2 | C |

TABLE 1-continued
| Cmpd No. | Structure | Name | MH+ | Activity |
|---|---|---|---|---|
| 394 | 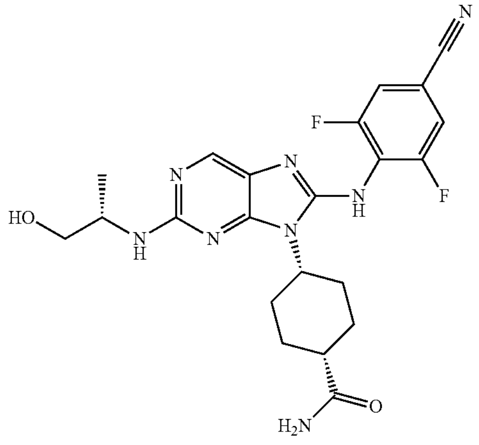 [SMILES: C[C@@H](CO)Nc1ncc2nc(Nc3c(F)cc(C#N)cc3F)n([C@H]3CC[C@@H](C(N)=O)CC3)c2n1] | (1R,4s)-4-(8-(4-cyano-2,6-difluorophenylamino)-2-((S)-1-hydroxypropan-2-ylamino)-9H-purin-9-yl)cyclohexanecarboxamide | 471.2 | A |
| 395 | 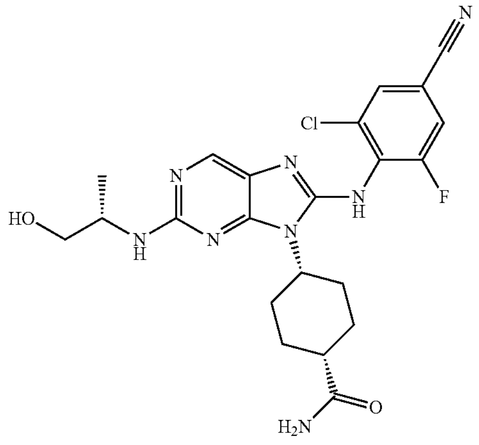 [SMILES: C[C@@H](CO)Nc1ncc2nc(Nc3c(F)cc(C#N)cc3Cl)n([C@H]3CC[C@@H](C(N)=O)CC3)c2n1] | (1R,4s)-4-(8-(2-chloro-4-cyano-6-fluorophenylamino)-2-((S)-1-hydroxypropan-2-ylamino)-9H-purin-9-yl)cyclohexanecarboxamide | 487.2 | A |
| 396 | 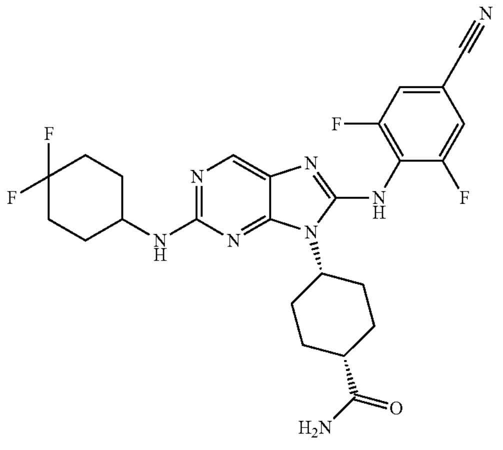 [SMILES: N#Cc1cc(F)c(Nc2nc3cnc(NC4CCC(F)(F)CC4)nc3n2[C@H]2CC[C@@H](C(N)=O)CC2)c(F)c1] | (1s,4s)-4-(8-(4-cyano-2,6-difluorophenylamino)-2-(4,4-difluorocyclohexylamino)-9H-purin-9-yl)cyclohexanecarboxamide | 531.3 | B |

TABLE 1-continued
| Cmpd No. | Structure | Name | MH+ | Activity |
|---|---|---|---|---|
| 397 | 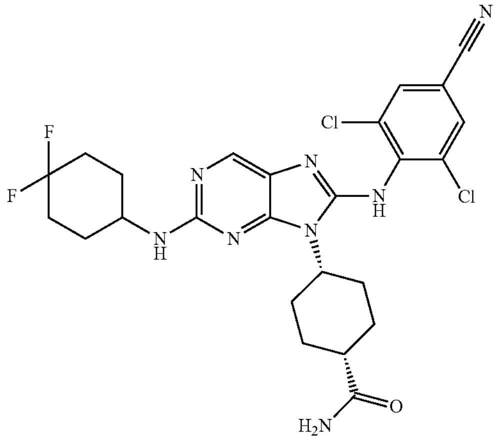 | (1s,4s)-4-(8-(2,6-dichloro-4-cyanophenylamino)-2-(4,4-difluorocyclohexyl)amino)-9H-purin-9-yl)cyclohexanecarboxamide | 563.2 | D |
| 398 | 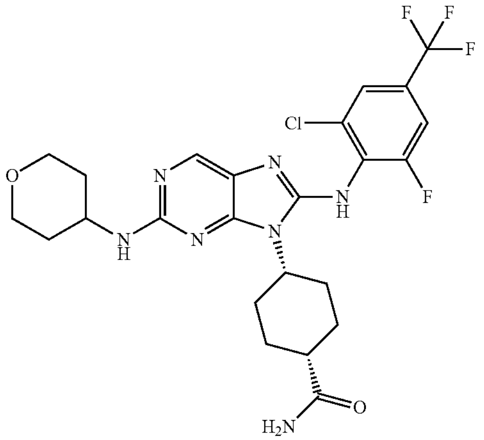 [SMILES: NC(=O)[C@H]1CC[C@@H](n2c(Nc3c(F)cc(C(F)(F)F)cc3Cl)nc3cnc(NC4CCOCC4)nc32)CC1] | (1s,4s)-4-(8-(2-chloro-6-fluoro-4-(trifluoromethyl)phenylamino)-2-(tetrahydro-2H-pyran-4-ylamino)-9H-purin-9-yl)cyclohexanecarboxamide | 556.2 | B |
| 399 | 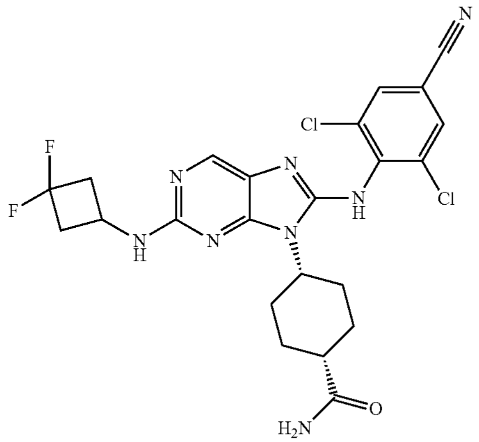 [SMILES: N#Cc1cc(Cl)c(Nc2nc3cnc(NC4CC(F)(F)C4)nc3n2[C@H]2CC[C@@H](C(N)=O)CC2)c(Cl)c1] | (1s,4s)-4-(8-(2,6-dichloro-4-cyanophenylamino)-2-(3,3-difluorocyclobutylamino)-9H-purin-9-yl)cyclohexanecarboxamide | 535.2 | C |

TABLE 1-continued
| Cmpd No. | Structure | Name | MH+ | Activity |
|---|---|---|---|---|
| 400 | 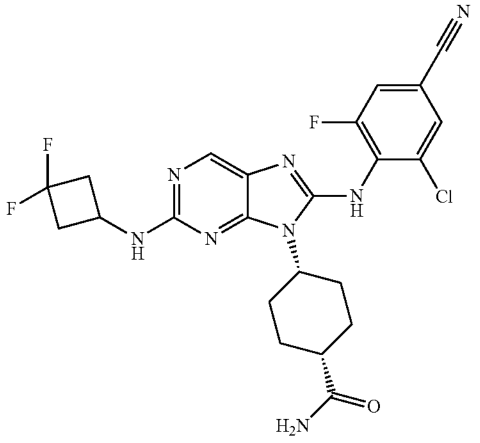 [SMILES: N#Cc1cc(F)c(Nc2nc3cnc(NC4CC(F)(F)C4)nc3n2[C@H]2CC[C@@H](C(N)=O)CC2)c(Cl)c1] | (1s,4s)-4-(8-(2-chloro-4-cyano-6-fluorophenylamino)-2-(3,3-difluorocyclobutylamino)-9H-purin-9-yl)cyclohexanecarboxamide | 519.2 | B |
| 401 | 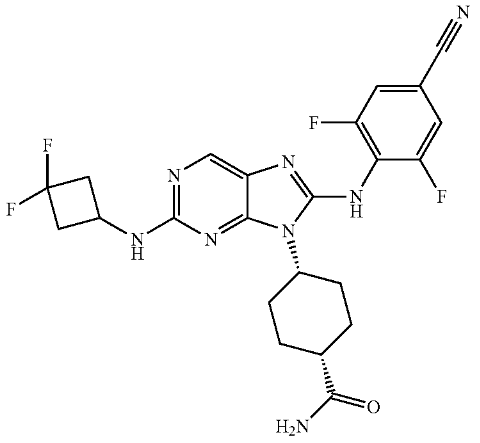 [SMILES: N#Cc1cc(F)c(Nc2nc3cnc(NC4CC(F)(F)C4)nc3n2[C@H]2CC[C@@H](C(N)=O)CC2)c(F)c1] | (1s,4s)-4-(8-(4-cyano-2,6-difluorophenylamino)-2-(3,3-difluorocyclobutylamino)-9H-purin-9-yl)cyclohexanecarboxamide | 503.2 | A |
| 402 | 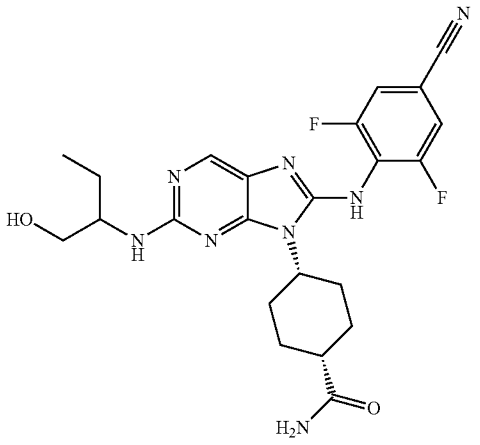 [SMILES: CCC(CO)Nc1ncc2nc(Nc3c(F)cc(C#N)cc3F)n([C@H]3CC[C@@H](C(N)=O)CC3)c2n1] | (1R,4s)-4-(8-(4-cyano-2,6-difluorophenylamino)-2-((S)-1-hydroxybutna-2-ylamino)-9H-purin-9-yl)cyclohexanecarboxamide | 485.3 | A |

TABLE 1-continued

| Cmpd No. | Structure | Name | MH+ | Activity |
|---|---|---|---|---|
| 403 | 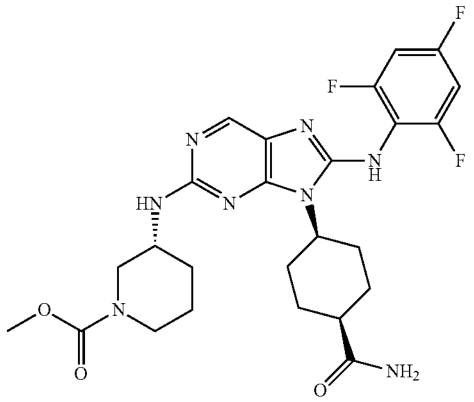 [SMILES: COC(=O)N1CCC[C@@H](Nc2ncc3nc(Nc4c(F)cc(F)cc4F)n([C@H]4CC[C@@H](C(N)=O)CC4)c3n2)C1] | (R)-methyl 3-(9-((1s,4S)-4-carbamoylcyclohexyl)-8-(2,4,6-trifluorophenylamino)-9H-purin-2-ylamino)piperidine-1-carboxylate | 547.3 | A |
| 404 | 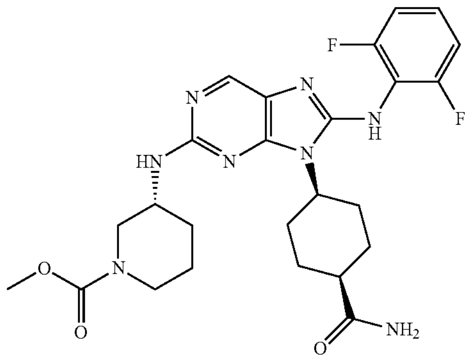 [SMILES: COC(=O)N1CCC[C@@H](Nc2ncc3nc(Nc4c(F)cccc4F)n([C@H]4CC[C@@H](C(N)=O)CC4)c3n2)C1] | (R)-methyl 3-(9-((1s,4S)-4-carbamoylcyclohexyl)-8-(2,6-difluorophenylamino)-9H-purin-2-ylamino)piperidine-1-carboxylate | 529.2 | A |
| 405 | 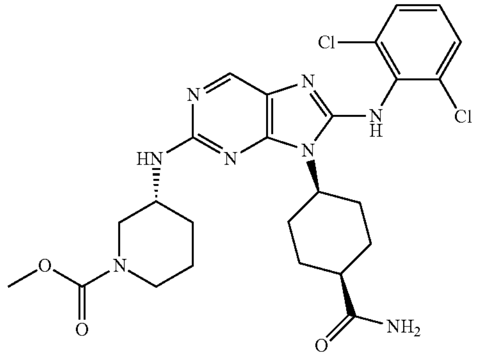 [SMILES: COC(=O)N1CCC[C@@H](Nc2ncc3nc(Nc4c(Cl)cccc4Cl)n([C@H]4CC[C@@H](C(N)=O)CC4)c3n2)C1] | (R)-methyl 3-(9-((1s,4S)-4-carbamoylcyclohexyl)-8-(2,6-dichlorophenylamino)-9H-purin-2-ylamino)piperidine-1-carboxylate | 561.2 | A |
| 406 | 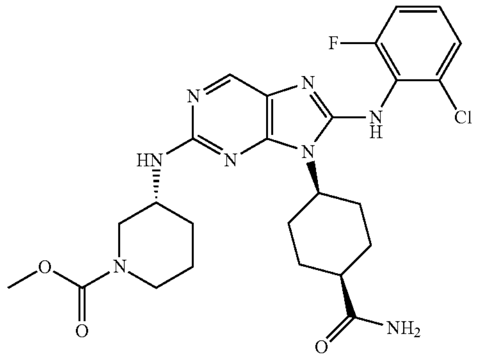 | (R)-methyl 3-((9-((1s,4S)-4-carbamoylcyclohexyl)-8-(2-chloro-6-fluorophenylamino)-9H-purin-2-ylamino)piperidine-1-carboxylate | 545.2 | A |

TABLE 1-continued

| Cmpd No. | Structure | Name | MH+ | Ac-tivi-ty |
|---|---|---|---|---|
| 407 | 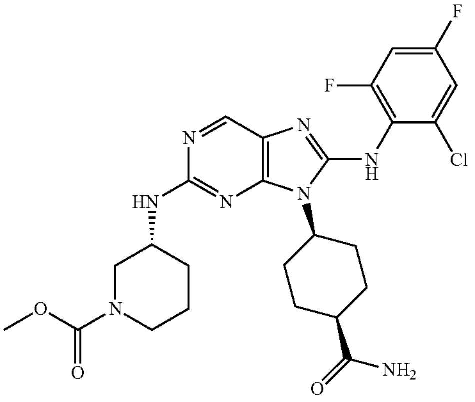 | (R)-methyl 3-(9-((1s,4S)-4-carbamoylcyclohexyl)-8-(2-chloro-4,6-difluorophenylamino)-9H-purin-2-ylamino)piperidine-1-carboxylate | 563.2 | A |
| 408 | 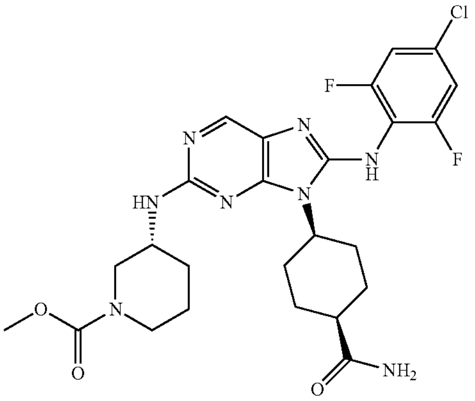 [SMILES: COC(=O)N1CCC[C@@H](Nc2ncc3nc(Nc4c(F)cc(F)cc4Cl)n([C@H]4CC[C@@H](C(N)=O)CC4)c3n2)C1] | (R)-methyl 3-(9-((1s,4S)-4-carbamoylcyclohexyl)-8-(4-chloro-2,6-difluorophenylamino)-9H-purin-2-ylamino)piperidine-1-carboxylate | 563.2 | B |
| 409 | 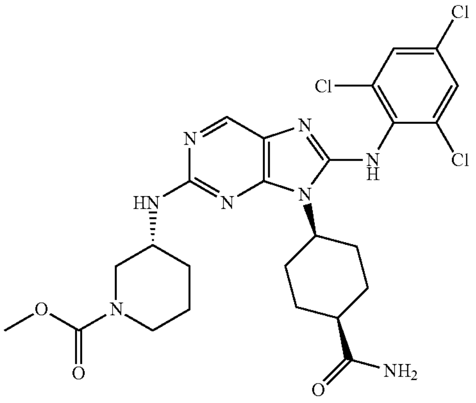 [SMILES: COC(=O)N1CCC[C@@H](Nc2ncc3nc(Nc4c(Cl)cc(Cl)cc4Cl)n([C@H]4CC[C@@H](C(N)=O)CC4)c3n2)C1] | (R)-methyl 3-(9-((1s,4S)-4-carbamoylcyclohexyl)-8-(2,4,6-trichlorophenylamino)-9H-purin-2-ylamino)piepridine-1-carboxylate | 595.2 | B |

TABLE 1-continued

| Cmpd No. | Structure | Name | MH+ | Activity |
|---|---|---|---|---|
| 410 | 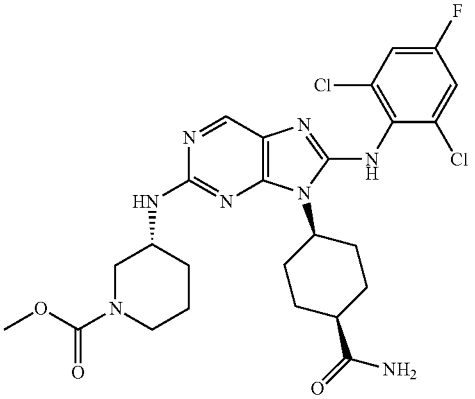 | (R)-methyl 3-(9-((1s,4S)-4-carbamoylcyclohexyl)-8-(2,6-dichloro-4-fluorophenylamino)-9H-purin-2-ylamino)piperidine-1-carboxylate | 579.1 | A |
| 411 | 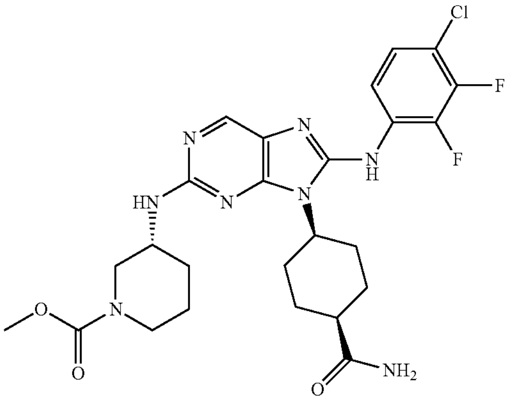 [SMILES: COC(=O)N1CCC[C@@H](Nc2ncc3nc(Nc4ccc(Cl)c(F)c4F)n([C@H]4CC[C@@H](C(N)=O)CC4)c3n2)C1] | (R)-methyl 3-(9-((1s,4S)-4-carbamoylcyclohexyl)-8-(4-chloro-2,3-difluorophenylamino)-9H-purin-2-ylamino)piperidine-1-carboxylate | 563.2 | A |
| 412 | 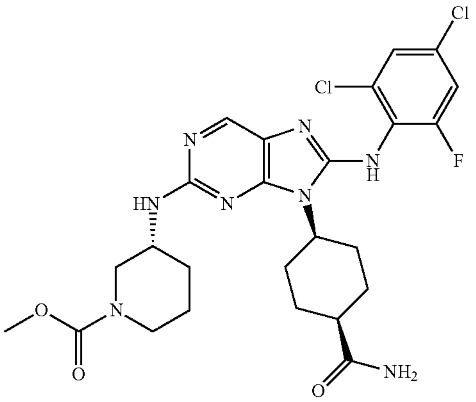 [SMILES: COC(=O)N1CCC[C@@H](Nc2ncc3nc(Nc4c(F)cc(Cl)cc4Cl)n([C@H]4CC[C@@H](C(N)=O)CC4)c3n2)C1] | (R)-methyl 3-(9-((1s,4S)-4-carbamoylcyclohexyl)-8-(2,4-dichloro-6-fluorophenylamino)-9H-purin-2-ylamino)piperidine-1-carboxylate | 579.2 | C |

TABLE 1-continued

| Cmpd No. | Structure | Name | MH+ | Ac-tivi-ty |
|---|---|---|---|---|
| 413 | 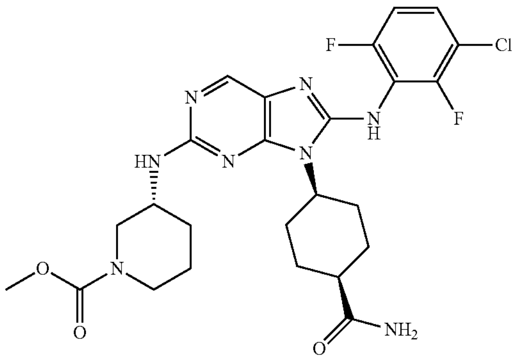 [SMILES: COC(=O)N1CCC[C@@H](Nc2ncc3nc(Nc4c(F)ccc(Cl)c4F)n([C@H]4CC[C@@H](C(N)=O)CC4)c3n2)C1] | (R)-methyl 3-(9-((1s,4S)-4-carbamoylcyclohexyl)-8-(3-chloro-2,6-difluorophenylamino)-9H-purin-2-ylamino)piperidine-1-carboxylate | 563.3 | A |
| 414 | 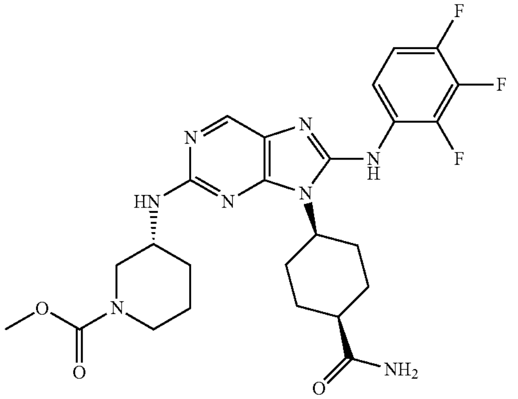 [SMILES: COC(=O)N1CCC[C@@H](Nc2ncc3nc(Nc4ccc(F)c(F)c4F)n([C@H]4CC[C@@H](C(N)=O)CC4)c3n2)C1] | (R)-methyl 3-(9-((1s,4S)-4-carbamoylcyclohexyl)-8-(2,3,4-trifluorophenylamino)-9H-purin-2-ylamino)piperidine-1-carboxylate | 574.2 | A |
| 415 | 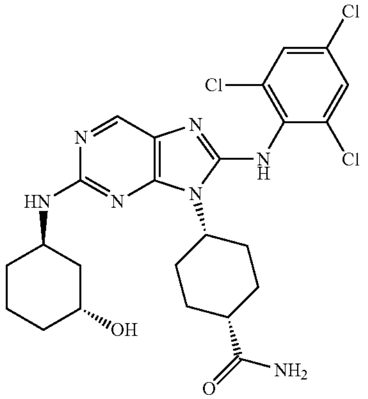 | (1S,4s)-4-(2-((1R,3R)-3-hydroxycyclohexylamino)-8-(2,4,6-trichlorophenylamino)-9H-purin-9-yl)cyclohexanecarboxamide | 552.1 | B |
| 416 | 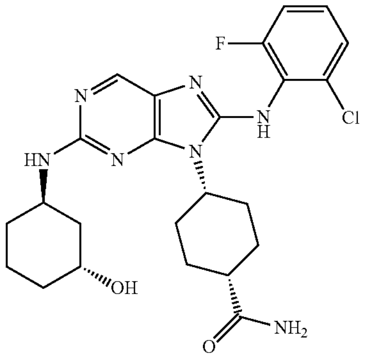 [SMILES: NC(=O)[C@H]1CC[C@@H](n2c(Nc3c(F)cccc3Cl)nc3cnc(N[C@@H]4CCC[C@@H](O)C4)nc32)CC1] | (1S,4s)-4-(8-(2-chloro-6-fluorophenylamino)-2-((1R,3R)-3-hydroxycyclohexylamino)-9H-purin-9-yl)cyclohexanecarboxamide | 502.2 | A |

TABLE 1-continued
| Cmpd No. | Structure | Name | MH+ | Activity |
|---|---|---|---|---|
| 417 | 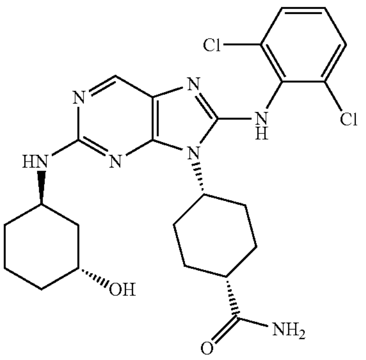 [SMILES: NC(=O)[C@H]1CC[C@@H](n2c(Nc3c(Cl)cccc3Cl)nc3cnc(N[C@@H]4CCC[C@@H](O)C4)nc32)CC1] | (1S,4s)-4-(8-(2,6-dichlorophenylamino)-2-((1R,3R)-3-hydroxycyclohexylamino)-9H-purin-9-yl)cyclohexanecarboxamide | 518.1 | A |
| 418 | 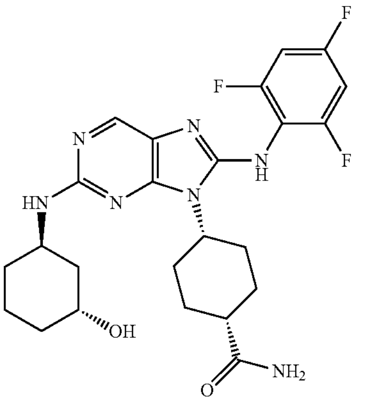 [SMILES: NC(=O)[C@H]1CC[C@@H](n2c(Nc3c(F)cc(F)cc3F)nc3cnc(N[C@@H]4CCC[C@@H](O)C4)nc32)CC1] | (1S,4s)-4-(2-((1R,3R)-3-hydroxycyclohexylamino)-8-(2,4,6-trifluorophenylamino)-9H-purin-9-yl)cyclohexanecarboxamide | 504.2 | A |
| 419 | 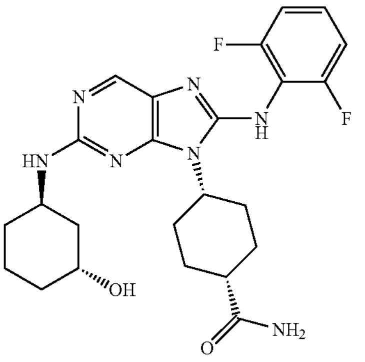 [SMILES: NC(=O)[C@H]1CC[C@@H](n2c(Nc3c(F)cccc3F)nc3cnc(N[C@@H]4CCC[C@@H](O)C4)nc32)CC1] | (1S,4s)-4-(8-(2,6-difluorophenylamino)-2-((1R,3R)-3-hydroxycyclohexylamino)-9H-purin-9-yl)cyclohexanecarboxamide | 486.2 | A |

TABLE 1-continued
| Cmpd No. | Structure | Name | MH+ | Activity |
|---|---|---|---|---|
| 420 | 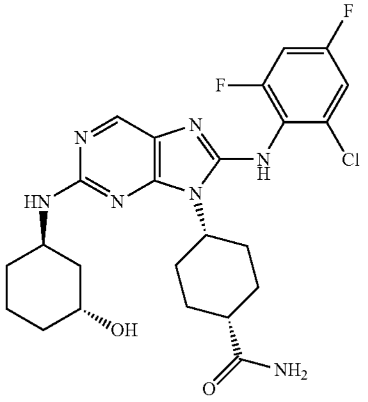 | (1S,4s)-4-(8-(2-chloro-4,6-difluorophenylamino)-2-((1R,3R)-3-hydroxycyclohexylamino)-9H-purin-9-yl)cyclohexanecarboxamide | 520.2 | A |
| 421 | 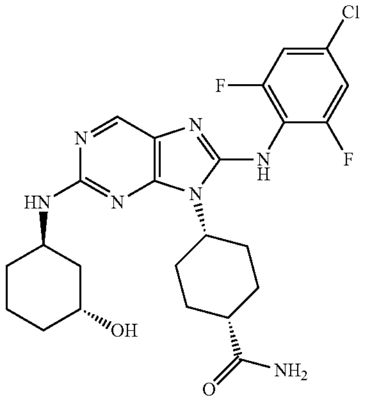 [SMILES: NC(=O)[C@H]1CC[C@@H](n2c(Nc3c(F)cc(Cl)cc3F)nc3cnc(N[C@@H]4CCC[C@@H](O)C4)nc32)CC1] | (1S,4s)-4-(8-(4-chloro-2,6-difluorophenylamino)-2-((1R,3R)-3-hydroxycyclohexylamino)-9H-purin-9-yl)cyclohexanecarobxamide | 520.1 | A |
| 422 | 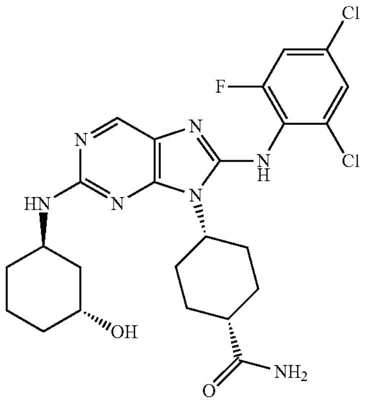 [SMILES: NC(=O)[C@H]1CC[C@@H](n2c(Nc3c(F)cc(Cl)cc3Cl)nc3cnc(N[C@@H]4CCC[C@@H](O)C4)nc32)CC1] | (1S,4s)-4-(8-(2,4-dichloro-6-fluorophenylamino)-2-((1R,3R)-3-hydroxycyclohexylamino)-9H-purin-9-yl)cyclohexanecarboxamide | 536.1 | B |

TABLE 1-continued
| Cmpd No. | Structure | Name | MH+ | Activity |
|---|---|---|---|---|
| 423 | 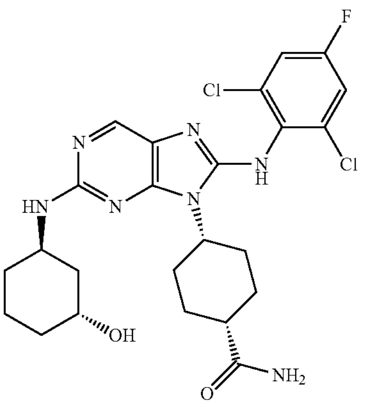 [SMILES: NC(=O)[C@H]1CC[C@@H](n2c(Nc3c(Cl)cc(F)cc3Cl)nc3cnc(N[C@@H]4CCC[C@@H](O)C4)nc32)CC1] | (1S,4s)-4-(8-(2,6-dichloro-4-fluorophenylamino)-2-((1R,3R)-3-hydroxycyclohexylamino)-9H-purin-9-yl)cyclohexanecarboxamide | 536 | B |
| 424 | 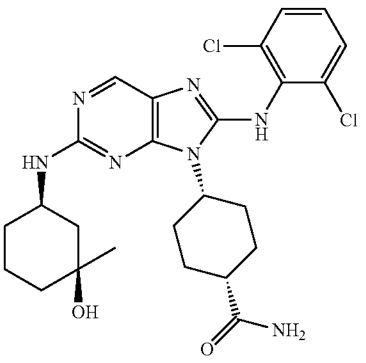 [SMILES: C[C@]1(O)CCC[C@@H](Nc2ncc3nc(Nc4c(Cl)cccc4Cl)n([C@H]4CC[C@@H](C(N)=O)CC4)c3n2)C1] | (1S,4s)-4-(8-(2,6-dichlorophenylamino)-2-((1R,3S)-3-hydroxy-3-methylcyclohexylamino)-9H-purin-9-yl)cyclohexanecarboxamide | 532.2 | A |
| 425 | 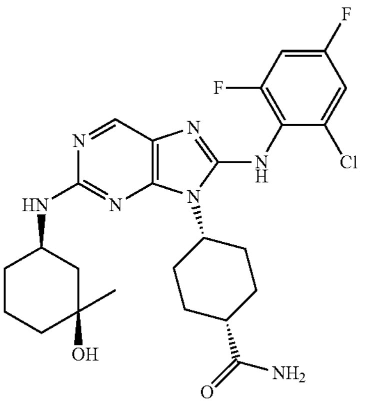 | (1S,4s)-4-(8-(2-chloro-4,6-difluorophenylamino)-2-((1R,3S)-3-hydroxy-3-methylcyclohexylamino)-9H-purin-9-yl)cyclohexanecarboxamide | 534.2 | A |

TABLE 1-continued

| Cmpd No. | Structure | Name | MH+ | Activity |
|---|---|---|---|---|
| 426 | 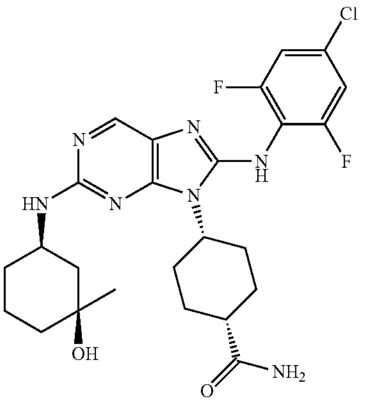 [SMILES: C[C@]1(O)CCC[C@@H](Nc2ncc3nc(Nc4c(F)cc(Cl)cc4F)n([C@H]4CC[C@@H](C(N)=O)CC4)c3n2)C1] | (1S,4s)-4-(8-(4-chloro-2,6-difluorophenylamino)-2-((1R,3S)-3-hydroxy-3-methylcyclohexylamino)-9H-purin-9-yl)cyclohexanecarboxamide | 534.2 | A |
| 427 | 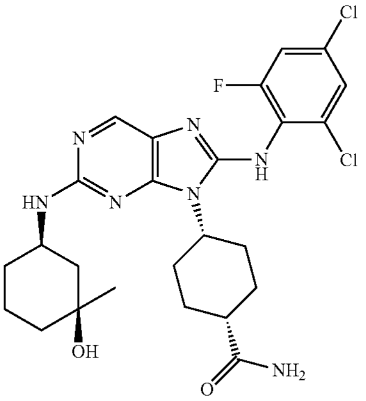 [SMILES: C[C@]1(O)CCC[C@@H](Nc2ncc3nc(Nc4c(Cl)cc(F)cc4Cl)n([C@H]4CC[C@@H](C(N)=O)CC4)c3n2)C1] | (1S,4s)-4-(8-(2,4-dichloro-6-fluorophenylamino)-2-((1R,3S)-3-hydroxy-3-methylcyclohexylamino)-9H-purin-9-yl)cyclohexanecarboxamide | 550.2 | B |
| 428 | 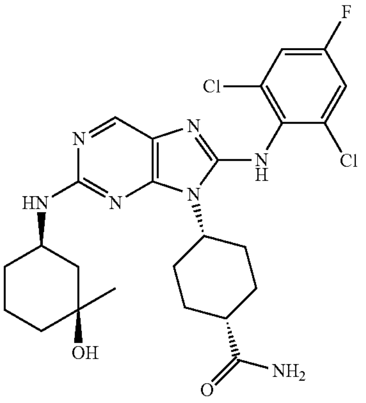 | (1S,4s)-4-(8-(2,6-dichloro-4-fluorophenylamino)-2-((1R,3S)-3-hydroxy-3-methylcyclohexylamino)-9H-purin-9-yl)cyclohexanecarboxamide | 550.2 | A |

TABLE 1-continued
| Cmpd No. | Structure | Name | MH+ | Ac-tivi-ty |
|---|---|---|---|---|
| 429 | 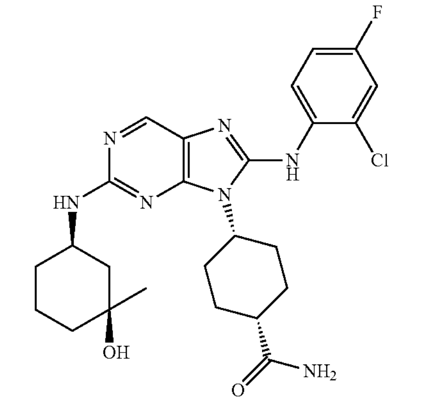 [SMILES: C[C@]1(O)CCC[C@@H](Nc2ncc3nc(Nc4ccc(F)cc4Cl)n([C@H]4CC[C@@H](C(N)=O)CC4)c3n2)C1] | (1S,4s)-4-(8-(2-chloro-4-fluorophenylamino)-2-((1R,3S)-3-hydroxy-3-methylcyclohexylamino)-9H-purin-9-yl)cyclohexanecarboxamide | 516.1 | A |
| 430 | 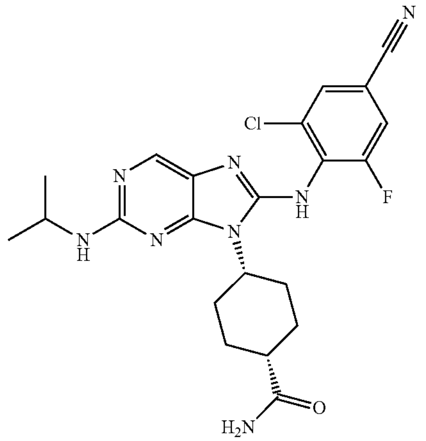 [SMILES: CC(C)Nc1ncc2nc(Nc3c(F)cc(C#N)cc3Cl)n([C@H]3CC[C@@H](C(N)=O)CC3)c2n1] | (1s,4s)-4-(8-(2-chloro-4-cyano-6-fluorophenylamino)-2-(isopropylamino)-9H-purin-9-yl)cyclohexanecarboxamide | 471.2 | B |
| 431 | 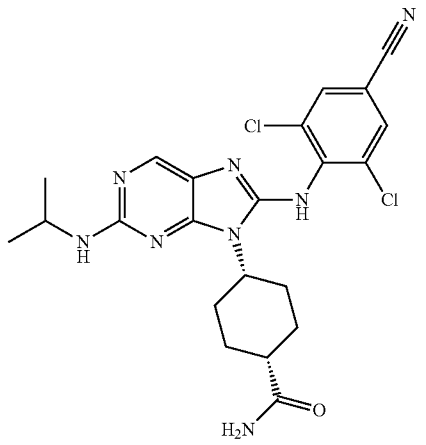 [SMILES: CC(C)Nc1ncc2nc(Nc3c(Cl)cc(C#N)cc3Cl)n([C@H]3CC[C@@H](C(N)=O)CC3)c2n1] | (1s,4s)-4-(8-(2,6-dichloro-4-cyanophenylamino)-2-(isopropylamino)-9H-purin-9-yl)cyclohexanecarboxamide | 487.2 | B |

TABLE 1-continued
| Cmpd No. | Structure | Name | MH+ | Activity |
| --- | --- | --- | --- | --- |
| 432 | 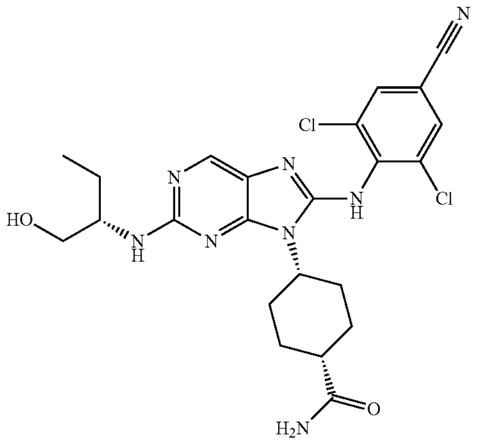 | (1R,4s)-4-(8-(2,6-dichloro-4-cyanophenylamino)-2-((S)-1-hydroxybutan-2-ylamino)-9H-purin-9-yl)-cyclohexanecarboxamide | 517.3 | B |
| 433 | 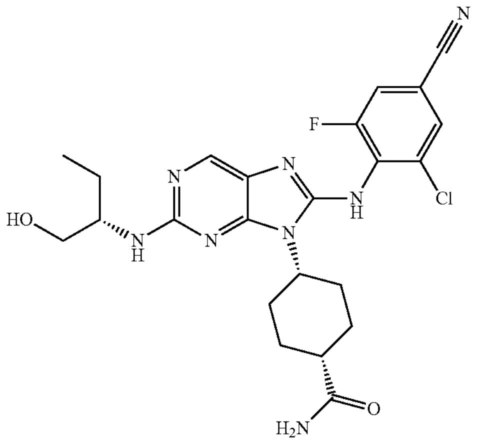 | (1R,4s)-4-(8-(2-chloro-4-cyano-6-fluorophenylamino)-2-((S)-1-hydroxybutan-2-ylamino)-9H-purin-9-yl)cyclohexanecarboxamide | 501.2 | A |
| 434 | 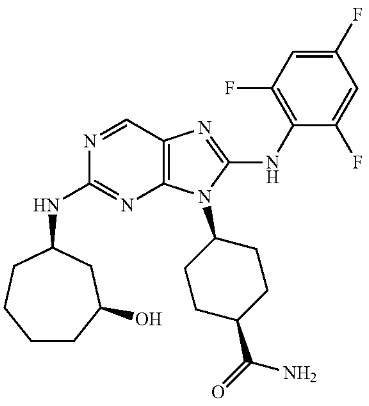 [SMILES: NC(=O)[C@H]1CC[C@@H](n2c(Nc3c(F)cc(F)cc3F)nc3cnc(N[C@@H]4CCCC[C@H](O)C4)nc32)CC1] | (1S,4s)-4-(2-((1R,3S)-3-hydroxycycloheptylamino)-8-(2,4,6-trifluorophenylamino)-9H-purin-9-yl)cyclohexanecarboxamide | 518.2 | A |

TABLE 1-continued

| Cmpd No. | Structure | Name | MH+ | Activity |
|---|---|---|---|---|
| 435 | 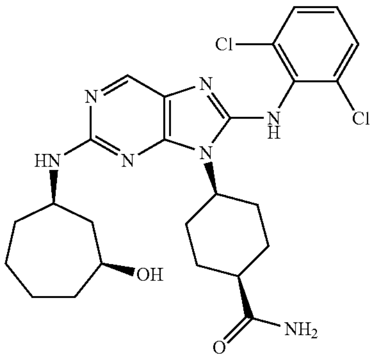 [SMILES: NC(=O)[C@H]1CC[C@@H](n2c(Nc3c(Cl)cccc3Cl)nc3cnc(N[C@@H]4CCCC[C@H](O)C4)nc32)CC1] | (1S,4s)-4-(8-(2,6-dichlorophenylamino)-2-((1R,3S)-3-hydroxycycloheptylamino)-9H-purin-9-yl)cyclohexanecarboxamide | 532.2 | A |
| 436 | 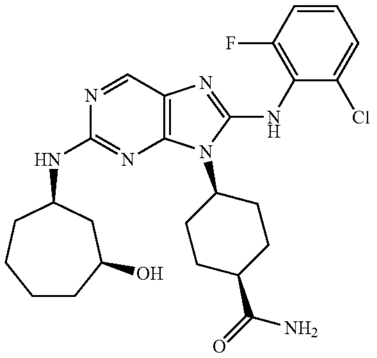 [SMILES: NC(=O)[C@H]1CC[C@@H](n2c(Nc3c(F)cccc3Cl)nc3cnc(N[C@@H]4CCCC[C@H](O)C4)nc32)CC1] | (1S,4s)-4-(8-(2-chloro--fluorophenylamino)-2-((1R,3S)-3-hydroxycycloheptylamino)-9H-purin-9-yl)cyclohexanecarboxamide | 516.3 | A |
| 437 | 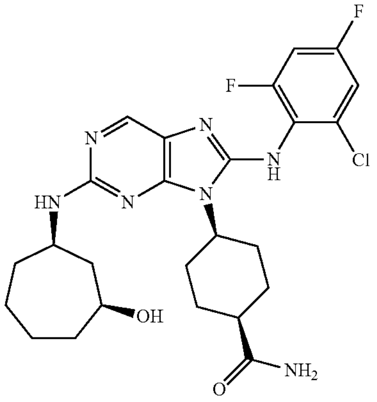 [SMILES: NC(=O)[C@H]1CC[C@@H](n2c(Nc3c(F)cc(F)cc3Cl)nc3cnc(N[C@@H]4CCCC[C@H](O)C4)nc32)CC1] | (1S,4s)-4-(8-(2-chloro-4,6-difluorophenylamino)-2-((1R,3S)-3-hydroxycycloheptylamino)-9H-purin-9-yl)cyclohexanecarboxamide | 534.2 | A |
| 438 | 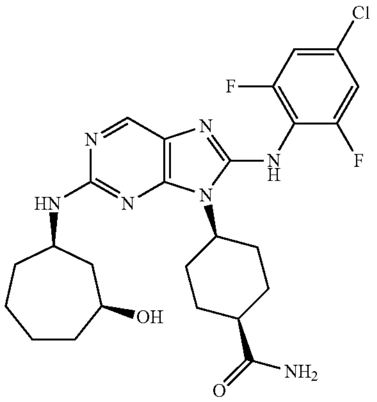 | (1S,4s)-4-(8-(4-chloro-2,6-difluorophenylamino)-2-((1R,3S)-3-hydroxycycloheptylamino)-9H-purin-9-yl)cylcohexanecarboxamide | 534 | A |

TABLE 1-continued
| Cmpd No. | Structure | Name | MH+ | Activity |
|---|---|---|---|---|
| 439 | 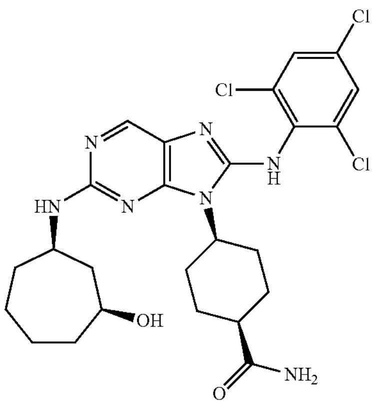 | (1S,4s)-4-(2-((1R,3S)-3-hydroxycycloheptylamino)-8-(2,4,6-trichlorophenylamino)-9H-purin-9-yl)cyclohexanecarboxamide | 566.1 | A |
| 440 | 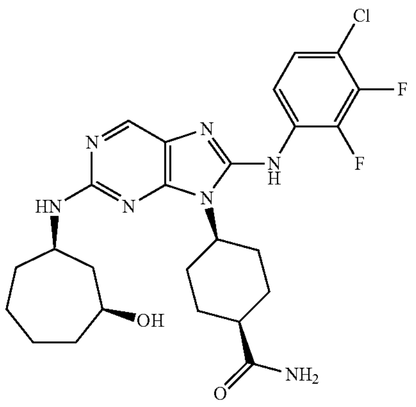 [SMILES: NC(=O)[C@H]1CC[C@@H](n2c(Nc3ccc(Cl)c(F)c3F)nc3cnc(N[C@@H]4CCCC[C@H](O)C4)nc32)CC1] | (1S,4S)-4-(8-(4-chloro-2,3-difluorophenylamino)-2-((1R,3S)-3-hydroxycycloheptylamino)-9H-purin-9-yl)cyclohexanecarboxamide | 534.2 | A |
| 441 | 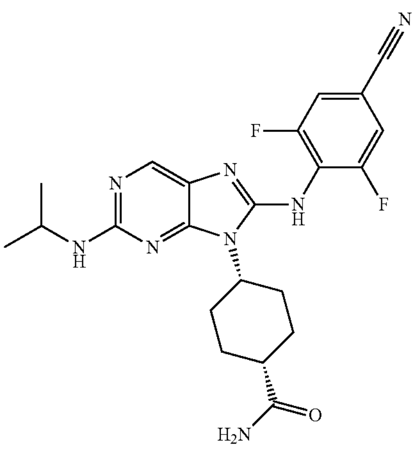 [SMILES: CC(C)Nc1ncc2nc(Nc3c(F)cc(C#N)cc3F)n([C@H]3CC[C@@H](C(N)=O)CC3)c2n1] | (1s,4s)-4-(8-(4-cyano-2,6-difluorophenylamino)-2-(isopropylamino)-9H-purin-9-yl)cyclohexanecarboxamide | 455.3 | B |

TABLE 1-continued
| Cmpd No. | Structure | Name | MH+ | Activity |
|---|---|---|---|---|
| 442 | 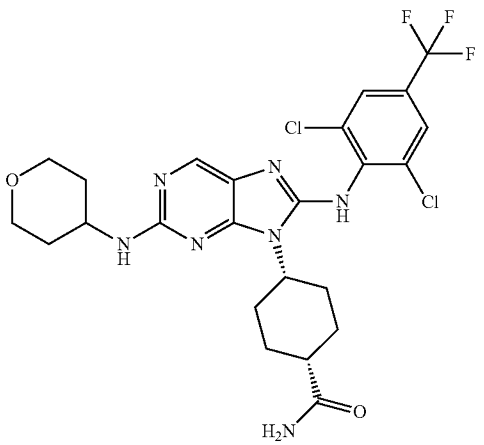 | (1s,4s)-4-(8-(2,6-dichloro-4-(trifluoromethyl)phenylamino)-2-(tetrahydro-2H-pyran-4-ylamino)-9H-purin-9-yl)cyclohexanecarboxamide | 572.3 | C |
| 443 | 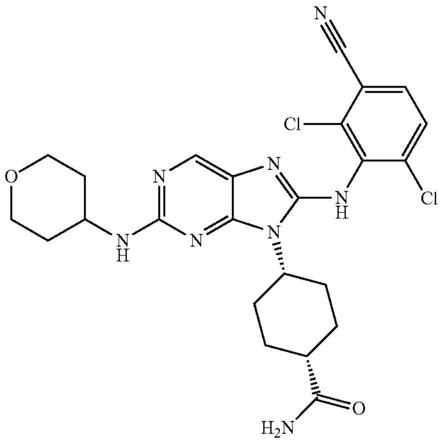 [SMILES: N#Cc1ccc(Cl)c(Nc2nc3cnc(NC4CCOCC4)nc3n2[C@H]2CC[C@@H](C(N)=O)CC2)c1Cl] | (1s,4s)-4-(8-(2,6-dichloro-3-cyanophenylamino)-2-(tetrahydro-2H-pyran-4-ylamino)-9H-purin-9-yl)cyclohexanecarboxamide | 529.2 | A |
| 444 | 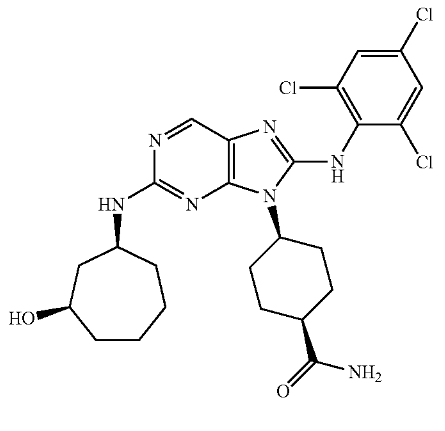 [SMILES: NC(=O)[C@H]1CC[C@@H](n2c(Nc3c(Cl)cc(Cl)cc3Cl)nc3cnc(N[C@H]4CCCC[C@@H](O)C4)nc32)CC1] | (1R,4s)-4-(2-((1S,3R)-3-hydroxycylcoheptylamino)-8-(2,4,6-trichlorophenylamino)-9H-purin-9-yl)cyclohexanecarboxamide | 566 | A |

TABLE 1-continued

| Cmpd No. | Structure | Name | MH+ | Activity |
| --- | --- | --- | --- | --- |
| 445 | 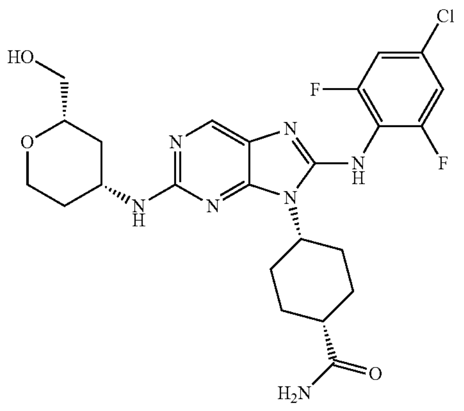 [SMILES: NC(=O)[C@H]1CC[C@@H](n2c(Nc3c(F)cc(Cl)cc3F)nc3cnc(N[C@@H]4CCO[C@H](CO)C4)nc32)CC1] | (1S,4s)-4-(8-(4-chloro-2,6-difluorophenylamino)-2-((2S,4R)-2-(hydroxymethyl)tetrahydro-2H-pyran-4-ylamino)-9H-purin-9-yl)cyclohexanecarboxamide | 536.3 | C |
| 446 | 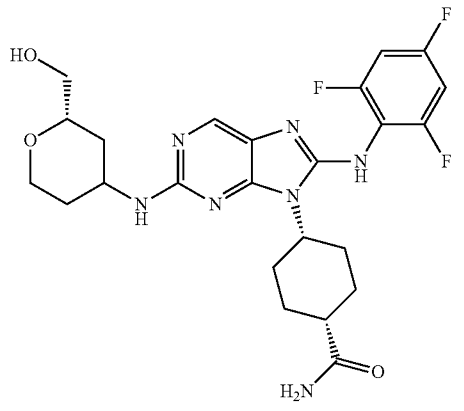 [SMILES: NC(=O)[C@H]1CC[C@@H](n2c(Nc3c(F)cc(F)cc3F)nc3cnc(NC4CCO[C@H](CO)C4)nc32)CC1] | (1S,4s)-4-(2-((2S,4R)-2-(hydroxymethyl)tetrahydro-2H-pyran-4-ylamino)-8-(2,4,6-trifluorophenylamino)-9H-purin-9-yl)cyclohexanecarboxamide | 520.3 | A |
| 447 | 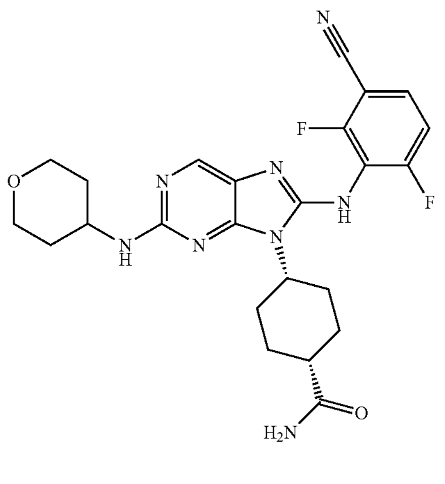 [SMILES: N#Cc1ccc(F)c(Nc2nc3cnc(NC4CCOCC4)nc3n2[C@H]2CC[C@@H](C(N)=O)CC2)c1F] | (1s,4s)-4-(8-(3-cyano-2,6-difluorophenylamino)-2-(tetrahydro-2H-pyran-4-ylamino)-9H-purin-9-yl)cyclohexanecarboxamide | 497.3 | A |

TABLE 1-continued
| Cmpd No. | Structure | Name | MH+ | Activity |
|---|---|---|---|---|
| 448 | 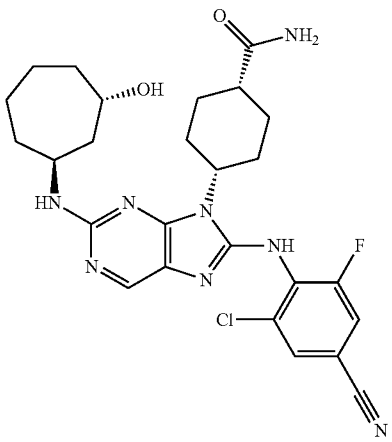 [SMILES: N#Cc1cc(F)c(Nc2nc3cnc(N[C@H]4CCCC[C@H](O)C4)nc3n2[C@H]2CC[C@@H](C(N)=O)CC2)c(Cl)c1] | (1R,4s)-4-(8-(2-chloro-4-cyano-6-fluorophenylamino)-2-((1S,3S)-3-hydroxycycloheptylamino)-9H-purin-9-yl)cyclohexanecarboxamide | 541.3 | A |
| 449 | 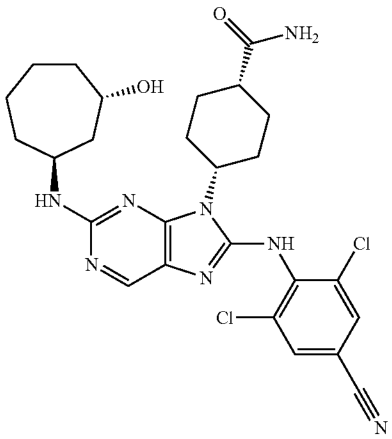 [SMILES: N#Cc1cc(Cl)c(Nc2nc3cnc(N[C@H]4CCCC[C@H](O)C4)nc3n2[C@H]2CC[C@@H](C(N)=O)CC2)c(Cl)c1] | (1R,4s)-4-(8-(2,6-dichloro-4-cyanophenylamino)-2-((1S,3S)-3-hydroxycycloheptylamino)-9H-purin-9-yl)cyclohexanecarboxamide | 557.3 | A |
| 450 | 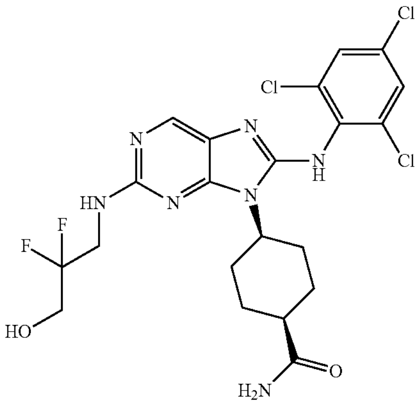 [SMILES: NC(=O)[C@H]1CC[C@@H](n2c(Nc3c(Cl)cc(Cl)cc3Cl)nc3cnc(NCC(F)(F)CO)nc32)CC1] | (1s,4s)-4-(2-(2,2-difluoro-3-hydroxypropylamino)-8-(2,4,6-trichlorophenylamino)-9H-purin-9-yl)cyclohexanecarboxamide | 548.2 | A |

TABLE 1-continued
| Cmpd No. | Structure | Name | MH+ | Activity |
|---|---|---|---|---|
| 451 | 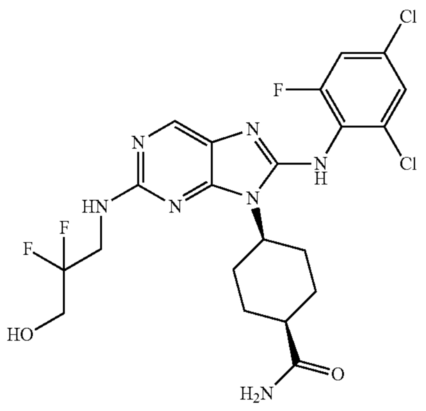 [SMILES: NC(=O)[C@H]1CC[C@@H](n2c(Nc3c(F)cc(Cl)cc3Cl)nc3cnc(NCC(F)(F)CO)nc32)CC1] | (1s,4s)-4-(8-(2,4-dichloro-6-fluorophenylamino)-2-(2,2-difluoro-3-hydroxypropylamino)-9H-purin-9-yl)cyclohexanecarboxamide | 532.2 | A |
| 452 | 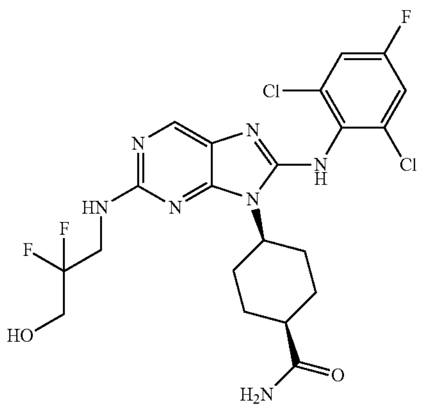 | (1s,4s)-4-(8-(2,6-dichloro-4-fluorophenylamino)-2-(2,2-difluoro-3-hydroxypropylamino)-9H-purin-9-yl)cylcohexanecarboxamide | 532 | A |
| 453 | 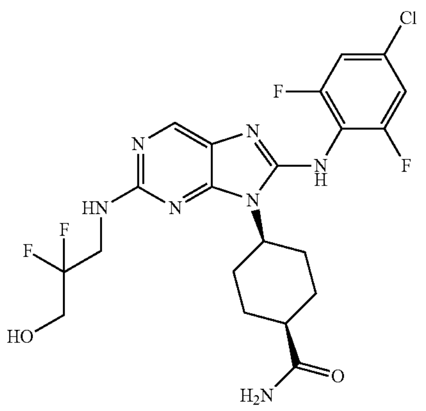 [SMILES: NC(=O)[C@H]1CC[C@@H](n2c(Nc3c(F)cc(Cl)cc3F)nc3cnc(NCC(F)(F)CO)nc32)CC1] | (1s,4s)-4-(8-(4-chloro-2,6-difluorophenylamino)-2-(2,2-difluoro-3-hydroxypropylamino)-9H-purin-9-yl)cyclohexanecarboxamide | 516.2 | A |

TABLE 1-continued

| Cmpd No. | Structure | Name | MH+ | Activity |
|---|---|---|---|---|
| 454 | 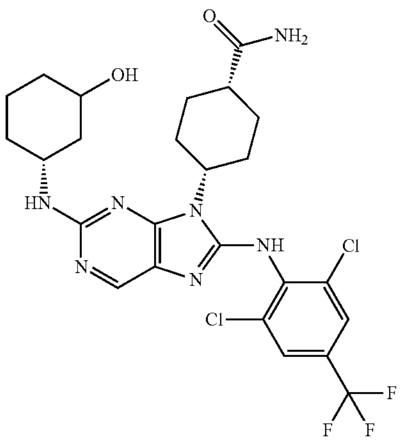 [SMILES: NC(=O)[C@H]1CC[C@@H](n2c(Nc3c(Cl)cc(C(F)(F)F)cc3Cl)nc3cnc(N[C@@H]4CCCC(O)C4)nc32)CC1] | (1S,4s)-4-(8-(2,6-dichloro-4-(trifluoromethyl)phenylamino)-2-((1R,3S)-3-hydroxycyclohexylamino)-9H-purin-9-yl)cyclohexanecarboxamide | 586.2 | B |
| 455 | 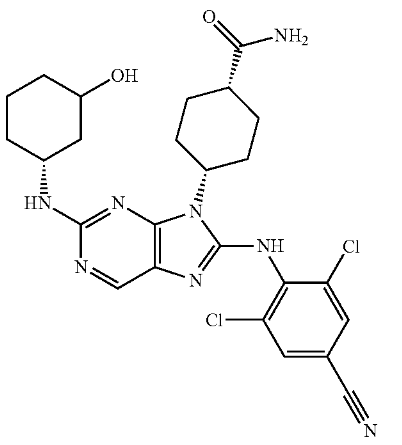 [SMILES: N#Cc1cc(Cl)c(Nc2nc3cnc(N[C@@H]4CCCC(O)C4)nc3n2[C@H]2CC[C@@H](C(N)=O)CC2)c(Cl)c1] | (1S,4s)-4-(8-(2,6-dichloro-4-cyanophenylamino)-2-((1R,3S)-3-hydroxycyclohexylamino)-9H-purin-9-yl)cyclohexanecarboxamide | 543.2 | D |
| 456 | 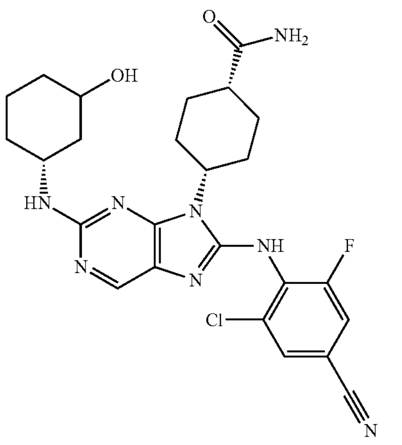 [SMILES: N#Cc1cc(F)c(Nc2nc3cnc(N[C@@H]4CCCC(O)C4)nc3n2[C@H]2CC[C@@H](C(N)=O)CC2)c(Cl)c1] | (1S,4s)-4-(8-(2-chloro-4-cyano-6-fluorophenylamino)-2-((1R,3S)-3-hydroxycyclohexylamino)-9H-purin-9-yl)cyclohexanecarboxamide | 527.3 | B |

TABLE 1-continued
| Cmpd No. | Structure | Name | MH+ | Activity |
| --- | --- | --- | --- | --- |
| 457 | 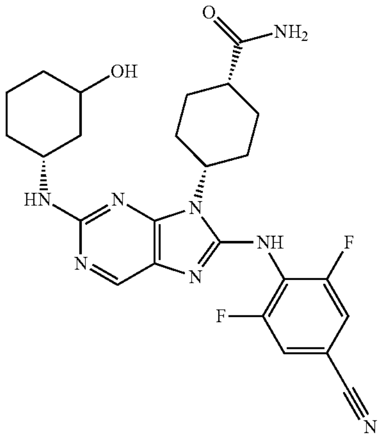 [SMILES: N#Cc1cc(F)c(Nc2nc3cnc(N[C@@H]4CCCC(O)C4)nc3n2[C@H]2CC[C@@H](C(N)=O)CC2)c(F)c1] | (1S,4s)-4-(8-(4-cyano-2,6-difluorophenylamino)-2-((1R,3S)-3-hydroxycyclohexylamino)-9H-purin-9-yl)cyclohexanecarboxamide | 511.4 | A |
| 458 | 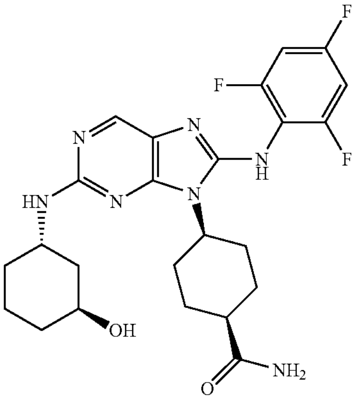 [SMILES: NC(=O)[C@H]1CC[C@@H](n2c(Nc3c(F)cc(F)cc3F)nc3cnc(N[C@H]4CCC[C@H](O)C4)nc32)CC1] | (1R,4s)-4-(2-((1S,3S)-3-hydroxycyclohexylamino)-8-(2,4,6-trifluorophenylamino)-9H-purin-9-yl)cyclohexanecarboxamide | 504.2 | A |
| 459 | 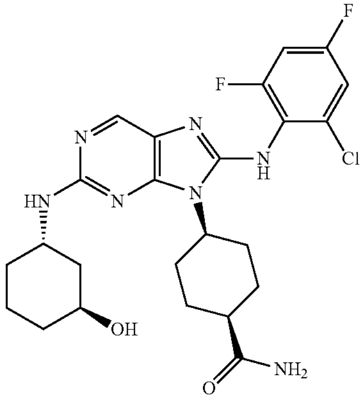 [SMILES: NC(=O)[C@H]1CC[C@@H](n2c(Nc3c(F)cc(F)cc3Cl)nc3cnc(N[C@H]4CCC[C@H](O)C4)nc32)CC1] | (1R,4s)-4-(8-(2-chloro-4,6-difluorophenylamino)-2-((1S,3S)-3-hydroxycyclohexylamino)-9H-purin-9-yl)cyclohexanecarboxamide | 520.2 | A |

TABLE 1-continued
| Cmpd No. | Structure | Name | MH+ | Activity |
|---|---|---|---|---|
| 460 | 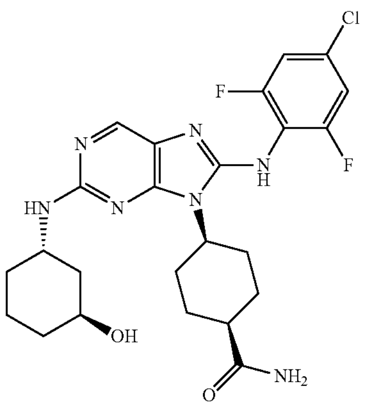 | (1R,4s)-4-(8-(4-chloro-2,6-difluorophenylamino)-2-((1S,3S)-3-hydroxycyclohexylamino)-9H-purin-9-yl)cyclohexanecarboxamide | 520.2 | A |
| 461 | 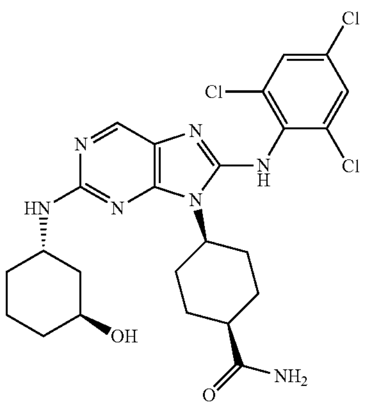 | (1R,4s)-4-(2-((1S,3S)-3-hydroxycyclohexylamino)-8-(2,4,6-trichlorophenylamino)-9H-purin-9-yl)cyclohexanecarboxamide | 552.1 | A |
| 462 | 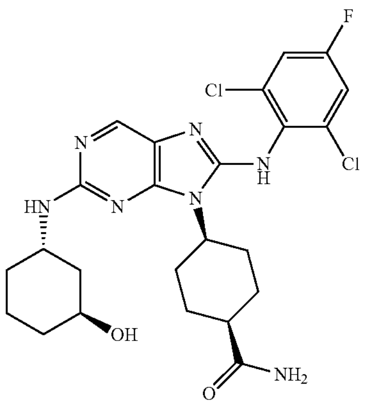 [SMILES: NC(=O)[C@H]1CC[C@@H](n2c(Nc3c(Cl)cc(F)cc3Cl)nc3cnc(N[C@H]4CCC[C@H](O)C4)nc32)CC1] | (1R,4s)-4-(8-(2,6-dichloro-4-fluorophenylamino)-2-((1S,3S)-3-hydroxycyclohexylamino)-9H-purin-9-yl)cyclohexanecarboxamide | 536.1 | A |

TABLE 1-continued
| Cmpd No. | Structure | Name | MH+ | Activity |
|---|---|---|---|---|
| 463 | 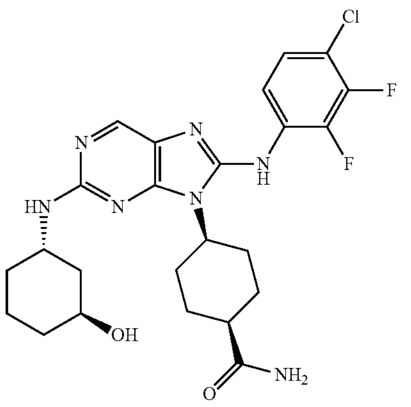 [SMILES: NC(=O)[C@H]1CC[C@@H](n2c(Nc3ccc(Cl)c(F)c3F)nc3cnc(N[C@H]4CCC[C@H](O)C4)nc32)CC1] | (1R,4s)-4-(8-(4-chloro-2,3-difluorophenylamino)-2-((1S,3S)-3-hydroxycyclohexylamino)-9H-purin-9-yl)cyclohexanecarboxamide | 520.1 | A |
| 464 | 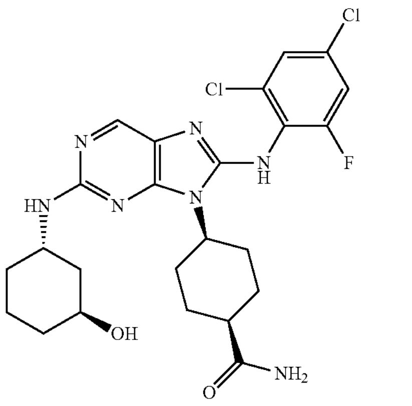 [SMILES: NC(=O)[C@H]1CC[C@@H](n2c(Nc3c(F)cc(Cl)cc3Cl)nc3cnc(N[C@H]4CCC[C@H](O)C4)nc32)CC1] | (1R,4s)-4-(8-(2,4-dichloro-6-fluorophenylamino)-2-((1S,3S)-3-hydroxycyclohexylamino)-9H-purin-9-yl)cyclohexanecarboxamide | 536.1 | B |
| 465 | 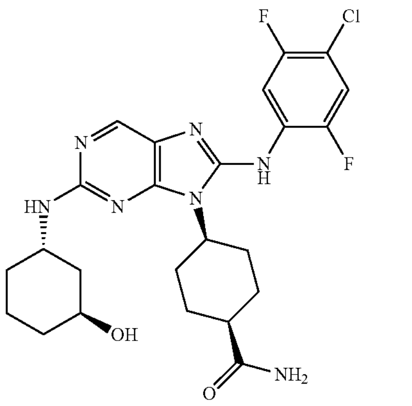 [SMILES: NC(=O)[C@H]1CC[C@@H](n2c(Nc3cc(F)c(Cl)cc3F)nc3cnc(N[C@H]4CCC[C@H](O)C4)nc32)CC1] | (1R,4s)-4-(8-(4-chloro-2,5-difluorophenylamino)-2-((1S,3S)-3-hydroxycyclohexylamino)-9H-purin-9-yl)cyclohexanecarboxamide | 520.2 | A |

TABLE 1-continued
| Cmpd No. | Structure | Name | MH+ | Activity |
| --- | --- | --- | --- | --- |
| 466 | 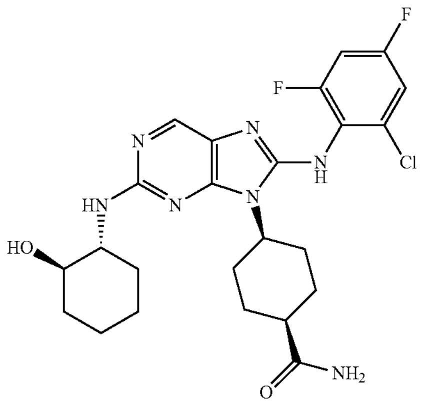 [SMILES: NC(=O)[C@H]1CC[C@@H](n2c(Nc3c(F)cc(F)cc3Cl)nc3cnc(N[C@@H]4CCCC[C@H]4O)nc32)CC1] | (1S,4s)-4-(8-(2-chloro-4,6-difluorophenylamino)-2-((1R,2R)-2-hydroxycyclohexylamino)-9H-purin-9-yl)cyclohexanecarboxamide | 520.2 | A |
| 467 | 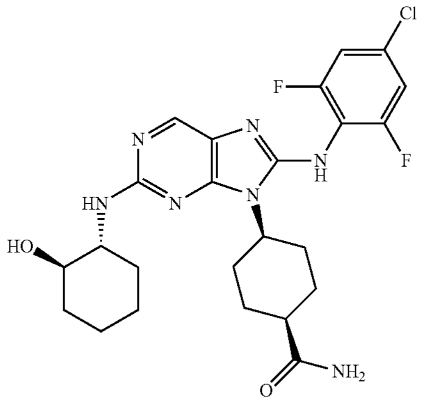 [SMILES: NC(=O)[C@H]1CC[C@@H](n2c(Nc3c(F)cc(Cl)cc3F)nc3cnc(N[C@@H]4CCCC[C@H]4O)nc32)CC1] | (1S,4s)-4-(8-(4-chloro-2,6-difluorophenylamino)-2-((1R,2R)-2-hydroxycyclohexylamino)-9H-purin-9-yl)cyclohexanecarboxamide | 520.1 | A |
| 468 | 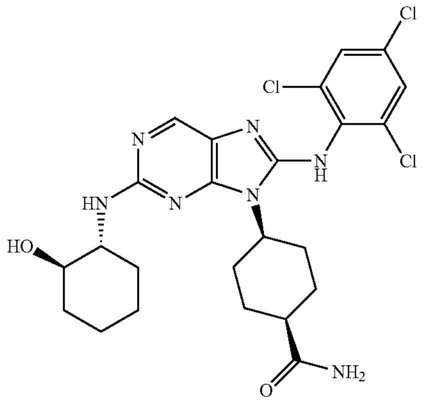 [SMILES: NC(=O)[C@H]1CC[C@@H](n2c(Nc3c(Cl)cc(Cl)cc3Cl)nc3cnc(N[C@@H]4CCCC[C@H]4O)nc32)CC1] | (1S,4S)-4-(2-((1R,2R)-2-hydroxycyclohexylamino)-8-(2,4,6-trichlorophenylamino)-9H-purin-9-yl)cyclohexanecarboxamide | 552.1 | A |

TABLE 1-continued
| Cmpd No. | Structure | Name | MH+ | Activity |
| --- | --- | --- | --- | --- |
| 469 | 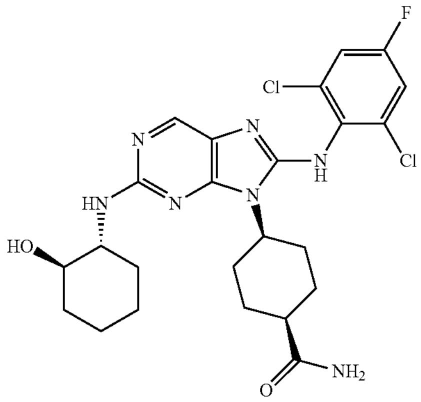 [SMILES: NC(=O)[C@H]1CC[C@@H](n2c(Nc3c(Cl)cc(F)cc3Cl)nc3cnc(N[C@@H]4CCCC[C@H]4O)nc32)CC1] | (1S,4s)-4-(8-(2,6-dichlroo-4-fluuorophenylamino)-2-((1R,2R)-2-hydroxycyclohexylamino)-9H-purin-9-yl)cyclohexanecarboxamide | 536.1 | A |
| 470 | 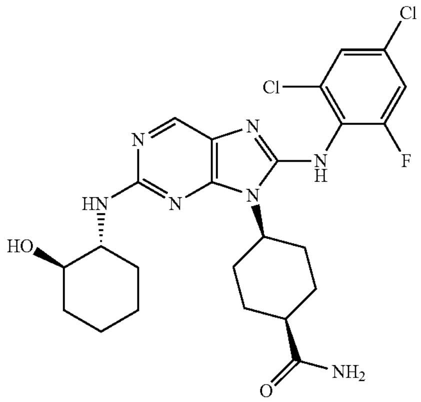 [SMILES: NC(=O)[C@H]1CC[C@@H](n2c(Nc3c(F)cc(Cl)cc3Cl)nc3cnc(N[C@@H]4CCCC[C@H]4O)nc32)CC1] | (1S,4s)-4-(8-(2,4-dichloro-6-fluorophenylamino)-2-((1R,2R)-2-hydroxycyclohexylamino)-9H-purin-9-yl)cyclohexanecarboxamide | 536.1 | A |
| 471 | 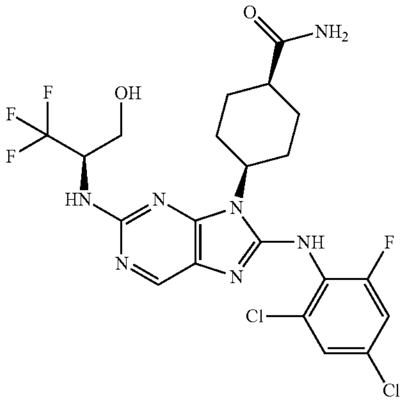 [SMILES: NC(=O)[C@H]1CC[C@@H](n2c(Nc3c(F)cc(Cl)cc3Cl)nc3cnc(N[C@H](CO)C(F)(F)F)nc32)CC1] | (1S,4s)-4-(8-(2,4-dichloro-6-fluorophenylamino)-2-((R)-1,1,1-trifluoro-3-hydroxypropan-2-ylamino)-9H-purin-9-yl)cyclohexanecarboxamide | 550.2 | A |

TABLE 1-continued

| Cmpd No. | Structure | Name | MH+ | Activity |
|---|---|---|---|---|
| 472 | 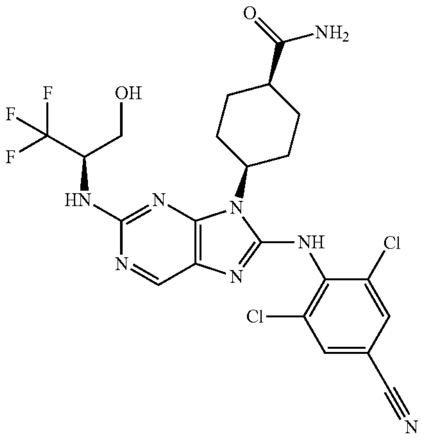 [SMILES: N#Cc1cc(Cl)c(Nc2nc3cnc(N[C@H](CO)C(F)(F)F)nc3n2[C@H]2CC[C@@H](C(N)=O)CC2)c(Cl)c1] | (1S,4s)-4-(8-(2,6-dichlroo-4-cyanophenylamino)-2-((R)-1,1,1-trifluoro-3-hydroxypropan-2-ylamino)-9H-purin-9-yl)cyclohexanecarboxamide | 557.2 | A |
| 473 | 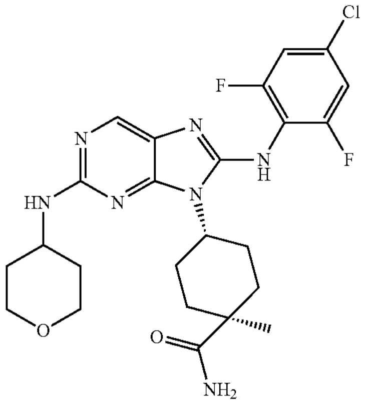 [SMILES: C[C@]1(C(N)=O)CC[C@H](n2c(Nc3c(F)cc(Cl)cc3F)nc3cnc(NC4CCOCC4)nc32)CC1] | (1r,4r)-4-(8-(4-chloro-2,6-difluorophenylamino)-2-(tetrahydro-2H-pyran-4-ylamino)-9H-purin-9-yl)-1-methylcyclohexanecarboxamide | 520.2 | A |
| 474 | 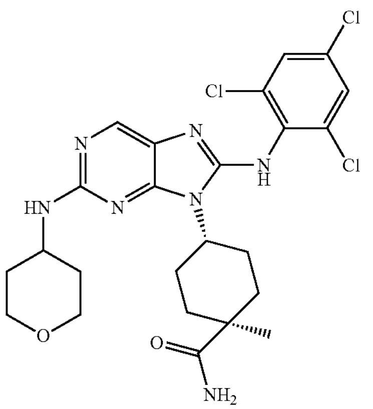 [SMILES: C[C@]1(C(N)=O)CC[C@H](n2c(Nc3c(Cl)cc(Cl)cc3Cl)nc3cnc(NC4CCOCC4)nc32)CC1] | (1r,4r)-1-methyl-4-(2-(tetrahydro-2H-pyran-4-ylamino)-8-(2,,46-trichlorophenylamino)-9H-purin-9-yl)cyclohexanecarboxamide | 552.2 | A |

TABLE 1-continued

| Cmpd No. | Structure | Name | MH+ | Activity |
|---|---|---|---|---|
| 475 | 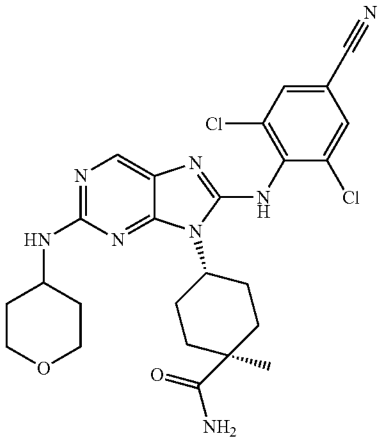 [SMILES: C[C@]1(C(N)=O)CC[C@H](n2c(Nc3c(Cl)cc(C#N)cc3Cl)nc3cnc(NC4CCOCC4)nc32)CC1] | (1r,4r)-4-(8-(2,6-dichloro-4-cyanophenylamino)-2-(tetrahydro-2H-pyran-4-ylamino)-9H-purin-9-yl)-1-methylcyclohexanecarboxamide | 543.2 | B |
| 476 | 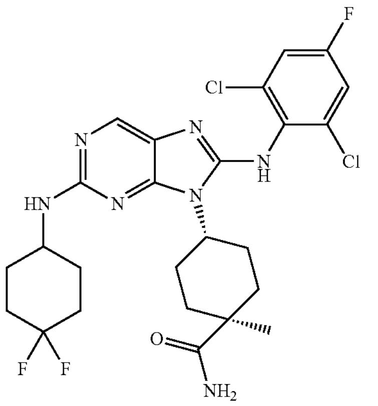 [SMILES: C[C@]1(C(N)=O)CC[C@H](n2c(Nc3c(Cl)cc(F)cc3Cl)nc3cnc(NC4CCC(F)(F)CC4)nc32)CC1] | (1r,4r)-4-(8-(2,6-dichloro-4-fluorophenylamino)-2-(4,4-difluorocyclohexylamino)-9H-purin-9-yl)-1-methylcyclohexanecarboxamide | 570.2 | A |
| 477 | 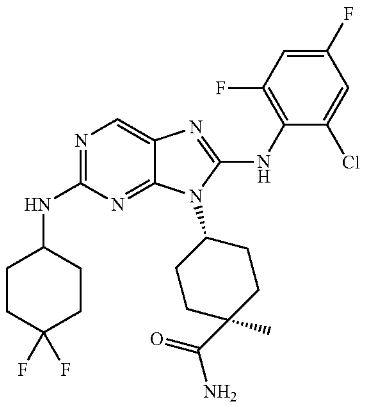 [SMILES: C[C@]1(C(N)=O)CC[C@H](n2c(Nc3c(F)cc(F)cc3Cl)nc3cnc(NC4CCC(F)(F)CC4)nc32)CC1] | (1r,4r)-4-(8-(2-chloro-4,6-difluorophenylamino)-2-(4,4-difluorocyclohexylamino)-9H-purin-9-yl)-1-methylcyclohexanecarboxamide | 554.2 | A |

TABLE 1-continued

| Cmpd No. | Structure | Name | MH+ | Activity |
| --- | --- | --- | --- | --- |
| 478 | 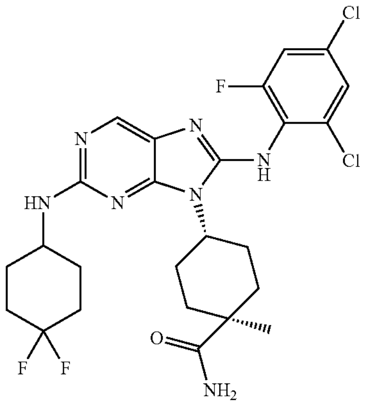 [SMILES: C[C@]1(C(N)=O)CC[C@H](n2c(Nc3c(F)cc(Cl)cc3Cl)nc3cnc(NC4CCC(F)(F)CC4)nc32)CC1] | (1r,4r)-4-(8-(2,4-dichloro-6-fluorophenylamino)-2-(4,4-difluorocyclohexylamino)-9H-purin-9-yl)-1-methylcyclohexanecarboxamide | 570.2 | A |
| 479 | 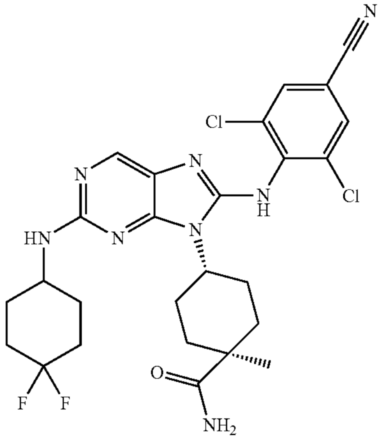 [SMILES: C[C@]1(C(N)=O)CC[C@H](n2c(Nc3c(Cl)cc(C#N)cc3Cl)nc3cnc(NC4CCC(F)(F)CC4)nc32)CC1] | (1r,4r)-4-(8-(2,6-dichloro-4-cyanophenylamino)-2-(4,4-difluorocyclohexylamino)-9H-purin-9-yl)-1-methylcyclohexanecarboxamide | 577.2 | A |
| 480 | 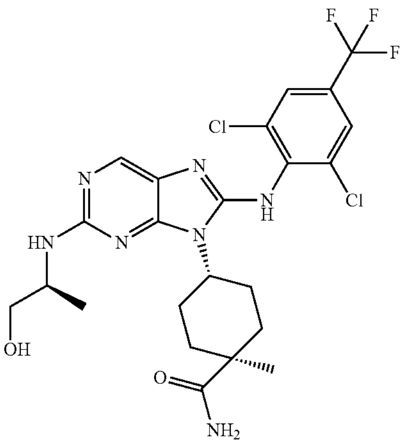 [SMILES: C[C@@H](CO)Nc1ncc2nc(Nc3c(Cl)cc(C(F)(F)F)cc3Cl)n([C@H]3CC[C@](C)(C(N)=O)CC3)c2n1] | (1S,4r)-4-(8-(2,6-dichloro-4-(trifluoromethyl)phenylamino)-2-((S)-1-hydroxypropan-2-ylamino)-9H-purin-9-yl)-1-methylcyclohexanecarboxamide | 560.2 | A |

TABLE 1-continued
| Cmpd No. | Structure | Name | MH+ | Activity |
|---|---|---|---|---|
| 481 | 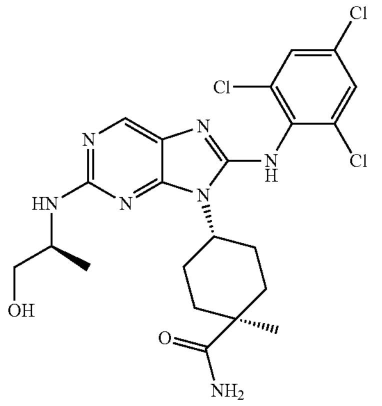 [SMILES: C[C@@H](CO)Nc1ncc2nc(Nc3c(Cl)cc(Cl)cc3Cl)n([C@H]3CC[C@](C)(C(N)=O)CC3)c2n1] | (1S,4r)-4-(2-((S)-1-hydroxypropan-2-ylamino)-8-(2,4,6-trichlorophenylamino)-9H-purin-9-yl)-1-methylcyclohexanecarboxamide | 526.2 | A |
| 482 | 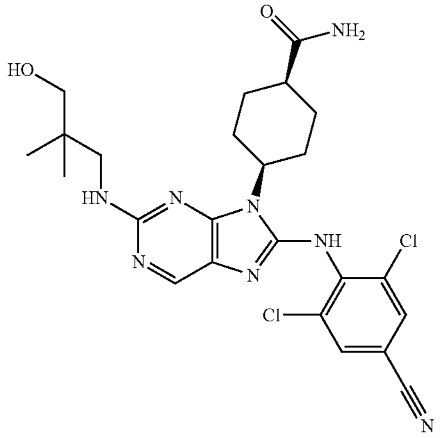 [SMILES: CC(C)(CO)CNc1ncc2nc(Nc3c(Cl)cc(C#N)cc3Cl)n([C@H]3CC[C@@H](C(N)=O)CC3)c2n1] | (1s,4s)-4-(8-(2,6-dichlroo-4-cyanophenylamino)-2-(3-hydroxy-2,2-dimethylpropylamino)-9H-purin-9-yl)cyclohexanecarboxamide | 531.2 | A |
| 483 | 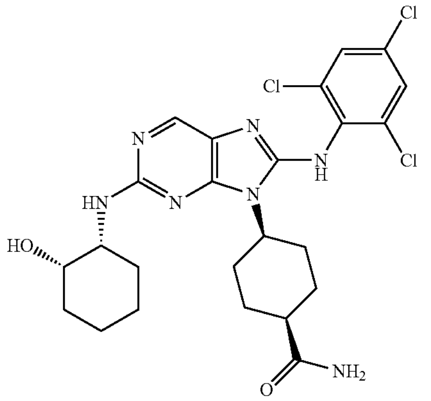 [SMILES: NC(=O)[C@H]1CC[C@@H](n2c(Nc3c(Cl)cc(Cl)cc3Cl)nc3cnc(N[C@@H]4CCCC[C@@H]4O)nc32)CC1] | (1S,4s)-4-(2-((1R,2S)-2-hydroxycyclohexylamino)-8-(2,4,6-trichlorophenylamino)-9H-purin-9-yl)cyclohexanecarboxamide | 552.2 | A |

TABLE 1-continued
| Cmpd No. | Structure | Name | MH+ | Activity |
|---|---|---|---|---|
| 484 | 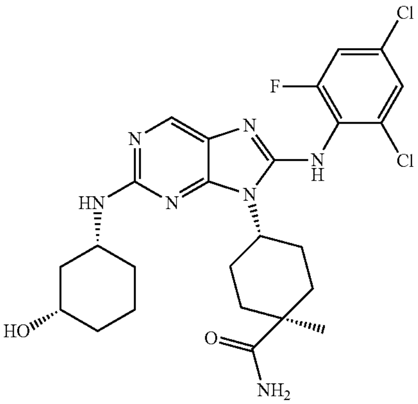 [SMILES: C[C@]1(C(N)=O)CC[C@H](n2c(Nc3c(F)cc(Cl)cc3Cl)nc3cnc(N[C@@H]4CCC[C@H](O)C4)nc32)CC1] | (1R,4r)-4-(8-(2,4-dichloro-6-fluorophenylamino)-2-((1R,3S)-3-hydroxycyclohexylamino)-9H-purin-9-yl)-1-methylcyclohexanecarboxamide | 550.2 | A |
| 485 | 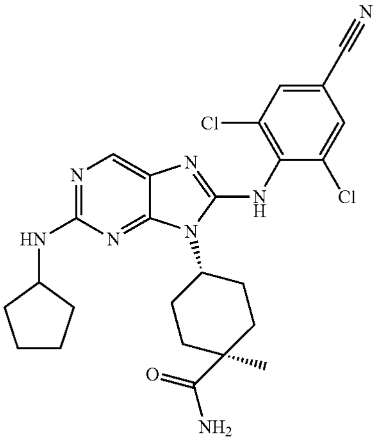 [SMILES: C[C@]1(C(N)=O)CC[C@H](n2c(Nc3c(Cl)cc(C#N)cc3Cl)nc3cnc(NC4CCCC4)nc32)CC1] | (1r,4r)-4-(2-(cyclopentylamino)-8-(2,6-dichloro-4-cyanophenylamino)-9H-purin-9-yl)-1-methylcyclohexanecarboxamide | 527.2 | B |
| 486 | 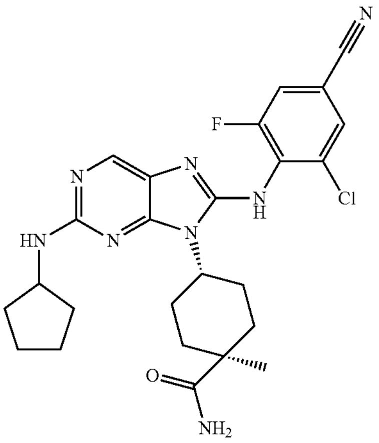 [SMILES: C[C@]1(C(N)=O)CC[C@H](n2c(Nc3c(F)cc(C#N)cc3Cl)nc3cnc(NC4CCCC4)nc32)CC1] | (1r,4r)-4-(8-(2-chloro-4-cyano-6-fluorophenylamino)-2-(cyclopentylamino)-9H-purin-9-yL)-1-methylcyclohexanecarboxamide | 511.3 | B |

TABLE 1-continued
| Cmpd No. | Structure | Name | MH+ | Activity |
|---|---|---|---|---|
| 487 | 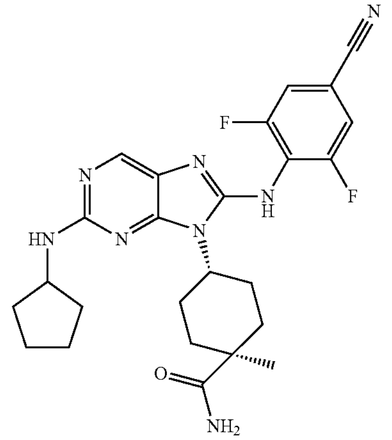 [SMILES: C[C@]1(C(N)=O)CC[C@H](n2c(Nc3c(F)cc(C#N)cc3F)nc3cnc(NC4CCCC4)nc32)CC1] | (1r,4r)-4-(8-(4-cyano-2,6-difluorophenylamino)-2-(cyclopentylamino)-9H-purin-9-yl)-1-methylcyclohexanecarboxamide | 495.2 | A |
| 488 | 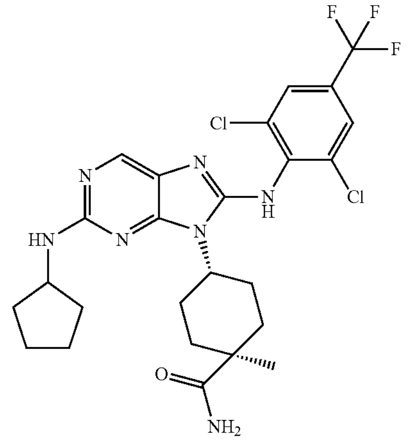 [SMILES: C[C@]1(C(N)=O)CC[C@H](n2c(Nc3c(Cl)cc(C(F)(F)F)cc3Cl)nc3cnc(NC4CCCC4)nc32)CC1] | (1r,4r)-4-(2-(cyclopentylamino)-8-(2,6-dichloro-4-(trifluoromethyl)phenylamino)-9H-purin-9-yl)-1-methylcyclohexanecarboxamide | 570.2 | A |
| 489 | 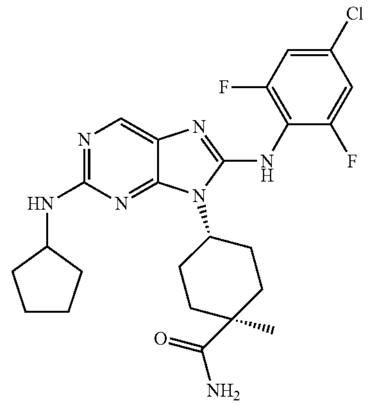 [SMILES: C[C@]1(C(N)=O)CC[C@H](n2c(Nc3c(F)cc(Cl)cc3F)nc3cnc(NC4CCCC4)nc32)CC1] | (1r,4r)-4-(8-(4-chloro-2,6-difluorophenylamino)-2-(cyclopentylamino)-9H-purin-9-yl)-1-methylcyclohexanecarboxamide | 504.2 | A |

TABLE 1-continued
| Cmpd No. | Structure | Name | MH+ | Activity |
|---|---|---|---|---|
| 490 | 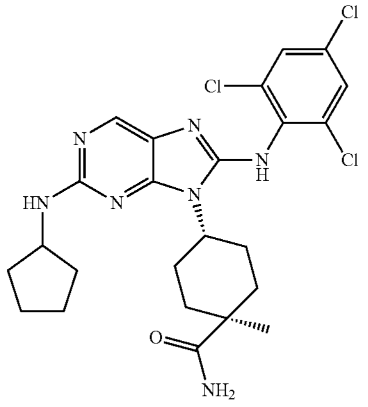 [SMILES: C[C@]1(C(N)=O)CC[C@H](n2c(Nc3c(Cl)cc(Cl)cc3Cl)nc3cnc(NC4CCCC4)nc32)CC1] | (1r,4r)-4-(2-(cyclopentylamino)-8-(2,4,6-trichlorophenylamino)-9H-purin-9-yl)-1-methylcyclohexanecarboxamide | 536.2 | A |
| 491 | 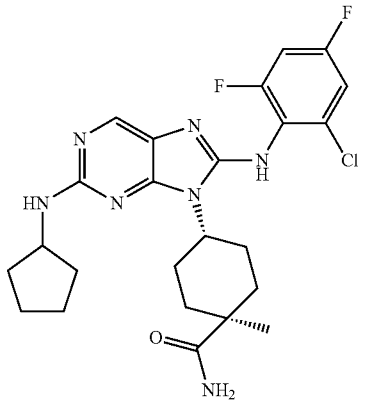 [SMILES: C[C@]1(C(N)=O)CC[C@H](n2c(Nc3c(F)cc(F)cc3Cl)nc3cnc(NC4CCCC4)nc32)CC1] | (1r,4r)-4-(8-(2-chloro-4,6-difluorophenylamino)-2-(cyclopentylamino)-9H-purin-9-yl)-1-methylcyclohexanecarboxamide | 504.3 | A |
| 492 | 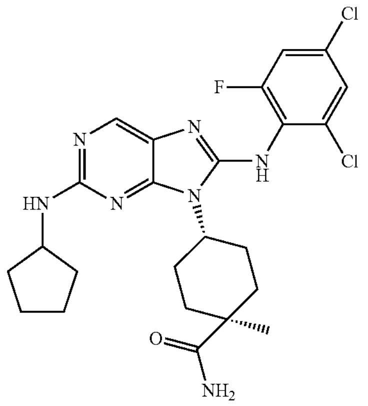 [SMILES: C[C@]1(C(N)=O)CC[C@H](n2c(Nc3c(F)cc(Cl)cc3Cl)nc3cnc(NC4CCCC4)nc32)CC1] | (1r,4r)-4-(2-(cyclopentyalmino)-8-(2,4-dichloro-6-fluorophenylamino)-9H-purin-9-yl)-1-methylcyclohexanecarboxamide | 520.2 | B |

TABLE 1-continued
| Cmpd No. | Structure | Name | MH+ | Activity |
| --- | --- | --- | --- | --- |
| 493 | 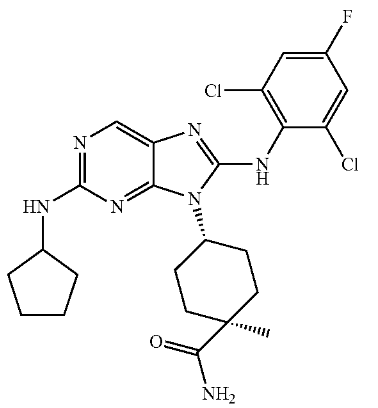 [SMILES: C[C@]1(C(N)=O)CC[C@H](n2c(Nc3c(Cl)cc(F)cc3Cl)nc3cnc(NC4CCCC4)nc32)CC1] | (1r,4r)-4-(2-(cyclopentylamino)-8-(2,6-dichloro-4-fluorophenylamino)-9H-purin-9-yl)-1-methylcyclohexanecarboxamide | 520.2 | A |
| 494 | 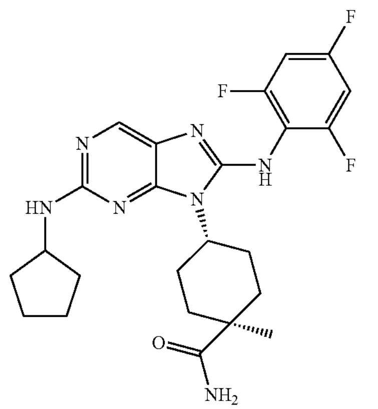 [SMILES: C[C@]1(C(N)=O)CC[C@H](n2c(Nc3c(F)cc(F)cc3F)nc3cnc(NC4CCCC4)nc32)CC1] | (1r,4r)-4-(2-(cyclopentylamino)-8-(2,4,6-trifluorophenylamino)-9H-purin-9-yl)-1-methylcyclohexanecarboxamide | 488.3 | A |
| 495 | 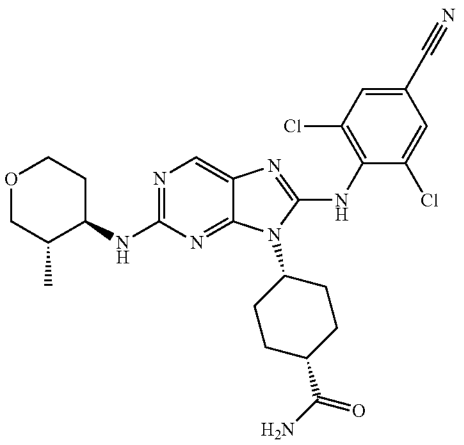 [SMILES: C[C@@H]1COCC[C@H]1Nc1ncc2nc(Nc3c(Cl)cc(C#N)cc3Cl)n([C@H]3CC[C@@H](C(N)=O)CC3)c2n1] | (1S,4s)-4-(8-(2,6-dichloro-4-cyanophenylamino)-2-((3S,4R)-3-methyltetrahydro-2H-pyran-4-ylamino)-9H-purin-9-yl)cyclohexanecarboxamide | 543.3 | D |

TABLE 1-continued

| Cmpd No. | Structure | Name | MH+ | Activity |
|---|---|---|---|---|
| 496 | 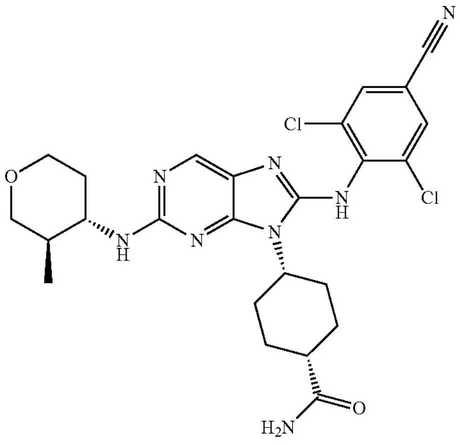 | (1R,4s)-4-(8-(2,6-dichloro-4-cyanophenylamino)-2-((3R,4S)-3-methyltetrahydro-2H-pyran-4-ylamino)-9H-purin-9-yl)cyclohexanecarboxamide | 543.2 | C |
| 497 | 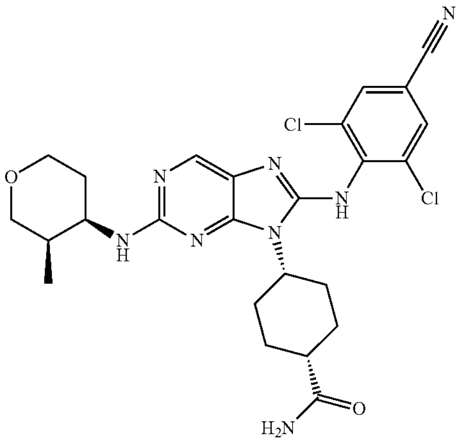 [SMILES: C[C@H]1COCC[C@H]1Nc1ncc2nc(Nc3c(Cl)cc(C#N)cc3Cl)n([C@H]3CC[C@@H](C(N)=O)CC3)c2n1] | (1S,4s)-4-(8-(2,6-dichloro-4-cyanophenylamino)-2-((3R,4R)-3-methyltetrahydro-2H-pyran-4-ylamino)-9H-purin-9-yl)cyclohexanecarboxamide | 543.3 | D |
| 498 | 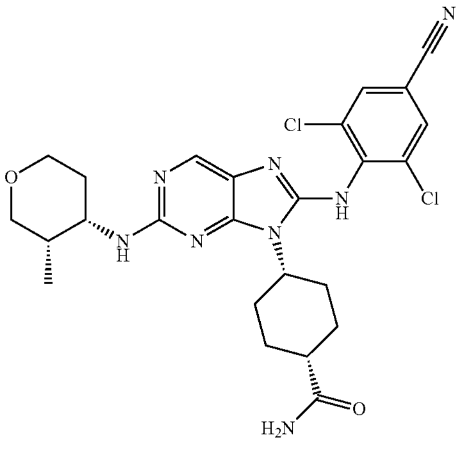 | (1R,4s)-4-(8-(2,6-dichloro-4-cyanophenylamino)-2-((3S,4S)-3-methyltetrahydro-2H-pyran--4 ylamino)-9H-purin-9-yl)cyclohexanecarboxamide | 543.3 | C |

TABLE 1-continued
| Cmpd No. | Structure | Name | MH+ | Activity |
| --- | --- | --- | --- | --- |
| 499 | 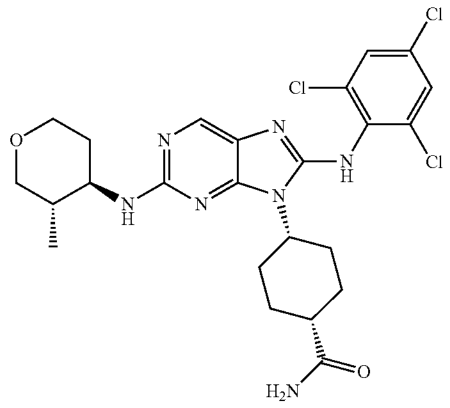 [SMILES: C[C@@H]1COCC[C@H]1Nc1ncc2nc(Nc3c(Cl)cc(Cl)cc3Cl)n([C@H]3CC[C@@H](C(N)=O)CC3)c2n1] | (1S,4s)-4-(2-((3S,4R)-3-methyltetrahydro-2H-pyran-4-ylamino)-8-(2,4,6-trichlorophenylamino)-9H-purin-9-yl)cyclohexanecarboxamide | 552.2 | D |
| 500 | 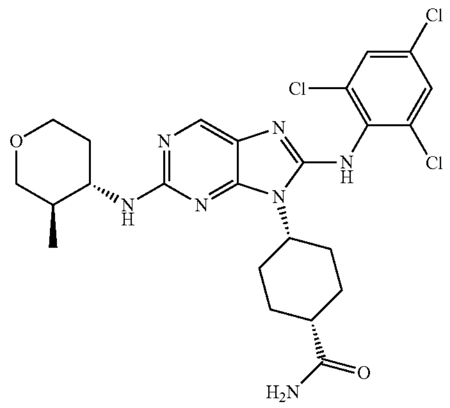 [SMILES: C[C@H]1COCC[C@@H]1Nc1ncc2nc(Nc3c(Cl)cc(Cl)cc3Cl)n([C@H]3CC[C@@H](C(N)=O)CC3)c2n1] | (1R,4s)-4-(2-((3R,4S)-3-methyltetrahydro-2H-pyran-4-ylamino)-8-(2,4,6-trichlorophenylamino)-9H-purin-9-yl)cyclohexanecarboxamide | 552.2 | B |
| 501 | 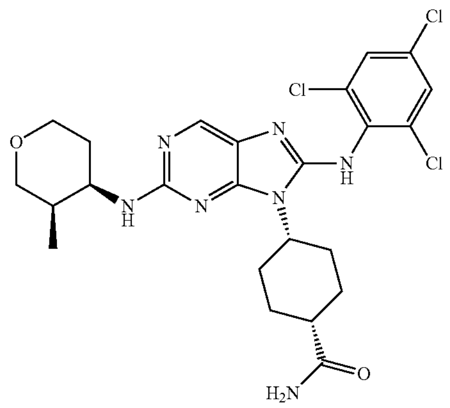 [SMILES: C[C@H]1COCC[C@H]1Nc1ncc2nc(Nc3c(Cl)cc(Cl)cc3Cl)n([C@H]3CC[C@@H](C(N)=O)CC3)c2n1] | (1S,4s)-4-(2-((3R,4R)-3-methyltetrahydro-2H-pyran-4-ylamino)-8-(2,4,6-trichlorophenylamino)-9H-purin-9-yl)cyclohexanecarboxamide | 552.2 | C |

TABLE 1-continued

| Cmpd No. | Structure | Name | MH+ | Activity |
|---|---|---|---|---|
| 502 | 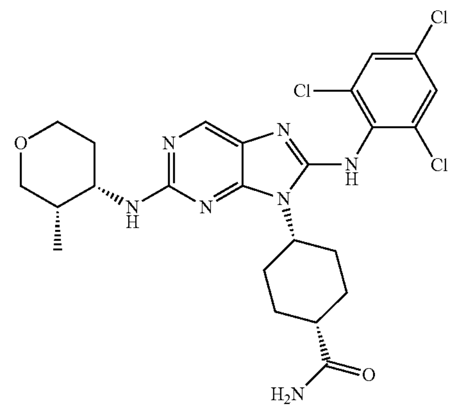 [SMILES: C[C@@H]1COCC[C@@H]1Nc1ncc2nc(Nc3c(Cl)cc(Cl)cc3Cl)n([C@H]3CC[C@@H](C(N)=O)CC3)c2n1] | (1R,4s)-4-(2-((3S,4S)-3-methyltetrahydro-2H-pyran-4-ylamino)-8-(2,4,6-trichlorophenylamino)-9H-purin-9-yl)cyclohexanecarboxamide | 552.2 | C |
| 503 | 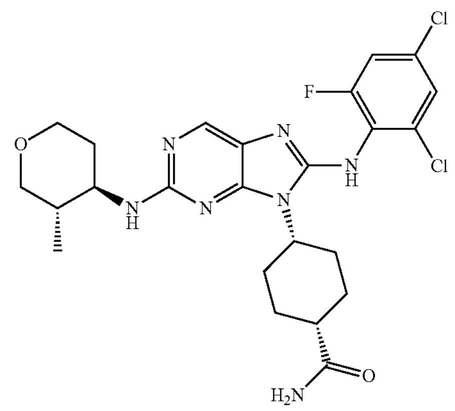 | (1S,4s)-4-(8-(2,4-dichloro-6-fluorophenylamino)-2-((3S,4R)-3-methyltetrahydro-2H-pyran-4-ylamino)-9H-purin-9-yl)cyclohexanecarboxamide | 536.2 | D |
| 504 | 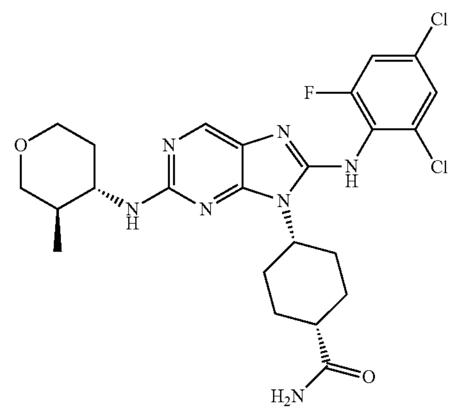 [SMILES: C[C@H]1COCC[C@@H]1Nc1ncc2nc(Nc3c(F)cc(Cl)cc3Cl)n([C@H]3CC[C@@H](C(N)=O)CC3)c2n1] | (1R,4S)-4-(8-(2,4-dichloro-6-fluorophenylamino)-2-((3R,4S)-3-methyltetrahydro-2H-pyran-4-ylamino)-9H-purin-9-yl)cyclohexanecarboxamide | 536.2 | B |

TABLE 1-continued

| Cmpd No. | Structure | Name | MH+ | Activity |
| --- | --- | --- | --- | --- |
| 505 | 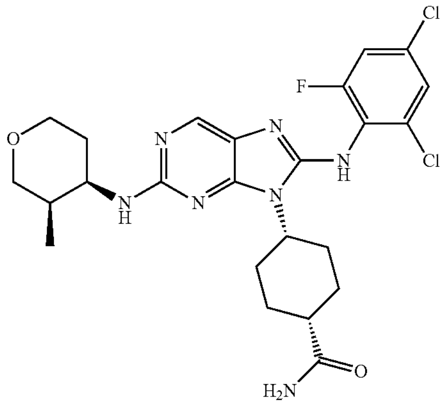 [SMILES: C[C@H]1COCC[C@H]1Nc1ncc2nc(Nc3c(F)cc(Cl)cc3Cl)n([C@H]3CC[C@@H](C(N)=O)CC3)c2n1] | (1S,4s)-4-(8-(2,4-dichloro-6-fluorophenylamino)-2-((3R,4R)-3-methyltetrahydro-2H-pyran-4-ylamino)-9H-purin-9-yl)cyclohexanecarboxamide | 536.2 | C |
| 506 | 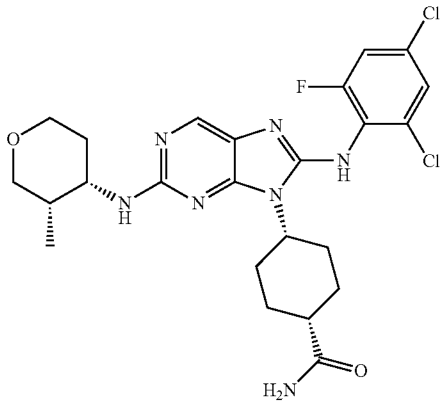 | (1R,4s)-4-(8-(2,4-dichloro-6-fluorophenylamino)-2-((3S,4S)-3-methyltetrahydro-2H-pyran-4-ylamino)-9H-purin-9-yl)cyclohexanecarboxamide | 536.2 | C |
| 507 | 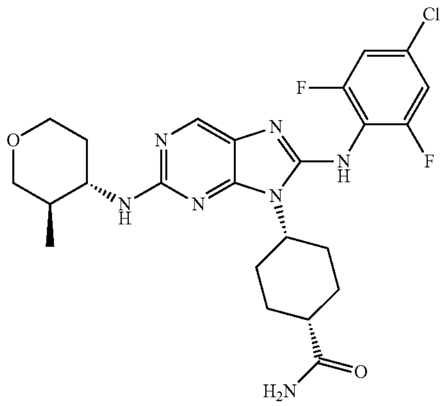 [SMILES: C[C@H]1COCC[C@@H]1Nc1ncc2nc(Nc3c(F)cc(Cl)cc3F)n([C@H]3CC[C@@H](C(N)=O)CC3)c2n1] | (1R,4s)-4-(8-(4-chloro-2,6-difluorophenylamino)-2-((3R,4S)-3-methyltetrahydro-2H-pyran-4-ylamino)-9H-purin-9-yl)cyclohexanecarboxamide | 520.3 | A |

TABLE 1-continued

| Cmpd No. | Structure | Name | MH+ | Activity |
|---|---|---|---|---|
| 508 | 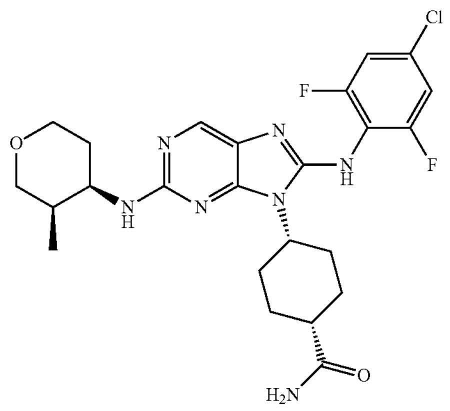 [SMILES: C[C@H]1COCC[C@H]1Nc1ncc2nc(Nc3c(F)cc(Cl)cc3F)n([C@H]3CC[C@@H](C(N)=O)CC3)c2n1] | (1S,4s)-4-(8-(4-chloro-2,6-difluorophenylamino)-2-((3R,4R)-3-methyltetrahydro-2H-pyran-4-ylamino)-9H-purin-9-yl)cyclohexanecarboxamide | 520.3 | B |
| 509 | 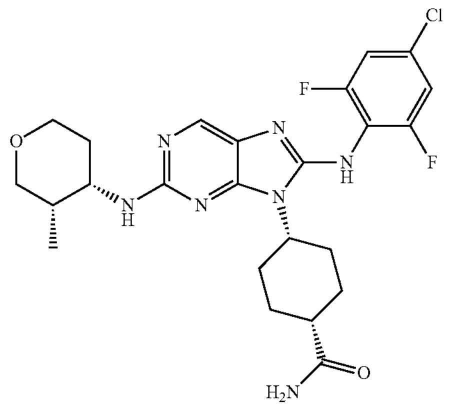 | (1R,4S)-4-(8-(4-chloro-2,6-difluorophenylamino)-2-((3S,4S)-3-methyltetrahydro-2H-pyran-4-ylamino)-9H-purin-9-yl)cyclohexanecarboxamide | 520.3 | B |
| 510 | 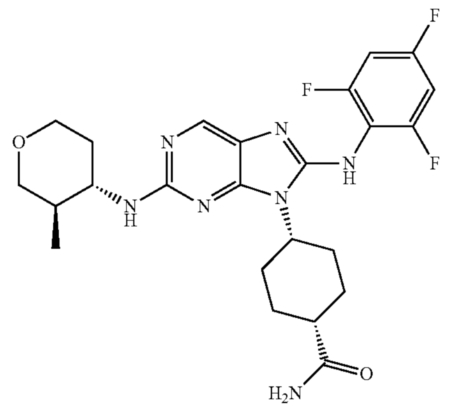 | (1R,4s)-4-(2-((3R,4S)-3-methyltetrahydro-2H-pyran-4-ylamino)-8-(2,4,6-trifluorophenylamino)-9H-purin-9-yl)cyclohexanecarboxamide | 504.3 | A |

TABLE 1-continued
| Cmpd No. | Structure | Name | MH+ | Activity |
|---|---|---|---|---|
| 511 | 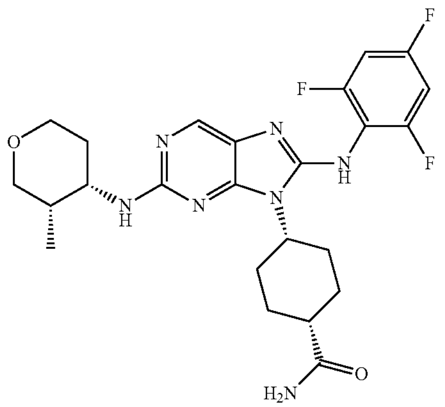 | (1R,4s)-4-(2-((3S,4S)-3-methyltetrahydro-2H-pyran-4-ylamino)-8-(2,4,6-trifluorophenylamino)-9H-purin-9-yl)cyclohexanecarboxamide | 504.3 | B |
| 512 | 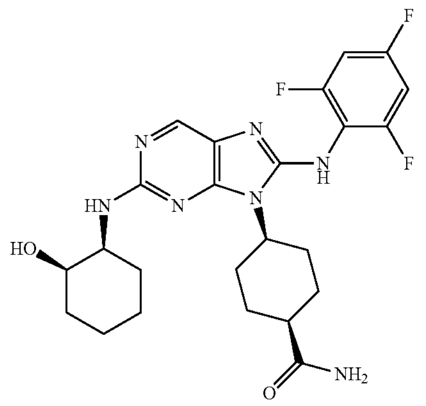 [SMILES: NC(=O)[C@H]1CC[C@@H](n2c(Nc3c(F)cc(F)cc3F)nc3cnc(N[C@H]4CCCC[C@H]4O)nc32)CC1] | (1R,4s)-4-(2-((1S,2R)-2-hydroxycyclohexylamino)-8-(2,4,6-trifluorophenylamino)-9H-purin-9-yl)cyclohexanecarboxamide | 504.1 | A |
| 513 | 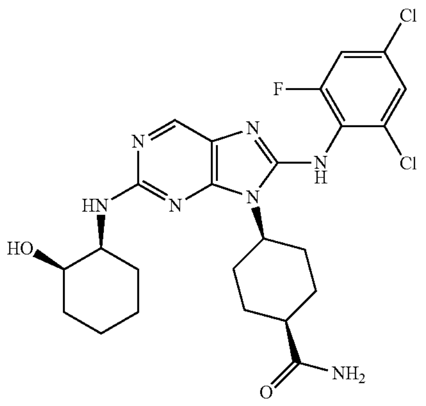 | (1R,4s)-4-(8-(2,4-dichloro-6-fluorophenylamino)-2-((1S,2R)-2-hydroxycyclohexylamino)-9H-purin-9-yl)cyclohexanecarboxamide | 536.1 | A |

TABLE 1-continued
| Cmpd No. | Structure | Name | MH+ | Activity |
|---|---|---|---|---|
| 514 | 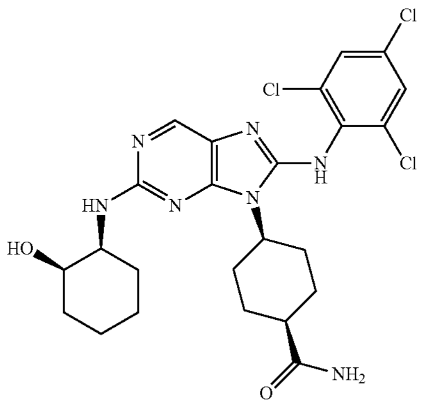 | (1R,4s)-4-(2-((1S,2R)-2-hydroxycyclohexylamino)-8-(2,4,6-trichlorophenylamino)-9H-purin-9-yl)cyclohexanecarboxamide | 552.1 | A |
| 515 | 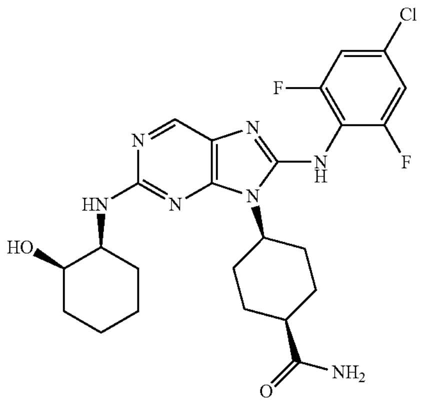 | (1R,4s)-4-(8-(4-chloro-2,6-difluorophenylamino)-2-((1S,2R)-2-hydroxycyclohexylamino)-9H-purin-9-yl)cyclohexanecarboxamide | 520.1 | A |
| 516 | 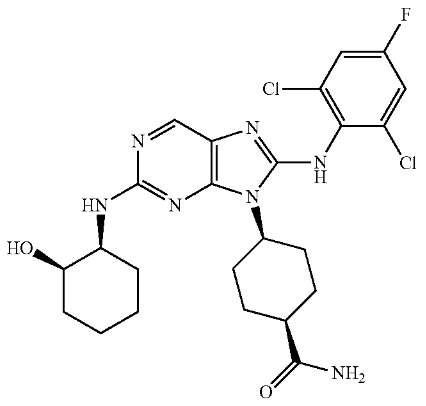 [SMILES: NC(=O)[C@H]1CC[C@@H](n2c(Nc3c(Cl)cc(Cl)cc3Cl)nc3cnc(N[C@H]4CCCC[C@H]4O)nc32)CC1] | (1R,4s)-4-(8-(2,6-dichloro-4-fluorophenylamino)-2-((1S,2R)-2-hydroxycyclohexylamino)-9H-purin-9-yl)cyclohexanecarboxamide | 536.1 | A |

TABLE 1-continued
| Cmpd No. | Structure | Name | MH+ | Activity |
|---|---|---|---|---|
| 517 | 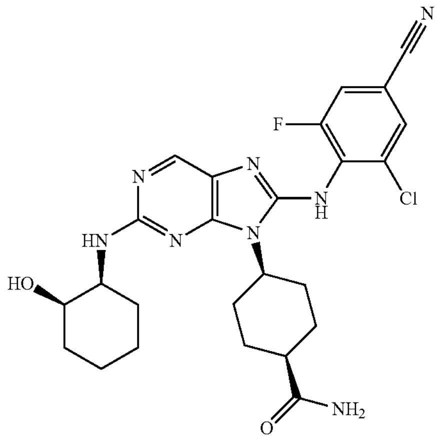 [SMILES: N#Cc1cc(F)c(Nc2nc3cnc(N[C@H]4CCCC[C@H]4O)nc3n2[C@H]2CC[C@@H](C(N)=O)CC2)c(Cl)c1] | (1R,4s)-4-(8-(2-chloro-4-cyano-6-fluorophenylamino)-2-((1S,2R)-2-hydroxycyclohexylamino)-9H-purin-9-yl)cyclohexanecarboxamide | 527.1 | A |
| 518 | 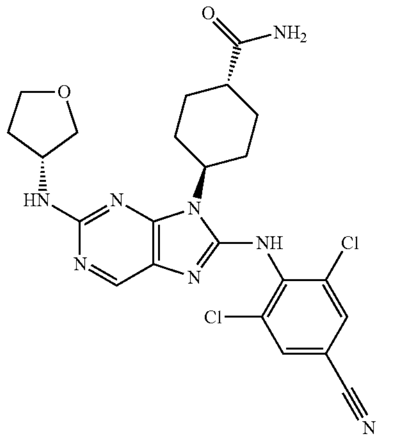 [SMILES: N#Cc1cc(Cl)c(Nc2nc3cnc(N[C@@H]4CCOC4)nc3n2[C@H]2CC[C@H](C(N)=O)CC2)c(Cl)c1] | (1S,4s)-4-(8-(2,6-dichloro-4-cyanophenylamino)-2-((R)-tetrahydrofuran-3-ylamino)-9H-purin-9-yl)cyclohexanecarboxamide | 515.2 | C |
| 519 | 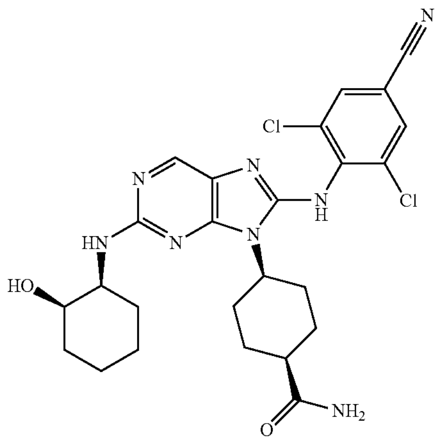 [SMILES: N#Cc1cc(Cl)c(Nc2nc3cnc(N[C@H]4CCCC[C@H]4O)nc3n2[C@H]2CC[C@@H](C(N)=O)CC2)c(Cl)c1] | (1R,4s)-4-(8-(2,6-dichloro-4-cyanophenylamino)-2-((1S,2R)-2-hydroxycyclohexylamino)-9H-purin-9-yl)cyclohexanecarboxamide | 543.2 | A |

TABLE 1-continued
| Cmpd No. | Structure | Name | MH+ | Activity |
| --- | --- | --- | --- | --- |
| 520 | 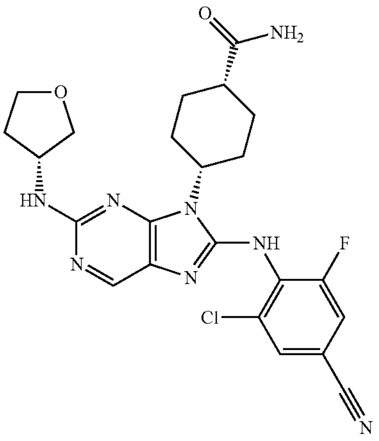 [SMILES: N#Cc1cc(F)c(Nc2nc3cnc(N[C@@H]4CCOC4)nc3n2[C@H]2CC[C@@H](C(N)=O)CC2)c(Cl)c1] | (1S,4s)-4-(8-(2-chloro-4-cyano-6-fluorophenylamino)-2-((R)-tetrahydrofuran-3-ylamino)-9H-purin-9-yl)cyclohexanecarboxamide | 499.2 | C |
| 521 | 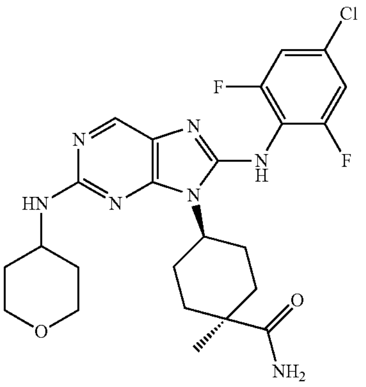 [SMILES: C[C@]1(C(N)=O)CC[C@@H](n2c(Nc3c(F)cc(Cl)cc3F)nc3cnc(NC4CCOCC4)nc32)CC1] | (1s,4s)-4-(8-(4-chloro-2,6-difluorophenylamino)-2-(tetrahydro-2H-pyran-4-ylamino)-9H-purin-9-yl)-1-methylcyclohexanecarboxamide | 520.2 | D |
| 522 | 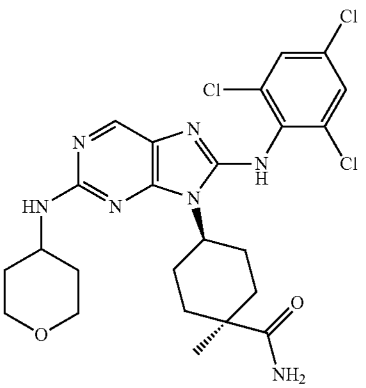 [SMILES: C[C@]1(C(N)=O)CC[C@@H](n2c(Nc3c(Cl)cc(Cl)cc3Cl)nc3cnc(NC4CCOCC4)nc32)CC1] | (1s,4s)-1-methyl-4-(2-(tetrahydro-2H-pyran-4-ylamino)-8-(2,4,6-trichlorophenylamino)-9H-purin-9-yl)cyclohexanecarboxamide | 552.1 | D |

TABLE 1-continued

| Cmpd No. | Structure | Name | MH+ | Activity |
|---|---|---|---|---|
| 523 | 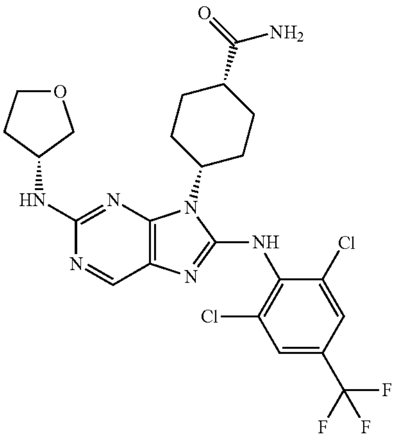 [SMILES: NC(=O)[C@H]1CC[C@@H](n2c(Nc3c(Cl)cc(C(F)(F)F)cc3Cl)nc3cnc(N[C@@H]4CCOC4)nc32)CC1] | (1S,4s)-4-(8-(2,6-dichloro-4-(trifluoromethyl)phenylamino)-2-((R)-tetrahydrofuran-3-ylamino)-9H-purin-9-yl)cyclohexanecarboxamide | 558.1 | A |
| 524 | 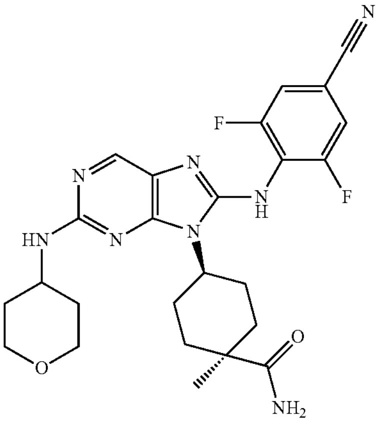 [SMILES: C[C@]1(C(N)=O)CC[C@@H](n2c(Nc3c(F)cc(C#N)cc3F)nc3cnc(NC4CCOCC4)nc32)CC1] | (1s,4s)-4-(8-(4-cyano-2,6-difluorophenylamino)-2-(tetrahydro-2H-pyran-4-ylamino)-9H-purin-9-yl)-1-methylcyclohexanecarboxamide | 511.2 | D |
| 525 | 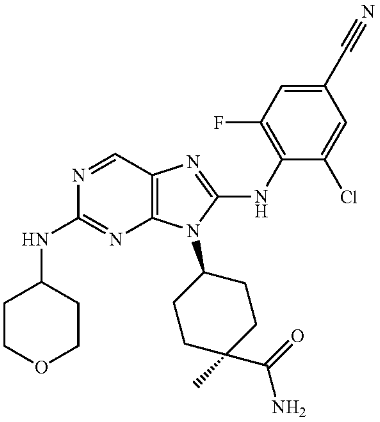 | (1s,4s)-4-(8-(2-chloro-4-cyano-6-fluorophenylamino)-2-(tetrahydro-2H-pyran-4-ylamino)-9H-purin-9-yl)-1-methylcyclohexanecarboxamide | 527.1 | D |

TABLE 1-continued

| Cmpd No. | Structure | Name | MH+ | Activity |
|---|---|---|---|---|
| 526 | 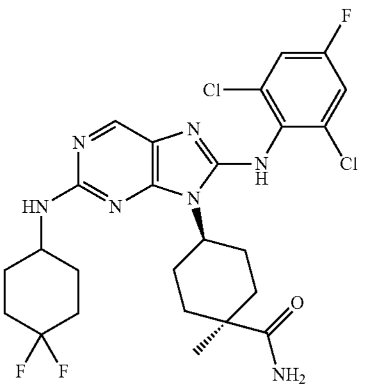 | (1s,4s)-4-(8-(2,6-dichloro-4-fluorophenylamino)-2-(4,4-difluorocyclohexylamino)-9H-purin-9-yl)-1-methylcyclohexanecarboxamide | 570.1 | D |
| 527 | 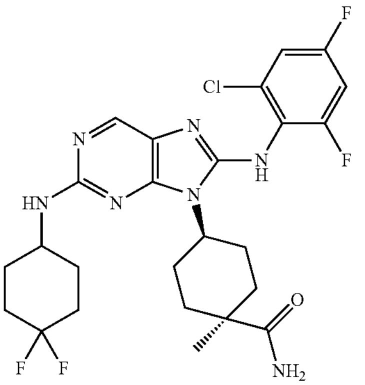 [SMILES: C[C@]1(C(N)=O)CC[C@@H](n2c(Nc3c(F)cc(F)cc3Cl)nc3cnc(NC4CCC(F)(F)CC4)nc32)CC1] | (1s,4s)-4-(8-(2-chloro-4,6-difluorophenylamino)-2-(4,4-difluorocyclohexylamino)-9H-purin-9-yl)-1-methylcyclohexanecarboxamide | 554.1 | D |
| 528 | 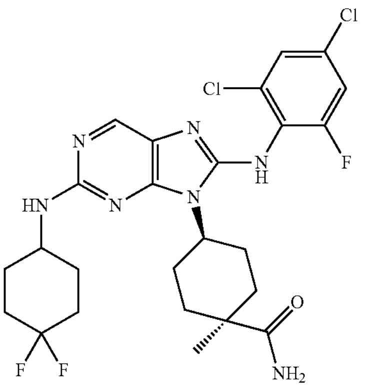 [SMILES: C[C@]1(C(N)=O)CC[C@@H](n2c(Nc3c(F)cc(Cl)cc3Cl)nc3cnc(NC4CCC(F)(F)CC4)nc32)CC1] | (1s,4s)-4-(8-(2,4-dichloro-6-fluorophenylamino)-2-(4,4-difluorocyclohexylamino)-9H-purin-9-yl)-1-methylcyclohexanecarboxamide | 570.1 | D |

TABLE 1-continued
| Cmpd No. | Structure | Name | MH+ | Activity |
| --- | --- | --- | --- | --- |
| 529 | 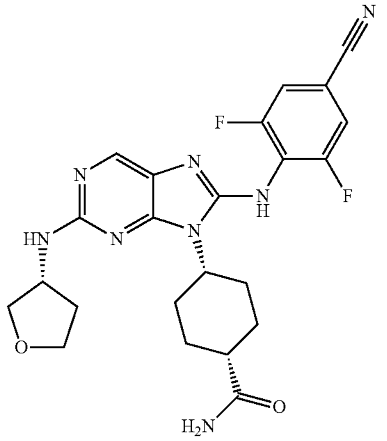 [SMILES: N#Cc1cc(F)c(Nc2nc3cnc(N[C@@H]4CCOC4)nc3n2[C@H]2CC[C@@H](C(N)=O)CC2)c(F)c1] | (1S,4s)-4-(8-(4-cyano-2,6-difluorophenylamino)-2-((R)-tetrahydrofuran-3-ylamino)-9H-purin-9-yl)cyclohexanecarboxamide | 483 | A |
| 530 | 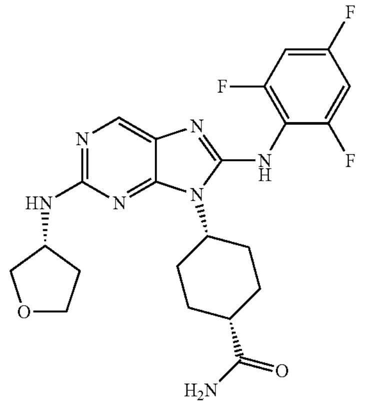 [SMILES: NC(=O)[C@H]1CC[C@@H](n2c(Nc3c(F)cc(F)cc3F)nc3cnc(N[C@@H]4CCOC4)nc32)CC1] | (1S,4s)-4-(2-((R)-tetrahydrofuran-3-ylamino)-8-(2,4,6-trifluorophenylamino)-9H-purin-9-yl)cyclohexanecarboxamide | 476.2 | B |
| 531 | 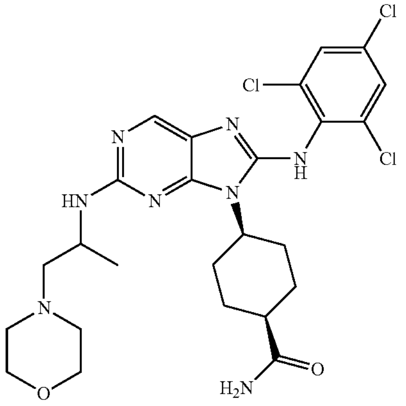 [SMILES: CC(CN1CCOCC1)Nc1ncc2nc(Nc3c(Cl)cc(Cl)cc3Cl)n([C@H]3CC[C@@H](C(N)=O)CC3)c2n1] | (1s,4s)-4-(2-(1-morpholinopropan-2-ylamino)-8-(2,4,6-trichlorophenylamino)-9H-purin-9-yl)cyclohexanecarboxamide | 581.1 | A |

TABLE 1-continued

| Cmpd No. | Structure | Name | MH+ | Activity |
| --- | --- | --- | --- | --- |
| 532 | 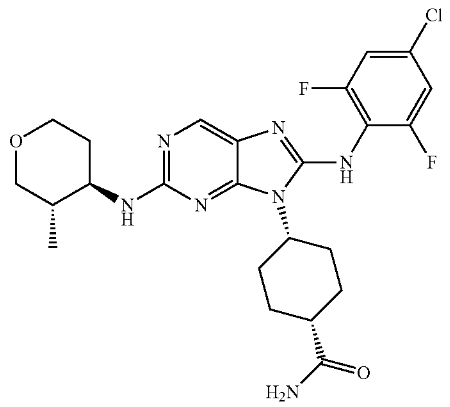 [SMILES: C[C@@H]1COCC[C@H]1Nc1ncc2nc(Nc3c(F)cc(Cl)cc3F)n([C@H]3CC[C@@H](C(N)=O)CC3)c2n1] | (1S,4s)-4-(8-(4-chloro-2,6-difluorophenylamino)-2-((3S,4R)-3-methyltetrahydro-2H-pyran-4-ylamino)-9H-purin-9-yl)cyclohexanecarboxamide | 520.3 | C |
| 533 | 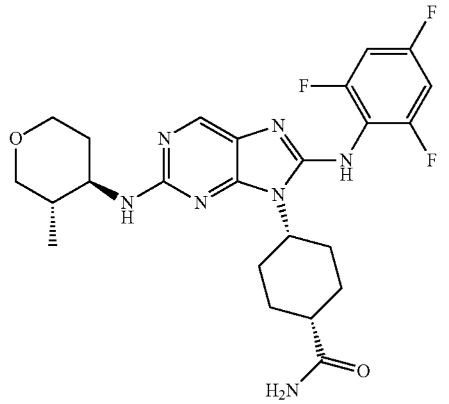 [SMILES: C[C@@H]1COCC[C@H]1Nc1ncc2nc(Nc3c(F)cc(F)cc3F)n([C@H]3CC[C@@H](C(N)=O)CC3)c2n1] | (1S,4s)-4-(2-((3S,4R)-3-methyltetrahydro-2H-pyran-4-ylamino)-8-(2,4,6-trifluorophenylamino)-9H-purin-9-yl)cyclohexanecarboxamide | 504.3 | D |
| 534 | 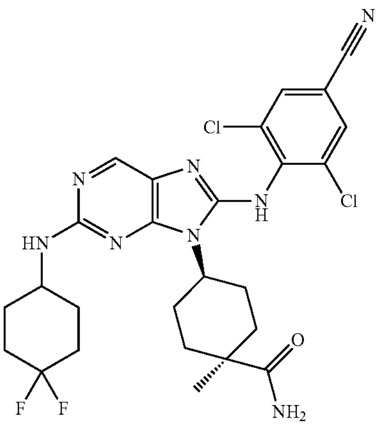 [SMILES: C[C@]1(C(N)=O)CC[C@@H](n2c(Nc3c(Cl)cc(C#N)cc3Cl)nc3cnc(NC4CCC(F)(F)CC4)nc32)CC1] | (1s,4s)-4-(8-(2,6-dichloro-4-cyanophenylamino)-2-(4,4-difluorocyclohexylamino)-9H-purin-9-yl)-1-methylcyclohexanecarboxamide | 577.2 | D |

TABLE 1-continued
| Cmpd No. | Structure | Name | MH+ | Activity |
|---|---|---|---|---|
| 535 | 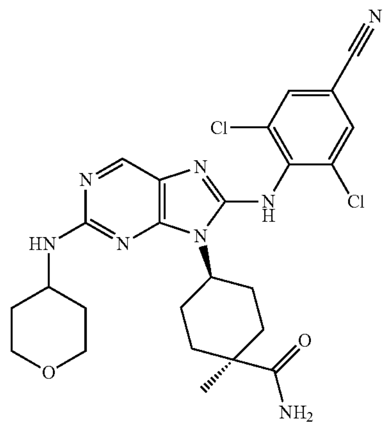 [SMILES: C[C@]1(C(N)=O)CC[C@@H](n2c(Nc3c(Cl)cc(C#N)cc3Cl)nc3cnc(NC4CCOCC4)nc32)CC1] | (1s,4s)-4-(8-(2,6-dichloro-4-cyanophenylamino)-2-(tetrahydro-2H-pyran-4-ylamino)-9H-purin-9-yl)-1-methylcyclohexanecarboxamide | 543.2 | D |
| 536 | 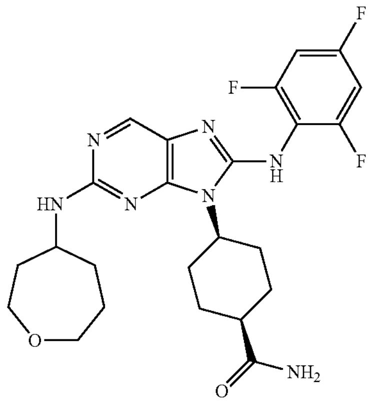 [SMILES: NC(=O)[C@H]1CC[C@@H](n2c(Nc3c(F)cc(F)cc3F)nc3cnc(NC4CCCOCC4)nc32)CC1] | (1s,4s)-4-(2-(oxepan-4-ylamino)-8-(2,4,6-trifluorophenylamino)-9H-purin-9-yl)cyclohexanecarboxamide | 504.2 | B |
| 537 | 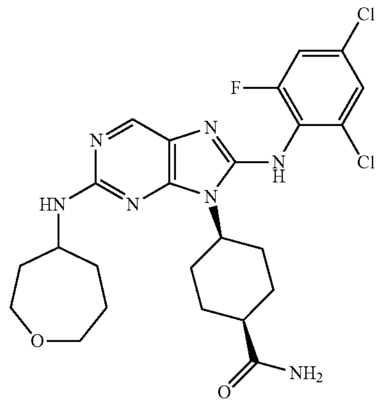 | (1s,4s)-4-(8-(2,4-dichloro-6-fluorophenylamino)-2-(oxepan-4-ylamino)-9H-purin-9-yl)cyclohexanecarboxamide | 536.1 | D |

TABLE 1-continued
| Cmpd No. | Structure | Name | MH+ | Activity |
|---|---|---|---|---|
| 538 | 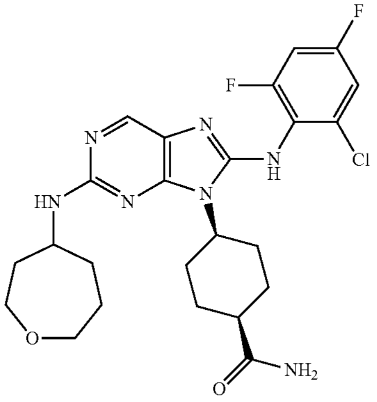 [SMILES: NC(=O)[C@H]1CC[C@@H](n2c(Nc3c(F)cc(F)cc3Cl)nc3cnc(NC4CCCOCC4)nc32)CC1] | (1s,4s)-4-(8-(2-chloro-4,6-difluorophenylamino)-2-(oxepan-4-ylamino)-9H-purin-9-yl)cyclohexanecarboxamide | 520.2 | C |
| 539 | 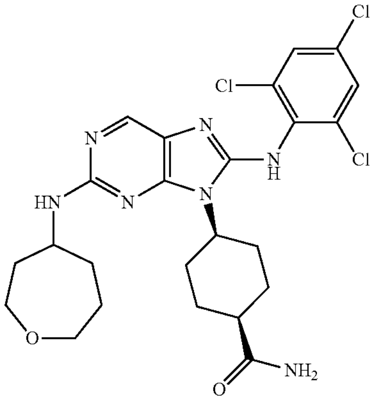 | (1s,4s)-4-(2-(oxepan-4-ylamino)-8-(2,4,6-trichlorophenylamino)-9H-purin-9-yl)cyclohexanecarboxamide | 554.1 | D |
| 540 | 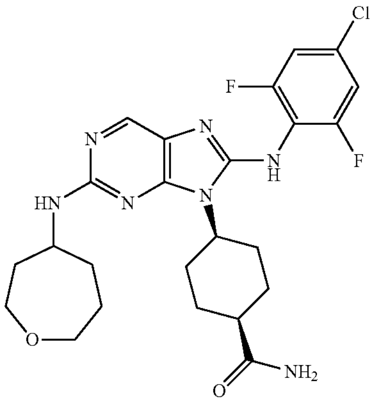 | (1s,4s)-4-(8-(4-chloro-2,6-difluorophenylamino)-2-(oxepan-4-ylamino)-9H-purin-9-yl)cyclohexanecarboxamide | 520.2 | C |

TABLE 1-continued
| Cmpd No. | Structure | Name | MH+ | Activity |
|---|---|---|---|---|
| 541 | 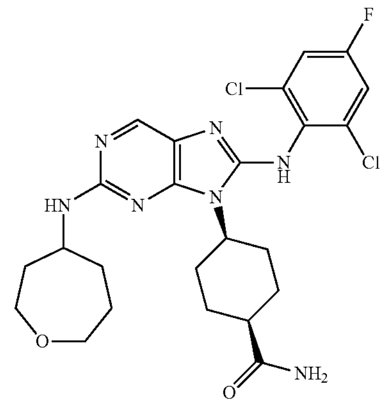 [SMILES: NC(=O)[C@H]1CC[C@@H](n2c(Nc3c(Cl)cc(F)cc3Cl)nc3cnc(NC4CCCOCC4)nc32)CC1] | (1s,4s)-4-(8-(2,6-dichloro-4-fluorophenylamino)-2-(oxepan-4-ylamino)-9H-purin-9-yl)cyclohexanecarboxamide | 536.1 | B |
| 542 | 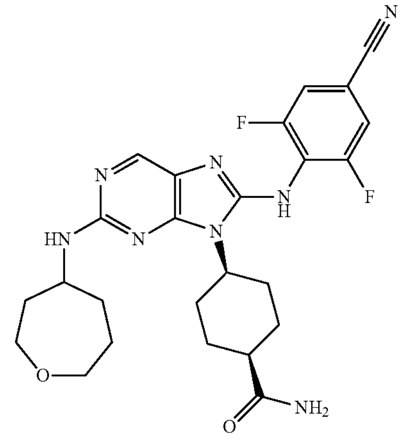 [SMILES: N#Cc1cc(F)c(Nc2nc3cnc(NC4CCCOCC4)nc3n2[C@H]2CC[C@@H](C(N)=O)CC2)c(F)c1] | (1s,4s)-4-(8-(4-cyano-2,6-difluorophenylamino)-2-(oxepan-4-ylamino)-9H-purin-9-yl)cyclohexanecarboxamide | 511.2 | A |
| 543 | 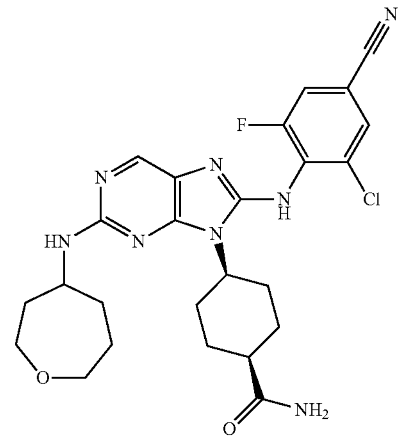 [SMILES: N#Cc1cc(F)c(Nc2nc3cnc(NC4CCCOCC4)nc3n2[C@H]2CC[C@@H](C(N)=O)CC2)c(Cl)c1] | (1s,4s)-4-(8-(2-chloro-4-cyano-6-fluorophenylamino)-2-(oxepan-4-ylamino)-9H-purin-9-yl)cyclohexanecarboxamide | 527.2 | D |

TABLE 1-continued
| Cmpd No. | Structure | Name | MH+ | Activity |
|---|---|---|---|---|
| 544 | 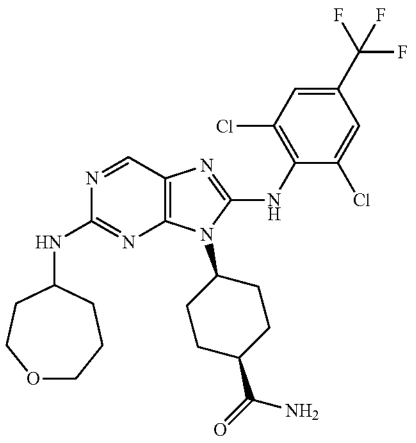 [SMILES: NC(=O)[C@H]1CC[C@@H](n2c(Nc3c(Cl)cc(C(F)(F)F)cc3Cl)nc3cnc(NC4CCCOCC4)nc32)CC1] | (1s,4s)-4-(8-(2,6-dichloro-4-(trifluoromethyl)phenylamino)-2-(oxepan-4-ylamino)-9H-purin-9-yl)cyclohexanecarboxamide | 586.2 | A |
| 545 | 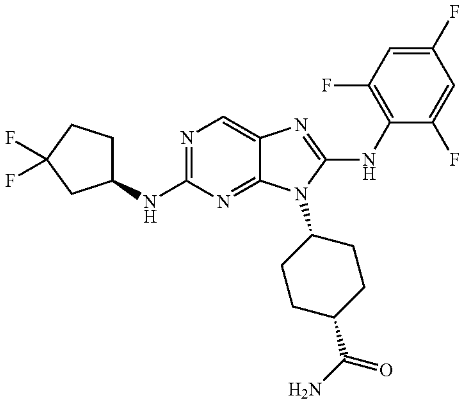 [SMILES: NC(=O)[C@H]1CC[C@@H](n2c(Nc3c(F)cc(F)cc3F)nc3cnc(N[C@@H]4CCC(F)(F)C4)nc32)CC1] | (1S,4s)-4-(2-((R)-3,3-difluorocyclopentylamino)-8-(2,4,6-trifluorophenylamino)-9H-purin-9-yl)cyclohexanecarboxamide | 510.3 | D |
| 546 | 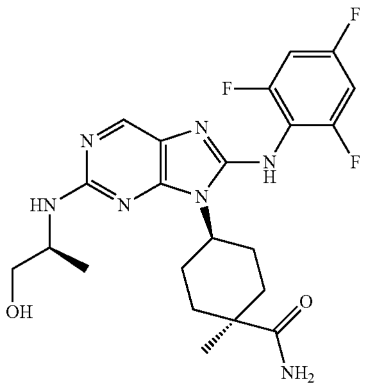 [SMILES: C[C@@H](CO)Nc1ncc2nc(Nc3c(F)cc(F)cc3F)n([C@H]3CC[C@@](C)(C(N)=O)CC3)c2n1] | (1R,4s)-4-(2-((S)-1-hydroxypropan-2-ylamino)-8-(2,4,6-trifluorophenylamino)-9H-purin-9-yl)-1-methylcyclohexanecarboxamide | 478.2 | C |

TABLE 1-continued
| Cmpd No. | Structure | Name | MH+ | Activity |
|---|---|---|---|---|
| 547 | 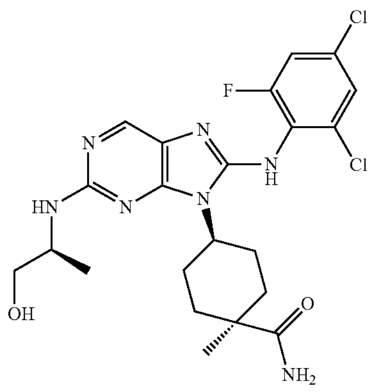 [SMILES: C[C@@H](CO)Nc1ncc2nc(Nc3c(F)cc(Cl)cc3Cl)n([C@H]3CC[C@@](C)(C(N)=O)CC3)c2n1] | (1R,4s)-4-(8-(2,4-dichloro-6-fluorophenylamino)-2-((S)-1-hydroxypropan-2-ylamino)-9H-puriin-9-yl)-1-methylcyclohexanecarboxamide | 510.2 | D |
| 548 | 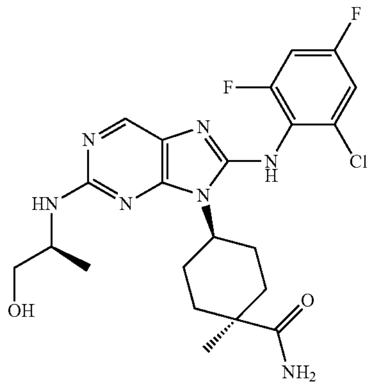 | (1R,4s)-4-(8-(2-chloro-4,6-difluorophenylamino)-2-((S)-1-hydroxypropan-2-ylamino)-9H-purin-9-yl)-1-methylcyclohexanecarboxamide | 494.2 | D |
| 549 | 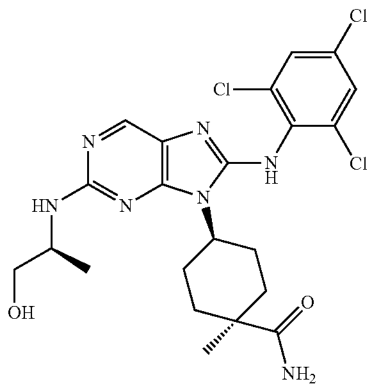 [SMILES: C[C@@H](CO)Nc1ncc2nc(Nc3c(Cl)cc(Cl)cc3Cl)n([C@H]3CC[C@@](C)(C(N)=O)CC3)c2n1] | (1R,4s)-4-(2-((S)-1-hydroxypropan-2-ylamino)-8-(2,4,6-trichlorophenylamino)-9H-purin-9-yl)-1-methylcyclohexanecarboxamide | 526.1 | D |

TABLE 1-continued

| Cmpd No. | Structure | Name | MH+ | Activity |
|---|---|---|---|---|
| 550 | 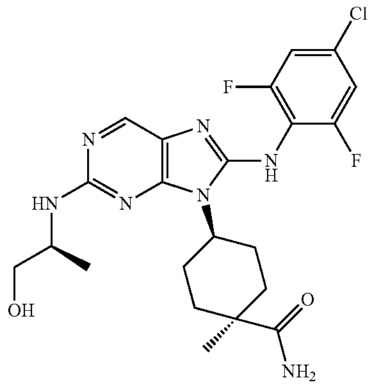 [SMILES: C[C@@H](CO)Nc1ncc2nc(Nc3c(F)cc(Cl)cc3F)n([C@H]3CC[C@@](C)(C(N)=O)CC3)c2n1] | (1R,4s)-4-(8-(4-chloro-2,6-difluorophenylamino)-2-((S)-1-hydroxypropan-2-ylamino)-9H-purin-9-yl)-1-methylcyclohexanecarboxamide | 494.1 | D |
| 551 | 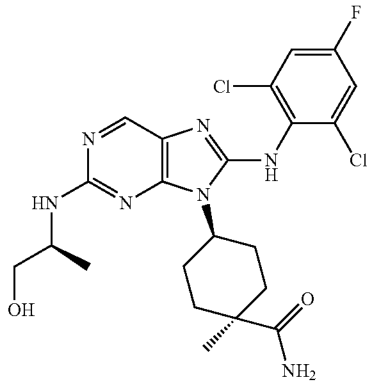 | (1R,4s)-4-(8-(2,6-dichloro-4-fluorophenylamino)-2-((S)-1-hydroxypropan-2-ylamino)-9H-purin-9-yl)-1-methylcyclohexanecarboxamide | 510.2 | D |
| 552 | 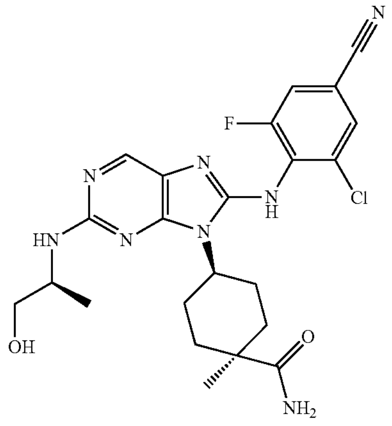 [SMILES: C[C@@H](CO)Nc1ncc2nc(Nc3c(F)cc(C#N)cc3Cl)n([C@H]3CC[C@@](C)(C(N)=O)CC3)c2n1] | (1R,4s)-4-(8-(2-chloro-4-cyano-6-fluorophenylamino)-2-((S)-1-hydroxypropan-2-ylamino)-9H-purin-9-yl)-1-methylcyclohexanecarboxamide | 501.1 | D |

TABLE 1-continued
| Cmpd No. | Structure | Name | MH+ | Activity |
|---|---|---|---|---|
| 553 | 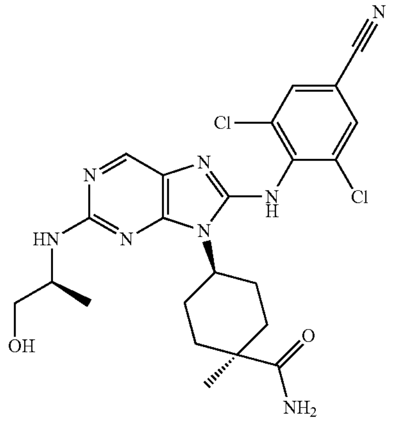 [SMILES: C[C@@H](CO)Nc1ncc2nc(Nc3c(Cl)cc(C#N)cc3Cl)n([C@H]3CC[C@@](C)(C(N)=O)CC3)c2n1] | (1R,4s)-4-(8-(2,6-dichloro-4-cyanophenylamino)-2-((S)-1-hydroxypropan-2-ylamino)-9H-purin-9-yl)-1-methylcyclohexanecarboxamide | 517.2 | D |
| 554 | 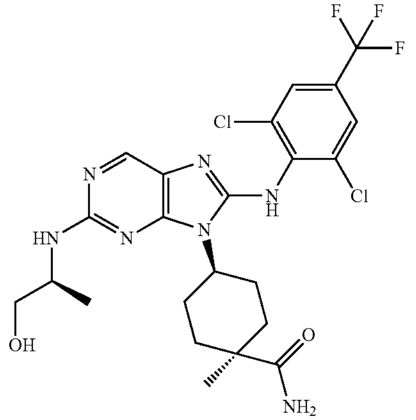 [SMILES: C[C@@H](CO)Nc1ncc2nc(Nc3c(Cl)cc(C(F)(F)F)cc3Cl)n([C@H]3CC[C@@](C)(C(N)=O)CC3)c2n1] | (1R,4s)-4-(8-(2,6-dichloro-4-(trifluoromethyl)phenylamino)-2-((S)-1-hydroxypropan-2-ylamino)-9H-purin-9-yl)-1-methylcyclohexanecarboxamide | 560.1 | B |
| 555 | 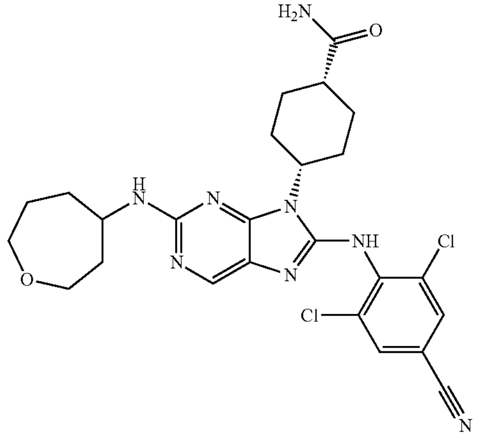 [SMILES: N#Cc1cc(Cl)c(Nc2nc3cnc(NC4CCCOCC4)nc3n2[C@H]2CC[C@@H](C(N)=O)CC2)c(Cl)c1] | (1s,4s)-4-(8-(2,6-dichloro-4-cyanophenylamino)-2-(oxepan-4-ylamino)-9H-purin-9-yl)cyclohexanecarboxamide | 543.2 | D |

TABLE 1-continued
| Cmpd No. | Structure | Name | MH+ | Activity |
|---|---|---|---|---|
| 556 | 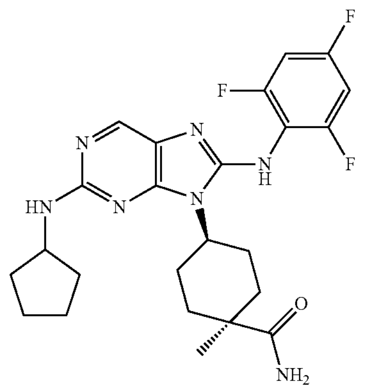 [SMILES: C[C@]1(C(N)=O)CC[C@@H](n2c(Nc3c(F)cc(F)cc3F)nc3cnc(NC4CCCC4)nc32)CC1] | (1s,4s)-4-(2-(cyclopentyalmino)-8-(2,4,6-trifluorophenylamino)-9H-purin-9-yl)-1-methylcyclohexanecarboxamide | 488.1 | D |
| 557 | 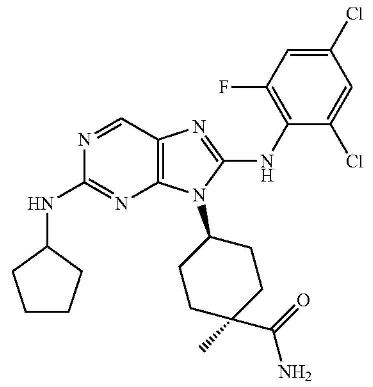 | (1s,4s)-4-(2-(cyclopentylamino)-8-(2,4-dichloro-6-fluorophenylamino)-9H-purin-9-yl)-1-methylcyclohexanecarboxamide | 520.1 | D |
| 558 | 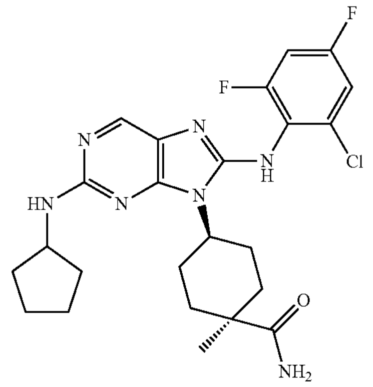 | (1s,4s)-4-(8-(2-chloro-4,6-difluorophenylamino)-2-(cyclopentylamino)-9H-purin-9-yl)-1-methylcyclohexanecarboxamide | 504.3 | D |

TABLE 1-continued
| Cmpd No. | Structure | Name | MH+ | Activity |
|---|---|---|---|---|
| 559 | 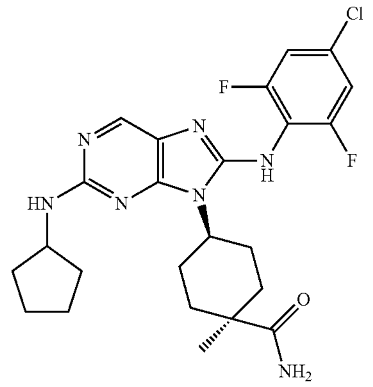 | (1s,4s)-4-(8-(4-chloro-2,6-difluorophenylamino)-2-(cyclopentylamino)-9H-purin-9-yl)-1-methylcyclohexanecarboxamide | 504.3 | C |
| 560 | 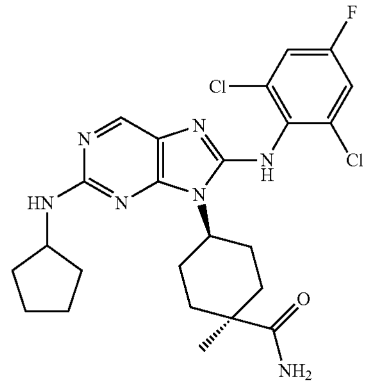 | (1s,4s)-4-(2-(cyclopentylamino)-8-(2,6-dichloro-4-fluorophenylamino)-9H-purin-9-yl)-1-methylcyclohexanecarboxamide | 520.2 | C |
| 561 | 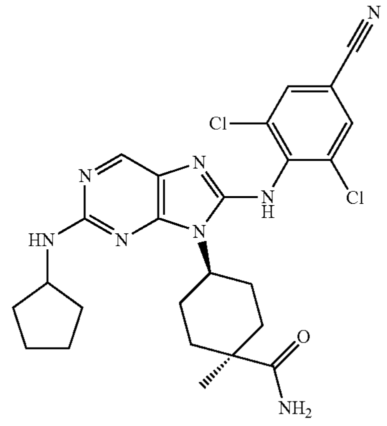 | (1s,4s)-4-(2-(cyclopentylamino)-8-(2,6-dichloro-4-cyanophenylamino)-9H-purin-9-yl)-1-methylcyclohexanecarboxamide | 527.1 | D |

TABLE 1-continued

| Cmpd No. | Structure | Name | MH+ | Activity |
|---|---|---|---|---|
| 562 | 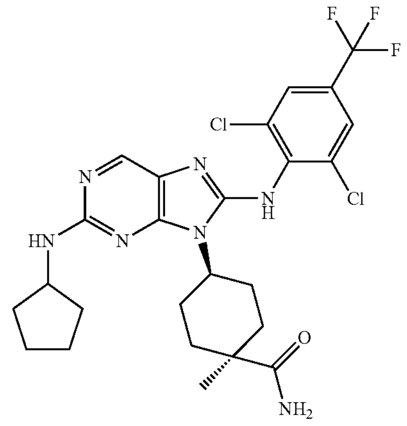 [SMILES: C[C@]1(C(N)=O)CC[C@@H](n2c(Nc3c(Cl)cc(C(F)(F)F)cc3Cl)nc3cnc(NC4CCCC4)nc32)CC1] | (1s,4s)-4-(2-(cyclopentylamino)-8-(2,6-dichloro-4-(trifluoromethyl)phenylamino)-9H-purin-9-yl)-1-methylcyclohexanecarboxamide | 570.1 | A |
| 563 | 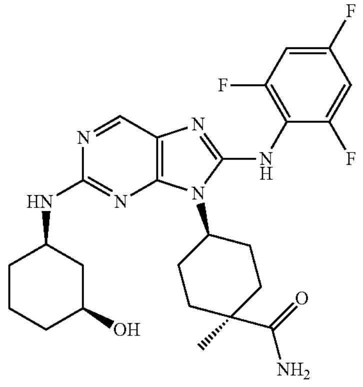 [SMILES: C[C@]1(C(N)=O)CC[C@@H](n2c(Nc3c(F)cc(F)cc3F)nc3cnc(N[C@@H]4CCC[C@H](O)C4)nc32)CC1] | (1S,4s)-4-(2-((1R,3S)-3-hydroxycyclohexylamino)-8-(2,4,6-trifluorophenylamino)-9H-purin-9-yl)-1-methylcyclohexanecarboxamide | 518.2 | A |
| 564 | 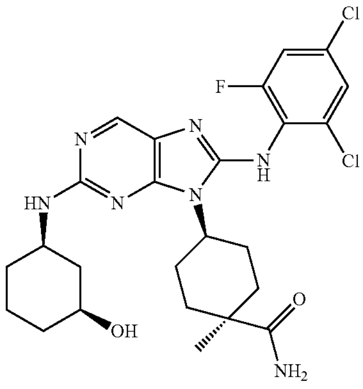 | (1S,4s)-4-(8-(2,4-dichloro-6-fluorophenylamino)-2-((1R,3S)-3-hydroxycyclohexylamino)-9H-purin-9-yl)-1-methylcyclohexanecarboxamide | 550.2 | D |

TABLE 1-continued

| Cmpd No. | Structure | Name | MH+ | Activity |
|---|---|---|---|---|
| 565 | 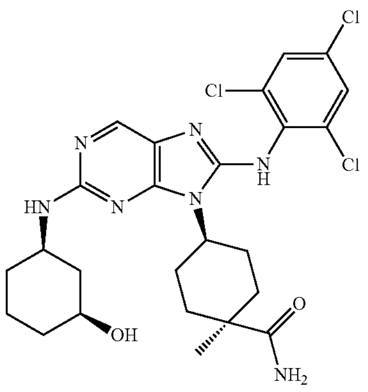 [SMILES: C[C@]1(C(N)=O)CC[C@@H](n2c(Nc3c(Cl)cc(Cl)cc3Cl)nc3cnc(N[C@@H]4CCC[C@H](O)C4)nc32)CC1] | (1S,4s)-4-(2-((1R,3S)-3-hydroxycyclohexylamino)-8-(2,4,6-trichlorophenylamino)-9H-purin-9-yl)-1-methylcyclohexanecarboxamide | 567.1 | D |
| 566 | 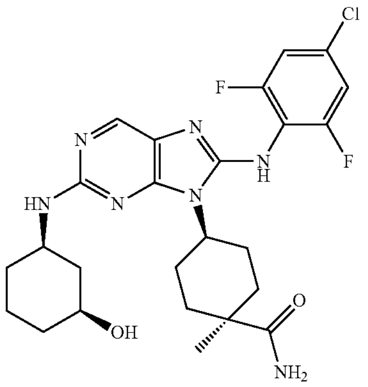 | (1S,4s)-4-(8-(4-chloro-2,6-difluorophenylamino)-2-((1R,3S)-3-hydroxycyclohexylamino)-9H-purin-9-yl)-1-methylcyclohexanecarboxamide | 534.2 | C |
| 567 | 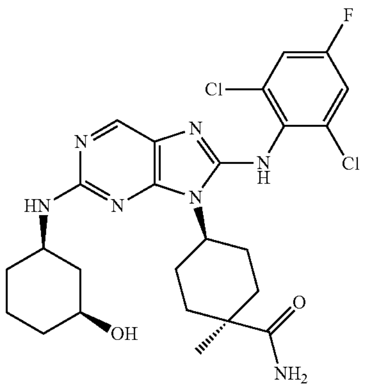 | (1S,4s)-4-(8-(2,6-dichloro-4-fluorophenylamino)-2-((1R,3S)-3-hydroxycyclohexylamino)-9H-purin-9-yl)-1-methylcyclohexanecarboxamide | 550.2 | B |

TABLE 1-continued

| Cmpd No. | Structure | Name | MH+ | Activity |
|---|---|---|---|---|
| 568 | 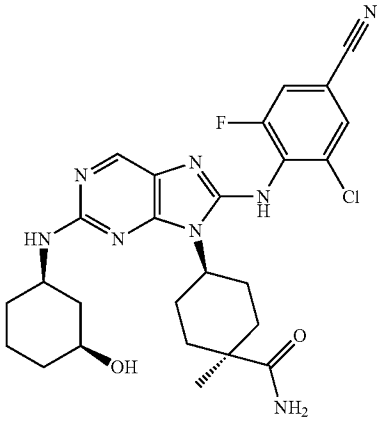 [SMILES: C[C@]1(C(N)=O)CC[C@@H](n2c(Nc3c(F)cc(C#N)cc3Cl)nc3cnc(N[C@@H]4CCC[C@H](O)C4)nc32)CC1] | (1S,4s)-4-(8-(2-chloro-4-cyano-6-fluorophenylamino)-2-((1R,3S)-3-hydroxycyclohexylamino)-9H-purin-9-yl)-1-methylcyclohexanecarboxamide | 541.2 | C |
| 569 | 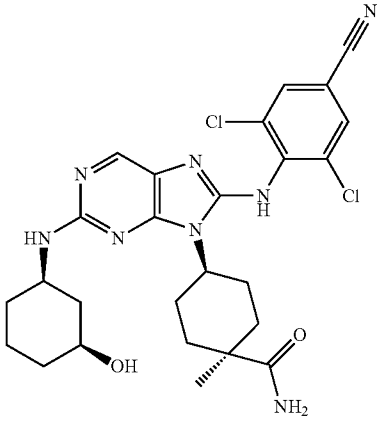 [SMILES: C[C@]1(C(N)=O)CC[C@@H](n2c(Nc3c(Cl)cc(C#N)cc3Cl)nc3cnc(N[C@@H]4CCC[C@H](O)C4)nc32)CC1] | (1S,4s)-4-(8-(2,6-dichloro-4-cyanophenylamino)-2-((1R,3S)-3-hydroxycyclohexylamino)-9H-purin-9-yl)-1-methylcyclohexanecarboxamide | 557.1 | D |
| 570 | 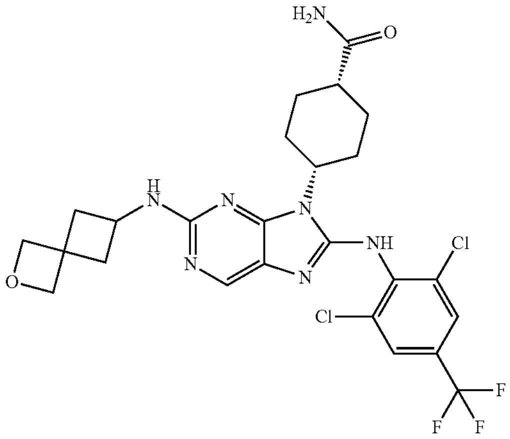 [SMILES: NC(=O)[C@H]1CC[C@@H](n2c(Nc3c(Cl)cc(C(F)(F)F)cc3Cl)nc3cnc(NC4CC5(COC5)C4)nc32)CC1] | (1s,4s)-4-(2-(2-oxaspiro[3.3]heptan-6-ylamino)-8-(2,6-dichloro-4-(trifluoromethyl)phenylamino)-9H-purin-9-yl)cyclohexanecarboxamide | 584.2 | A |

TABLE 1-continued
| Cmpd No. | Structure | Name | MH+ | Activity |
|---|---|---|---|---|
| 571 | 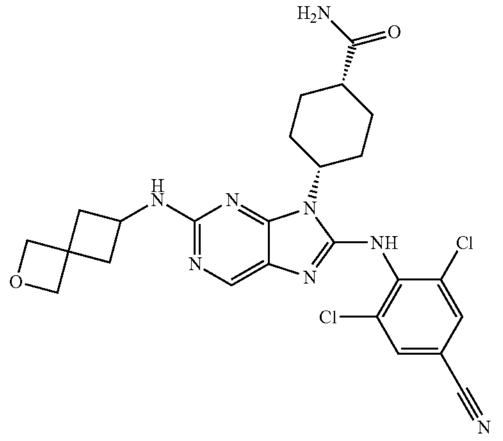 [SMILES: N#Cc1cc(Cl)c(Nc2nc3cnc(NC4CC5(COC5)C4)nc3n2[C@H]2CC[C@@H](C(N)=O)CC2)c(Cl)c1] | (1s,4s)-4-(2-(2-oxaspiro[3.3]heptan-6-ylamino)-8-(2,6-dichloro-4-cyanophenylamino)-9H-purin-9-yl)cyclohexanecarboxamide | 541.2 | C |
| 572 | 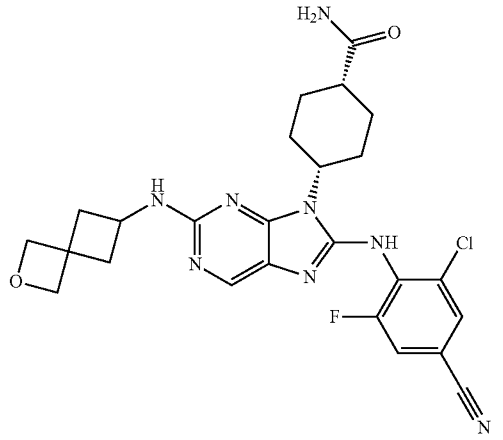 [SMILES: N#Cc1cc(F)c(Nc2nc3cnc(NC4CC5(COC5)C4)nc3n2[C@H]2CC[C@@H](C(N)=O)CC2)c(Cl)c1] | (1s,4s)-4-(2-(2-oxaspiro[3.3]heptan-6-ylamino)-8-(2-chloro-4-cyano-6-fluorophenylamino)-9H-purin-9-yl)cyclohexanecarboxamide | 525.2 | B |
| 573 | 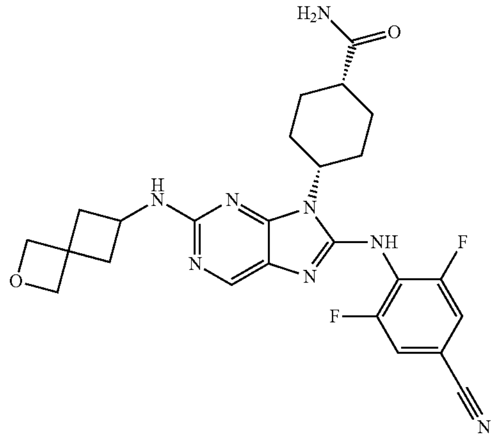 [SMILES: N#Cc1cc(F)c(Nc2nc3cnc(NC4CC5(COC5)C4)nc3n2[C@H]2CC[C@@H](C(N)=O)CC2)c(F)c1] | (1s,4s)-4-(2-(2-oxaspiro[3.3]heptan-6-ylamino)-8-(4-cyano-2,6-difluorophenylamino)-9H-purin-9-yl)cyclohexanecarboxamide | 509.2 | A |

TABLE 1-continued
| Cmpd No. | Structure | Name | MH+ | Activity |
| --- | --- | --- | --- | --- |
| 574 | 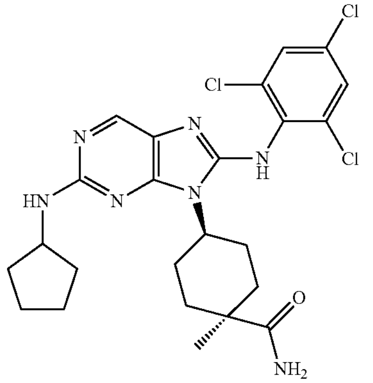 [SMILES: C[C@]1(C(N)=O)CC[C@@H](n2c(Nc3c(Cl)cc(Cl)cc3Cl)nc3cnc(NC4CCCC4)nc32)CC1] | (1s,4s)-4-(2-(cyclopentylamino)-8-(2,4,6-trichlorophenylamino)-9H-purin-9-yl)-1-methylcyclohexanecarboxamide | 536 | C |
| 575 | 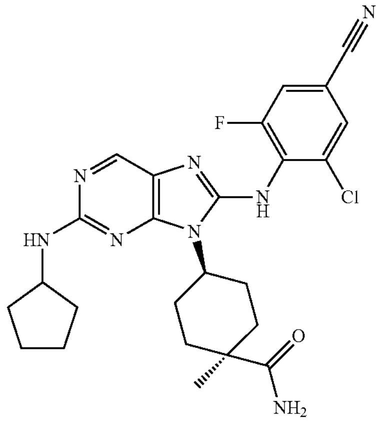 [SMILES: C[C@]1(C(N)=O)CC[C@@H](n2c(Nc3c(F)cc(C#N)cc3Cl)nc3cnc(NC4CCCC4)nc32)CC1] | (1s,4s)-4-(8-(2-chloro-4-cyano-6-fluorophenylamino)-2-(cyclopentylamino)-9H-purin-9-yl)-1-methylcyclohexanecarboxamide | 511.2 | D |
| 576 | 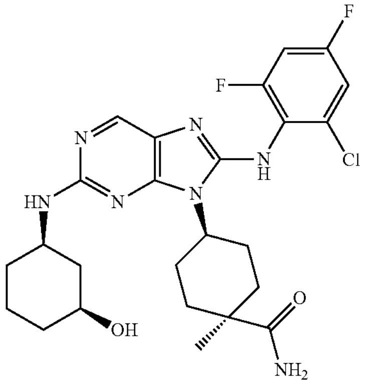 [SMILES: C[C@]1(C(N)=O)CC[C@@H](n2c(Nc3c(F)cc(F)cc3Cl)nc3cnc(N[C@@H]4CCC[C@H](O)C4)nc32)CC1] | (1S,4s)-4-(8-(2-chloro-4,6-difluorophenylamino)-2-((1R,3S)-3-hydroxycyclohexylamino)-9H-purin-9-yl)-1-methylcyclohexanecarboxamide | 534.2 | C |

TABLE 1-continued

| Cmpd No. | Structure | Name | MH+ | Activity |
|---|---|---|---|---|
| 577 | 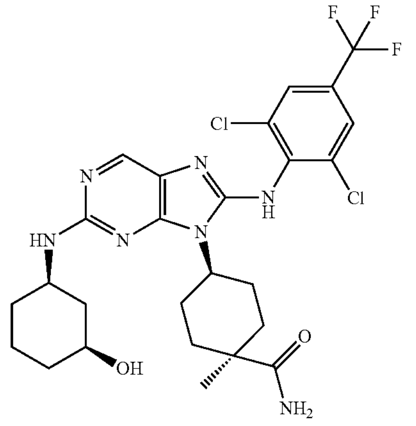 [SMILES: C[C@]1(C(N)=O)CC[C@@H](n2c(Nc3c(Cl)cc(C(F)(F)F)cc3Cl)nc3cnc(N[C@@H]4CCC[C@H](O)C4)nc32)CC1] | (1S,4s)-4-(8-(2,6-dichloro-4-(trifluoromethyl)phenylamino)-2-((1R,3S)-3-hydroxycyclohexylamino)-9H-purin-9-yl)-1-methylcyclohexanecarboxamide | 600.1 | A |
| 578 | 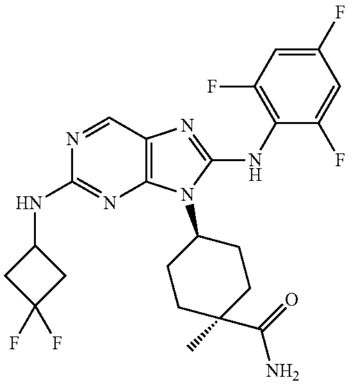 [SMILES: C[C@]1(C(N)=O)CC[C@@H](n2c(Nc3c(F)cc(F)cc3F)nc3cnc(NC4CC(F)(F)C4)nc32)CC1] | (1s,4s)-4-(2-(3,3-difluorocyclobutylamino)-8-(2,4,6-trifluorophenylamino)-9H-purin-9-yl)-1-methylcyclohexanecarboxamide | 510.2 | D |
| 579 | 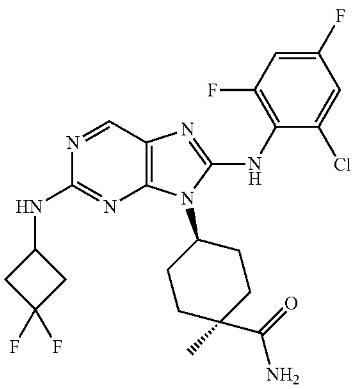 [SMILES: C[C@]1(C(N)=O)CC[C@@H](n2c(Nc3c(F)cc(F)cc3Cl)nc3cnc(NC4CC(F)(F)C4)nc32)CC1] | (1s,4s)-4-(8-(2-chloro-4,6-difluorophenylamino)-2-(3,3-difluorocyclobutylamino)-9H-purin-9-yl)-1-methylcyclohexanecarboxamide | 526.2 | D |

TABLE 1-continued

| Cmpd No. | Structure | Name | MH+ | Activity |
|---|---|---|---|---|
| 580 | 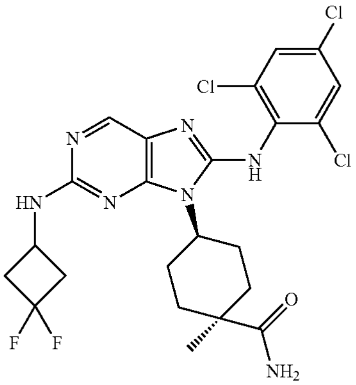 [SMILES: C[C@]1(C(N)=O)CC[C@@H](n2c(Nc3c(Cl)cc(Cl)cc3Cl)nc3cnc(NC4CC(F)(F)C4)nc32)CC1] | (1s,4s)-4-(2-(3,3-difluorocyclobutylamino)-8-(2,4,6-trichlorophenylamino)-9H-purin-9-yl)-1-methylcyclohexanecarboxamide | 588.2 | C |
| 581 | 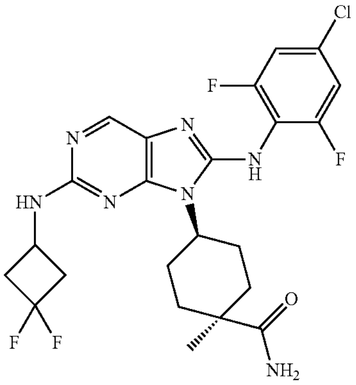 [SMILES: C[C@]1(C(N)=O)CC[C@@H](n2c(Nc3c(F)cc(Cl)cc3F)nc3cnc(NC4CC(F)(F)C4)nc32)CC1] | (1s,4s)-4-(8-(4-chloro-2,6-difluorophenylamino)-2-(3,3-difluorocyclobutylamino)-9H-purin-9-yl)-1-methylcyclohexanecarboxamide | 526.2 | D |
| 582 | 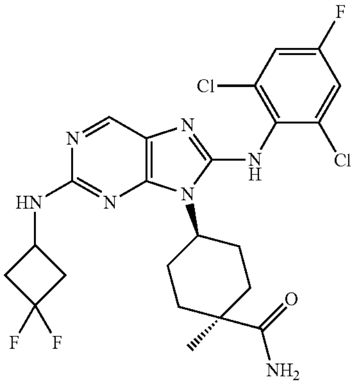 [SMILES: C[C@]1(C(N)=O)CC[C@@H](n2c(Nc3c(Cl)cc(F)cc3Cl)nc3cnc(NC4CC(F)(F)C4)nc32)CC1] | (1s,4s)-4-(8-(2,6-dichloro-4-fluorophenylamino)-2-(3,3-difluorocyclobutylamino)-9H-purin-9-yl)-1-methylcyclohexanecarboxamide | 542.2 | D |

TABLE 1-continued

| Cmpd No. | Structure | Name | MH+ | Activity |
|---|---|---|---|---|
| 583 | 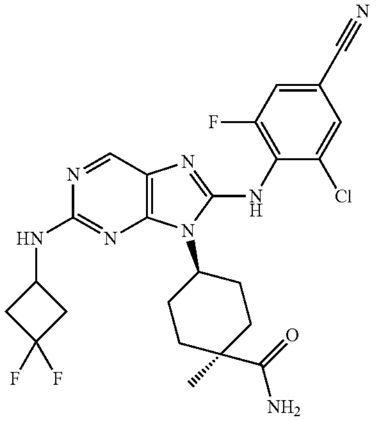 [SMILES: C[C@]1(C(N)=O)CC[C@@H](n2c(Nc3c(F)cc(C#N)cc3Cl)nc3cnc(NC4CC(F)(F)C4)nc32)CC1] | (1s,4s)-4-(8-(2-chloro-4-cyano-6-fluorophenylamino)-2-(3,3-difluorocyclobutylamino)-9H-purin-9-yl)-1-methylcyclohexanecarboxamide | 533.2 | D |
| 584 | 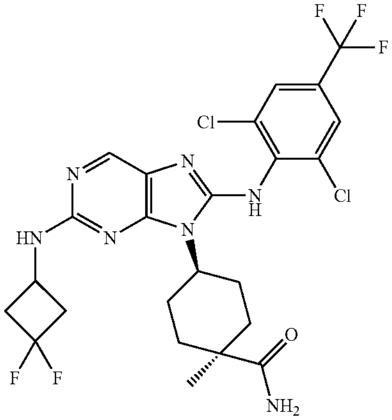 [SMILES: C[C@]1(C(N)=O)CC[C@@H](n2c(Nc3c(Cl)cc(C(F)(F)F)cc3Cl)nc3cnc(NC4CC(F)(F)C4)nc32)CC1] | (1s,4s)-4-(8-(2,6-dichloro-4-(trifluoromethyl)phenylamino)-2-(3,3-difluorocyclobutylamino)-9H-purin-9-yl)-1-methylcyclohexanecarboxamide | 592 | A |
| 585 | 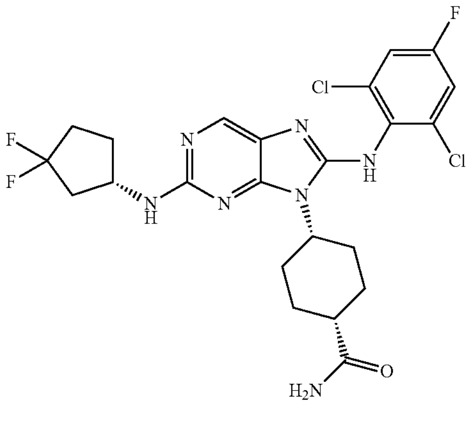 | (1R,4s)-4-(8-(2,6-dichloro-4-fluorophenylamino)-2-((S)-3,3-difluorocyclopentylamino)-9H-purin-9-yl)cyclohexanecarboxamide | 542.2 | B |

TABLE 1-continued
| Cmpd No. | Structure | Name | MH+ | Activity |
|---|---|---|---|---|
| 586 | 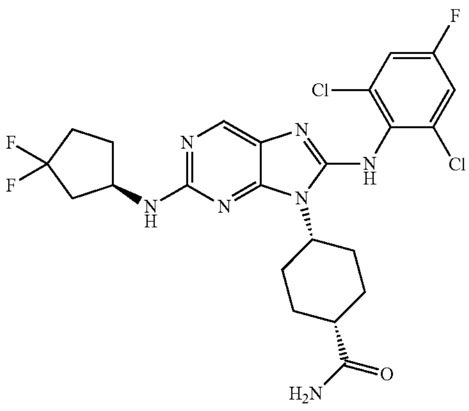 | (1S,4s)-4-(8-(2,6-dichloro-4-fluorophenylamino)-2-((R)-3,3-difluorocyclopentylamino)-9H-purin-9-yl)cyclohexanecarboxamide | 542.2 | D |
| 587 | 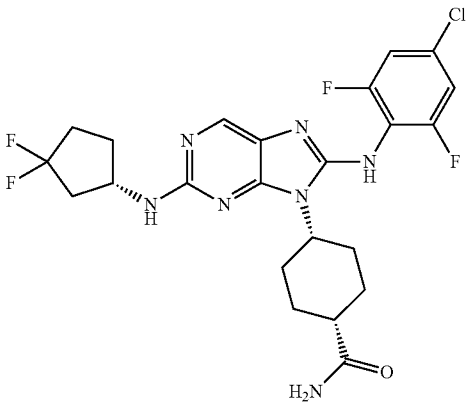 [SMILES: NC(=O)[C@H]1CC[C@@H](n2c(Nc3c(F)cc(Cl)cc3F)nc3cnc(N[C@H]4CCC(F)(F)C4)nc32)CC1] | (1R,4s)-4-(8-(4-chloro-2,6-difluorophenylamino)-2-((S)-3,3-difluorocyclopentylamino)-9H-purin-9-yl)cyclohexanecarboxamide | 526.2 | C |
| 588 | 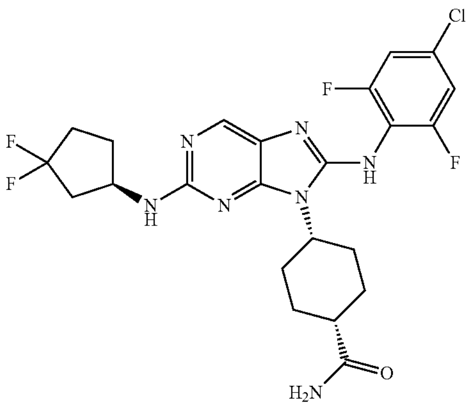 [SMILES: NC(=O)[C@H]1CC[C@@H](n2c(Nc3c(F)cc(Cl)cc3F)nc3cnc(N[C@@H]4CCC(F)(F)C4)nc32)CC1] | (1S,4s)-4-(8-(4-chloro-2,6-difluorophenylamino)-2-((R)-3,3-difluorocyclopentylamino)-9H-purin-9-yl)cyclohexanecarboxamide | 526.2 | D |

TABLE 1-continued
| Cmpd No. | Structure | Name | MH+ | Activity |
|---|---|---|---|---|
| 589 | 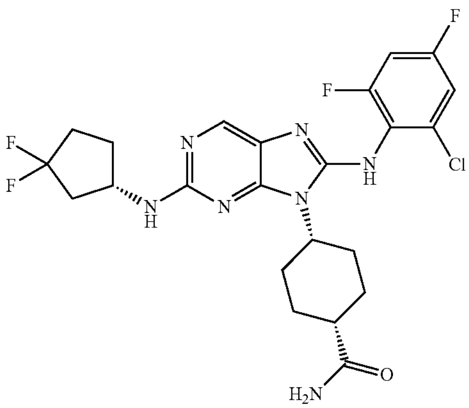 | (1R,4s)-4-(8-(2-chloro-4,6-difluorophenylamino)-2-((S)-3,3-difluorocyclopentylamino)-9H-purin-9-yl)cyclohexanecarboxamide | 526.2 | C |
| 590 | 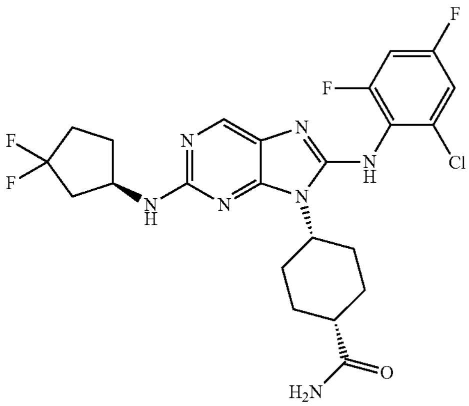 | (1S,4s)-4-(8-(2-chloro-4,6-difluorophenylamino)-2-((R)-3,3-difluorocyclopentylamino)-9H-purin-9-yl)cyclohexanecarboxamide | 526.2 | D |
| 591 | 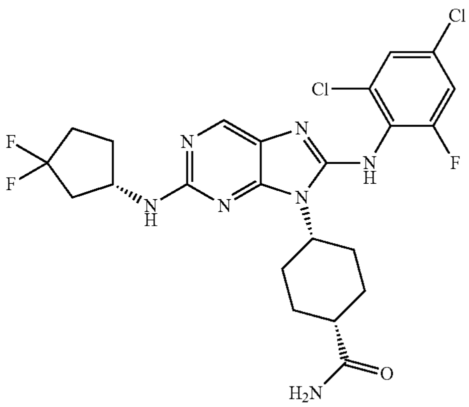 [SMILES: NC(=O)[C@H]1CC[C@@H](n2c(Nc3c(F)cc(Cl)cc3Cl)nc3cnc(N[C@H]4CCC(F)(F)C4)nc32)CC1] | (1R,4s)-4-(8-(2,4-dichloro-6-fluorophenylamino)-2-((S)-3,3-difluorocyclopentylamino)-9H-purian-9-yl)cyclohexanecarboxamide | 542.2 | C |

TABLE 1-continued
| Cmpd No. | Structure | Name | MH+ | Activity |
| --- | --- | --- | --- | --- |
| 592 | 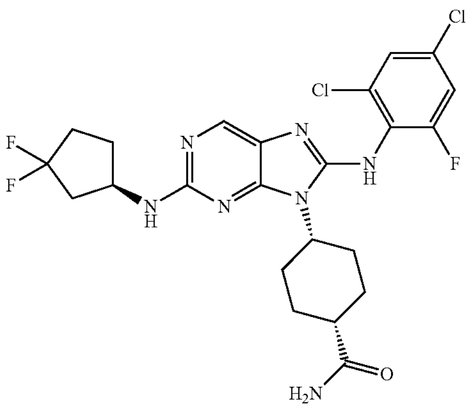 [SMILES: NC(=O)[C@H]1CC[C@@H](n2c(Nc3c(F)cc(Cl)cc3Cl)nc3cnc(N[C@@H]4CCC(F)(F)C4)nc32)CC1] | (1S,4s)-4-(8-(2,4-dichloro-6-fluorophenylamino)-2-((R)-3,3-difluorocyclopentylamino)-9H-purin-9-yl)cyclohexanecarboxamide | 542.2 | D |
| 593 | 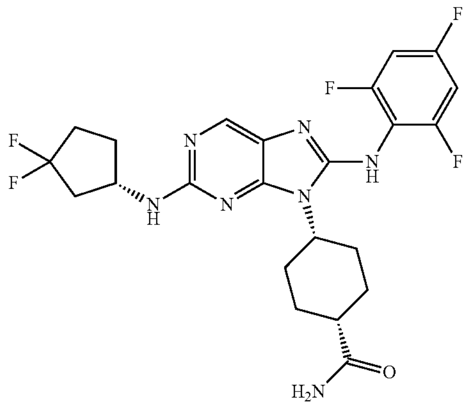 [SMILES: NC(=O)[C@H]1CC[C@@H](n2c(Nc3c(F)cc(F)cc3F)nc3cnc(N[C@H]4CCC(F)(F)C4)nc32)CC1] | (1R,4s)-4-(2-((S)-3,3-difluorocyclopentylamino)-8-(2,4,6-trifluorophenylamino)-9H-purin-9-yl)cyclohexanecarboxamide | 510.3 | C |
| 594 | 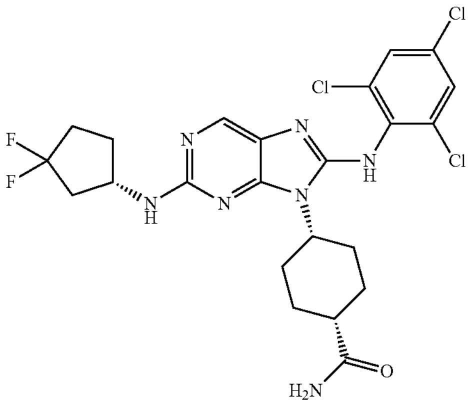 [SMILES: NC(=O)[C@H]1CC[C@@H](n2c(Nc3c(Cl)cc(Cl)cc3Cl)nc3cnc(N[C@H]4CCC(F)(F)C4)nc32)CC1] | (1R,4s)-4-(2-((S)-3,3-difluorocyclopentylamino)-8-(2,4,6-trichlorophenylamino)-9H-purin-9-yl)cyclohexanecarboxamide | 560.2 | C |

TABLE 1-continued

| Cmpd No. | Structure | Name | MH+ | Activity |
|---|---|---|---|---|
| 595 | 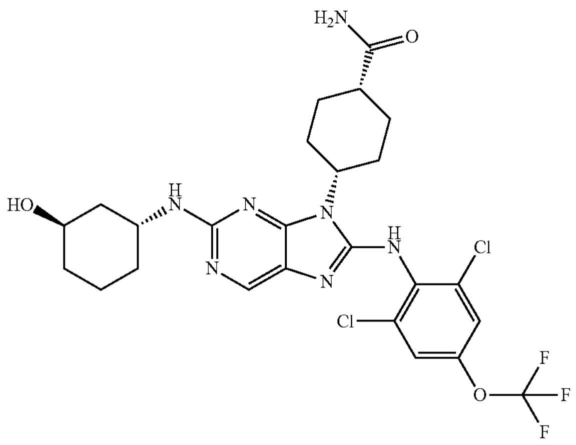 [SMILES: NC(=O)[C@H]1CC[C@@H](n2c(Nc3c(Cl)cc(OC(F)(F)F)cc3Cl)nc3cnc(N[C@@H]4CCC[C@@H](O)C4)nc32)CC1] | (1S,4s)-4-(8-(2,6-dichloro-4-(trifluoromethoxy)phenylamino)-2-((1R,3S)-3-hydroxycyclohexylamino)-9H-purin-9-yl)cyclohexanecarboxamide | 602.1 | A |
| 596 | 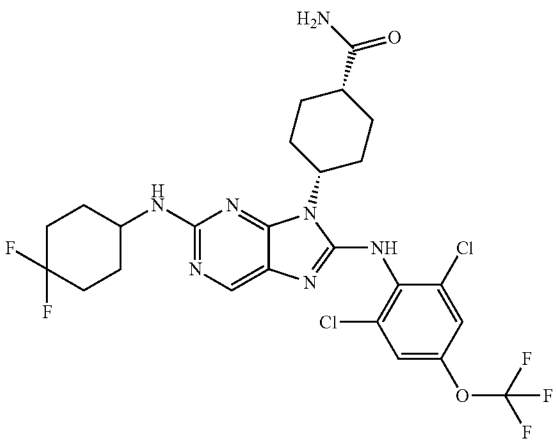 [SMILES: NC(=O)[C@H]1CC[C@@H](n2c(Nc3c(Cl)cc(OC(F)(F)F)cc3Cl)nc3cnc(NC4CCC(F)(F)CC4)nc32)CC1] | (1s,4s)-4-(8-(2,6-dichloro-4-(trifluoromethoxy)phenylamino)-2-(4,4-difluorocyclohexylamino)-9H-purin-9-yl)cyclohexanecarboxamide | 622.1 | A |
| 597 | 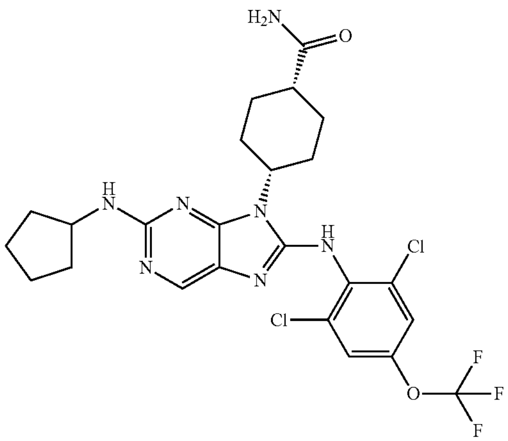 [SMILES: NC(=O)[C@H]1CC[C@@H](n2c(Nc3c(Cl)cc(OC(F)(F)F)cc3Cl)nc3cnc(NC4CCCC4)nc32)CC1] | (1s,4s)-4-(2-(cyclopentylamino)-8-(2,6-dichloro-4-(trifluoromethoxy)phenylamino)-9H-purin-9-yl)cyclohexanecarboxamide | 572.2 | A |

TABLE 1-continued
| Cmpd No. | Structure | Name | MH+ | Activity |
|---|---|---|---|---|
| 598 | 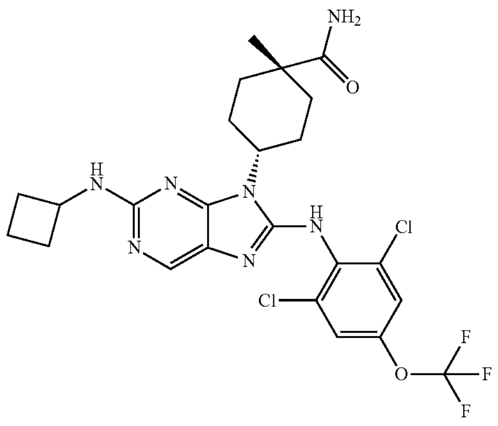 [SMILES: C[C@]1(C(N)=O)CC[C@@H](n2c(Nc3c(Cl)cc(OC(F)(F)F)cc3Cl)nc3cnc(NC4CCC4)nc32)CC1] | (1s,4s)-4-(2-(cyclobutylamino)-8-(2,6-dichloro-4-(trifluoromethoxy)phenylamino)-9H-purin-9-yl)-1-methylcyclohexanecarboxamide | 572.2 | A |
| 599 | 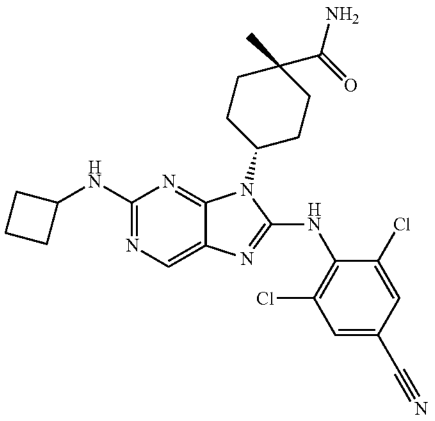 [SMILES: C[C@]1(C(N)=O)CC[C@@H](n2c(Nc3c(Cl)cc(C#N)cc3Cl)nc3cnc(NC4CCC4)nc32)CC1] | (1s,4s)-4-(2-(cyclobutylamino)-8-(2,6-dichloro-4-cyanophenylamino)-9H-purin-9-yl)-1-methylcyclohexanecarboxamide | 513.2 | D |
| 600 | 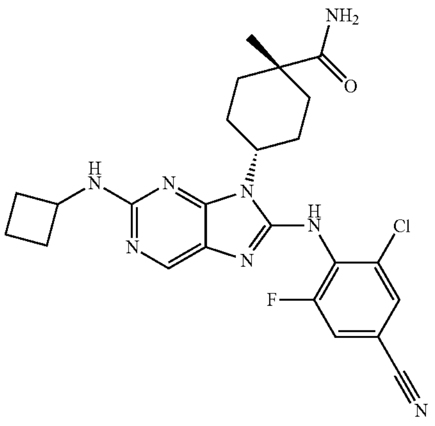 [SMILES: C[C@]1(C(N)=O)CC[C@@H](n2c(Nc3c(F)cc(C#N)cc3Cl)nc3cnc(NC4CCC4)nc32)CC1] | (1s,4s)-4-(8-(2-chloro-4-cyano-6-fluorophenylamino)-2-(cyclobutylamino)-9H-purin-9-yl)-1-methylcyclohexanecarboxamide | 497.3 | D |

TABLE 1-continued
| Cmpd No. | Structure | Name | MH+ | Ac-tivi-ty |
|---|---|---|---|---|
| 601 | 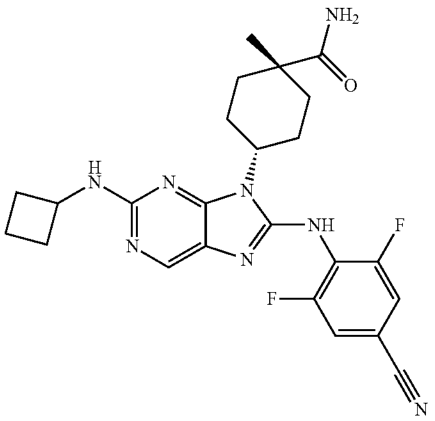 [SMILES: C[C@]1(C(N)=O)CC[C@@H](n2c(Nc3c(F)cc(C#N)cc3F)nc3cnc(NC4CCC4)nc32)CC1] | (1s,4s)-4-(8-(4-cyano-2,6-difluorophenylamino)-2-(cyclobutylamino)-9H-purin-9-yl)-1-methylcyclohexanecarboxamide | 481.3 | D |
| 602 | 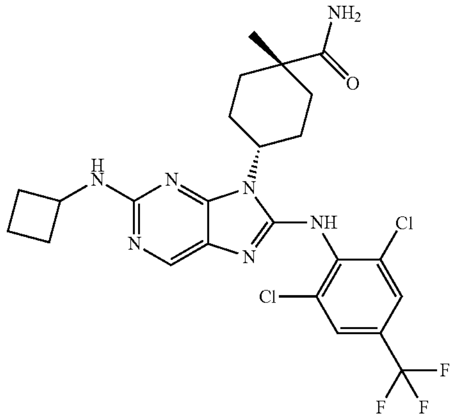 [SMILES: C[C@]1(C(N)=O)CC[C@@H](n2c(Nc3c(Cl)cc(C(F)(F)F)cc3Cl)nc3cnc(NC4CCC4)nc32)CC1] | (1s,4s)-4-(2-(cyclobutylamino)-8-(2,6-dichloro-4-(trifluoromethyl)phenylamino)-9H-purin-9-yl)-1-methylcyclohexanecarboxamide | 556 | A |
| 603 | 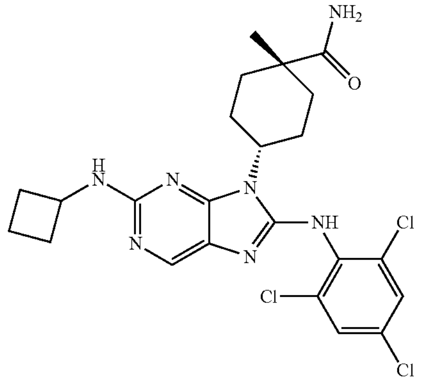 | (1s,4s)-4-(2-(cyclobutylamino)-8-(2,4,6-trichlorophenylamino)-9H-purin-9-yl)-1-methylcyclohexanecarboxamide | 522.2 | D |

TABLE 1-continued

| Cmpd No. | Structure | Name | MH+ | Activity |
|---|---|---|---|---|
| 604 | 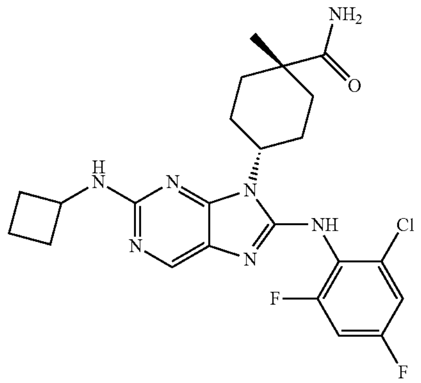 | (1s,4s)-4-(8-(2-chloro-4,6-difluorophenylamino)-2-(cyclobutylamino)-9H-purin-9-yl)-1-methylcyclohexanecarboxamide | 490.2 | D |
| 605 | 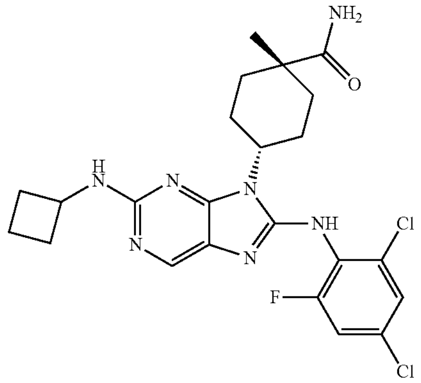 [SMILES: C[C@]1(C(N)=O)CC[C@@H](n2c(Nc3c(F)cc(F)cc3Cl)nc3cnc(NC4CCC4)nc32)CC1] | (1s,4s)-4-(2-(cyclobutylamino)-8-(2,4-dichloro-6-fluorophenylamino)-9H-purin-9-yl)-1-methylcyclohexanecarboxamide | 506.2 | D |
| 606 | 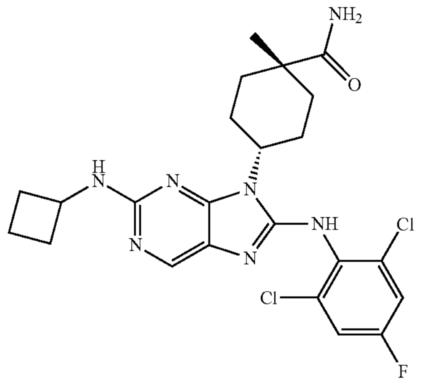 [SMILES: C[C@]1(C(N)=O)CC[C@@H](n2c(Nc3c(Cl)cc(F)cc3Cl)nc3cnc(NC4CCC4)nc32)CC1] | (1s,4s)-4-(2-(cyclobutylamino)-8-(2,6-dichloro-4-fluorophenylamino)-9H-purin-9-yl)-1-methylcyclohexanecarboxamide | 506.2 | D |
| 607 | 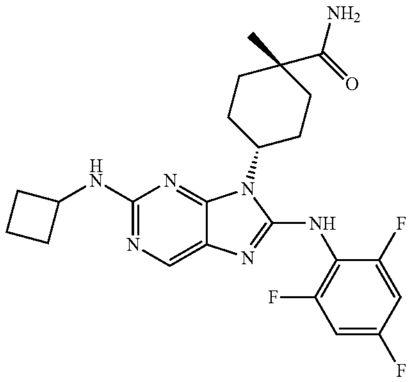 [SMILES: C[C@]1(C(N)=O)CC[C@@H](n2c(Nc3c(F)cc(F)cc3F)nc3cnc(NC4CCC4)nc32)CC1] | (1s,4s)-4-(2-(cyclobutylamino)-8-(2,4,6-trifluorophenylamino)-9H-purin-9-yl)-1-methylcyclohexanecarboxamide | 474.2 | D |

TABLE 1-continued
| Cmpd No. | Structure | Name | MH+ | Activity |
|---|---|---|---|---|
| 608 | 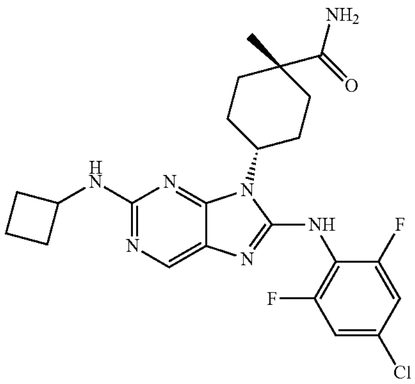 [SMILES: C[C@]1(C(N)=O)CC[C@@H](n2c(Nc3c(F)cc(Cl)cc3F)nc3cnc(NC4CCC4)nc32)CC1] | (1s,4s)-4-(8-(4-chloro-2,6-difluorophenylamino)-2-(cyclobutylamino)-9H-purin-9-yl)-1-methylcyclohexanecarboxamide | 490 | D |
| 609 | 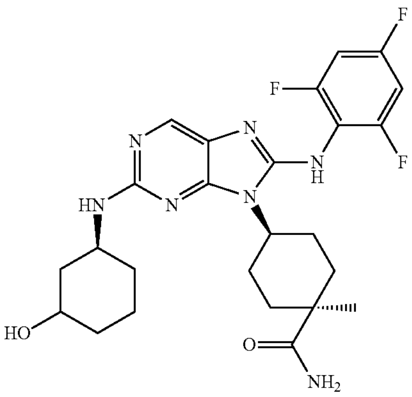 [SMILES: C[C@]1(C(N)=O)CC[C@@H](n2c(Nc3c(F)cc(F)cc3F)nc3cnc(N[C@H]4CCCC(O)C4)nc32)CC1] | (1R,4s)-4-(2-((1S,3S)-3-hydroxycyclohexylamino)-8-(2,4,6-trifluorophenylamino)-9H-purin-9-yl)-1-methylcyclohexanecarboxamide | 518 | C |
| 610 | 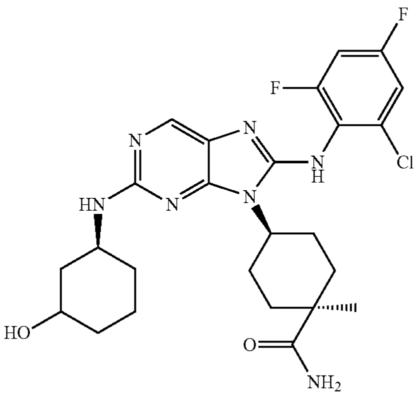 | (1R,4s)-4-(8-(2-chloro-4,6-difluorophenylamino)-2-((1S,3S)-3-hydroxycyclohexylamino)-9H-purin-9-yl)-1-methylcyclohexanecarboxamide | 534 | C |

TABLE 1-continued

| Cmpd No. | Structure | Name | MH+ | Activity |
|---|---|---|---|---|
| 611 | 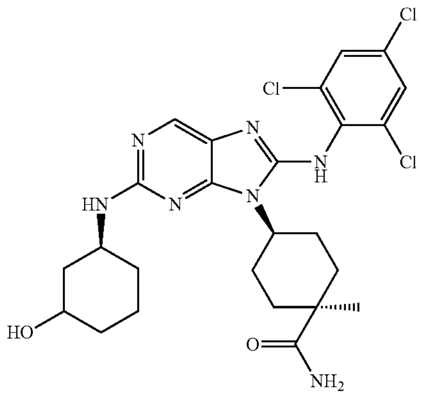 [SMILES: C[C@]1(C(N)=O)CC[C@@H](n2c(Nc3c(Cl)cc(Cl)cc3Cl)nc3cnc(N[C@H]4CCCC(O)C4)nc32)CC1] | (1R,4s)-4-(2-((1S,3S)-3-hydroxycyclohexylamino)-8-(2,4,6-trichlorophenylamino)-9H-purin-9-yl)-1-methylcyclohexanecarboxamide | 566.2 | D |
| 612 | 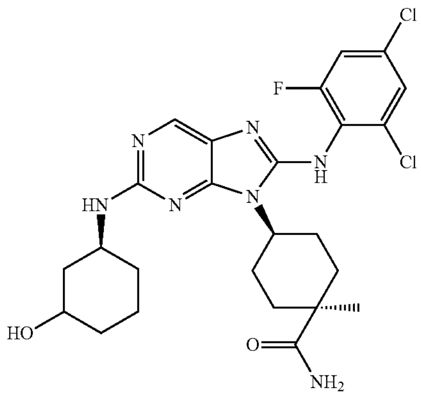 [SMILES: C[C@]1(C(N)=O)CC[C@@H](n2c(Nc3c(F)cc(Cl)cc3Cl)nc3cnc(N[C@H]4CCCC(O)C4)nc32)CC1] | (1R,4s)-4-(8-(2,4-dichloro-6-fluorophenylamino)-2-((1S,3S)-3-hydroxycyclohexylamino)-9H-purin-9-yl)-1-methylcyclohexanecarboxamide | 550.1 | D |
| 613 | 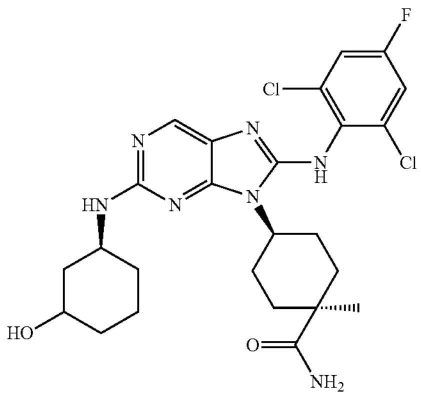 | (1R,4s)-4-(8-(2,6-dichloro-4-fluorophenylamino)-2-((1S,3S)-3-hydroxycyclohexylamino)-9H-purin-9-yl)-1-methylcyclohexanecarboxamide | 550.1 | D |

TABLE 1-continued

| Cmpd No. | Structure | Name | MH+ | Activity |
|---|---|---|---|---|
| 614 | 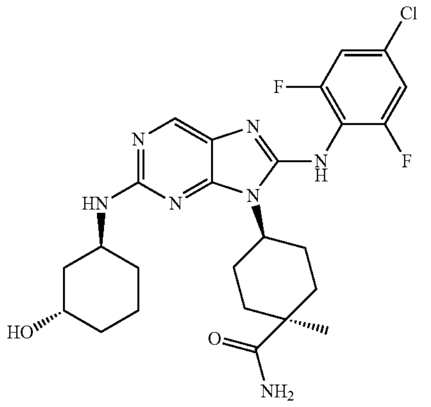 [SMILES: C[C@]1(C(N)=O)CC[C@@H](n2c(Nc3c(F)cc(Cl)cc3F)nc3cnc(N[C@H]4CCC[C@H](O)C4)nc32)CC1] | (1R,4s)-4-(8-(4-chloro-2,6-difluorophenylamino)-2-((1S,3S)-3-hydroxycyclohexylamino)-9H-purin-9-yl)-1-methylcyclohexanecarboxamide | 534.2 | D |
| 615 | 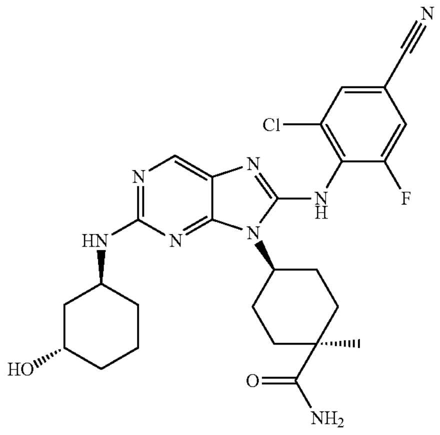 [SMILES: C[C@]1(C(N)=O)CC[C@@H](n2c(Nc3c(F)cc(C#N)cc3Cl)nc3cnc(N[C@H]4CCC[C@H](O)C4)nc32)CC1] | (1R,4s)-4-(8-(2-chloro-4-cyano-6-fluorophenylamino)-2-((1S,3S)-3-hydroxycyclohexylamino)-9H-purin-9-yl)-1-methylcyclohexanecarboxamide | 541.3 | D |
| 616 | 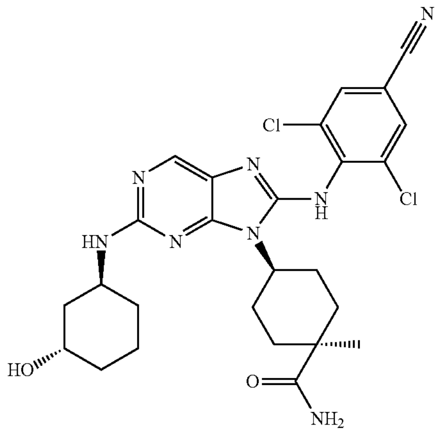 [SMILES: C[C@]1(C(N)=O)CC[C@@H](n2c(Nc3c(Cl)cc(C#N)cc3Cl)nc3cnc(N[C@H]4CCC[C@H](O)C4)nc32)CC1] | (1R,4s)-4-(8-(2,6-dichloro-4-cyanophenylamino)-2-((1S,3S)-3-hydroxycyclohexylamino)-9H-purin-9-yl)-1-methylcyclohexanecarboxamide | 557.2 | D |

TABLE 1-continued
| Cmpd No. | Structure | Name | MH+ | Activity |
|---|---|---|---|---|
| 617 | 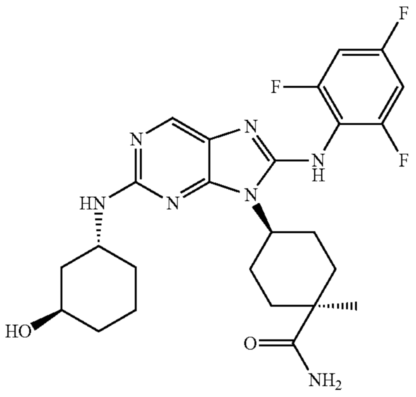 [SMILES: C[C@]1(C(N)=O)CC[C@@H](n2c(Nc3c(F)cc(F)cc3F)nc3cnc(N[C@@H]4CCC[C@@H](O)C4)nc32)CC1] | (1S,4s)-4-(2-((1R,3R)-3-hydroxycyclohexylamino)-8-(2,4,6-trifluorophenylamino)-9H-purin-9-yl)-1-methylcyclohexanecarboxamide | 518.3 | A |
| 618 | 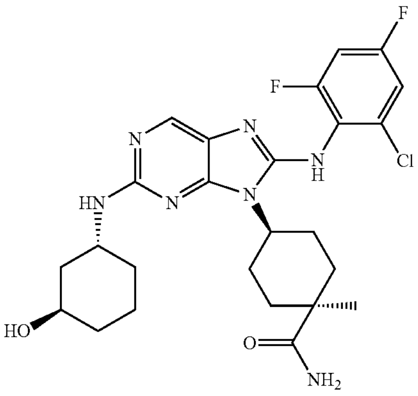 | (1S,4s)-4-(8-(2-chloro-4,6-difluorophenylamino)-2-((1R,3R)-3-hydroxycyclohexylamino)-9H-purin-9-yl)-1-methylcyclohexanecarboxamide | 534.2 | B |
| 619 | 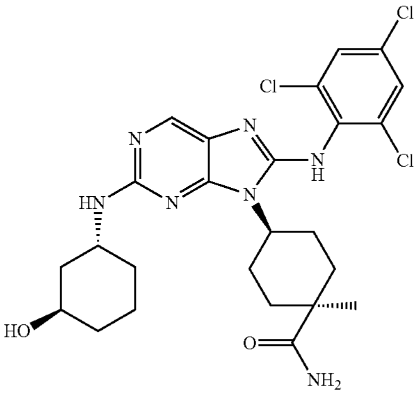 [SMILES: C[C@]1(C(N)=O)CC[C@@H](n2c(Nc3c(Cl)cc(Cl)cc3Cl)nc3cnc(N[C@@H]4CCC[C@@H](O)C4)nc32)CC1] | (1S,4s)-4-(2-((1R,3R)-3-hydroxycyclohexylamino)-8-(2,4,6-trichlorophenylamino)-9H-purin-9-yl)-1-methylcyclohexanecarboxamide | 566.2 | B |

TABLE 1-continued

| Cmpd No. | Structure | Name | MH+ | Ac-tivi-ty |
|---|---|---|---|---|
| 620 | 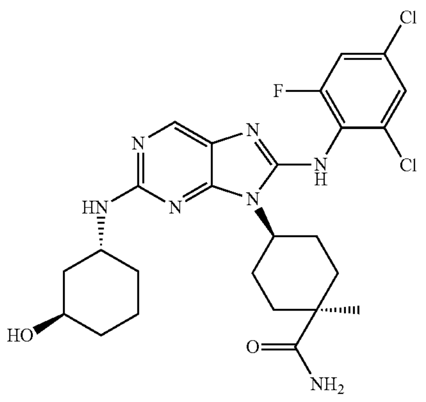 [SMILES: C[C@]1(C(N)=O)CC[C@@H](n2c(Nc3c(F)cc(Cl)cc3Cl)nc3cnc(N[C@@H]4CCC[C@@H](O)C4)nc32)CC1] | (1S,4s)-4-(8-(2,4-dichloro-6-fluorophenylamino)-2-((1R,3R)-3-hydroxycyclohexylamino)-9H-purin-9-yl)-1-methylcyclohexanecarboxamide | 550.2 | B |
| 621 | 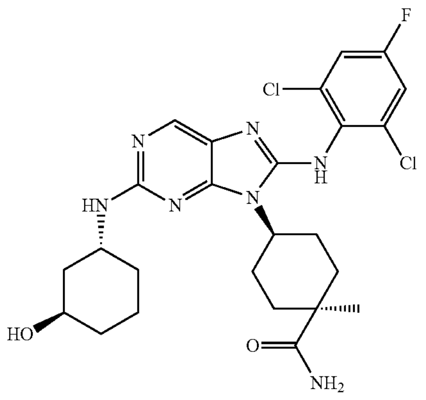 [SMILES: C[C@]1(C(N)=O)CC[C@@H](n2c(Nc3c(Cl)cc(F)cc3Cl)nc3cnc(N[C@@H]4CCC[C@@H](O)C4)nc32)CC1] | (1S,4s)-4-(8-(2,6-dichloro--fluorophenylamino)-2-((1R,3R)-3-hydroxycyclohexylamino)-9H-purin-9-yl)-1-methylcyclohexanecarboxamide | 550.2 | A |
| 622 | 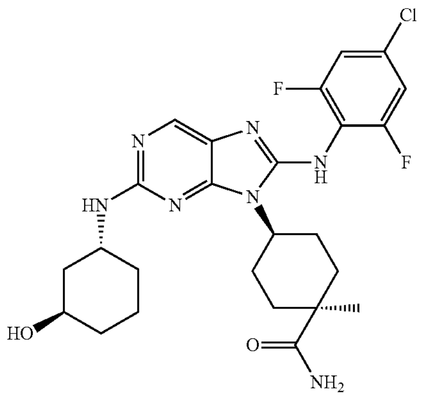 [SMILES: C[C@]1(C(N)=O)CC[C@@H](n2c(Nc3c(F)cc(Cl)cc3F)nc3cnc(N[C@@H]4CCC[C@@H](O)C4)nc32)CC1] | (1S,4s)-4-(8-(4-chloro-2,6-difluorophenylamino)-2-((1R,3R)-3-hydroxycyclohexylamino)-9H-purin-9-yl)-1-methylcyclohexanecarboxamide | 534.2 | B |

TABLE 1-continued

| Cmpd No. | Structure | Name | MH+ | Activity |
|---|---|---|---|---|
| 623 | 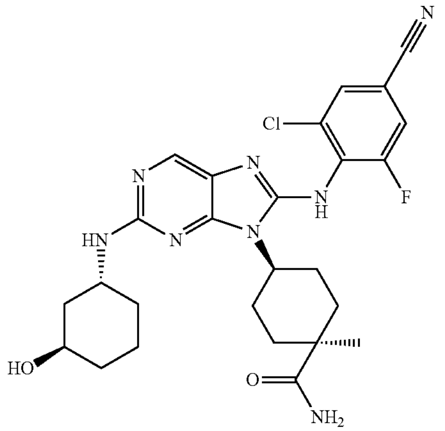 [SMILES: C[C@]1(C(N)=O)CC[C@@H](n2c(Nc3c(F)cc(C#N)cc3Cl)nc3cnc(N[C@@H]4CCC[C@@H](O)C4)nc32)CC1] | (1S,4s)-4-(8-(2-chloro-4-cyano-6-fluorophenylamino)-2-((1R,3R)-3-hydroxycyclohexylamino)-9H-purin-9-yl)-1-methylcyclohexanecarboxamide | 541.2 | C |
| 624 | 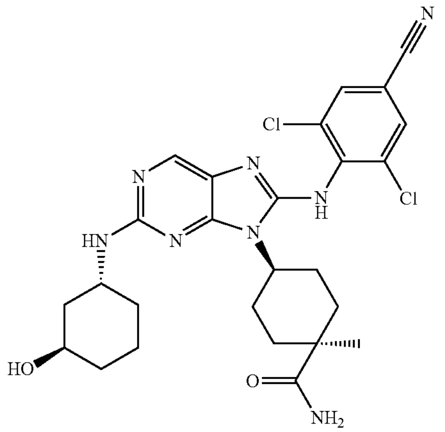 | (1S,4s)-4-(8-(2,6-dichloro-4-cyanophenylamino)-2-((1R,3R)-3-hydroxycyclohexylamino)-9H-purin-9-yl)-1-methylcyclohexanecarboxamide | 557.2 | C |
| 625 | 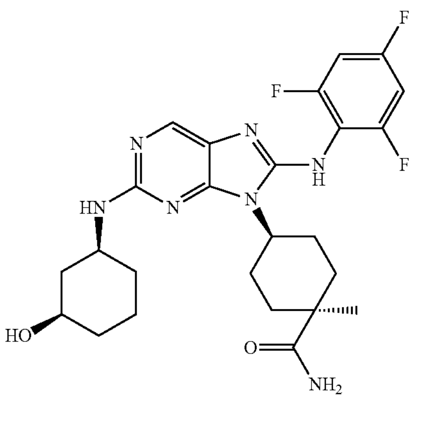 [SMILES: C[C@]1(C(N)=O)CC[C@@H](n2c(Nc3c(F)cc(F)cc3F)nc3cnc(N[C@H]4CCC[C@@H](O)C4)nc32)CC1] | (1R,4s)-4-(2-((1S,3R)-3-hydroxycyclohexylamino)-8-(2,4,6-trifluorophenylamino)-9H-purin-9-yl)-1-methylcyclohexanecarboxamide | 518.2 | A |

TABLE 1-continued

| Cmpd No. | Structure | Name | MH+ | Activity |
|---|---|---|---|---|
| 626 | 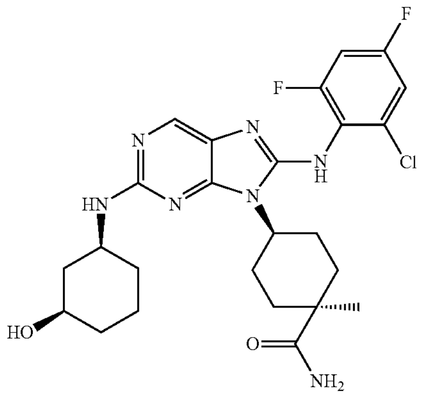 [SMILES: C[C@]1(C(N)=O)CC[C@@H](n2c(Nc3c(F)cc(F)cc3Cl)nc3cnc(N[C@H]4CCC[C@@H](O)C4)nc32)CC1] | (1R,4s)-4-(8-(2-chloro-4,6-difluorophenylamino)-2-((1S,3R)-3-hydroxycyclohexylamino)-9H-purin-9-yl)-1-methylcyclohexanecarboxamide | 534.2 | B |
| 627 | 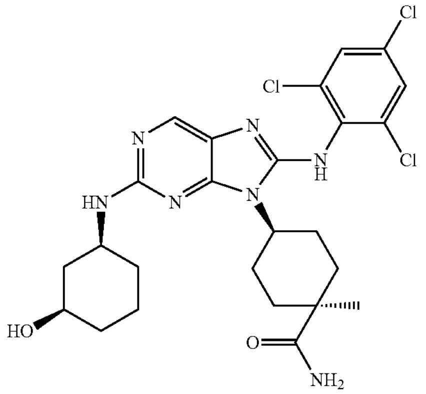 [SMILES: C[C@]1(C(N)=O)CC[C@@H](n2c(Nc3c(Cl)cc(Cl)cc3Cl)nc3cnc(N[C@H]4CCC[C@@H](O)C4)nc32)CC1] | (1R,4s)-4-(2-((1S,3R)-3-hydroxycyclohexylamino)-8-(2,4,6-trichlorophenylamino)-9H-purin-9-yl)-1-methylcyclohexanecarboxamide | 566.2 | D |
| 628 | 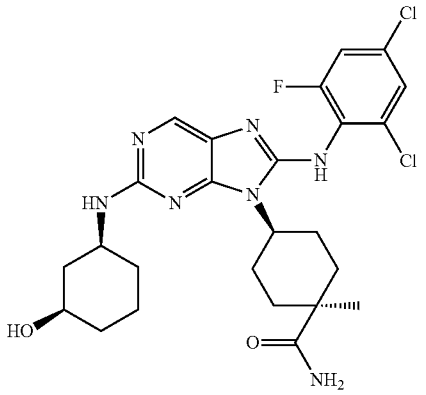 [SMILES: C[C@]1(C(N)=O)CC[C@@H](n2c(Nc3c(F)cc(Cl)cc3Cl)nc3cnc(N[C@H]4CCC[C@@H](O)C4)nc32)CC1] | (1R,4s)-4-(8-(2,4-dichloro-6-fluorophenylamino)-2-((1S,3R)-3-hydroxycyclohexylamino)-9H-purin-9-yl)-1-methylcyclohexanecarboxamide | 550.2 | D |

TABLE 1-continued

| Cmpd No. | Structure | Name | MH+ | Activity |
|---|---|---|---|---|
| 629 | 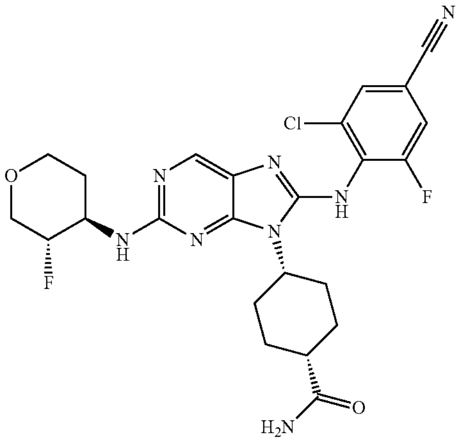 | (1S,4s)-4-(8-(2-chloro-4-cyano-6-fluorophenylamino)-2-((3S,4R)-3-fluorotetrahydro-2H-pyran-4-ylamino)-9H-purin-9-yl)cyclohexanecarboxamide | 531.2 | D |
| 630 | 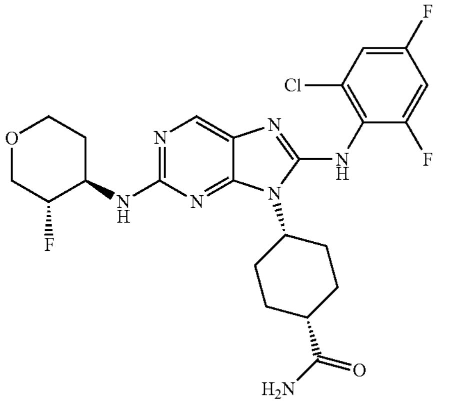 | (1S,4s)-4-(8-(2-chloro-4,6-difluorophenylamino)-2-((3S,4R)-3-fluorotetrahydro-2H-pyran-4-ylamino)-9H-purin-9-yl)cyclohexanecarboxamide | 524.2 | D |
| 631 | 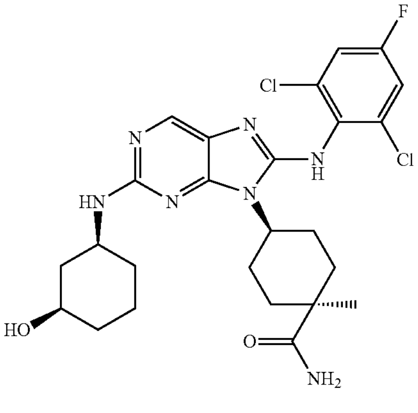 | (1R,4s)-4-(8-(2,6-dichloro-4-fluorophenylamino)-2-((1S,3R)-3-hydroxycyclohexylamino)-9H-purin-9-yl)-1-methylcyclohexanecarboxamide | 550.2 | B |

TABLE 1-continued

| Cmpd No. | Structure | Name | MH+ | Activity |
|---|---|---|---|---|
| 632 | 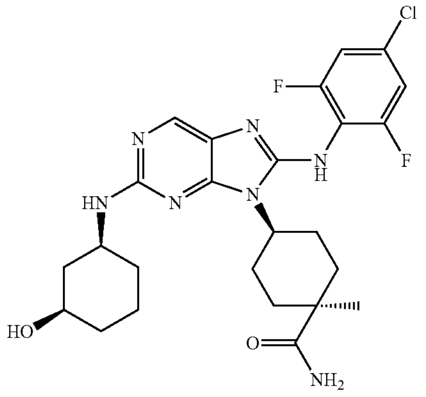 [SMILES: C[C@]1(C(N)=O)CC[C@@H](n2c(Nc3c(F)cc(Cl)cc3F)nc3cnc(N[C@H]4CCC[C@@H](O)C4)nc32)CC1] | (1R,4s)-4-(8-(4-chloro-2,6-difluorophenylamino)-2-((1S,3R)-3-hydroxycyclohexylamino)-9H-purin-9-yl)-1-methylcyclohexanecarboxamide | 534.2 | B |
| 633 | 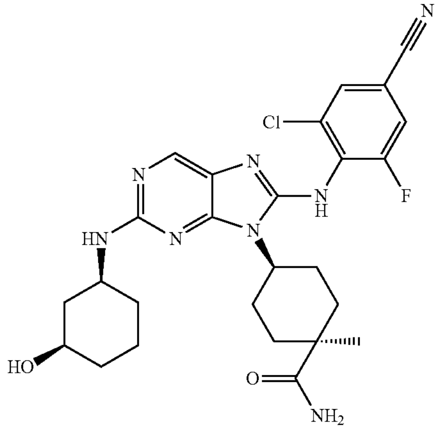 [SMILES: C[C@]1(C(N)=O)CC[C@@H](n2c(Nc3c(F)cc(C#N)cc3Cl)nc3cnc(N[C@H]4CCC[C@@H](O)C4)nc32)CC1] | (1R,4s)-4-(8-(2-chloro-4-cyano-6-fluorophenylamino)-2-((1S,3R)-3-hydroxycyclohexylamino)-9H-purin-9-yl)-1-methylcyclohexanecarboxamide | 541 | B |
| 634 | 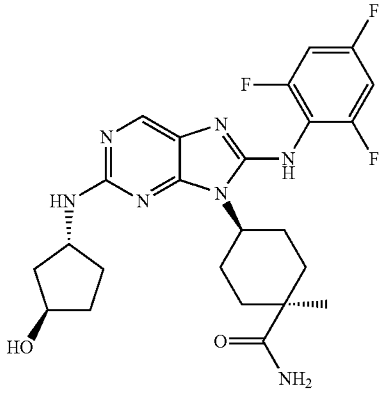 [SMILES: C[C@]1(C(N)=O)CC[C@@H](n2c(Nc3c(F)cc(F)cc3F)nc3cnc(N[C@@H]4CC[C@@H](O)C4)nc32)CC1] | (1S,4s)-4-(2-((1R,3R)-3-hydroxycyclopentylamino)-8-(2,4,6-trifluorophenylamino)-9H-purin-9-yl)-1-methylcyclohexanecarboxamide | 504 | B |

TABLE 1-continued

| Cmpd No. | Structure | Name | MH+ | Activity |
|---|---|---|---|---|
| 635 | 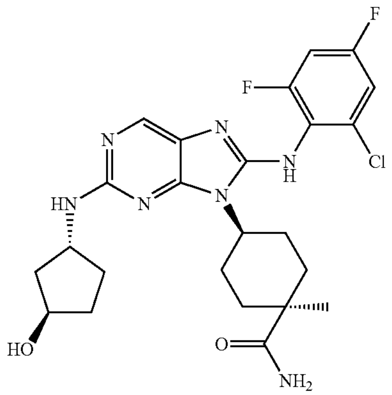 | (1S,4s)-4-(8-(2-chloro-4,6-difluorophenylamino)-2-((1R,3R)-3-hydroxycyclopentylamino)-9H-purin-9-yl)-1-methylcyclohexanecarboxamide | 520 | C |
| 636 | 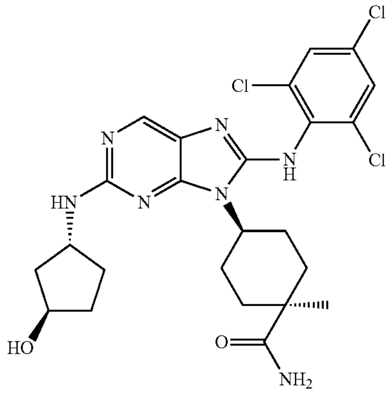 [SMILES: C[C@]1(C(N)=O)CC[C@@H](n2c(Nc3c(Cl)cc(Cl)cc3Cl)nc3cnc(N[C@@H]4CC[C@@H](O)C4)nc32)CC1] | (1S,4s)-4-(2-((1R,3R)-3-hydroxycyclopentylamino)-8-(2,4,6-trichlorophenylamino)-9H-purin-9-yl)-1-methylcyclohexanecarboxamide | 552.2 | D |
| 637 | 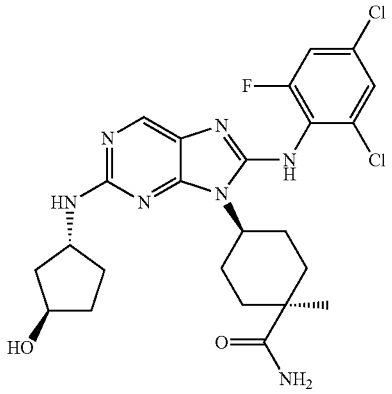 [SMILES: C[C@]1(C(N)=O)CC[C@@H](n2c(Nc3c(F)cc(Cl)cc3Cl)nc3cnc(N[C@@H]4CC[C@@H](O)C4)nc32)CC1] | (1S,4s)-4-(8-(2,4-dichloro-6-fluorophenylamino)-2-((1R,3R)-3-hydroxycyclopentylamino)-9H-purin-9-yl)-1-methylcyclohexanecarboxamide | 536.2 | D |

TABLE 1-continued

| Cmpd No. | Structure | Name | MH+ | Ac-tivi-ty |
|---|---|---|---|---|
| 638 | 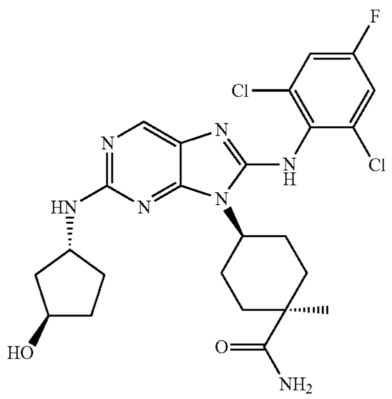 | (1S,4s)-4-(8-(2,6-dichloro-4-fluorophenylamino)-2-((1R,3R)-3-hydroxycyclopentylamino)-9H-purin-9-yl)-1-methylcyclohexanecarboxamide | 536.2 | D |
| 639 | 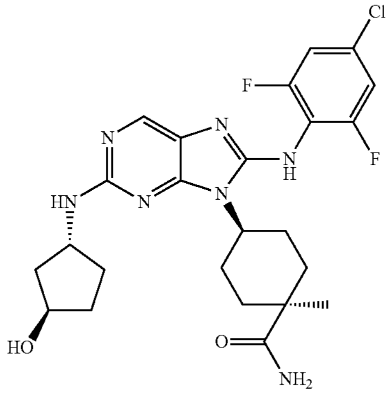 [SMILES: C[C@]1(C(N)=O)CC[C@@H](n2c(Nc3c(F)cc(Cl)cc3F)nc3cnc(N[C@@H]4CC[C@@H](O)C4)nc32)CC1] | (1S,4s)-4-(8-(4-chloro-2,6-difluorophenylamino)-2-((1R,3R)-3-hydroxycyclopentylamino)-9H-purin-9-yl)-1-methylcyclohexanecarboxamide | 520.2 | D |
| 640 | 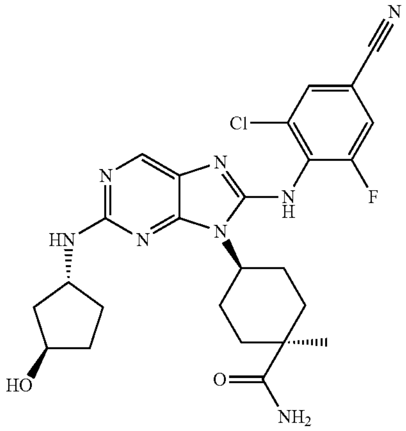 [SMILES: C[C@]1(C(N)=O)CC[C@@H](n2c(Nc3c(F)cc(C#N)cc3Cl)nc3cnc(N[C@@H]4CC[C@@H](O)C4)nc32)CC1] | (1S,4s)-4-(8-(2-chloro-4-cyano-6-fluorophenylamino)-2-((1R,3R)-3-hydroxycyclopentylamino)-9H-purin-9-yl)-1-methylcyclohexanecarboxamide | 527.2 | D |

TABLE 1-continued

| Cmpd No. | Structure | Name | MH+ | Ac-tivi-ty |
|---|---|---|---|---|
| 641 | 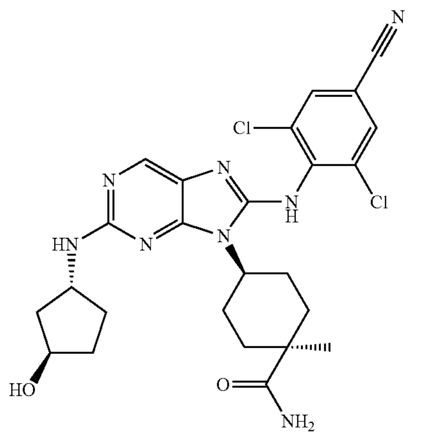 [SMILES: C[C@]1(C(N)=O)CC[C@@H](n2c(Nc3c(Cl)cc(C#N)cc3Cl)nc3cnc(N[C@@H]4CC[C@@H](O)C4)nc32)CC1] | (1S,4s)-4-(8-(2,6-dichloro-4-cyanophenylamino)-2-((1R,3R)-3-hydroxycyclopentylamino)-9H-purin-9-yl)-1-methylcyclohexanecarboxamide | 543.2 | D |
| 642 | 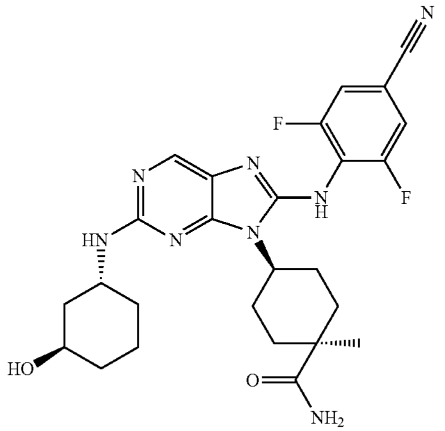 [SMILES: C[C@]1(C(N)=O)CC[C@@H](n2c(Nc3c(F)cc(C#N)cc3F)nc3cnc(N[C@@H]4CCC[C@@H](O)C4)nc32)CC1] | (1S,4s)-4-(8-(4-cyano-2,6-difluorophenylamino)-2-((1R,3R)-3-hydroxycyclohexylamino)-9H-purin-9-yl)-1-methylcyclohexanecarboxamide | 525.2 | A |
| 643 | 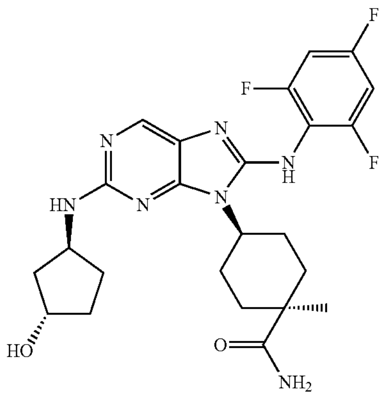 [SMILES: C[C@]1(C(N)=O)CC[C@@H](n2c(Nc3c(F)cc(F)cc3F)nc3cnc(N[C@H]4CC[C@H](O)C4)nc32)CC1] | (1R,4s)-4-(2-((1S,3S)-3-hydroxycyclopentylamino)-8-(2,4,6-trifluorophenylamino)-9H-purin-9-yl)-1-methylcyclohexanecarboxamide | 504 | B |

TABLE 1-continued

| Cmpd No. | Structure | Name | MH+ | Activity |
|---|---|---|---|---|
| 644 | 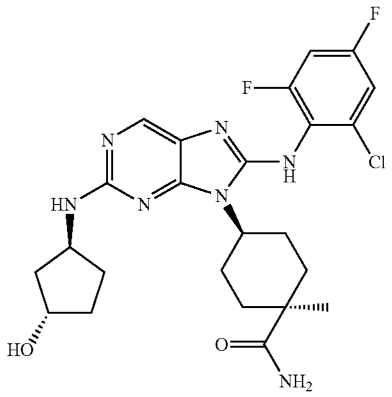 | (1R,4s)-4-(8-(2-chloro-4,6-difluorophenylamino)-2-((1S,3S)-3-hydroxycyclopentylamino)-9H-purin-9-yl)-1-methylcyclohexanecarboxamide | 520.2 | C |
| 645 | 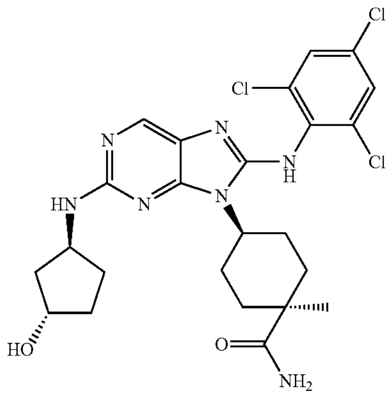 [SMILES: C[C@]1(C(N)=O)CC[C@@H](n2c(Nc3c(Cl)cc(Cl)cc3Cl)nc3cnc(N[C@H]4CC[C@H](O)C4)nc32)CC1] | (1R,4s)-4-(2-((1S,3S)-3-hydroxycyclopentylamino)-8-(2,4,6-trichlorophenylamino)-9H-purin-9-yl)-1-methylcyclohexanecarboxamide | 552.2 | B |
| 646 | 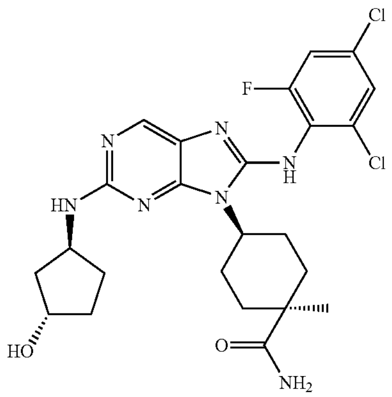 [SMILES: C[C@]1(C(N)=O)CC[C@@H](n2c(Nc3c(F)cc(Cl)cc3Cl)nc3cnc(N[C@H]4CC[C@H](O)C4)nc32)CC1] | (1R,4s)-4-(8-(2,4-dichloro-6-fluorophenylamino)-2-((1S,3S)-3-hydroxycyclopentyalmino)-9H-purin-9-yl)-1-methylcyclohexanecarboxamide | 536.2 | C |

TABLE 1-continued

| Cmpd No. | Structure | Name | MH+ | Ac-tivi-ty |
|---|---|---|---|---|
| 647 | 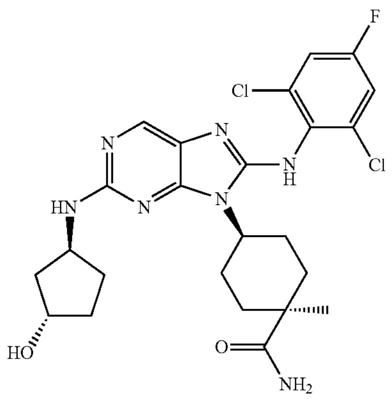 | (1R,4s)-4-(8-(2,6-dichloro-4-fluorophenylamino)-2-((1S,3S)-3-hydroxycyclopentylamino)-9H-purin-9-yl)-1-methylcyclohexanecarboxamide | 536.2 | B |
| 648 | 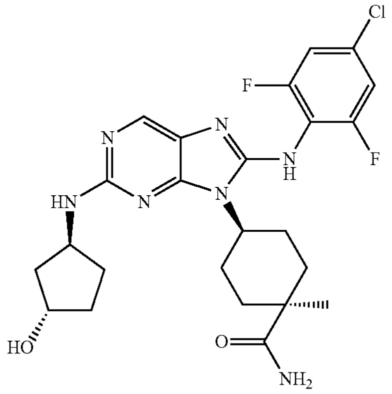 [SMILES: C[C@]1(C(N)=O)CC[C@@H](n2c(Nc3c(F)cc(Cl)cc3F)nc3cnc(N[C@H]4CC[C@H](O)C4)nc32)CC1] | (1R,4s)-4-(8-(4-chloro-2,6-difluorophenylamino)-2-((1S,3S)-3-hydroxycyclopentylamino)-9H-purin-9-yl)-1-methylcyclohexanecarboxamide | 520.2 | A |
| 649 | 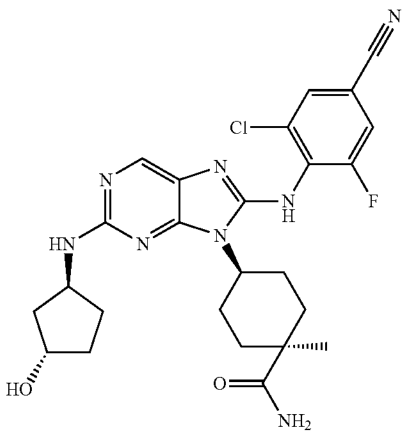 [SMILES: C[C@]1(C(N)=O)CC[C@@H](n2c(Nc3c(F)cc(C#N)cc3Cl)nc3cnc(N[C@H]4CC[C@H](O)C4)nc32)CC1] | (1R,4s)-4-(8-(2-chloro-4-cyano-6-fluorophenylamino)-2-((1S,3S)-3-hydroxycyclopentylamino)-9H-purin-9-yl)-1-methylcyclohexanecarboxamide | 527.2 | C |

TABLE 1-continued

| Cmpd No. | Structure | Name | MH+ | Activity |
|---|---|---|---|---|
| 650 | 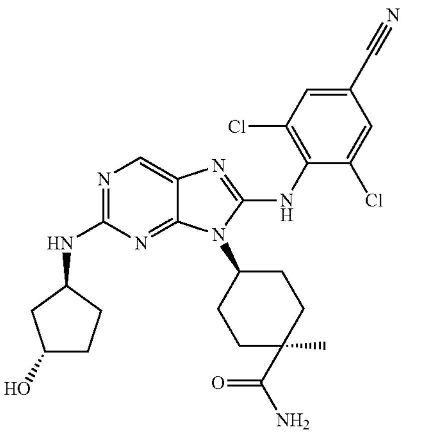 [SMILES: C[C@]1(C(N)=O)CC[C@@H](n2c(Nc3c(Cl)cc(C#N)cc3Cl)nc3cnc(N[C@H]4CC[C@H](O)C4)nc32)CC1] | (1R,4s)-4-(8-(2,6-dichloro-4-cyanophenylamino)-2-((1S,3S)-3-hydroxycyclopentylamino)-9H-purin-9-yl)-1-methylcyclohexanecarboxamide | 543.2 | C |
| 651 | 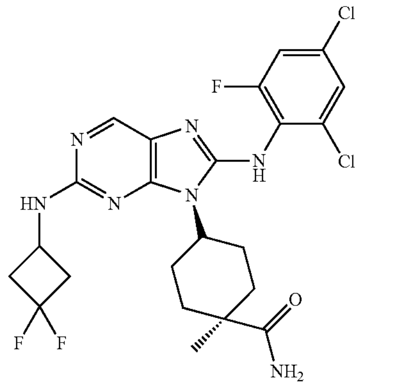 | (1s,4s)-4-(8-(2,4-dichloro-6-fluorophenylamino)-2-(3,3-difluorocyclobutylamino)-9H-purin-9-yl)-1-methylcyclohexanecarboxamide | 542.1 | D |
| 652 | 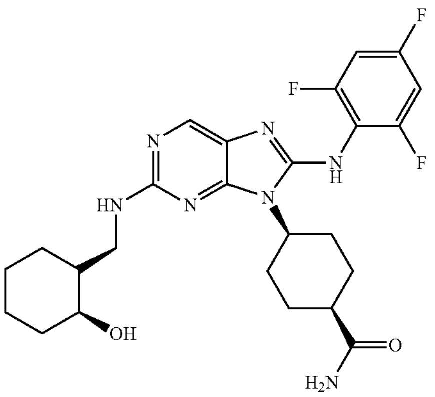 | (1R,4s)-4-(2-(((1S,2S)-2-hydroxycyclohexayl)methylamino)-8-(2,4,6-trifluorophenylamino)-9H-purin-9-yl)cyclohexanecarboxamide | 518.3 | A |

TABLE 1-continued

| Cmpd No. | Structure | Name | MH+ | Activity |
|---|---|---|---|---|
| 653 | 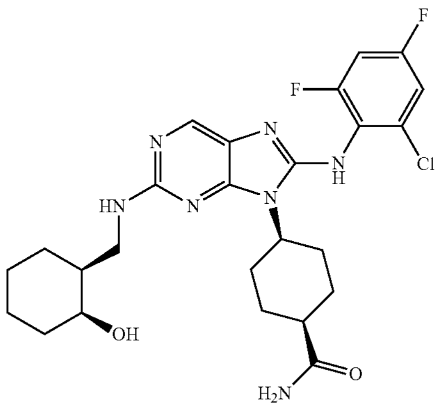 | (1R,4s)-4-(8-(2-chloro-4,6-difluorophenylamino)-2-(((1S,2S)-2-hydroxycyclohexyl)methylamino)-9H-purin-9-yl)cyclohexanecarboxamide | 534.2 | A |
| 654 | 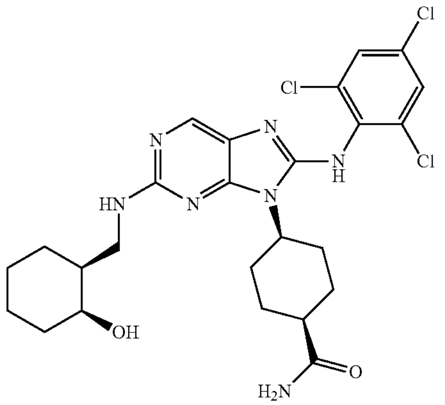 [SMILES: NC(=O)[C@H]1CC[C@@H](n2c(Nc3c(Cl)cc(Cl)cc3Cl)nc3cnc(NC[C@@H]4CCCC[C@@H]4O)nc32)CC1] | (1R,4s)-4-(2-(((1S,2S)-2-hydroxycyclohexyl)methylamino)-8-(2,4,6-trichlorophenylamino)-9H-purin-9-yl)cyclohexanecarboxamide | 566.2 | A |
| 655 | 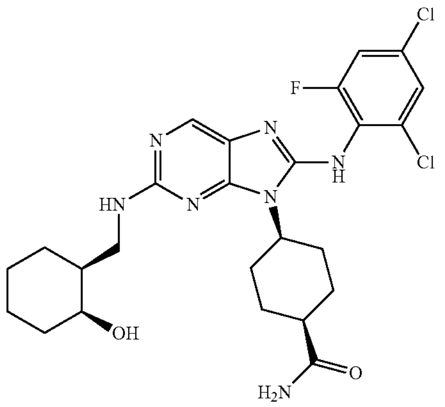 [SMILES: NC(=O)[C@H]1CC[C@@H](n2c(Nc3c(F)cc(Cl)cc3Cl)nc3cnc(NC[C@@H]4CCCC[C@@H]4O)nc32)CC1] | (1R,4s)-4-(8-(2,4-dichloro-6-fluorophenylamino)-2-(((1S,2S)-2-hydroxycyclohexyl)methylamino)-9H-purin-9-yl)cyclohexanecarboxamide | 550.2 | A |

TABLE 1-continued

| Cmpd No. | Structure | Name | MH+ | Activity |
|---|---|---|---|---|
| 656 | 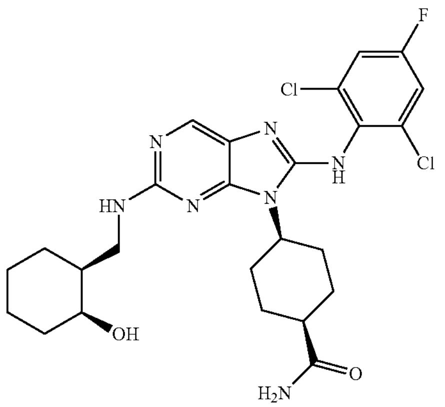 | (1R,4s)-4-(8-(2,6-dichloro-4-fluorophenylamino)-2-(((1S,2S)-2-hydroxycyclohexyl)methylamino)-9H-purin-9-yl)cyclohexanecarboxamide | 550.2 | A |
| 657 | 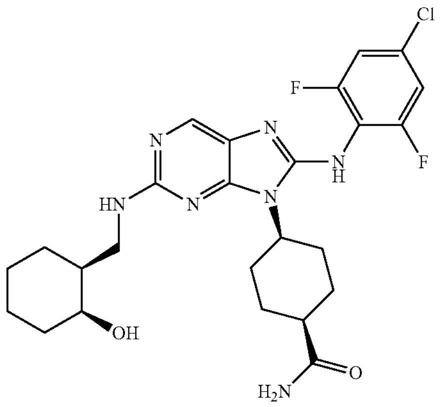 [SMILES: NC(=O)[C@H]1CC[C@@H](n2c(Nc3c(F)cc(Cl)cc3F)nc3cnc(NC[C@@H]4CCCC[C@@H]4O)nc32)CC1] | (1R,4s)-4-(8-(4-chloro-2,6-difluorophenylamino)-2-(((1S,2S)-2-hydroxycyclohexyl)methylamino)-9H-purin-9-yl)cyclohexanecarboxamide | 534.2 | A |
| 658 | 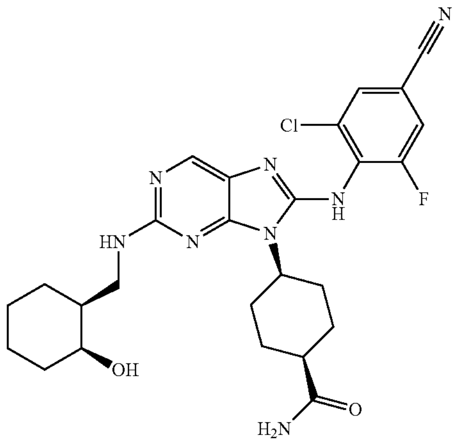 [SMILES: N#Cc1cc(F)c(Nc2nc3cnc(NC[C@@H]4CCCC[C@@H]4O)nc3n2[C@H]2CC[C@@H](C(N)=O)CC2)c(Cl)c1] | (1R,4s)-4-(8-(2-chloro-4-cyano-6-fluorophenylamino)-2-(((1S,2S)-2-hydroxycyclohexyl)methylamino)-9H-purin-9-yl)cyclohexanecarboxamide | 541.3 | A |

TABLE 1-continued

| Cmpd No. | Structure | Name | MH+ | Activity |
|---|---|---|---|---|
| 659 | 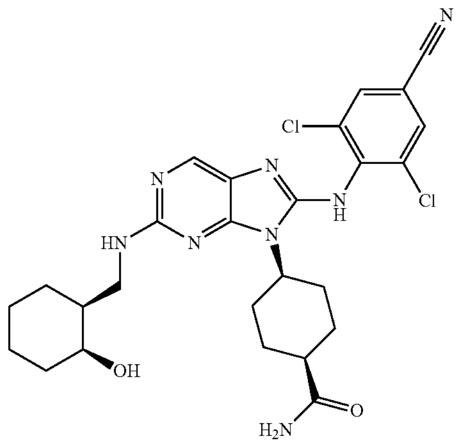 [SMILES: N#Cc1cc(Cl)c(Nc2nc3cnc(NC[C@@H]4CCCC[C@@H]4O)nc3n2[C@H]2CC[C@@H](C(N)=O)CC2)c(Cl)c1] | (1R,4s)-4-(8-(2,6-dichloro-4-cyanophenylamino)-2-(((1S,2S)-2-hydroxycyclohexyl)methylamino)-9H-purin-9-yl)cyclohexanecarboxamide | 557.2 | A |
| 660 | 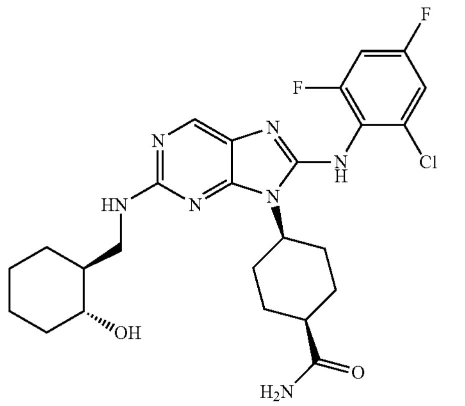 | (1R,4s)-4-(8-(2-chloro-4,6-difluorophenylamino)-2-(((1S,2R)-2-hydroxycyclohexyl)methylamino)-9H-purin-9-yl)cyclohexanecarboxamide | 534.2 | A |
| 661 | 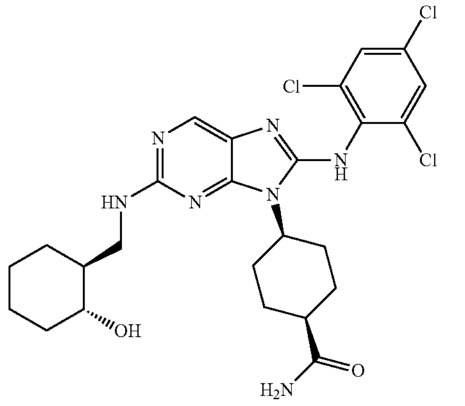 [SMILES: NC(=O)[C@H]1CC[C@@H](n2c(Nc3c(Cl)cc(Cl)cc3Cl)nc3cnc(NC[C@@H]4CCCC[C@H]4O)nc32)CC1] | (1R,4s)-4-(2-(((1S,2R)-2-hydroxycyclohexyl)methylamino)-8-(2,4,6-trichlorophenylamino)-9H-purin-9-yl)cyclohexanecarboxamide | 566.2 | A |

TABLE 1-continued

| Cmpd No. | Structure | Name | MH+ | Activity |
|---|---|---|---|---|
| 662 | 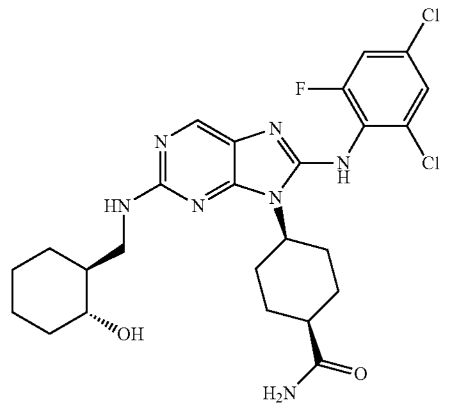 [SMILES: NC(=O)[C@H]1CC[C@@H](n2c(Nc3c(F)cc(Cl)cc3Cl)nc3cnc(NC[C@@H]4CCCC[C@H]4O)nc32)CC1] | (1R,4s)-4-(8-(2,4-dichloro-6-fluorophenylamino)-2-(((1S,2R)-2-hydroxycyclohexyl)methylamino)-9H-purin-9-yl)cyclohexanecarboxamide | 550.2 | A |
| 663 | 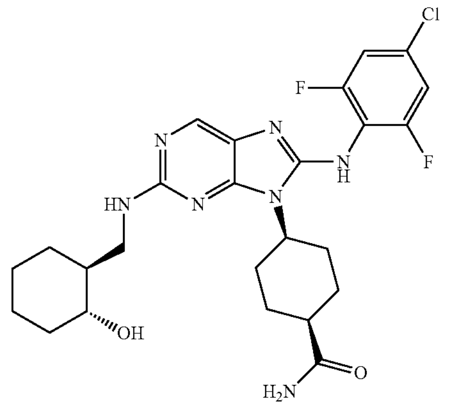 [SMILES: NC(=O)[C@H]1CC[C@@H](n2c(Nc3c(F)cc(Cl)cc3F)nc3cnc(NC[C@@H]4CCCC[C@H]4O)nc32)CC1] | (1R,4s)-4-(8-(4-chloro-2,6-difluorophenylamino)-2-(((1S,2R)-2-hydroxycyclohexyl)methylamino)-9H-purin-9-yl)cyclohexanecarboxamide | 534 | A |
| 664 | 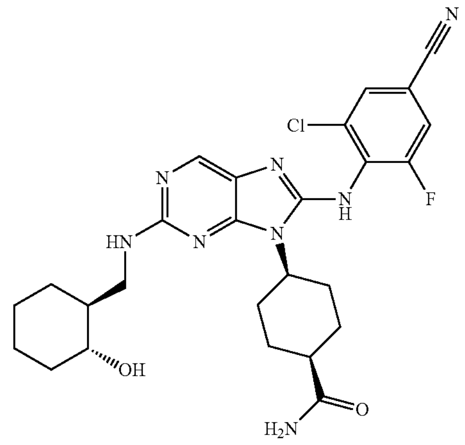 [SMILES: N#Cc1cc(F)c(Nc2nc3cnc(NC[C@@H]4CCCC[C@H]4O)nc3n2[C@H]2CC[C@@H](C(N)=O)CC2)c(Cl)c1] | (1R,4s)-4-(8-(2-chloro-4-cyano-6-fluorophenylamino)-2-(((1S,2R)-2-hydroxycyclohexyl)methylamino)-9H-purin-9-yl)cyclohexanecarboxamide | 541.2 | A |

TABLE 1-continued

| Cmpd No. | Structure | Name | MH+ | Ac-tivi-ty |
|---|---|---|---|---|
| 665 | 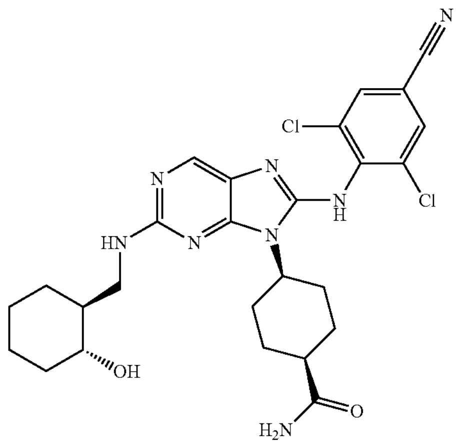 [SMILES: N#Cc1cc(Cl)c(Nc2nc3cnc(NC[C@@H]4CCCC[C@H]4O)nc3n2[C@H]2CC[C@@H](C(N)=O)CC2)c(Cl)c1] | (1R,4s)-4-(8-(2,6-dichloro-4-cyanophenylamino)-2-(((1S,2R)-2-hydroxycyclohexyl)methylamino)-9H-purin-9-yl)cyclohexanecarboxamide | 557.2 | A |
| 666 | 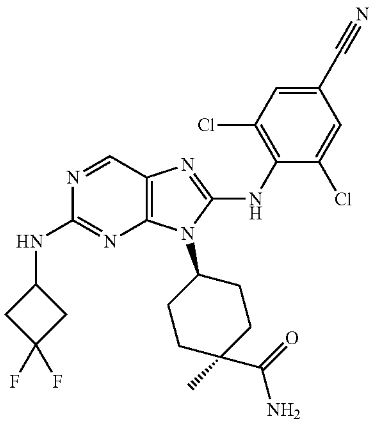 | (1s,4s)-4-(8-(2,6-dichloro-4-cyanophenylamino)-2-(3,3-difluorocyclobutylamino)-9H-purin-9-yl)-1-methylcyclohexanecarboxamide | 549.2 | D |
| 667 | 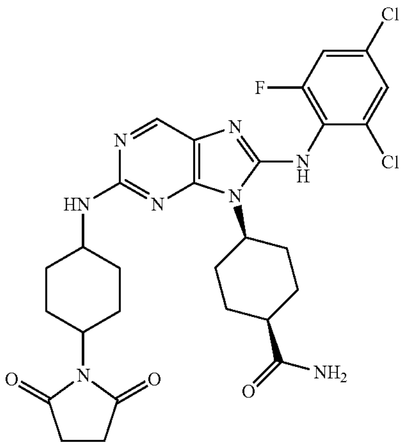 [SMILES: NC(=O)[C@H]1CC[C@@H](n2c(Nc3c(F)cc(Cl)cc3Cl)nc3cnc(NC4CCC(N5C(=O)CCC5=O)CC4)nc32)CC1] | (1s,4s)-4-(8-(2,4-dichloro-6-fluorophenylamino)-2-(4-(2,5-dioxopyrrolidin-1-yl)cyclohexylamino)-9H-purin-9-yl)cyclohexanecarboxamide | 617.1 | A |

TABLE 1-continued

| Cmpd No. | Structure | Name | MH+ | Activity |
|---|---|---|---|---|
| 668 | 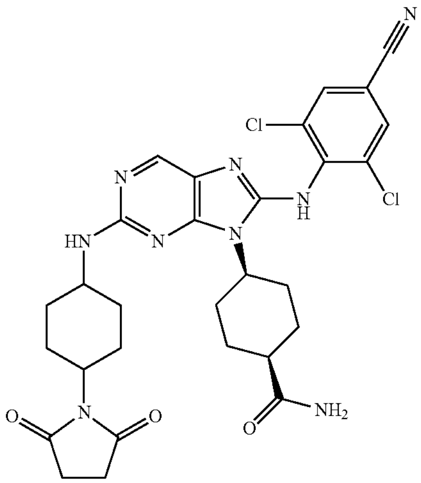 [SMILES: N#Cc1cc(Cl)c(Nc2nc3cnc(NC4CCC(N5C(=O)CCC5=O)CC4)nc3n2[C@H]2CC[C@@H](C(N)=O)CC2)c(Cl)c1] | (1s,4s)-4-(8-(2,6-dichloro-4-cyanophenylamino)-2-(4-(2,5-dioxopyrrolidin-1-yl)cyclohexylamino)-9H-purin-9-yl)cyclohexanecarboxamide | 624.2 | A |
| 669 | 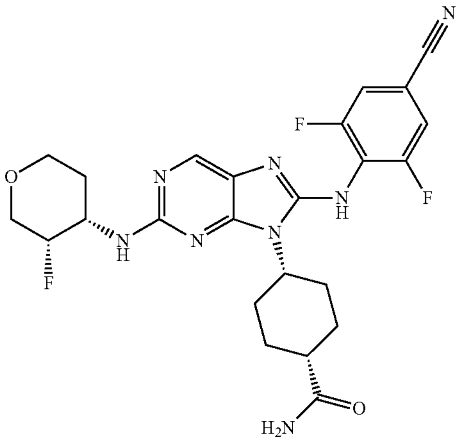 [SMILES: N#Cc1cc(F)c(Nc2nc3cnc(N[C@H]4CCOC[C@H]4F)nc3n2[C@H]2CC[C@@H](C(N)=O)CC2)c(F)c1] | (1R,4s)-4-(8-(4-cyano-2,6-difluorophenylamino)-2-((3S,4S)-3-fluorotetrahydro-2H-pyran-4-ylamino)-9H-purin-9-yl)cyclohexanecarboxamide | 515.2 | B |
| 670 | 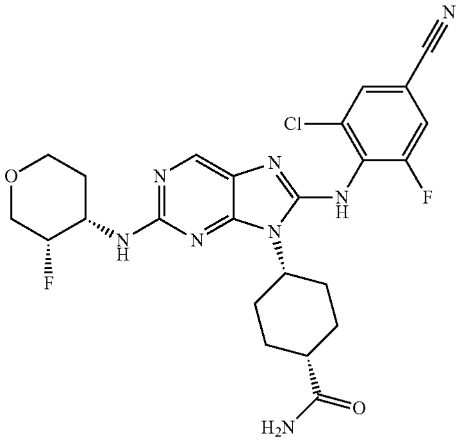 [SMILES: N#Cc1cc(F)c(Nc2nc3cnc(N[C@H]4CCOC[C@H]4F)nc3n2[C@H]2CC[C@@H](C(N)=O)CC2)c(Cl)c1] | (1R,4s)-4-(8-(2-chloro-4-cyano-6-fluorophenylamino)-2-((3S,4S)-3-fluorotetrahydro-2H-pyran-4-ylamino)-9H-purin-9-yl)cyclohexanecarboxamide | 531.2 | D |

TABLE 1-continued

| Cmpd No. | Structure | Name | MH+ | Ac-tivi-ty |
|---|---|---|---|---|
| 671 | 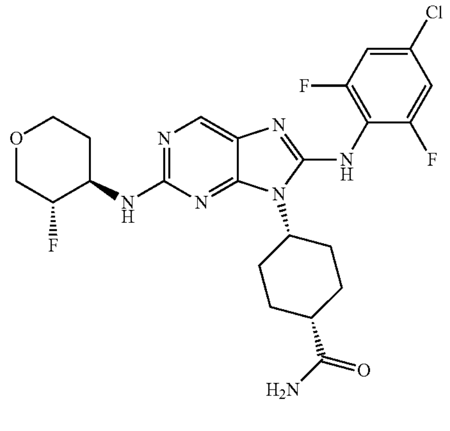 [SMILES: NC(=O)[C@H]1CC[C@@H](n2c(Nc3c(F)cc(Cl)cc3F)nc3cnc(N[C@@H]4CCOC[C@H]4F)nc32)CC1] | (1S,4s)-4-(8-(4-chloro-2,6-difluorophenylamino)-2-((3S,4R)-3-fluorotetrahydro-2H-pyran-4-ylamino)-9H-purin-9-yl)cyclohexanecarboxamide | 524.2 | D |
| 672 | 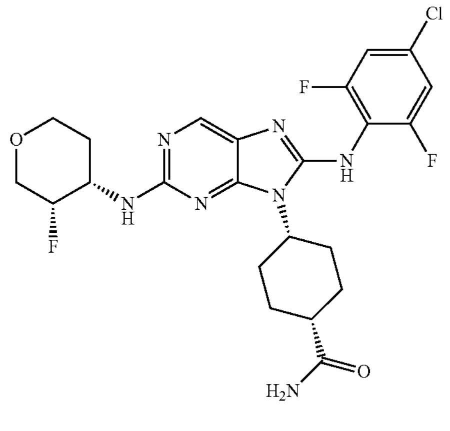 [SMILES: NC(=O)[C@H]1CC[C@@H](n2c(Nc3c(F)cc(Cl)cc3F)nc3cnc(N[C@H]4CCOC[C@H]4F)nc32)CC1] | (1R,4s)-4-(8-(4-chloro-2,6-difluorophenylamino)-2-((3S,4S)-3-fluorotetrahydro-2H-pyran-4-ylamino)-9H-purin-9-yl)cyclohexanecarboxamide | 524.2 | D |
| 673 | 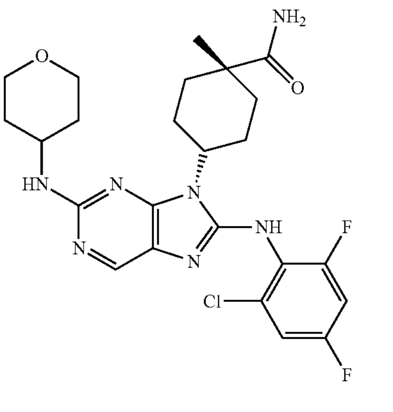 | (1s,4s)-4-(8-(2-chloro-4,6-difluorophenylamino)-2-(tetrahydro-2H-pyran-4-ylamino)-9H-purin-9-yl)-1-methylcyclohexanecarboxamide | 520.1 | D |

TABLE 1-continued

| Cmpd No. | Structure | Name | MH+ | Activity |
|---|---|---|---|---|
| 674 | 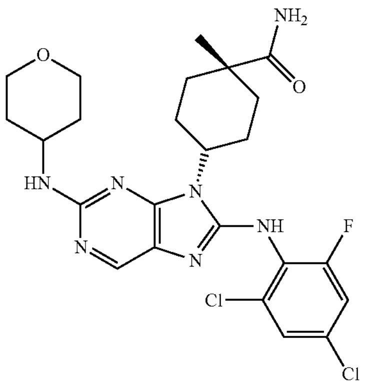 | (1s,4s)-4-(8-(2,4-dichloro-6-fluorophenylamino)-2-(tetrahydro-2H-pyran-4-ylamino)-9H-purin-9-yl)-1-methylcyclohexanecarboxamide | 536.1 | D |
| 675 | 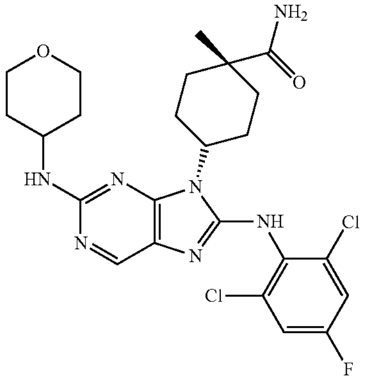 | (1s,4s)-4-(8-(2,6-dichloro-4-fluorophenylamino)-2-(tetrahydro-2H-pyran-4-ylamino)-9H-purin-9-yl)-1-methylcyclohexanecarboxamide | 536.1 | D |
| 676 | 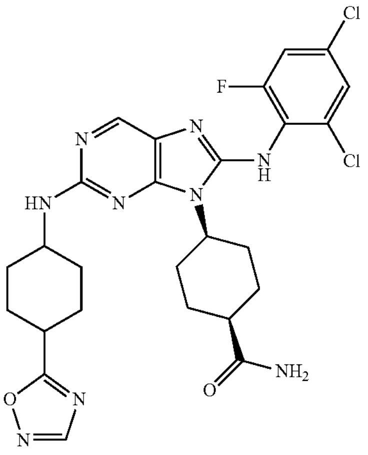 [SMILES: NC(=O)[C@H]1CC[C@@H](n2c(Nc3c(F)cc(Cl)cc3Cl)nc3cnc(NC4CCC(c5ncno5)CC4)nc32)CC1] | (1s,4s)-4-(2-(4-(1,2,4-oxadiazol-5-yl)cyclohexylamino)-8-(2,4-dichloro-6-fluorophenylamino)-9H-purin-9-yl)cyclohexanecarboxamide | 558.1 | A |

TABLE 1-continued
| Cmpd No. | Structure | Name | MH+ | Activity |
| --- | --- | --- | --- | --- |
| 677 | 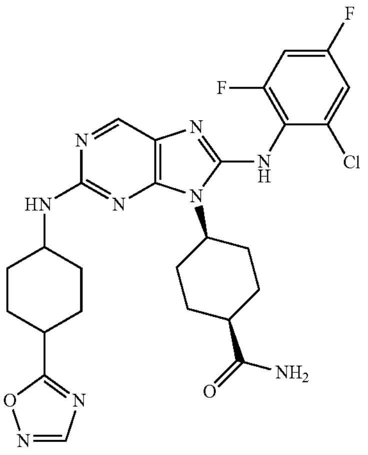 [SMILES: NC(=O)[C@H]1CC[C@@H](n2c(Nc3c(F)cc(F)cc3Cl)nc3cnc(NC4CCC(c5ncno5)CC4)nc32)CC1] | (1s,4s)-4-(2-(4-(1,2,4-oxadiazol-5-yl)cyclohexylamino)-8-(2-chloro-4,6-difluorophenylamino)-9H-purin-9-yl)cyclohexanecarboxamide | 572.1 | A |
| 678 | 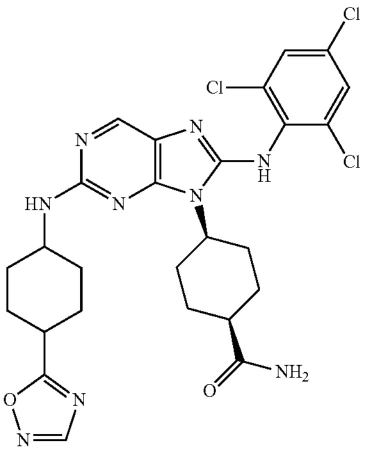 [SMILES: NC(=O)[C@H]1CC[C@@H](n2c(Nc3c(Cl)cc(Cl)cc3Cl)nc3cnc(NC4CCC(c5ncno5)CC4)nc32)CC1] | (1s,4s)-4-(2-(4-(1,2,4-oxadiazol-5-yl)cyclohexylamino)-8-(2,4,6-trichlorophenylamino)-9H-purin-9-yl)cyclohexanecarboxamide | 604.1 | A |
| 679 | 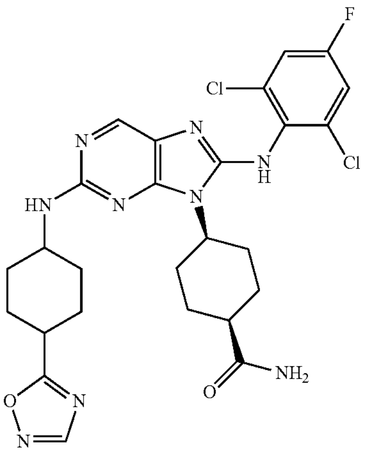 [SMILES: NC(=O)[C@H]1CC[C@@H](n2c(Nc3c(Cl)cc(F)cc3Cl)nc3cnc(NC4CCC(c5ncno5)CC4)nc32)CC1] | (1s,4s)-4-(2-(4-(1,2,4-oxadiazol-5-yl)cyclohexylamino)-8-(2,6-dichloro-4-fluorophenylamino)-9H-purin-9-yl)cyclohexanecarboxamide | 588.1 | A |

TABLE 1-continued

| Cmpd No. | Structure | Name | MH+ | Activity |
|---|---|---|---|---|
| 680 | 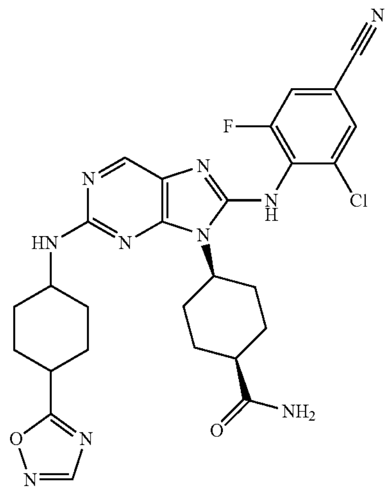 [SMILES: N#Cc1cc(F)c(Nc2nc3cnc(NC4CCC(c5ncno5)CC4)nc3n2[C@H]2CC[C@@H](C(N)=O)CC2)c(Cl)c1] | (1s,4s)-4-(2-(4-(1,2,4-oxadiazol-5-yl)cyclohexylamino)-8-(2-chloro-4-cyano-6-fluorophenylamino)-9H-purin-9-yl)cyclohexanecarboxamide | 579.2 | A |
| 681 | 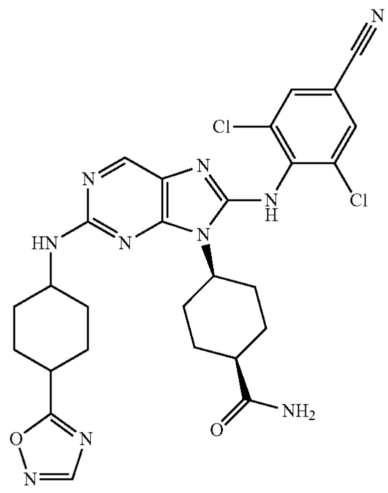 [SMILES: N#Cc1cc(Cl)c(Nc2nc3cnc(NC4CCC(c5ncno5)CC4)nc3n2[C@H]2CC[C@@H](C(N)=O)CC2)c(Cl)c1] | (1s,4s)-4-(2-(4-(1,2,4-oxadiazol-5-yl)cyclohexylamino)-8-(2,6-dichloro-4-cyanophenylamino)-9H-purin-9-yl)cyclohexanecarboxamide | 595.1 | A |
| 682 | 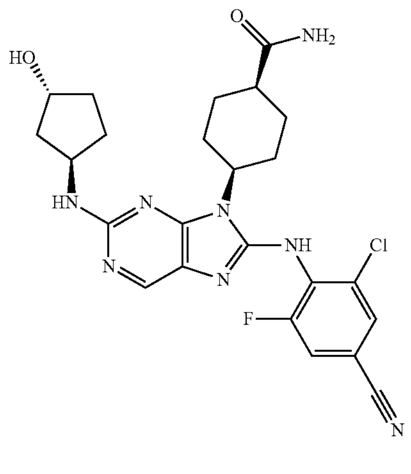 [SMILES: N#Cc1cc(F)c(Nc2nc3cnc(N[C@@H]4CC[C@@H](O)C4)nc3n2[C@H]2CC[C@@H](C(N)=O)CC2)c(Cl)c1] | (1S,4s)-4-(8-(2-chloro-4-cyano-6-fluorophenylamino)-2-((1R,3R)-3-hydroxycyclopentylamino)-9H-purin-9-yl)cyclohexanecarboxamide | 513 | D |

TABLE 1-continued
| Cmpd No. | Structure | Name | MH+ | Activity |
| --- | --- | --- | --- | --- |
| 683 | 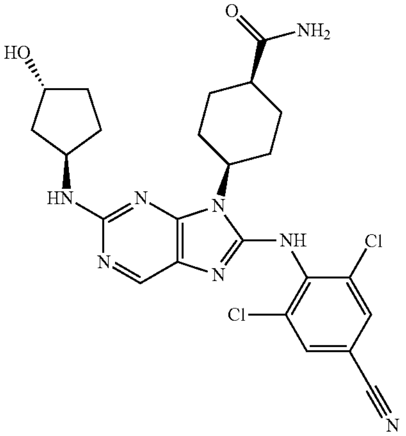 [SMILES: N#Cc1cc(Cl)c(Nc2nc3cnc(N[C@@H]4CC[C@@H](O)C4)nc3n2[C@H]2CC[C@@H](C(N)=O)CC2)c(Cl)c1] | (1S,4s)-4-(8-(2,6-dichloro-4-cyanophenylamino)-2-((1R,3R)-3-hydroxycyclopentylamino)-9H-purin-9-yl)cyclohexanecarboxamide | 529.2 | D |
| 684 | 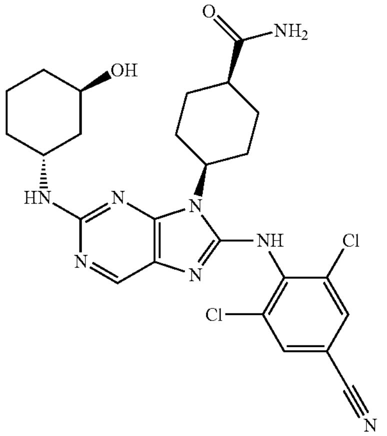 [SMILES: N#Cc1cc(Cl)c(Nc2nc3cnc(N[C@@H]4CCC[C@@H](O)C4)nc3n2[C@H]2CC[C@@H](C(N)=O)CC2)c(Cl)c1] | (1S,4s)-4-(8-(2,6-dichloro-4-cyanophenylamino)-2-((1R,3R)-3-hydroxycyclohexylamino)-9H-purin-9-yl)cyclohexanecarboxamide | 543.2 | B |
| 685 | 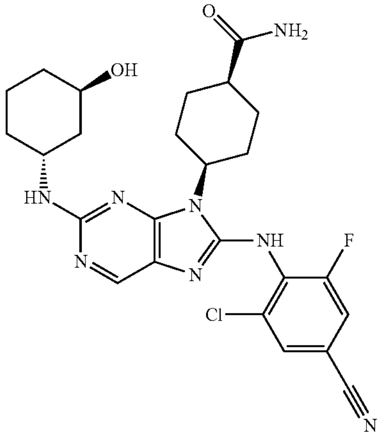 [SMILES: N#Cc1cc(F)c(Nc2nc3cnc(N[C@@H]4CCC[C@@H](O)C4)nc3n2[C@H]2CC[C@@H](C(N)=O)CC2)c(Cl)c1] | (1S,4s)-4-(8-(2-chloro-4-cyano-6-fluorophenylamino)-2-((1R,3R)-3-hydroxycyclohexylamino)-9H-purin-9-yl)cyclohexanecarboxamide | 527.1 | B |

TABLE 1-continued
| Cmpd No. | Structure | Name | MH+ | Activity |
|---|---|---|---|---|
| 686 | 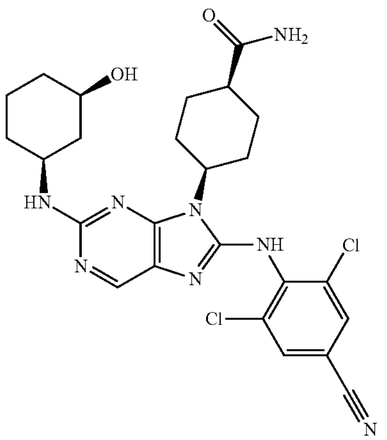 [SMILES: N#Cc1cc(Cl)c(Nc2nc3cnc(N[C@H]4CCC[C@@H](O)C4)nc3n2[C@H]2CC[C@@H](C(N)=O)CC2)c(Cl)c1] | (1R,4s)-4-(8-(2,6-dichloro-4-cyanophenylamino)-2-((1S,3R)-3-hydroxycyclohexylamino)-9H-purin-9-yl)cyclohexanecarboxamide | 543.2 | B |
| 687 | 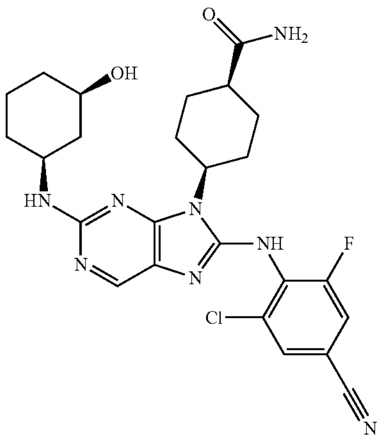 [SMILES: N#Cc1cc(F)c(Nc2nc3cnc(N[C@H]4CCC[C@@H](O)C4)nc3n2[C@H]2CC[C@@H](C(N)=O)CC2)c(Cl)c1] | (1R,4s)-4-(8-(2-chloro-4-cyano-6-fluorophenylamino)-2-((1S,3R)-3-hydroxycyclohexylamino)-9H-purin-9-yl)cyclohexanecarboxamide | 527.1 | A |
| 688 | 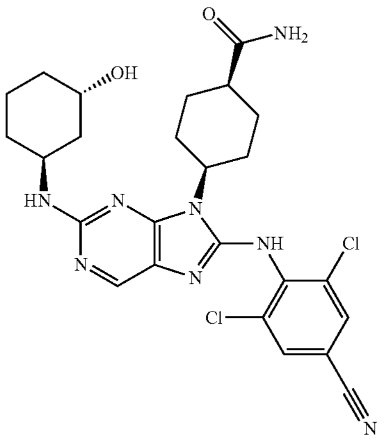 [SMILES: N#Cc1cc(Cl)c(Nc2nc3cnc(N[C@H]4CCC[C@H](O)C4)nc3n2[C@H]2CC[C@@H](C(N)=O)CC2)c(Cl)c1] | (1R,4s)-4-(8-(2,6-dichloro-4-cyanophenylamino)-2-((1S,3S)-3-hydroxycyclohexylamino)-9H-purin-9-yl)cyclohexanecarboxamide | 543.2 | C |

TABLE 1-continued
| Cmpd No. | Structure | Name | MH+ | Activity |
|---|---|---|---|---|
| 689 | 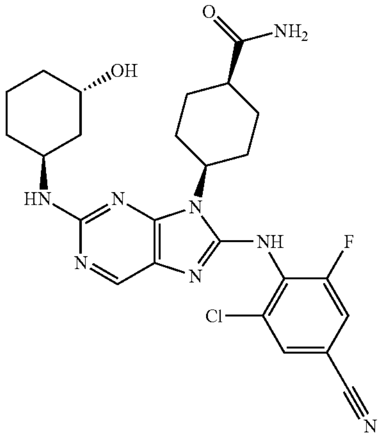 [SMILES: N#Cc1cc(F)c(Nc2nc3cnc(N[C@H]4CCC[C@H](O)C4)nc3n2[C@H]2CC[C@@H](C(N)=O)CC2)c(Cl)c1] | (1R,4s)-4-(8-(2-chloro-4-cyano-6-fluorophenylamino)-2-((1S,3S)-3-hydroxycyclohexylamino)-9H-purin-9-yl)cyclohexanecarboxamide | 527.1 | C |
| 690 | 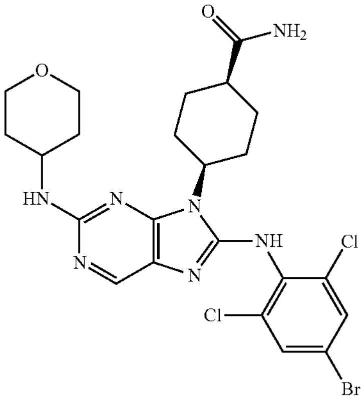 [SMILES: NC(=O)[C@H]1CC[C@@H](n2c(Nc3c(Cl)cc(Br)cc3Cl)nc3cnc(NC4CCOCC4)nc32)CC1] | (1s,4s)-4-(8-(4-bromo-2,6-dichlorophenylamino)-2-(tetrahydro-2H-pyran-4-ylamino)-9H-purin-9-yl)cyclohexanecarboxamide | 584 | D |
| 691 | 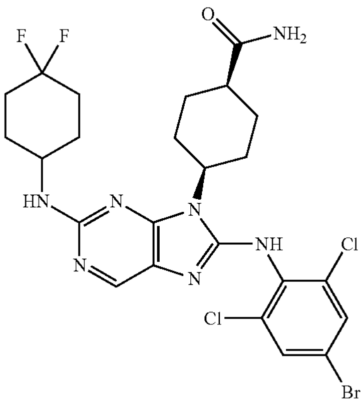 [SMILES: NC(=O)[C@H]1CC[C@@H](n2c(Nc3c(Cl)cc(Br)cc3Cl)nc3cnc(NC4CCC(F)(F)CC4)nc32)CC1] | (1s,4s)-4-(8-(4-bromo-2,6-dichlorophenylamino)-2-(4,4-difluorocyclohexylamino)-9H-purin-9-yl)cyclohexanecarboxamide | 618 | B |

TABLE 1-continued
| Cmpd No. | Structure | Name | MH+ | Activity |
|---|---|---|---|---|
| 692 | 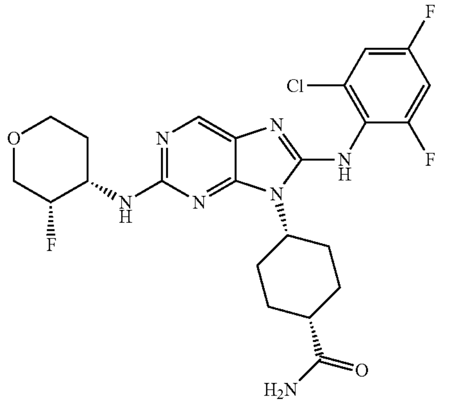 [SMILES: NC(=O)[C@H]1CC[C@@H](n2c(Nc3c(F)cc(F)cc3Cl)nc3cnc(N[C@H]4CCOC[C@H]4F)nc32)CC1] | (1R,4s)-4-(8-(2-chloro-4,6-difluorophenylamino)-2-((3S,4S)-3-fluorotetrahydro-2H-pyran-4-ylamino)-9H-purin-9-yl)cyclohexanecarboxamide | 524.2 | D |
| 693 | 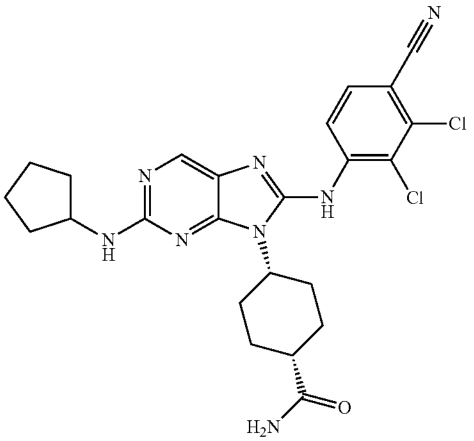 [SMILES: N#Cc1ccc(Nc2nc3cnc(NC4CCCC4)nc3n2[C@H]2CC[C@@H](C(N)=O)CC2)c(Cl)c1Cl] | (1s,4s)-4-(2-(cyclopentylamino)-8-(2,3-dichloro-4-cyanophenylamino)-9H-purin-9-yl)cyclohexanecarboxamide | 513.2 | A |
| 694 | 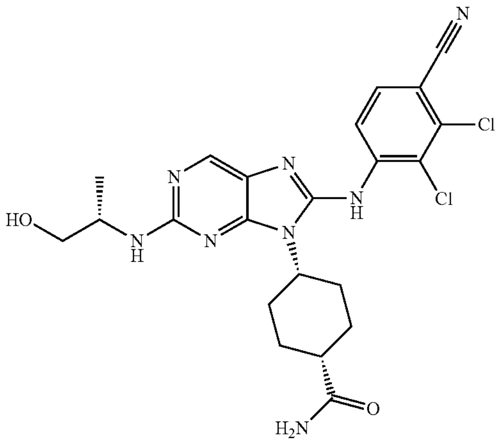 [SMILES: C[C@@H](CO)Nc1ncc2nc(Nc3ccc(C#N)c(Cl)c3Cl)n([C@H]3CC[C@@H](C(N)=O)CC3)c2n1] | (1R,4s)-4-(8-(2,3-dichloro-4-cyanophenylamino)-2-((S)-1-hydroxypropan-2-ylamino)-9H-purin-9-yl)cyclohexanecarboxamide | 503.2 | A |

TABLE 1-continued
| Cmpd No. | Structure | Name | MH+ | Activity |
|---|---|---|---|---|
| 695 | 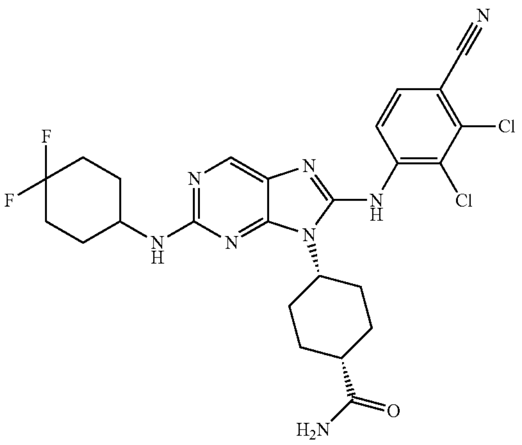 [SMILES: N#Cc1ccc(Nc2nc3cnc(NC4CCC(F)(F)CC4)nc3n2[C@H]2CC[C@@H](C(N)=O)CC2)c(Cl)c1Cl] | (1s,4s)-4-(8-(2,3-dichloro-4-cyanophenylamino)-2-(4,4-difluorocyclohexylamino)-9H-purin-9-yl)cyclohexanecarboxamide | 563.2 | A |
| 696 | 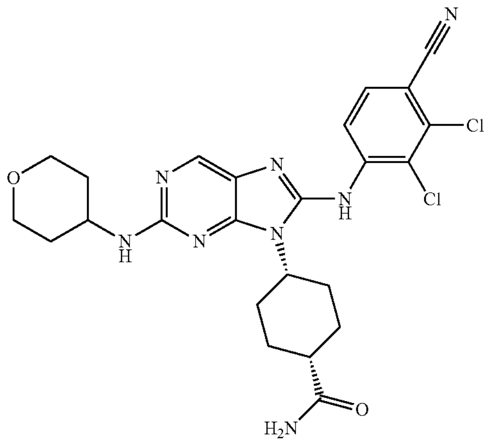 [SMILES: N#Cc1ccc(Nc2nc3cnc(NC4CCOCC4)nc3n2[C@H]2CC[C@@H](C(N)=O)CC2)c(Cl)c1Cl] | (1s,4s)-4-(8-(2,3-dichloro-4-cyanophenylamino)-2-(tetrahydro-2H-pyran-4-ylamino)-9H-purin-9-yl)cyclohexanecarboxamide | 529.2 | B |
| 697 | 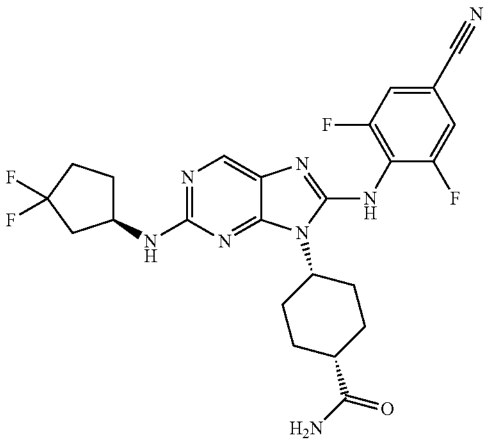 [SMILES: N#Cc1cc(F)c(Nc2nc3cnc(N[C@@H]4CCC(F)(F)C4)nc3n2[C@H]2CC[C@@H](C(N)=O)CC2)c(F)c1] | (1S,4s)-4-(8-(4-cyano-2,6-difluorophenylamino)-2-((R)-3,3-difluorocyclopentylamino)-9H-purin-9-yl)cyclohexanecarboxamide | 517.2 | C |

TABLE 1-continued
| Cmpd No. | Structure | Name | MH+ | Activity |
|---|---|---|---|---|
| 698 | 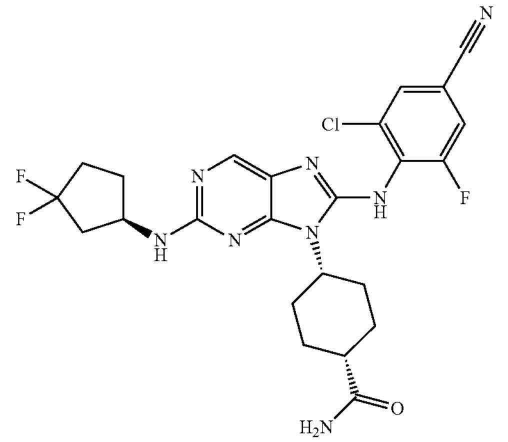 [SMILES: N#Cc1cc(F)c(Nc2nc3cnc(N[C@@H]4CCC(F)(F)C4)nc3n2[C@H]2CC[C@@H](C(N)=O)CC2)c(Cl)c1] | (1S,4s)-4-(8-(2-chloro-4-cyano-6-fluorophenylamino)-2-((R)-3,3-difluorocyclopentylamino)-9H-purin-9-yl)cyclohexanecarboxamide | 553.2 | D |
| 699 | 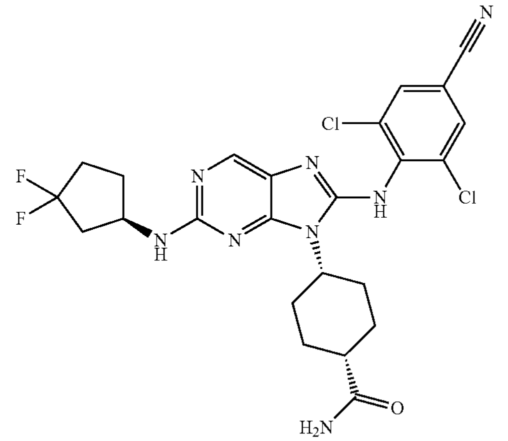 [SMILES: N#Cc1cc(Cl)c(Nc2nc3cnc(N[C@@H]4CCC(F)(F)C4)nc3n2[C@H]2CC[C@@H](C(N)=O)CC2)c(Cl)c1] | (1S,4s)-4-(8-(2,6-dichloro-4-cyanophenylamino)-2-((R)-3,3-difluorocyclopentylamino)-9H-purin-9-yl)cyclohexanecarboxamide | 549.2 | C |
| 700 | 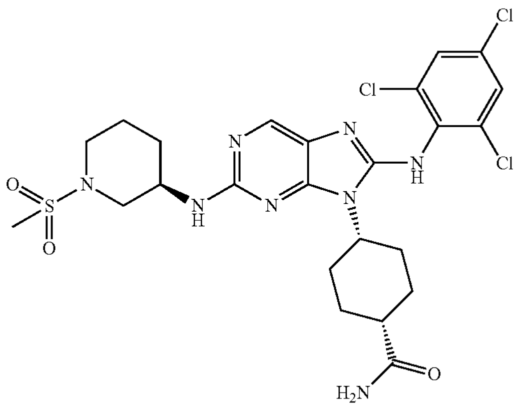 [SMILES: CS(=O)(=O)N1CCC[C@@H](Nc2ncc3nc(Nc4c(Cl)cc(Cl)cc4Cl)n([C@H]4CC[C@@H](C(N)=O)CC4)c3n2)C1] | (1S,4s)-4-(2-((R)-1-(methylsulfonyl)piperidin-3-ylamino)-8-(2,4,6-trichlorophenylamino)-9H-purin-9-yl)cyclohexanecarboxamide | 615.2 | B |

TABLE 1-continued

| Cmpd No. | Structure | Name | MH+ | Activity |
|---|---|---|---|---|
| 701 | 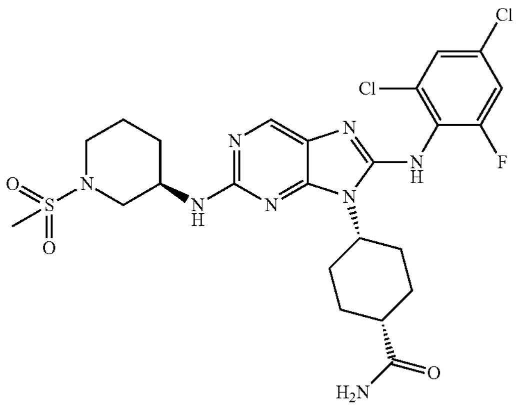 [SMILES: CS(=O)(=O)N1CCC[C@@H](Nc2ncc3nc(Nc4c(F)cc(Cl)cc4Cl)n([C@H]4CC[C@@H](C(N)=O)CC4)c3n2)C1] | (1S,4s)-4-(8-(2,4-dichloro-6-fluorophenylamino)-2-((R)-1-(methylsulfonyl)piperidin-3-ylamino)-9H-purin-9-yl)cyclohexanecarboxamide | 599.2 | B |
| 702 | 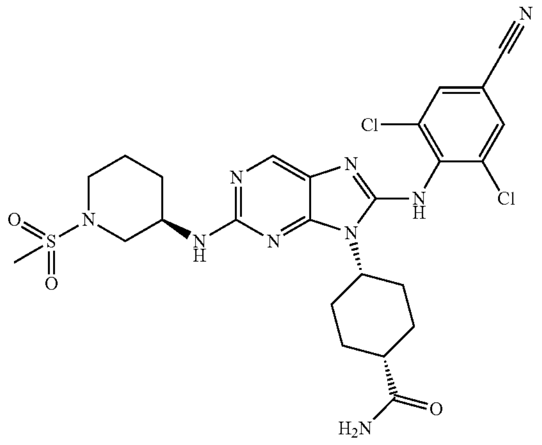 [SMILES: CS(=O)(=O)N1CCC[C@@H](Nc2ncc3nc(Nc4c(Cl)cc(C#N)cc4Cl)n([C@H]4CC[C@@H](C(N)=O)CC4)c3n2)C1] | (1S,4s)-4-(8-(2,6-dichloro-4-cyanophenylamino)-2-((R)-1-(methylsulfonyl)piperidin-3-ylamino)-9H-purin-9-yl)cyclohexanecarboxamide | 606.2 | A |
| 703 | 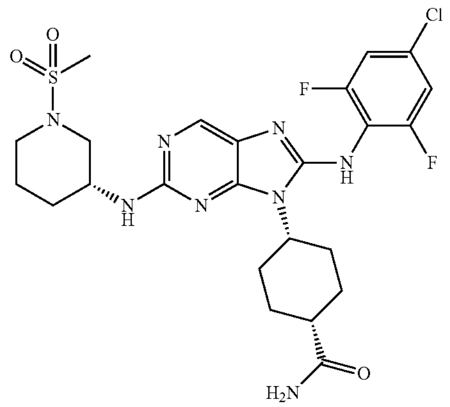 [SMILES: CS(=O)(=O)N1CCC[C@@H](Nc2ncc3nc(Nc4c(F)cc(Cl)cc4F)n([C@H]4CC[C@@H](C(N)=O)CC4)c3n2)C1] | (1S,4s)-4-(8-(4-chloro-2,6-difluorophenylamino)-2-((R)-1-(methylsulfonyl)piperidin-3-ylamino)-9H-purin-9-yl)cyclohexanecarboxamide | 583.2 | A |

TABLE 1-continued

| Cmpd No. | Structure | Name | MH+ | Activity |
|---|---|---|---|---|
| 704 | 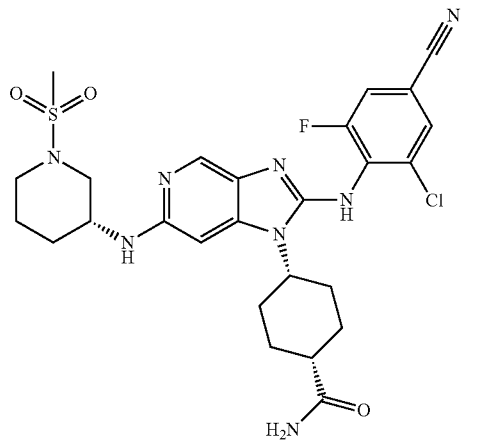 [SMILES: CS(=O)(=O)N1CCC[C@@H](Nc2cc3c(cn2)nc(Nc2c(F)cc(C#N)cc2Cl)n3[C@H]2CC[C@@H](C(N)=O)CC2)C1] | (1S,4s)-4-(8-(2-chloro-4-cyano-6-fluorophenylamino)-2-((R)-1-(methylsulfonyl)piperidin-3-ylamino)-9H-purin-9-yl)cyclohexanecarboxamide | 590.2 | A |
| 705 | 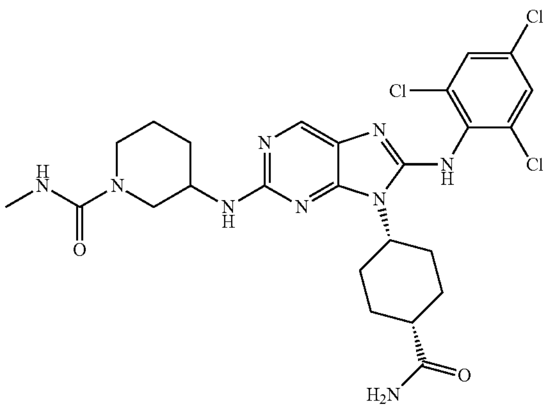 [SMILES: CNC(=O)N1CCCC(Nc2ncc3nc(Nc4c(Cl)cc(Cl)cc4Cl)n([C@H]4CC[C@@H](C(N)=O)CC4)c3n2)C1] | (R)-3-(9-((1s,4s)-4-carbamoylcyclohexyl)-8-(2,4,6-trichlorophenylamino)-9H-purin-2-ylamino)-N-methylpiperidine-1-carboxamide | 594.6 | A |
| 706 | 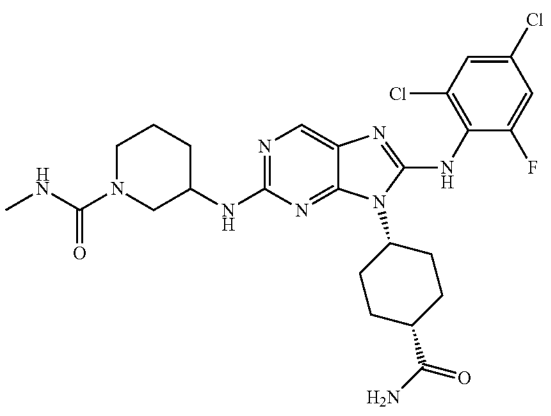 [SMILES: CNC(=O)N1CCCC(Nc2ncc3nc(Nc4c(F)cc(Cl)cc4Cl)n([C@H]4CC[C@@H](C(N)=O)CC4)c3n2)C1] | (R)-3-(9-((1s,4S)-4-carbamoylcyclohexyl)-8-(2,4-dichloro-6-fluorophenylamino)-9H-purin-2-ylamino)-N-methylpiperidine-1-carboxamide | 578.2 | A |

TABLE 1-continued

| Cmpd No. | Structure | Name | MH+ | Activity |
|---|---|---|---|---|
| 707 | 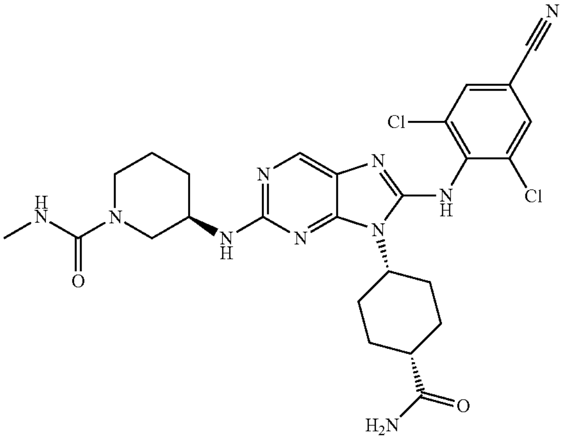 [SMILES: CNC(=O)N1CCC[C@@H](Nc2ncc3nc(Nc4c(Cl)cc(C#N)cc4Cl)n([C@H]4CC[C@@H](C(N)=O)CC4)c3n2)C1] | (R)-3-(9-((1s,4S)-4-carbamoylcyclohexyl)-8-(2,6-dichloro-4-cyanophenylamino)-9H-purin-2-ylamino)-N-methylpiperidine-1-carboxamide | 585.2 | A |
| 708 | 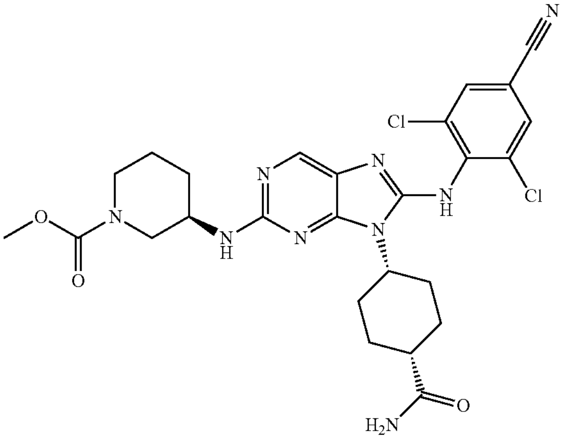 [SMILES: COC(=O)N1CCC[C@@H](Nc2ncc3nc(Nc4c(Cl)cc(C#N)cc4Cl)n([C@H]4CC[C@@H](C(N)=O)CC4)c3n2)C1] | (R)-methyl 3-(9-((1s,4S)-4-carbamoylcyclohexyl)-8-(2,6-dichloro-4-cyanophenylamino)-9H-purin-2-ylamino)piperidine-1-carboxylate | 586.2 | C |
| 709 | 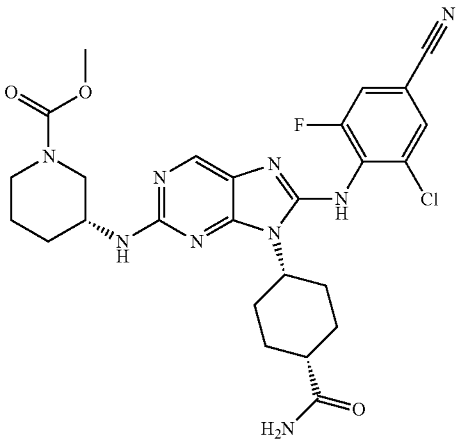 [SMILES: COC(=O)N1CCC[C@@H](Nc2ncc3nc(Nc4c(F)cc(C#N)cc4Cl)n([C@H]4CC[C@@H](C(N)=O)CC4)c3n2)C1] | (R)-methyl 3-(9-((1s,4S)-4-carbamoylcyclohexyl)-8-(2-chloro-4-cyano-6-fluorophenylamino)-9H-purin-2-ylamino)piperidine-1-carboxylate | 570.2 | B |

TABLE 1-continued
| Cmpd No. | Structure | Name | MH+ | Activity |
|---|---|---|---|---|
| 710 | 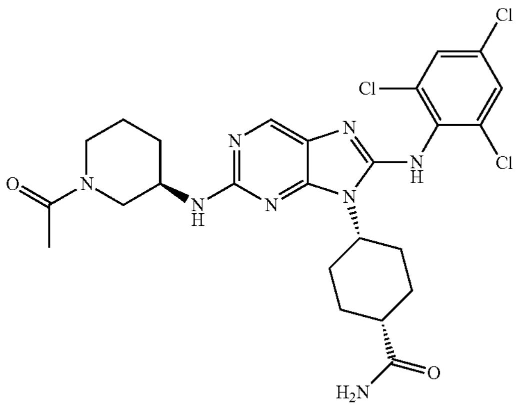 [SMILES: CC(=O)N1CCC[C@@H](Nc2ncc3nc(Nc4c(Cl)cc(Cl)cc4Cl)n([C@H]4CC[C@@H](C(N)=O)CC4)c3n2)C1] | (1S,4s)-4-(2-((R)-1-acetylpiperidin-3-ylamino)-8-(2,4,6-trichlorophenylamino)-9H-purin-9-yl)cyclohexanecarboxamide | 579.2 | A |
| 711 | 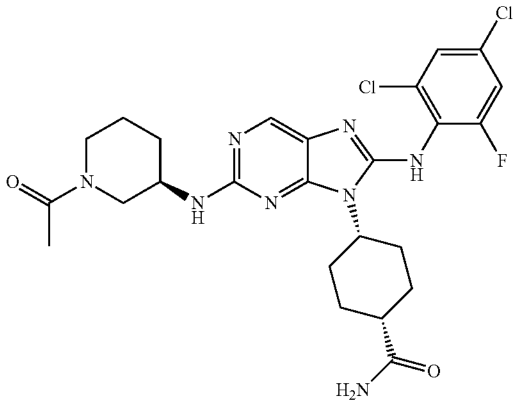 [SMILES: CC(=O)N1CCC[C@@H](Nc2ncc3nc(Nc4c(F)cc(Cl)cc4Cl)n([C@H]4CC[C@@H](C(N)=O)CC4)c3n2)C1] | (1S,4s)-4-(2-((R)-1-acetylpiperidin-3-ylamino)-8-(2,4-dichloro-6-fluorophenylamino)-9H-purin-9-yl)cyclohexanecarboxamide | 563.2 | A |
| 712 | 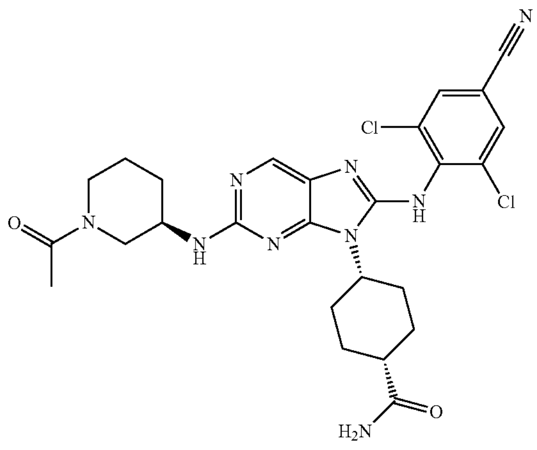 [SMILES: CC(=O)N1CCC[C@@H](Nc2ncc3nc(Nc4c(Cl)cc(C#N)cc4Cl)n([C@H]4CC[C@@H](C(N)=O)CC4)c3n2)C1] | (1S,4s)-4-(2-((R)-1-acetylpiperidin-3-ylamino)-8-(2,6-dichloro-4-cyanophenylamino)-9H-purin-9-yl)cyclohexanecarboxamide | 570.2 | A |

TABLE 1-continued

| Cmpd No. | Structure | Name | MH+ | Activity |
|---|---|---|---|---|
| 713 | 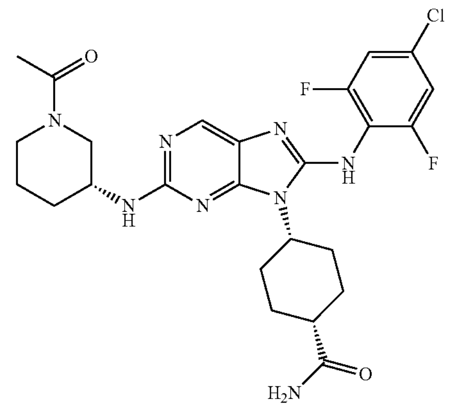 [SMILES: CC(=O)N1CCC[C@@H](Nc2ncc3nc(Nc4c(F)cc(Cl)cc4F)n([C@H]4CC[C@@H](C(N)=O)CC4)c3n2)C1] | (1S,4s)-4-(2-((R)-1-acetylpiperidin-3-ylamino)-8-(4-chloro-2,6-difluorophenylamino)-9H-purin-9-yl)cyclohexanecarboxamide | 547.2 | A |
| 714 | 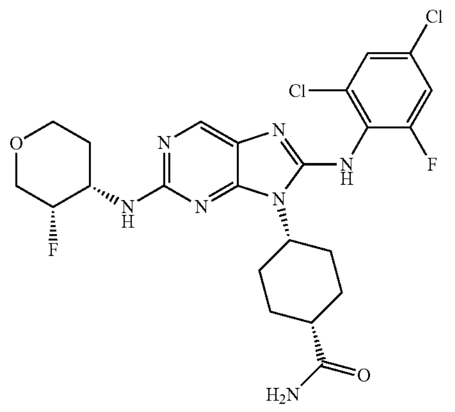 [SMILES: NC(=O)[C@H]1CC[C@@H](n2c(Nc3c(F)cc(Cl)cc3Cl)nc3cnc(N[C@H]4CCOC[C@H]4F)nc32)CC1] | (1R,4s)-4-(8-(2,4-dichloro-6-fluorophenylamino)-2-((3S,4S)-3-fluorotetrahydro-2H-pyran-4-ylamino)-9H-purin-9-yl)cyclohexanecarboxamide | 540.2 | D |
| 715 | 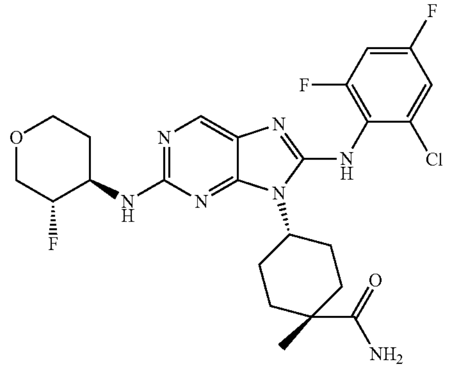 [SMILES: C[C@]1(C(N)=O)CC[C@@H](n2c(Nc3c(F)cc(F)cc3Cl)nc3cnc(N[C@@H]4CCOC[C@H]4F)nc32)CC1] | (1S,4s)-4-(8-(2-chloro-4,6-difluorophenylamino)-2-((3S,4R)-3-fluorotetrahydro-2H-pyran-4-ylamino)-9H-purin-9-yl)-1-methylcyclohexanecarboxamide | 538.2 | D |

TABLE 1-continued

| Cmpd No. | Structure | Name | MH+ | Activity |
|---|---|---|---|---|
| 716 | 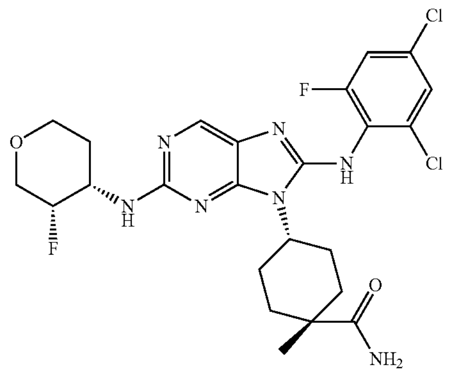 [SMILES: C[C@]1(C(N)=O)CC[C@@H](n2c(Nc3c(F)cc(Cl)cc3Cl)nc3cnc(N[C@H]4CCOC[C@H]4F)nc32)CC1] | (1R,4s)-4-(8-(2,4-dichloro-6-fluorophenylamino)-2-((3S,4S)-3-fluorotetrahydro-2H-pyran-4-ylamino)-9H-purin-9-yl)-1-methylcyclohexanecarboxamide | 554.2 | D |
| 717 | 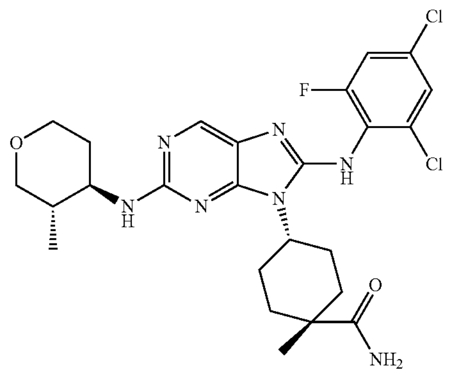 [SMILES: C[C@@H]1COCC[C@H]1Nc1ncc2nc(Nc3c(F)cc(Cl)cc3Cl)n([C@H]3CC[C@@](C)(C(N)=O)CC3)c2n1] | (1S,4s)-4-(8-(2,4-dichloro-6-fluorophenylamino)-2-((3S,4R)-3-methyltetrahydro-2H-pyran-4-ylamino)-9H-purin-9-yl)-1-methylcyclohexanecarboxamide | 550.2 | D |
| 718 | 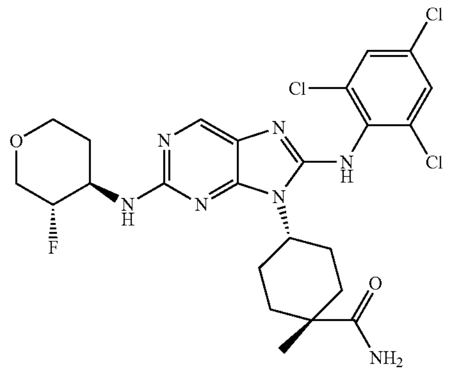 [SMILES: C[C@]1(C(N)=O)CC[C@@H](n2c(Nc3c(Cl)cc(Cl)cc3Cl)nc3cnc(N[C@@H]4CCOC[C@H]4F)nc32)CC1] | (1S,4s)-4-(2-((3S,4R)-3-fluorotetrahydro-2H-pyran-4-ylamino)-8-(2,4,6-trichlorophenylamino)-9H-purin-9-yl)-1-methylcyclohexanecarboxamide | 570.1 | D |
| 719 | 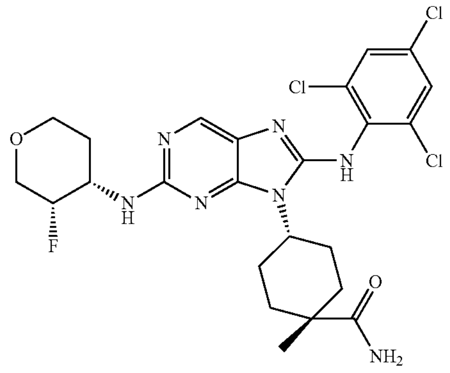 [SMILES: C[C@]1(C(N)=O)CC[C@@H](n2c(Nc3c(Cl)cc(Cl)cc3Cl)nc3cnc(N[C@H]4CCOC[C@H]4F)nc32)CC1] | (1R,4s)-4-(2-((3S,4S)-3-fluorotetrahydro-2H-pyran-4-ylamino)-8-(2,4,6-trichlorophenylamino)-9H-purin-9-yl)-1-methylcyclohexanecarboxamide | 570.1 | D |

TABLE 1-continued

| Cmpd No. | Structure | Name | MH+ | Activity |
|---|---|---|---|---|
| 720 | 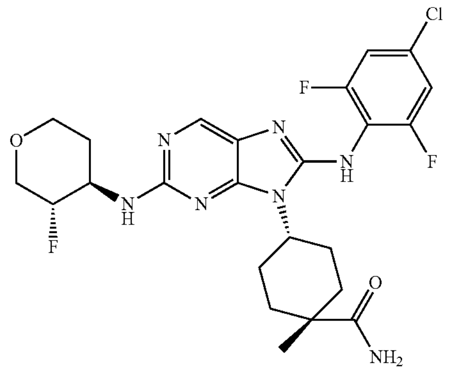 [SMILES: C[C@]1(C(N)=O)CC[C@@H](n2c(Nc3c(F)cc(Cl)cc3F)nc3cnc(N[C@@H]4CCOC[C@H]4F)nc32)CC1] | (1S,4s)-4-(8-(4-chloro-2,6-difluorophenylamino)-2-((3S,4R)-3-fluorotetrahydro-2H-pyran-4-ylamino)-9H-purin-9-yl)-1-methylcyclohexanecarboxamide | 538.2 | D |
| 721 | 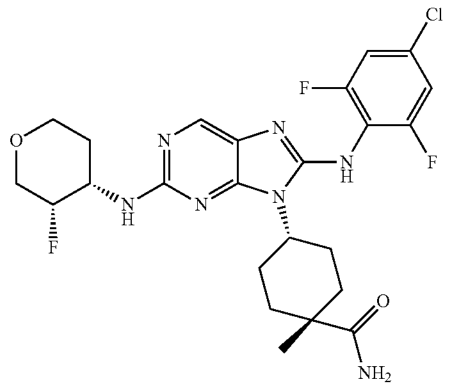 [SMILES: C[C@]1(C(N)=O)CC[C@@H](n2c(Nc3c(F)cc(Cl)cc3F)nc3cnc(N[C@H]4CCOC[C@H]4F)nc32)CC1] | (1R,4s)-4-(8-(4-chloro-2,6-difluorophenylamino)-2-((3S,4S)-3-fluorotetrahydro-2H-pyran-4-ylamino)-9H-purin-9-yl)-1-methylcyclohexanecarboxamide | 538.2 | D |
| 722 | 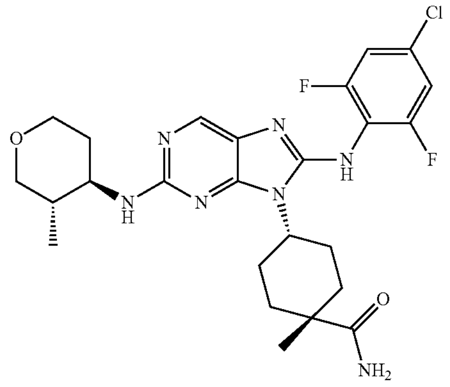 [SMILES: C[C@@H]1COCC[C@H]1Nc1ncc2nc(Nc3c(F)cc(Cl)cc3F)n([C@H]3CC[C@@](C)(C(N)=O)CC3)c2n1] | (1S,4s)-4-(8-(4-chloro-2,6-difluorophenylamino)-2-((3S,4R)-3-methyltetrahydro-2H-pyran-4-ylamino)-9H-purin-9-yl)-1-methylcyclohexanecarboxamide | 534.2 | D |

TABLE 1-continued

| Cmpd No. | Structure | Name | MH+ | Activity |
|---|---|---|---|---|
| 723 | 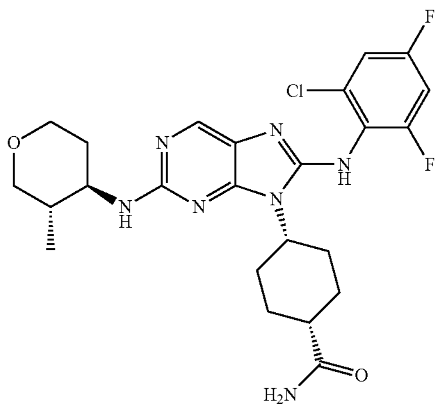 | (1S,4s)-4-(8-(2-chloro-4,6-difluorophenylamino)-2-((3S,4R)-3-methyltetrahydro-2H-pyran-4-ylamino)-9H-purin-9-yl)cyclohexanecarboxamide | 520.2 | D |
| 724 | 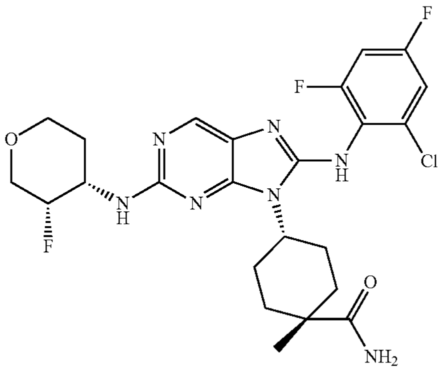 | (1R,4S)-4-(8-(2-chloro-4,6-difluorophenylamino)-2-((3S,4S)-3-fluorotetrahydro-2H-pyran-4-ylamino)-9H-purin-9-yl)-1-methylcyclohexanecarboxamide | 538.2 | D |
| 725 | 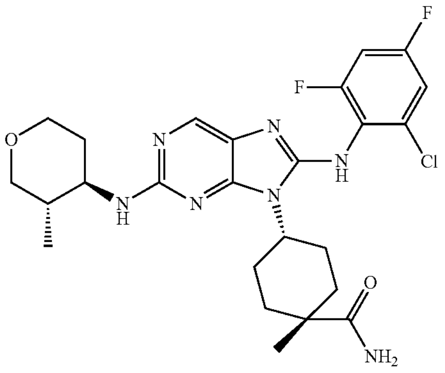 | (1S,4s)-4-(8-(2-chloro-4,6-difluorophenylamino)-2-((3S,4R)-3-methyltetrahydro-2H-pyran-4-ylamino)-9H-purin-9-yl)-1-methylcyclohexanecarboxamide | 535.2 | D |
| 726 | 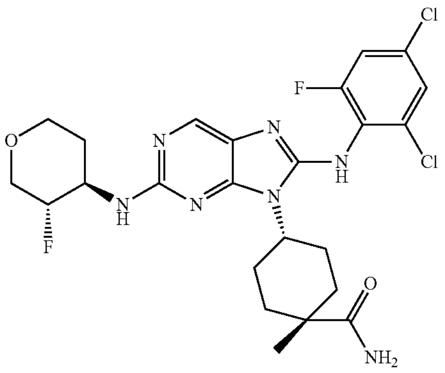 | (1S,4s)-4-(8-(2,4-dichloro-6-fluorophenylamino)-2-((3S,4R)-3-fluorotetrahydro-2H-pyran-4-ylamino)-9H-purin-9-yl)-1-methylcyclohexanecarboxamide | 554.2 | D |

TABLE 1-continued

| Cmpd No. | Structure | Name | MH+ | Ac-tivi-ty |
|---|---|---|---|---|
| 727 | 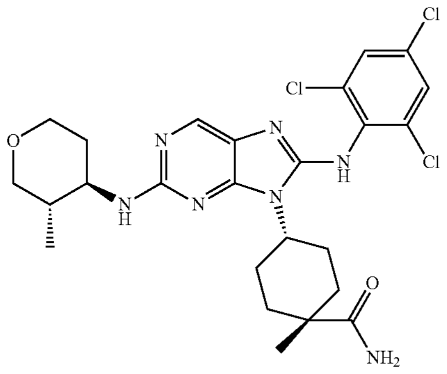 | (1S,4s)-1-methyl-4-(2-((3S,4R)-3-methyltetrahydro-2H-pyran-4-ylamino)-8-(2,4,6-trichlorophenylamino)-9H-purin-9-yl)cyclohexanecarboxamide | 566.2 | D |
| 728 | 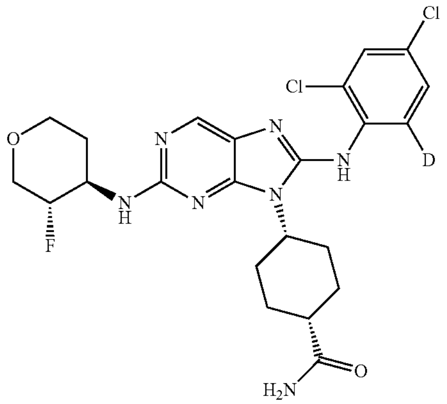 [SMILES: [2H]c1cc(Cl)cc(Cl)c1Nc1nc2cnc(N[C@@H]3CCOC[C@H]3F)nc2n1[C@H]1CC[C@@H](C(N)=O)CC1] | (1S,4s)-4-(8-(2,4-dichloro-6-fluorophenylamino)-2-((3S,4R)-3-fluorotetrahydro-2H-pyran-4-ylamino)-9H-purin-9-yl)cyclohexanecarboxamide | 540.2 | D |
| 729 | 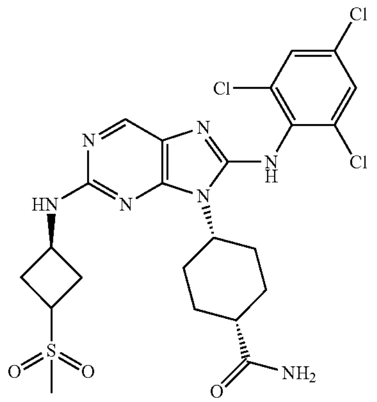 | (1s,4s)-4-(2-(3-(methylsulfonyl)cyclobutylamino)-8-(2,4,6,-trichlorophenylamino)-9H-purin-9-yl)cyclohexanecarboxamide | 586 | A |

TABLE 1-continued
| Cmpd No. | Structure | Name | MH+ | Activity |
|---|---|---|---|---|
| 730 | 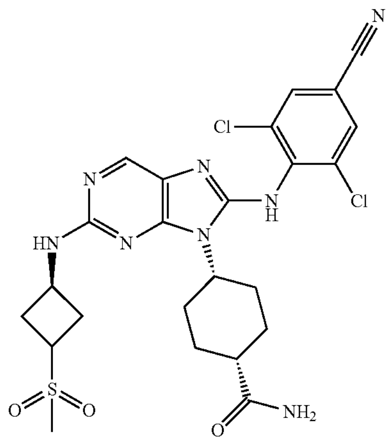 | (1s,4s)-4-(8-(2,6-dichloro-4-cyanophenylamino)-2-(3-(methylsulfonyl)cyclobutylamino)-9H-purin-9-yl)cyclohexanecarboxamide | 577.2 | A |
| 731 | 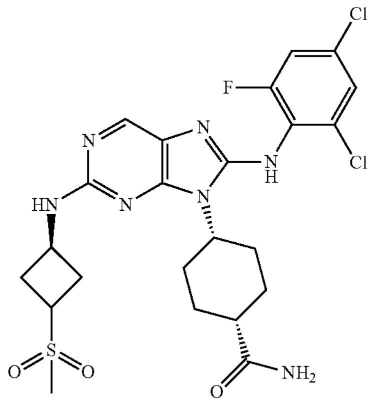 | (1s,4s)-4-(8-(2,4-dichloro-6-fluorophenylamino)-2-(3-(methylsulfonyl)cyclobutylamino)-9H-purin-9-yl)cyclohexanecarboxamide | 570.2 | A |
| 732 | 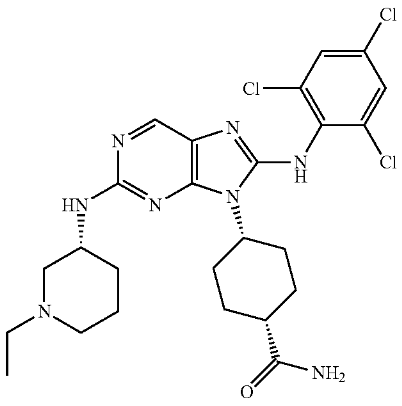 [SMILES: CCN1CCC[C@@H](Nc2ncc3nc(Nc4c(Cl)cc(Cl)cc4Cl)n([C@H]4CC[C@@H](C(N)=O)CC4)c3n2)C1] | (1S,4s)-4-(2-((R)-1-ethylpiperidin-3-ylamino)-8-(2,4,6-trichlorophenylamino)-9H-purin-9-yl)cyclohexanecarboxamide | 567.2 | A |

TABLE 1-continued
| Cmpd No. | Structure | Name | MH+ | Ac-tivi-ty |
|---|---|---|---|---|
| 733 | 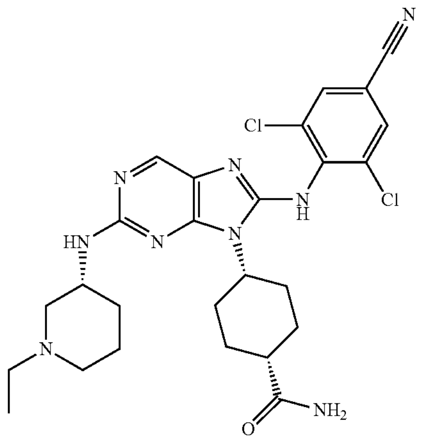 [SMILES: CCN1CCC[C@@H](Nc2ncc3nc(Nc4c(Cl)cc(C#N)cc4Cl)n([C@H]4CC[C@@H](C(N)=O)CC4)c3n2)C1] | (1S,4s)-4-(8-(2,6-dichloro-4-cyanophenylamino)-2-((R)-1-ethylpiperidin-3-ylamino)-9H-purin-9-yl)cyclohexanecarboxamide | 556.2 | A |
| 734 | 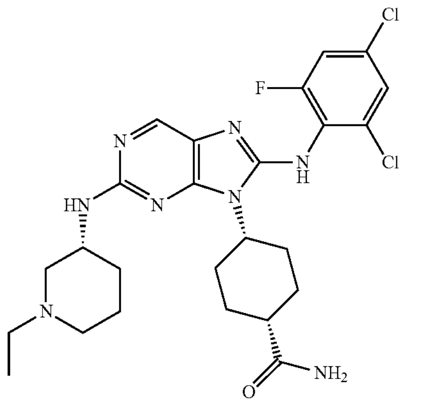 [SMILES: CCN1CCC[C@@H](Nc2ncc3nc(Nc4c(F)cc(Cl)cc4Cl)n([C@H]4CC[C@@H](C(N)=O)CC4)c3n2)C1] | (1S,4s)-4-(8-(2,4-dichloro-6-fluorophenylamino)-2-((R)-1-ethylpiperidin-3-ylamino)-9H-purin-9-yl)cyclohexanecarboxamide | 549.2 | A |
| 735 | 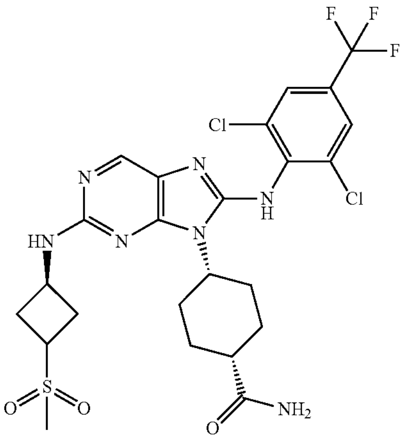 | (1s,4s)-4-(8-(2,6-dichloro-4-(trifluoromethyl)phenylamino)-2-(3-(methylsulfonyl)cyclobutylamino)-9H-purin-9-yl)cyclohexanecarboxamide | 620.2 | A |

TABLE 1-continued
| Cmpd No. | Structure | Name | MH+ | Activity |
|---|---|---|---|---|
| 736 | 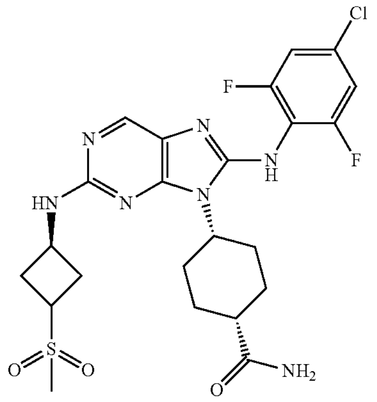 | (1s,4s)-4-(8-(4-chloro-2,6-difluorophenylamino)-2-(3-(methylsulfonyl)cyclobutylamino)-9H-purin-9-yl)cyclohexanecarboxamide | 554 | A |
| 737 | 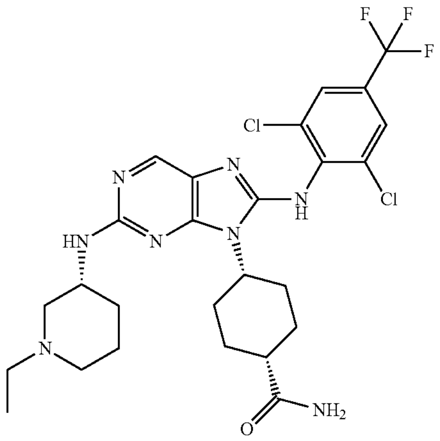 [SMILES: CCN1CCC[C@@H](Nc2ncc3nc(Nc4c(Cl)cc(C(F)(F)F)cc4Cl)n([C@H]4CC[C@@H](C(N)=O)CC4)c3n2)C1] | (1S,4s)-4-(8-(2,6-dichloro-4-(trifluoromethyl)phenylamino)-2-((R)-1-ethylpiperidin-3-ylamino)-9H-purin-9-yl)cyclohexanecarboxamide | 599.2 | A |
| 738 | 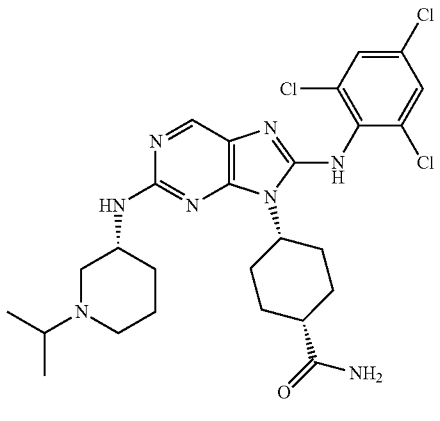 [SMILES: CC(C)N1CCC[C@@H](Nc2ncc3nc(Nc4c(Cl)cc(Cl)cc4Cl)n([C@H]4CC[C@@H](C(N)=O)CC4)c3n2)C1] | (1S,4s)-4-(2-((R)-1-isopropylpiperidin-3-ylamino)-8-(2,4,6-trichlorophenylamino)-9H-purin-9-yl)cyclohexanecarboxamide | 579.2 | A |

TABLE 1-continued
| Cmpd No. | Structure | Name | MH+ | Activity |
|---|---|---|---|---|
| 739 | 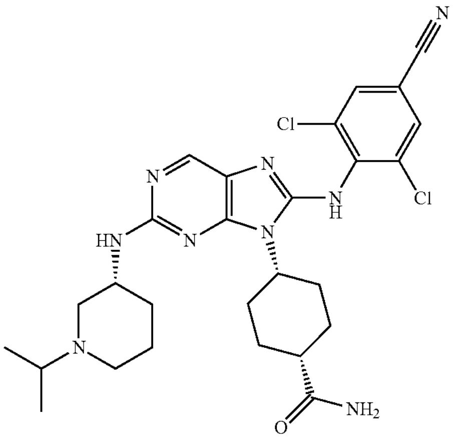 [SMILES: CC(C)N1CCC[C@@H](Nc2ncc3nc(Nc4c(Cl)cc(C#N)cc4Cl)n([C@H]4CC[C@@H](C(N)=O)CC4)c3n2)C1] | (1S,4s)-4-(8-(2,6-dichloro-4-cyanophenylamino)-2-((R)-1-isopropylpiperidin-3-ylamino)-9H-purin-9-yl)cyclohexanecarboxamide | 570.2 | A |
| 740 | 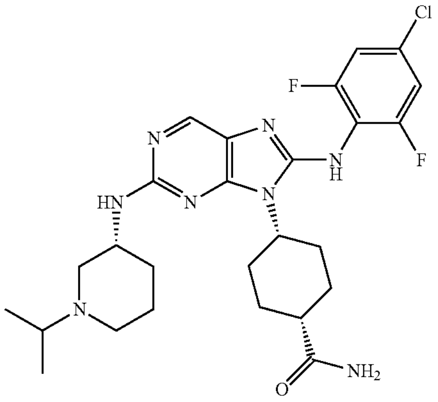 [SMILES: CC(C)N1CCC[C@@H](Nc2ncc3nc(Nc4c(F)cc(Cl)cc4F)n([C@H]4CC[C@@H](C(N)=O)CC4)c3n2)C1] | (1S,4s)-4-(8-(4-chloro-2,6-difluorophenylamino)-2-((R)-1-isopropylpiperidin-3-ylamino)-9H-purin-9-yl)cyclohexanecarboxamide | 547.2 | A |
| 741 | 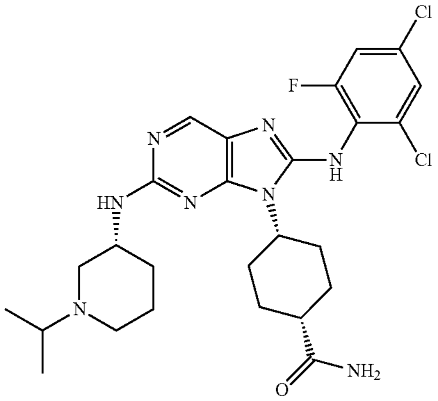 [SMILES: CC(C)N1CCC[C@@H](Nc2ncc3nc(Nc4c(F)cc(Cl)cc4Cl)n([C@H]4CC[C@@H](C(N)=O)CC4)c3n2)C1] | (1S,4s)-4-(8-(2,4-dichloro-6-fluorophenylamino)-2-((R)-1-isopropylpiperidin-3-ylamino)-9H-purin-9-yl)cyclohexanecarboxamide | 563.2 | A |

TABLE 1-continued
| Cmpd No. | Structure | Name | MH+ | Activity |
|---|---|---|---|---|
| 742 | 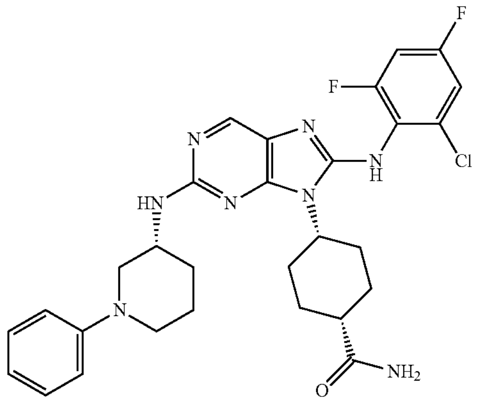 [SMILES: NC(=O)[C@H]1CC[C@@H](n2c(Nc3c(F)cc(F)cc3Cl)nc3cnc(N[C@@H]4CCCN(c5ccccc5)C4)nc32)CC1] | (1S,4s)-4-(8-(2-chloro-4,6-difluorophenylamino)-2-((R)-1-phenylpiperidin-3-ylamino)-9H-purin-9-yl)cyclohexanecarboxamide | 581.2 | A |
| 743 | 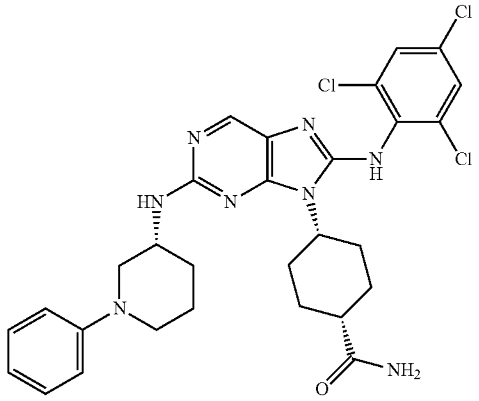 [SMILES: NC(=O)[C@H]1CC[C@@H](n2c(Nc3c(Cl)cc(Cl)cc3Cl)nc3cnc(N[C@@H]4CCCN(c5ccccc5)C4)nc32)CC1] | (1S,4s)-4-(2-((R)-1-phenylpiperidin-3-ylamino)-8-(2,4,6-trichlorophenylamino)-9H-purin-9-yl)cyclohexanecarboxamide | 613.2 | A |
| 744 | 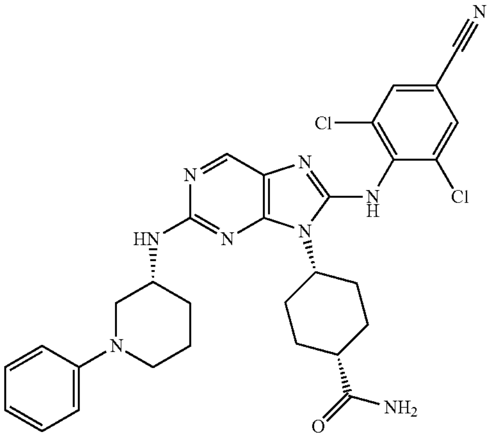 [SMILES: N#Cc1cc(Cl)c(Nc2nc3cnc(N[C@@H]4CCCN(c5ccccc5)C4)nc3n2[C@H]2CC[C@@H](C(N)=O)CC2)c(Cl)c1] | (1S,4s)-4-(8-(2,6-dichloro-4-cyanophenylamino)-2-((R)-1-phenylpiperidin-3-ylamino)-9H-purin-9-yl)cyclohexanecarboxamide | 604.2 | A |

TABLE 1-continued
| Cmpd No. | Structure | Name | MH+ | Activity |
|---|---|---|---|---|
| 745 | 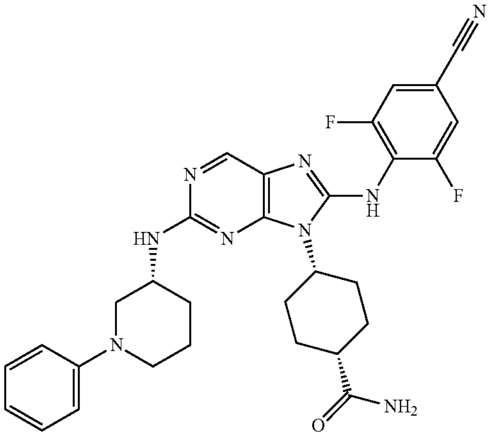 [SMILES: N#Cc1cc(F)c(Nc2nc3cnc(N[C@@H]4CCCN(c5ccccc5)C4)nc3n2[C@H]2CC[C@@H](C(N)=O)CC2)c(F)c1] | (1S,4s)-4-(8-(4-cyano-2,6-difluorophenylamino)-2-((R)-1-phenylpiperidin-3-ylamino)-9H-purin-9-yl)cyclohexanecarboxamide | 572.2 | A |
| 746 | 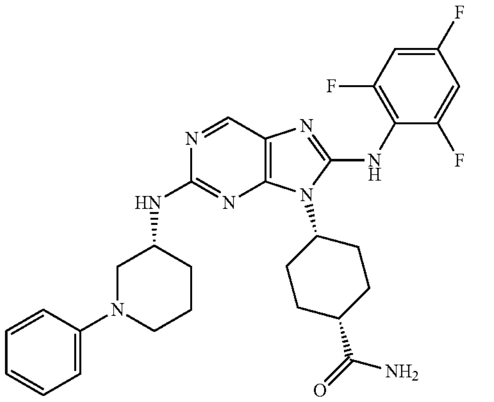 [SMILES: NC(=O)[C@H]1CC[C@@H](n2c(Nc3c(F)cc(F)cc3F)nc3cnc(N[C@@H]4CCCN(c5ccccc5)C4)nc32)CC1] | (1S,4s)-4-(2-((R)-1-phenylpiperidin-3-ylamino)-8-(2,4,6-trifluorophenylamino)-9H-purin-9-yl)cyclohexanecarboxamide | 566.2 | A |
| 747 | 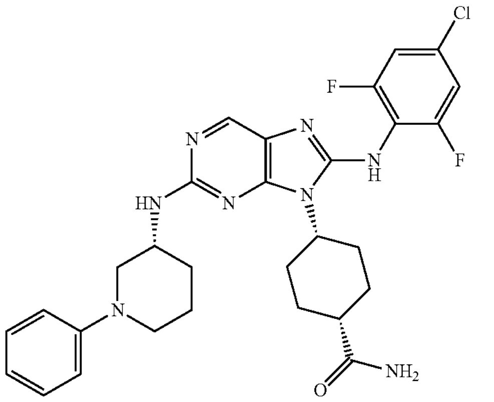 [SMILES: NC(=O)[C@H]1CC[C@@H](n2c(Nc3c(F)cc(Cl)cc3F)nc3cnc(N[C@@H]4CCCN(c5ccccc5)C4)nc32)CC1] | (1S,4S)-4-(8-(4-chloro-2,6-difluorophenylamino)-2-((R)-1-phenylpiperidin-3-ylamino)-9H-purin-9-yl)cyclohexanecarboxamide | 581.2 | A |

TABLE 1-continued
| Cmpd No. | Structure | Name | MH+ | Activity |
|---|---|---|---|---|
| 748 | 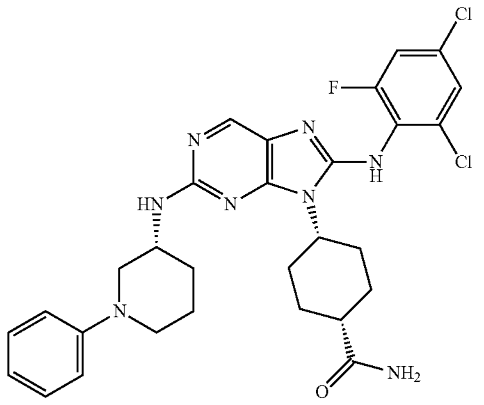 [SMILES: NC(=O)[C@H]1CC[C@@H](n2c(Nc3c(F)cc(Cl)cc3Cl)nc3cnc(N[C@@H]4CCCN(c5ccccc5)C4)nc32)CC1] | (1S,4s)-4-(8-(2,4-dichloro-6-fluorophenylamino)-2-((R)-1-phenylpiperidin-3-ylamino)-9H-purin-9-yl)cyclohexanecarboxamide | 597.2 | A |
| 749 | 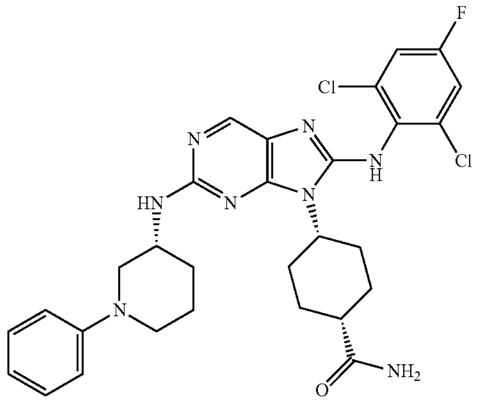 [SMILES: NC(=O)[C@H]1CC[C@@H](n2c(Nc3c(Cl)cc(F)cc3Cl)nc3cnc(N[C@@H]4CCCN(c5ccccc5)C4)nc32)CC1] | (1S,4s)-4-(8-(2,6-dichloro-4-fluorophenylamino)-2-((R)-1-phenylpiperidin-3-ylamino)-9H-purin-9-yl)cyclohexanecarboxamide | 597.2 | A |
| 750 | 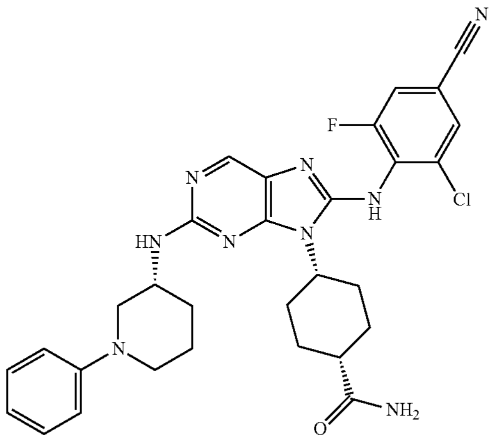 | (1S,4s)-4-(8-(2-chloro-4-cyano-6-fluorophenylamino)-2-((R)-1-phenylpiperidin-3-ylamino)-9H-purin-9-yl)cyclohexanecarboxamide | 588.2 | A |

TABLE 1-continued
| Cmpd No. | Structure | Name | MH+ | Activity |
|---|---|---|---|---|
| 751 | 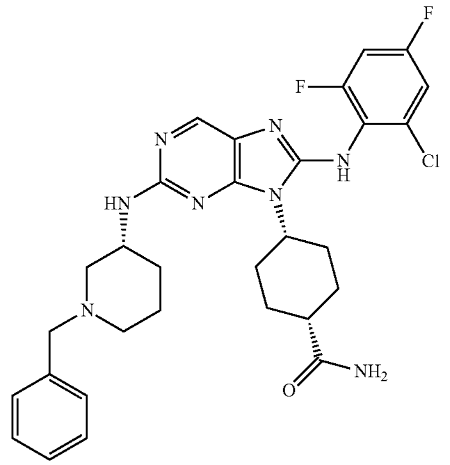 [SMILES: NC(=O)[C@H]1CC[C@@H](n2c(Nc3c(F)cc(F)cc3Cl)nc3cnc(N[C@@H]4CCCN(Cc5ccccc5)C4)nc32)CC1] | (1S,4s)-4-(2-((R)-1-benzylpiperidin-3-ylamino)-8-(2-chloro-4,6-difluorophenylamino)-9H-purin-9-yl)cyclohexanecarboxamide | 595.2 | A |
| 752 | 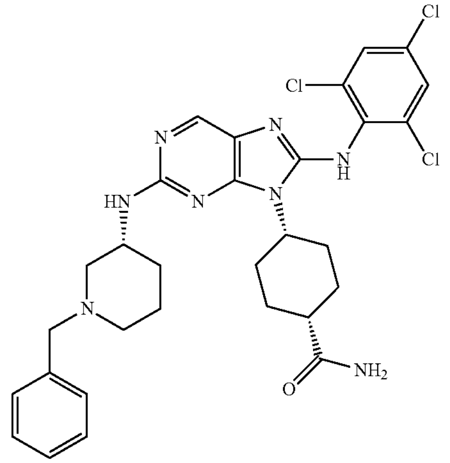 [SMILES: NC(=O)[C@H]1CC[C@@H](n2c(Nc3c(Cl)cc(Cl)cc3Cl)nc3cnc(N[C@@H]4CCCN(Cc5ccccc5)C4)nc32)CC1] | (1S,4s)-4-(2-((R)-1-benzylpiperidin-3-ylamino)-8-(2,4,6-trichlorophenylamino)-9H-purin-9-yl)cyclohexanecarboxamide | 629.2 | A |
| 753 | 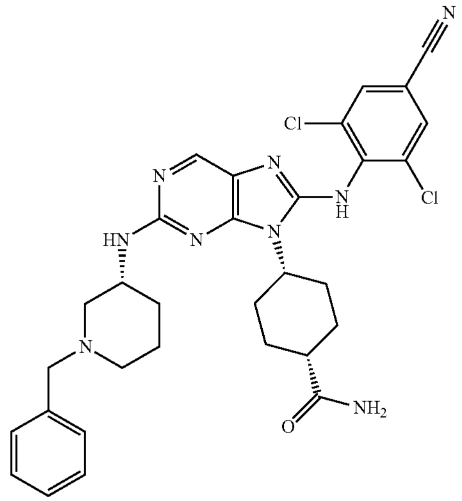 [SMILES: N#Cc1cc(Cl)c(Nc2nc3cnc(N[C@@H]4CCCN(Cc5ccccc5)C4)nc3n2[C@H]2CC[C@@H](C(N)=O)CC2)c(Cl)c1] | (1S,4s)-4-(2-((R)-1-benzylpiperidin-3-ylamino)-8-(2,6-dichloro-4-cyanophenylamino)-9H-purin-9-yl)cyclohexanecarboxamide | 618.2 | A |

TABLE 1-continued
| Cmpd No. | Structure | Name | MH+ | Activity |
|---|---|---|---|---|
| 754 | 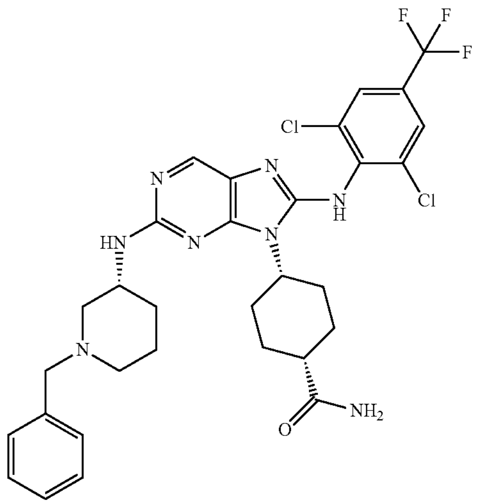 [SMILES: NC(=O)[C@H]1CC[C@@H](n2c(Nc3c(Cl)cc(C(F)(F)F)cc3Cl)nc3cnc(N[C@@H]4CCCN(Cc5ccccc5)C4)nc32)CC1] | (1S,4s)-4-(2-((R)-1-benzylpiperidin-3-ylamino)-8-(2,6-dichloro-4-(trifluoromethyl)phenylamino)-9H-purin-9-yl)cyclohexanecarboxamide | 661.2 | A |
| 755 | 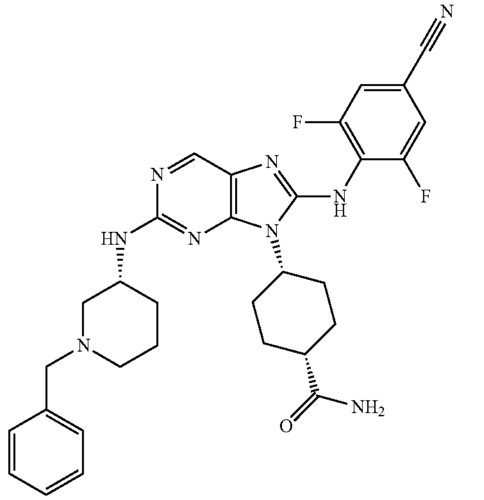 [SMILES: N#Cc1cc(F)c(Nc2nc3cnc(N[C@@H]4CCCN(Cc5ccccc5)C4)nc3n2[C@H]2CC[C@@H](C(N)=O)CC2)c(F)c1] | (1S,4s)-4-(2-((R)-1-benzylpiperidin-3-ylamino)-8-(4-cyano-2,6-difluorophenylamino)-9H-purin-9-yl)cyclohexanecarboxamide | 586.4 | A |
| 756 | 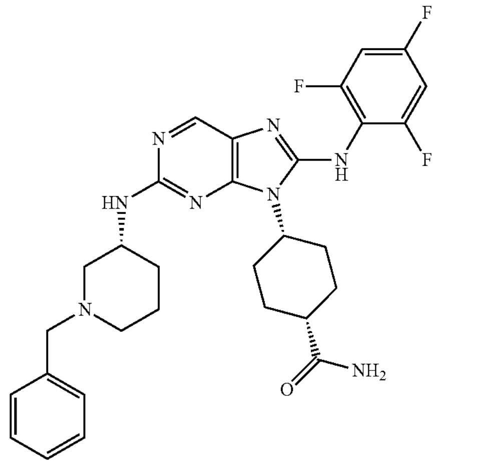 [SMILES: NC(=O)[C@H]1CC[C@@H](n2c(Nc3c(F)cc(F)cc3F)nc3cnc(N[C@@H]4CCCN(Cc5ccccc5)C4)nc32)CC1] | (1S,4s)-4-(2-((R)-1-benzylpiperidin-3-ylamino)-8-(2,4,6-trifluorophenylamino)-9H-purin-9-yl)cyclohexanecarboxamide | 579.2 | A |

TABLE 1-continued
| Cmpd No. | Structure | Name | MH+ | Activity |
|---|---|---|---|---|
| 757 | 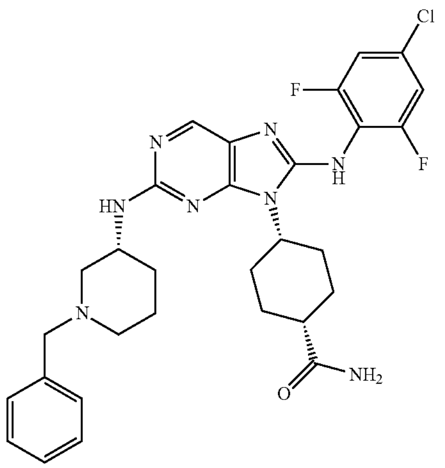 [SMILES: NC(=O)[C@H]1CC[C@@H](n2c(Nc3c(F)cc(Cl)cc3F)nc3cnc(N[C@@H]4CCCN(Cc5ccccc5)C4)nc32)CC1] | (1S,4s)-4-(2-((R)-1-benzylpiperidin-3-ylamino)-8-(4-chloro-2,6-difluorophenylamino)-9H-purin-9-yl)cyclohexanecarboxamide | 595.2 | A |
| 758 | 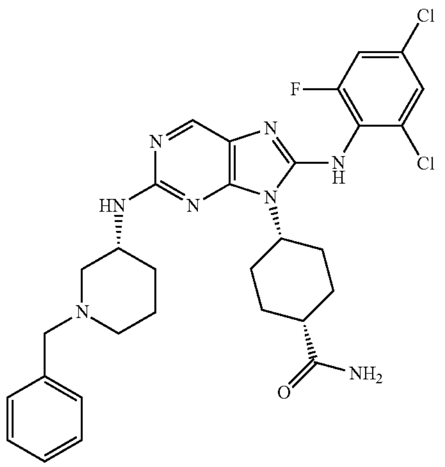 [SMILES: NC(=O)[C@H]1CC[C@@H](n2c(Nc3c(F)cc(Cl)cc3Cl)nc3cnc(N[C@@H]4CCCN(Cc5ccccc5)C4)nc32)CC1] | (1S,4s)-4-(2-((R)-1-benzylpiperidin-3-ylamino)-8-(2,4-dichloro-6-fluorophenylamino)-9H-purin-9-yl)cyclohexanecarboxamide | 611.2 | A |
| 759 | 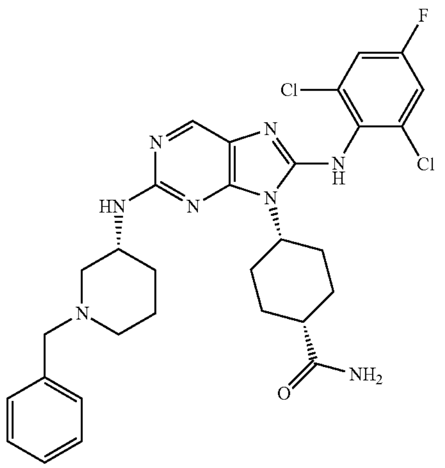 [SMILES: NC(=O)[C@H]1CC[C@@H](n2c(Nc3c(Cl)cc(F)cc3Cl)nc3cnc(N[C@@H]4CCCN(Cc5ccccc5)C4)nc32)CC1] | (1S,4s)-4-(2-((R)-1-benzylpiperidin-3-ylamino)-8-(2,6-dichloro-4-fluorophenylamino)-9H-purin-9-yl)cyclohexanecarboxamide | 611.2 | A |

TABLE 1-continued

| Cmpd No. | Structure | Name | MH+ | Activity |
|---|---|---|---|---|
| 760 | 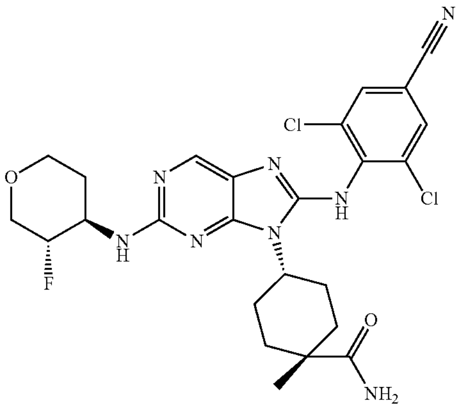 [SMILES: C[C@]1(C(N)=O)CC[C@@H](n2c(Nc3c(Cl)cc(C#N)cc3Cl)nc3cnc(N[C@@H]4CCOC[C@H]4F)nc32)CC1] | (1S,4s)-4-(8-(2,6-dichloro-4-cyanophenylamino)-2-((3S,4R)-3-fluorotetrahydro-2H-pyran-4-ylamino)-9H-purin-9-yl)-1-methylcyclohexanecarboxamide | 561.2 | D |
| 761 | 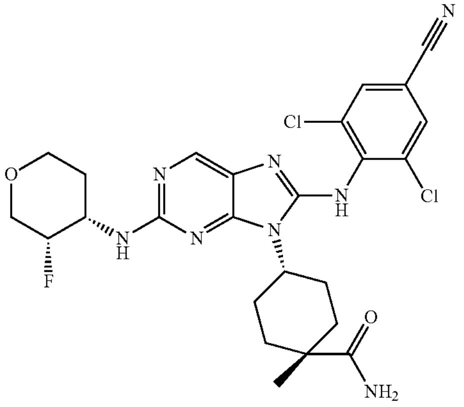 [SMILES: C[C@]1(C(N)=O)CC[C@@H](n2c(Nc3c(Cl)cc(C#N)cc3Cl)nc3cnc(N[C@H]4CCOC[C@H]4F)nc32)CC1] | (1R,4s)-4-(8-(2,6-dichloro-4-cyanophenylamino)-2-((3S,4S)-3-fluorotetrahydro-2H-pyran-4-ylamino)-9H-purin-9-yl)-1-methylcyclohexanecarboxamide | 561.2 | D |
| 762 | 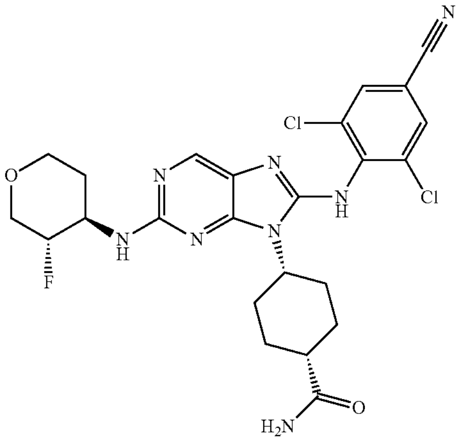 | (1S,4s)-4-(8-(2,6-dichloro-4-cyanophenylamino)-2-((3S,4R)-3-fluorotetrahydro-2H-pyran-4-ylamino)-9H-purin-9-yl)cyclohexanecarboxamide | 547.2 | D |

TABLE 1-continued

| Cmpd No. | Structure | Name | MH+ | Activity |
|---|---|---|---|---|
| 763 | 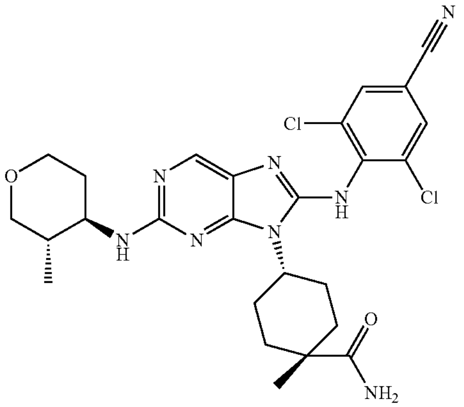 | (1S,4s)-4-(8-(2,6-dichloro-4-cyanophenylamino)-2-((3S,4R)-3-methyltetrahydro-2H-pyran-4-ylamino)-9H-purin-9-yl)-1-methylcyclohexanecarboxamide | 557.2 | D |
| 764 | 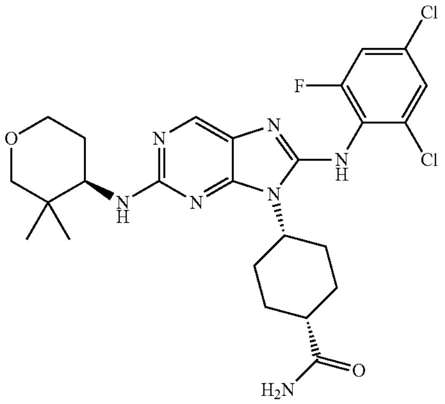 | (1S,4s)-4-(8-(2,4-dichloro-6-fluorophenylamino)-2-((R)-3,3-dimethyltetrahydro-2H-pyran-4-ylamino)-9H-purin-9-yl)cyclohexanecarboxamide | 551.2 | B |
| 765 | 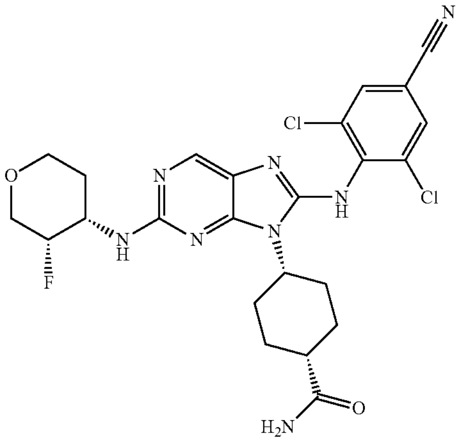 | (1R,4s)-4-(8-(2,6-dichloro-4-cyanophenylamino)-2-((3S,4S)-3-fluorotetrahydro-2H-pyran-4-ylamino)-9H-purin-9-yl)cyclohexanecarboxamide | 548.1 | D |

TABLE 1-continued

| Cmpd No. | Structure | Name | MH+ | Activity |
|---|---|---|---|---|
| 766 | 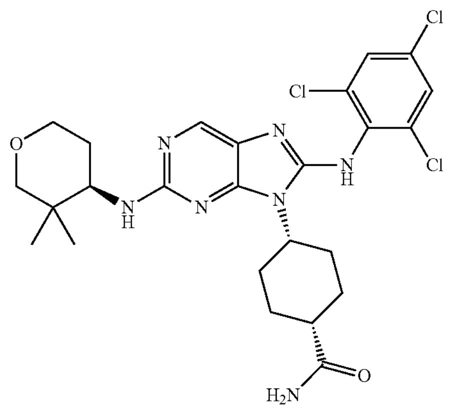 [SMILES: CC1(C)COCC[C@H]1Nc1ncc2nc(Nc3c(Cl)cc(Cl)cc3Cl)n([C@H]3CC[C@@H](C(N)=O)CC3)c2n1] | (1S,4s)-4-(2-((R)-3,3-dimethyltetrahydro-2H-pyran-4-ylamino)-8-(2,4,6-trichlorophenylamino)-9H-purin-9-yl)cyclohexanecarboxamide | 567.2 | B |
| 767 | 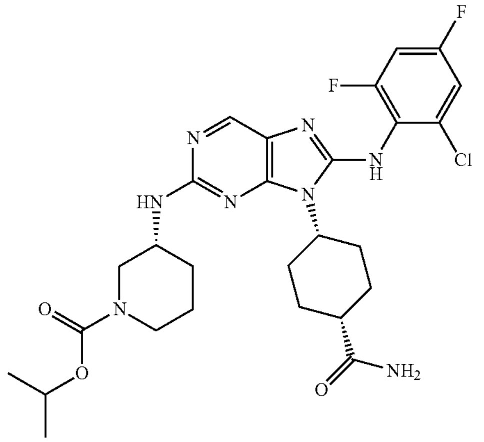 [SMILES: CC(C)OC(=O)N1CCC[C@@H](Nc2ncc3nc(Nc4c(F)cc(F)cc4Cl)n([C@H]4CC[C@@H](C(N)=O)CC4)c3n2)C1] | (R)-isopropyl 3-(9-((1s,4S)-4-carbamoylcyclohexyl)-8-(2-chloro-4,6-difluorophenylamino)-9H-purin-2-ylamino)piperidine-1-carboxamide | 591.2 | A |
| 768 | 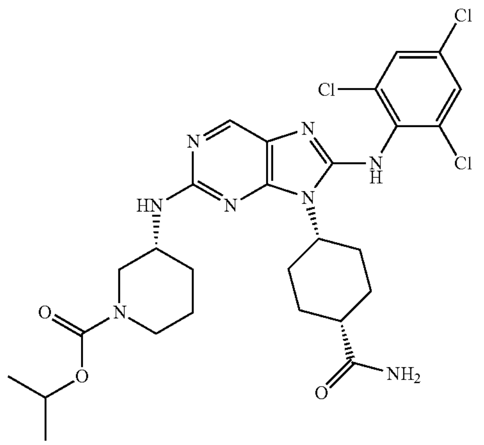 [SMILES: CC(C)OC(=O)N1CCC[C@@H](Nc2ncc3nc(Nc4c(Cl)cc(Cl)cc4Cl)n([C@H]4CC[C@@H](C(N)=O)CC4)c3n2)C1] | (R)-isopropyl 3-(9-((1s,4S)-4-carbamoylcyclohexyl)-8-(2,4,6-trichlorophenylamino)-9H-purin-2-ylamino)piperidine-1-carboxylate | 623.2 | B |

TABLE 1-continued

| Cmpd No. | Structure | Name | MH+ | Activity |
|---|---|---|---|---|
| 769 | 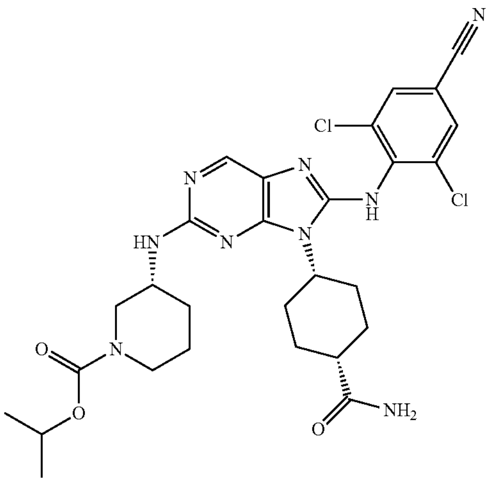 [SMILES: CC(C)OC(=O)N1CCC[C@@H](Nc2ncc3nc(Nc4c(Cl)cc(C#N)cc4Cl)n([C@H]4CC[C@@H](C(N)=O)CC4)c3n2)C1] | (R)-isopropyl 3-(9-((1s,4S)-4-carbamoylcyclohexyl)-8-(2,6-dichloro-4-cyanophenylamino)-9H-purin-2-ylamino)piperidine-1-carboxylate | 614.2 | B |
| 770 | 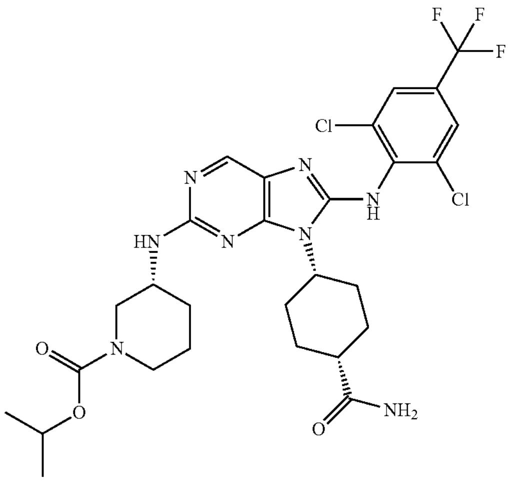 [SMILES: CC(C)OC(=O)N1CCC[C@@H](Nc2ncc3nc(Nc4c(Cl)cc(C(F)(F)F)cc4Cl)n([C@H]4CC[C@@H](C(N)=O)CC4)c3n2)C1] | (R)-isopropyl 3-(9-((1s,4S)-4-carbamoylcyclohexyl)-8-(2,6-dichloro-4-(trifluoromethyl)phenylamino)-9H-purin-2-ylamino)piperidine-1-carboxamide | 657.2 | A |
| 771 | 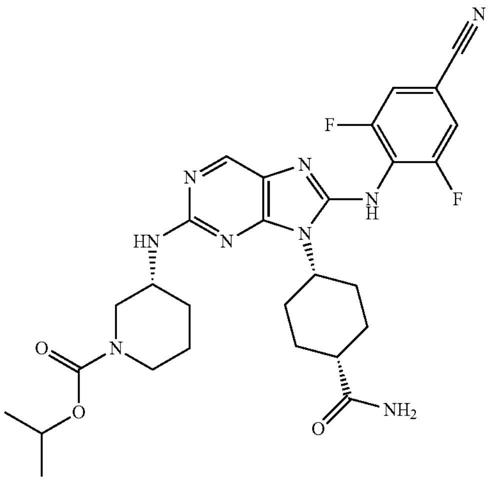 [SMILES: CC(C)OC(=O)N1CCC[C@@H](Nc2ncc3nc(Nc4c(F)cc(C#N)cc4F)n([C@H]4CC[C@@H](C(N)=O)CC4)c3n2)C1] | (R)-isopropyl 3-(9-((1s,4S)-4-carbamoylcyclohexyl)-8-(4-cyano-2,6-difluorophenylamino)-9H-purin-2-ylamino)piperidine-1-carboxylate | 582.2 | A |

TABLE 1-continued

| Cmpd No. | Structure | Name | MH+ | Activity |
|---|---|---|---|---|
| 772 | 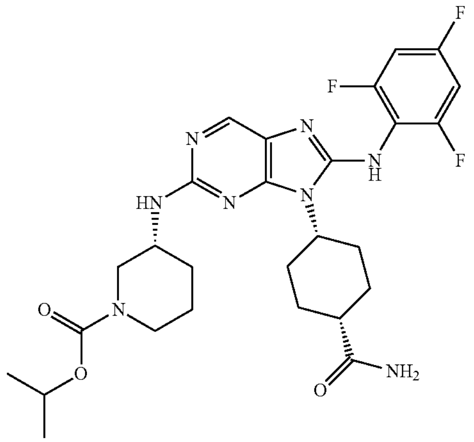 [SMILES: CC(C)OC(=O)N1CCC[C@@H](Nc2ncc3nc(Nc4c(F)cc(F)cc4F)n([C@H]4CC[C@@H](C(N)=O)CC4)c3n2)C1] | (R)-isopropyl 3-(9-((1s,4S)-4-carbamoylcyclohexyl)-8-(2,4,6-trifluorophenylamino)-9H-purin-2-ylamino)-piperidine-1-carboxylate | 575.2 | A |
| 773 | 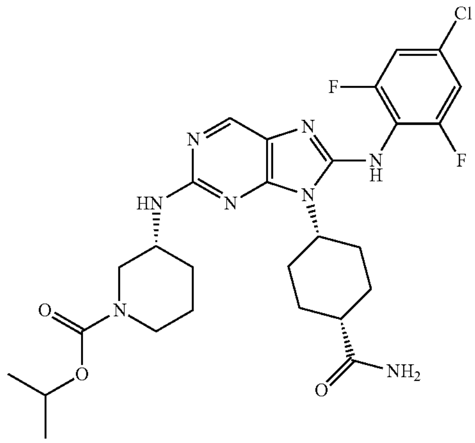 | (R)-isopropyl 3-(9-((1s,4S)-4-carbamoylcyclohexyl)-8-(4-chloro-2,6-difluorophenylamino)-9H-purin-2-ylamino)piperidine-1-carboxylate | 591.2 | B |
| 774 | 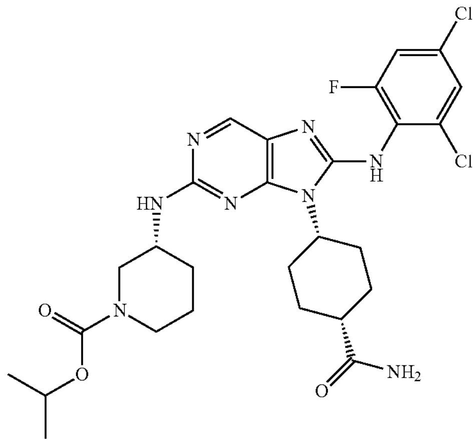 [SMILES: CC(C)OC(=O)N1CCC[C@@H](Nc2ncc3nc(Nc4c(F)cc(Cl)cc4Cl)n([C@H]4CC[C@@H](C(N)=O)CC4)c3n2)C1] | (R)-isopropyl 3-(9-((1s,4S)-4-carbamoylcyclohexyl)-8-(2,4-dichloro-6-fluorophenylamino)-9H-purin-2-ylamino)piperidine-1-carboxylate | 607.2 | C |

TABLE 1-continued

| Cmpd No. | Structure | Name | MH+ | Activity |
|---|---|---|---|---|
| 775 | 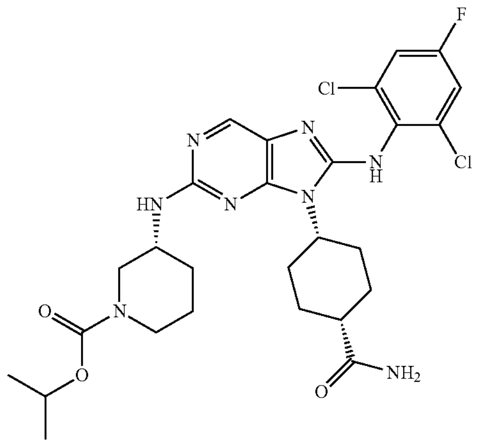 [SMILES: CC(C)OC(=O)N1CCC[C@@H](Nc2ncc3nc(Nc4c(Cl)cc(F)cc4Cl)n([C@H]4CC[C@@H](C(N)=O)CC4)c3n2)C1] | (R)-isopropyl 3-(9-((1s,4S)-4-carbamoylcyclohexyl)-8-(2,6-dichloro-4-fluorophenylamino)-9H-purin-2-ylamino)piperidine-1-carboxylate | 607.2 | A |
| 776 | 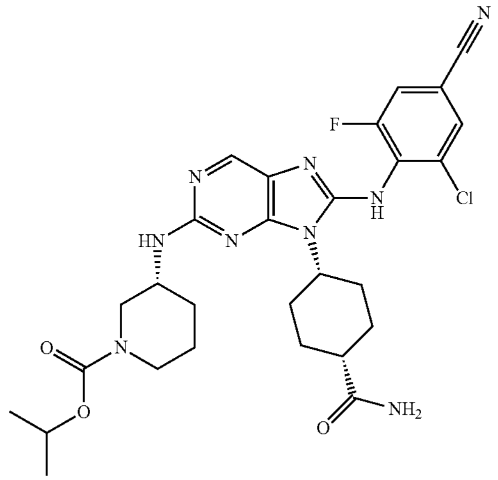 [SMILES: CC(C)OC(=O)N1CCC[C@@H](Nc2ncc3nc(Nc4c(F)cc(C#N)cc4Cl)n([C@H]4CC[C@@H](C(N)=O)CC4)c3n2)C1] | (R)-isopropyl 3-(9-((1s,4S)-4-carbamoylcyclohexyl)-8-(2-chloro-4-cyano-6-fluorophenylamino)-9H-purin-2-ylamino)piperidine-1-carboxylate | 582.2 | B |
| 777 | 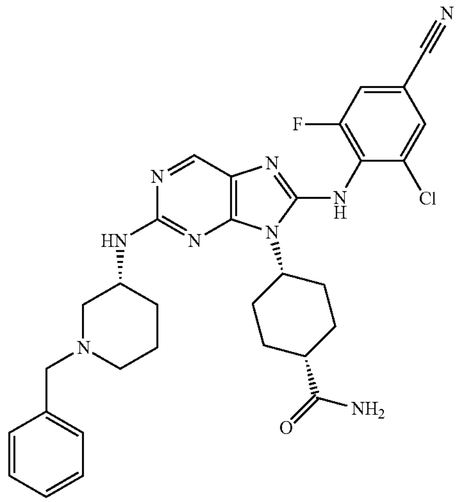 | (1S,4s)-4-(2-((R)-1-benzylpiperidin-3-ylamino)-8-(2-chloro-4-cyano-6-fluorophenylamino)-9H-purin-9-yl)cyclohexanecarboxamide | 602.2 | A |

TABLE 1-continued

| Cmpd No. | Structure | Name | MH+ | Activity |
|---|---|---|---|---|
| 778 | 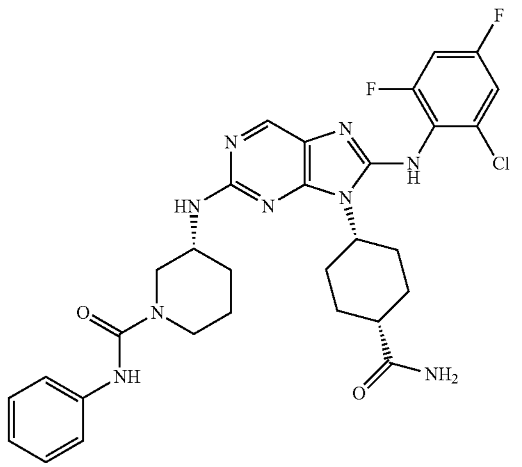 [SMILES: NC(=O)[C@H]1CC[C@@H](n2c(Nc3c(F)cc(F)cc3Cl)nc3cnc(N[C@@H]4CCCN(C(=O)Nc5ccccc5)C4)nc32)CC1] | (R)-3-(9-((1s,4S)-4-carbamoylcyclohexyl)-8-(2-chloro-4,6-difluorophenylamino)-9H-purin-2-ylamino)-N-phenylpiperidine-1-carboxamide | 624.2 | A |
| 779 | 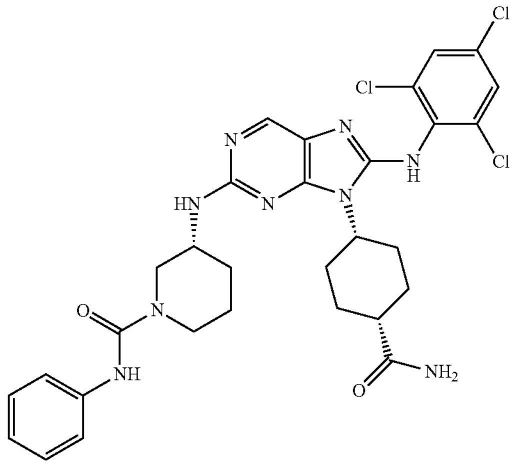 [SMILES: NC(=O)[C@H]1CC[C@@H](n2c(Nc3c(Cl)cc(Cl)cc3Cl)nc3cnc(N[C@@H]4CCCN(C(=O)Nc5ccccc5)C4)nc32)CC1] | (R)-3-(9-((1s,4S)-4-carbamoylcyclohexyl)-8-(2,4,6-trichlorophenylamino)-9H-purin-2-ylamino)-N-phenylpiperidine-1-carboxamide | 656.2 | B |
| 780 | 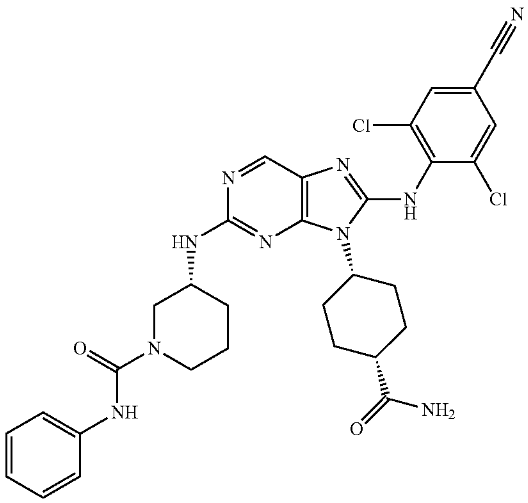 [SMILES: N#Cc1cc(Cl)c(Nc2nc3cnc(N[C@@H]4CCCN(C(=O)Nc5ccccc5)C4)nc3n2[C@H]2CC[C@@H](C(N)=O)CC2)c(Cl)c1] | (R)-3-(9-((1s,4S)-4-carbamoylcyclohexyl)-8-(2,6-dichloro-4-cyanophenylamino)-9H-purin-2-ylamino)-N-phenylpiperidine-1-carboxamide | 647.2 | A |

TABLE 1-continued

| Cmpd No. | Structure | Name | MH+ | Activity |
|---|---|---|---|---|
| 781 | 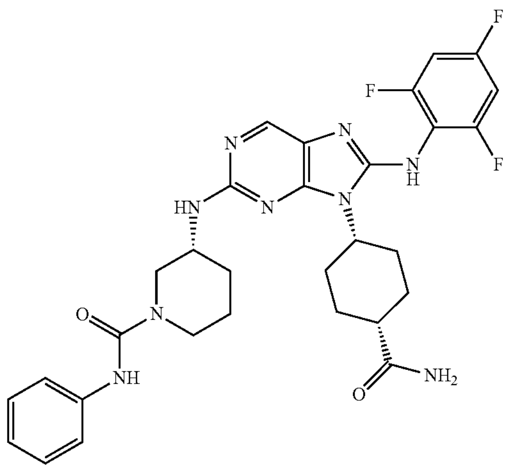 [SMILES: NC(=O)[C@H]1CC[C@@H](n2c(Nc3c(F)cc(F)cc3F)nc3cnc(N[C@@H]4CCCN(C(=O)Nc5ccccc5)C4)nc32)CC1] | (R)-3-(9-((1s,4S)-4-carbamoylcyclohexyl)-8-(2,4,6-trifluorophenylamio)-9H-purin-2-ylamino)-N-phenylpiperidine-1-carboxamide | 608.2 | A |
| 782 | 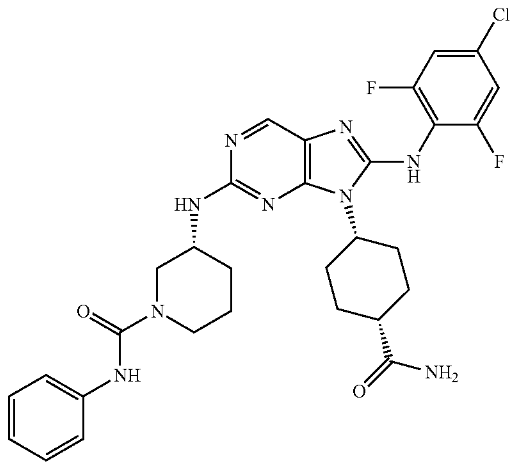 [SMILES: NC(=O)[C@H]1CC[C@@H](n2c(Nc3c(F)cc(Cl)cc3F)nc3cnc(N[C@@H]4CCCN(C(=O)Nc5ccccc5)C4)nc32)CC1] | (R)-3-(9-((1s,4S)-4-carbamoylcyclohexyl)-8-(4-chloro-2,6-difluorophenylamino)-9H-purin-2-ylamino)-N-phenylpiperidine-1-carboxamide | 624.2 | A |
| 783 | 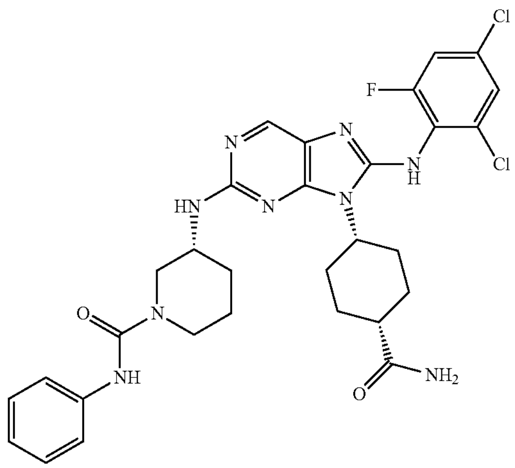 [SMILES: NC(=O)[C@H]1CC[C@@H](n2c(Nc3c(F)cc(Cl)cc3Cl)nc3cnc(N[C@@H]4CCCN(C(=O)Nc5ccccc5)C4)nc32)CC1] | (R)-3-(9-((1s,4S)-4-carbamoylcyclohexyl)-8-(2,4-dichloro-6-fluorophenylamino)-9H-purin-2-ylamino)-N-phenylpiperidine-1-carboxamide | 640.2 | A |

TABLE 1-continued

| Cmpd No. | Structure | Name | MH+ | Activity |
|---|---|---|---|---|
| 784 | 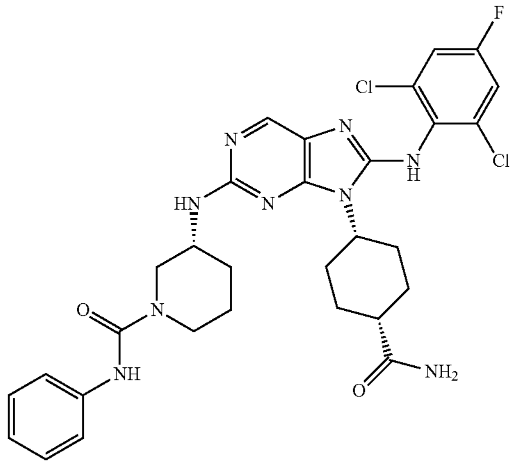 [SMILES: NC(=O)[C@H]1CC[C@@H](n2c(Nc3c(Cl)cc(F)cc3Cl)nc3cnc(N[C@@H]4CCCN(C(=O)Nc5ccccc5)C4)nc32)CC1] | (R)-3-(9-((1s,4S)-4-carbamoylcyclohexyl)-8-(2,6-dichloro-4-fluorophenylamino)-9H-purin-2-ylamino)-N-phenylpiperidine-1-carboxamide | 640.2 | A |
| 785 | 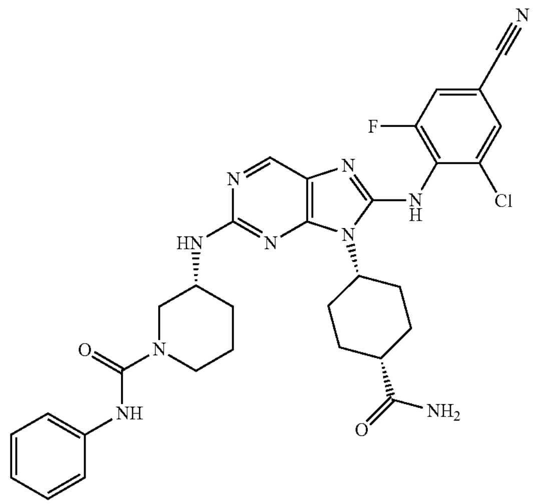 [SMILES: N#Cc1cc(F)c(Nc2nc3cnc(N[C@@H]4CCCN(C(=O)Nc5ccccc5)C4)nc3n2[C@H]2CC[C@@H](C(N)=O)CC2)c(Cl)c1] | (R)-3-(9-((1s,4S)-4-carbamoylcyclohexyl)-8-(2-chloro-4-cyano-6-fluorophenylamino)-9H-purin-2-ylamino)-N-phenylpiperidine-1-carboxamide | 631.2 | A |
| 786 | 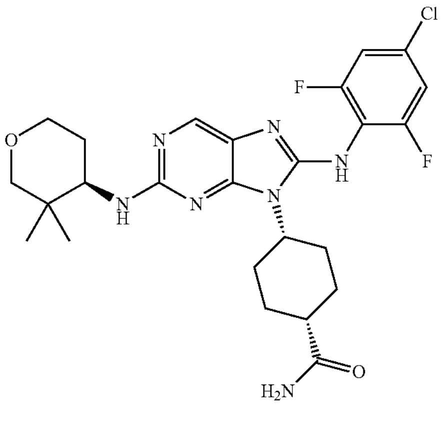 [SMILES: CC1(C)COCC[C@H]1Nc1ncc2nc(Nc3c(F)cc(Cl)cc3F)n([C@H]3CC[C@@H](C(N)=O)CC3)c2n1] | (1S,4s)-4-(8-(4-chloro-2,6-difluorophenylamino)-2-((R)-3,3-dimethyltetrahydro-2H-pyran-4-ylamino)-9H-purin-9-yl)cyclohexanecarboxamide | 535.2 | A |

TABLE 1-continued
| Cmpd No. | Structure | Name | MH+ | Activity |
| --- | --- | --- | --- | --- |
| 787 | 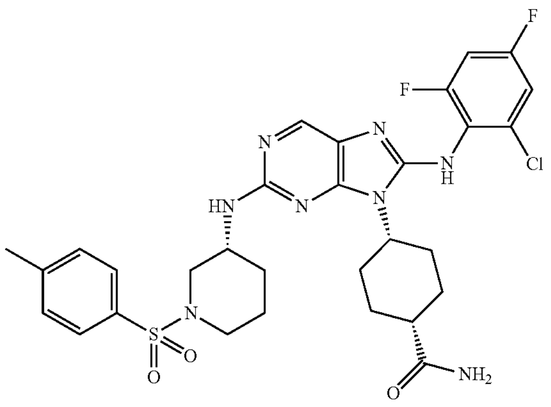 [SMILES: Cc1ccc(S(=O)(=O)N2CCC[C@@H](Nc3ncc4nc(Nc5c(F)cc(F)cc5Cl)n([C@H]5CC[C@@H](C(N)=O)CC5)c4n3)C2)cc1] | (1S,4s)-4-(8-(2-chloro-4,6-difluorophenylamino)-2-((R)-1-tosylpiperidin-3-ylamino)-9H-purin-9-yl)cyclohexanecarboxamide | 659.2 | A |
| 788 | 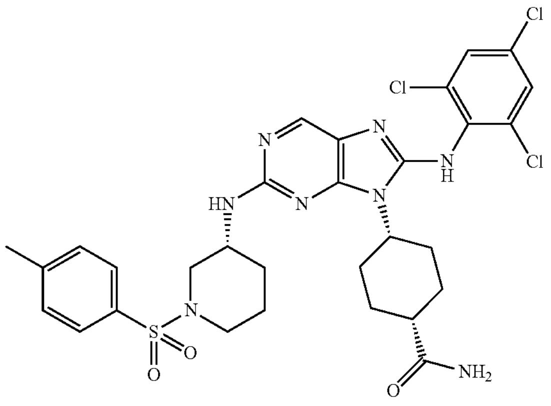 | (1S,4s)-4-(2-((R)-1-tosylpiperidin-3-ylamino)-8-(2,4,6-trichlorophenylamino)-9H-purin-9-yl)cyclohexanecarboxamide | 691.2 | A |
| 789 | 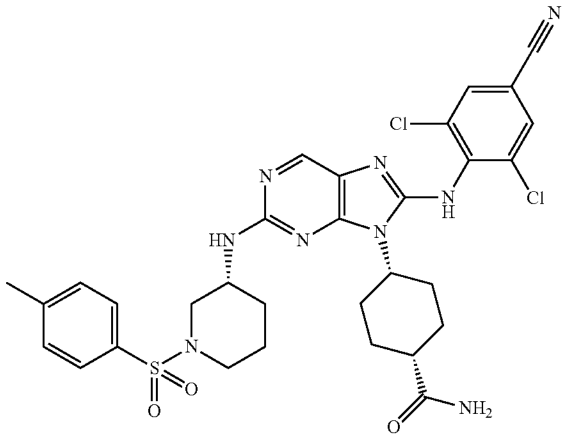 [SMILES: Cc1ccc(S(=O)(=O)N2CCC[C@@H](Nc3ncc4nc(Nc5c(Cl)cc(C#N)cc5Cl)n([C@H]5CC[C@@H](C(N)=O)CC5)c4n3)C2)cc1] | (1S,4s)-4-(8-(2,6-dichloro-4-cyanophenylamino)-2-((R)-1-tosylpiperidin-3-ylamino)-9H-purin-9-yl)cyclohexanecarboxamide | 682.2 | A |

TABLE 1-continued
| Cmpd No. | Structure | Name | MH+ | Ac-tivi-ty |
|---|---|---|---|---|
| 790 | 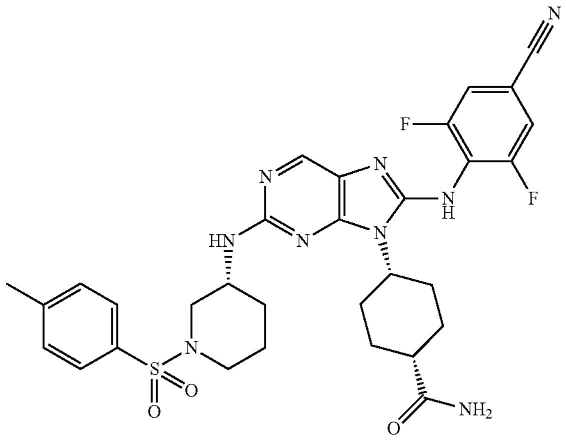 [SMILES: Cc1ccc(S(=O)(=O)N2CCC[C@@H](Nc3ncc4nc(Nc5c(F)cc(C#N)cc5F)n([C@H]5CC[C@@H](C(N)=O)CC5)c4n3)C2)cc1] | (1S,4s)-4-(8-(4-cyano-2,6-difluorophenylamino)-2-((R)-1-tosylpiperidin-3-ylamino)-9H-purin-9-yl)cyclohexanecarboxamide | 650.2 | A |
| 791 | 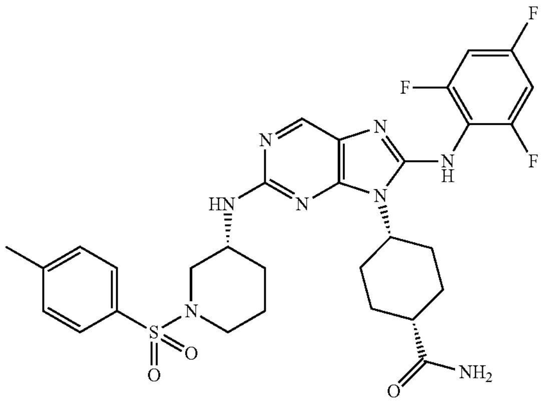 [SMILES: Cc1ccc(S(=O)(=O)N2CCC[C@@H](Nc3ncc4nc(Nc5c(F)cc(F)cc5F)n([C@H]5CC[C@@H](C(N)=O)CC5)c4n3)C2)cc1] | (1S,4s)-4-(2-((R)-1-tosylpiperidin-3-ylamino)-8-(2,4,6-trifluorophenylamino)-9H-purin-9-yl)cyclohexanecarboxamide | 643.2 | A |
| 792 | 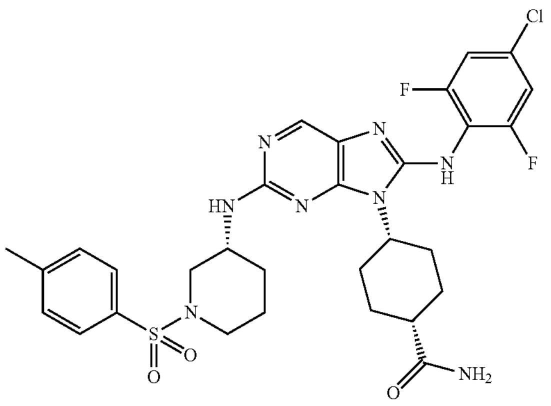 | (1S,4s)-4-(8-(4-chloro-2,6-difluorophenylamino)-2-((R)-1-tosylpiperidin-3-ylamino)-9H-purin-9-yl)cyclohexanecarboxamide | 659.2 | A |

TABLE 1-continued
| Cmpd No. | Structure | Name | MH+ | Activity |
|---|---|---|---|---|
| 793 | 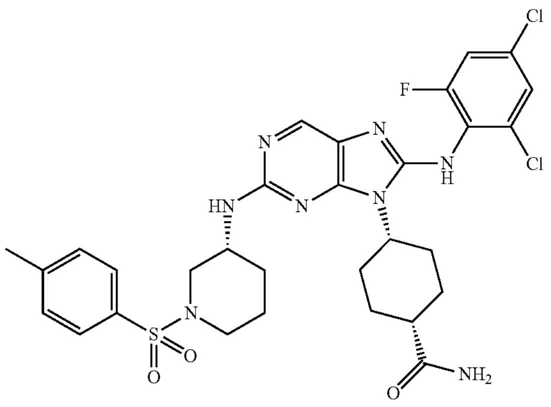 | (1S,4s)-4-(8-(2,4-dichloro-6-fluorophenylamino)-2-((R)-1-tosylpiperidin-3-ylamino)-9H-purin-9-yl)cyclohexanecarboxamide | 675.2 | A |
| 794 | 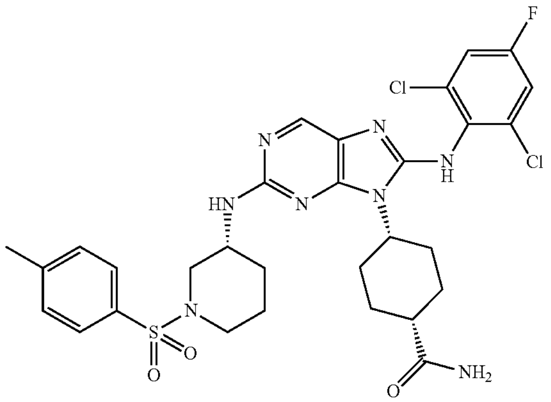 [SMILES: Cc1ccc(S(=O)(=O)N2CCC[C@@H](Nc3ncc4nc(Nc5c(Cl)cc(F)cc5Cl)n([C@H]5CC[C@@H](C(N)=O)CC5)c4n3)C2)cc1] | (1S,4s)-4-(8-(2,6-dichloro-4-fluorophenylamino)-2-((R)-1-tosylpiperidin-3-ylamino)-9H-purin-9-yl)cyclohexanecarboxamide | 675.2 | A |
| 795 | 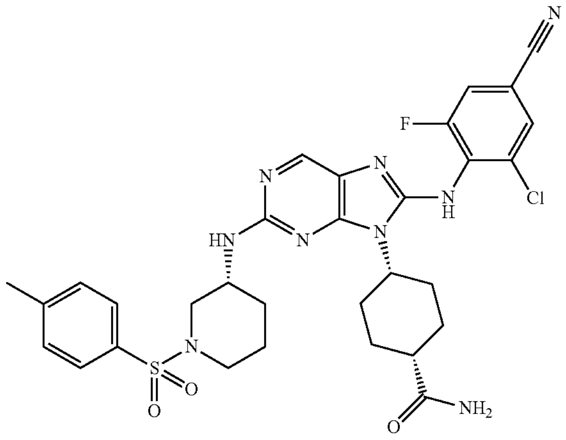 | (1S,4s)-4-(8-(2-chloro-4-cyano-6-fluorophenylamino)-2-((R)-1-tosylpiperidin-3-ylamino)-9H-purin-9-yl)cyclohexanecarboxamide | 666.2 | A |

TABLE 1-continued

| Cmpd No. | Structure | Name | MH+ | Activity |
|---|---|---|---|---|
| 796 | 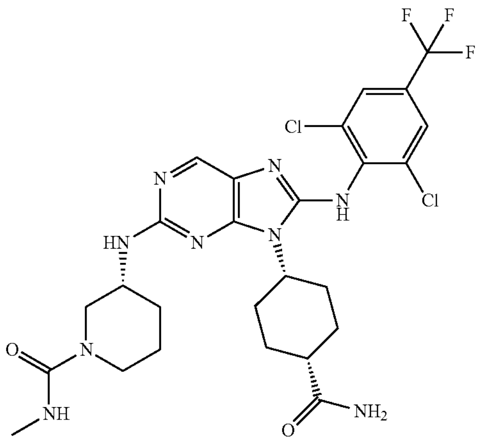 [SMILES: CNC(=O)N1CCC[C@@H](Nc2ncc3nc(Nc4c(Cl)cc(C(F)(F)F)cc4Cl)n([C@H]4CC[C@@H](C(N)=O)CC4)c3n2)C1] | (R)-3-(9-((1s,4S)-4-carbamoylcyclohexyl)-8-(2,6-dichloro-4-(trifluoromethyl)phenylamino)-9H-purin-2-ylamino)-N-methylpiperidine-1-carboxamide | 628.2 | A |
| 797 | 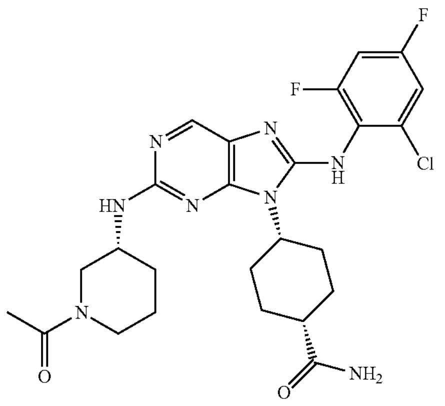 [SMILES: CC(=O)N1CCC[C@@H](Nc2ncc3nc(Nc4c(F)cc(F)cc4Cl)n([C@H]4CC[C@@H](C(N)=O)CC4)c3n2)C1] | (1S,4s)-4-(2-((R)-1-acetylpiperidin-3-ylamino)-8-(2-chloro-4,6-difluorophenylamino)-9H-purin-9-yl)cyclohexanecarboxamide | 547.2 | A |
| 798 | 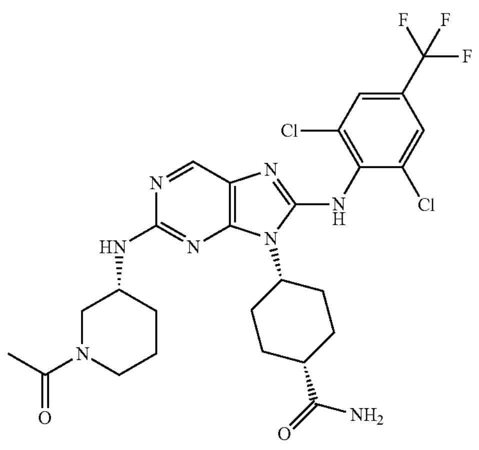 [SMILES: CC(=O)N1CCC[C@@H](Nc2ncc3nc(Nc4c(Cl)cc(C(F)(F)F)cc4Cl)n([C@H]4CC[C@@H](C(N)=O)CC4)c3n2)C1] | (1S,4s)-4-(2-((R)-1-acetylpiperidin-3-ylamino)-8-(2,6-dichloro-4-(trifluoromethyl)phenylamino)-9H-purin-9-yl)cyclohexanecarboxamide | 613.2 | A |

TABLE 1-continued
| Cmpd No. | Structure | Name | MH+ | Activity |
|---|---|---|---|---|
| 799 | 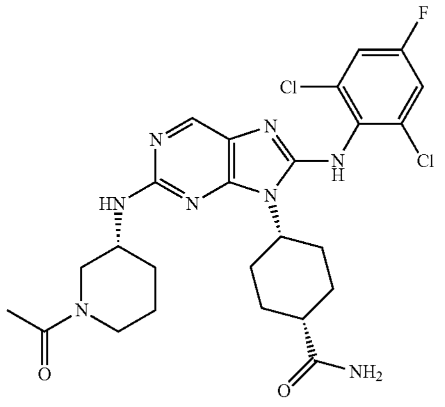 [SMILES: CC(=O)N1CCC[C@@H](Nc2ncc3nc(Nc4c(Cl)cc(F)cc4Cl)n([C@H]4CC[C@@H](C(N)=O)CC4)c3n2)C1] | (1S,4s)-4-(2-((R)-1-acetylpiperidin-3-ylamino)-8-(2,6-dichloro-4-fluorophenylamino)-9H-purin-9-yl)cyclohexanecarboxamide | 563.2 | A |
| 800 | 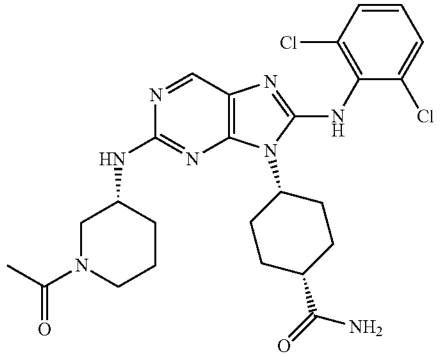 [SMILES: CC(=O)N1CCC[C@@H](Nc2ncc3nc(Nc4c(Cl)cccc4Cl)n([C@H]4CC[C@@H](C(N)=O)CC4)c3n2)C1] | (1S,4s)-4-(2-((R)-1-acetylpiperidin-3-ylamino)-8-(2,6-dichlorophenylamino)-9H-purin-9-yl)cyclohexanecarboxamide | 545.2 | A |
| 801 | 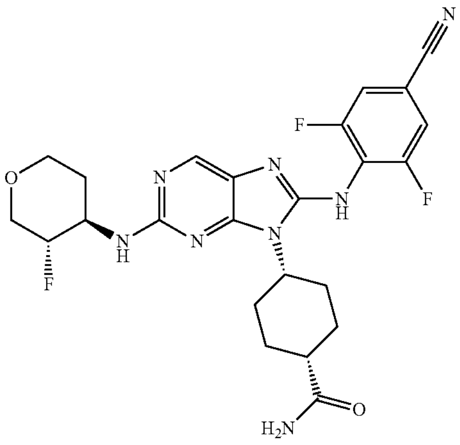 [SMILES: N#Cc1cc(F)c(Nc2nc3cnc(N[C@@H]4CCOC[C@H]4F)nc3n2[C@H]2CC[C@@H](C(N)=O)CC2)c(F)c1] | (1S,4s)-4-(8-(4-cyano-2,6-difluorophenylamino)-2-((3S,4R)-3-fluorotetrahydro-2H-pyran-4-ylamino)-9H-purin-9-yl)cyclohexanecarboxamide | 515.3 | D |

TABLE 1-continued

| Cmpd No. | Structure | Name | MH+ | Activity |
| --- | --- | --- | --- | --- |
| 802 | 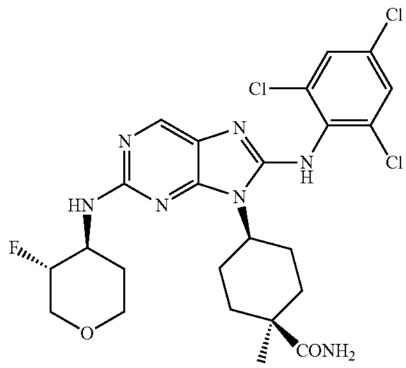 [SMILES: C[C@]1(C(N)=O)CC[C@@H](n2c(Nc3c(Cl)cc(Cl)cc3Cl)nc3cnc(N[C@H]4CCOC[C@@H]4F)nc32)CC1] | (1R,4s)-4-(2-(((3R,4S)-3-fluorotetrahydro-2H-pyran-4-yl)amino)-8-((2,4,6-trichlorophenyl)amino)-9H-purin-9-yl)-1-methylcyclohexane-1-carboxamide | 571.0 | D |

A number of references have been cited, the disclosures of which are incorporated herein by reference in their entirety.

What is claimed is:

1. A method for treating melanoma, comprising administering to a patient having melanoma an effective amount of a compound of formula (I):

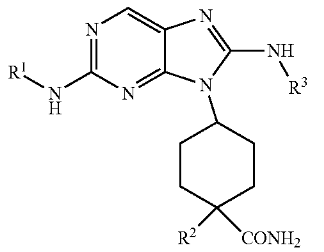

(I)

or a pharmaceutically acceptable salt, tautomer, stereoisomer or enantiomer thereof, wherein:

$R^1$ is substituted or unsubstituted $C_{1-8}$ alkyl, substituted or unsubstituted cycloalkyl, substituted or unsubstituted cycloalkylalkyl, or substituted or unsubstituted non-aromatic heterocyclyl;

$R^2$ is H or substituted or unsubstituted $C_{1-3}$ alkyl;

$R^3$ is phenyl, substituted with one or more halogen, optionally further substituted with one or more substituents independently selected from substituted or unsubstituted $C_{1-3}$ alkyl, CN, and —OR', wherein each R' is independently substituted or unsubstituted $C_{1-3}$ alkyl;

wherein when an alkyl group is substituted, it is substituted with a substituent selected from the group consisting of chloro; iodo; bromo; fluoro; alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; acyl; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; $B(OH)_2$; and O(alkyl)aminocarbonyl;

wherein when a group other than an alkyl group is substituted, it is substituted with a substituent selected from the group consisting of chloro; iodo; bromo; fluoro; alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; acyl; ester; urea; urethane; oxime; hydroxylamine; alkoxyamine; aryloxyamine; aralkoxyamine; N-oxide; hydrazine; hydrazide; hydrazone; azide; isocyanate; isothiocyanate; cyanate; thiocyanate; oxo; $B(OH)_2$, O(alkyl)aminocarbonyl; cycloalkyl, which may be monocyclic or fused or non-fused polycyclic, or a heterocyclyl, which may be monocyclic or fused or non-fused polycyclic; monocyclic or fused or non-fused polycyclic aryl or heteroaryl; aryloxy; aralkyloxy; heterocyclyloxy; and heterocyclylalkoxy; and provided that the compound is not 4-[2-[(1-methylethyl)amino]-8-[(2,4,6-trifluorophenyl)amino]-9H-purin-9-yl]-cis-cyclohexanecarboxamide, or 4-[8-[(2,4-difluorophenyl)amino]-2-[(trans-4-hydroxycyclohexyl)amino]-9H-purin-9-yl]-cis-cyclohexanecarboxamide, wherein said compound of formula (I) is administered to said patient one to four times a day in a dose of about 0.005 mg/kg to about 10 mg/kg of said patient's body weight.

2. The method of claim 1, wherein the dose is about 0.01 mg/kg to about 5 mg/kg of said patient's body weight, about 0.05 mg/kg to about 1 mg/kg of said patient's body weight, about 0.1 mg/kg to about 0.75 mg/kg of said patient's body weight or about 0.25 mg/kg to about 0.5 mg/kg of said patient's body weight.

3. The method of claim 1, wherein the dose is about 0.25 mg/kg to about 0.5 mg/kg of said patient's body weight.

4. The method of claim 1, wherein $R^1$ is oxetanyl, tetrahydrofuranyl, tetrahydropyranyl, tetrahydro-thiopyrandioxide, piperidyl, oxepanyl, or oxaspiroheptyl, optionally substituted with one or more substituents independently selected from F, OH, $SO_2CH_3$, $SO_2$-tosyl, $C(=O)CH_3$, $C(=O)OCH_3$, $C(=O)O$-tert-butyl, $C(=O)O$-isopropyl, $C(=O)NHCH_3$, $C(=O)NH$-phenyl, methyl, ethyl, isopropyl, $CH_2OH$, phenyl, pyridyl, or benzyl.

5. The method of claim 1, wherein $R^2$ is $CH_3$.

6. The method of claim 1, wherein $R^3$ is 2,4,6-trihalogen substituted phenyl.

7. The method of claim 1, wherein the compound is (1s,4s)-4-(8-(3-chlorophenylamino)-2-(isopropylamino)-9H-purin-9-yl)cyclohexanecarboxamide.

8. The method of claim 1, wherein the compound is (1R,4s)-4-(8-(2,4-dichloro-6-fluorophenylamino)-2-((S)-1-hydroxypropan-2-ylamino)-9H-purin-9-yl)cyclohexanecarboxamide.

9. The method of claim 1, wherein the compound is (1R,4s)-4-(8-(2,4-dichloro-6-fluorophenylamino)-2-((S)-1-hydroxypropan-2-ylamino)-9H-purin-9-yl)-1-methylcyclohexanecarboxamide.

10. The method of claim 1, wherein the compound is (1R,4s)-4-(8-(2,6-dichloro-4-cyanophenylamino)-2-((S)-1-hydroxypropan-2-ylamino)-9H-purin-9-yl)cyclohexanecarboxamide.

11. The method of claim 1, wherein the compound is (1s,4s)-4-(2-(cyclobutylamino)-8-(2,6-dichloro-4-cyanophenylamino)-9H-purin-9-yl)cyclohexanecarboxamide.

12. The method of claim 1, wherein the compound is (1s,4s)-4-(2-(cyclobutylamino)-8-(2,6-dichloro-4-cyanophenylamino)-9H-purin-9-yl)-1-methylcyclohexanecarboxamide.

13. The method of claim 1, wherein the compound is (1s,4s)-4-(2-(3,3-difluorocyclobutylamino)-8-(2,4,6-trifluorophenylamino)-9H-purin-9-yl)-1-methylcyclohexanecarboxamide.

14. The method of claim 1, wherein the compound is (1s,4s)-4-(2-(cyclopentylamino)-8-(2,6-dichloro-4-cyanophenylamino)-9H-purin-9-yl)cyclohexanecarboxamide.

15. The method of claim 1, wherein the compound is (1S,4s)-4-(8-(2,6-dichloro-4-fluorophenylamino)-2-((R)-3,3-difluorocyclopentylamino)-9H-purin-9-yl)cyclohexanecarboxamide.

16. The method of claim 1, wherein the compound is (1R,4s)-4-(2-(((3R,4 S)-3-fluorotetrahydro-2H-pyran-4-yl)amino)-8-((2,4,6-trichlorophenyl)amino)-9H-purin-9-yl)-1-methylcyclohexane-1-carboxamide.

17. The method of claim 1, wherein the compound is (1R,4S)-4-(8-(2,4-dichloro-6-fluorophenyl amino)-2-((1 S,3R)-3-hydroxycyclohexylamino)-9H-purin-9-yl)-1-methylcyclohexanecarboxamide.

18. The method of claim 1, wherein the compound is (1S,4s)-4-(2-(((3 S,4R)-3-fluorotetrahydro-2H-pyran-4-yl)amino)-8-((2,4,6-trichlorophenyl)amino)-9H-purin-9-yl)-1-methylcyclohexane-1-carboxamide.

19. The method of claim 1, wherein the compound is (1S,4s)-4-(8-((4-chloro-2,6-difluorophenyl)amino)-2-(((3 S,4R)-3-methyltetrahydro-2H-pyran-4-yl)amino)-9H-purin-9-yl)cyclohexane-1-carboxamide.

20. The method of claim 1, wherein the compound is (1s,4s)-4-(8-(4-chloro-2,6-difluorophenyl)amino)-2-((tetrahydro-2H-pyran-4-yl)amino)-9H-purin-9-yl)cyclohexane-1-carboxamide.

* * * * *